US008168418B2

(12) United States Patent
Barnett et al.

(10) Patent No.: US 8,168,418 B2
(45) Date of Patent: May 1, 2012

(54) EXPRESSION OF HIV POLYPEPTIDES AND PRODUCTION OF VIRUS-LIKE PARTICLES

(76) Inventors: Susan W Barnett, San Francisco, CA (US); Jan Zur Megede, San Francisco, CA (US); Indresh Srivastava, Concord, CA (US); Ying Lian, Vallejo, CA (US); Karin Hartog, Piedmont, CA (US); Hong Liu, Castro Valley, CA (US); Catherine Greer, Oakland, CA (US); Mark Selby, San Francisco, CA (US); Christopher Walker, Blacklick, OH (US)

( * ) Notice: Subject to any disclaimer, the term of this patent is extended or adjusted under 35 U.S.C. 154(b) by 0 days.

(21) Appl. No.: 12/770,905

(22) Filed: Apr. 30, 2010
(Under 37 CFR 1.47)

(65) Prior Publication Data
US 2011/0065146 A1    Mar. 17, 2011

Related U.S. Application Data

(60) Division of application No. 12/026,619, filed on Feb. 6, 2008, now Pat. No. 7,718,401, which is a division of application No. 10/387,336, filed on Mar. 11, 2003, now Pat. No. 7,348,177, which is a continuation of application No. 09/475,515, filed on Dec. 30, 1999, now Pat. No. 6,602,705.

(60) Provisional application No. 60/114,495, filed on Dec. 31, 1998, provisional application No. 60/168,471, filed on Dec. 1, 1999.

(51) Int. Cl.
*C12N 7/00* (2006.01)
*A61K 39/21* (2006.01)
(52) U.S. Cl. .................... 435/235.1; 424/208.1
(58) Field of Classification Search ................ None
See application file for complete search history.

(56) References Cited

U.S. PATENT DOCUMENTS

| 4,652,639 | A | 3/1987 | Stabinsky |
| 4,861,707 | A | 8/1989 | Ivanoff et al. |
| RE33,653 | E | 7/1991 | Mark et al. |
| 5,032,510 | A | 7/1991 | Kovacevic et al. |
| 5,082,767 | A | 1/1992 | Hatfield et al. |
| 5,128,319 | A | 7/1992 | Arlinghaus |
| 5,130,247 | A | 7/1992 | Kniskern et al. |
| 5,156,949 | A | 10/1992 | Luciw et al. |
| 5,256,767 | A | 10/1993 | Salk et al. |
| 5,304,472 | A | 4/1994 | Bass et al. |
| 5,364,773 | A | 11/1994 | Paoletti et al. |
| 5,419,900 | A | 5/1995 | Lane et al. |
| 5,503,833 | A | 4/1996 | Redmond et al. |
| 5,550,280 | A | 8/1996 | Dao-Cong et al. |
| 5,637,677 | A | 6/1997 | Greene et al. |
| 5,665,569 | A | 9/1997 | Ohno |
| 5,665,720 | A | 9/1997 | Young et al. |
| 5,670,152 | A | 9/1997 | Weiner et al. |
| 5,683,864 | A | 11/1997 | Houghton et al. |
| 5,686,078 | A | 11/1997 | Becker et al. |
| 5,688,688 | A | 11/1997 | Luciw et al. |
| 5,693,755 | A | 12/1997 | Buonagurio et al. |
| 5,712,088 | A | 1/1998 | Houghton et al. |
| 5,714,596 | A | 2/1998 | Houghton et al. |
| 5,728,520 | A | 3/1998 | Weiner et al. |
| 5,741,492 | A | 4/1998 | Hurwitz et al. |
| 5,750,373 | A | 5/1998 | Garrard et al. |
| 5,766,845 | A | 6/1998 | Weiner et al. |
| 5,786,464 | A | 7/1998 | Seed |
| 5,792,459 | A | 8/1998 | Haigwood |
| 5,795,737 | A | 8/1998 | Seed et al. |
| 5,817,637 | A | 10/1998 | Weiner et al. |
| 5,837,242 | A | 11/1998 | Holliger et al. |
| 5,837,818 | A | 11/1998 | Buonagurio et al. |
| 5,840,313 | A | 11/1998 | Vahlne et al. |
| 5,846,546 | A | 12/1998 | Hurwitz et al. |
| 5,853,736 | A | 12/1998 | Becker et al. |
| 5,858,675 | A | 1/1999 | Hillman et al. |
| 5,859,193 | A | 1/1999 | Devare et al. |
| 5,866,320 | A | 2/1999 | Rovinski et al. |
| 5,871,747 | A | 2/1999 | Gengoux-Sedlik et al. |
| 5,876,724 | A | 3/1999 | Girard |
| 5,876,731 | A | 3/1999 | Sia et al. |
| 5,879,907 | A | 3/1999 | Aberg et al. |
| 5,879,925 | A | 3/1999 | Rovinski et al. |
| 5,889,176 | A | 3/1999 | Rovinski et al. |
| 5,932,445 | A | 8/1999 | Lal et al. |

(Continued)

FOREIGN PATENT DOCUMENTS
EP    187041    7/1986
(Continued)

OTHER PUBLICATIONS

Adams et al., "The Expression of Hybrid Hiv:ty Virus-like Particles in Yeast," Nature 329:68-70 (1987).
Anderson, et al., "Human Gene Therapy," Nature 392(6679 Suppl):25-30 (1998).
Andre et al., "Increased Immune Response Elicited by DNA Vaccination with a Synthetic gp120 Sequence with Optimized Codon Usage," J. Virology 72(2):1497-1503 (1998).
Arthur, et al., "Serological Responses in Chimpanzees Inoculated with Human Immunodeficiency Virus Glycoprotein (Gp120) Subunit Vaccine," Proc Natl Acad Sci USA 84(23):8583-8587 (1987).
Azevedo et al., "Main Features of DNA-Based Immunization Vectors," Braz J Med Biol Res. 32(2):147-153 (1999).

(Continued)

*Primary Examiner* — Stacy B. Chen
(74) *Attorney, Agent, or Firm* — Regina Bautista; Helen Lee

(57) ABSTRACT

The present invention relates to the efficient expression of HIV polypeptides in a variety of cell types, including, but not limited to, mammalian, insect, and plant cells. Synthetic expression cassettes encoding the HIV Gag-containing polypeptides are described, as are uses of the expression cassettes in applications including DNA immunization, generation of packaging cell lines, and production of Env-, tat- or Gag-containing proteins. The invention provides methods of producing Virus-Like Particles (VLPs), as well as, uses of the VLPs including, but not limited to, vehicles for the presentation of antigens and stimulation of immune response in subjects to whom the VLPs are administered.

14 Claims, 131 Drawing Sheets

U.S. PATENT DOCUMENTS

| | | | |
|---|---|---|---|
| 5,951,975 A | 9/1999 | Falo, Jr. et al. |
| 5,955,342 A | 9/1999 | Rovinski et al. |
| 5,965,726 A | 10/1999 | Pavlakis et al. |
| 5,972,596 A | 10/1999 | Pavlakis et al. |
| 6,001,977 A | 12/1999 | Chang et al. |
| 6,004,763 A | 12/1999 | Gengoux et al. |
| 6,025,125 A | 2/2000 | Rovinski et al. |
| 6,060,273 A | 5/2000 | Dirks et al. |
| 6,060,587 A | 5/2000 | Weiner et al. |
| 6,063,384 A | 5/2000 | Morrow et al. |
| 6,074,636 A | 6/2000 | Nichols |
| 6,080,408 A | 6/2000 | Rovinski et al. |
| 6,087,486 A | 7/2000 | Weiner et al. |
| 6,090,388 A | 7/2000 | Wang |
| 6,093,800 A | 7/2000 | Reiter et al. |
| 6,096,505 A | 8/2000 | Selby et al. |
| 6,099,847 A | 8/2000 | Tobin et al. |
| 6,114,148 A | 9/2000 | Seed et al. |
| 6,132,973 A | 10/2000 | Lal et al. |
| 6,139,833 A | 10/2000 | Burgess et al. |
| 6,140,059 A | 10/2000 | Schawaller |
| 6,146,635 A | 11/2000 | Cano et al. |
| 6,172,201 B1 | 1/2001 | Weiner et al. |
| 6,174,666 B1 | 1/2001 | Pavlakis et al. |
| 6,214,804 B1 | 4/2001 | Felgner et al. |
| 6,291,157 B1 | 9/2001 | Rovinski et al. |
| 6,291,664 B1 | 9/2001 | Pavlakis et al. |
| 6,316,253 B1 | 11/2001 | Innis et al. |
| 6,331,404 B1 | 12/2001 | Berman et al. |

FOREIGN PATENT DOCUMENTS

| | | |
|---|---|---|
| EP | 199301 | 10/1986 |
| EP | 242216 | 10/1987 |
| EP | 314317 | 5/1989 |
| EP | 449116 | 10/1991 |
| EP | 617132 | 9/1994 |
| EP | 449116 | 10/1999 |
| WO | WO 86/03224 | 6/1986 |
| WO | WO 87/02775 | 5/1987 |
| WO | WO 88/00471 | 1/1988 |
| WO | WO 88/10300 | 12/1988 |
| WO | WO 89/01940 | 3/1989 |
| WO | WO 89/02277 | 3/1989 |
| WO | WO 89/02922 | 4/1989 |
| WO | WO 89/03222 | 4/1989 |
| WO | WO 90/00556 | 1/1990 |
| WO | WO 90/02568 | 3/1990 |
| WO | WO 90/03984 | 4/1990 |
| WO | WO 90/10438 | 9/1990 |
| WO | WO 90/11092 | 10/1990 |
| WO | WO 90/11359 | 10/1990 |
| WO | WO 90/12094 | 10/1990 |
| WO | WO 90/15141 | 12/1990 |
| WO | WO 91/04273 | 4/1991 |
| WO | WO 91/06319 | 5/1991 |
| WO | WO 91/07425 | 5/1991 |
| WO | WO 91/07510 | 5/1991 |
| WO | WO 91/13360 | 9/1991 |
| WO | WO 91/13906 | 9/1991 |
| WO | WO 91/15238 | 10/1991 |
| WO | WO 91/15512 | 10/1991 |
| WO | WO 91/16926 | 11/1991 |
| WO | WO 91/18928 | 12/1991 |
| WO | WO 91/19803 | 12/1991 |
| WO | WO 92/03475 | 3/1992 |
| WO | WO 92/04046 | 3/1992 |
| WO | 9205798 A1 | 4/1992 |
| WO | WO 92/05799 | 4/1992 |
| WO | WO 93/02102 | 2/1993 |
| WO | WO 93/04090 | 3/1993 |
| WO | WO 93/08836 | 5/1993 |
| WO | WO 93/14789 | 8/1993 |
| WO | WO 93/20212 | 10/1993 |
| WO | WO 93/21346 | 10/1993 |
| WO | WO 93/23569 | 11/1993 |
| WO | WO 94/04574 | 3/1994 |
| WO | WO 94/07922 | 4/1994 |
| WO | WO 94/11523 | 5/1994 |
| WO | WO 94/13804 | 6/1994 |
| WO | WO 94/15621 | 7/1994 |
| WO | WO 94/16060 | 7/1994 |
| WO | WO 94/16737 | 8/1994 |
| WO | WO 94/18221 | 8/1994 |
| WO | WO 94/20141 | 9/1994 |
| WO | WO 94/20640 | 9/1994 |
| WO | WO 94/22477 | 10/1994 |
| WO | WO 94/26293 | 11/1994 |
| WO | WO 94/29339 | 12/1994 |
| WO | WO 95/03407 | 2/1995 |
| WO | WO 95/04818 | 2/1995 |
| WO | WO 95/11317 | 4/1995 |
| WO | WO 95/11701 | 5/1995 |
| WO | WO 95/24485 | 9/1995 |
| WO | WO 95/25124 | 9/1995 |
| WO | WO 95/27505 | 10/1995 |
| WO | WO 95/29700 | 11/1995 |
| WO | WO 95/33206 | 12/1995 |
| WO | WO 95/33835 | 12/1995 |
| WO | WO 96/02273 | 2/1996 |
| WO | WO 96/02557 | 2/1996 |
| WO | WO 96/04382 | 2/1996 |
| WO | WO 96/09066 | 3/1996 |
| WO | WO 96/09378 | 3/1996 |
| WO | WO 96/16178 | 5/1996 |
| WO | WO 96/20732 | 7/1996 |
| WO | WO 96/23509 | 8/1996 |
| WO | WO 96/25177 | 8/1996 |
| WO | WO 96/30523 | 10/1996 |
| WO | WO 96/40290 | 12/1996 |
| WO | WO 97/03198 | 1/1997 |
| WO | WO 97/11605 | 4/1997 |
| WO | WO 97/26009 | 7/1997 |
| WO | WO 97/31115 | 8/1997 |
| WO | WO 97/48370 | 12/1997 |
| WO | WO 98/08539 | 3/1998 |
| WO | WO 98/12207 | 3/1998 |
| WO | WO 98/34640 | 8/1998 |
| WO | WO 98/41536 | 9/1998 |
| WO | WO 98/41645 | 9/1998 |
| WO | WO 98/43182 | 10/1998 |
| WO | WO 98/48843 | 11/1998 |
| WO | WO 98/59074 | 12/1998 |
| WO | WO 99/02694 | 1/1999 |
| WO | WO 99/06599 | 2/1999 |
| WO | WO 99/09412 | 2/1999 |
| WO | WO 99/12416 | 3/1999 |
| WO | WO 99/13864 | 3/1999 |
| WO | WO 99/16883 | 4/1999 |
| WO | WO 99/33346 | 7/1999 |
| WO | WO 99/41397 | 8/1999 |
| WO | WO 99/41398 | 8/1999 |
| WO | WO 99/52463 | 10/1999 |
| WO | WO 99/53960 | 10/1999 |
| WO | WO 99/67395 | 12/1999 |
| WO | WO 00/08043 | 2/2000 |
| WO | WO 00/15819 | 3/2000 |
| WO | WO 00/18929 | 4/2000 |
| WO | WO 00/21556 | 4/2000 |
| WO | WO 00/29561 | 5/2000 |
| WO | WO 00/39302 | 7/2000 |
| WO | WO 00/39303 | 7/2000 |
| WO | WO 00/39304 | 7/2000 |
| WO | WO 00/44926 | 8/2000 |
| WO | WO 00/65076 | 11/2000 |
| WO | WO 00/66179 | 11/2000 |
| WO | WO 00/67761 | 11/2000 |
| WO | WO 00/67787 | 11/2000 |
| WO | WO 00/71561 | 11/2000 |
| WO | WO 01/02607 | 1/2001 |
| WO | WO 01/12223 | 2/2001 |
| WO | WO 01/16342 | 3/2001 |
| WO | WO 01/19958 | 3/2001 |
| WO | WO 01/21270 | 3/2001 |
| WO | WO 01/26681 | 4/2001 |
| WO | WO 01/29225 | 4/2001 |
| WO | WO 01/36614 | 5/2001 |

| WO | WO 01/42308 | 6/2001 |
| WO | WO 01/43693 | 6/2001 |
| WO | WO 01/45748 | 6/2001 |
| WO | WO 01/46408 | 6/2001 |
| WO | WO 01/47955 | 7/2001 |
| WO | WO 01/54701 | 8/2001 |
| WO | WO 01/54719 | 8/2001 |
| WO | WO 01/60393 | 8/2001 |
| WO | WO 01/60838 | 8/2001 |
| WO | 0204493 A2 | 1/2002 |
| WO | WO 03/004620 | 1/2003 |

OTHER PUBLICATIONS

Baker et al., "Structures of Bovine and Human Papillomaviruses. Analysis by Cryoelectron Microscopy and Three-dimensional Image Reconstruction," Biophys. J. 60:1445-1456 (1991).
Barr, et al., "Antigenicity and Immunogenicity of Domains of the Human Immunodeficiency Virus (HIV) Envelope Polypeptide Expressed in the Yeast *Saccharomyces cerevisiae*," Vaccine 5(2):90-101 (1987).
Barre-Sinoussi et al., Science 220:868-871 (1983).
Barrett, et al., "Large-scale production and purification of a vaccinia recombinant-derived HIV-1 gp160 and analysis of its immunogenicity," AIDS Res Hum Retroviruses 5(2):159-71 (1989).
Beard, W. A., et al.,"Role of the "Helix Clamp" in HIV-1 Reverse Transcriptase Catalytic Cycling as Revealed by Alanine-Scanning Mutagenesis," Journal of Biological Chemistry 271(21):12213-12220 (1996).
Berger, P.B., "New Directions in Research: Report from the 10th International Conference on AIDS," Canadian Medical Association Journal 152(12):1991-1995 (1995).
Berman, et al., "Expression and Immunogenicity of the Extracellular Domain of the Human Immunodeficiency Virus Type 1 Envelope Glycoprotein, gp160," J Virol. 63(8):3489-3498 (1989).
Berman, et al., "Human Immunodeficiency Virus Type 1 Challenge of Chimpanzees Immunized with Recombinant Envelope Glycoprotein gp120," Proc Natl Acad Sci USA 85(14):5200-5204 (1988).
Birx and Redfield, "HIV Vaccine Therapy," Int J Immunopharmacol. 13(1):129-132 (1991).
Bolognesi et al., Ann. Int. Med. 8(7):603-611 (1994).
Bolognesi, D.P., "Progress in Vaccines Against AIDS," Science 246:1233-1234 (1989).
Borrow, et al., "Virus-Specific CD8+ Cytotoxic T-Lymphocyte Activity Associated with Control of Viremia in Primary Human Immunodeficiency Virus Type 1 Infection," J. Virol. 68(9):6103-6110 (1994).
Borsetti et al., J. Virol. 72(11):9313-9317 (1998).
Bourgault, et al., "Cytotoxic T-Cell Response and AIDS-Free Survival in Simian Immunodeficiency Virus-Infected Macaques," AIDS. 7 (Suppl 2):S73-S79 (1993).
Brown et al., "Chimeric Parvovirus B19 Capsids for the Presentation of Foreign Epitopes," Virology 198477:488 (1994).
Bujacz, G., et al., "The Catalytic Domain of Human Immunodeficiency Virus Integrase: Ordered Active Site in the F185H Mutant," Febs Letters 398(2-3):175-178 (1996).
Burton et al., "Why Do We Not Have an HIV Vaccine and How Can We Make One?" Nat Med. 4(5 Suppl):495-498 (1998).
Burton et al., AIDS 11(Suppl. A):S87-S98 (1997).
Cao et al., J. Virol. 71(12):9808-9812 (1997).
Carmichael et al., "Quantitative Analysis of the Human Immunodeficiency Virus Type 1 (Hiv-1)-specific Cytotoxic T Lymphocyte (Ctl) Response at Different Stages of Hiv-1 Infection: Differential Ctl Responses to Hiv-1 and Epstein-barr Virus in Late Disease," J Exp Med. 177(2):249-256 (1993).
Chazal N. et al., "Phenotypic Characterization of Insertion Mutants of the Human Immunodeficiency Virus Type 1 Gag Precursor Expressed in Recombinant Baculovirus-infected Cells," Virology 68(1):111-122 (1994).
Cheng-Mayer, PNAS USA 86:8575-8579 (1989).
Ciernik et al., "Induction of Cytotoxic T Lymphocytes and Antitumor Immunity with Dna Vaccines Expressing Single T Cell Epitopes," J. Immunol. 156(7):2369-2375 (1996).

Clavel et al., "Isolation of a New Human Retrovirus from West African Patients with AIDS," Science 233:343-346 (1986).
Clavel et al., "Molecular Cloning and Polymorphism of the Human Immune Deficiency Virus Type 2," Nature 324:691-695 (1986).
Daar et al., "Transient High Levels of Viremia in Patients with Primary Human Immunodeficiency Virus Type 1 Infection," N Engl J Med. 324(14):961-964 (1991).
Davey et al., "Subcutaneous administration of interleukin-2 in human immunodeficiency virus type 1-infected persons," J Infect Dis. 175(4):781-789 (1997).
Davies J. F., et al., "Crystal structure of the ribonuclease H domain of HIV-1 reverse transcriptase," Science 252(5002):88-95 (1991).
Deminie et al., "Evaluation of Reverse Transcriptase and Protease Inhibitors in Two-drug Combinations Against Human Immunodeficiency Virus Replication," Antimicrob Agents Chemother. 40(6):1346-1351 (1996).
Desai et al., "Molecular Cloning and Primary Nucleotide Sequence Analysis of a Distinct Human Immunodeficiency Virus Isolate Reveal Significant Divergence in its Genomic Sequence," Proc. Natl. Acad. Sci. USA 83:8380-8384 (1986).
Doe et al., "Induction of HIV-1 Envelope (gp120)-Specific Cytotoxic T Lymphocyte Responses in Mice by Recombinant CHO Cell-Derived gp120 is Enhanced by Enzymatic Removal of N-Linked Glycans," Eur. J. Immunol. 24:2369-2376 (1994).
Doe, B. and Walker, C.M. "HIV-1 p24 Gag-Specific Cytotoxic T-Lymphocyte Responses in Mice," AIDS 10(7):793-794 (1996).
D'Souza et al., J. Infect. Dis. 176:1056-1062 (1997).
Dyda F., et al., "Crystal Structure of the Catalytic Domain of HIV-1 Integrase: Similarity to Other Polynucleotidyl Transferases," Science 266(5193):1981-1986 (1994).
Earl et al., "Isolate- and Group-specific Immune Responses to the Envelope Protein of Human Immunodeficiency Virus Induced by a Live Recombinant Vaccinia Virus in Macaques," AIDS Res Hum Retroviruses 5(1):23-32 (1989).
Earl et al., J. Virol. 65:31-41 (1991).
Earl et al., PNAS USA 87:648-652 (1990).
Edelman, R., "Vaccine Adjuvants," Rev Infect Dis. 2(3):370-383 (1980).
Engelman, A. et al., "Structure-based Mutagenesis of the Catalytic Domain of Human Immunodeficiency Virus Type 1 Integrase," Journal of Virology 71(5):3507-3514 (1997).
Esnouf et al., "Mechanism of Inhibition of HIV-1 Reverse Transcriptase by Nonnucleoside Inhibitors," Structural Biology 2(4)303-308 (1995).
Evans et al., "An Engineered Poliovirus Chimaera Elicits Broadly Reactive Hiv-1 Neutralizing Antibodies," Nature 339(6223):385-388 (1989).
Faust et al., "Outpatient Biopsies of the Palatine Tonsil: Access to Lymphoid Tissue for Assessment of Human Immunodeficiency Virus RNA Titers," Otolaryngol Head Neck Surg. 114(4):593-598 (1996).
Fennie et al., "Model for Intracellular Folding of the Human Immunodeficiency Virus Type 1 gp120," J Virol. 63(2):639-646 (1989).
Ferre et al., "Combination Therapies Against HIV-1 Infection:Exploring the Concept of Combining Antiretroviral Drug Treatments with HIV-1 Immune-Based Therapies in Asymptomatic Individuals," AIDS Patient Care STDS 10(6):357-361 (1996).
Fiore et al., Virol. 204, 297-303, 1994.
Fisher, et al., "Biologically diverse molecular variants within a single HIV-1 isolate," Nature 334:444-447 (1988).
Fox et al., "No Winners Against AIDS," Bio/Technology 12(2):128 (1994).
Freed, Virology 251:1-15 (1998).
Garnier, L. et al., "Particle Size Determinants in the Human Immunodeficiency Virus Type 1 Gag Protein," J Virol 72(6):4667-4677 (1998).
Goldgur, Y. et al., "Three New Structures of the Core Domain of HIV-1 Integrase: an Active Site That Binds Magnesium," Proceedings of the National Academy of Sciences of the United States of America 95(16):9150-9154 (1998).
Goudsmit et al., "Human Immunodeficiency Virus Type 1 Neutralization Epitope with Conserved Architecture Elicits Early Type-specific Antibodies in Experimentally Infected Chimpanzees," Proc. Natl. Acad. Sci. USA 85:4478-4482 (1988).
Greene, "AIDS and the Immune System," Scientific American Sep.: 9-105 (1993).
Griffiths J.C. et al., "Hybrid Human Immunodeficiency Virus Gag Particles as an Antigen Carrier System: Induction of Cytotoxic T-cell and Humoral Responses by a Gag:V3 Fusion," J. Virol. 67(6):3191-3198 (1993).
Grimison B. and Laurence, J., "Immunodominant Epitope Regions of HIV-1 Reverse Transcriptase: Correlations with HIV-1+ Serum IgG Inhibitory to Polymerase Activity and With Disease Progression," Journal of Acquired Immune Deficiency Syndromes and Human Retrovirology 9(1):58-68 (1995).
Gurgo et al., "Envelope Sequences of Two New United States HIV-1 Isolates," Virology 164:531-536 (1988).
Gurunathan et al., "CD40 Ligand/Trimer DNA Enhances Both Humoral and Cellular Immune Responses and Induces Protective Immunity to Infectious and Tumor Challenge," J Immunol. 161(9):4563-4571 (1998).
Guyader et al., "Genome Organization and Transactivation of the Human Immunodeficiency Virus Type 2," Nature 326:661-669 (1987).
Haas et al., "Cytotoxin T-Cell Responses to HIV-1 Reverse Transcriptase, Integrase and Protease," AIDS, 12:1427-1436 (1998).
Haas et al., Current Biology 6(3):315-324 (1996).
Hagensee et al., "Three-dimensional Structure of Vaccinia Virus-produced Human Papillomavirus Type 1 Capsids," J. Virol. 68:4503-4505 (1994).
Hahn et al., "Genetic Variation in HTLV-III/LAV Over Time in Patients with AIDS or at Risk for AIDS," Science 232:1548-1553 (1986).
Hamajima, et al., "The Combination of DNA and Peptide Vaccines Induces Strong Immunities Against HIV-1 in Both Humoral and CMI," 11.sup.th International AIDS Conference, Vancouver, Britich Columbia, Jul. 7-12; 11:6 (abstract No. Mo.A.151) (1996).
Hammer et al., "Issues in Combination Antiretroviral Therapy: a Review," J Acquir Immune Defic Syndr. 7(Suppl 2):S24-S37 (1994).
Haynes et al., "Toward an Understanding of the Correlates of Protective Immunity to Hiv Infection" Science 271:324-328 (1996).
Haynes et al., "Update on the Issues of Hiv Vaccine Development," Ann Med. 28(1):39-41 (1996).
Heeney et al., "Beta-chemokines and Neutralizing Antibody Titers Correlate with Sterilizing Immunity Generated in HIV-1 Vaccinated Macaques," Proc Natl Acad Sci USA 95(18):10803-10808 (1998).
Hickman, A. B., et al., "Biophysical and enzymatic properties of the catalytic domain of HIV-1 integrase," Journal of Biological Chemistry 269(46):29279-29287 (1994).
Ho et al., "Human Immunodeficiency Virus Neutralizing Antibodies Recognize Several Conserved Domains on the Envelope Glycoproteins," J Virol. 61(6):2024-2028 (1987).
Hu et al., Science 255:456-459 (1992).
Jacobo-Molina, A. et al., "Crystal Structure of Human Immunodeficiency Virus Type 1 Reverse Transcriptase Complexed with Double-stranded DNA at 3.0 A Resolution Shows Bent DNA," Proceedings of the National Academy of Sciences of the United States of America 90(13):6320-6324 (1993).
Javaherian et al., PNAS USA 86:6786-6792 (1989).
Jeffs et al., J. Gen. Virol. 77:1403-1410 (1996).
Kang et al., PNAS USA 88:6171-6175 (1991).
Katz, R. A. and Skalka, A. M., "The Retroviral Enzymes," Annual Review of Biochemistry 63:133-73 (1994).
Keefer, et al., "Safety and Immunogenicity of Env 2-3, a Human Immunodeficiency Virus Type 1 Candidate Vaccine, in Combination with a Novel Adjuvant, MTP-PE/MF59. NIAID AIDS Vaccine Evaluation Group," AIDS Res Hum Retroviruses. 12(8):683-693 (1996).
Kent, et al., "A Recombinant Avipoxvirus HIV-1 Vaccine Expressing Interferon-Gamma is Safe and Immunogenic in Macaques," Vaccine 18:2250-2256 (2000).
Kimbauer et al., "Efficient Self-assembly of Human Papillomavirus Type 16 L1 and L1-L2 into Virus-Like Particles," J. Virol. 67:6929-6936 (1993).

Klenerman, et al., "Original Antigenic Sin Impairs Cytotoxic T Lymphocyte Responses to Viruses Bearing Variant Epitopes," Nature 394(6692):482-485 (1998).
Koff and Schultz, "Progress and Challenges Toward and AIDS Vaccine: Brother, Can You Spare A Paradigm?" J. Clinical Immunology 16(3):127-133 (1996).
Koff et al., "Development and Testing of AIDS Vaccines," Science 241:426-432 (1988).
Kohl et al., "Active Human Immunodeficiency Virus Protease Is Required for Viral Infectivity," PNAS USA 85:4686-4690 (1988).
Kohlstaedt, L. A. et al., "Crystal Structure at 3.5 A Resolution of HIV-1 Reverse Transcriptase Complexed with an Inhibitor," Science 256(5065):1783-1790 (1992).
Koup et al., "Temporal Association of Cellular Immune Responses with the Initial Control of Viremia in Primary Human Immunodeficiency Virus Type 1 Syndrome," J Virol. 68(7):4650-4655 (1994).
Kovacs et al., "Controlled Trial of Interleukin-2 Infusions in Patients Infected with the Human Immunodeficiency Virus," N Engl J Med. 335(18):1350-1356 (1996).
Kovacs et al., "Increases in CD4 T Lymphocytes with Intermittent Courses of Interleukin-2 in Patients with Human Immunodeficiency Virus Infection," New England J. Med. 332(9):567-575 (1995).
Krausslich et al., "Proceessing of in Vitro-synthesized Gag Precursor Proteins of Human Immunodeficiency Virus (HIV) Type 1 by HIV Proteinase Generated in *Escherichia coli*," J. Virol. 62:4393-4397 (1988).
Kreuter J., et al., "Mode of Action of Immunological Adjuvants: Some Physicochemical Factors Influencing the Effectivity of Polyacrylic Adjuvants," Infect Immun. 19(2):667-675 (1978).
Krug, M. S. and Berger, S. L., "Reverse Transcriptase from Human Immunodeficiency Virus: a Simple Template-primer Binding Site Serves Two Physically Separable Catalytic Functions," Biochemistry 30(44):10614-10623 (1991).
Kwong et al., Nature 393:648-659 (1998).
Lalvani A. et al., "Rapid effector Function in CD8+ Memory T Cells," J. Exp. Med. 186:859-865 (1997).
Lasky et al., "Delineation of a Region of the Human Immunodeficiency Virus Type 1 gp120 Glycoprotein Critical for Interaction with the CD4 Receptor," Cell 50(6):975-985 (1987).
Levy et al., "Isolation of Lymphocytopathic Retroviruses from San Francisco Patients with AIDS," Science 225:840-842 (1984).
Littman et al., "Unusual Intron in the Immunoglobulin Domain of the Newly Isolated Murine CD4 (L3T4) Gene," Nature 325(6103):453-455 (1987).
Looney et al., "Type-restricted Neutralization of Molecular Clones of Human Immunodeficiency Virus," Science 241:357-359 (1988).
Lu et al., "Immunogenicity of DNA vaccines expressing human immunodeficiency virus type 1 envelope glycoprotein with and without deletions in the V1/2 and V3 regions," AIDS Research and Human Retroviruses 14(2):151-155 (1998).
Maddon et al., "The Isolation and Nucleotide Sequence of a Cdna Encoding the T Cell Surface Protein T4: a New Member of the Immunoglobulin Gene Family," Cell 42(1):93-104 (1985).
Maignan, S., et al. "Crystal Structures of the Catalytic Domain of HIV-1 Integrase Free and Complexed with its Metal Cofactor: High Level of Similarity of the Active Site with Other Viral Integrases," Journal of Molecular Biology 282(2):359-368 (1998).
Mammano et al., J. Virol. 68(8):4927-4936 (1994).
Manca et al., "Antigenicity of Hiv-derived T Helper Determinants in the Context of Carrier Recombinant Proteins: Effect on T Helper Cell Repertoire Selection," Eur J Immunol. 26(10):2411-2469 (1996).
Mascola et al., J. Infect. Dis. 169:48-54 (1994).
Matsushita et al., J. Virol. 62:2107-2144 (1988).
Matthews PNAS USA 83:9709-9713 (1986).
Mazumder, A., et al., "Effects of nucleotide analogues on human immunodeficiency virus type 1 integrase," Molecular Pharmacology 49(4):621-628 (1996).
Mazza et al., "Recombinant Interleukin-2 (Ril-2) in Acquired Immune Deficiency Syndrome (Aids): Preliminary Report in Patients with Lymphoma Associated with Hiv Infection," Eur J Haematol. 49(1):1-6 (1992).

McCluskie et al., "Route and method of delivery of DNA vaccine influence immune responses in mice and non-human primates," Mol. Med. 5, 287-300, 1999.

McComack et al., "HIV Protease Substrate Conformation: Modulation by Cyclophilin A," FEBS Letts 414:84-88 (1997).

McDougal et al., J Immunol. 137:2937-2944 (1986).

Mcheyzer-Williams, M.G. et al, "Enumeration and Characterization of Memory Cells in the Th Compartment," Immunol. Rev. 150:5-21 (1996).

McMichael, A.J. and O'Callaghan, C.A., "A New Look at T Cells," J. Exp. Med. 187(9)1367-1371 (1998).

Modrow et al., "Computer-assisted Analysis of Envelope Protein Sequences of Seven Human Immunodeficiency Virus Isolates: Prediction of Antigenic Epitopes in Conserved and Variable Regions," J. Virol. 61(2):570-578 (1987).

Montagnier et al., "Human T-Cell Leukemia Viruses: The Family of Human T-Lymphotropic Retroviruses: Their Role in Malignancies and Association with AIDS," Gallo, Essex & Gross, eds., pp. 363-379 (1984).

Monteflori et al., AIDS Res. Hum. Retroviruses 15(8):689-698 (1999).

Myers et al., "Human Retroviruses and AIDS," published by the Los Alamos National Laboratory, Los Alamos, NM, 1991, pp. I-A-48 to I-A-56 and II-77 to II-88.

Nara et al., J. Virol. 62:2622-2628 (1988).

Nathanson et al., "Biological Considerations in the Development of a Human Immunodeficiency Virus Vaccine," J Infect Dis. 182(2):579-589 (2000).

Novitsky et al., "Molecular Cloning and Phylogenetic Analysis of Human Immunodeficiency Virus Type 1 Subtype C: a Set of 23 Full-Length Clones from Botswana," J. Virol. 73(5):4427-4432 (1999).

Nowak and Bangham, "Population Dynamics of Immune Responses to Persistent Viruses," Science 272(5258):74-79 (1996).

Odile et al., "Anti-HIV Active Immunization, Evidence for Persistent Cell Mediated Immunity after a 2 Year Follow Up," Eighth International Conference on AIDS/III STD World Congress Amsterdam, The Netherlands Jul. 19-24, 1992, Abstract No. MOB 0024.

Okuda et al., "Induction of Potent Humoral and Cell-mediated Immune Responses Following Direct Injection of DNA Encoding the HIV Type 1 Env and Rev gene Products," AIDS Res Hum Retroviruses. 11(8):933-943 (1995).

Palaniappan, C. et al., "Mutations Within the Primer Grip Region of HIV-1 Reverse Transcriptase Result in Loss of Rnase H Function," Journal of Biological Chemistry 272(17):11157-11164 (1997).

Palker et al., PNAS USA 85:1932-1936 (1988).

Park et al., "Overexpression of The Gag-pol Precursor From Human Immunodeficiency Virus Type 1 Proviral Genomes Results in Efficient Proteolytic Processing in The Absence of Virion Production," J. Virol. 65:5111 (1991).

Patel et al., "Insights into DNA Polymerization Mechanisms from Structure and Function Analysis of HIV-1 Reverse Transcriptase," Biochemistry 34:5351-5363 (1995).

Peng et al., AIDS 11:587-595 (1997).

Perelson et al., "Decay Characteristics of HIV-1-infected Compartments During Combination Therapy," Nature 387, 188-91, 1997.

Popovic et al., "Detection, Isolation, and Continuous Production of Cytopathic Retroviruses (HTLV-III) from Patients with AIDS and Pre-AIDS," Science 224:497-500 (1984).

Putney et al., Science 234:1392-1395 (1986).

Pyle et al., "Immune Response to Immunostimulatory Complexes (ISCOMs) Prepared from Human Immunodeficiency Virus Type 1 (HIV-1) of the HIV-1 External Envelope Glycoprotein (gp120)," Vaccine 7(5):465-473 (1989).

Ratner et al., Nature 313:277-284 (1985).

Redfield and Birx, "Hiv-specific Vaccine Therapy: Concepts, Status, and Future Directions,"AIDS Res Hum Retroviruses 8(6):1051-1058 (1992).

Reicin, A.S. et al., "Linker Insertion Mutations in the Human Immunodeficiency Virus Type 1 Gag Gene: Effects on Virion Particle Assembly, Release, and Infectivity," J. Virol. 69(2):642-650 (1995).

Robert-Guroff et al., Nature (London) 316:72-74 (1985).

Robey, et al., "Prospect for Prevention of Human Immunodeficiency Virus Infection: Purified 120-kDa Envelope Glycoprotein Induces Neutralizing Antibody," Proc Natl Acad Sci USA 83(18):7023-7027 (1986).

Rodgers, D. W. et al., "The Structure of Unliganded Reverse Transcriptase from the Human Immunodeficiency Virus Type 1," Proceesing of the National Academy of Sciences of the United State of America 92(4):1222-1226 (1995).

Rushe et al., PNAS USA 85:3198-3202 (1988).

Saag and Kuritzkes, "Strategies for Continuing Antiretroviral Therapy," Intl AIDS Society USA 4(2):16-19 (1996).

Saag, et al., "Extensive Variation of Human Immunodeficiency Virus Type-1 in vivo," Nature 334:440-444 (1988).

Salk et al., "Prospects for the Control of Aids by Immunizing Seropositive Individuals," Nature 327(6122):473-476 (1987).

Sanchez-Pescador et al., Science 227(4686):484-492 (1985).

Schernthaner, et al., "Endosperm-specific Activity of a Zein Gene Promoter in Transgenic Tobacco Plants," The EMBO J. 7:1249-1259 (1988).

Schneider et al., "Inactivation of the human immunodeficiency virus type 1 inhibitory elements allows rev-independent expression of gag and gag/protease and particle formation," J. Virology 71(7):4892-4903 (1997).

Schulhafer et al., "Acquired Immunodeficiency Syndrome: Molecular Biology and its Therapeutic Intervention (review)," In Vivo 3(2):61-78 (1989).

Sheng N. and Dennis, D., "Active Site Labeling of HIV-1 Reverse Transcriptase," Biochemistry 32(18):4938-4942 (1993).

Smith et al., "Blocking of HIV-1 infectivity by a soluble, secreted form on the CD4 antigen," Science 238(4834):1704-1707 (1987).

Spence R. A., et al., "Mechanism of Inhibition of HIV-1 Reverse Transcriptase by Nonnucleotide Inhibitors," Science 267(5200):988-993 (1995).

Srinivasan et al., "Molecular Characterization of Human immunodeficiency Virus from Zaire: Nucleotide Sequence Analysis Identifies Conserved and Variable Domains in the Envelope Gene," Gene 52:71-82 (1987).

Stamatatos et al., "An envelope modification that renders a primary, neutralization-resistant clade B human immunodeficiency virus type 1 isolate highly susceptible to neutralization by sera from other clades," J. Virology 72(10):7840-7845 (1998).

Stamatatos et al., AIDS Res. Hum. Retroviruses 14(13):1129-1139 (1998).

Starcich et al., "Identification and Characterization of Conserved and Variable Regions in the Envelope Gene of HTLV-III/LAV, the Retroviruses of AIDS," Cell 45:637-648 (1986).

Steimer et al., "Genetically Engineered Human Immunodeficiency Envelope Glycoprotein Gp120 Produced in Yeast Is the Target of Neutralizing Antibodies," Vaccines 87:236-241 (1987).

Sternberg et al., "Prediction of Antigenic Determinants and Secondary Structures of the Major Aids Virus Proteins," FEBS Letters 218(2):231-237 (1987).

Thali et al., J. Virol. 67(7):3978-3988 (1993).

Tindle et al., "Chimeric Hepatitis B Core Antigen Particles Containing B- and Th-epitopes of Human Papillomavirus Type 16 E7 Protein Induce Specific Antibody and T-helper Responses in Immunised Mice," Virology 200:547-557 (1994).

Trokla et al., J. Virol. 69(11):6609-6617 (1995).

Vacca et al., "L-735,524: an Orally Bioavailable Human Immunodeficiency Virus Type 1 Protease Inhibitor," Proc Natl Acad Sci USA 91(9):4096-4100 (1994).

Verma et al., "Gene therapy—Promises, Problems and Prospects," Nature 389(6648):239-242 (1997).

Vilmer et al., "Isolation of New Lymphotropic Retrovirus from Two Siblings with Haemophilia B, One with AIDS," The Lancet 1:753 (1984).

Wagner et al., "Assembly and Extracellular Release of Chimeric HIV-1 PR55gag Retrovirus-like Particles," Virology 200:162-175 (1994).

Wagner et al., "Construction, Expression, and Immunogenicity of Chimeric HIV-1 Virus-like Particles," Virology 220:128-140 (1996).

Wagner R., et al., "Studies on Processing, Particle Formation, and Immunogenicity of the HIV-1 gag Gene Product: a Possible Component of a HIV Vaccine," Arch Virol. 127:117-137 (1992).

Wakefield, J. K. et al., "In Vitro Enzymatic Activity of Human Immunodeficiency Virus Type 1 Reverse Transcriptase Mutants in the Highly Conserved YMDD Amino Acid Motif Correlates with the Infectious Potential of the Proviral Genome," Journal of Virology 66(11):6806-6812 (1992).

Wan et al., "Autoprocessing: an Essential Step for the Activation of HIV-1 Protease," Biochem. J. 316:569-573 (1996).

Wang C. et al., "Analysis of Minimal Human Immunodeficiency Virus Type 1 Gag Coding Sequences Capable of Virus-like Particle Assembly and Release," J Virol 72(10): 7950-7959 (1998).

Wang et al., "Induction of Humoral and Cellular Immune Responses to the Human Immuno-deficiency Type 1 Virus in Nonhuman Primates by in Vivo DNA Inoculation," Virology 211(1):102-112 (1995).

Wang et al., Virology 200:524-534 (1994).

Weiss et al., Nature (London) 316:69-72 (1985).

Weiss et al., Nature (London) 324:572-575 (1986).

Williamson, et al., "Designing HIV-1 Subtype C Vaccines for South Africa," South African Journal of Science, 96:318-324 (2000).

Wu X., et al., "Targeting foreign proteins to human immunodeficiency virus particles via fusion with Vpr and Vpx," J. Virol. 69(6):3389-3398 (1995).

Wyatt et al., J. Virol. 69(9):5723-5733 (1995).

Wyatt et al., Nature 393:705-711 (1998).

Yeni et al., "Antiretroviral and Immune-based Therapies: Update," AIDS 7(Suppl 1):5173-5184 (1993).

Yenofsky et al., "A Mutant Neomycin Phosphotransferase II Gene Reduces the Resistance of Transformants to Antibiotic Selection Pressure," Proc. Natl. Acad. Sci. USA 87:3435-3439 (1990).

Youmo et al., "Nucleotide Sequence Analysis of the Env Gene of a New Zairian Isolate of HIV-1," AIDS Res Hum Retroviruses 4(3):165-73 (1988).

Zagury et al., "One-year Follow-up of Vaccine Therapy in Hiv-infected Immune-deficient Individuals: a New Strategy," J. Acquired Immune Deficiency Syndromes 5:676-681 (1992).

Zagury et al., "Progress Report IV on Aids Vaccine in Human: Phase I Clinical Trial in Hiv Infected Patients," VII International Conference on AIDS, Florence Jun. 16-21, 1991, Abstract No. M.A. 67.

Zhang Y., et al., "Analysis of the Assembly Function of the Human Immunodeficiency Virus Type 1 Gag Protein Nucleocapsid Domain," J Virol 72(3):1782-1789 (1998).

Zhu et al., Science 261:1179-1181 (1993).

zur Megede et al., "Increased Expression and Immunogenicity of Sequence-modified Human Immunodeficiency Virus Type 1 Gag Gene," J Virol. 74(6):2628-2635 (2000).

GenBank Accession No. AF110985, Apr. 20, 2000.

GenBank Accession No. AF110967, Oct. 15, 2001 (first seen in GenBank on Mar. 3, 1999).

GenBank Accession No. AF110968, Oct. 15, 2001 (first seen in GenBank on Mar. 3, 1999).

GenBank Accession No. AF110975, Oct. 15, 2001 (first seen in GenBank on Mar. 3, 1999).

GenBank Accession No. M60524, Aug. 2, 1993.

Chapman et al., (1991) "Effect of intron A from human cytomegalovirus (Towne) immediate-early gene on heterologous expression in mammalian cells," Nucleic Acids Research, vol. 19, No. 14, pp. 3979-3986.

O'Hagan et al., (Oct. 2001) "Induction of Potent Immune Responses by Cationic Microparticles with Adsorbed Human Immunodeficiency Virus DNA Vaccines," Journal of Virology, vol. 75, No. 19, pp. 9037-9043.

Nabel, G.J., (2002) "HIV vaccine strategies," Vaccine, vol. 20, No. 15, pp. 1945-1947.

```
orig.gagSF2
ATGGGTGCGAGAGCGTCGGTATTAAGCGGGGGAGAATTAGATAAATGGGAAAAAATTCGGTTAAGGCCAGGGGGAAAG Inact.1
AAAAAATATAAGTTAAAACATATAGTATGGGCAAGCAGGGAGCTAGAACGATTCGCAGTCAATCCTGGCCTGTTAGAA
  G  G  C   C    G C  C Inact.2
ACATCAGAAGGCTGCAGACAAATATTGGGACAGCTACAGCCATCCCTTCAGACAGGATCAGAAGAACTTAGATCATTA
                                                              G   C        C Inact.3
TATAATACAGTAGCAACCCTCTATTGTGTACATCAAAGGATAGATGTAAAAGACACCAAGGAAGCTTTAGAGAAGATA
    C                           C GC    C      C  G Inact.4
GAGGAAGAGCAAAACAAAAGTAAGAAAAAGGCACAGCAAGCAGCAGCTGCAGCTGGCACAGGAAACAGCAGCCAGGTC
                GTCC         G      C           G

AGCCAAAATTACCCTATAGTGCAGAACCTACAGGGGCAAATGGTACATCAGGCCATATCACCTAGAACTTTAAATGCA

TGGGTAAAAGTAGTAGAAGAAAAGGCTTTCAGCCCAGAAGTAATACCCATGTTTTCAGCATTATCAGAAGGAGCCACC

Inact.5
CCACAAGATTTAAACACCATGCTAAACACAGTGGGGGGACATCAAGCAGCCATGCAAATGTTAAAAGAGACTATCAAT
    G  CC G       G  T   C

GAGGAAGCTGCAGAATGGGATAGAGTGCATCCAGTGCATGCAGGGCCTATTGCACCAGGCCAAATGAGAGAACCAAGG

GGAAGTGACATAGCAGGAACTACTAGTACCCTTCAGGAACAAATAGGATGGATGACAAATAATCCACCTATCCCAGTA

Inact.6                            Inact.7
GGAGAAATCTATAAAAGATGGATAATCCTGGGATTAAATAAAATAGTAAGAATGTATAGCCCTACCAGCATTCTGGAC
    G  C  G  G                G  C  G  C  G  G ATAAGACAAGGACCAAAGGAACCCTTTAGAGATTATGTAGACCGGTTCTATAAAACTCTAAGAGCGAACAAGCTTCA
                                                        T
                                                                      Inact.8
CAGGATGTAAAAAATTGGATGACAGAAACCTTGTTGGTCCAAAATGCAAACCCAGATTGTAAGACTATTTTAAAAGCA
                                                                C  CC G   T TTGGGACCAGCAGCTACACTAGAAGAAATGATGACAGCATGTCAGGGAGTGGGGGGACCCGGCCATAAAGCAAGAGTT
   C  C

TTGGCTGAAGCCATGAGCCAAGTAACAAATCCAGCTAACATAATGATGCAGAGAGGCAATTTTAGGAACCAAAGAAAG

ACTGTTAAGTGTTTCAATTGTGGCAAAGAAGGGCACATAGCCAAAAATTGCAGGGCCCCTAGGAAAAAGGGCTGTTGG

AGATGTGGAAGGGAAGGACACCAAATGAAAGATTGCACTGAGAGACAGGCTAATTTTTTAGGGAAGATCTGGCCTTCC

TACAAGGGAAGGCCAGGGAATTTTCTTCAGAGCAGACCAGAGCCAACAGCCCCACCAGAAGAGAGCTTCAGGTTTGGG

GAGGAGAAAACAACTCCCTCTCAGAAGCAGGAGCCCATAGACAAGGAACTGTATCCTTTAACTTCCCTCAGATCACTC

TTTGGCAACGACCCCTCGTCACAATAA
```

FIG. 1 native HIV-1SF2 gag-protease

→ From here codon optimization + inactivation (GP1) and (GP2)

ATGGGTGCGAGAGCGTCGGTATTAAGCGGGGGAGAATTAGATAAATGGGAAAAAATTCGGTTAAGGCCAGGGGGAAAG

| Inact.1 |
AAAAAATATAAGTTAAAACATATAGTATGGGCAAGCAGGGAGCTAGAACGATTCGCAGTCAATCCTGGCCTGTTAGAA
  G   G   C   C    G C   C ACATCAGAAGGCTGCAGACAAATATTGGGACAGCTACAGCCATCCCTTCAGACAGGATCAGAAGAACTTAGATCATTA
                                                                G  G  C   C

| Inact.2 |                  | Inact.3 |
TATAATACAGTAGCAACCCTCTATTGTGTACATCAAAGGATAGATGTAAAAGACACCAAGGAAGCTTTAGAGAAGATA
    C                         C  GC    C       C    G GAGGAAGAGCAAAACAAAAGTAAGAAAAAGGCACAGCAAGCAGCAGCTGCAGCTGGCACAGGAAACAGCAGCCAGGTC
              | Inact.4 |
              GTCC       G   C      G

AGCCAAAATTACCCTATAGTGCAGAACCTACAGGGGCAAATGGTACATCAGGCCATATCACCTAGAACTTTAAATGCA

TGGGTAAAAGTAGTAGAAGAAAAGGCTTTCAGCCCAGAAGTAATACCCATGTTTTCAGCATTATCAGAAGGAGCCACC

| Inact.5 |
CCACAAGATTTAAACACCATGCTAAACACAGTGGGGGGACATCAAGCAGCCATGCAAATGTTAAAAGAGACTATCAAT
    G   CC  G      G   T G       G

GAGGAAGCTGCAGAATGGGATAGAGTGCATCCAGTGCATGCAGGGCCTATTGCACCAGGCCAAATGAGAGAACCAAGG

GGAAGTGACATAGCAGGAACTACTAGTACCCTTCAGGAACAAATAGGATGGATGACAAATAATCCACCTATCCCAGTA

| Inact.6 |
GGAGAAATCTATAAAAGATGGATAATCCTGGGATTAAATAAAATAGTAAGAATGTATAGCCCTACCAGCATTCTGGAC
     G   C  G              G C G C  G ATAAGACAAGGACCAAAGGAACCCTTTAGAGATTATGTAGACCGGTTCTATAAAACTCTAAGAGC[C]GAACAAGCTTCA
                                                                 T CAGGATGTAAAAAATTGGATGACAGAAACCTTGTTGGTCCAAAATGCAAACCCAGATTGTAAGAC TATTTTAAAAGCA
                                                         | Inact.7 |
                                                         C  CC  G  G  T

| Inact.7 |
TTGGGACCAGCAGCTACACTAGAAGAAATGATGACAGCATGTCAGGGAGTGGGGGGACCCGGCCATAAAGCAAGAGTT
C  C  C      G

| Inact.8 |                          | Inact.9 |
TTGGCTGAAGCCATGAGCCAAGTAACAAATCCAGCTAACATAATGATGCAGAGAGGCAATTTTAGGAACCAAAGAAAG
   C G    G         G   G   G  C  G  G            C   CC          GC  G

| Inact.9 |                       | Inact.10 |
ACTGTTAAGTGTTTCAATTGTGGCAAAGAAGGGCACATAGCCAAAAATTGCAGGGCCCCTAGGAAAAAGGGCTGTTGG
   C   C   C                       CC    GG   C   C       CC      G

AGATGTGGAAGGGAAGGACACCAAATGAAAGATTGCACTGAGAGACAGGCTAATTTTTTAGGGAAGATCTGGCCTTCC

→ From here no changes to native sequence (GP1) and (GP2)

TACAAGGGAAGGCCAGGGAATTTTCTTCAGAGCAGACCAGAGCCAACAGCCCCACCAGAAGAGAGCTTCAGGTTTGGG

GAGGAGAAAACAACTCCCTCTCAGAAGCAGGAGCCGATAGACAAGGAACTGTATCCTTTAACTTCCCTCAGATCACTC
                                    → From here codon optimization + inactivation (GP1)
                                    | Inact.11 or only inactivation (GP2) |
TTTGGCAACGACCCCTCGTCACAATAAGGATAGGGGGGCAACTAAAGGAAGCTCTATTAGATACAGGAGCAGATGATA
                          G    C        C       G  GC  C

| Inact.12 |
CAGTATTAGAAGAAATGAATTTGCCAGGAAAATGGAAACCAAAAATGATAGGGGGAATTGGAGGTTTTATCAAAGTAA
                                                          G  C  GC C      G  G

| Inact.12 |
GACAGTACGATCAGATACCTGTAGAAATCTGTGGACATAAAGCTATAGGTACAGTATTAGTAGGACCTACACCTGTCA
    G      C

| Inact.13 |                    | Inact.14 |
ACATAATTGGAAGAAATCTGTTGACTCAGATTGGTTGTACTTTAAATTTCCCCATTAGTCCTATTGAAACTGTACCAG
                        C    C   C    C  G  C              C  C      G G  G  C

| Inact.14 |
TAAAATTAAAGCCAGGAATGGATGGCCCAAAAGTTAAGCAATGGCCATTGTAA
G  G       GG       C      CG     G

FIG. 2

```
                            10         20         30         40         50
GagPol.ModSF    1 ATGGGCGCCC GCGCCAGCGT GCTGAGCGGC GGCGAGCTGG ACAAGTGGGA   50
GagProt.ModS    1 ATGGGCGCCC GCGCCAGCGT GCTGAGCGGC GGCGAGCTGG ACAAGTGGGA   50
Gag.ModSF2      1 ATGGGCGCCC GCGCCAGCGT GCTGAGCGGC GGCGAGCTGG ACAAGTGGGA   50

60         70         80         90        100
GagPol.ModSF   51 GAAGATCCGC CTGCGCCCCG GCGGCAAGAA GAAGTACAAG CTGAAGCACA  100
GagProt.ModS   51 GAAGATCCGC CTGCGCCCCG GCGGCAAGAA GAAGTACAAG CTGAAGCACA  100
Gag.ModSF2     51 GAAGATCCGC CTGCGCCCCG GCGGCAAGAA GAAGTACAAG CTGAAGCACA  100

110        120        130        140        150
GagPol.ModSF  101 TCGTGTGGGC CAGCCGCGAG CTGGAGCGCT TCGCCCGTGAA CCCCGGCCTG  150
GagProt.ModS  101 TCGTGTGGGC CAGCCGCGAG CTGGAGCGCT TCGCCCGTGAA CCCCGGCCTG  150
Gag.ModSF2    101 TCGTGTGGGC CAGCCGCGAG CTGGAGCGCT TCGCCCGTGAA CCCCGGCCTG  150

160        170        180        190        200
GagPol.ModSF  151 CTGGAGACCA GCGAGGGCTG CCGCCAGATC CTGGGCCAGC TGCAGCCCAG  200
GagProt.ModS  151 CTGGAGACCA GCGAGGGCTG CCGCCAGATC CTGGGCCAGC TGCAGCCCAG  200
Gag.ModSF2    151 CTGGAGACCA GCGAGGGCTG CCGCCAGATC CTGGGCCAGC TGCAGCCCAG  200

210        220        230        240        250
GagPol.ModSF  201 CCTGCAGACC GGCAGCGAGG AGCTGCGCAG CCTGTACAAC ACCGTGGCCA  250
GagProt.ModS  201 CCTGCAGACC GGCAGCGAGG AGCTGCGCAG CCTGTACAAC ACCGTGGCCA  250
Gag.ModSF2    201 CCTGCAGACC GGCAGCGAGG AGCTGCGCAG CCTGTACAAC ACCGTGGCCA  250

260        270        280        290        300
GagPol.ModSF  251 CCCTGTACTG CGTGCACCAG CGCATCGACG TCAAGGACAC CAAGGAGGCC  300
GagProt.ModS  251 CCCTGTACTG CGTGCACCAG CGCATCGACG TCAAGGACAC CAAGGAGGCC  300
Gag.ModSF2    251 CCCTGTACTG CGTGCACCAG CGCATCGACG TCAAGGACAC CAAGGAGGCC  300

310        320        330        340        350
GagPol.ModSF  301 CTGGAGAAGA TCGAGGAGGA GCAGAACAAG TCCAAGAAGA AGGCCCAGCA  350
GagProt.ModS  301 CTGGAGAAGA TCGAGGAGGA GCAGAACAAG TCCAAGAAGA AGGCCCAGCA  350
Gag.ModSF2    301 CTGGAGAAGA TCGAGGAGGA GCAGAACAAG TCCAAGAAGA AGGCCCAGCA  350

360        370        380        390        400
GagPol.ModSF  351 GGCCGCCGCC CCGCCGCCGCA CCGGCAACAG CAGCCAGGTG AGCCAGAACT  400
GagProt.ModS  351 GGCCGCCGCC CCGCCGCCGCA CCGGCAACAG CAGCCAGGTG AGCCAGAACT  400
Gag.ModSF2    351 GGCCGCCGCC CCGCCGCCGCA CCGGCAACAG CAGCCAGGTG AGCCAGAACT  400

410        420        430        440        450
GagPol.ModSF  401 ACCCCATCGT GCAGAACCTG CAGGGCCAGA TGGTGCACCA GGCCATCAGC  450
GagProt.ModS  401 ACCCCATCGT GCAGAACCTG CAGGGCCAGA TGGTGCACCA GGCCATCAGC  450
Gag.ModSF2    401 ACCCCATCGT GCAGAACCTG CAGGGCCAGA TGGTGCACCA GGCCATCAGC  450
```

| | | 460 | 470 | 480 | 490 | 500 | |
|---|---|---|---|---|---|---|---|
| GagPol.ModSF | 451 | CCCCGCACCC | TGAACGCCTG | GGTGAAGGTG | GTGGAGGAGA | AGGCCTTCAG | 500 |
| GagProt.ModS | 451 | CCCCGCACCC | TGAACGCCTG | GGTGAAGGTG | GTGGAGGAGA | AGGCCTTCAG | 500 |
| Gag.ModSF2 | 451 | CCCCGCACCC | TGAACGCCTG | GGTGAAGGTG | GTGGAGGAGA | AGGCCTTCAG | 500 |
| | | 510 | 520 | 530 | 540 | 550 | |
| GagPol.ModSF | 501 | CCCGAGGTG | ATCCCCATGT | TCAGCGCCCT | GAGCGAGGGC | GCCACCCCCC | 550 |
| GagProt.ModS | 501 | CCCGAGGTG | ATCCCCATGT | TCAGCGCCCT | GAGCGAGGGC | GCCACCCCCC | 550 |
| Gag.ModSF2 | 501 | CCCGAGGTG | ATCCCCATGT | TCAGCGCCCT | GAGCGAGGGC | GCCACCCCCC | 550 |
| | | 560 | 570 | 580 | 590 | 600 | |
| GagPol.ModSF | 551 | AGGACCTGAA | CACGATGTTG | AACACCGTGG | GCGGCCACCA | GGCCGCCATG | 600 |
| GagProt.ModS | 551 | AGGACCTGAA | CACGATGTTG | AACACCGTGG | GCGGCCACCA | GGCCGCCATG | 600 |
| Gag.ModSF2 | 551 | AGGACCTGAA | CACGATGTTG | AACACCGTGG | GCGGCCACCA | GGCCGCCATG | 600 |
| | | 610 | 620 | 630 | 640 | 650 | |
| GagPol.ModSF | 601 | CAGATGCTGA | AGGAGACCAT | CAACGAGGAG | GCCGCCGAGT | GGGACCGCGT | 650 |
| GagProt.ModS | 601 | CAGATGCTGA | AGGAGACCAT | CAACGAGGAG | GCCGCCGAGT | GGGACCGCGT | 650 |
| Gag.ModSF2 | 601 | CAGATGCTGA | AGGAGACCAT | CAACGAGGAG | GCCGCCGAGT | GGGACCGCGT | 650 |
| | | 660 | 670 | 680 | 690 | 700 | |
| GagPol.ModSF | 651 | GCACCCCGTG | CACGCCGGCC | CCATCGCCCC | CGGCCAGATG | CGGGAGCCCC | 700 |
| GagProt.ModS | 651 | GCACCCCGTG | CACGCCGGCC | CCATCGCCCC | CGGCCAGATG | CGGGAGCCCC | 700 |
| Gag.ModSF2 | 651 | GCACCCCGTG | CACGCCGGCC | CCATCGCCCC | CGGCCAGATG | CGGGAGCCCC | 700 |
| | | 710 | 720 | 730 | 740 | 750 | |
| GagPol.ModSF | 701 | GCGGCAGCGA | CATCGCCGGC | ACCACCAGCA | CCCTGCAGGA | GCAGATCGGC | 750 |
| GagProt.ModS | 701 | GCGGCAGCGA | CATCGCCGGC | ACCACCAGCA | CCCTGCAGGA | GCAGATCGGC | 750 |
| Gag.ModSF2 | 701 | GCGGCAGCGA | CATCGCCGGC | ACCACCAGCA | CCCTGCAGGA | GCAGATCGGC | 750 |
| | | 760 | 770 | 780 | 790 | 800 | |
| GagPol.ModSF | 751 | TGGATGACCA | ACAACCCCCC | CATCCCCGTG | GGCGAGATCT | ACAAGCGGTG | 800 |
| GagProt.ModS | 751 | TGGATGACCA | ACAACCCCCC | CATCCCCGTG | GGCGAGATCT | ACAAGCGGTG | 800 |
| Gag.ModSF2 | 751 | TGGATGACCA | ACAACCCCCC | CATCCCCGTG | GGCGAGATCT | ACAAGCGGTG | 800 |
| | | 810 | 820 | 830 | 840 | 850 | |
| GagPol.ModSF | 801 | GATCATCCTG | GGCCTGAACA | AGATCGTGCG | GATGTACAGC | CCCACCAGCA | 850 |
| GagProt.ModS | 801 | GATCATCCTG | GGCCTGAACA | AGATCGTGCG | GATGTACAGC | CCCACCAGCA | 850 |
| Gag.ModSF2 | 801 | GATCATCCTG | GGCCTGAACA | AGATCGTGCG | GATGTACAGC | CCCACCAGCA | 850 |
| | | 860 | 870 | 880 | 890 | 900 | |
| GagPol.ModSF | 851 | TCCTGGACAT | CCGGCAGGGC | CCCAAGGAGC | CCTTCCGCGA | CTACGTGGAC | 900 |
| GagProt.ModS | 851 | TCCTGGACAT | CCGGCAGGGC | CCCAAGGAGC | CCTTCCGCGA | CTACGTGGAC | 900 |
| Gag.ModSF2 | 851 | TCCTGGACAT | CCGGCAGGGC | CCCAAGGAGC | CCTTCCGCGA | CTACGTGGAC | 900 |

```
GagPol.ModSF   901  CGCTTCTACA  AGACCCTGCG  CGCTGAGCAG  GCCAGCCAGG  ACGTGAAGAA   950
GagProt.ModS   901  CGCTTCTACA  AGACCCTGCG  CGCTGAGCAG  GCCAGCCAGG  ACGTGAAGAA   950
Gag.ModSF2     901  CGCTTCTACA  AGACCCTGCG  CGCTGAGCAG  GCCAGCCAGG  ACGTGAAGAA   950
                         910         920         930         940         950

GagPol.ModSF   951  CTGGATGACC  GAGACCCTGC  TGGTGCAGAA  CGCCAACCCC  GACTGCAAGA  1000
GagProt.ModS   951  CTGGATGACC  GAGACCCTGC  TGGTGCAGAA  CGCCAACCCC  GACTGCAAGA  1000
Gag.ModSF2     951  CTGGATGACC  GAGACCCTGC  TGGTGCAGAA  CGCCAACCCC  GACTGCAAGA  1000
                         960         970         980         990        1000

GagPol.ModSF  1001  CCATCCTGAA  GGCTCTCGGC  CCCGCGGCCA  CCCTGGAGGA  GATGATGACC  1050
GagProt.ModS  1001  CCATCCTGAA  GGCTCTCGGC  CCCGCGGCCA  CCCTGGAGGA  GATGATGACC  1050
Gag.ModSF2    1001  CCATCCTGAA  GGCTCTCGGC  CCCGCGGCCA  CCCTGGAGGA  GATGATGACC  1050
                        1010        1020        1030        1040        1050

GagPol.ModSF  1051  GCCTGCCAGG  GCGTGGGCGG  CCCCGGCCAC  AAGGCCCGCG  TGCTGGCCGA  1100
GagProt.ModS  1051  GCCTGCCAGG  GCGTGGGCGG  CCCCGGCCAC  AAGGCCCGCG  TGCTGGCCGA  1100
Gag.ModSF2    1051  GCCTGCCAGG  GCGTGGGCGG  CCCCGGCCAC  AAGGCCCGCG  TGCTGGCCGA  1100
                        1060        1070        1080        1090        1100

GagPol.ModSF  1101  GGGCGATGAGC  CAGGTGACGA  ACCCGGCGAC  CATCATGATG  CAGCGCGGCA  1150
GagProt.ModS  1101  GGGCGATGAGC  CAGGTGACGA  ACCCGGCGAC  CATCATGATG  CAGCGCGGCA  1150
Gag.ModSF2    1101  GGGCGATGAGC  CAGGTGACGA  ACCCGGCGAC  CATCATGATG  CAGCGCGGCA  1150
                        1110        1120        1130        1140        1150

GagPol.ModSF  1151  ACTTCCGCAA  CCAGCGGAAG  ACCGTCAAGT  GCTTCAACTG  CGGCAAGGAG  1200
GagProt.ModS  1151  ACTTCCGCAA  CCAGCGGAAG  ACCGTCAAGT  GCTTCAACTG  CGGCAAGGAG  1200
Gag.ModSF2    1151  ACTTCCGCAA  CCAGCGGAAG  ACCGTCAAGT  GCTTCAACTG  CGGCAAGGAG  1200
                        1160        1170        1180        1190        1200

GagPol.ModSF  1201  GGCCACACCG  CCAGGAACTG  CCGCGCCCCC  CGCAAGAAGG  GCTGCTGGCG  1250
GagProt.ModS  1201  GGCCACACCG  CCAGGAACTG  CCGCGCCCCC  CGCAAGAAGG  GCTGCTGGCG  1250
Gag.ModSF2    1201  GGCCACACCG  CCAGGAACTG  CCGCGCCCCC  CGCAAGAAGG  GCTGCTGGCG  1250
                        1210        1220        1230        1240        1250

GagPol.ModSF  1251  CTGCGGCCGC  GAAGGACACC  AAATGAAAGA  TTGCACTGAG  AGACAGGCTA  1300
GagProt.ModS  1251  CTGCGGCCGC  GAAGGACACC  AAATGAAAGA  TTGCACTGAG  AGACAGGCTA  1300
Gag.ModSF2    1251  CTGCGGCCGC  GAGGGACACC  AGATGAAGGA  CTGCACCGAG  CGCCAGGCCA  1300
                        1260        1270        1280        1290        1300

Gag

FIG. 7D

| | | 1360 | 1370 | 1380 | 1390 | 1400 | |
|---|---|---|---|---|---|---|---|
| GagPol.ModSF | 1351 | CTTCAGAGCA | GACCAGAGCC | AACAGCCCCA | CCAGAAGAGA | GCTTCAGGTT | 1400 |
| GagProt.ModS | 1351 | CTTCAGAGCA | GACCAGAGCC | AACAGCCCCA | CCAGAAGAGA | GCTTCAGGTT | 1400 |
| Gag.ModSF2 | 1351 | CTGCAGAGCC | GCCCCGAGCC | CACCGCCCCC | CCCGAGGAGA | GCTTCCGCTT | 1400 |
| | | 1410 | 1420 | 1430 | 1440 | 1450 | |
| GagPol.ModSF | 1401 | TGGGGAGGAG | AAAACAACTC | CCTCTCAGAA | GCAGGAGCCG | ATAGACAAGG | 1450 |
| GagProt.ModS | 1401 | TGGGGAGGAG | AAAACAACTC | CCTCTCAGAA | GCAGGAGCCG | ATAGACAAGG | 1450 |
| Gag.ModSF2 | 1401 | CGGCGAGGAG | AAGACCACCC | CCAGCCAGAA | GCAGGAGCCC | ATCGACAAGG | 1450 |
| | | 1460 | 1470 | 1480 | 1490 | 1500 | |
| GagPol.ModSF | 1451 | AACTGTATCC | TTTAACTTCC | CTCAGATCAC | TCTTTGGCAA | CGACCCCTCG | 1500 |
| GagProt.ModS | 1451 | AACTGTATCC | TTTAACTTCC | CTCAGATCAC | TCTTTGGCAA | CGACCCCTCG | 1500 |
| Gag.ModSF2 | 1451 | AGTGTACCC | CCTGACCAGC | CTGCCAGC | TGTTCGGCAA | CGACCCCAGC | 1500 |
| | | 1510 | 1520 | 1530 | 1540 | 1550 | |
| GagPol.ModSF | 1501 | TCACAGTAAG | GATCGGCGGC | CAGCTCAAGG | AGGGCTGCT | CGACACCGGC | 1550 |
| GagProt.ModS | 1501 | TCACAGTAAG | GATCGGCGGC | CAGCTCAAGG | AGGGCTGCT | CGACACCGGC | 1550 |
| Gag.ModSF2 | 1501 | AGCCAGTAA. | .......... | .......... | .......... | .......... | 1550 |
| | | 1560 | 1570 | 1580 | 1590 | 1600 | |
| GagPol.ModSF | 1551 | GCCGACGACA | CCGTGCTGGA | GGAGATGAAC | CTGCCCGGCA | AGTGGAAGCC | 1600 |
| GagProt.ModS | 1551 | GCCGACGACA | CCGTGCTGGA | GGAGATGAAC | CTGCCCGGCA | AGTGGAAGCC | 1600 |
| Gag.ModSF2 | 1551 | .......... | .......... | .......... | .......... | .......... | 1600 |
| | | 1610 | 1620 | 1630 | 1640 | 1650 | |
| GagPol.ModSF | 1601 | CAAGATGATC | GGCGGGATCG | GGGGCTTCAT | CAAGGTGCGG | CAGTACGACC | 1650 |
| GagProt.ModS | 1601 | CAAGATGATC | GGCGGGATCG | GGGGCTTCAT | CAAGGTGCGG | CAGTACGACC | 1650 |
| Gag.ModSF2 | 1601 | .......... | .......... | .......... | .......... | .......... | 1650 |
| | | 1660 | 1670 | 1680 | 1690 | 1700 | |
| GagPol.ModSF | 1651 | AGATCCCCGT | GGAGATCTGC | GGCCACAAGG | CCATCGGCAC | CGTGCTGGTG | 1700 |
| GagProt.ModS | 1651 | AGATCCCCGT | GGAGATCTGC | GGCCACAAGG | CCATCGGCAC | CGTGCTGGTG | 1700 |
| Gag.ModSF2 | 1651 | .......... | .......... | .......... | .......... | .......... | 1700 |
| | | 1710 | 1720 | 1730 | 1740 | 1750 | |
| GagPol.ModSF | 1701 | GGCCCCACCC | CCGTGAACAT | CATCGGCCGC | AACCTGCTGA | CCCAGATCGG | 1750 |
| GagProt.ModS | 1701 | GGCCCCACCC | CCGTGAACAT | CATCGGCCGC | AACCTGCTGA | CCCAGATCGG | 1750 |
| Gag.ModSF2 | 1701 | .......... | .......... | .......... | .......... | .......... | 1750 |
| | | 1760 | 1770 | 1780 | 1790 | 1800 | |
| GagPol.ModSF | 1751 | CTGCACCCTG | AACTTCCCCA | TCAGCCCCAT | CGAGACGGTG | CCCGTGAAGC | 1800 |
| GagProt.ModS | 1751 | CTGCACCCTG | AACTTCCCCA | TCAGCCCCAT | CGAGACGGTG | CCCGTGAAGC | 1800 |
| Gag.ModSF2 | 1751 | .......... | .......... | .......... | .......... | .......... | 1800 |

```
                         1810       1820       1830       1840       1850
GagPol.ModSF  1801  TGAAGCCGGG GATGGACGGC CCCAAGGTCA AGCAGTGGCC CCTGACCGAG  1850
GagProt.ModS  1801  TGAAGCCGGG GATGGACGGC CCCAAGGTCA AGCAGTGGCC CCTGTAA...  1850
Gag.ModSF2    1801  .......... .......... .......... .......... ..........  1850

1860       1870       1880       1890       1900
GagPol.ModSF  1851  GAGAAGATCA AGGCCCTGGT GGAGATCTGC ACCGAGATGG AGAAGGAGGG  1900
GagProt.ModS  1851  .......... .......... .......... .......... ..........  1900
Gag.ModSF2    1851  .......... .......... .......... .......... ..........  1900

1910       1920       1930       1940       1950
GagPol.ModSF  1901  CAAGATCAGC AAGATCGGCC CCGAGAACCC CTACAACACC CCCGTGTTCG  1950
GagProt.ModS  1901  .......... .......... .......... .......... ..........  1950
Gag.ModSF2    1901  .......... .......... .......... .......... ..........  1950

1960       1970       1980       1990       2000
GagPol.ModSF  1951  CCATCAAGAA GAAGGACAGC ACCAAGTGGC GCAAGCTGGT GGACTTCCGC  2000
GagProt.ModS  1951  .......... .......... .......... .......... ..........  2000
Gag.ModSF2    1951  .......... .......... .......... .......... ..........  2000

2010       2020       2030       2040       2050
GagPol.ModSF  2001  GAGCTGAACA AGCGCACCCA GGACTTCTGG GAGGTGCAGC TGGGCATCCC  2050
GagProt.ModS  2001  .......... .......... .......... .......... ..........  2050
Gag.ModSF2    2001  .......... .......... .......... .......... ..........  2050

2060       2070       2080       2090       2100
GagPol.ModSF  2051  CCACCCCGCC GGCCTGAAGA AGAAGAAGAG CGTGACCGTG CTGGACGTGG  2100
GagProt.ModS  2051  .......... .......... .......... .......... ..........  2100
Gag.ModSF2    2051  .......... .......... .......... .......... ..........  2100

2110       2120       2130       2140       2150
GagPol.ModSF  2101  GCGACGCCTA CTTCAGCGTG CCCCTGGACA AGGACTTCCG CAAGTACACC  2150
GagProt.ModS  2101  .......... .......... .......... .......... ..........  2150
Gag.ModSF2    2101  .......... .......... .......... .......... ..........  2150

2160       2170       2180       2190       2200
GagPol.ModSF  2151  GCCTTCACCA TCCCCAGCAT CAACAACGAG ACCCCCGGCA TCCGCTACCA  2200
GagProt.ModS  2151  .......... .......... .......... .......... ..........  2200
Gag.ModSF2    2151  .......... .......... .......... .......... ..........  2200

2210       2220       2230       2240       2250
GagPol.ModSF  2201  GTACAACGTG CTGCCCCAGG GCTGGAAGGG CAGCCCCGCC ATCTTCCAGA  2250
GagProt.ModS  2201  .......... .......... .......... .......... ..........  2250
Gag.ModSF2    2201  .......... .......... .......... .......... ..........  2250
```

FIG. 7E

| | | | | | | |
|---|---|---|---|---|---|---|
| GagPol.ModSF | 2251 | GCAGCATGAC | CAAGATCCTG | GAGCCCTTCC | GCAAGCAGAA | CCCCGACATC | 2300 |
| GagProt.Mods | 2251 | ........... | ........... | ........... | ........... | ........... | 2300 |
| Gag.ModSF2 | 2251 | ........... | ........... | ........... | ........... | ........... | 2300 |
| GagPol.ModSF | 2301 | GTGATCTACC | AGTACATGGA | CGACCTGTAC | GTGGGCAGCG | ACCTGGAGAT | 2350 |
| GagProt.Mods | 2301 | ........... | ........... | ........... | ........... | ........... | 2350 |
| Gag.ModSF2 | 2301 | ........... | ........... | ........... | ........... | ........... | 2350 |
| GagPol.ModSF | 2351 | CGGCCAGCAC | CGCACCAAGA | TCGAGGAGCT | GCGCCAGCAG | CTGCTGCGCT | 2400 |
| GagProt.Mods | 2351 | ........... | ........... | ........... | ........... | ........... | 2400 |
| Gag.ModSF2 | 2351 | ........... | ........... | ........... | ........... | ........... | 2400 |
| GagPol.ModSF | 2401 | GGGGCTTCAC | CACCCCCGAC | AAGAAGCACC | AGAAGGAGCC | CCCCTTCCTG | 2450 |
| GagProt.Mods | 2401 | ........... | ........... | ........... | ........... | ........... | 2450 |
| Gag.ModSF2 | 2401 | ........... | ........... | ........... | ........... | ........... | 2450 |
| GagPol.ModSF | 2451 | TGGATGGGCT | ACGAGCTGCA | CCCCGACAAG | TGGACCGTGC | AGCCCATCAT | 2500 |
| GagProt.Mods | 2451 | ........... | ........... | ........... | ........... | ........... | 2500 |
| Gag.ModSF2 | 2451 | ........... | ........... | ........... | ........... | ........... | 2500 |
| GagPol.ModSF | 2501 | GCTGCCCGAG | AAGGACAGCT | GGACCGTGAA | CGACATCCAG | AAGCTGGTGG | 2550 |
| GagProt.Mods | 2501 | ........... | ........... | ........... | ........... | ........... | 2550 |
| Gag.ModSF2 | 2501 | ........... | ........... | ........... | ........... | ........... | 2550 |
| GagPol.ModSF | 2551 | GCAAGCTGAA | CTGGGCCAGC | CAGATCTACG | CCGGCATCAA | GGTGAAGCAG | 2600 |
| GagProt.Mods | 2551 | ........... | ........... | ........... | ........... | ........... | 2600 |
| Gag.ModSF2 | 2551 | ........... | ........... | ........... | ........... | ........... | 2600 |
| GagPol.ModSF | 2601 | CTGTGCAAGC | TGCTGCGCGG | CACCAAGGCC | CTGACCGAGG | TGATCCCCCT | 2650 |
| GagProt.Mods | 2601 | ........... | ........... | ........... | ........... | ........... | 2650 |
| Gag.ModSF2 | 2601 | ........... | ........... | ........... | ........... | ........... | 2650 |
| GagPol.ModSF | 2651 | GACCGAGGAG | GCCGAGCTGG | AGCTGGCCGA | GAACCGCGAG | ATCCTGAAGG | 2700 |
| GagProt.Mods | 2651 | ........... | ........... | ........... | ........... | ........... | 2700 |
| Gag.ModSF2 | 2651 | ........... | ........... | ........... | ........... | ........... | 2700 |

FIG. 7F

```
GagPol.ModSF 2701 AGCCCGTGCA CGAGGTGTAC TACGACCCCA GCAAGGACCT GGTGGGCCGAG 2750
GagProt.Mods 2701 .......... .......... .......... .......... ..........  2750
Gag.ModSF2   2701 .......... .......... .......... .......... ..........  2750

GagPol.ModSF 2751 ATCCAGAAGC AGGGCCAGGG CCAGTGGACC TACCAGATCT ACCAGGAGCC 2800
GagProt.Mods 2751 .......... .......... .......... .......... ..........  2800
Gag.ModSF2   2751 .......... .......... .......... .......... ..........  2800

GagPol.ModSF 2801 CTTCAAGAAC CTGAAGACCG GCAAGTACGC CCGGCATGCGC GGCGCCCACA 2850
GagProt.Mods 2801 .......... .......... .......... .......... ..........  2850
Gag.ModSF2   2801 .......... .......... .......... .......... ..........  2850

GagPol.ModSF 2851 CCAACGACGT GAAGCAGCTG ACCGAGGCCG TGCAGAAGGT GAGCACCGAG 2900
GagProt.Mods 2851 .......... .......... .......... .......... ..........  2900
Gag.ModSF2   2851 .......... .......... .......... .......... ..........  2900

GagPol.ModSF 2901 AGCATCGTGA TCTGGGGCAA GATCCCCAAG TTCAAGCTGC CCATCCAGAA 2950
GagProt.Mods 2901 .......... .......... .......... .......... ..........  2950
Gag.ModSF2   2901 .......... .......... .......... .......... ..........  2950

GagPol.ModSF 2951 GGAGACCTGG GAGGCCTGGT GGATGGAGTA CTGGCAGGCC ACCTGGATCC 3000
GagProt.Mods 2951 .......... .......... .......... .......... ..........  3000
Gag.ModSF2   2951 .......... .......... .......... .......... ..........  3000

GagPol.ModSF 3001 CCGAGTGGGA GTTCGTGAAC ACCCCCCCC TGGTGAAGCT GTGGTACCAG 3050
GagProt.Mods 3001 .......... .......... .......... .......... ..........  3050
Gag.ModSF2   3001 .......... .......... .......... .......... ..........  3050

GagPol.ModSF 3051 CTGGAGAAGG AGCCCATCGT GGGGCGCGAG ACCTTCTACG TGGACGGCGC 3100
GagProt.Mods 3051 .......... .......... .......... .......... ..........  3100
Gag.ModSF2   3051 .......... .......... .......... .......... ..........  3100

GagPol.ModSF 3101 CGCCAACCGC GAGACCAAGC TGGGCAAGGC CGGCTACGTG ACCGACCGCG 3150
GagProt.Mods 3101 .......... .......... .......... .......... ..........  3150
Gag.ModSF2   3101 .......... .......... .......... .......... ..........  3150
```

FIG. 7G

| | | | | | | |
|---|---|---|---|---|---|---|
| GagPol.ModSF | 3151 | GCCGCCAGAA | GGTGGTGAGC | ATCGCCGACA | CCACCAACCA | GAAGACCGAG | 3200 |
| GagProt.ModS | 3151 | ·········· | ·········· | ·········· | ·········· | ·········· | 3200 |
| Gag.ModSF2   | 3151 | ·········· | ·········· | ·········· | ·········· | ·········· | 3200 |
| GagPol.ModSF | 3201 | CTGCAGGCCA | TCCACCTGGC | CCTGCAGGAC | AGCGGCCTGG | AGGTGAACAT | 3250 |
| GagProt.ModS | 3201 | ·········· | ·········· | ·········· | ·········· | ·········· | 3250 |
| Gag.ModSF2   | 3201 | ·········· | ·········· | ·········· | ·········· | ·········· | 3250 |
| GagPol.ModSF | 3251 | CGTGACCGAC | AGCCAGTACG | CCCTGGGCAT | CATCCCAGGCC | CAGCCCGACA | 3300 |
| GagProt.ModS | 3251 | ·········· | ·········· | ·········· | ·········· | ·········· | 3300 |
| Gag.ModSF2   | 3251 | ·········· | ·········· | ·········· | ·········· | ·········· | 3300 |
| GagPol.ModSF | 3301 | AGAGCGAGAG | CGAGCTGGTG | AGCCAGATCA | TCGAGCAGCT | GATCAAGAAG | 3350 |
| GagProt.ModS | 3301 | ·········· | ·········· | ·········· | ·········· | ·········· | 3350 |
| Gag.ModSF2   | 3301 | ·········· | ·········· | ·········· | ·········· | ·········· | 3350 |
| GagPol.ModSF | 3351 | GAGAAGGTGT | ACCTGGCCTG | GGTGCCCGCC | CACAAGGGCA | TCGGCGGCAA | 3400 |
| GagProt.ModS | 3351 | ·········· | ·········· | ·········· | ·········· | ·········· | 3400 |
| Gag.ModSF2   | 3351 | ·········· | ·········· | ·········· | ·········· | ·········· | 3400 |
| GagPol.ModSF | 3401 | CGAGCAGGTG | GACAAGCTGG | TGAGCGCCGG | CATCCGCAAG | GTGCTGTTCC | 3450 |
| GagProt.ModS | 3401 | ·········· | ·········· | ·········· | ·········· | ·········· | 3450 |
| Gag.ModSF2   | 3401 | ·········· | ·········· | ·········· | ·········· | ·········· | 3450 |
| GagPol.ModSF | 3451 | TGAACGGCAT | CGACAAGGCC | CAGGAGGAGC | ACGAGAAGTA | CCACAGCAAC | 3500 |
| GagProt.ModS | 3451 | ·········· | ·········· | ·········· | ·········· | ·········· | 3500 |
| Gag.ModSF2   | 3451 | ·········· | ·········· | ·········· | ·········· | ·········· | 3500 |
| GagPol.ModSF | 3501 | TGGCGCGCCA | TGGCCAGCGA | CTTCAACCTG | CCCCCCGTGG | TGGCCAAGGA | 3550 |
| GagProt.ModS | 3501 | ·········· | ·········· | ·········· | ·········· | ·········· | 3550 |
| Gag.ModSF2   | 3501 | ·········· | ·········· | ·········· | ·········· | ·········· | 3550 |
| GagPol.ModSF | 3551 | GATCGTGGCC | AGCTGCGACA | AGTGCCAGCT | GAAGGGCGAG | GCCATGCACG | 3600 |
| GagProt.ModS | 3551 | ·········· | ·········· | ·········· | ·········· | ·········· | 3600 |
| Gag.ModSF2   | 3551 | ·········· | ·········· | ·········· | ·········· | ·········· | 3600 |

FIG. 7H

```
GagPol.ModSF 3601 GCCAGGTGGA CTGCAGCCCC GGCATCTGGC AGCTGGACTG CACCCACCTG 3650
GagProt.ModS 3601 .......... .......... .......... .......... .......... 3650
Gag.ModSF2   3601 .......... .......... .......... .......... .......... 3650

GagPol.ModSF 3651 GAGGGCAAGA TCATCCTGGT GGCCGTGCAC GTGGCCAGCG GCTACATCGA 3700
GagProt.ModS 3651 .......... .......... .......... .......... .......... 3700
Gag.ModSF2   3651 .......... .......... .......... .......... .......... 3700

GagPol.ModSF 3701 GGCCGAGGTG ATCCCCGCCG AGACCGGCCA GGAGACCGCC TACTTCCTGC 3750
GagProt.ModS 3701 .......... .......... .......... .......... .......... 3750
Gag.ModSF2   3701 .......... .......... .......... .......... .......... 3750

GagPol.ModSF 3751 TGAAGCTGGC CGGCCGCTGG CCCGTGAAGA CCATCCACAC CGACAACGGC 3800
GagProt.ModS 3751 .......... .......... .......... .......... .......... 3800
Gag.ModSF2   3751 .......... .......... .......... .......... .......... 3800

GagPol.ModSF 3801 AGCAACTTCA CCAGCACCAC CGTGAAGGCC GCCTGCTGGT GGGCCGGCAT 3850
GagProt.ModS 3801 .......... .......... .......... .......... .......... 3850
Gag.ModSF2   3801 .......... .......... .......... .......... .......... 3850

GagPol.ModSF 3851 CAAGCAGGAG TTCGGCATCC CCTACAACCC CCAGAGCCAG GGCGTGGTGG 3900
GagProt.ModS 3851 .......... .......... .......... .......... .......... 3900
Gag.ModSF2   3851 .......... .......... .......... .......... .......... 3900

GagPol.ModSF 3901 AGAGCATGAA CAACGAGCTG AAGAAGATCA TCGGCCAGGT GCGGGACCAG 3950
GagProt.ModS 3901 .......... .......... .......... .......... .......... 3950
Gag.ModSF2   3901 .......... .......... .......... .......... .......... 3950

GagPol.ModSF 3951 GCCGAGCACC TGAAGACCGC CGTGCAGATG GCCGTGTTCA TCCACAACTT 4000
GagProt.ModS 3951 .......... .......... .......... .......... .......... 4000
Gag.ModSF2   3951 .......... .......... .......... .......... .......... 4000

GagPol.ModSF 4001 CAAGCGCAAG GGCGGCATCG GCGGCTACAG CGCCGGCGAG CGCATCGTGG 4050
GagProt.ModS 4001 .......... .......... .......... .......... .......... 4050
Gag.ModSF2   4001 .......... .......... .......... .......... .......... 4050
```

```
GagPol.ModSF 4051 ACATCATCGC CACCGACATC CAGACCAAGG AGCTGCAGAA GCAGATCACC 4100
GagProt.Mods 4051 .......... .......... .......... .......... .......... 4100
Gag.ModSF2   4051 .......... .......... .......... .......... .......... 4100

GagPol.ModSF 4101 AAGATCCAGA ACTTCCGCGT GTACTACCGC GACAACAAGG ACCCCCTGTG 4150
GagProt.Mods 4101 .......... .......... .......... .......... .......... 4150
Gag.ModSF2   4101 .......... .......... .......... .......... .......... 4150

GagPol.ModSF 4151 GAAGGGCCCC GCCAAGCTGC TGTGGAAGGG CGAGGGCGCC GTGGTGATCC 4200
GagProt.Mods 4151 .......... .......... .......... .......... .......... 4200
Gag.ModSF2   4151 .......... .......... .......... .......... .......... 4200

GagPol.ModSF 4201 AGGACAACAG CGACATCAAG GTGGTGCCCC GCCGCAAGGC CAAGATCATC 4250
GagProt.Mods 4201 .......... .......... .......... .......... .......... 4250
Gag.ModSF2   4201 .......... .......... .......... .......... .......... 4250

GagPol.ModSF 4251 CGCGACTACG GCAAGCAGAT GGCCGGCGAC GACTGCGTGG CCAGCCGCCA 4300
GagProt.Mods 4251 .......... .......... .......... .......... .......... 4300
Gag.ModSF2   4251 .......... .......... .......... .......... .......... 4300

GagPol.ModSF 4301 GGACGAGGAC TAG....... .......... .......... .......... 4350
GagProt.Mods 4301 .......... .......... .......... .......... .......... 4350
Gag.ModSF2   4301 .......... .......... .......... .......... .......... 4350
```

FIG. 12A native HIV-1SF2 gag-polymerase

ATGGGTGCGAGAGCGTCGGTATTAAGCGGGGGAGAATTAGATAAATGGGAAAAAATTCGGTTAAGGCCAGGGGGAAAG

| Inact.1 |
AAAAATATAAGTTAAAACATATAGTGGGGAGCAGGGAGCTAGAACGATTCGCAGTCAATCCTGGCCTGTTAGAA
 G C C   G  C                                    Inact.2
                                          AGAACTTAGATCATTA
                                          G G C       C ACATCAGAAGGCTGCAGACAAATATTGGGACAGCTACAGCCATCCCTTCAGACAGATCAGAAGAAGCTTTAGAGAAGATA
 Inact.2
 C

| Inact.3 |
TATAATACAGTAGCAACCCTCTATTGTGTACATCAAAGAATAGTGTAAAAGACACCAAGGACAGCCAGGTC
             C  GC   C   G
                    | Inact.4 |
GAGGAAGAGCAAAACAAAAGTAAGAAAAAGGCACAGCAAGCAGCAGCTGCCA

```
AGATATGTACAGAAATGGAAAGGAAGGGGAAATTTCAAAAATTGGGCCTGAAATCCATACAATACTCCAGTATTTG
CTATAAAGAAAAGACAGTACTAAATGGAGAAAACTAGTAGATTTCAGAGAACTTAATAAAAGAACTCAAGACTTCT
GGGAAGTTCAGTTAGGAATACCACACCCCGCAGGGTTAAAAAAGAAAAAATCAGTAACAGTATTGGATGTGGGTGATG
CATACTTTTCAGTTCCCTTAGATAAAGACTTTAGAAAGTATACTGCATTTACCATACCTAGTATAAACAATGAGACAC
CAGGATTAGATATCAGTACAATGTGCTGCCACAGGATGGAAAGATCACCAGCAATATTCCAAGTAGCATGACAA
AAATCTTAGAGCCTTTTAGAAAACAGAATCCAGACAATACTTATCTATCAATGGATGATTTGTATGTAGGATCTG
ACTTAGAAATAGGGCAGCATAGAACAAAAATAGAGGAACTGAGAACATCTGTTGAGGTGGGATTTACCACACCAG
ACAAAAAACATCAGAAGAACCTCCATTCCTTTGGATGGGTTATGAACTCCTGATAAATGACAGTACAGCCTA
TAATGCTGCCAGAAAAAGACAGCTGGACTGTCAATGACATACAGAAGTTAGTGGAAAATTGAATTGGGCAAGTCAGA
TTTATGCAGGGATTAAAGTAAAGCAGTTATGTAAACTCCTTAGAGGAACCAAAGCACTAACAGAAGTAATACCACTAA
CAGAAGAAGCAGAGCTAGAACTGGCAGAAAACAGGGAGATTCTAAAAGAACCAGTACATGGAGTATATTATGACCAT
CAAAAGACTTAGTAGCAGAAATACAGAAGCAGGGCAAGCCAATGGACATATCAAATTTATCAGAGCCATTTAAAA
ATCTGAAAACAGGAAGTATGCAAGGATGAGGGGTGCCCACACTAAATTCCTAAATGATGTAAAACAGTTAACAAAAGCAGTGCAAA
AAGTATCCACAGAAAGCATAGTAATATGGGGAAAGATTCCTAAATTTAAACTACCCATACAAAAGGAAACATGGGAAG
CATGGTGGATGGAGTATTGGCAAGCTACCTGGATTCCTGAGTTTGTCAATACCCCTCCCTTAGTGAAATTAT
GGTACCAGTTAGAGAAAGAACCCATAGTAGGAGCAGAGACTTTCTATGTAGATGGGGCAGCTAATAGGGAGACTAAAT
TAGGAAAAGCAGGATATGTTACTGACAGAGGAAGACAAAAAGTTGTCTCCATAGCTGACACAACAAATCAGAAGACTG
AATTACAAGCAATTCATCTAGCTTTGCAGGATTCGGGATTAGAAGTAAACATAGTAACAGACTCACAATATGCATTAG
GAATCATTCAAGCACAACCAGATAAGAGTGAATCAGAGTTAGTCAGTCAAATAATAGAGCAGTTAATAAAAAGGAAA
AGGTCTACCTGGCATGGGTACCAGCACACAAAGGAATTGGAGGAAATGAACAAGTAGATAAATTAGTCAGTGCTGGAA
TCAGGAAAGTACTATTTTTGAACCTGCCACCTGTGGATGGAATAGCCAAGGAAATATGAGCAGTGTACACATCC
AAGCCATGCATGGACAAGTAGACTGTAGTCCAGGAATATGGCAACTAGATTGTACACACTTAGAAGGAAAAATTATCC
TGGTAGCAGTTCATGTAGCCAGTGGATATATAGAAGCAGAAGTTATTCCAGCAGAGACAGGGCAGGAAACAGCATATT
TTCTCTTAAAATTAGCAGGAAGATGGCCAGTAAAAACAATACATACAGACAATGGCAGCAATTTCACCAGTACTACGG
TTAAGGCCGCCTGTTGGTGGGCGGGATCAAGCAGGAATTTCCCTACAATCCCCAAAGTCAAGGAGTAGTAG
AATCTATGAATAAAGAATTAAAGAAAATTATAGGACAGGTAAGAGATCAGGCTGAACACCTTAAGACAGCACAAAA
TGGCAGTATTCATCCACAATTTAAAAGAAAAGGGGGGATTGGGGGATACAGTGCAGGGGAAAGAATACAAGACATAA
TAGCAATAGACATACAAACTAAAGAACTACAAAAACAAATTACAAAAATTCAAAATTTTCGGGTTTATTACAAGAGACA
ACAAAGATCCCCTTTGGAAAGGACCAGCAAGCTTCTCTGGAAAGGTGAAGGGGCAGTAGTAATACAAGATAATAGTG
ACATAAAGTAGTGCCAAGAAGAAAGCAAAAATCATTAGGGATTATGGAAAACAGATGGCAGGTGATGATTGTGTGG
CAAGTAGACAGGATGAGGATTAG
``` gp120wtSF162

GTAGAAAAATTGTGGGTCACAGTCTATTATGGGGTACCTGTGTGTGGAAAGAAGCAACCACCACTCTATTTT
GTGCATCAGATGCTAAAGCATGCTAAAAGCCTATGACACAGAGGTACATAATGTCTGGGCCACACATGCCTGTGTACCCAC
AGACCCTAACCCACCAAGAATAGTATTGGAAAATGTGACAGAAAATTTAACATGTGGAAAATAACATG
GTAGAACAGATGC gp140wtSF162

GTAGAAAAATTGTGGGTCACAGTCTATTATGGGTACCTGTGTGAAGAAGAAGCAACCACCACTCTATTTT
GTGCATCAGATGCTAAAGCATATGACACAGAGGTACATAATGTCTGGGCCACACATGCCTGTGTACCCAC
AGACCCTAACCCACAAGAAGATAGTATTGGAAATGTGACAGAAAATTTAACATGTGGAAAATAACATG
GTAGAACAGATGCATGAGGATATAATCAGTTTATGGGATCAAAGTCTAAAGCCATGTGTAAAGTTAACCC
CACTCTGTGTTACTCTACATTGCACTAATTTGAAGAATGCTACTAATACCAAGAGTAGTAGTTGGAAAGA
GATGGAC gp160wtSF162

```
GTAGAAAAATTGTGGGTCACAGTCTATTATGGGGTACCTGTGTGGAAAGAAGCAACCACCACTCTATTTT
GTGCATCAGATGCTAAAGCCTATGACACAGAGGTACATAATGTCTGGGCCACACATGCCTGTGTACCCAC
AGACCCTAACCCACAAGAAATAGTATTGGAAAATGTGACAGAAAATTTTAACATGTGGAAAAATAACATG
GTAGAACAGATGCATGAGGATATAATCAGTTTATGGGATCAAAGTCTAAAGCCATGTGTAAAGTTAACCC
CACTCTGTGTTACTCTACATTGCACTAATTTGAAGAATGCTACTAATACCAAGAGTAGTAATTGGAAAGA
GATGGACAGAGGAGAAATAAAAAATTGCTCTTTCAAGGTCACCACAAGCATAAGAAATAAGATGCAGAAA
GAATATGCACTTTTTTATAAACTTGATGTAGTACCAATAGATAATGATAATACAAGCTATAAATTGATAA
ATTGTAACACCTCAGTCATTACACAGGCCTGTCCAAAGGTATCCTTTGAACCAATTCCCATACATTATTG
TGCCCCGGCTGGTTTTGCGATTCTAAAGTGTAATGATAAGAAGTTCAATGGATCAGGACCATGTACAAAT
GTCAGCACAGTACAATGTACACATGGAATTAGGCCAGTAGTGTCAACTCAATTGCTGTTAAATGGCAGTC
TAGCAGAAGAAGGGGTAGTAATTAGATCTGAAAATTTCACAGACAATGCTAAAACTATAATAGTACAGCT
GAAGGAATCTGTAGAAATTAATTGTACAAGACCTAACAATAATACAAGAAAAAGTATAACTATAGGACCG
GGGAGAGCATTTTATGCAACAGGAGACATAATAGGAGATATAAGACAAGCACATTGTAACATTAGTGGAG
AAAAATGGAATAACACTTTAAAACAGATAGTTACAAAATTACAAGCACAATTTGGGAATAAAACAATAGT
CTTTAAGCAATCCTCAGGAGGGGACCCAGAAATTGTAATGCACAGTTTTAATTGTGGAGGGGAATTTTTC
TACTGTAATTCAACACAGCTTTTTAATAGTACTTGGAATAATACTATAGGGCCAAATAACACTAATGGAA
CTATCACACTCCCATGCAGAATAAAACAAATTATAAACAGGTGGCAGGAAGTAGGAAAAGCAATGTATGC
CCCTCCCATCAGAGGACAAATTAGATGCTCATCAAATATTACAGGACTGCTATTAACAAGAGATGGTGGT
AAAGAGATCAGTAACACCACCGAGATCTTCAGACCTGGAGGTGGAGATATGAGGGACAATTGGAGAAGTG
AATTATATAAATATAAAGTAGTAAAAATTGAGCCATTAGGAGTAGCACCCACCAAGGCAAAGAGAAGAGT
GGTGCAGAGAGAAAAAAGAGCAGTGACGCTAGGAGCTATGTTCCTTGGGTTCTTGGGAGCAGCAGGAAGC
ACTATGGGCGCACGGTCACTGACGCTGACGGTACAGGCCAGACAATTATTGTCTGGTATAGTGCAACAGC
AGAACAATTTGCTGAGAGCTATTGAGGCGCAACAGCATCTGTTGCAACTCACAGTCTGGGGCATCAAGCA
GCTCCAGGCAAGAGTCCTGGCTGTGGAAAGATACCTAAAGGATCAACAGCTCCTAGGGATTTGGGGTTGC
TCTGGAAAACTCATTTGCACCACTGCTGTGCCTTGGAATGCTAGTTGGAGTAATAAATCTCTGGATCAGA
TTTGGAATAACATGACCTGGATGGAGTGGGAGAGAGAAATTGACAATTACACAAACTTAATATACACCTT
AATTGAAGAATCGCAGAACCAACAAGAAAAGAATGAACAAGAATTATTAGAATTGGATAAGTGGGCAAGT
TTGTGGAATTGGTTTGACATATCAAAATGGCTGTGGTATATAAAAATATTCATAATGATAGTAGGAGGTT
TAGTAGGTTTAAGGATAGTTTTTACTGTGCTTTCTATAGTGAATAGAGTTAGGCAGGGATACTCACCATT
ATCATTTCAGACCCGCTTCCCAGCCCCAAGGGGACCCGACAGGCCCGAAGGAATCGAAGAAGAAGGTGGA
GAGAGAGACAGAGACAGATCCAGTCCATTAGTGCATGGATTATTAGCACTCATCTGGGACGATCTACGGA
GCCTGTGCCTCTTCAGCTACCACCGCTTGAGAGACTTAATCTTGATTGCAGCGAGGATTGTGGAACTTCT
GGGACGCAGGGGGTGGGAAGCCCTCAAGTATTGGGGGAATCTCCTGCAGTATTGGATTCAGGAACTAAAG
AATAGTGCTGTTAGTTTGTTTGATGCCATAGCTATAGCAGTAGCTGAGGGGACAGATAGGATTATAGAAG
TAGCACAAAGAATTGGTAGAGCTTTTCTCCACATACCTAGAAGAATAAGACAGGGCTTTGAAAGGGCTTT
GCTATAA
```

FIG. 18

(SEQ ID NO:32)

gp120.modSF162 gaattcgccaccatggatgcaatgaagagagggctctgctgtgtgctgctgctgtgtggagcagtc
ttcgtttcgcccagcgccgtggagaagctgtgggtgaccgtgtactacggcgtgcccgtgtggaag
gaggccaccaccaccctgttctgcgccagcgacgccaaggcctacgacaccgaggtgcacaacgtg
tgggccacccacgcctgcgtgcccaccgaccccaacccccaggagatcgtgctggagaacgtgacc
gagaacttcaacatgtggaagaacaacatggtggagcagatgcacgaggacatcatcagcctgtgg
gaccagagcctgaagccctgcgtgaagctgacccccctgtgcgtgaccctgcactgcaccaacctg
aagaacgccaccaacaccaagagcagcaactggaaggagatggaccgcggcgagatcaagaactgc
agcttcaaggtgaccaccagcatccgcaacaagatgcagaaggagtacgccctgttctacaagctg
gacgtggtgcccatcgacaacgacaacaccagctacaagctgatcaactgcaacaccagcgtgatc
acccaggcctgccccaaggtgagcttcgagcccatccccatccactactgcgcccccgccggcttc
gccatcctgaagtgcaacgacaagaagttcaacggcagcggcccctgcaccaacgtgagcaccgtg
cagtgcacccacggcatccgccccgtggtgagcacccagctgctgctgaacggcagcctggccgag
gagggcgtggtgatccgcagcgagaacttcaccgacaacgccaagaccatcatcgtgcagctgaag
gagagcgtggagatcaactgcacccgccccaacaacaacacccgcaagagcatcaccatcggcccc
ggccgcgccttctacgccaccggcgacatcatcggcgacatccgccaggcccactgcaacatcagc
ggcgagaagtggaacaacaccctgaagcagatcgtgaccaagctgcaggcccagttcggcaacaag
accatcgtgttcaagcagagcagcggcggcgaccccgagatcgtgatgcacagcttcaactgcggc
ggcgagttcttctactgcaacagcacccagctgttcaacagcacctggaacaacaccatcggcccc
aacaacaccaacggcaccatcaccctgccctgccgcatcaagcagatcatcaaccgctggcaggag
gtgggcaaggccatgtacgcccccccatccgcggccagatccgctgcagcagcaacatcaccggc
ctgctgctgacccgcgacggcggcaaggagatcagcaacaccaccgagatcttccgccccggcggc
ggcgacatgcgcgacaactggcgcagcgagctgtacaagtacaaggtggtgaagatcgagcccctg
ggcgtggcccccaccaaggccaagcgccgcgtggtgcagcgcgagaagcgctaactcgag

FIG. 19
(SEQ ID NO:33)

gp120.modSF162.delV2 gaattcgcc gp120.modSF162.delV1V2

```
gaattcgccaccatggatgcaatgaagagagaggctctgtgtgtctgt gp140.modSF162

```
gaattcgccaccatggatgcaatgaagagagggctctgctgtgtgctgctgctgtgtggagcagtc
ttcgtttcgcccagcgccgtggagaagctgtgggtgaccgtgtactacggcgtgcccgtgtggaag
gaggccaccaccaccctgttctgcgccagcgacgccaaggcctacgacaccgaggtgcacaacgtg
tgggccacccacgcctgcgtgcccaccgaccccaaccccaggagatcgtgctggagaacgtgacc
gagaacttcaacatgtggaagaacaacatggtggagcagatgcacgaggacatcatcagcctgtgg
gaccagagcctgaagccctgcgtgaagctgacccccctgtgcgtgaccctgcactgcaccaacctg
aagaacgccaccaacaccaagagcagcaactggaaggagatggaccgcggcgagatcaagaactgc
agcttcaaggtgaccaccagcatccgcaacaagatgcagaaggagtacgccctgttctacaagctg
gacgtggtgcccatcgacaacgacaacaccagctacaagctgatcaactgcaacaccagcgtgatc
acccaggcctgccccaaggtgagcttcgagcccatccccatccactactgcgccccgccggcttc
gccatcctgaagtgcaacgacaagaagttcaacggcagcggcccctgcaccaacgtgagcaccgtg
cagtgcacccacggcatccgccccgtggtgagcacccagctgctgctgaacggcagcctggccgag
gagggcgtggtgatccgcagcgagaacttcaccgacaacgccaagaccatcatcgtgcagctgaag
gagagcgtggagatcaactgcacccgccccaacaacaacacccgcaagagcatcaccatcggcccc
ggccgcgccttctacgccaccggcgacatcatcggcgacatccgccaggcccactgcaacatcagc
ggcgagaagtggaacaacaccctgaagcagatcgtgaccaagctgcaggcccagttcggcaacaag
accatcgtgttcaagcagagcagcggcggcgaccccgagatcgtgatgcacagcttcaactgcggc
ggcgagttcttctactgcaacagcacccagctgttcaacagcacctggaacaacaccatcggcccc
aacaacaccaacggcaccatcaccctgccctgccgcatcaagcagatcatcaaccgctggcaggag
gtgggcaaggccatgtacgcccccccatccgcggccagatccgctgcagcagcaacatcaccggc
ctgctgctgacccgcgacggcggcaaggagatcagcaacaccaccgagatcttccgccccggcggc
ggcgacatgcgcgacaactggcgcagcgagctgtacaagtacaaggtggtgaagatcgagcccctg
ggcgtggccccaccaaggccaagcgccgcgtggtgcagcgcgagaagcgcgccgtgaccctgggc
gccatgttcctgggcttcctgggcgccgcggcagcaccatgggcgcccgcagcctgacccTgacc
gtgcaggcccgccagctgctgagcggcatcgtgcagcagcagaacaacctgctgcgcgccatcgag
gcccagcagcacctgctgcagctgaccgtgtggggcatcaagcagctgcaggcccgcgtgctggcc
gtggagcgctacctgaaggaccagcagctgctgggcatctggggctgcagcggcaagctgatctgc
accaccgccgtgccctggaacgccagctggagcaacaagagcctggaccagatctggaacaacatg
acctggatggagtgggagcgcgagatcgacaactacaccaacctgatctaccctgatcgaggag
agccagaaccagcaggagaagaacgagcaggagctgctggagctggacaagtgggccagcctgtgg
aactggttcgacatcagcaagtggctgtggtacatctaactcgag
```

FIG. 23
(SEQ ID NO:36)

gp140.modSF162.delV2 gaattcgccaccatggatgcaatgaagagagggctctgctgtgtgctgctgctgtgtggagcagtc
ttcgtttcgcccagcgccgtggagaagctgtgggtgaccgtgtactacggcgtgcccgtgtggaag
gaggccaccaccaccctgttctgcgccagcgacgccaaggcctacgacaccgaggtgcacaacgtg
tgggccacccacgcctgcgtgcccaccgaccccaaccccaggagatcgtgctggagaacgtgacc
gagaacttcaacatgtggaagaacaacatggtggagcagatgcacgaggacatcatcagcctgtgg
gaccagagcctgaagccctgcgtgaagctgacccccctgtgcgtgaccctgcactgcaccaacctg
aagaacgccaccaacaccaagagcagcaactggaaggagatggaccgcggcgagatcaagaactgc
agcttcaaggtgggcgccggcaagctgatcaactgcaacaccagcgtgatcacccaggcctgcccc
aaggtgagcttcgagcccatccccatccactactgcgccccgccggcttcgccatcctgaagtgc
aacgacaagaagttcaacggcagcggccctgcaccaacgtgagcaccgtgcagtgcacccacggc
atccgccgtggtgagcacccagctgctgctgaacggcagcctggccgaggagggcgtggtgatc
cgcagcgagaacttcaccgacaacgccaagaccatcatcgtgcagctgaaggagagcgtggagatc
aactgcacccgccccaacaacaacacccgcaagagcatcaccatcggcccggccgcgccttctac
gccaccggcgacatcatcggcgacatccgccaggcccactgcaacatcagcggcgagaagtggaac
aacaccctgaagcagatcgtgaccaagctgcaggcccagttcggcaacaagaccatcgtgttcaag
cagagcagcggcggcgaccccgagatcgtgatgcacagcttcaactgcggcggcgagttcttctac
tgcaacagcacccagctgttcaacagcacctggaacaacaccatcggccccaacaacaccaacggc
accatcaccctgccctgccgcatcaagcagatcatcaaccgctggcaggaggtgggcaaggccatg
tacgccccccccatccgcggccagatccgctgcagcagcaacatcaccggcctgctgctgacccgc
gacggcggcaaggagatcagcaacaccaccgagatcttccgccccggcggcggcgacatgcgcgac
aactggcgcagcgagctgtacaagtacaaggtggtgaagatcgagcccctgggcgtggcccccacc
aaggccaagcgccgcgtggtgcagcgcgagaagcgcgccgtgaccctgggcgccatgttcctgggc
ttcctgggcgccgccggcagcaccatgggcgcccgcagcctgaccctgaccgtgcaggcccgccag
ctgctgagcggcatcgtgcagcagcagaacaacctgctgcgcgccatcgaggcccagcagcacctg
ctgcagctgaccgtgtggggcatcaagcagctgcaggcccgcgtgctggccgtggagcgctacctg
aaggaccagcagctgctgggcatctggggctgcagcggcaagctgatctgcaccaccgccgtgccc
tggaacgccagctggagcaacaagagcctggaccagatctggaacaacatgacctggatggagtgg
gagcgcgagatcgacaactacaccaacctgatctacaccctgatcgaggagagccagaaccagcag
gagaagaacgagcaggagctgctggagctggacaagtgggccagcctgtggaactggttcgacatc
agcaagtggctgtggtacatctaactcgag

FIG. 24
(SEQ ID NO:37)

gp140.modSF162.delV1V2 gaattcgccaccatggatgcaatgaagagagggctctgctgtgtgctgctgctgtgtggagcagtc
ttcgtttcgcccagcgccgtggagaagctgtgggtgaccgtgtactacggcgtgcccgtgtggaag
gaggccaccaccaccctgttctgcgccagcgacgccaaggcctacgacaccgaggtgcacaacgtg
tgggccacccacgcctgcgtgcccaccgaccccaaccccaggagatcgtgctggagaacgtgacc
gagaacttcaacatgtggaagaacaacatggtggagcagatgcacgaggacatcatcagcctgtgg
gaccagagcctgaagccctgcgtgaagctgaccccctgtgcgtgggcgccggcaactgccagacc
agcgtgatcacccaggcctgccccaaggtgagcttcgagcccatccccatccactactgcgccccc
gccggcttcgccatcctgaagtgcaacgacaagaagttcaacggcagcggccctgcaccaacgtg
agcaccgtgcagtgcacccacggcatccgcccgtggtgagcacccagctgctgctgaacggcagc
ctggccgaggagggcgtggtgatccgcagcgagaacttcaccgacaacgccaagaccatcatcgtg
cagctgaaggagagcgtggagatcaactgcacccgccccaacaacaacacccgcaagagcatcacc
atcggccccggccgcgccttctacgccaccggcgacatcatcggcgacatccgccaggcccactgc
aacatcagcggcgagaagtggaacaacaccctgaagcagatcgtgaccaagctgcaggcccagttc
ggcaacaagaccatcgtgttcaagcagagcagcggcggcgaccccgagatcgtgatgcacagcttc
aactgcggcggcgagttcttctactgcaacagcacccagctgttcaacagcacctggaacaacacc
atcggccccaacaacaccaacggcaccatcaccctgccctgccgcatcaagcagatcatcaaccgc
tggcaggaggtgggcaaggccatgtacgcccccccatccgcggccagatccgctgcagcagcaac
atcaccggcctgctgctgacccgcgacggcggcaaggagatcagcaacaccaccgagatcttccgc
cccggcggcggcgacatgcgcgacaactggcgcagcgagctgtacaagtacaaggtggtgaagatc
gagcccctgggcgtggccccaccaaggccaagcgccgcgtggtgcagcgcgagaagcgcgccgtg
accctgggcgccatgttcctgggcttcctgggcgccgccggcagcaccatgggcgcccgcagcctg
accctgaccgtgcaggccgccagctgctgagcggcatcgtgcagcagcagaacaacctgctgcgc
gccatcgaggcccagcagcacctgctgcagctgaccgtgtggggcatcaagcagctgcaggcccgc
gtgctggccgtggagcgctacctgaaggaccagcagctgctgggcatctggggctgcagcggcaag
ctgatctgcaccaccgccgtgccctggaacgccagctggagcaacaagagcctggaccagatctgg
aacaacatgacctggatggagtgggagcgcgagatcgacaactacaccaacctgatctacaccctg
atcgaggagagccagaaccagcaggagaagaacgagcaggagctgctggagctggacaagtgggcc
agcctgtggaactggttcgacatcagcaagtggctgtggtacatctaactcgag

FIG. 25
(SEQ ID NO:38)

gp140.mut.modSF162

```
gaattcgccaccatggatgcaatgaagagagggctctgctgtgtgctgctgctgtgtggagcagtc
ttcgtttcgcccagcgccgtggagaagctgtgggtgaccgtgtactacggcgtgcccgtgtggaag
gaggccaccaccaccctgttctgcgccagcgacgccaaggcctacgacaccgaggtgcacaacgtg
tgggccacccacgcctgcgtgcccaccgaccccaaccccaggagatcgtgctggagaacgtgacc
gagaacttcaacatgtggaagaacaacatggtggagcagatgcacgaggacatcatcagcctgtgg
gaccagagcctgaagccctgcgtgaagctgaccccctgtgcgtgaccctgcactgcaccaacctg
aagaacgccaccaacaccaagagcagcaactggaaggagatggaccgcggcgagatcaagaactgc
agcttcaaggtgaccaccagcatccgcaacaagatgcagaaggagtacgccctgttctacaagctg
gacgtggtgcccatcgacaacgacaacaccagctacaagctgatcaactgcaacaccagcgtgatc
acccaggcctgccccaaggtgagcttcgagcccatccccatccactactgcgccccgccggcttc
gccatcctgaagtgcaacgacaagaagttcaacggcagcggccctgcaccaacgtgagcaccgtg
cagtgcacccacggcatccgccccgtggtgagcacccagctgctgctgaacggcagcctggccgag
gagggcgtggtgatccgcagcgagaacttcaccgacaacgccaagaccatcatcgtgcagctgaag
gagagcgtggagatcaactgcacccgccccaacaacaacacccgcaagagcatcaccatcggcccc
ggccgcgccttctacgccaccggcgacatcatcggcgacatccgccaggcccactgcaacatcagc
ggcgagaagtggaacaacaccctgaagcagatcgtgaccaagctgcaggcccagttcggcaacaag
accatcgtgttcaagcagagcagcggcggcgaccccgagatcgtgatgcacagcttcaactgcggc
ggcgagttcttctactgcaacagcacccagctgttcaacagcacctggaacaacaccatcggcccc
aacaacaccaacggcaccatcaccctgccctgccgcatcaagcagatcatcaaccgctggcaggag
gtgggcaaggccatgtacgccccccccatccgcggccagatccgctgcagcagcaacatcaccggc
ctgctgctgacccgcgacggcggcaaggagatcagcaacaccaccgagatcttccgccccggcggc
ggcgacatgcgcgacaactggcgcagcgagctgtacaagtacaaggtggtgaagatcgagcccctg
ggcgtggcccccaccaaggccaagcgccgcgtggtgcagcgcgagaagagcgccgtgaccctgggc
gccatgttcctgggcttcctgggcgccgccggcagcaccatgggcgcccgcagcctgaccctgacc
gtgcaggccgccagctgctgagcggcatcgtgcagcagcagaacaacctgctgcgcgccatcgag
gcccagcagcacctgctgcagctgaccgtgtggggcatcaagcagctgcaggcccgcgtgctggcc
gtggagcgctacctgaaggaccagcagctgctgggcatctggggctgcagcggcaagctgatctgc
accaccgccgtgccctggaacgccagctggagcaacaagagcctggaccagatctggaacaacatg
acctggatggagtgggagcgcgagatcgacaactacaccaacctgatctacaccctgatcgaggag
agccagaaccagcaggagaagaacgagcaggagctgctggagctggacaagtgggccagcctgtgg
aactggttcgacatcagcaagtggctgtggtacatctaactcgag
```

FIG. 26
(SEQ ID NO:39)

gp140.mut.modSF162.delV2

```
gaattcgccaccatggatgcaatgaagagagggctctgctgtgtgctgctgctgtgtggagcagtc
ttcgtttcgcccagcgccgtggagaagctgtggtgaccgtgtactacggcgtgcccgtgtggaag
gaggccaccaccaccctgttctgcgccagcgacgccaaggcctacgacaccgaggtgcacaacgtg
tgggccacccacgcctgcgtgcccaccgaccccaaccccaggagatcgtgctggagaacgtgacc
gagaacttcaacatgtggaagaacaacatggtggagcagatgcacgaggacatcatcagcctgtgg
gaccagagcctgaagccctgcgtgaagctgacccccgtgcgtgaccctgcactgcaccaacctg
aagaacgccaccaacaccaagagcagcaactggaaggagatggaccgcggcgagatcaagaactgc
agcttcaaggtgggcgccggcaagctgatcaactgcaacaccagcgtgatcacccaggcctgcccc
aaggtgagcttcgagcccatccccatccactactgcgcccccgccggcttcgccatcctgaagtgc
aacgacaagaagttcaacggcagcggccctgcaccaacgtgagcaccgtgcagtgcacccacggc
atccgcccgtggtgagcacccagctgctgctgaacggcagcctggccgaggagggcgtggtgatc
cgcagcgagaacttcaccgacaacgccaagaccatcatcgtgcagctgaaggagagcgtggagatc
aactgcacccgccccaacaacaacacccgcaagagcatcaccatcggccccggccgcgccttctac
gccaccggcgacatcatcggcgacatccgccaggcccactgcaacatcagcggcgagaagtggaac
aacaccctgaagcagatcgtgaccaagctgcaggcccagttcggcaacaagaccatcgtgttcaag
cagagcagcggcggcgaccccgagatcgtgatgcacagcttcaactgcggcggcgagttcttctac
tgcaacagcacccagctgttcaacagcacctggaacaacaccatcggccccaacaacaccaacggc
accatcaccctgccctgccgcatcaagcagatcatcaaccgctggcaggaggtgggcaaggccatg
tacgccccccccatccgcggccagatccgctgcagcagcaacatcaccggcctgctgctgacccgc
gacggcggcaaggagatcagcaacaccaccgagatcttccgccccggcggcggcgacatgcgcgac
aactggcgcagcgagctgtacaagtacaaggtggtgaagatcgagcccctgggcgtggcccccacc
aaggccaagcgccgcgtggtgcagcgcgagaagagcgccgtgaccctgggcgccatgttcctgggc
ttcctgggcgccgccggcagcaccatgggcgcccgcagcctgacccctgaccgtgcaggcccgccag
ctgctgagcggcatcgtgcagcagcagaacaacctgctgcgcgccatcgaggcccagcagcacctg
ctgcagctgaccgtgtggggcatcaagcagctgcaggcccgcgtgctggccgtggagcgctacctg
aaggaccagcagctgctgggcatctggggctgcagcggcaagctgatctgcaccaccgccgtgccc
tggaacgccagctggagcaacaagagcctggaccagatctggaacaacatgacctggatggagtgg
gagcgcgagatcgacaactacaccaacctgatctacaccctgatcgaggagagccagaaccagcag
gagaagaacgagcaggagctgctggagctggacaagtgggccagcctgtggaactggttcgacatc
agcaagtggctgtggtacatctaactcgag
```

FIG. 27

(SEQ ID NO:40)

gp140.mut.modSF162.delV1V2

```
gaattcgccaccatggatgcaatgaagagagggctctgctgtgtgctgctgctgtgtggagcagtc
ttcgtttcgcccagcgccgtggagaagctgtgggtgaccgtgtactacggcgtgcccgtgtggaag
gaggccaccaccaccctgttctgcgccagcgacgccaaggcctacgacaccgaggtgcacaacgtg
tgggccacccacgcctgcgtgcccaccgaccccaaccccaggagatcgtgctggagaacgtgacc
gagaacttcaacatgtggaagaacaacatggtggagcagatgcacgaggacatcatcagcctgtgg
gaccagagcctgaagccctgcgtgaagctgacccccctgtgcgtgggcgccggcaactgccagacc
agcgtgatcacccaggcctgccccaaggtgagcttcgagcccatccccatccactactgcgccccc
gccggcttcgccatcctgaagtgcaacgacaagaagttcaacggcagcggcccctgcaccaacgtg
agcaccgtgcagtgcacccacggcatccgcccgtggtgagcacccagctgctgctgaacggcagc
ctggccgaggagggcgtggtgatccgcagcgagaacttcaccgacaacgccaagaccatcatcgtg
cagctgaaggagagcgtggagatcaactgcacccgccccaacaacaacacccgcaagagcatcacc
atcggccccggccgcgccttctacgccaccggcgacatcatcggcgacatcgccaggcccactgc
aacatcagcggcgagaagtggaacaacaccctgaagcagatcgtgaccaagctgcaggcccagttc
ggcaacaagaccatcgtgttcaagcagagcagcggcggcgaccccgagatcgtgatgcacagcttc
aactgcggcggcgagttcttctactgcaacagcacccagctgttcaacagcacctggaacaacacc
atcggccccaacaacaccaacggcaccatcacctgccctgccgcatcaagcagatcatcaaccgc
tggcaggaggtgggcaaggccatgtacgccccccccatccgcggccagatccgctgcagcagcaac
atcaccggcctgctgctgacccgcgacggcggcaaggagatcagcaacaccaccgagatcttccgc
cccggcggcggcgacatgcgcgacaactggcgcagcgagctgtacaagtacaaggtggtgaagatc
gagcccctgggcgtggcccccaccaaggccaagcgccgcgtggtgcagcgcgagaagagcgccgtg
accctgggcgccatgttcctgggcttcctgggcgccgccggcagcaccatgggcgcccgcagcctg
accctgaccgtgcaggcccgccagctgctgagcggcatcgtgcagcagcagaacaacctgctgcgc
gccatcgaggcccagcagcacctgctgcagctgaccgtgtggggcatcaagcagctgcaggcccgc
gtgctggccgtggagcgctacctgaaggaccagcagctgctgggcatctggggctgcagcggcaag
ctgatctgcaccaccgccgtgccctggaacgccagctggagcaacaagagcctggaccagatctgg
aacaacatgacctggatggagtgggagcgcgagatcgacaactacaccaacctgatctacaccctg
atcgaggagagccagaaccagcaggagaagaacgagcaggagctgctggagctggacaagtgggcc
agcctgtggaactggttcgacatcagcaagtggctgtggtacatctaactcgag
```

FIG. 28
(SEQ ID NO:41)

gp140.mut7.modSF162 gaattcgccaccatggatgcaatgaagagagggctctgctgtgtgctgctgctgtgtggagcagtc
ttcgtttcgcccagcgccgtggagaagctgtgggtgaccgtgtactacggcgtgcccgtgtggaag
gaggccaccaccaccctgttctgcgccagcgacgccaaggcctacgacaccgaggtgcacaacgtg
tgggccacccacgcctgcgtgcccaccgaccccaaccccaggagatcgtgctggagaacgtgacc
gagaacttcaacatgtggaagaacaacatggtggagcagatgcacgaggacatcatcagcctgtgg
gaccagagcctgaagccctgcgtgaagctgacccccctgtgcgtgaccctgcactgcaccaacctg
aagaacgccaccaacaccaagagcagcaactggaaggagatggaccgcggcgagatcaagaactgc
agcttcaaggtgaccaccagcatccgcaacaagatgcagaaggagtacgccctgttctacaagctg
gacgtggtgcccatcgacaacgacaacaccagctacaagctgatcaactgcaacaccagcgtgatc
acccaggcctgccccaaggtgagcttcgagcccatccccatccactactgcgcccccgccggcttc
gccatcctgaagtgcaacgacaagaagttcaacggcagcggcccctgcaccaacgtgagcaccgtg
cagtgcacccacggcatccgccccgtggtgagcacccagctgctgctgaacggcagcctggccgag
gagggcgtggtgatccgcagcgagaacttcaccgacaacgccaagaccatcatcgtgcagctgaag
gagagcgtggagatcaactgcacccgccccaacaacaacacccgcaagagcatcaccatcggcccc
ggccgcgccttctacgccaccggcgacatcatcggcgacatccgccaggccactgcaacatcagc
ggcgagaagtggaacaacaccctgaagcagatcgtgaccaagctgcaggcccagttcggcaacaag
accatcgtgttcaagcagagcagcggcggcgaccccgagatcgtgatgcacagcttcaactgcggc
ggcgagttcttctactgcaacagcacccagctgttcaacagcacctggaacaacaccatcggcccc
aacaacaccaacggcaccatcaccctgccctgccgcatcaagcagatcatcaaccgctggcaggag
gtgggcaaggccatgtacgccccccccatccgcggccagatccgctgcagcagcaacatcaccggc
ctgctgctgacccgcgacggcggcaaggagatcagcaacaccaccgagatcttccgccccggcggc
ggcgacatgcgcgacaactggcgcagcgagctgtacaagtacaaggtggtgaagatcgagcccctg
ggcgtggcccccaccaaggccatcagcagcgtggtgcagagcgagaagagcgccgtgacc ctgggc
gccatgttcctgggcttcctgggcgccgccggcagcaccatgggcgcccgcagcctgaccctgacc
gtgcaggcccgccagctgctgagcggcatcgtgcagcagcagaacaacctgctgcgcgccatcgag
gccagcagcacctgctgcagctgaccgtgtggggcatcaagcagctgcaggcccgcgtgctggcc
gtggagcgctacctgaaggaccagcagctgctgggcatctggggctgcagcggcaagctgatctgc
accaccgccgtgccctggaacgccagctggagcaacaagagcctggaccagatctggaacaacatg
acctggatggagtgggagcgcgagatcgacaactacaccaacctgatctacaccctgatcgaggag
agccagaaccagcaggagaagaacgagcaggagctgctggagctggacaagtgggccagcctgtgg
aactggttcgacatcagcaagtggctgtggtacatctaactcgag
```

FIG. 29
(SEQ ID NO:42)

gp140.mut7.modSF162.delV2 gaattcgccaccatggatgcaatgaagagagggctctgctgtgtgctgctgctgtgtggagcagtc
ttcgtttcgcccagcgccgtggagaagctgtgggtgaccgtgtactacggcgtgcccgtgtggaag
gaggccaccaccaccctgttctgcgccagcgacgccaaggcctacgacaccgaggtgcacaacgtg
tgggccacccacgcctgcgtgcccaccgaccccaaccccaggagatcgtgctggagaacgtgacc
gagaacttcaacatgtggaagaacaacatggtggagcagatgcacgaggacatcatcagcctgtgg
gaccagagcctgaagccctgcgtgaagctgaccccctgtgcgtgaccctgcactgcaccaacctg
aagaacgccaccaacaccaagagcagcaactggaaggagatggaccgcggcgagatcaagaactgc
agcttcaaggtgggcgccggcaagctgatcaactgcaacaccagcgtgatcacccaggcctgcccc
aaggtgagcttcgagcccatccccatccactactgcgcccccgccggcttcgccatcctgaagtgc
aacgacaagaagttcaacggcagcggcccctgcaccaacgtgagcaccgtgcagtgcacccacggc
atccgccccgtggtgagcacccagctgctgctgaacggcagcctggccgaggagggcgtggtgatc
cgcagcgagaacttcaccgacaacgccaagaccatcatcgtgcagctgaaggagagcgtggagatc
aactgcacccgccccaacaacaacacccgcaagagcatcaccatcggccccggccgcgccttctac
gccaccggcgacatcatcggcgacatccgccaggcccactgcaacatcagcggcgagaagtggaac
aacaccctgaagcagatcgtgaccaagctgcaggcccagttcggcaacaagaccatcgtgttcaag
cagagcagcggcggcgaccccgagatcgtgatgcacagcttcaactgcggcggcgagttcttctac
tgcaacagcacccagctgttcaacagcacctggaacaacaccatcggccccaacaacaccaacggc
accatcaccctgccctgccgcatcaagcagatcatcaaccgctggcaggaggtgggcaaggccatg
tacgccccccccatccgcggccagatccgctgcagcagcaacatcaccggcctgctgctgacccgc
gacggcggcaaggagatcagcaacaccaccgagatcttcgccccggcggcggcgacatgcgcgac
aactggcgcagcgagctgtacaagtacaaggtggtgaagatcgagcccctgggcgtggcccccacc
aaggccatcagcagcgtggtgcagagcgagaagagcgccgtgacgctgggcgccatgttcctgggc
ttcctgggcgccgccggcagcaccatgggcgcccgcagcctgaccctgaccgtgcaggcccgccag
ctgctgagcggcatcgtgcagcagcagaacaacctgctgcgcgccatcgaggcccagcagcacctg
ctgcagctgaccgtgtggggcatcaagcagctgcaggcccgcgtgctggccgtggagcgctacctg
aaggaccagcagctgctgggcatctggggctgcagcggcaagctgatctgcaccaccgccgtgccc
tggaacgccagctggagcaacaagagcctggaccagatctggaacaacatgacctggatggagtgg
gagcgcgagatcgacaactacaccaacctgatctacaccctgatcgaggagagccagaaccagcag
gagaagaacgagcaggagctgctggagctggacaagtgggccagcctgtggaactggttcgacatc
agcaagtggctgtggtacatctaactcgag

FIG. 30
(SEQ ID NO:43)

gp140.mut7.modSF162.delV1V2

```
gaattcgccaccatggatgcaatgaagagagggctctgctgtgtgctgctgctgtgggagcagtc
ttcgtttcgcccagcgccgtggagaagctgtgggtgaccgtgtactacggcgtgcccgtgtggaag
gaggccaccaccaccctgttctgcgccagcgacgccaaggcctacgacaccgaggtgcacaacgtg
tgggccacccacgcctgcgtgcccaccgacccaaccccaggagatcgtgctggagaacgtgacc
gagaacttcaacatgtggaagaacaacatggtggagcagatgcacgaggacatcatcagcctgtgg
gaccagagcctgaagccctgcgtgaagctgacccccctgtgcgtgggcgccggcaactgccagacc
agcgtgatcacccaggcctgccccaaggtgagcttcgagcccatccccatccactactgcccccc
gccggcttcgccatcctgaagtgcaacgacaagaagttcaacggcagcggccctgcaccaacgtg
agcaccgtgcagtgcacccacggcatccgcccgtggtgagcacccagctgctgctgaacggcagc
ctggccgaggagggcgtggtgatccgcagcgagaacttcaccgacaacgccaagaccatcatcgtg
cagctgaaggagagcgtggagatcaactgcacccgccccaacaacaacacccgcaagagcatcacc
atcggccccggccgcgccttctacgccaccggcgacatcatcggcgacatccgccaggccactgc
aacatcagcggcgagaagtggaacaacaccctgaagcagatcgtgaccaagctgcaggcccagttc
ggcaacaagaccatcgtgttcaagcagagcagcggcggcgaccccgagatcgtgatgcacagcttc
aactgcggcggcgagttcttctactgcaacagcacccagctgttcaacagcacctggaacaacacc
atcggccccaacaacaccaacggcaccatcaccctgccctgccgcatcaagcagatcatcaaccgc
tggcaggaggtgggcaaggccatgtacgcccccccatccgcggccagatccgctgcagcagcaac
atcaccggcctgctgctgacccgcgacggcggcaaggagatcagcaacaccaccgagatcttccgc
cccggcggcggcgacatgcgcgacaactggcgcagcgagctgtacaagtacaaggtggtgaagatc
gagcccctgggcgtggcccccaccaaggccatcagcagcgtggtgcagagcgagaagagcgccgtg
accctgggcgccatgttcctgggcttcctgggcgccgccggcagcaccatgggcgcccgcagcctg
accctgaccgtgcaggcccgccagctgctgagcggcatcgtgcagcagcagaacaacctgctgcgc
gccatcgaggcccagcagcacctgctgcagctgaccgtgtggggcatcaagcagctgcaggcccgc
gtgctggccgtggagcgctacctgaaggaccagcagctgctgggcatctggggctgcagcggcaag
ctgatctgcaccaccgccgtgccctggaacgccagctggagcaacaagagcctggaccagatctgg
aacaacatgacctggatggagtgggagcgcgagatcgacaactacaccaacctgatctacaccctg
atcgaggagagccagaaccagcaggagaagaacgagcaggagctgctggagctggacaagtgggcc
agcctgtggaactggttcgacatcagcaagtggctgtggtacatctaactcgag
```

FIG. 31

(SEQ ID NO:44)

gp140.mut8.modSF162 gaattcgccaccatggatgcaatgaagagagggctctgctgtgtgctgctgctgtgtggagcagtc
ttcgtttcgcccagcgccgtggagaagctgtgggtgaccgtgtactacggcgtgcccgtgtggaag
gaggccaccaccaccctgttctgcgccagcgacgccaaggcctacgacaccgaggtgcacaacgtg
tgggccacccacgcctgcgtgcccaccgaccccaaccccaggagatcgtgctggagaacgtgacc
gagaacttcaacatgtggaagaacaacatggtggagcagatgcacgaggacatcatcagcctgtgg
gaccagagcctgaagccctgcgtgaagctgaccccctgtgcgtgaccctgcactgcaccaacctg
aagaacgccaccaacaccaagagcagcaactggaaggagatggaccgcggcgagatcaagaactgc
agcttcaaggtgaccaccagcatccgcaacaagatgcagaaggagtacgccctgttctacaagctg
gacgtggtgcccatcgacaacgacaacaccagctacaagctgatcaactgcaacaccagcgtgatc
acccaggcctgccccaaggtgagcttcgagcccatccccatccactactgcgccccgccggcttc
gccatcctgaagtgcaacgacaagaagttcaacggcagcggccctgcaccaacgtgagcaccgtg
cagtgcacccacggcatccgccccgtggtgagcacccagctgctgctgaacggcagcctggccgag
gagggcgtggtgatccgcagcgagaacttcaccgacaacgccaagaccatcatcgtgcagctgaag
gagagcgtggagatcaactgcacccgccccaacaacaacacccgcaagagcatcaccatcggcccc
ggccgcgccttctacgccaccggcgacatcatcggcgacatccgccaggccactgcaacatcagc
ggcgagaagtggaacaacaccctgaagcagatcgtgaccaagctgcaggcccagttcggcaacaag
accatcgtgttcaagcagagcagcggcggcgaccccgagatcgtgatgcacagcttcaactgcggc
ggcgagttcttctactgcaacagcacccagctgttcaacagcacctggaacaacaccatcggcccc
aacaacaccaacggcaccatcaccctgccctgccgcatcaagcagatcatcaaccgctggcaggag
gtgggcaaggccatgtacgcccccccatccgcggccagatccgctgcagcagcaacatcaccggc
ctgctgctgacccgcgacggcggcaaggagatcagcaacaccaccgagatcttccgccccggcggc
ggcgacatgcgcgacaactggcgcagcgagctgtacaagtacaaggtggtgaagatcgagcccctg
ggcgtggcccccaccatcgccatcagcagcgtggtgcagagcgagaagagcgccgtgaccctgggc
gccatgttcctgggcttcctgggcgccgccggcagcaccatgggcgcccgcagcctgaccctgacc
gtgcaggcccgccagctgctgagcggcatcgtgcagcagcagaacaacctgctgcgcgccatcgag
gccagcagcacctgctgcagctgaccgtgtggggcatcaagcagctgcaggcccgcgtgctggcc
gtggagcgctacctgaaggaccagcagctgctgggcatctggggctgcagcggcaagctgatctgc
accaccgccgtgccctggaacgccagctggagcaacaagagcctggaccagatctggaacaacatg
acctggatggagtgggagcgcgagatcgacaactacaccaacctgatctacaccctgatcgaggag
agccagaaccagcaggagaagaacgagcaggagctgctggagctggacaagtgggccagcctgtgg
aactggttcgacatcagcaagtggctgtggtacatctaactcgag

FIG. 32
(SEQ ID NO:45)

gp140.mut8.modSF162.delV2

```
gaattcgccaccatggatgcaatgaagagagggctctgctgtgtgctgctgctgtgtggagcagtc
ttcgtttcgcccagcgccgtggagaagctgtgggtgaccgtgtactacggcgtgcccgtgtggaag
gaggccaccaccaccctgttctgcgccagcgacgccaaggcctacgacaccgaggtgcacaacgtg
tgggccacccacgcctgcgtgcccaccgaccccaaccccaggagatcgtgctggagaacgtgacc
gagaacttcaacatgtggaagaacaacatggtggagcagatgcacgaggacatcatcagcctgtgg
gaccagagcctgaagccctgcgtgaagctgaccccctgtgcgtgacctgcactgcaccaacctg
aagaacgccaccaacaccaagagcagcaactggaaggagatggaccgcggcgagatcaagaactgc
agcttcaaggtgggcgccggcaagctgatcaactgcaacaccagcgtgatcacccaggcctgcccc
aaggtgagcttcgagcccatccccatccactactgcgcccctgccggcttcgccatcctgaagtgc
aacgacaagaagttcaacggcagcggccctgcaccaacgtgagcaccgtgcagtgcacccacggc
atccgccccgtggtgagcacccagctgctgctgaacggcagcctggccgaggagggcgtggtgatc
cgcagcgagaacttcaccgacaacgccaagaccatcatcgtgcagctgaaggagagcgtggagatc
aactgcacccgccccaacaacaacaccegcaagagcataccatcggccccggccgcgccttctac
gccaccggcgacatcatcggcgacatccgccaggccactgcaacatcagcggcgagaagtggaac
aacaccctgaagcagatcgtgaccaagctgcaggcccagttcggcaacaagaccatcgtgttcaag
cagagcagcggcggcgaccccgagatcgtgatgcacagcttcaactgcggcggcgagttcttctac
tgcaacagcacccagctgttcaacagcacctggaacaacaccatcggccccaacaacaccaacggc
accatcaccctgccctgccgcatcaagcagatcatcaaccgctggcaggaggtgggcaaggccatg
tacgcccccccatccgcggccagatccgctgcagcagcaacatcaccggcctgctgctgacccgc
gacggcggcaaggagatcagcaacaccaccgagatcttccgccccggcggcggcgacatgcgcgac
aactggcgcagcgagctgtacaagtacaaggtggtgaagatcgagcccctgggcgtggcccccacc
atcgccatcagcagcgtggtgcagagcgagaagagcgccgtgaccctgggcgccatgttcctgggc
ttcctgggcgccgccggcagcaccatgggcgcccgcagcctgaccctgaccgtgcaggcccgccag
ctgctgagcggcatcgtgcagcagcagaacaacctgctgcgcgccatcgaggcccagcagcacctg
ctgcagctgaccgtgtggggcatcaagcagctgcaggcccgcgtgctggccgtggagcgctacctg
aaggaccagcagctgctgggcatctggggctgcagcggcaagctgatctgcaccaccgccgtgccc
tggaacgccagctggagcaacaagagcctggaccagatctggaacaacatgacctggatggagtgg
gagcgcgagatcgacaactacaccaacctgatctacaccctgatcgaggagagccagaaccagcag
gagaagaacgagcaggagctgctggagctggacaagtgggccagcctgtggaactggttcgacatc
agcaagtggctgtggtacatctaactcgag
```

FIG. 33

(SEQ ID NO:46)

gp140.mut8.modSF162.delV1V2

```
gaattcgccaccatggatgcaatgaagagagggctctgctgtgtgctgctgctgtgtggagcagtc
ttcgtttcgcccagcgccgtggagaagctgtgggtgaccgtgtactacggcgtgcccgtgtggaag
gaggccaccaccaccctgttctgcgccagcgacgccaaggcctacgacaccgaggtgcacaacgtg
tgggccacccacgcctgcgtgcccaccgaccccaaccccaggagatcgtgctggagaacgtgacc
gagaacttcaacatgtggaagaacaacatggtggagcagatgcacgaggacatcatcagcctgtgg
gaccagagcctgaagccctgcgtgaagctgacccccctgtgcgtgggcgccggcaactgccagacc
agcgtgatcacccaggcctgccccaaggtgagcttcgagcccatccccatccactactgcgccccc
gccggcttcgccatcctgaagtgcaacgacaagaagttcaacggcagcggccctgcaccaacgtg
agcaccgtgcagtgcacccacggcatccgcccgtggtgagcacccagctgctgctgaacggcagc
ctggccgaggagggcgtggtgatccgcagcgagaacttcaccgacaacgccaagaccatcatcgtg
cagctgaaggagagcgtggagatcaactgcacccgccccaacaacaacacccgcaagagcatcacc
atcggccccggccgcgccttctacgccaccggcgacatcatcggcgacatccgccaggcccactgc
aacatcagcggcgagaagtggaacaacacccctgaagcagatcgtgaccaagctgcaggcccagttc
ggcaacaagaccatcgtgttcaagcagagcagcggcggcgaccccgagatcgtgatgcacagcttc
aactgcggcggcgagttcttctactgcaacagcacccagctgttcaacagcacctggaacaacacc
atcggccccaacaacaccaacggcaccatcaccctgccctgccgcatcaagcagatcatcaaccgc
tggcaggaggtgggcaaggccatgtacgccccccccatccgcggccagatccgctgcagcagcaac
atcaccggcctgctgctgacccgcgacggcggcaaggagatcagcaacaccaccgagatcttccgc
cccggcggcggcgacatgcgcgacaactggcgcagcgagctgtacaagtacaaggtggtgaagatc
gagccctgggcgtggcccccaccatcgccatcagcagcgtggtgcagagcgagaagagcgccgtg
accctgggcgccatgttcctgggcttcctgggcgccgccggcagcaccatgggcgcccgcagcctg
accctgaccgtgcaggcccgccagctgctgagcggcatcgtgcagcagcagaacaacctgctgcgc
gccatcgaggcccagcagcacctgctgcagctgaccgtgtggggcatcaagcagctgcaggcccgc
gtgctggccgtggagcgctacctgaaggaccagcagctgctgggcatctggggctgcagcggcaag
ctgatctgcaccaccgccgtgccctggaacgccagctggagcaacaagagcctggaccagatctgg
aacaacatgacctggatggagtgggagcgcgagatcgacaactacaccaacctgatctacaccctg
atcgaggagagccagaaccagcaggagaagaacgagcaggagctgctggagctggacaagtgggcc
agcctgtggaactggttcgacatcagcaagtggctgtggtacatctaactcgag
```

FIG. 34

(SEQ ID NO:47)

gp160.modSF162 gaattcgccaccatggatgcaatgaagagagggctctgctgtgtgctgctgctgtgtggagcagtc
ttcgtttcgcccagcgccgtggagaagctgtgggtgaccgtgtactacggcgtgcccgtgtggaag
gaggccaccaccaccctgttctgcgccagcgacgccaaggcctacgacaccgaggtgcacaacgtg
tgggccacccacgcctgcgtgcccaccgaccccaaccccaggagatcgtgctggagaacgtgacc
gagaacttcaacatgtggaagaacaacatggtggagcagatgcacgaggacatcatcagcctgtgg
gaccagagcctgaagccctgcgtgaagctgacccccctgtgcgtgaccctgcactgcaccaacctg
aagaacgccaccaacaccaagagcagcaactggaaggagatggaccgcggcgagatcaagaactgc
agcttcaaggtgaccaccagcatccgcaacaagatgcagaaggagtacgccctgttctacaagctg
gacgtggtgcccatcgacaacgacaacaccagctacaagctgatcaactgcaacaccagcgtgatc
acccaggcctgccccaaggtgagcttcgagcccatccccatccactactgcgcccccgccggcttc
gccatcctgaagtgcaacgacaagaagttcaacggcagcggcccctgcaccaacgtgagcaccgtg
cagtgcacccacggcatccgccccgtggtgagcacccagctgctgctgaacggcagcctggccgag
gagggcgtggtgatccgcagcgagaacttcaccgacaacgccaagaccatcatcgtgcagctgaag
gagagcgtggagatcaactgcacccgccccaacaacaacacccgcaagagcatcaccatcggcccc
ggccgcgccttctacgccaccggcgacatcatcggcgacatccgccaggcccactgcaacatcagc
ggcgagaagtggaacaacaccctgaagcagatcgtgaccaagctgcaggcccagttcggcaacaag
accatcgtgttcaagcagagcagcggcggcgaccccgagatcgtgatgcacagcttcaactgcggc
ggcgagttcttctactgcaacagcacccagctgttcaacagcacctggaacaacaccatcggcccc
aacaacaccaacggcaccatcaccctgccctgccgcatcaagcagatcatcaaccgctggcaggag
gtgggcaaggccatgtacgccccccccatccgcggccagatccgctgcagcagcaacatcaccggc
ctgctgctgacccgcgacggcggcaaggagatcagcaacaccaccgagatcttccgccccggcggc
ggcgacatgcgcgacaactggcgcagcgagctgtacaagtacaaggtggtgaagatcgagcccctg
ggcgtggcccccaccaaggccaagcgccgcgtggtgcagcgcgagaagcgcgccgtgaccctgggc
gccatgttcctgggcttcctgggcgccgccggcagcaccatgggcgcccgcagcctgacccctgacc
gtgcaggcccgccagctgctgagcggcatcgtgcagcagcagaacaacctgctgcgcgccatcgag
gcccagcagcacctgctgcagctgaccgtgtggggcatcaagcagctgcaggcccgcgtgctggcc
gtggagcgctacctgaaggaccagcagctgctgggcatctggggctgcagcggcaagctgatctgc
accaccgccgtgccctggaacgccagctggagcaacaagagcctggaccagatctggaacaacatg
acctggatggagtgggagcgcgagatcgacaactacaccaacctgatctacaccctgatcgaggag
agccagaaccagcaggagaagaacgagcaggagctgctggagctggacaagtgggccagcctgtgg
aactggttcgacatcagcaagtggctgtggtacatcaagatcttcatcatgatcgtgggcggcctg
gtgggcctgcgcatcgtgttcaccgtgctgagcatcgtgaaccgcgtgcgccagggctacagcccc
ctgagcttccagacccgcttccccgcccccgcggccccgaccgccccgagggcatcgaggaggag
ggcggcgagcgcgaccgcgaccgcagcagccccctggtgcacggcctgctggccctgatctgggac
gacctgcgcagcctgtgcctgttcagctaccaccgcctgcgcgacctgatcctgatcgccgcccgc
atcgtggagctgctgggccgccgcggctgggaggccctgaagtactggggcaacctgctgcagtac
tggatccaggagctgaagaacagcgccgtgagcctgttcgacgccatcgccatcgccgtggccgag
ggcaccgaccgcatcatcgaggtgcccagcgcatcggccgcgccttcctgcacatccccgccgc
atccgccagggcttcgagcgcgccctgctgtaactcgag

FIG. 35
(SEQ ID NO:48)

gp160.modSF162.delV2 gaattcgccaccatggatgcaatgaagagagggctctgctgtgtgctgctgctgtgtggagcagtc
ttcgtttcgcccagcgccgtggagaagctgtgggtgaccgtgtactacggcgtgcccgtgtggaag
gaggccaccaccaccctgttctgcgccagcgacgccaaggcctacgacaccgaggtgcacaacgtg
tgggccacccacgcctgcgtgcccaccgaccccaaccccaggagatcgtgctggagaacgtgacc
gagaacttcaacatgtggaagaacaacatggtggagcagatgcacgaggacatcatcagcctgtgg
gaccagagcctgaagccctgcgtgaagctgaccccctgtgcgtgaccctgcactgcaccaacctg
aagaacgccaccaacaccaagagcagcaactggaaggagatggaccgcggcgagatcaagaactgc
agcttcaaggtgggcgccggcaagctgatcaactgcaacaccagcgtgatcacccaggcctgcccc
aaggtgagcttcgagcccatccccatccactactgcgccccgccggcttcgccatcctgaagtgc
aacgacaagaagttcaacggcagcggccctgcaccaacgtgagcaccgtgcagtgcacccacggc
atccgccccgtggtgagcacccagctgctgctgaacggcagcctggccgaggagggcgtggtgatc
cgcagcgagaacttcaccgacaacgccaagaccatcatcgtgcagctgaaggagagcgtggagatc
aactgcacccgccccaacaacaacacccgcaagagcatcaccatcggccccggccgcgccttctac
gccaccggcgacatcatcggcgacatccgccaggccactgcaacatcagcggcgagaagtggaac
aacaccctgaagcagatcgtgaccaagctgcaggccagttcggcaacaagaccatcgtgttcaag
cagagcagcggcggcgaccccgagatcgtgatgcacagcttcaactgcggcggcgagttcttctac
tgcaacagcacccagctgttcaacagcacctggaacaacaccatcggccccaacaacaccaacggc
accatcaccctgccctgccgcatcaagcagatcatcaaccgctggcaggaggtgggcaaggccatg
tacgccccccccatccgcggccagatccgctgcagcagcaacatcaccggcctgctgctgacccgc
gacggcggcaaggagatcagcaacaccaccgagatcttccgccccggcggcggcgacatgcgcgac
aactggcgcagcgagctgtacaagtacaaggtggtgaagatcgagcccctgggcgtggcccccacc
aaggccaagcgccgcgtggtgcagcgcgagaagcgcgccgtgaccctgggcgccatgttcctgggc
ttcctgggcgccgccggcagcaccatgggcgcccgcagcctgaccctgaccgtgcaggcccgccag
ctgctgagcggcatcgtgcagcagcagaacaacctgctgcgcgccatcgaggcccagcagcacctg
ctgcagctgaccgtgtggggcatcaagcagctgcaggcccgcgtgctggccgtggagcgctacctg
aaggaccagcagctgctgggcatctggggctgcagcggcaagctgatctgcaccaccgccgtgccc
tggaacgccagctggagcaacaagagcctggaccagatctggaacaacatgacctggatggagtgg
gagcgcgagatcgacaactacaccaacctgatctacaccctgatcgaggagagccagaaccagcag
gagaagaacgagcaggagctgctggagctggacaagtgggccagcctgtggaactggttcgacatc
agcaagtggctgtggtacatcaagatcttcatcatgatcgtgggcggcctggtgggcctgcgcatc
gtgttcaccgtgctgagcatcgtgaaccgcgtgcgccagggctacagccccctgagcttccagacc
cgcttccccgccccgcggccccgaccgccccgagggcatcgaggaggagggcggcgagcgcgac
cgcgaccgcagcagccccctggtgcacggcctgctggccctgatctgggacgacctgcgcagcctg
tgcctgttcagctaccaccgcctgcgcgacctgatcctgatcgccgcccgcatcgtggagctgctg
ggccgccgcggctgggaggccctgaagtactggggcaacctgctgcagtactggatccaggagctg
aagaacagcgccgtgagcctgttcgacgccatcgccatcgccgtggccgagggcaccgaccgcatc
atcgaggtggcccagcgcatcggccgcgccttcctgcacatccccgccgcatccgccagggcttc
gagcgcgccctgctgtaactcgag

FIG. 36
(SEQ ID NO:49)

gp160.modSF162.delV1V2

```
gaattcgccaccatggatgcaatgaagagagggctctgctgtgtgctgctgctgtgtggagcagtc
ttcgtttcgcccagcgccgtggagaagctgtgggtgaccgtgtactacggcgtgcccgtgtggaag
gaggccaccaccaccctgttctgcgccagcgacgccaaggcctacgacaccgaggtgcacaacgtg
tgggccacccacgcctgcgtgcccaccgaccccaaccccaggagatcgtgctggagaacgtgacc
gagaacttcaacatgtggaagaacaacatggtggagcagatgcacgaggacatcatcagcctgtgg
gaccagagcctgaagccctgcgtgaagctgaccccctgtgcgtgggcgccggcaactgccagacc
agcgtgatcacccaggcctgccccaaggtgagcttcgagcccatccccatccactactgcccccc
gccggcttcgccatcctgaagtgcaacgacaagaagttcaacggcagcggccctgcaccaacgtg
agcaccgtgcagtgcacccacggcatccgcccgtggtgagcacccagctgctgctgaacggcagc
ctggccgaggagggcgtggtgatccgcagcgagaacttcaccgacaacgccaagaccatcatcgtg
cagctgaaggagagcgtggagatcaactgcacccgccccaacaacaacacccgcaagagcatcacc
atcggccccggccgcgccttctacgccaccggcgacatcatcggcgacatccgccaggccactgc
aacatcagcggcgagaagtggaacaacaccctgaagcagatcgtgaccaagctgcaggcccagttc
ggcaacaagaccatcgtgttcaagcagagcagcggcggcgaccccgagatcgtgatgcacagcttc
aactgcggcggcgagttcttctactgcaacagcacccagctgttcaacagcacctggaacaacacc
atcggccccaacaacaccaacggcaccatcaccctgccctgccgcatcaagcagatcatcaaccgc
tggcaggaggtgggcaaggccatgtacgcccccccatccgcggccagatccgctgcagcagcaac
atcaccggcctgctgctgacccgcgacggcggcaaggagatcagcaacaccaccgagatcttccgc
cccggcggcggcgacatgcgcgacaactggcgcagcgagctgtacaagtacaaggtggtgaagatc
gagcccctgggcgtggcccccaccaaggccaagcgccgcgtggtgcagcgcgagaagcgcgccgtg
accctgggcgccatgttcctgggcttcctgggcgccgccggcagcaccatgggcgcccgcagcctg
accctgaccgtgcaggccgccagctgctgagcggcatcgtgcagcagcagaacaacctgctgcgc
gccatcgaggcccagcagcacctgctgcagctgaccgtgtggggcatcaagcagctgcaggcccgc
gtgctggccgtggagcgctacctgaaggaccagcagctgctgggcatctggggctgcagcggcaag
ctgatctgcaccaccgccgtgccctggaacgccagctggagcaacaagagcctggaccagatctgg
aacaacatgacctggatggagtgggagcgcgagatcgacaactacaccaacctgatctacaccctg
atcgaggagagccagaaccagcaggagaagaacgagcaggagctgctggagctggacaagtgggcc
agcctgtggaactggttcgacatcagcaagtggctgtggtacatcaagatcttcatcatgatcgtg
ggcggcctggtgggcctgcgcatcgtgttcaccgtgctgagcatcgtgaaccgcgtgcgccagggc
tacagccccctgagcttccagacccgcttccccgcccccgcggccccgaccgccccgagggcatc
gaggaggagggcggcgagcgcgaccgcgaccgcagcagccccctggtgcacggcctgctggccctg
atctgggacgacctgcgcagcctgtgcctgttcagctaccaccgcctgcgcgacctgatcctgatc
gccgcccgcatcgtggagctgctgggccgccgcggctggaggccctgaagtactggggcaacctg
ctgcagtactggatccaggagctgaagaacagcgccgtgagcctgttcgacgccatcgccatcgcc
gtggccgagggcaccgaccgcatcatcgaggtggcccagcgcatcggccgcgccttcctgcacatc
ccccgccgcatccgccagggcttcgagcgcgccctgctgtaactcgag
```

FIG. 37

(SEQ ID NO:50)

gp120wtUS4

ACAACAGTCTTGTGGGTCACAGTCTATTATGGGGTACCTGTGTGGAAAGAAG
CAACCACCACTCTGTTTTGTGCATCAGATGCTAAAGCATACAAAGCAGAGGC
ACATAACGTCTGGGCTACACATGCCTGTGTACCCACAGACCCCAACCCACAG
GAAGTAAATTTAACAAATGTGACAGAAAATTTTAACATGTGGAAAAATAACA
TGGTGGAACAGATGCATGAGGATATAATCAGTTTATGGATCAAAGCCTAAA
GCCATGTGTAAAATTAACCCCACTCTGTGTTACTTTAAATTGTACTGATAAGT
TGACAGGTAGTACTAATGGCACAAATAGTACTAGTGGCACTAATAGTACTAG
TGGCACTAATAGTACTAGTACTAATAGTACTGATAGTTGGGAAAAGATGCCA
GAAGGAGAAATAAAAAACTGCTCTTTCAATATCACCACAAGTGTAAGAGATA
AAGTGCAGAAAGAATATTCTCTCTTCTATAAACTTGATGTAGTACCAATAGAT
AATGATAATGCTAGCTATAGATTGATAAATTGTAATACCTCAGTCATTACACA
AGCCTGTCCAAAGGTATCTTTTGAACCAATTCCCATACATTATTGTGCCCCGG
CTGGTTTTGCGATTCTAAAGTGTAAAGATAAGAAGTTCAATGGAACAGGACC
ATGTAAAAATGTCAGCACAGTACAATGCACACATGGAATTAGACCAGTAGTA
TCAACTCAACTGCTGTTAAATGGCAGTCTAGCAGAAGAAGAGATAGTACTTA
GATCTGAAAATTTCACAGACAATGCTAAAACCATAATAGTACAGCTGAATGA
ATCTGTAGAAATTAATTGTATAAGACCCAACAATAATACAAGAAAAGTATA
CATATAGGACCAGGGAGAGCATTTATGCAACAGGTGATATAATAGGAGACA
TAAGACAAGCACATTGTAACATTAGTAAAGCAAACTGGACTAACACTTTAGA
ACAGATAGTTGAAAAATTAAGAGAACAATTTGGGAATAATAAAACAATAATC
TTTAATTCATCCTCAGGAGGGGACCCAGAAATTGTATTTCACAGTTTTAATTG
TGGAGGGGAATTTTTCTATTGTAATACATCACAACTATTTAATAGTACCTGGA
ATATTACTGAAGAGGTAAATAAGACTAAAGAAAATGACACTATCATACTCCC
ATGCAGAATAAGACAAATTATAAACATGTGGCAAGAAGTAGGAAAAGCAAT
GTATGCCCCTCCCATCAGAGGACAAATTAAATGTTCATCAAATATTACAGGG
CTGCTATTAACTAGAGATGGTGGTACTAACAATAATAGGACGAACGACACCG
AGACCTTCAGACCTGGGGGAGGAAACATGAAGGACAATTGGAGAAGTGAAT
TATATAAATATAAAGTAGTAAGAATTGAACCATTAGGAGTAGCACCCACCCA
GGCAAAGAGAAGAGTGGTGCAAAGAGAGAAAGA

FIG. 38
(SEQ ID NO:51)

gp140wtUS4

ACAACAGTCTTGTGGGTCACAGTCTATTATGGGGTACCTGTGTGGAAAGAAG
CAACCACCACTCTGTTTTGTGCATCAGATGCTAAAGCATACAAAGCAGAGGC
ACATAACGTCTGGGCTACACATGCCTGTGTACCCACAGACCCCAACCCACAG
GAAGTAAATTTAACAAATGTGACAGAAAATTTTAACATGTGGAAAAATAACA
TGGTGGAACAGATGCATGAGGATATAATCAGTTTATGGATCAAAGCCTAAA
GCCATGTGTAAAATTAACCCCACTCTGTGTTACTTTAAATTGTACTGATAAGT
TGACAGGTAGTACTAATGGCACAAATAGTACTAGTGGCACTAATAGTACTAG
TGGCACTAATAGTACTAGTACTAATAGTACTGATAGTTGGGAAAAGATGCCA
GAAGGAGAAATAAAAAACTGCTCTTTCAATATCACCACAAGTGTAAGAGATA
AAGTGCAGAAAGAATATTCTCTCTTCTATAAACTTGATGTAGTACCAATAGAT
AATGATAATGCTAGCTATAGATTGATAAATTGTAATACCTCAGTCATTACACA
AGCCTGTCCAAAGGTATCTTTTGAACCAATTCCCATACATTATTGTGCCCCGG
CTGGTTTTGCGATTCTAAAGTGTAAAGATAAGAAGTTCAATGGAACAGGACC
ATGTAAAAATGTCAGCACAGTACAATGCACACATGGAATTAGACCAGTAGTA
TCAACTCAACTGCTGTTAAATGGCAGTCTAGCAGAAGAAGAGATAGTACTTA
GATCTGAAAATTTCACAGACAATGCTAAAACCATAATAGTACAGCTGAATGA
ATCTGTAGAAATTAATTGTATAAGACCCAACAATAATACAAGAAAAGTATA
CATATAGGACCAGGGAGAGCATTTTATGCAACAGGTGATATAATAGGAGACA
TAAGACAAGCACATTGTAACATTAGTAAAGCAAACTGGACTAACACTTTAGA
ACAGATAGTTGAAAAATTAAGAGAACAATTTGGGAATAATAAACAATAATC
TTTAATTCATCCTCAGGAGGGGACCCAGAAATTGTATTTCACAGTTTTAATTG
TGGAGGGGAATTTTTCTATTGTAATACATCACAACTATTTAATAGTACCTGGA
ATATTACTGAAGAGGTAAATAAGACTAAAGAAAATGACACTATCATACTCCC
ATGCAGAATAAGACAAATTATAAACATGTGGCAAGAAGTAGGAAAAGCAAT
GTATGCCCCTCCCATCAGAGGACAAATTAAATGTTCATCAAATATTACAGGG
CTGCTATTAACTAGAGATGGTGGTACTAACAATAATAGGACGAACGACACCG
AGACCTTCAGACCTGGGGGAGGAAACATGAAGGACAATTGGAGAAGTGAAT
TATATAAATATAAAGTAGTAAGAATTGAACCATTAGGAGTAGCACCCACCCA
GGCAAAGAGAAGAGTGGTGCAAAGAGAGAAAGAGCAGTGGGACTAGGAG
CTTTGTTCATTGGGTTCTTGGGAGCAGCAGGAAGCACTATGGGCGCAGCGTC
AGTGACGCTGACGGTACAGGCCAGACAATTATTGTCTGGTATAGTGCAACAG
CAGAACAATTTGCTGAGAGCTATTGAGGCGCAACAGCATCTGTTGCAACTCA
CGGTCTGGGGCATCAAACAGCTCCAGGCAAGAATCCTGGCTGTGGAAAGATA
CCTAAAGGATCAACAGCTCCTAGGGATTTGGGGTTGCTCTGGAAAACTCATTT
GCACCACTACTGTGCCTTGGAACTCTAGTTGGAGTAATAAATCTCTGACTGAG
ATTTGGGATAATATGACCTGGATGGAGTGGGAAGAGAAATTGGCAATTATA
CAGGCTTAATATACAATTTAATTGAAATAGCACAAAACCAGCAAGAAAAGAA
TGAACAAGAATTATTGGAATTAGACAAGTGGGCAAGTTTGTGGAATTGGTTT
GATATAACAAACTGGCTGTGGTATATA

FIG. 39
(SEQ ID NO:52)

gp160wtUS4

ACAACAGTCTTGTGGGTCACAGTCTATTATGGGGTACCTGTGTGGAAAGAAG
CAACCACCACTCTGTTTTGTGCATCAGATGCTAAAGCATACAAAGCAGAGGC
ACATAACGTCTGGGCTACACATGCCTGTGTACCCACAGACCCCAACCCACAG
GAAGTAAATTTAACAAATGTGACAGAAAATTTTAACATGTGGAAAAATAACA
TGGTGGAACAGATGCATGAGGATATAATCAGTTTATGGATCAAAGCCTAAA
GCCATGTGTAAAATTAACCCCACTCTGTGTTACTTTAAATTGTACTGATAAGT
TGACAGGTAGTACTAATGGCACAAATAGTACTAGTGGCACTAATAGTACTAG
TGGCACTAATAGTACTAGTACTAATAGTACTGATAGTTGGGAAAAGATGCCA
GAAGGAGAAATAAAAAACTGCTCTTTCAATATCACCACAAGTGTAAGAGATA
AAGTGCAGAAAGAATATTCTCTCTTCTATAAACTTGATGTAGTACCAATAGAT
AATGATAATGCTAGCTATAGATTGATAAATTGTAATACCTCAGTCATTACACA
AGCCTGTCCAAAGGTATCTTTTGAACCAATTCCCATACATTATTGTGCCCCGG
CTGGTTTTGCGATTCTAAAGTGTAAAGATAAGAAGTTCAATGGAACAGGACC
ATGTAAAAATGTCAGCACAGTACAATGCACACATGGAATTAGACCAGTAGTA
TCAACTCAACTGCTGTTAAATGGCAGTCTAGCAGAAGAAGAGATAGTACTTA
GATCTGAAAATTTCACAGACAATGCTAAAACCATAATAGTACAGCTGAATGA
ATCTGTAGAAATTAATTGTATAAGACCCAACAATAATACAAGAAAAGTATA
CATATAGGACCAGGGAGAGCATTTTATGCAACAGGTGATATAATAGGAGACA
TAAGACAAGCACATTGTAACATTAGTAAAGCAAACTGGACTAACACTTTAGA
ACAGATAGTTGAAAAATTAAGAGAACAATTTGGGAATAATAAAACAATAATC
TTTAATTCATCCTCAGGAGGGGACCCAGAAATTGTATTTCACAGTTTTAATTG
TGGAGGGGAATTTTTCTATTGTAATACATCACAACTATTTAATAGTACCTGGA
ATATTACTGAAGAGGTAAATAAGACTAAAGAAAATGACACTATCATACTCCC
ATGCAGAATAAGACAAATTATAAACATGTGGCAAGAAGTAGGAAAAGCAAT
GTATGCCCCTCCCATCAGAGGACAAATTAAATGTTCATCAAATATTACAGGG
CTGCTATTAACTAGAGATGGTGGTACTAACAATAATAGGACGAACGACACCG
AGACCTTCAGACCTGGGGGAGGAAACATGAAGGACAATTGGAGAAGTGAAT
TATATAAATATAAAGTAGTAAGAATTGAACCATTAGGAGTAGCACCCACCCA
GGCAAAGAGAAGAGTGGTGCAAAGAGAGAAAAGAGCAGTGGGACTAGGAG
CTTTGTTCATTGGGTTCTTGGGAGCAGCAGGAAGCACTATGGGCGCAGCGTC
AGTGACGCTGACGGTACAGGCCAGACAATTATTGTCTGGTATAGTGCAACAG
CAGAACAATTTGCTGAGAGCTATTGAGGCGCAACAGCATCTGTTGCAACTCA
CGGTCTGGGGCATCAAACAGCTCCAGGCAAGAATCCTGGCTGTGGAAAGATA
CCTAAAGGATCAACAGCTCCTAGGGATTTGGGGTTGCTCTGGAAAACTCATTT
GCACCACTACTGTGCCTTGGAACTCTAGTTGGAGTAATAAATCTCTGACTGAG
ATTTGGGATAATATGACCTGGATGGAGTGGGAAAGAGAAATTGGCAATTATA
CAGGCTTAATATACAATTTAATTGAAATAGCACAAAACCAGCAAGAAAAGAA
TGAACAAGAATTATTGGAATTAGACAAGTGGGCAAGTTTGTGGAATTGGTTT
GATATAACAAACTGGCTGTGGTATATAAGAATATTCATAATGATAGTAGGAG
GCTTGATAGGTTTAAGAATAGTTTTGCTGTACTTTCTATAGTGAATAGAGTT
AGGCAGGGATACTCACCAATATCATTGCAGACCCGCCTCCCAGCTCAGAGGG

FIG. 40A
(SEQ ID NO:53)

```
GACCCGACAGGCCCGAAGGAATCGAAGAAGAAGGTGGAGAGAGAGACAGA
GACAGATCCAATCGATTAGTGCATGGATTATTGGCACTCATCTGGGACGATCT
GCGGAGCCTGTGCCTCTTCAGCTACCACCGCTTGAGAGACTTACTCTTGATTG
TAGCGAGGATTGTGGAACTTCTGGGACGCAGGGGGTGGGAAGCCCTCAAGTA
TTGGTGGAATCTCCTGCAGTATTGGAGTCAGGAGCTAAAGAGTAGTGCTGTT
AGTTTGTTTAATGCCACAGCAATAGCAGTAGCTGAAGGGACAGATAGGATTA
TAGAAATAGTACAAAGAATTTTTAGAGCTGTAATTCACATACCTAGAAGAAT
AAGACAGGGCTTGGAGAGGGCTTTACTATAA
```

FIG. 40B
(SEQ ID NO:53)

gp120.modUS4

GAATTCGCCACCATGGATGCAATGAAGAGAGGGCTCTGCTGTG gp120.mod.US4.del128-194

GAATTCGCCACCATGGATGCAATGAAGAGAGGGCTCTGCTGTGTGCTGCTGCTGTGTGG
AGCAGTCTTCGTTTCGCCCAGCGCCACCACCGTGCTGTGGGTGACCGTGTACTACGGCG
TGCCCGTGTGGAAGGAGGCCACCACCACCCTGTTCTGCGCCAGCGACGCCAAGGCTTAC
AAGGCCGAGGCCCACAACGTGTGGGCCACCCACGCCTGCGTGCCCACCGACCCCAACCC
CCAGGAGGTGAACCTGACCAACGTGACCGAGAACTTCAACATGTGGAAGAACAACATGG
TGGAGCAGATGCATGAGGACATCATCAGCCTGTGGGACCAGAGCCTGAAGCCCTGCGTG
AAGCTGACCCCCCTGTGCGTGGGGGCAGGGAACTGCGAGACCAGCGTGATCACCCAGGC
CTGCCCCAAGGTGAGCTTCGAGCCCATCCCCATCCACTACTGCGCCCCCGCCGGCTTCG
CCATCCTGAAGTGCAAGGACAAGAAGTTCAACGGCACCGGCCCCTGCAAGAACGTGAGC
ACCGTGCAGTGCACCCACGGCATCCGCCCCGTGGTGAGCACCCAGCTGCTGCTGAACGG
CAGCCTGGCCGAGGAGGAGATCGTGCTGCGCTCCGAGAACTTCACCGACAACGCCAAGA
CCATCATCGTGCAGCTGAACGAGTCCGTGGAGATCAACTGCATCCGCCCCAACAACAAC
ACGCGTAAGAGCATCCACATCGGCCCCGGCCGCGCCTTCTACGCCACCGGCGACATCAT
CGGCGACATCCGCCAGGCCCACTGCAACATCAGCAAGGCCAACTGGACCAACACCCTCG
AGCAGATCGTGGAGAAGCTGCGCGAGCAGTTCGGCAACAACAAGACCATCATCTTCAAC
AGCAGCAGCGGCGGCGACCCCGAGATCGTGTTCCACAGCTTCAACTGCGGCGGCGAGTT
CTTCTACTGCAACACCAGCCAGCTGTTCAACAGCACCTGGAACATCACCGAGGAGGTGA
ACAAGACCAAGGAGAACGACACCATCATCCTGCCCTGCCGCATCCGCCAGATCATCAAC
ATGTGGCAGGAGGTGGGCAAGGCCATGTACGCCCCCCCCATCCGCGGCCAGATCAAGTG
CAGCAGCAATATTACCGGCCTGCTGCTGACCCGCGACGGCGGCACCAACAACAACCGCA
CCAACGACACCGAGACCTTCCGCCCCGGCGGCGGCAACATGAAGGACAACTGGCGCAGC
GAGCTGTACAAGTACAAGGTGGTGCGCATCGAGCCCCTGGGCGTGGCCCCCACCCAGGC
CAAGCGCCGCGTGGTGCAGCGCGAGAAGCGCTAAGATATCGGATCCTCTAGA

FIG. 42

(SEQ ID NO:55)

gp140.modUS4

GAATTCGCCACCATGGATGCAATGAAGAGAGGGCTCTGCTGTGTGCTGCTGCTGTGTGGAGCA
GTCTTCGTTTCGCCCAGCGCCACCACCGTGCTGTGGGTGACCGTGTACTACGGCGTGCCCGTG
TGGAAGGAGGCCACCACCACCCTGTTCTGCGCCAGCGACGCCAAGGCTTACAAGGCCGAGGC
CCACAACGTGTGGGCCACCCACGCCTGCGTGCCCACCGACCCCAACCCCCAGGAGGTGAACC
TGACCAACGTGACCGAGAACTTCAACATGTGGAAGAACAACATGGTGGAGCAGATGCATGAG
GACATCATCAGCCTGTGGGACCAGAGCCTGAAGCCCTGCGTGAAGCTGACCCCCCTGTGCGTG
ACCCTGAACTGCACCGACAAGCTGACCGGCAGCACCAACGGCACCAACAGCACCAGCGGCAC
CAACAGCACCAGCGGCACCAACAGCACCAGCACCAACAGCACCGACAGCTGGGAGAAGATG
CCCGAGGGCGAGATCAAGAACTGCAGCTTCAACATCACCACCAGCGTGCGCGACAAGGTGCA
GAAGGAGTACAGCCTGTTCTACAAGCTGGACGTGGTGCCCATCGACAACGACAACGCCAGCT
ACCGCCTGATCAACTGCAACACCAGCGTGATCACCCAGGCCTGCCCCAAGGTGAGCTTCGAGC
CCATCCCCATCCACTACTGCGCCCCCGCCGGCTTCGCCATCCTGAAGTGCAAGGACAAGAAGT
TCAACGGCACCGGCCCCTGCAAGAACGTGAGCACCGTGCAGTGCACCCACGGCATCCGCCCC
GTGGTGAGCACCCAGCTGCTGCTGAACGGCAGCCTGGCCGAGGAGGAGATCGTGCTGCGCTC
CGAGAACTTCACCGACAACGCCAAGACCATCATCGTGCAGCTGAACGAGTCCGTGGAGATCA
ACTGCATCCGCCCCAACAACAACACGCGTAAGAGCATCCACATCGGCCCCGGCCGCGCCTTCT
ACGCCACCGGCGACATCATCGGCGACATCCGCCAGGCCCACTGCAACATCAGCAAGGCCAAC
TGGACCAACACCCTCGAGCAGATCGTGGAGAAGCTGCGCGAGCAGTTCGGCAACAACAAGAC
CATCATCTTCAACAGCAGCAGCGGCGGCGACCCCGAGATCGTGTTCCACAGCTTCAACTGCGG
CGGCGAGTTCTTCTACTGCAACACCAGCCAGCTGTTCAACAGCACCTGGAACATCACCGAGGA
GGTGAACAAGACCAAGGAGAACGACACCATCATCCTGCCCTGCCGCATCCGCCAGATCATCA
ACATGTGGCAGGAGGTGGGCAAGGCCATGTACGCCCCCCCCATCCGCGGCCAGATCAAGTGC
AGCAGCAATATTACCGGCCTGCTGCTGACCCGCGACGGCGGCACCAACAACAACCGCACCAA
CGACACCGAGACCTTCCGCCCCGGCGGCGGCAACATGAAGGACAACTGGCGCAGCGAGCTGT
ACAAGTACAAGGTGGTGCGCATCGAGCCCCTGGGCGTGGCCCCCACCCAGGCCAAGCGCCGC
GTGGTGCAGCGCGAGAAGCGCGCCGTGGGCCTGGGCGCCCTGTTCATCGGCTTCCTGGGCGCC
GCCGGGAGCACCATGGGCGCCGCCTCCGTGACCCTGACCGTGCAGGCCCGCCAGCTGCTGAG
CGGCATCGTGCAGCAGCAGAACAACCTGCTGCGCGCCATCGAGGCCCAGCAGCACCTGCTGC
AGCTGACCGTGTGGGGCATCAAGCAGCTGCAGGCCCGCATCCTGGCCGTGGAGCGCTACCTG
AAGGACCAGCAGCTGCTGGGCATCTGGGGCTGCAGCGGCAAGCTGATCTGCACCACCACCGT
GCCCTGGAACAGCAGCTGGAGCAACAAGAGCCTGACCGAGATCTGGGACAACATGACCTGGA
TGGAGTGGGAGCGCGAGATCGGCAACTACACCGGCCTGATCTACAACCTGATCGAGATCGCC
CAGAACCAGCAGGAGAAGAACGAGCAGGAGCTGCTGGAGCTGGACAAGTGGGCCAGCCTGT
GGAACTGGTTCGACATCACCAACTGGCTGTGGTACATCTAAGATATCGGATCCTCTAGA

FIG. 43
(SEQ ID NO:56)

gp140.mut.modUS4

GAATTCGCCACCATGGATGCAATGAAGAGAGGGCTCTGCTGT gp140.TM.modUS4

GAATTCGCCACCATGGATGCAATGAAGAGAGGGCTCTGCTGTGTGCTGCTGCTGTGTGGAGCA
GTCTTCGTTTCGCCCAGCGCCACCACCGTGCTGTGGGTGACCGTGTACTACGGCGTGCCCGTG
TGGAAGGAGGCCACCACCACCCTGTTCTGCGCCAGCGACGCCAAGGCTTACAAGGCCGAGGC
CCACAACGTGTGGGCCACCCACGCCTGCGTGCCCACCGACCCCAACCCCCAGGAGGTGAACC
TGACCAACGTGACCGAGAACTTCAACATGTGGAAGAACAACATGGTGGAGCAGATGCATGAG
GACATCATCAGCCTGTGGGACCAGAGCCTGAAGCCCTGCGTGAAGCTGACCCCCTGTGCGTG
ACCCTGAACTGCACCGACAAGCTGACCGGCAGCACCAACGGCACCAACAGCACCAGCGGCAC
CAACAGCACCAGCGGCACCAACAGCACCAGCACCAACAGCACCGACAGCTGGGAGAAGATG
CCCGAGGGCGAGATCAAGAACTGCAGCTTCAACATCACCACCAGCGTGCGCGACAAGGTGCA
GAAGGAGTACAGCCTGTTCTACAAGCTGGACGTGGTGCCCATCGACAACGACAACGCCAGCT
ACCGCCTGATCAACTGCAACACCAGCGTGATCACCCAGGCCTGCCCCAAGGTGAGCTTCGAGC
CCATCCCCATCCACTACTGCGCCCCCGCCGGCTTCGCCATCCTGAAGTGCAAGGACAAGAAGT
TCAACGGCACCGGCCCCTGCAAGAACGTGAGCACCGTGCAGTGCACCCACGGCATCCGCCCC
GTGGTGAGCACCCAGCTGCTGCTGAACGGCAGCCTGGCCGAGGAGGAGATCGTGCTGCGCTC
CGAGAACTTCACCGACAACGCCAAGACCATCATCGTGCAGCTGAACGAGTCCGTGGAGATCA
ACTGCATCCGCCCCAACAACAACACGCGTAAGAGCATCCACATCGGCCCCGGCCGCGCCTTCT
ACGCCACCGGCGACATCATCGGCGACATCCGCCAGGCCCACTGCAACATCAGCAAGGCCAAC
TGGACCAACACCCTCGAGCAGATCGTGGAGAAGCTGCGCGAGCAGTTCGGCAACAACAAGAC
CATCATCTTCAACAGCAGCAGCGGCGGCGACCCCGAGATCGTGTTCCACAGCTTCAACTGCGG
CGGCGAGTTCTTCTACTGCAACACCAGCCAGCTGTTCAACAGCACCTGGAACATCACCGAGGA
GGTGAACAAGACCAAGGAGAACGACACCATCATCCTGCCCTGCCGCATCCGCCAGATCATCA
ACATGTGGCAGGAGGTGGGCAAGGCCATGTACGCCCCCCCCATCCGCGGCCAGATCAAGTGC
AGCAGCAATATTACCGGCCTGCTGCTGACCCGCGACGGCGGCACCAACAACAACCGCACCAA
CGACACCGAGACCTTCCGCCCCGGCGGCGGCAACATGAAGGACAACTGGCGCAGCGAGCTGT
ACAAGTACAAGGTGGTGCGCATCGAGCCCCTGGGCGTGGCCCCCACCCAGGCCAAGCGCCGC
GTGGTGCAGCGCGAGAAGCGCGCCGTGGGCCTGGGCGCCCTGTTCATCGGCTTCCTGGGCGCC
GCCGGGAGCACCATGGGCGCCGCCTCCGTGACCCTGACCGTGCAGGCCCGCCAGCTGCTGAG
CGGCATCGTGCAGCAGCAGAACAACCTGCTGCGCGCCATCGAGGCCCAGCAGCACCTGCTGC
AGCTGACCGTGTGGGGCATCAAGCAGCTGCAGGCCCGCATCCTGGCCGTGGAGCGCTACCTG
AAGGACCAGCAGCTGCTGGGCATCTGGGGCTGCAGCGGCAAGCTGATCTGCACCACCACCGT
GCCCTGGAACAGCAGCTGGAGCAACAAGAGCCTGACCGAGATCTGGGACAACATGACCTGGA
TGGAGTGGGAGCGCGAGATCGGCAACTACACCGGCCTGATCTACAACCTGATCGAGATCGCC
CAGAACCAGCAGGAGAAGAACGAGCAGGAGCTGCTGGAGCTGGACAAGTGGGCCAGCCTGT
GGAACTGGTTCGACATCACCAACTGGCTGTGGTACATCCGCATCTTCATCATGATCGTGGGCG
GCCTGATCGGCCTGCGCATCGTGTTCGCCGTGCTGAGCATCGTGTAAGATATCGGATCCTCTA
GA

FIG. 45
(SEQ ID NO:58)

Gp140modUS4.DV1V2

```
GAATTCGCCACCATGGATGCAATGAAGAGAGGGCTCTGCTGTGTGCTGCTGC
TGTGTGGAGCAGTCTTCGTTTCGCCCAGCGCCACCACCGTGCTGTGGGTGACC
GTGTACTACGGCGTGCCCGTGTGGAAGGAGGCCACCACCACCCTGTTCTGCG
CCAGCGACGCCAAGGCTTACAAGGCCGAGGCCCACAACGTGTGGGCCACCCA
CGCCTGCGTGCCCACCGACCCCAACCCCCAGGAGGTGAACCTGACCAACGTG
ACCGAGAACTTCAACATGTGGAAGAACAACATGGTGGAGCAGATGCATGAG
GACATCATCAGCCTGTGGGACCAGAGCCTGAAGCCCTGCGTGGGCGCCGGCC
AGGCCTGCCCCAAGGTGAGCTTCGAGCCCATCCCCATCCACTACTGCGCCCC
CGCCGGCTTCGCCATCCTGAAGTGCAAGGACAAGAAGTTCAACGGCACCGGC
CCCTGCAAGAACGTGAGCACCGTGCAGTGCACCCACGGCATCCGCCCCGTGG
TGAGCACCCAGCTGCTGCTGAACGGCAGCCTGGCCGAGGAGGAGATCGTGCT
GCGCTCCGAGAACTTCACCGACAACGCCAAGACCATCATCGTGCAGCTGAAC
GAGTCCGTGGAGATCAACTGCATCCGCCCCAACAACAACACGCGTAAGAGCA
TCCACATCGGCCCCGGCCGCGCCTTCTACGCCACCGGCGACATCATCGGCGA
CATCCGCCAGGCCCACTGCAACATCAGCAAGGCCAACTGGACCAACACCCTC
GAGCAGATCGTGGAGAAGCTGCGCGAGCAGTTCGGCAACAACAAGACCATC
ATCTTCAACAGCAGCAGCGGCGGCGACCCCGAGATCGTGTTCCACAGCTTCA
ACTGCGGCGGCGAGTTCTTCTACTGCAACACCAGCCAGCTGTTCAACAGCAC
CTGGAACATCACCGAGGAGGTGAACAAGACCAAGGAGAACGACACCATCAT
CCTGCCCTGCCGCATCCGCCAGATCATCAACATGTGGCAGGAGGTGGGCAAG
GCCATGTACGCCCCCCCCATCCGCGGCCAGATCAAGTGCAGCAGCAATATTA
CCGGCCTGCTGCTGACCCGCGACGGCGGCACCAACAACAACCGCACCAACGA
CACCGAGACCTTCCGCCCCGGCGGCGGCAACATGAAGGACAACTGGCGCAGC
GAGCTGTACAAGTACAAGGTGGTGCGCATCGAGCCCCTGGGCGTGGCCCCCA
CCCAGGCCAAGCGCCGCGTGGTGCAGCGCGAGAAGCGCGCCGTGGGCCTGG
GCGCCCTGTTCATCGGCTTCCTGGGCGCCGCCGGGAGCACCATGGGCGCCGC
CTCCGTGACCCTGACCGTGCAGGCCCGCCAGCTGCTGAGCGGCATCGTGCAG
CAGCAGAACAACCTGCTGCGCGCCATCGAGGCCCAGCAGCACCTGCTGCAGC
TGACCGTGTGGGGCATCAAGCAGCTGCAGGCCCGCATCCTGGCCGTGGAGCG
CTACCTGAAGGACCAGCAGCTGCTGGGCATCTGGGGCTGCAGCGGCAAGCTG
ATCTGCACCACCACCGTGCCCTGGAACAGCAGCTGGAGCAACAAGAGCCTGA
CCGAGATCTGGGACAACATGACCTGGATGGAGTGGGAGCGCGAGATCGGCA
ACTACACCGGCCTGATCTACAACCTGATCGAGATCGCCCAGAACCAGCAGGA
GAAGAACGAGCAGGAGCTGCTGGAGCTGGACAAGTGGGCCAGCCTGTGGAA
CTGGTTCGACATCACCAACTGGCTGTGGTACATCTAAGATATCGGATCCTCTA
GA
```

FIG. 46

(SEQ ID NO:59)

Gp140modUS4.DV2

GAATTCGCCACCATGGATGCAATGAAGAGAGGGCTCTGCTGTGTGCTGCTGC
TGTGTGGAGCAGTCTTCGTTTCGCCCAGCGCCACCACCGTGCTGTGGGTGACC
GTGTACTACGGCGTGCCCGTGTGGAAGGAGGCCACCACCACCCTGTTCTGCG
CCAGCGACGCCAAGGCTTACAAGGCCGAGGCCCACAACGTGTGGGCCACCCA
CGCCTGCGTGCCCACCGACCCCAACCCCCAGGAGGTGAACCTGACCAACGTG
ACCGAGAACTTCAACATGTGGAAGAACAACATGGTGGAGCAGATGCATGAG
GACATCATCAGCCTGTGGGACCAGAGCCTGAAGCCCTGCGTGAAGCTGACCC
CCCTGTGCGTGACCCTGAACTGCACCGACAAGCTGACCGGCAGCACCAACGG
CACCAACAGCACCAGCGGCACCAACAGCACCAGCGGCACCAACAGCACCAG
CACCAACAGCACCGACAGCTGGGAGAAGATGCCCGAGGGCGAGATCAAGAA
CTGCAGCTTCAACATCGGCGCCGGCCGCCTGATCAACTGCAACACCAGCGTG
ATCACCCAGGCCTGCCCCAAGGTGAGCTTCGAGCCCATCCCCATCCACTACT
GCGCCCCCGCCGGCTTCGCCATCCTGAAGTGCAAGGACAAGAAGTTCAACGG
CACCGGCCCCTGCAAGAACGTGAGCACCGTGCAGTGCACCCACGGCATCCGC
CCCGTGGTGAGCACCCAGCTGCTGCTGAACGGCAGCCTGGCCGAGGAGGAGA
TCGTGCTGCGCTCCGAGAACTTCACCGACAACGCCAAGACCATCATCGTGCA
GCTGAACGAGTCCGTGGAGATCAACTGCATCCGCCCCAACAACAACACGCGT
AAGAGCATCCACATCGGCCCCGGCCGCGCCTTCTACGCCACCGGCGACATCA
TCGGCGACATCCGCCAGGCCCACTGCAACATCAGCAAGGCCAACTGGACCAA
CACCCTCGAGCAGATCGTGGAGAAGCTGCGCGAGCAGTTCGGCAACAACAA
GACCATCATCTTCAACAGCAGCAGCGGCGGCGACCCCGAGATCGTGTTCCAC
AGCTTCAACTGCGGCGGCGAGTTCTTCTACTGCAACACCAGCCAGCTGTTCAA
CAGCACCTGGAACATCACCGAGGAGGTGAACAAGACCAAGGAGAACGACAC
CATCATCCTGCCCTGCCGCATCCGCCAGATCATCAACATGTGGCAGGAGGTG
GGCAAGGCCATGTACGCCCCCCCCATCCGCGGCCAGATCAAGTGCAGCAGCA
ATATTACCGGCCTGCTGCTGACCCGCGACGGCGGCACCAACAACAACCGCAC
CAACGACACCGAGACCTTCCGCCCCGGCGGCGGCAACATGAAGGACAACTG
GCGCAGCGAGCTGTACAAGTACAAGGTGGTGCGCATCGAGCCCCTGGGCGTG
GCCCCCACCCAGGCCAAGCGCCGCGTGGTGCAGCGCGAGAAGCGCGCCGTG
GGCCTGGGCGCCCTGTTCATCGGCTTCCTGGGCGCCGCCGGGAGCACCATGG
GCGCCGCCTCCGTGACCCTGACCGTGCAGGCCCGCCAGCTGCTGAGCGGCAT
CGTGCAGCAGCAGAACAACCTGCTGCGCGCCATCGAGGCCCAGCAGCACCTG
CTGCAGCTGACCGTGTGGGGCATCAAGCAGCTGCAGGCCCGCATCCTGGCCG
TGGAGCGCTACCTGAAGGACCAGCAGCTGCTGGGCATCTGGGGCTGCAGCGG
CAAGCTGATCTGCACCACCACCGTGCCCTGGAACAGCAGCTGGAGCAACAAG
AGCCTGACCGAGATCTGGGACAACATGACCTGGATGGAGTGGGAGCGCGAG
ATCGGCAACTACACCGGCCTGATCTACAACCTGATCGAGATCGCCCAGAACC
AGCAGGAGAAGAACGAGCAGGAGCTGCTGGAGCTGGACAAGTGGGCCAGCC
TGTGGAACTGGTTCGACATCACCAACTGGCTGTGGTACATCTAAGATATCGG
ATCCTCTAGA

FIG. 47
(SEQ ID NO:60)

Gp140modmutUS4.DV1V2

GAATTCGCCACCATGGATGCAATGAAGAGAGGGCTCTGCTGTGTGCTGCTGC
TGTGTGGAGCAGTCTTCGTTTCGCCCAGCGCCACCACCGTGCTGTGGGTGACC
GTGTACTACGGCGTGCCCGTGTGGAAGGAGGCCACCACCACCCTGTTCTGCG
CCAGCGACGCCAAGGCTTACAAGGCCGAGGCCCACAACGTGTGGGCCACCC
ACGCCTGCGTGCCCACCGACCCCAACCCCCAGGAGGTGAACCTGACCAACGT
GACCGAGAACTTCAACATGTGGAAGAACAACATGGTGGAGCAGATGCATGA
GGACATCATCAGCCTGTGGGACCAGAGCCTGAAGCCCTGCGTGGGCGCCGGC
CAGGCCTGCCCCAAGGTGAGCTTCGAGCCCATCCCCATCCACTACTGCGCCC
CCGCCGGCTTCGCCATCCTGAAGTGCAAGGACAAGAAGTTCAACGGCACCGG
CCCCTGCAAGAACGTGAGCACCGTGCAGTGCACCCACGGCATCCGCCCCGTG
GTGAGCACCCAGCTGCTGCTGAACGGCAGCCTGGCCGAGGAGGAGATCGTGC
TGCGCTCCGAGAACTTCACCGACAACGCCAAGACCATCATCGTGCAGCTGAA
CGAGTCCGTGGAGATCAACTGCATCCGCCCCAACAACAACACGCGTAAGAGC
ATCCACATCGGCCCCGGCCGCGCCTTCTACGCCACCGGCGACATCATCGGCG
ACATCCGCCAGGCCCACTGCAACATCAGCAAGGCCAACTGGACCAACACCCT
CGAGCAGATCGTGGAGAAGCTGCGCGAGCAGTTCGGCAACAACAAGACCAT
CATCTTCAACAGCAGCAGCGGCGGCGACCCCGAGATCGTGTTCCACAGCTTC
AACTGCGGCGGCGAGTTCTTCTACTGCAACACCAGCCAGCTGTTCAACAGCA
CCTGGAACATCACCGAGGAGGTGAACAAGACCAAGGAGAACGACACCATCA
TCCTGCCCTGCCGCATCGCCAGATCATCAACATGTGGCAGGAGGTGGGCAA
GGCCATGTACGCCCCCCCCATCCGCGGCCAGATCAAGTGCAGCAGCAATATT
ACCGGCCTGCTGCTGACCCGCGACGGCGGCACCAACAACAACCGCACCAACG
ACACCGAGACCTTCCGCCCCGGCGGCGGCAACATGAAGGACAACTGGCGCA
GCGAGCTGTACAAGTACAAGGTGGTGCGCATCGAGCCCCTGGGCGTGGCCCC
CACCCAGGCCAAGCGCCGCGTGGTGCAGCGCGAGAAGAGCGCCGTGGGCCT
GGGCGCCCTGTTCATCGGCTTCCTGGGCGCCGCCGGGAGCACCATGGGCGCC
GCCTCCGTGACCCTGACCGTGCAGGCCCGCCAGCTGCTGAGCGGCATCGTGC
AGCAGCAGAACAACCTGCTGCGCGCCATCGAGGCCCAGCAGCACCTGCTGCA
GCTGACCGTGTGGGGCATCAAGCAGCTGCAGGCCCGCATCCTGGCCGTGGAG
CGCTACCTGAAGGACCAGCAGCTGCTGGGCATCTGGGGCTGCAGCGGCAAGC
TGATCTGCACCACCACCGTGCCCTGGAACAGCAGCTGGAGCAACAAGAGCCT
GACCGAGATCTGGGACAACATGACCTGGATGGAGTGGGAGCGCGAGATCGG
CAACTACACCGGCCTGATCTACAACCTGATCGAGATCGCCCAGAACCAGCAG
GAGAAGAACGAGCAGGAGCTGCTGGAGCTGGACAAGTGGGCCAGCCTGTGG
AACTGGTTCGACATCACCAACTGGCTGTGGTACATCTAAGATATCGGATCCTC
TAGA

FIG. 48

(SEQ ID NO:61)

gp140.mod.US4.del128-194

GAATTCGCCACCATGGATGCAATGAAGAGAGGGCTCTGCTGTGTGCTGCTGCTGTGTGG
AGCAGTCTTCGTTTCGCCCAGCGCCACCACCGTGCTGTGGGTGACCGTGTACTACGGCG
TGCCCGTGTGGAAGGAGGCCACCACCACCCTGTTCTGCGCCAGCGACGCCAAGGCTTAC
AAGGCCGAGGCCCACAACGTGTGGGCCACCCACGCCTGCGTGCCCACCGACCCCAACCC
CCAGGAGGTGAACCTGACCAACGTGACCGAGAACTTCAACATGTGGAAGAACAACATGG
TGGAGCAGATGCATGAGGACATCATCAGCCTGTGGGACCAGAGCCTGAAGCCCTGCGTG
AAGCTGACCCCCTGTGCGTGGGGCAGGGAACTGCGAGACCAGCGTGATCACCCAGGC
CTGCCCCAAGGTGAGCTTCGAGCCCATCCCCATCCACTACTGCGCCCCGCCGGCTTCG
CCATCCTGAAGTGCAAGGACAAGAAGTTCAACGGCACCGGCCCTGCAAGAACGTGAGC
ACCGTGCAGTGCACCCACGGCATCCGCCCCGTGGTGAGCACCCAGCTGCTGCTGAACGG
CAGCCTGGCCGAGGAGGAGATCGTGCTGCGCTCCGAGAACTTCACCGACAACGCCAAGA
CCATCATCGTGCAGCTGAACGAGTCCGTGGAGATCAACTGCATCCGCCCCAACAACAAC
ACGCGTAAGAGCATCCACATCGGCCCCGGCCGCGCCTTCTACGCCACCGGCGACATCAT
CGGCGACATCCGCCAGGCCCACTGCAACATCAGCAAGGCCAACTGGACCAACACCCTCG
AGCAGATCGTGGAGAAGCTGCGCGAGCAGTTCGGCAACAACAAGACCATCATCTTCAAC
AGCAGCAGCGGCGGCGACCCCGAGATCGTGTTCCACAGCTTCAACTGCGGCGGCGAGTT
CTTCTACTGCAACACCAGCCAGCTGTTCAACAGCACCTGGAACATCACCGAGGAGGTGA
ACAAGACCAAGGAGAACGACACCATCATCCTGCCCTGCCGCATCCGCCAGATCATCAAC
ATGTGGCAGGAGGTGGGCAAGGCCATGTACGCCCCCCCCATCCGCGGCCAGATCAAGTG
CAGCAGCAATATTACCGGCCTGCTGCTGACCCGCGACGGCGGCACCAACAACAACCGCA
CCAACGACACCGAGACCTTCCGCCCCGGCGGCGGCAACATGAAGGACAACTGGCGCAGC
GAGCTGTACAAGTACAAGGTGGTGCGCATCGAGCCCCTGGGCGTGGCCCCCACCCAGGC
CAAGCGCCGCGTGGTGCAGCGCGAGAAGCGCGCCGTGGGCCTGGGCGCCCTGTTCATCG
GCTTCCTGGGCGCCGCCGGGAGCACCATGGGCGCCGCCTCCGTGACCCTGACCGTGCAG
GCCCGCCAGCTGCTGAGCGGCATCGTGCAGCAGCAGAACAACCTGCTGCGCGCCATCGA
GGCCCAGCAGCACCTGCTGCAGCTGACCGTGTGGGGCATCAAGCAGCTGCAGGCCCGCA
TCCTGGCCGTGGAGCGCTACCTGAAGGACCAGCAGCTGCTGGGCATCTGGGGCTGCAGC
GGCAAGCTGATCTGCACCACCACCGTGCCCTGGAACAGCAGCTGGAGCAACAAGAGCCT
GACCGAGATCTGGGACAACATGACCTGGATGGAGTGGGAGCGCGAGATCGGCAACTACA
CCGGCCTGATCTACAACCTGATCGAGATCGCCCAGAACCAGCAGGAGAAGAACGAGCAG
GAGCTGCTGGAGCTGGACAAGTGGGCCAGCCTGTGGAACTGGTTCGACATCACCAACTG
GCTGTGGTACATCTAAGATATCGGATCCTCTAGA

FIG. 49
(SEQ ID NO:62)

gp140.mut.mod.US4.del128-194

```
GAATTCGCCACCATGGATGCAATGAAGAGAG gp160.modUS4

GAATTCGCCACCATGGATGCAATGAAGAGAGGGCTCTGCTGTGTGCTGCTGCTGTGTGGAGCA
GTCTTCGTTTCGCCCAGCGCCACCACCGTGCTGTGGGTGACCGTGTACTACGGCGTGCCCGTG
TGGAAGGAGGCCACCACCACCCTGTTCTGCGCCAGCGACGCCAAGGCTTACAAGGCCGAGGC
CCACAACGTGTGGGCCACCCACGCCTGCGTGCCCACCGACCCCAACCCCCAGGAGGTGAACC
TGACCAACGTGACCGAGAACTTCAACATGTGGAAGAACAACATGGTGGAGCAGATGCATGAG
GACATCATCAGCCTGTGGGACCAGAGCCTGAAGCCCTGCGTGAAGCTGACCCCCCTGTGCGTG
ACCCTGAACTGCACCGACAAGCTGACCGGCAGCACCAACGGCACCAACAGCACCAGCGGCAC
CAACAGCACCAGCGGCACCAACAGCACCAGCACCAACAGCACCGACAGCTGGGAGAAGATG
CCCGAGGGCGAGATCAAGAACTGCAGCTTCAACATCACCACCAGCGTGCGCGACAAGGTGCA
GAAGGAGTACAGCCTGTTCTACAAGCTGGACGTGGTGCCCATCGACAACGACAACGCCAGCT
ACCGCCTGATCAACTGCAACACCAGCGTGATCACCCAGGCCTGCCCCAAGGTGAGCTTCGAGC
CCATCCCCATCCACTACTGCGCCCCCGCCGGCTTCGCCATCCTGAAGTGCAAGGACAAGAAGT
TCAACGGCACCGGCCCCTGCAAGAACGTGAGCACCGTGCAGTGCACCCACGGCATCCGCCCC
GTGGTGAGCACCCAGCTGCTGCTGAACGGCAGCCTGGCCGAGGAGGAGATCGTGCTGCGCTC
CGAGAACTTCACCGACAACGCCAAGACCATCATCGTGCAGCTGAACGAGTCCGTGGAGATCA
ACTGCATCCGCCCCAACAACAACACGCGTAAGAGCATCCACATCGGCCCCGGCCGCGCCTTCT
ACGCCACCGGCGACATCATCGGCGACATCCGCCAGGCCCACTGCAACATCAGCAAGGCCAAC
TGGACCAACACCCTCGAGCAGATCGTGGAGAAGCTGCGCGAGCAGTTCGGCAACAACAAGAC
CATCATCTTCAACAGCAGCAGCGGCGGCGACCCCGAGATCGTGTTCCACAGCTTCAACTGCGG
CGGCGAGTTCTTCTACTGCAACACCAGCCAGCTGTTCAACAGCACCTGGAACATCACCGAGGA
GGTGAACAAGACCAAGGAGAACGACACCATCATCCTGCCCTGCCGCATCCGCCAGATCATCA
ACATGTGGCAGGAGGTGGGCAAGGCCATGTACGCCCCCCCCATCCGCGGCCAGATCAAGTGC
AGCAGCAATATTACCGGCCTGCTGCTGACCCGCGACGGCGGCACCAACAACAACCGCACCAA
CGACACCGAGACCTTCCGCCCCGGCGGCGGCAACATGAAGGACAACTGGCGCAGCGAGCTGT
ACAAGTACAAGGTGGTGCGCATCGAGCCCCTGGGCGTGGCCCCCACCCAGGCCAAGCGCCGC
GTGGTGCAGCGCGAGAAGCGCGCCGTGGGCCTGGGCGCCCTGTTCATCGGCTTCCTGGGCGCC
GCCGGGAGCACCATGGGCGCCGCCTCCGTGACCCTGACCGTGCAGGCCCGCCAGCTGCTGAG
CGGCATCGTGCAGCAGCAGAACAACCTGCTGCGCGCCATCGAGGCCCAGCAGCACCTGCTGC
AGCTGACCGTGTGGGGCATCAAGCAGCTGCAGGCCCGCATCCTGGCCGTGGAGCGCTACCTG
AAGGACCAGCAGCTGCTGGGCATCTGGGGCTGCAGCGGCAAGCTGATCTGCACCACCACCGT
GCCCTGGAACAGCAGCTGGAGCAACAAGAGCCTGACCGAGATCTGGGACAACATGACCTGGA
TGGAGTGGGAGCGCGAGATCGGCAACTACACCGGCCTGATCTACAACCTGATCGAGATCGCC
CAGAACCAGCAGGAGAAGAACGAGCAGGAGCTGCTGGAGCTGGACAAGTGGGCCAGCCTGT
GGAACTGGTTCGACATCACCAACTGGCTGTGGTACATCCGCATCTTCATCATGATCGTGGGCG
GCCTGATCGGCCTGCGCATCGTGTTCGCCGTGCTGAGCATCGTGAACCGCGTGCGCCAGGGCT
ACAGCCCCATCAGCCTGCAGACCCGCCTGCCCGCCCAGCGCGGCCCCGACCGCCCCGAGGGC
ATCGAGGAGGAGGGCGGCGAGCGCGACCGCGACCGCAGCAACCGCCTGGTGCACGGCCTGCT
GGCCCTGATCTGGGACGACCTGCGCAGCCTGTGCCTGTTCAGCTACCACCGCCTGCGCGACCT
GCTGCTGATCGTGGCCCGCATCGTGGAGCTGCTGGGCCGCCGCGGCTGGGAGGCCCTGAAGT
ACTGGTGGAACCTGCTGCAGTACTGGAGCCAGGAGCTGAAGAGCAGCGCCGTGAGCCTGTTC
AACGCCACCGCCATCGCCGTGGCCGAGGGCACCGACCGCATCATCGAGATCGTGCAGCGCAT
CTTCCGCGCCGTGATCCACATCCCCCGCCGCATCCGCCAGGGCCTGGAGCGCGCCCTGCTGTA
AGATATCGGATCCTCTAGA

FIG. 51
(SEQ ID NO:64)

gp160.modUS4.delV1

GAATTCGCCACCATGGATGCAATGAAGAGAGGGCTCTGCTGTGTGCTGCTGCTGTGTGGAGCA
GTCTTCGTTTCGCCCAGCGCCACCACCGTGCTGTGGGTGACCGTGTACTACGGCGTGCCCGTG
TGGAAGGAGGCCACCACCACCCTGTTCTGCGCCAGCGACGCCAAGGCTTACAAGGCCGAGGC
CCACAACGTGTGGGCCACCCACGCCTGCGTGCCCACCGACCCCAACCCCCAGGAGGTGAACC
TGACCAACGTGACCGAGAACTTCAACATGTGGAAGAACAACATGGTGGAGCAGATGCATGAG
GACATCATCAGCCTGTGGGACCAGAGCCTGAAGCCCTGCGTGAAGCTGACCCCCCTGTGCGTG
ACCCTGAACTGCACCGACAAGCTGGGCGCCGGCGGCGAGATCAAGAACTGCAGCTTCAACAT
CACCACCAGCGTGCGCGACAAGGTGCAGAAGGAGTACAGCCTGTTCTACAAGCTGGACGTGG
TGCCCATCGACAACGACAACGCCAGCTACCGCCTGATCAACTGCAACACCAGCGTGATCACCC
AGGCCTGCCCCAAGGTGAGCTTCGAGCCCATCCCCATCCACTACTGCGCCCCCGCCGGCTTCG
CCATCCTGAAGTGCAAGGACAAGAAGTTCAACGGCACCGGCCCCTGCAAGAACGTGAGCACC
GTGCAGTGCACCCACGGCATCCGCCCCGTGGTGAGCACCCAGCTGCTGCTGAACGGCAGCCTG
GCCGAGGAGGAGATCGTGCTGCGCTCCGAGAACTTCACCGACAACGCCAAGACCATCATCGT
GCAGCTGAACGAGTCCGTGGAGATCAACTGCATCCGCCCCAACAACAACACGCGTAAGAGCA
TCCACATCGGCCCCGGCCGCGCCTTCTACGCCACCGGCGACATCATCGGCGACATCCGCCAGG
CCCACTGCAACATCAGCAAGGCCAACTGGACCAACACCCTCGAGCAGATCGTGGAGAAGCTG
CGCGAGCAGTTCGGCAACAACAAGACCATCATCTTCAACAGCAGCAGCGGCGGCGACCCCGA
GATCGTGTTCCACAGCTTCAACTGCGGCGGCGAGTTCTTCTACTGCAACACCAGCCAGCTGTT
CAACAGCACCTGGAACATCACCGAGGAGGTGAACAAGACCAAGGAGAACGACACCATCATCC
TGCCCTGCCGCATCCGCCAGATCATCAACATGTGGCAGGAGGTGGGCAAGGCCATGTACGCC
CCCCCCATCCGCGGCCAGATCAAGTGCAGCAGCAATATTACCGGCCTGCTGCTGACCCGCGAC
GGCGGCACCAACAACAACCGCACCAACGACACCGAGACCTTCCGCCCCGGCGGCGGCAACAT
GAAGGACAACTGGCGCAGCGAGCTGTACAAGTACAAGGTGGTGCGCATCGAGCCCCTGGGCG
TGGCCCCCACCCAGGCCAAGCGCCGCGTGGTGCAGCGCGAGAAGCGCGCCGTGGGCCTGGGC
GCCCTGTTCATCGGCTTCCTGGGCGCCGCCGGGAGCACCATGGGCGCCGCCTCCGTGACCCTG
ACCGTGCAGGCCCGCCAGCTGCTGAGCGGCATCGTGCAGCAGCAGAACAACCTGCTGCGCGC
CATCGAGGCCCAGCAGCACCTGCTGCAGCTGACCGTGTGGGGCATCAAGCAGCTGCAGGCCC
GCATCCTGGCCGTGGAGCGCTACCTGAAGGACCAGCAGCTGCTGGGCATCTGGGGCTGCAGC
GGCAAGCTGATCTGCACCACCACCGTGCCCTGGAACAGCAGCTGGAGCAACAAGAGCCTGAC
CGAGATCTGGGACAACATGACCTGGATGGAGTGGGAGCGCGAGATCGGCAACTACACCGGCC
TGATCTACAACCTGATCGAGATCGCCCAGAACCAGCAGGAGAAGAACGAGCAGGAGCTGCTG
GAGCTGGACAAGTGGGCCAGCCTGTGGAACTGGTTCGACATCACCAACTGGCTGTGGTACATC
CGCATCTTCATCATGATCGTGGGCGGCCTGATCGGCCTGCGCATCGTGTTCGCCGTGCTGAGC
ATCGTGAACCGCGTGCGCCAGGGCTACAGCCCCATCAGCCTGCAGACCCGCCTGCCCGCCCAG
CGCGGCCCCGACCGCCCCGAGGGCATCGAGGAGGAGGGCGGCGAGCGCGACCGCGACCGCA
GCAACCGCCTGGTGCACGGCCTGCTGGCCCTGATCTGGGACGACCTGCGCAGCCTGTGCCTGT
TCAGCTACCACCGCCTGCGCGACCTGCTGCTGATCGTGGCCCGCATCGTGGAGCTGCTGGGCC
GCCGCGGCTGGGAGGCCCTGAAGTACTGGTGGAACCTGCTGCAGTACTGGAGCCAGGAGCTG
AAGAGCAGCGCCGTGAGCCTGTTCAACGCCACCGCCATCGCCGTGGCCGAGGGCACCGACCG
CATCATCGAGATCGTGCAGCGCATCTTCCGCGCCGTGATCCACATCCCCCGCCGCATCCGCCA
GGGCCTGGAGCGCGCCCTGCTGTAAGATATCGGATCCTCTAGA

FIG. 52

(SEQ ID NO:65)

gp160.mod.US4.delV2

```
GAATTCGCCACCATGGATGCAATGAAGAGAGGGCTCTGCTGTGTGCTGCTGCTGTGTGG
AGCAGTCTTCGTTTCGCCCAGCGCCACCACCGTGCTGTGGGTGACCGTGTACTACGGCG
TGCCCGTGTGGAAGGAGGCCACCACCACCCTGTTCTGCGCCAGCGACGCCAAGGCTTAC
AAGGCCGAGGCCCACAACGTGTGGGCCACCCACGCCTGCGTGCCCACCGACCCCAACCC
CCAGGAGGTGAACCTGACCAACGTGACCGAGAACTTCAACATGTGGAAGAACAACATGG
TGGAGCAGATGCATGAGGACATCATCAGCCTGTGGGACCAGAGCCTGAAGCCCTGCGTG
AAGCTGACCCCCCTGTGCGTGACCCTGAACTGCACCGACAAGCTGACCGGCAGCACCAA
CGGCACCAACAGCACCAGCGGCACCAACAGCACCAGCGGCACCAACAGCACCAGCACCA
ACAGCACCGACAGCTGGGAGAAGATGCCCGAGGGCGAGATCAAGAACTGCAGCTTCAAC
ATCGGCGCCGGCCGCCTGATCAACTGCAACACCAGCGTGATCACCCAGGCCTGCCCCAA
GGTGAGCTTCGAGCCCATCCCCATCCACTACTGCGCCCCCGCCGGCTTCGCCATCCTGA
AGTGCAAGGACAAGAAGTTCAACGGCACCGGCCCTGCAAGAACGTGAGCACCGTGCAG
TGCACCCACGGCATCCGCCCCGTGGTGAGCACCCAGCTGCTGCTGAACGGCAGCCTGGC
CGAGGAGGAGATCGTGCTGCGCTCCGAGAACTTCACCGACAACGCCAAGACCATCATCG
TGCAGCTGAACGAGTCCGTGGAGATCAACTGCATCCGCCCCAACAACAACACGCGTAAG
AGCATCCACATCGGCCCCGGCCGCGCCTTCTACGCCACCGGCGACATCATCGGCGACAT
CCGCCAGGCCCACTGCAACATCAGCAAGGCCAACTGGACCAACACCCTCGAGCAGATCG
TGGAGAAGCTGCGCGAGCAGTTCGGCAACAACAAGACCATCATCTTCAACAGCAGCAGC
GGCGGCGACCCCGAGATCGTGTTCCACAGCTTCAACTGCGGCGGCGAGTTCTTCTACTG
CAACACCAGCCAGCTGTTCAACAGCACCTGGAACATCACCGAGGAGGTGAACAAGACCA
AGGAGAACGACACCATCATCCTGCCCTGCCGCATCCGCCAGATCATCAACATGTGGCAG
GAGGTGGGCAAGGCCATGTACGCCCCCCCCATCCGCGGCCAGATCAAGTGCAGCAGCAA
TATTACCGGCCTGCTGCTGACCCGCGACGGCGGCACCAACAACAACCGCACCAACGACA
CCGAGACCTTCCGCCCCGGCGGCGGCAACATGAAGGACAACTGGCGCAGCGAGCTGTAC
AAGTACAAGGTGGTGCGCATCGAGCCCCTGGGCGTGGCCCCCACCCAGGCCAAGCGCCG
CGTGGTGCAGCGCGAGAAGCGCGCCGTGGGCCTGGGCGCCCTGTTCATCGGCTTCCTGG
GCGCCGCCGGGAGCACCATGGGCGCCGCCTCCGTGACCCTGACCGTGCAGGCCCGCCAG
CTGCTGAGCGGCATCGTGCAGCAGCAGAACAACCTGCTGCGCGCCATCGAGGCCCAGCA
GCACCTGCTGCAGCTGACCGTGTGGGGCATCAAGCAGCTGCAGGCCCGCATCCTGGCCG
TGGAGCGCTACCTGAAGGACCAGCAGCTGCTGGGCATCTGGGGCTGCAGCGGCAAGCTG
ATCTGCACCACCACCGTGCCCTGGAACAGCAGCTGGAGCAACAAGAGCCTGACCGAGAT
CTGGGACAACATGACCTGGATGGAGTGGGAGCGCGAGATCGGCAACTACACCGGCCTGA
TCTACAACCTGATCGAGATCGCCCAGAACCAGCAGGAGAAGAACGAGCAGGAGCTGCTG
GAGCTGGACAAGTGGGCCAGCCTGTGGAACTGGTTCGACATCACCAACTGGCTGTGGTA
CATCCGCATCTTCATCATGATCGTGGGCGGCCTGATCGGCCTGCGCATCGTGTTCGCCG
TGCTGAGCATCGTGAACCGCGTGCGCCAGGGCTACAGCCCCATCAGCCTGCAGACCCGC
CTGCCCGCCAGCGCGGCCCCGACCGCCCCGAGGGCATCGAGGAGGAGGGCGGCGAGCG
CGACCGCGACCGCAGCAACCGCCTGGTGCACGGCCTGCTGGCCCTGATCTGGGACGACC
TGCGCAGCCTGTGCCTGTTCAGCTACCACCGCCTGCGCGACCTGCTGCTGATCGTGGCC
CGCATCGTGGAGCTGCTGGGCCGCCGCGGCTGGGAGGCCCTGAAGTACTGGTGGAACCT
GCTGCAGTACTGGAGCCAGGAGCTGAAGAGCAGCGCCGTGAGCCTGTTCAACGCCACCG
CCATCGCCGTGGCCGAGGGCACCGACCGCATCATCGAGATCGTGCAGCGCATCTTCCGC
GCCGTGATCCACATCCCCGCCGCATCCGCCAGGGCCTGGAGCGCGCCCTGCTGTAAGA
TATCGGATCCTCTAGA
```

FIG. 53
(SEQ ID NO:66)

gp160.modUS4delV1/2

```
GAATTCGCCACCATGGATGCAATGAAGAGAGGGCTCTGCTGTGTGCTGCTGCTGTGGAGCA
GTCTTCGTTTCGCCCAGCGCCACCACCGTGCTGTGGGTGACCGTGTACTACGGCGTGCCCGTG
TGGAAGGAGGCCACCACCACCCTGTTCTGCGCCAGCGACGCCAAGGCTTACAAGGCCGAGGC
CCACAACGTGTGGGCCACCCACGCCTGCGTGCCCACCGACCCCAACCCCCAGGAGGTGAACC
TGACCAACGTGACCGAGAACTTCAACATGTGGAAGAACAACATGGTGGAGCAGATGCATGAG
GACATCATCAGCCTGTGGGACCAGAGCCTGAAGCCCTGCGTGGGCGCCGGCCAGGCCTGCCC
CAAGGTGAGCTTCGAGCCCATCCCCATCCACTACTGCGCCCCGCCGGCTTCGCCATCCTGAA
GTGCAAGGACAAGAAGTTCAACGGCACCGGCCCCTGCAAGAACGTGAGCACCGTGCAGTGCA
CCCACGGCATCCGCCCCGTGGTGAGCACCCAGCTGCTGCTGAACGGCAGCCTGGCCGAGGAG
GAGATCGTGCTGCGCTCCGAGAACTTCACCGACAACGCCAAGACCATCATCGTGCAGCTGAA
CGAGTCCGTGGAGATCAACTGCATCCGCCCCAACAACAACACGCGTAAGAGCATCCACATCG
GCCCCGGCCGCGCCTTCTACGCCACCGGCGACATCATCGGCGACATCCGCCAGGCCCACTGCA
ACATCAGCAAGGCCAACTGGACCAACACCCTCGAGCAGATCGTGGAGAAGCTGCGCGAGCAG
TTCGGCAACAACAAGACCATCATCTTCAACAGCAGCAGCGGCGGCGACCCCGAGATCGTGTT
CCACAGCTTCAACTGCGGCGGCGAGTTCTTCTACTGCAACACCAGCCAGCTGTTCAACAGCAC
CTGGAACATCACCGAGGAGGTGAACAAGACCAAGGAGAACGACACCATCATCCTGCCCTGCC
GCATCCGCCAGATCATCAACATGTGGCAGGAGGTGGGCAAGGCCATGTACGCCCCCCCCATC
CGCGGCCAGATCAAGTGCAGCAGCAATATTACCGGCCTGCTGCTGACCCGCGACGGCGGCAC
CAACAACAACCGCACCAACGACACCGAGACCTTCCGCCCCGGCGGCGGCAACATGAAGGACA
ACTGGCGCAGCGAGCTGTACAAGTACAAGGTGGTGCGCATCGAGCCCCTGGGCGTGGCCCCC
ACCCAGGCCAAGCGCCGCGTGGTGCAGCGCGAGAAGCGCGCCGTGGGCCTGGGCGCCCTGTT
CATCGGCTTCCTGGGCGCCGCCGGGAGCACCATGGGCGCCGCCTCCGTGACCCTGACCGTGCA
GGCCCGCCAGCTGCTGAGCGGCATCGTGCAGCAGCAGAACAACCTGCTGCGCGCCATCGAGG
CCCAGCAGCACCTGCTGCAGCTGACCGTGTGGGGCATCAAGCAGCTGCAGGCCCGCATCCTG
GCCGTGGAGCGCTACCTGAAGGACCAGCAGCTGCTGGGCATCTGGGGCTGCAGCGGCAAGCT
GATCTGCACCACCACCGTGCCCTGGAACAGCAGCTGGAGCAACAAGAGCCTGACCGAGATCT
GGGACAACATGACCTGGATGGAGTGGGAGCGCGAGATCGGCAACTACACCGGCCTGATCTAC
AACCTGATCGAGATCGCCCAGAACCAGCAGGAGAAGAACGAGCAGGAGCTGCTGGAGCTGG
ACAAGTGGGCCAGCCTGTGGAACTGGTTCGACATCACCAACTGGCTGTGGTACATCCGCATCT
TCATCATGATCGTGGGCGGCCTGATCGGCCTGCGCATCGTGTTCGCCGTGCTGAGCATCGTGA
ACCGCGTGCGCCAGGGCTACAGCCCCATCAGCCTGCAGACCCGCCTGCCCGCCCAGCGCGGC
CCCGACCGCCCCGAGGGCATCGAGGAGGAGGGCGGCGAGCGCGACCGCGACCGCAGCAACC
GCCTGGTGCACGGCCTGCTGGCCCTGATCTGGGACGACCTGCGCAGCCTGTGCCTGTTCAGCT
ACCACCGCCTGCGCGACCTGCTGCTGATCGTGGCCCGCATCGTGGAGCTGCTGGGCCGCCGCG
GCTGGGAGGCCCTGAAGTACTGGTGGAACCTGCTGCAGTACTGGAGCCAGGAGCTGAAGAGC
AGCGCCGTGAGCCTGTTCAACGCCACCGCCATCGCCGTGGCCGAGGGCACCGACCGCATCATC
GAGATCGTGCAGCGCATCTTCCGCGCCGTGATCCACATCCCCCGCCGCATCCGCCAGGGCCTG
GAGCGCGCCCTGCTGTAAGATATCGGATCCTCTAGA
```

FIG. 54
(SEQ ID NO:67)

gp160.modUS4 del 128-194

GAATTCGCCACCATGGATGCAATGAAGAGAGGGCTCTGCTGTGTGCTGCTGCTGTGTGGAGCA
GTCTTCGTTTCGCCCAGCGCCACCACCGTGCTGTGGGTGACCGTGTACTACGGCGTGCCCGTG
TGGAAGGAGGCCACCACCACCCTGTTCTGCGCCAGCGACGCCAAGGCTTACAAGGCCGAGGC
CCACAACGTGTGGGCCACCCACGCCTGCGTGCCCACCGACCCCAACCCCCAGGAGGTGAACC
TGACCAACGTGACCGAGAACTTCAACATGTGGAAGAACAACATGGTGGAGCAGATGCATGAG
GACATCATCAGCCTGTGGGACCAGAGCCTGAAGCCCTGCGTGAAGCTGACCCCCCTGTGCGTG
GGGGCAGGGAACTGCGAGACCAGCGTGATCACCCAGGCCTGCCCCAAGGTGAGCTTCGAGCC
CATCCCCATCCACTACTGCGCCCCCGCCGGCTTCGCCATCCTGAAGTGCAAGGACAAGAAGTT
CAACGGCACCGGCCCCTGCAAGAACGTGAGCACCGTGCAGTGCACCCACGGCATCCGCCCCG
TGGTGAGCACCCAGCTGCTGCTGAACGGCAGCCTGGCCGAGGAGGAGATCGTGCTGCGCTCC
GAGAACTTCACCGACAACGCCAAGACCATCATCGTGCAGCTGAACGAGTCCGTGGAGATCAA
CTGCATCCGCCCCAACAACAACACGCGTAAGAGCATCCACATCGGCCCCGGCCGCGCCTTCTA
CGCCACCGGCGACATCATCGGCGACATCCGCCAGGCCCACTGCAACATCAGCAAGGCCAACT
GGACCAACACCCTCGAGCAGATCGTGGAGAAGCTGCGCGAGCAGTTCGGCAACAACAAGACC
ATCATCTTCAACAGCAGCAGCGGCGGCGACCCCGAGATCGTGTTCCACAGCTTCAACTGCGGC
GGCGAGTTCTTCTACTGCAACACCAGCCAGCTGTTCAACAGCACCTGGAACATCACCGAGGAG
GTGAACAAGACCAAGGAGAACGACACCATCATCCTGCCCTGCCGCATCCGCCAGATCATCAA
CATGTGGCAGGAGGTGGGCAAGGCCATGTACGCCCCCCCCATCCGCGGCCAGATCAAGTGCA
GCAGCAATATTACCGGCCTGCTGCTGACCCGCGACGGCGGCACCAACAACAACCGCACCAAC
GACACCGAGACCTTCCGCCCCGGCGGCGGCAACATGAAGGACAACTGGCGCAGCGAGCTGTA
CAAGTACAAGGTGGTGCGCATCGAGCCCCTGGGCGTGGCCCCCACCCAGGCCAAGCGCCGCG
TGGTGCAGCGCGAGAAGCGCGCCGTGGGCCTGGGCGCCCTGTTCATCGGCTTCCTGGGCGCCG
CCGGGAGCACCATGGGCGCCGCCTCCGTGACCCTGACCGTGCAGGCCCGCCAGCTGCTGAGC
GGCATCGTGCAGCAGCAGAACAACCTGCTGCGCGCCATCGAGGCCCAGCAGCACCTGCTGCA
GCTGACCGTGTGGGGCATCAAGCAGCTGCAGGCCCGCATCCTGGCCGTGGAGCGCTACCTGA
AGGACCAGCAGCTGCTGGGCATCTGGGGCTGCAGCGGCAAGCTGATCTGCACCACCACCGTG
CCCTGGAACAGCAGCTGGAGCAACAAGAGCCTGACCGAGATCTGGGACAACATGACCTGGAT
GGAGTGGGAGCGCGAGATCGGCAACTACACCGGCCTGATCTACAACCTGATCGAGATCGCCC
AGAACCAGCAGGAGAAGAACGAGCAGGAGCTGCTGGAGCTGGACAAGTGGGCCAGCCTGTG
GAACTGGTTCGACATCACCAACTGGCTGTGGTACATCCGCATCTTCATCATGATCGTGGGCGG
CCTGATCGGCCTGCGCATCGTGTTCGCCGTGCTGAGCATCGTGAACCGCGTGCGCCAGGGCTA
CAGCCCCATCAGCCTGCAGACCCGCCTGCCCGCCCAGCGCGGCCCCGACCGCCCCGAGGGCA
TCGAGGAGGAGGGCGGCGAGCGCGACCGCGACCGCAGCAACCGCCTGGTGCACGGCCTGCTG
GCCCTGATCTGGGACGACCTGCGCAGCCTGTGCCTGTTCAGCTACCACCGCCTGCGCGACCTG
CTGCTGATCGTGGCCCGCATCGTGGAGCTGCTGGGCCGCCGCGGCTGGGAGGCCCTGAAGTAC
TGGTGGAACCTGCTGCAGTACTGGAGCCAGGAGCTGAAGAGCAGCGCCGTGAGCCTGTTCAA
CGCCACCGCCATCGCCGTGGCCGAGGGCACCGACCGCATCATCGAGATCGTGCAGCGCATCTT
CCGCGCCGTGATCCACATCCCCCGCCGCATCCGCCAGGGCCTGGAGCGCGCCCTGCTGTAAGA
TATCGGATCCTCTAGA

FIG. 55
(SEQ ID NO:68)

Env_US4_C4wt
GACACTATCATACTCCCATGCAGAATAAGACAAATTATAAACATGTGGCAAGAAGTAGG
AAAAGCAATGTATGCCCCTCCCATCAGAGGACAAATTAAATGTTCATCAAATATTACAG
GGCTGCTATTAACTAGAGATGGTGGT

FIG. 56
(SEQ ID NO:69)

Env_SF162_C4wt

GGAACTATCACACTCCCATGCAGAATAAAACAAATTATAAACAGGTGGCAGGAAGTAGG
AAAAGCAATGTATGCCCCTCCCATCAGAGGACAAATTAGATGCTCATCAAATATTACAG
GACTGCTATTAACAAGAGATGGTGGT

FIG. 57
(SEQ ID NO:70)

Env_US4_C4mod
GACACCATCATCCTGCCCTGCCGCATCCGCCAGATCATCAACATGTGGCAGGAGGTGGG
CAAGGCCATGTACGCCCCCCCCATCCGCGGCCAGATCAAGTGCAGCAGCAACATCACCG
GCCTGCTGCTGACCCGCGACGGCGGC

FIG. 58
(SEQ ID NO:71)

Env_SF162_C4mod
GGCACCATCACCCTGCCCTGCCGCATCAAGCAGATCATCAACCGCTGGCAGGAGGTGGG
CAAGGCCATGTACGCCCCCCCCATCCGCGGCCAGATCCGCTGCAGCAGCAACATCACCG
GCCTGCTGCTGACCCGCGACGGCGGC

FIG. 59
(SEQ ID NO:72)

gp160mod.us4.gag.modSF2
GAATTCGCCACCATGGATGCAATGAAGAGAGGGCTCTGCTGTGTGCTGCTGCTGTGTGGA
GCAGTCTTCGTTTCGCCCAGCGCCACCACCGTGCTGTGGGTGACCGTGTACTACGGCGTG
CCCGTGTGGAAGGAGGCCACCACCACCCTGTTCTGCGCCAGCGACGCCAAGGCTTACAAG
GCCGAGGCCCACAACGTGTGGGCCACCCACGCCTGCGTGCCCACCGACCCCAACCCCCAG
GAGGTGAACCTGACCAACGTGACCGAGAACTTCAACATGTGGAAGAACAACATGGTGGAG
CAGATGCATGAGGACATCATCAGCCTGTGGGACCAGAGCCTGAAGCCCTGCGTGAAGCTG
ACCCCCCTGTGCGTGACCCTGAACTGCACCGACAAGCTGACCGGCAGCACCAACGGCACC
AACAGCACCAGCGGCACCAACAGCACCAGCGGCACCAACAGCACCAGCACCAACAGCACC
GACAGCTGGGAGAAGATGCCCGAGGGCGAGATCAAGAACTGCAGCTTCAACATCACCACC
AGCGTGCGCGACAAGGTGCAGAAGGAGTACAGCCTGTTCTACAAGCTGGACGTGGTGCCC
ATCGACAACGACAACGCCAGCTACCGCCTGATCAACTGCAACACCAGCGTGATCACCCAG
GCCTGCCCCAAGGTGAGCTTCGAGCCCATCCCCATCCACTACTGCGCCCCCGCCGGCTTC
GCCATCCTGAAGTGCAAGGACAAGAAGTTCAACGGCACCGGCCCTGCAAGAACGTGAGC
ACCGTGCAGTGCACCCACGGCATCCGCCCCGTGGTGAGCACCCAGCTGCTGCTGAACGGC
AGCCTGGCCGAGGAGGAGATCGTGCTGCGCTCCGAGAACTTCACCGACAACGCCAAGACC
ATCATCGTGCAGCTGAACGAGTCCGTGGAGATCAACTGCATCCGCCCCAACAACAACACG
CGTAAGAGCATCCACATCGGCCCCGGCCGCGCCTTCTACGCCACCGGCGACATCATCGGC
GACATCCGCCAGGCCCACTGCAACATCAGCAAGGCCAACTGGACCAACACCCTCGAGCAG
ATCGTGGAGAAGCTGCGCGAGCAGTTCGGCAACAACAAGACCATCATCTTCAACAGCAGC
AGCGGCGGCGACCCCGAGATCGTGTTCCACAGCTTCAACTGCGGCGGCGAGTTCTTCTAC
TGCAACACCAGCCAGCTGTTCAACAGCACCTGGAACATCACCGAGGAGGTGAACAAGACC
AAGGAGAACGACACCATCATCCTGCCCTGCCGCATCGCCAGATCATCAACATGTGGCAG
GAGGTGGGCAAGGCCATGTACGCCCCCCCCATCCGCGGCCAGATCAAGTGCAGCAGCAAT
ATTACCGGCCTGCTGCTGACCCGCGACGGCGGCACCAACAACAACCGCACCAACGACACC
GAGACCTTCCGCCCCGGCGGCGGCAACATGAAGGACAACTGGCGCAGCGAGCTGTACAAG
TACAAGGTGGTGCGCATCGAGCCCCTGGGCGTGGCCCCCACCCAGGCCAAGCGCCGCGTG
GTGCAGCGCGAGAAGCGCGCCGTGGGCCTGGGCGCCCTGTTCATCGGCTTCCTGGGCGCC
GCCGGGAGCACCATGGGCGCCGCCTCCGTGACCCTGACCGTGCAGGCCCGCCAGCTGCTG
AGCGGCATCGTGCAGCAGCAGAACAACCTGCTGCGCGCCATCGAGGCCCAGCAGCACCTG
CTGCAGCTGACCGTGTGGGGCATCAAGCAGCTGCAGGCCCGCATCCTGGCCGTGGAGCGC
TACCTGAAGGACCAGCAGCTGCTGGGCATCTGGGGCTGCAGCGGCAAGCTGATCTGCACC
ACCACCGTGCCCTGGAACAGCAGCTGGAGCAACAAGAGCCTGACCGAGATCTGGGACAAC
ATGACCTGGATGGAGTGGGAGCGCGAGATCGGCAACTACACCGGCCTGATCTACAACCTG
ATCGAGATCGCCCAGAACCAGCAGGAGAAGAACGAGCAGGAGCTGCTGGAGCTGGACAAG
TGGGCCAGCCTGTGGAACTGGTTCGACATCACCAACTGGCTGTGGTACATCCGCATCTTC
ATCATGATCGTGGGCGGCCTGATCGGCCTGCGCATCGTGTTCGCCGTGCTGAGCATCGTG
AACCGCGTGCGCCAGGGCTACAGCCCCATCAGCCTGCAGACCCGCCTGCCCGCCCAGCGC
GGCCCCGACCGCCCCGAGGGCATCGAGGAGGAGGGCGGCGAGCGCGACCGCGACCGCAGC
AACCGCCTGGTGCACGGCCTGCTGGCCCTGATCTGGGACGACCTGCGCAGCCTGTGCCTG
TTCAGCTACCACCGCCTGCGCGACCTGCTGCTGATCGTGGCCCGCATCGTGGAGCTGCTG
GGCCGCCGCGGCTGGGAGGCCCTGAAGTACTGGTGGAACCTGCTGCAGTACTGGAGCCAG
GAGCTGAAGAGCAGCGCCGTGAGCCTGTTCAACGCCACCGCCATCGCCGTGGCCGAGGGC
ACCGACCGCATCATCGAGATCGTGCAGCGCATCTTCCGCGCCGTGATCCACATCCCCCGC
CGCATCCGCCAGGGCCTGGAGCGCGCCCTGCTGTAAGATATCGGATCCTCTAGAATTC

FIG. 61A
(SEQ ID NO:73)

```
CGCCCCCCCCCCCCCCCCCCCTCTCCCTCCCCCCCCCCTAACGTTACTGGCCGAAGCCGC
TTGGAATAAGGCCGGTGTGCGTTTGTCTATATGTTATTTTCCACCATATTGCCGTCTTTT
GGCAATGTGAGGGCCCGGAAACCTGGCCCTGTCTTCTTGACGAGCATTCCTAGGGGTCTT
TCCCCTCTCGCCAAAGGAATGCAAGGTCTGTTGAATGTCGTGAAGGAAGCAGTTCCTCTG
GAAGCTTCTTGAAGACAAACAACGTCTGTAGCGACCCTTTGCAGGCAGCGGAACCCCCCA
CCTGGCGACAGGTGCCTCTGCGGCCAAAAGCCACGTGTATAAGATACACCTGCAAAGGCG
GCACAACCCCAGTGCCACGTTGTGAGTTGGATAGTTGTGGAAAGAGTCAAATGGCTCTCC
TCAAGCGTATTCAACAAGGGGCTGAAGGATGCCCAGAAGGTACCCATTGTATGGGATCT
GATCTGGGGCCTCGGTGCACATGCTTTACATGTGTTTAGTCGAGGTTAAAAAAACGTCTA
GGCCCCCCGAACCACGGGGACGTGGTTTTCCTTTGAAAAACACGATAATACCATGGGCGC
CCGCGCCAGCGTGCTGAGCGGCGGCGAGCTGGACAAGTGGGAGAAGATCCGCCTGCGCCC
CGGCGGCAAGAAGAAGTACAAGCTGAAGCACATCGTGTGGGCCAGCCGCGAGCTGGAGCG
CTTCGCCGTGAACCCCGGCCTGCTGGAGACCAGCGAGGGCTGCCGCCAGATCCTGGGCCA
GCTGCAGCCCAGCCTGCAGACCGGCAGCGAGGAGCTGCGCAGCCTGTACAACACCGTGGC
CACCCTGTACTGCGTGCACCAGCGCATCGACGTCAAGGACACCAAGGAGGCCCTGGAGAA
GATCGAGGAGGAGCAGAACAAGTCCAAGAAGAAGGCCCAGCAGGCCGCCGCCGCCGCCGG
CACCGGCAACAGCAGCCAGGTGAGCCAGAACTACCCCATCGTGCAGAACCTGCAGGGCCA
GATGGTGCACCAGGCCATCAGCCCCCGCACCCTGAACGCCTGGGTGAAGGTGGTGGAGGA
GAAGGCCTTCAGCCCCGAGGTGATCCCCATGTTCAGCGCCCTGAGCGAGGGCGCCACCCC
CCAGGACCTGAACACGATGTTGAACACCGTGGGCGGCCACCAGGCCGCCATGCAGATGCT
GAAGGAGACCATCAACGAGGAGGCCGCCGAGTGGGACCGCGTGCACCCCGTGCACGCCGG
CCCCATCGCCCCCGGCCAGATGCGCGAGCCCCGCGGCAGCGACATCGCCGGCACCACCAG
CACCCTGCAGGAGCAGATCGGCTGGATGACCAACAACCCCCCATCCCCGTGGGCGAGAT
CTACAAGCGGTGGATCATCCTGGGCCTGAACAAGATCGTGCGGATGTACAGCCCCACCAG
CATCCTGGACATCCGCCAGGGCCCCAAGGAGCCCTTCCGCGACTACGTGGACCGCTTCTA
CAAGACCCTGCGCGCTGAGCAGGCCAGCCAGGACGTGAAGAACTGGATGACCGAGACCCT
GCTGGTGCAGAACGCCAACCCCGACTGCAAGACCATCCTGAAGGCTCTCGGCCCCGCGGC
CACCCTGGAGGAGATGATGACCGCCTGCCAGGGCGTGGGCGGCCCCGGCCACAAGGCCCG
CGTGCTGGCCGAGGCGATGAGCCAGGTGACGAACCCGGCGACCATCATGATGCAGCGCGG
CAACTTCCGCAACCAGCGGAAGACCGTCAAGTGCTTCAACTGCGGCAAGGAGGGCCACAC
CGCCAGGAACTGCCGCGCCCCCGCAAGAAGGGCTGCTGGCGCTGCGGCCGCGAGGGCCA
CCAGATGAAGGACTGCACCGAGCGCCAGGCCAACTTCCTGGGCAAGATCTGGCCCAGCTA
CAAGGGCCGCCCCGGCAACTTCCTGCAGAGCCGCCCCGAGCCCACCGCCCCCCCGAGGA
GAGCTTCCGCTTCGGCGAGGAGAAGACCACCCCCAGCCAGAAGCAGGAGCCCATCGACAA
GGAGCTGTACCCCCTGACCAGCCTGCGCAGCCTGTTCGGCAACGACCCCAGCAGCCAGTA
AGAATTCAGACTCGAGCAAGTCTAGA
```

FIG. 61B
(SEQ ID NO:73)

gp160mod.SF162.gag.modSF2

```
GAATTCGCCACCATGGATGCAATGAAGAGAGGGCTCTGCTGTGTGCTGCTGCTGTGTGG
AGCAGTCTTCGTTTCGCCCAGCGCCGTGGAGAAGCTGTGGGTGACCGTGTACTACGGCG
TGCCCGTGTGGAAGGAGGCCACCACCACCCTGTTCTGCGCCAGCGACGCCAAGGCCTAC
GACACCGAGGTGCACAACGTGTGGGCCACCCACGCCTGCGTGCCCACCGACCCCAACCC
CCAGGAGATCGTGCTGGAGAACGTGACCGAGAACTTCAACATGTGGAAGAACAACATGG
TGGAGCAGATGCACGAGGACATCATCAGCCTGTGGGACCAGAGCCTGAAGCCCTGCGTG
AAGCTGACCCCCTGTGCGTGACCCTGCACTGCACCAACCTGAAGAACGCCACCAACAC
CAAGAGCAGCAACTGGAAGGAGATGGACCGCGGCGAGATCAAGAACTGCAGCTTCAAGG
TGACCACCAGCATCCGCAACAAGATGCAGAAGGAGTACGCCCTGTTCTACAAGCTGGAC
GTGGTGCCCATCGACAACGACAACACCAGCTACAAGCTGATCAACTGCAACACCAGCGT
GATCACCCAGGCCTGCCCCAAGGTGAGCTTCGAGCCCATCCCCATCCACTACTGCGCCC
CCGCCGGCTTCGCCATCCTGAAGTGCAACGACAAGAAGTTCAACGGCAGCGGCCCCTGC
ACCAACGTGAGCACCGTGCAGTGCACCCACGGCATCCGCCCCGTGGTGAGCACCCAGCT
GCTGCTGAACGGCAGCCTGGCCGAGGAGGGCGTGGTGATCCGCAGCGAGAACTTCACCG
ACAACGCCAAGACCATCATCGTGCAGCTGAAGGAGAGCGTGGAGATCAACTGCACCCGC
CCCAACAACAACACCCGCAAGAGCATCACCATCGGCCCCGGCCGCGCCTTCTACGCCAC
CGGCGACATCATCGGCGACATCCGCCAGGCCCACTGCAACATCAGCGGCGAGAAGTGGA
ACAACACCCTGAAGCAGATCGTGACCAAGCTGCAGGCCCAGTTCGGCAACAAGACCATC
GTGTTCAAGCAGAGCAGCGGCGGCGACCCCGAGATCGTGATGCACAGCTTCAACTGCGG
CGGCGAGTTCTTCTACTGCAACAGCACCCAGCTGTTCAACAGCACCTGGAACAACACCA
TCGGCCCCAACAACACCAACGGCACCATCACCCTGCCCTGCCGCATCAAGCAGATCATC
AACCGCTGGCAGGAGGTGGGCAAGGCCATGTACGCCCCCCCATCCGCGGCCAGATCCG
CTGCAGCAGCAACATCACCGGCCTGCTGCTGACCCGCGACGGCGGCAAGGAGATCAGCA
ACACCACCGAGATCTTCCGCCCCGGCGGCGGCGACATGCGCGACAACTGGCGCAGCGAG
CTGTACAAGTACAAGGTGGTGAAGATCGAGCCCCTGGGCGTGGCCCCCACCAAGGCCAA
GCGCCGCGTGGTGCAGCGCGAGAAGCGCGCCGTGACCCTGGGCGCCATGTTCCTGGGCT
TCCTGGGCGCCGCCGGCAGCACCATGGGCGCCCGCAGCCTGACCCTGACCGTGCAGGCC
CGCCAGCTGCTGAGCGGCATCGTGCAGCAGCAGAACAACCTGCTGCGCGCCATCGAGGC
CCAGCAGCACCTGCTGCAGCTGACCGTGTGGGGCATCAAGCAGCTGCAGGCCCGCGTGC
TGGCCGTGGAGCGCTACCTGAAGGACCAGCAGCTGCTGGGCATCTGGGGCTGCAGCGGC
AAGCTGATCTGCACCACCGCCGTGCCCTGGAACGCCAGCTGGAGCAACAAGAGCCTGGA
CCAGATCTGGAACAACATGACCTGGATGGAGTGGGAGCGCGAGATCGACAACTACACCA
ACCTGATCTACACCCTGATCGAGGAGAGCCAGAACCAGCAGGAGAAGAACGAGCAGGAG
CTGCTGGAGCTGGACAAGTGGGCCAGCCTGTGGAACTGGTTCGACATCAGCAAGTGGCT
GTGGTACATCAAGATCTTCATCATGATCGTGGGCGGCCTGGTGGGCCTGCGCATCGTGT
TCACCGTGCTGAGCATCGTGAACCGCGTGCGCCAGGGCTACAGCCCCCTGAGCTTCCAG
ACCCGCTTCCCCGCCCCCGCGGCCCCGACCGCCCCGAGGGCATCGAGGAGGAGGGCGG
CGAGCGCGACCGCGACCGCAGCAGCCCCCTGGTGCACGGCCTGCTGGCCCTGATCTGGG
ACGACCTGCGCAGCCTGTGCCTGTTCAGCTACCACCGCCTGCGCGACCTGATCCTGATC
GCCGCCCGCATCGTGGAGCTGCTGGGCCGCCGCGGCTGGGAGGCCCTGAAGTACTGGGG
CAACCTGCTGCAGTACTGGATCCAGGAGCTGAAGAACAGCGCCGTGAGCCTGTTCGACG
CCATCGCCATCGCCGTGGCCGAGGGCACCGACCGCATCATCGAGGTGGCCCAGCGCATC
GGCCGCGCCTTCCTGCACATCCCCGCCGCATCCGCCAGGGCTTCGAGCGCGCCCTGCT
```

FIG. 62A
(SEQ ID NO:74)

```
GTAACTCGAGCAAGTCTAGAGAATTCCGCCCCCCCCCCCCCCCCCCCTCTCCCTCCCCC
CCCCCTAACGTTACTGGCCGAAGCCGCTTGGAATAAGGCCGGTGTGCGTTTGTCTATAT
GTTATTTTCCACCATATTGCCGTCTTTTGGCAATGTGAGGGCCCGGAAACCTGGCCCTG
TCTTCTTGACGAGCATTCCTAGGGGTCTTTCCCCTCTCGCCAAAGGAATGCAAGGTCTG
TTGAATGTCGTGAAGGAAGCAGTTCCTCTGGAAGCTTCTTGAAGACAAACAACGTCTGT
AGCGACCCTTTGCAGGCAGCGGAACCCCCCACCTGGCGACAGGTGCCTCTGCGGCCAAA
AGCCACGTGTATAAGATACACCTGCAAAGGCGGCACAACCCCAGTGCCACGTTGTGAGT
TGGATAGTTGTGGAAAGAGTCAAATGGCTCTCCTCAAGCGTATTCAACAAGGGGCTGAA
GGATGCCCAGAAGGTACCCCATTGTATGGGATCTGATCTGGGGCCTCGGTGCACATGCT
TTACATGTGTTTAGTCGAGGTTAAAAAAACGTCTAGGCCCCCCGAACCACGGGGACGTG
GTTTTCCTTTGAAAAACACGATAATACCATGGGCGCCCGCGCCAGCGTGCTGAGCGGCG
GCGAGCTGGACAAGTGGGAGAAGATCCGCCTGCGCCCCGGCGGCAAGAAGAAGTACAAG
CTGAAGCACATCGTGTGGGCCAGCCGCGAGCTGGAGCGCTTCGCCGTGAACCCCGGCCT
GCTGGAGACCAGCGAGGGCTGCCGCCAGATCCTGGGCCAGCTGCAGCCCAGCCTGCAGA
CCGGCAGCGAGGAGCTGCGCAGCCTGTACAACACCGTGGCCACCCTGTACTGCGTGCAC
CAGCGCATCGACGTCAAGGACACCAAGGAGGCCCTGGAGAAGATCGAGGAGGAGCAGAA
CAAGTCCAAGAAGAAGGCCCAGCAGGCCGCCGCCGCCGGCACCGGCAACAGCAGCC
AGGTGAGCCAGAACTACCCCATCGTGCAGAACCTGCAGGGCCAGATGGTGCACCAGGCC
ATCAGCCCCCGCACCCTGAACGCCTGGGTGAAGGTGGTGGAGGAGAAGGCCTTCAGCCC
CGAGGTGATCCCCATGTTCAGCGCCCTGAGCGAGGGCGCCACCCCCCAGGACCTGAACA
CGATGTTGAACACCGTGGGCGGCCACCAGGCCGCCATGCAGATGCTGAAGGAGACCATC
AACGAGGAGGCCGCCGAGTGGGACCGCGTGCACCCCGTGCACGCCGGCCCCATCGCCCC
CGGCCAGATGCGCGAGCCCCGCGGCAGCGACATCGCCGGCACCACCAGCACCCTGCAGG
AGCAGATCGGCTGGATGACCAACAACCCCCCCATCCCCGTGGGCGAGATCTACAAGCGG
TGGATCATCCTGGGCCTGAACAAGATCGTGCGGATGTACAGCCCCACCAGCATCCTGGA
CATCCGCCAGGGCCCCAAGGAGCCCTTCCGCGACTACGTGGACCGCTTCTACAAGACCC
TGCGCGCTGAGCAGGCCAGCCAGGACGTGAAGAACTGGATGACCGAGACCCTGCTGGTG
CAGAACGCCAACCCCGACTGCAAGACCATCCTGAAGGCTCTCGGCCCCGCGGCCACCCT
GGAGGAGATGATGACCGCCTGCCAGGGCGTGGGCGGCCCCGGCCACAAGGCCCGCGTGC
TGGCCGAGGCGATGAGCCAGGTGACGAACCCGGCGACCATCATGATGCAGCGCGGCAAC
TTCCGCAACCAGCGGAAGACCGTCAAGTGCTTCAACTGCGGCAAGGAGGGCCACACCGC
CAGGAACTGCCGCGCCCCCGCAAGAAGGGCTGCTGGCGCTGCGGCCGCGAGGGCCACC
AGATGAAGGACTGCACCGAGCGCCAGGCCAACTTCCTGGGCAAGATCTGGCCCAGCTAC
AAGGGCCGCCCCGGCAACTTCCTGCAGAGCCGCCCCGAGCCCACCGCCCCCCCGAGGA
GAGCTTCCGCTTCGGCGAGGAGAAGACCACCCCCAGCCAGAAGCAGGAGCCCATCGACA
AGGAGCTGTACCCCCTGACCAGCCTGCGCAGCCTGTTCGGCAACGACCCCAGCAGCCAG
TAAGAATTCAGACTCGAGCAAGTCTAGA
```

FIG. 62B
(SEQ ID NO:74)

gp160modUS4.delV1/V2.gag.modSF2

```
GAATTCGCCACCATGGATGCAATGAAGAGAGGGCTCTGCTGTGTGCTGCTGCTGTGTGGA
GCAGTCTTCGTTTCGCCCAGCGCCACCACCGTGCTGTGGGTGACCGTGTACTACGGCGTG
CCCGTGTGGAAGGAGGCCACCACCACCCTGTTCTGCGCCAGCGACGCCAAGGCTTACAAG
GCCGAGGCCCACAACGTGTGGGCCACCCACGCCTGCGTGCCCACCGACCCCAACCCCCAG
GAGGTGAACCTGACCAACGTGACCGAGAACTTCAACATGTGGAAGAACAACATGGTGGAG
CAGATGCATGAGGACATCATCAGCCTGTGGGACCAGAGCCTGAAGCCCTGCGTGGGCGCC
GGCCAGGCCTGCCCCAAGGTGAGCTTCGAGCCCATCCCCATCCACTACTGCGCCCCCGCC
GGCTTCGCCATCCTGAAGTGCAAGGACAAGAAGTTCAACGGCACCGGCCCCTGCAAGAAC
GTGAGCACCGTGCAGTGCACCCACGGCATCCGCCCCGTGGTGAGCACCCAGCTGCTGCTG
AACGGCAGCCTGGCCGAGGAGGAGATCGTGCTGCGCTCCGAGAACTTCACCGACAACGCC
AAGACCATCATCGTGCAGCTGAACGAGTCCGTGGAGATCAACTGCATCCGCCCCAACAAC
AACACGCGTAAGAGCATCCACATCGGCCCCGGCCGCGCCTTCTACGCCACCGGCGACATC
ATCGGCGACATCCGCCAGGCCCACTGCAACATCAGCAAGGCCAACTGGACCAACACCCTC
GAGCAGATCGTGGAGAAGCTGCGCGAGCAGTTCGGCAACAACAAGACCATCATCTTCAAC
AGCAGCAGCGGCGGCGACCCCGAGATCGTGTTCCACAGCTTCAACTGCGGCGGCGAGTTC
TTCTACTGCAACACCAGCCAGCTGTTCAACAGCACCTGGAACATCACCGAGGAGGTGAAC
AAGACCAAGGAGAACGACACCATCATCCTGCCCTGCCGCATCGCCAGATCATCAACATG
TGGCAGGAGGTGGGCAAGGCCATGTACGCCCCCCCCATCCGCGGCCAGATCAAGTGCAGC
AGCAATATTACCGGCCTGCTGCTGACCCGCGACGGCGGCACCAACAACAACCGCACCAAC
GACACCGAGACCTTCCGCCCCGGCGGCGGCAACATGAAGGACAACTGGCGCAGCGAGCTG
TACAAGTACAAGGTGGTGCGCATCGAGCCCCTGGGCGTGGCCCCCACCCAGGCCAAGCGC
CGCGTGGTGCAGCGCGAGAAGCGCGCCGTGGGCCTGGGCGCCCTGTTCATCGGCTTCCTG
GGCGCCGCCGGGAGCACCATGGGCGCCGCCTCCGTGACCCTGACCGTGCAGGCCCGCCAG
CTGCTGAGCGGCATCGTGCAGCAGCAGAACAACCTGCTGCGCGCCATCGAGGCCCAGCAG
CACCTGCTGCAGCTGACCGTGTGGGGCATCAAGCAGCTGCAGGCCCGCATCCTGGCCGTG
GAGCGCTACCTGAAGGACCAGCAGCTGCTGGGCATCTGGGGCTGCAGCGGCAAGCTGATC
TGCACCACCACCGTGCCCTGGAACAGCAGCTGGAGCAACAAGAGCCTGACCGAGATCTGG
GACAACATGACCTGGATGGAGTGGGAGCGCGAGATCGGCAACTACACCGGCCTGATCTAC
AACCTGATCGAGATCGCCCAGAACCAGCAGGAGAAGAACGAGCAGGAGCTGCTGGAGCTG
GACAAGTGGGCCAGCCTGTGGAACTGGTTCGACATCACCAACTGGCTGTGGTACATCCGC
ATCTTCATCATGATCGTGGGCGGCCTGATCGGCCTGCGCATCGTGTTCGCCGTGCTGAGC
ATCGTGAACCGCGTGCGCCAGGGCTACAGCCCCATCAGCCTGCAGACCCGCCTGCCCGCC
CAGCGCGGCCCCGACCGCCCCGAGGGCATCGAGGAGGAGGGCGGCGAGCGCGACCGCGAC
CGCAGCAACCGCCTGGTGCACGGCCTGCTGGCCCTGATCTGGGACGACCTGCGCAGCCTG
TGCCTGTTCAGCTACCACCGCCTGCGCGACCTGCTGCTGATCGTGGCCCGCATCGTGGAG
CTGCTGGGCCGCCGCGGCTGGGAGGCCCTGAAGTACTGGTGGAACCTGCTGCAGTACTGG
AGCCAGGAGCTGAAGAGCAGCGCCGTGAGCCTGTTCAACGCCACCGCCATCGCCGTGGCC
GAGGGCACCGACCGCATCATCGAGATCGTGCAGCGCATCTTCCGCGCCGTGATCCACATC
CCCCGCCGCATCCGCCAGGGCCTGGAGCGCGCCCTGCTGTAAGATATCGGATCCTCTAGA
GAATTCCGCCCCCCCCCCCCCCCCCCCCTCTCCCTCCCCCCCCCCTAACGTTACTGGCCGA
AGCCGCTTGGAATAAGGCCGGTGTGCGTTTGTCTATATGTTATTTTCCACCATATTGCCG
TCTTTTGGCAATGTGAGGGCCCGGAAACCTGGCCCTGTCTTCTTGACGAGCATTCCTAGG
GGTCTTTCCCCTCTCGCCAAAGGAATGCAAGGTCTGTTGAATGTCGTGAAGGAAGCAGTT
```

FIG. 63A
(SEQ ID NO:75)

```
CCTCTGGAAGCTTCTTGAAGACAAACAACGTCTGTAGCGACCCTTTGCAGGCAGCGGAAC
CCCCCACCTGGCGACAGGTGCCTCTGCGGCCAAAAGCCACGTGTATAAGATACACCTGCA
AAGGCGGCACAACCCCAGTGCCACGTTGTGAGTTGGATAGTTGTGGAAAGAGTCAAATGG
CTCTCCTCAAGCGTATTCAACAAGGGGCTGAAGGATGCCCAGAAGGTACCCCATTGTATG
GGATCTGATCTGGGGCCTCGGTGCACATGCTTTACATGTGTTTAGTCGAGGTTAAAAAAA
CGTCTAGGCCCCCGAACCACGGGGACGTGGTTTTCCTTTGAAAAACACGATAATACCAT
GGGCGCCCGCGCCAGCGTGCTGAGCGGCGGCGAGCTGGACAAGTGGGAGAAGATCCGCCT
GCGCCCCGGCGGCAAGAAGAAGTACAAGCTGAAGCACATCGTGTGGGCCAGCCGCGAGCT
GGAGCGCTTCGCCGTGAACCCCGGCCTGCTGGAGACCAGCGAGGGCTGCCGCCAGATCCT
GGGCCAGCTGCAGCCCAGCCTGCAGACCGGCAGCGAGGAGCTGCGCAGCCTGTACAACAC
CGTGGCCACCCTGTACTGCGTGCACCAGCGCATCGACGTCAAGGACACCAAGGAGGCCCT
GGAGAAGATCGAGGAGGAGCAGAACAAGTCCAAGAAGAAGGCCCAGCAGGCCGCCGCCGC
CGCCGGCACCGGCAACAGCAGCCAGGTGAGCCAGAACTACCCCATCGTGCAGAACCTGCA
GGGCCAGATGGTGCACCAGGCCATCAGCCCCGCACCCTGAACGCCTGGGTGAAGGTGGT
GGAGGAGAAGGCCTTCAGCCCCGAGGTGATCCCCATGTTCAGCGCCCTGAGCGAGGGCGC
CACCCCCCAGGACCTGAACACGATGTTGAACACCGTGGGCGGCCACCAGGCCGCCATGCA
GATGCTGAAGGAGACCATCAACGAGGAGGCCGCCGAGTGGGACCGCGTGCACCCCGTGCA
CGCCGGCCCCATCGCCCCCGGCCAGATGCGCGAGCCCCGCGGCAGCGACATCGCCGGCAC
CACCAGCACCCTGCAGGAGCAGATCGGCTGGATGACCAACAACCCCCCCATCCCCGTGGG
CGAGATCTACAAGCGGTGGATCATCCTGGGCCTGAACAAGATCGTGCGGATGTACAGCCC
CACCAGCATCCTGGACATCCGCCAGGGCCCCAAGGAGCCCTTCCGCGACTACGTGGACCG
CTTCTACAAGACCCTGCGCGCTGAGCAGGCCAGCCAGGACGTGAAGAACTGGATGACCGA
GACCCTGCTGGTGCAGAACGCCAACCCCGACTGCAAGACCATCCTGAAGGCTCTCGGCCC
CGCGGCCACCCTGGAGGAGATGATGACCGCCTGCCAGGGCGTGGGCGGCCCCGGCCACAA
GGCCCGCGTGCTGGCCGAGGCGATGAGCCAGGTGACGAACCCGGCGACCATCATGATGCA
GCGCGGCAACTTCCGCAACCAGCGGAAGACCGTCAAGTGCTTCAACTGCGGCAAGGAGGG
CCACACCGCCAGGAACTGCCGCGCCCCCGCAAGAAGGGCTGCTGGCGCTGCGGCCGCGA
GGGCCACCAGATGAAGGACTGCACCGAGCGCCAGGCAACTTCCTGGGCAAGATCTGGCC
CAGCTACAAGGGCCGCCCCGGCAACTTCCTGCAGAGCCGCCCCGAGCCCACCGCCCCCCC
CGAGGAGAGCTTCCGCTTCGGCGAGGAGAAGACCACCCCCAGCCAGAAGCAGGAGCCCAT
CGACAAGGAGCTGTACCCCCTGACCAGCCTGCGCAGCCTGTTCGGCAACGACCCCAGCAG
CCAGTAAGAATTCAGACTCGAGCAAGTCTAGA
```

FIG. 63B
(SEQ ID NO:75)

gp160.modSF162.delV2.gag.modSF2

GAATTCGCCACCATGGATGCAATGAAGAGAGGGCTCTGCTGTGTGCTGCTGCTGTGTGGA
GCAGTCTTCGTTTCGCCCAGCGCCGTGGAGAAGCTGTGGGTGACCGTGTACTACGGCGTG
CCCGTGTGGAAGGAGGCCACCACCACCCTGTTCTGCGCCAGCGACGCCAAGGCCTACGAC
ACCGAGGTGCACAACGTGTGGGCCACCCACGCCTGCGTGCCCACCGACCCCAACCCCCAG
GAGATCGTGCTGGAGAACGTGACCGAGAACTTCAACATGTGGAAGAACAACATGGTGGAG
CAGATGCACGAGGACATCATCAGCCTGTGGGACCAGAGCCTGAAGCCCTGCGTGAAGCTG
ACCCCCCTGTGCGTGACCCTGCACTGCACCAACCTGAAGAACGCCACCAACACCAAGAGC
AGCAACTGGAAGGAGATGGACCGCGGCGAGATCAAGAACTGCAGCTTCAAGGTGGGCGCC
GGCAAGCTGATCAACTGCAACACCAGCGTGATCACCCAGGCCTGCCCCAAGGTGAGCTTC
GAGCCCATCCCCATCCACTACTGCGCCCCCGCCGGCTTCGCCATCCTGAAGTGCAACGAC
AAGAAGTTCAACGGCAGCGGCCCCTGCACCAACGTGAGCACCGTGCAGTGCACCCACGGC
ATCCGCCCCGTGGTGAGCACCCAGCTGCTGCTGAACGGCAGCCTGGCCGAGGAGGGCGTG
GTGATCCGCAGCGAGAACTTCACCGACAACGCCAAGACCATCATCGTGCAGCTGAAGGAG
AGCGTGGAGATCAACTGCACCCGCCCCAACAACAACACCCGCAAGAGCATCACCATCGGC
CCCGGCCGCGCCTTCTACGCCACCGGCGACATCATCGGCGACATCCGCCAGGCCCACTGC
AACATCAGCGGCGAGAAGTGGAACAACACCCTGAAGCAGATCGTGACCAAGCTGCAGGCC
CAGTTCGGCAACAAGACCATCGTGTTCAAGCAGAGCAGCGGCGGCGACCCCGAGATCGTG
ATGCACAGCTTCAACTGCGGCGGCGAGTTCTTCTACTGCAACAGCACCCAGCTGTTCAAC
AGCACCTGGAACAACACCATCGGCCCCAACAACACCAACGGCACCATCACCCTGCCCTGC
CGCATCAAGCAGATCATCAACCGCTGGCAGGAGGTGGGCAAGGCCATGTACGCCCCCCCC
ATCCGCGGCCAGATCCGCTGCAGCAGCAACATCACCGGCCTGCTGCTGACCCGCGACGGC
GGCAAGGAGATCAGCAACACCACCGAGATCTTCCGCCCCGGCGGCGGCGACATGCGCGAC
AACTGGCGCAGCGAGCTGTACAAGTACAAGGTGGTGAAGATCGAGCCCCTGGGCGTGGCC
CCCACCAAGGCCAAGCGCCGCGTGGTGCAGCGCGAGAAGCGCGCCGTGACCCTGGGCGCC
ATGTTCCTGGGCTTCCTGGGCGCCGCCGGCAGCACCATGGGCGCCCGCAGCCTGACCCTG
ACCGTGCAGGCCCGCCAGCTGCTGAGCGGCATCGTGCAGCAGCAGAACAACCTGCTGCGC
GCCATCGAGGCCCAGCAGCACCTGCTGCAGCTGACCGTGTGGGGCATCAAGCAGCTGCAG
GCCCGCGTGCTGGCCGTGGAGCGCTACCTGAAGGACCAGCAGCTGCTGGGCATCTGGGGC
TGCAGCGGCAAGCTGATCTGCACCACCGCCGTGCCCTGGAACGCCAGCTGGAGCAACAAG
AGCCTGGACCAGATCTGGAACAACATGACCTGGATGGAGTGGGAGCGCGAGATCGACAAC
TACACCAACCTGATCTACACCCTGATCGAGGAGAGCCAGAACCAGCAGGAGAAGAACGAG
CAGGAGCTGCTGGAGCTGGACAAGTGGGCCAGCCTGTGGAACTGGTTCGACATCAGCAAG
TGGCTGTGGTACATCAAGATCTTCATCATGATCGTGGGCGGCCTGGTGGGCCTGCGCATC
GTGTTCACCGTGCTGAGCATCGTGAACCGCGTGCGCCAGGGCTACAGCCCCCTGAGCTTC
CAGACCCGCTTCCCCGCCCCCCGCGGCCCCGACCGCCCCGAGGGCATCGAGGAGGAGGGC
GGCGAGCGCGACCGCGACCGCAGCAGCCCCCTGGTGCACGGCCTGCTGGCCCTGATCTGG
GACGACCTGCGCAGCCTGTGCCTGTTCAGCTACCACCGCCTGCGCGACCTGATCCTGATC
GCCGCCCGCATCGTGGAGCTGCTGGGCCGCCGCGGCTGGGAGGCCCTGAAGTACTGGGGC
AACCTGCTGCAGTACTGGATCCAGGAGCTGAAGAACAGCGCCGTGAGCCTGTTCGACGCC
ATCGCCATCGCCGTGGCCGAGGGCACCGACCGCATCATCGAGGTGGCCCAGCGCATCGGC
CGCGCCTTCCTGCACATCCCCCGCCGCATCCGCCAGGGCTTCGAGCGCGCCCTGCTGTAA
CTCGAGCAAGTCTAGAGAATTCCGCCCCCCCCCCCCCCCCCCTCTCCCTCCCCCCCCC
TAACGTTACTGGCCGAAGCCGCTTGGAATAAGGCCGGTGTGCGTTTGTCTATATGTTATT
TTCCACCATATTGCCGTCTTTTGGCAATGTGAGGGCCCGGAAACCTGGCCCTGTCTTCTT

FIG. 64A (SEQ ID NO:76)

```
GACGAGCATTCCTAGGGGTCTTTCCCCTCTCGCCAAAGGAATGCAAGGTCTGTTGAATGT
CGTGAAGGAAGCAGTTCCTCTGGAAGCTTCTTGAAGACAAACAACGTCTGTAGCGACCCT
TTGCAGGCAGCGGAACCCCCCACCTGGCGACAGGTGCCTCTGCGGCCAAAAGCCACGTGT
ATAAGATACACCTGCAAAGGCGGCACAACCCCAGTGCCACGTTGTGAGTTGGATAGTTGT
GGAAAGAGTCAAATGGCTCTCCTCAAGCGTATTCAACAAGGGGCTGAAGGATGCCCAGAA
GGTACCCCATTGTATGGGATCTGATCTGGGCCTCGGTGCACATGCTTTACATGTGTTTA
GTCGAGGTTAAAAAAACGTCTAGGCCCCCGAACCACGGGGACGTGGTTTTCCTTTGAAA
AACACGATAATACCATGGGCGCCCGCGCCAGCGTGCTGAGCGGCGGCGAGCTGGACAAGT
GGGAGAAGATCCGCCTGCGCCCCGGCGGCAAGAAGAAGTACAAGCTGAAGCACATCGTGT
GGGCCAGCCGCGAGCTGGAGCGCTTCGCCGTGAACCCCGGCCTGCTGGAGACCAGCGAGG
GCTGCCGCCAGATCCTGGGCCAGCTGCAGCCCAGCCTGCAGACCGGCAGCGAGGAGCTGC
GCAGCCTGTACAACACCGTGGCCACCCTGTACTGCGTGCACCAGCGCATCGACGTCAAGG
ACACCAAGGAGGCCCTGGAGAAGATCGAGGAGGAGCAGAACAAGTCCAAGAAGAAGGCCC
AGCAGGCCGCCGCCGCCGCCGGCACCGGCAACAGCAGCCAGGTGAGCCAGAACTACCCCA
TCGTGCAGAACCTGCAGGGCCAGATGGTGCACCAGGCCATCAGCCCCCGCACCCTGAACG
CCTGGGTGAAGGTGGTGGAGGAGAAGGCCTTCAGCCCCGAGGTGATCCCCATGTTCAGCG
CCCTGAGCGAGGGCGCCACCCCCCAGGACCTGAACACGATGTTGAACACCGTGGGCGGCC
ACCAGGCCGCCATGCAGATGCTGAAGGAGACCATCAACGAGGAGGCCGCCGAGTGGGACC
GCGTGCACCCCGTGCACGCCGGCCCCATCGCCCCCGGCCAGATGCGCGAGCCCCGCGGCA
GCGACATCGCCGGCACCACCAGCACCCTGCAGGAGCAGATCGGCTGGATGACCAACAACC
CCCCCATCCCCGTGGGCGAGATCTACAAGCGGTGGATCATCCTGGGCCTGAACAAGATCG
TGCGGATGTACAGCCCCACCAGCATCCTGGACATCCGCCAGGGCCCCAAGGAGCCCTTCC
GCGACTACGTGGACCGCTTCTACAAGACCCTGCGCGCTGAGCAGGCCAGCCAGGACGTGA
AGAACTGGATGACCGAGACCCTGCTGGTGCAGAACGCCAACCCCGACTGCAAGACCATCC
TGAAGGCTCTCGGCCCCGCGGCCACCCTGGAGGAGATGATGACCGCCTGCCAGGGCGTGG
GCGGCCCCGGCCACAAGGCCCGCGTGCTGGCCGAGGCGATGAGCCAGGTGACGAACCCGG
CGACCATCATGATGCAGCGCGGCAACTTCCGCAACCAGCGGAAGACCGTCAAGTGCTTCA
ACTGCGGCAAGGAGGGCCACACCGCCAGGAACTGCCGCGCCCCCGCAAGAAGGGCTGCT
GGCGCTGCGGCCGCGAGGGCCACCAGATGAAGGACTGCACCGAGCGCCAGGCCAACTTCC
TGGGCAAGATCTGGCCCAGCTACAAGGGCCGCCCCGGCAACTTCCTGCAGAGCCGCCCCG
AGCCCACCGCCCCCCCGAGGAGAGCTTCCGCTTCGGCGAGGAGAAGACCACCCCCAGCC
AGAAGCAGGAGCCCATCGACAAGGAGCTGTACCCCCTGACCAGCCTGCGCAGCCTGTTCG
GCAACGACCCCAGCAGCCAGTAAGAATTCAGACTCGAGCAAGTCTAGA
```

FIG. 64B
(SEQ ID NO:76)

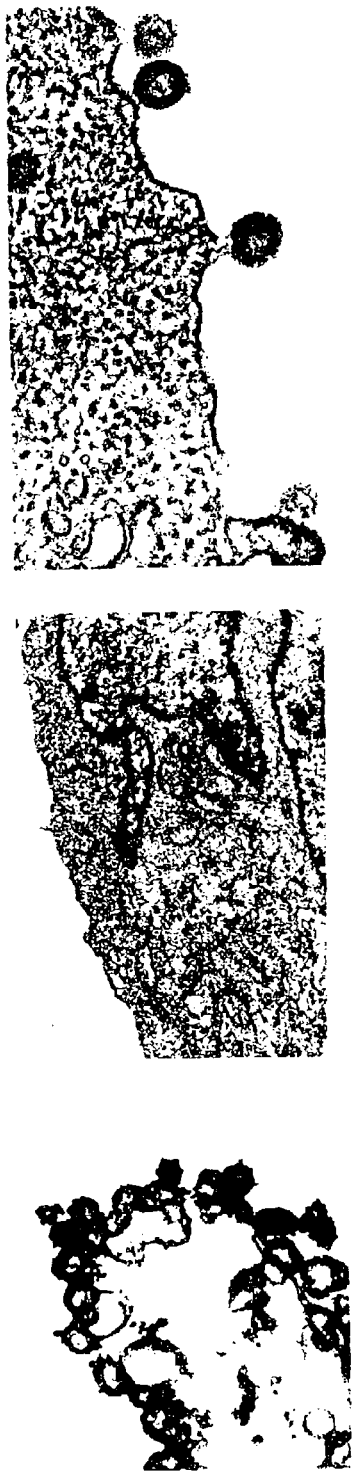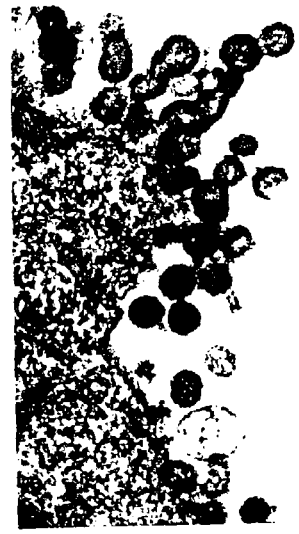
FIG. 65A  FIG. 65B  FIG. 65C  FIG. 65D  FIG. 65E  FIG. 65F

|  | | 1 | | 50 |
|---|---|---|---|---|
| gp160.modSF162 | (1) | GAATTCGCCACCATGGATGCAATGAAGAGAGGGCTCTGCTGTGTGCTGCT |
| gp160.modSF162.delV2 | (1) | GAATTCGCCACCATGGATGCAATGAAGAGAGGGCTCTGCTGTGTGCTGCT |
| gp160.modSF162.delV1V2 | (1) | GAATTCGCCACCATGGATGCAATGAAGAGAGGGCTCTGCTGTGTGCTGCT |
| gp140.modSF162 | (1) | GAATTCGCCACCATGGATGCAATGAAGAGAGGGCTCTGCTGTGTGCTGCT |
| gp140.mut7.modSF162 | (1) | GAATTCGCCACCATGGATGCAATGAAGAGAGGGCTCTGCTGTGTGCTGCT |
| gp140.mut8.modSF162 | (1) | GAATTCGCCACCATGGATGCAATGAAGAGAGGGCTCTGCTGTGTGCTGCT |
| gp120.modSF162 | (1) | GAATTCGCCACCATGGATGCAATGAAGAGAGGGCTCTGCTGTGTGCTGCT |
| Consensus | (1) | GAATTCGCCACCATGGATGCAATGAAGAGAGGGCTCTGCTGTGTGCTGCT |
|  | | 51 | | 100 |
| gp160.modSF162 | (51) | GCTGTGTGGAGCAGTCTTCGTTTCGCCCAGCGCCGCCGTGGAGAAGCTGTGGG |
| gp160.modSF162.delV2 | (51) | GCTGTGTGGAGCAGTCTTCGTTTCGCCCAGCGCCGCCGTGGAGAAGCTGTGGG |
| gp160.modSF162.delV1V2 | (51) | GCTGTGTGGAGCAGTCTTCGTTTCGCCCAGCGCCGCCGTGGAGAAGCTGTGGG |
| gp140.modSF162 | (51) | GCTGTGTGGAGCAGTCTTCGTTTCGCCCAGCGCCGCCGTGGAGAAGCTGTGGG |
| gp140.mut7.modSF162 | (51) | GCTGTGTGGAGCAGTCTTCGTTTCGCCCAGCGCCGCCGTGGAGAAGCTGTGGG |
| gp140.mut8.modSF162 | (51) | GCTGTGTGGAGCAGTCTTCGTTTCGCCCAGCGCCGCCGTGGAGAAGCTGTGGG |
| gp120.modSF162 | (51) | GCTGTGTGGAGCAGTCTTCGTTTCGCCCAGCGCCGCCGTGGAGAAGCTGTGGG |
| Consensus | (51) | GCTGTGTGGAGCAGTCTTCGTTTCGCCCAGCGCCGCCGTGGAGAAGCTGTGGG |
|  | | 101 | | 150 |
| gp160.modSF162 | (101) | TGACCGTGTACTACGGCGTGCCCGTGTGGAAGGAGGCCACCACCACCCTG |
| gp160.modSF162.delV2 | (101) | TGACCGTGTACTACGGCGTGCCCGTGTGGAAGGAGGCCACCACCACCCTG |
| gp160.modSF162.delV1V2 | (101) | TGACCGTGTACTACGGCGTGCCCGTGTGGAAGGAGGCCACCACCACCCTG |
| gp140.modSF162 | (101) | TGACCGTGTACTACGGCGTGCCCGTGTGGAAGGAGGCCACCACCACCCTG |
| gp140.mut7.modSF162 | (101) | TGACCGTGTACTACGGCGTGCCCGTGTGGAAGGAGGCCACCACCACCCTG |
| gp140.mut8.modSF162 | (101) | TGACCGTGTACTACGGCGTGCCCGTGTGGAAGGAGGCCACCACCACCCTG |
| gp120.modSF162 | (101) | TGACCGTGTACTACGGCGTGCCCGTGTGGAAGGAGGCCACCACCACCCTG |
| Consensus | (101) | TGACCGTGTACTACGGCGTGCCCGTGTGGAAGGAGGCCACCACCACCCTG |

```
gp120.modSF162      (251) TGGAGAACGTGACCGAGAACTTCAACATGTGGAAGAACAACATGGTGGAG
         Consensus  (251) TGGAGAACGTGACCGAGAACTTCAACATGTGGAAGAACAACATGGTGGAG
                                                                              350
       gp160.modSF162      (301) CAGATGCACGAGGAGACATCATCAGCCTGTGGGACCCAGAGCCTGAAGCCCTG
gp160.modSF162.delV2      (301) CAGATGCACGAGGAGACATCATCAGCCTGTGGGACCCAGAGCCTGAAGCCCTG
gp160.modSF162.delV1V2    (301) CAGATGCACGAGGAGACATCATCAGCCTGTGGGACCCAGAGCCTGAAGCCCTG
       gp140.modSF162      (301) CAGATGCACGAGGAGACATCATCAGCCTGTGGGACCCAGAGCCTGAAGCCCTG
   gp140.mut7.modSF162    (301) CAGATGCACGAGGAGACATCATCAGCCTGTGGGACCCAGAGCCTGAAGCCCTG
   gp140.mut8.modSF162    (301) CAGATGCACGAGGAGACATCATCAGCCTGTGGGACCCAGAGCCTGAAGCCCTG
       gp120.modSF162     (301) CAGATGCACGAGGAGACATCATCAGCCTGTGGGACCCAGAGCCTGAAGCCCTG
         Consensus        (301) CAGATGCACGAGGAGACATCATCAGCCTGTGGGACCCAGAGCCTGAAGCCCTG gp160.modSF162      (351) CGTGAAGCTGACCCCCCTGTGCGTGCGTGCGTG-----------------------
gp160.modSF162.delV2      (351) CGTGAAGCTGACCCCCCTGTGCGTGCGTGCGTG-----------------------
gp160.modSF162.delV1V2    (375) ----------------------------------
       gp140.modSF162      (401) CGTGAAGCTGACCCCCCTGTGCGTGCGTGCGTGCTGCACTGCACCAACCTGAAGA
   gp140.mut7.modSF162    (401) CGTGAAGCTGACCCCCCTGTGCGTGCGTGCGTGCTGCACTGCACCAACCTGAAGA
   gp140.mut8.modSF162    (401) CGTGAAGCTGACCCCCCTGTGCGTGCGTGCGTGCTGCACTGCACCAACCTGAAGA
       gp120.modSF162     (401) CGTGAAGCTGACCCCCCTGTGCGTGCGTGCGTGCTGCACTGCACCAACCTGAAGA
         Consensus        (351) CGTGAAGCTGACCCCCCTGTGCGTGCGTGCGTGCTGCACTGCACCAACCTGAAGA
                                                                              450
       gp160.modSF162      (401) ACGCCACCAACACCAAGAGCAGCAGCAACTGGAAGGAGATGGACCGCGGCGAG
gp160.modSF162.delV2      (401) ACGCCACCAACACCAAGAGCAGCAGCAACTGGAAGGAGATGGACCGCGGCGAG
gp160.modSF162.delV1V2    (375) ----------------------------------
       gp140.modSF162      (401) ACGCCACCAACACCAAGAGCAGCAGCAACTGGAAGGAGATGGACCGCGGCGAG
   gp140.mut7.modSF162    (401) ACGCCACCAACACCAAGAGCAGCAGCAACTGGAAGGAGATGGACCGCGGCGAG
   gp140.mut8.modSF162    (401) ACGCCACCAACACCAAGAGCAGCAGCAACTGGAAGGAGATGGACCGCGGCGAG
       gp120.modSF162     (401) ACGCCACCAACACCAAGAGCAGCAGCAACTGGAAGGAGATGGACCGCGGCGAG
         Consensus        (401) ACGCCACCAACACCAAGAGCAGCAGCAACTGGAAGGAGATGGACCGCGGCGAG
```

FIG. 66A-3

```
                      451                                                500
gp160.modSF162        (451) ATCAAGAACTGCAGCTTCAAGGTGACCACCAGCATCCGCAACAAGATGCA
gp160.modSF162.delV2  (451) ATCAAGAACTGCAGCTTCAAGGTGACCACCAGCATCCGCAACAAGATGCA
gp160.modSF162.delV1V2 (376) ----------------------------GGC-------------------
gp140.modSF162        (451) ATCAAGAACTGCAGCTTCAAGGTGACCACCAGCATCCGCAACAAGATGCA
gp140.mut7.modSF162   (451) ATCAAGAACTGCAGCTTCAAGGTGACCACCAGCATCCGCAACAAGATGCA
gp140.mut8.modSF162   (451) ATCAAGAACTGCAGCTTCAAGGTGACCACCAGCATCCGCAACAAGATGCA
gp120.modSF162        (451) ATCAAGAACTGCAGCTTCAAGGTGACCACCAGCATCCGCAACAAGATGCA
Consensus             (451) ATCAAGAACTGCAGCTTCAAGGTGACCACCAGCATCCGCAACAAGATGCA 501                                                550
gp160.modSF162        (501) GAAGGAGTACGCCCTGTTCTACAAGCTGGACGTGGTGCCCATCGACAACG
gp160.modSF162.delV2  (478) -----GCC------------------------------GG----------
gp160.modSF162.delV1V2 (379) -----GCC------------------------------GG----------
gp140.modSF162        (501) GAAGGAGTACGCCCTGTTCTACAAGCTGGACGTGGTGCCCATCGACAACG
gp140.mut7.modSF162   (501) GAAGGAGTACGCCCTGTTCTACAAGCTGGACGTGGTGCCCATCGACAACG
gp140.mut8.modSF162   (501) GAAGGAGTACGCCCTGTTCTACAAGCTGGACGTGGTGCCCATCGACAACG
gp120.modSF162        (501) GAAGGA

FIG. 66A-5

|       |       | 751 |                                                              | 800 |
|-------|-------|-----|--------------------------------------------------------------|-----|
| gp160.modSF162 | (751) | | GTGGTGAGCACCCAGCTGCTGCTGAACGGCAGCCTGGCCGAGGAGGCGT | |
| gp160.modSF162.delV2 | (670) | | GTGGTGAGCACCCAGCTGCTGCTGAACGGCAGCCTGGCCGAGGAGGCGT | |
| gp160.modSF162.delV1V2 | (562) | | GTGGTGAGCACCCAGCTGCTGCTGAACGGCAGCCTGGCCGAGGAGGCGT | |
| gp140.modSF162 | (751) | | GTGGTGAGCACCCAGCTGCTGCTGAACGGCAGCCTGGCCGAGGAGGCGT | |
| gp140.mut.modSF162 | (751) | | GTGGTGAGCACCCAGCTGCTGCTGAACGGCAGCCTGGCCGAGGAGGCGT | |
| gp140.mut7.modSF162 | (751) | | GTGG-GAGCACCCAGCTGCTGCTGAACGGCAGCCTGGCCGAGGAGGCGT | |
| gp140.mut8.modSF162 | (751) | | GTGGTGAGCACCCAGCTGCTGCTGAACGGCAGCCTGGCCGAGGAGGCGT | |
| gp120.modSF162 | (751) | | GTGGTGAGCACCCAGCTGCTGCTGAACGGCAGCCTGGCCGAGGAGGCGT | |
| Consensus | (751) | | GTGGTGAGCACCCAGCTGCTGCTGAACGGCAGCCTGGCCGAGGAGGCGT | |

|       |       | 801 |                                                              | 850 |
|-------|-------|-----|--------------------------------------------------------------|-----|
| gp160.modSF162 | (801) | | GGTGATCCGCAGCGAGAACTTCACCGACAACGCCAAGACCATCATCGTGC | |
| gp160.modSF162.delV2 | (720) | | GGTGATCCGCAGCGAGAACTTCACCGACAACGCCAAGACCATCATCGTGC | |
| gp160.modSF162.delV1V2 | (612) | | GGTGATCCGCAGCGAGAACTTCACCGACAACGCCAAGACCATCATCGTGC | |
| gp140.modSF162 | (801) | | GGTGATCCGCAGCGAGAACTTCACCGACAACGCCAAGACCATCATCGTGC | |
| gp140.mut.modSF162 | (801) | | GGTGATCCGCAGCGAGAACT-CACCGACAACGCCAAGACCATCATCGTGC | |
| gp140.mut7.modSF162 | (801) | | GGTGATCCGCAGCGAGAACTTCACCGACAACGCCAAGACCATCATCGTGC | |
| gp140.mut8.modSF162 | (801) | | GGTGATCCGCAGCGAGAACTTCACCGACAACGCCAAGACCATCATCGTGC | |
| gp120.modSF162 | (801) | | GGTGATCCGCAGCGAGAACTTCACCGACAACGCCAAGACCATCATCGTGC | |
| Consensus | (801) | | GGTGATCCGCAGCGAGAACTTCACCGACAACGCCAAGACCATCATCGTGC | |

|       |       | 851 |                                                              | 900 |
|-------|-------|-----|--------------------------------------------------------------|-----|
| gp160.modSF162 | (851) | | AGCTGAAGGAGAGCGTGGAGATCAACTGCACCCGCCCCAACAACAACACC | |
| gp160.modSF162.delV2 | (770) | | AGCTGAAGGAGAGCGTGGAGATCAACTGCACCCGCCCCAACAACAACACC | |
| gp160.modSF162.delV1V2 | (662) | | AGCTGAAGGAGAGCGTGGAGATCAACTGCACCCGCCCCAACAACAACACC | |

FIG. 66A-6

|  |  |  |
|---|---|---|
| gp140.modSF162 | (851) | AGCTGAAGGAGAGAGCGTGGAGATCAACTGCACCCGCCCCAACAACAACACC |
| gp140.mut.modSF162 | (851) | AGCTGAAGGAGAGAGCGTGGAGATCAACTGCACCCGCCCCAACAACAACACC |
| gp140.mut7.modSF162 | (851) | AGCTGAAGGAGAGAGCGTGGAGATCAACTGCACCCGCCCCAACAACAACACC |
| gp140.mut8.modSF162 | (851) | AGCTGAAGGAGAGAGCGTGGAGATCAACTGCACCCGCCCCAACAACAACACC |
| gp120.modSF162 | (851) | AGCTGAAGGAGAGAGCGTGGAGATCAACTGCACCCGCCCCAACAACAACACC |
| Consensus | (851) | AGCTGAAGGAGAGAGCGTGGAGATCAACTGCACCCGCCCCAACAACAACACC |
|  |  | 901   950 |
| gp160.modSF162 | (901) | CGCAAGAGAGCATCACCATCCGGCCCGCGCCGGCCTTCTACGCCACCGGCGA |
| gp160.modSF162.delV2 | (820) | CGCAAGAGAGCATCACCATCCGGCCCGCGCCGGCCTTCTACGCCACCGGCGA |
| gp160.modSF162.delV1V2 | (712) | CGCAAGAGAGCATCACCATCCGGCCCGCGCCGGCCTTCTACGCCACCGGCGA |
| gp140.modSF162 | (901) | CGCAAGAGAGCATCACCATCCGGCCCGCGCCGGCCTTCTACGCCACCGGCGA |
| gp140.mut7.modSF162 | (901) | CGCAAGAGAGCATCACCATCCGGCCCGCGCCGGCCTTCTACGCCACCGGCGA |
| gp140.mut8.modSF162 | (901) | CGCAAGAGAGCATCACCATCCGGCCCGCGCCGGCCTTCTACGCCACCGGCGA |
| gp120.modSF162 | (901) | CGCAAGAGAGCATCACCATCCGGCCCGCGCCGGCCTTCTACGCCACCGGCGA |
| Consensus | (901) | CGCAAGAGAGCATCACCATCCGGCCCGCGCCGGCCTTCTACGCCACCGGCGA |
|  |  | 951   1000 |
| gp160.modSF162 | (951) | CATCATCGGCGACATCCGGCAGGCCCACTGCAACATCAGCGGCGAGAAGT |
| gp160.modSF162.delV2 | (870) | CATCATCGGCGACATCCGGCAGGCCCACTGCAACATCAGCGGCGAGAAGT |
| gp160.modSF162.delV1V2 | (762) | CATCATCGGCGACATCCGGCAGGCCCACTGCAACATCAGCGGCGAGAAGT |
| gp140.modSF162 | (951) | CATCATCGGCGACATCCGGCAGGCCCACTGCAACATCAGCGGCGAGAAGT |
| gp140.mut7.modSF162 | (951) | CATCATCGGCGACATCCGGCAGGCCCACTGCAACATCAGCGGCGAGAAGT |
| gp140.mut8.modSF162 | (951) | CATCATCGGCGACATCCGGCAGGCCCACTGCAACATCAGCGGCGAGAAGT |
| gp120.modSF162 | (951) | CATCATCGGCGACATCCGGCAGGCCCACTGCAACATCAGCGGCGAGAAGT |
| Consensus | (951) | CATCATCGGCGACATCCGGCAGGCCCACTGCAACATCAGCGGCGAGAAGT |

FIG. 66A-7

```
                              1001                                                    1050
    gp160.modSF162     (1001) GGAACAACAACACCCTGAAGCAGCAGATCGTGACCAAGCTGCAGGCCCAGTTCGGC
gp160.modSF162.delV2    (920) GGAACAACAACACCCTGAAGCAGCAGATCGTGACCAAGCTGCAGGCCCAGTTCGGC
gp160.modSF162.delV1V2  (812) GGAACAACAACACCCTGAAGCAGCAGATCGTGACCAAGCTGCAGGCCCAGTTCGGC
    gp140.modSF162     (1001) GGAACAACAACACCCTGAAGCAGCAGATCGTGACCAAGCTGCAGGCCCAGTTCGGC
    gp140.mut7.modSF162 (1001) GGAACAACAACACCCTGAAGCAGCAGATCGTGACCAAGCTGCAGGCCCAGTTCGGC
    gp140.mut8.modSF162 (1001) GGAACAACAACACCCTGAAGCAGCAGATCGTGACCAAGCTGCAGGCCCAGTTCGGC
    gp120.modSF162     (1001) GGAACAACAACACCCTGAAGCAGCAGATCGTGACCAAGCTGCAGGCCCAGTTCGGC
          Consensus   (1001) GGAACAACAACACCCTGAAGCAGCAGATCGTGACCAAGCTGCAGGCCCAGTTCGGC 1051                                                    1100
    gp160.modSF162     (1051) AACAAGACCATCGTGTTCAAGCAGAGCAGCGGCGGCGACCCCGAGATCGT
gp160.modSF162.delV2    (970) AACAAGACCATCGTGTTCAAGCAGAGCAGCGGCGGCGACCCCGAGATCGT
gp160.modSF162.delV1V2  (862) AACAAGACCATCGTGTTCAAGCAGAGCAGCGGCGGCGACCCCGAGATCGT
    gp140.modSF162     (1051) AACAAGACCATCGTGTTCAAGCAGAGCAGCGGCGGCGACCCCGAGATCGT
    gp140.mut7.modSF162 (1051) AACAAGACCATCGTGTTCAAGCAGAGCAGCGGCGGCGACCCCGAGATCGT
    gp140.mut8.modSF162 (1051) AACAAGACCATCGTGTTCAAGCAGAGCAGCGGCGGCGACCCCGAGATCGT
    gp120.modSF162     (1051) AACAAGACCATCGTGTTCAAGCAGAGCAGCGGCGGCGACCCCGAGATCGT
          Consensus   (1051) AACAAGACCATCGTGTTCAAGCAGAGCAGCGGCGGCGACCCCGAGATCGT 1101                                                    1150
    gp160.modSF162     (1101) GATGCACAGCTTCAACTGCGGCGGCGAGTTCTTCTACTGCAACAGCACCC
gp160.modSF162.delV2   (1020) GATGCACAGCTTCAACTGCGGCGGCGAGTTCTTCTACTGCAACAGCACCC
gp160.modSF162.delV1V2  (912) GATGCACAGCTTCAACTGCGGCGGCGAGTTCTTCTACTGCAACAGCACCC
    gp140.modSF162     (1101) GATGCACAGCTTCAACTGCGGCGGCGAGTTCTTCTACTGCAACAGCACCC
    gp140.mut7.modSF162 (1101) GATGCACAGCTTCAACTGCGGCGGCGAGTTCTTCTACTGCAACAGCACCC
    gp140.mut8.modSF162 (1101) GATGCACAGCTTCAACTGCGGCGGCGAGTTCTTCTACTGCAACAGCACCC
    gp120.modSF162     (1101) GATGCACAGCTTCAACTGCGGCGGCGAGTTCTTCTACTGCAACAGCACCC
          Consensus   (1101) GATGCACAGCTTCAACTGCGGCGGCGAGTTCTTCTACTGCAACAGCACCC 1151                                                    1200
    gp160.modSF162     (1151) AGCTGTTCAACAGCACCTGGAACAACACCGGCCCCAACAACACCAAC
```

FIG. 66A-8

| | | |
|---|---|---|
| gp160.modSF162 | (1070) | AGCTGTTCAACAGCACCTGGAACAACAACACCATCGGCCCCAACAACAACACCAAC |
| gp160.modSF162.delV2 | (962) | AGCTGTTCAACAGCACCTGGAACAACAACACCATCGGCCCCAACAACAACACCAAC |
| gp140.modSF162 | (1151) | AGCTGTTCAACAGCACCTGGAACAACAACACCATCGGCCCCAACAACAACACCAAC |
| gp140.modSF162.delV2 | (1151) | AGCTGTTCAACAGCACCTGGAACAACAACACCATCGGCCCCAACAACAACACCAAC |
| gp160.modSF162.delV1V2 | (1151) | AGCTGTTCAACAGCACCTGGAACAACAACACCATCGGCCCCAACAACAACACCAAC |
| gp140.mut7.modSF162 | (1151) | AGCTGTTCAACAGCACCTGGAACAACAACACCATCGGCCCCAACAACAACACCAAC |
| gp140.mut8.modSF162 | (1151) | AGCTGTTCAACAGCACCTGGAACAACAACACCATCGGCCCCAACAACAACACCAAC |
| gp120.modSF162 | (1151) | AGCTGTTCAACAGCACCTGGAACAACAACACCATCGGCCCCAACAACAACACCAAC |
| Consensus | | AGCTGTTCAACAGCACCTGGAACAACAACACCATCGGCCCCAACAACAACACCAAC |
| | | 1250 |
| gp160.modSF162 | (1201) | GGCACCATCACCCTGCCCTGCCGCATCAAGCAGATCATCAACCGCTGGCA |
| gp160.modSF162.delV2 | (1120) | GGCACCATCACCCTGCCCTGCCGCATCAAGCAGATCATCAACCGCTGGCA |
| gp140.modSF162 | (1201) | GGCACCATCACCCTGCCCTGCCGCATCAAGCAGATCATCAACCGCTGGCA |
| gp140.modSF162.delV2 | (1201) | GGCACCATCACCCTGCCCTGCCGCATCAAGCAGATCATCAACCGCTGGCA |
| gp160.modSF162.delV1V2 | (1012) | GGCACCATCACCCTGCCCTGCCGCATCAAGCAGATCATCAACCGCTGGCA |
| gp140.mut7.modSF162 | (1201) | GGCACCATCACCCTGCCCTGCCGCATCAAGCAGATCATCAACCGCTGGCA |
| gp140.mut8.modSF162 | (1201) | GGCACCATCACCCTGCCCTGCCGCATCAAGCAGATCATCAACCGCTGGCA |
| gp120.modSF162 | (1201) | GGCACCATCACCCTGCCCTGCCGCATCAAGCAGATCATCAACCGCTGGCA |
| Consensus | (1201) | GGCACCATCACCCTGCCCTGCCGCATCAAGCAGATCATCAACCGCTGGCA |
| | | 1251                                          1300 |
| gp160.modSF162 | (1251) | GGAGGTGGGCAAGGCCATGTACGCCCCCATCCGCGGCCAGATCCGCT |
| gp160.modSF162.delV2 | (1170) | GGAGGTGGGCAAGGCCATGTACGCCCCCATCCGCGGCCAGATCCGCT |
| gp140.modSF162 | (1251) | GGAGGTGGGCAAGGCCATGTACGCCCCCATCCGCGGCCAGATCCGCT |
| gp140.modSF162.delV2 | (1251) | GGAGGTGGGCAAGGCCATGTACGCCCCCATCCGCGGCCAGATCCGCT |
| gp160.modSF162.delV1V2 | (1062) | GGAGGTGGGCAAGGCCATGTACGCCCCCATCCGCGGCCAGATCCGCT |
| gp140.mut7.modSF162 | (1251) | GGAGGTGGGCAAGGCCATGTACGCCCCCATCCGCGGCCAGATCCGCT |
| gp140.mut8.modSF162 | (1251) | GGAGGTGGGCAAGGCCATGTACGCCCCCATCCGCGGCCAGATCCGCT |
| gp120.modSF162 | (1251) | GGAGGTGGGCAAGGCCATGTACGCCCCCATCCGCGGCCAGATCCGCT |
| Consensus | (1251) | GGAGGTGGGCAAGGCCATGTACGCCCCCATCCGCGGCCAGATCCGCT |

FIG. 66A-9

```
                         1301                                                      1350
gp160.modSF162        (1301) GCAGCAGCAACATCACCGGCCTGCTGCTGACCCGCGACGGCGGCAAGGAG
gp160.modSF162.delV2  (1220) GCAGCAG

```
                          1451                                                          1500
gp160.modSF162       (1451) TGGGCGTGGCCCCCACCAAGGCCAAGCGCCGGTGGTGCAGCGCGAGAAG
gp160.modSF162.delV2 (1370) TGGGCGTGGCCCCC

FIG. 66A-12

```
                                1601                                              1650
gp160.modSF162          (1601) TGCTGAGCGGCATCGTGCAGCAGCAGAACAACCTGCTGCGCGCCATCGAG
gp160.modSF162.delV2    (1520) TGCTGAGCGGCATCGTGCAGCAGCAGAACAACCTGCTGCGCGCCATCGAG
gp160.modSF162.delV1V2  (1412) TGCTGAGCGGCATCGTGCAGCAGCAGA

```
gp120.modsF162    (    )  ------------------------------------------------
Consensus         (1701)  GGCCCGCGTGCTGGCCGTGGAGGCGCTACCTGAAGGACCAGCTGCTGG  1800
                                                  1751
gp160.modsF162    (1751)  GCATCTGGGGCTGCAGCGGCTGCAAGCTGATCTGCACCACCGCCGTGCCCCTGG
gp160.modsF162.delV2 (1670) GCATCTGGGGCTGCAGCGGCTGCAAGCTGATCTGCACCACCGCCGTGCCCCTGG
gp160.modsF162.delV1V2 (1562) GCATCTGGGGCTGCAGCGGCTGCAAGCTGATCTGCACCGCCGTGCCCCTGG
gp140.modsF162    (1751)  GCATCTGGGGCTGCAGCGGCTGCAAGCTGATCTGCACCACCGCCGTGCCCCTGG
gp140.mut.modsF162 (1751) GCATCTGGGGCTGCAGCGGCTGCAAGCTGATCTGCACCACCGCCGTGCCCCTGG
gp140.mut7.modsF162 (1751) GCATCTGGGGCTGCAGCGGCTGCAAGCTGATCTGCACCACCGCCGTGCCCCTGG
gp140.mut8.modsF162 (1751) GCATCTGGGGCTGCAGCGGCTGCAAGCTGATCTGCACCACCGCCGTGCCCCTGG
gp120.modsF162    (1513)  ------------------------------------------------
Consensus         (1751)  GCATCTGGGGCTGCAGCGGCTGCAAGCTGATCTGCACCACCGCCGTGCCCCTGG
                                                  1801                               1850
gp160.modsF162    (1801)  AACGCCAGCTGGAGCAACAAGAGCCTGGACCAGATCTGGAACAACATGAC
gp160.modsF162.delV2 (1720) AACGCCAGCTGGAGCAACAAGAGCCTGGACCAGATCTGGAACAACATGAC
gp160.modsF162.delV1V2 (1612) AACGCCAGCTGGAGCAACAAGAGCCTGGACCAGATCTGGAACAACATGAC
gp140.modsF162    (1801)  AACGCCAGCTGGAGCAACAAGAGCCTGGACCAGATCTGGAACAACATGAC
gp140.mut.modsF162 (1801) AACGCCAGCTGGAGCAACAAGAGCCTGGACCAGATCTGGAACAACATGAC
gp140.mut7.modsF162 (1801) AACGCCAGCTGGAGCAACAAGAGCCTGGACCAGATCTGGAACAACATGAC
gp140.mut8.modsF162 (1801) AACGCCAGCTGGAGCAACAAGAGCCTGGACCAGATCTGGAACAACATGAC
gp120.modsF162    (1513)  ------------------------------------------------
Consensus         (1801)  AACGCCAGCTGGAGCAACAAGAGCCTGGACCAGATCTGGAACAACATGAC
                                                  1851                               1900
gp160.modsF162    (1851)  CTGGATGGAGTGGGAGCGCGAGATCGACAACTACACCAACCTGATCTACA
gp160.modsF162.delV2 (1770) CTGGATGGAGTGGGAGCGCGAGATCGACAACTACACCAACCTGATCTACA
gp160.modsF162.delV1V2 (1662) CTGGATGGAGTGGGAGCGCGAGATCGACAACTACACCAACCTGATCTACA
gp140.modsF162    (1851)  CTGGATGGAGTGGGAGCGCGAGATCGACAACTACACCAACCTGATCTACA
gp140.mut.modsF162 (1851) CTGGATGGAGTGGGAGCGCGAGATCGACAACTACACCAACCTGATCTACA
gp140.mut7.modsF162 (1851) CTGGATGGAGTGGGAGCGCGAGATCGACAACTACACCAACCTGATCTACA
gp140.mut8.modsF162 (1851) CTGGATGGAGTGGGAGCGCGAGATCGACAACTACACCAACCTGATCTACA
gp120.modsF162    (1513)  ------------------------------------------------
Consensus         (1851)  CTGGATGGAGTGGGAGCGCGAGATCGACAACTACACCAACCTGATCTACA
```

```
gp140.mut7.modSF162    (2001) GTGGCTGTGGTACATCTAACTCGAG---------------------------
gp140.mut8.modSF162    (2001) GTGGCTGTGGTACATCTAACTCGAG---------------------------
gp120.modSF162         (1513) ----------------------------------------------------
gp160.modSF162         (2001) GTGGCTGTGGTACATCTAACTCGAG---------------------------
Consensus              (2001)                                                 2100

2051
gp160.modSF162         (2051) GCCTGCGCGATCGTGTTCACCGTGCTGAGCATCGTGAACCGCGTGCGCCAG
gp160.modSF162.delV2   (1970) GCCTGCGCGATCGTGTTCACCGTGCTGAGCATCGTGAACCGCGTGCGCCAG
gp160.modSF162.delV1V2 (1862) GCCTGCGCGATCGTGTTCACCGTGCTGAGCATCGTGAACCGCGTGCGCCAG
gp140.modSF162         (2026) GCCTGCGCGATCGTGTTCACCGTGCTGAGCATCGTGAACCGCGTGCGCCAG
gp140.mut7.modSF162    (2026) ----------------------------------------------------
gp140.mut8.modSF162    (2026) ----------------------------------------------------
gp120.modSF162         (1513) ----------------------------------------------------
Consensus              (2051)                                                 2150

2101
gp160.modSF162         (2101) GGCTACAGCCCCCTGAGCTTCCAGACCCGCTTCCCCGCCCCCGGCGGCCCC
gp160.modSF162.delV2   (2020) GGCTACAGCCCCCTGAGCTTCCAGACCCGCTTCCCCGCCCCCGGCGGCCCC
gp160.modSF162.delV1V2 (1912) GGCTACAGCCCCCTGAGCTTCCAGACCCGCTTCCCCGCCCCCGGCGGCCCC
gp140.modSF162         (2026) GGCTACAGCCCCCTGAGCTTCCAGACCCGCTTCCCCGCCCCCGGCGGCCCC
gp140.mut7.modSF162    (2026) ----------------------------------------------------
gp140.mut8.modSF162    (2026) ----------------------------------------------------
gp120.modSF162         (1513) ----------------------------------------------------
Consensus              (2101)                                                 2200

2151
gp160.modSF162         (2151) CGACCGCCCCGAGGGCATCGAGGAGGAGGGCGGCGAGCGCGACCGCGACC
gp160.modSF162.delV2   (2070) CGACCGCCCCGAGGGCATCGAGGAGGAGGGCGGCGAGCGCGACCGCGACC
gp160.modSF162.delV1V2 (1962) CGACCGCCCCGAGGGCATCGAGGAGGAGGGCGGCGAGCGCGACCGCGACC
gp140.modSF162         (2026) CGACCGCCCCGAGGGCATCGAGGAGGAGGGCGGCGAGCGCGACCGCGACC
gp140.mut7.modSF162    (2026) ----------------------------------------------------
gp140.mut8.modSF162    (2026) ----------------------------------------------------
gp120.modSF162         (1513) ----------------------------------------------------
Consensus              (2151)
```

FIG. 66A-15

```
                                    2201                                              2250
gp160.modSF162              (2201) GCAGCAGCCCCCTGGTGCACGGCCTGCTGGCCCTGATCTGGGACGACCTG
gp160.modSF162.delV

```
gp140.modSF162       (2026) ------------------------------------------------
gp140.mut7.modSF162  (2026) ------------------------------------------------
gp140.mut8.modSF162  (2026) ------------------------------------------------
gp160.modSF162.delV2 (2026) ------------------------------------------------
gp140.modSF162.delV1V2 (1513) ----------------------------------------------
gp120.modSF162       (2026) ------------------------------------------------
           Consensus (2301)                                             2400 gp160.modSF162       (2351) AGTACTGGGGCAACCTGCTGCAGTACTGGATCCAGGAGCTGAAGAACAGC
gp140.modSF162       (2270) AGTACTGGGGCAACCTGCTGCAGTACTGGATCCAGGAGCTGAAGAACAGC
gp140.mut7.modSF162  (2162) AGTACTGGGGCAACCTGCTGCAGTACTGGATCCAGGAGCTGAAGAACAGC
gp140.mut8.modSF162  (2026) ------------------------------------------------
gp160.modSF162.delV2 (2026) ------------------------------------------------
gp140.modSF162.delV1V2 (2026) --------------------------------------------
gp120.modSF162       (1513) ------------------------------------------------
           Consensus (2351)

gp160.modSF162       (2401) GCCGTGAGCCTGTTCGACGCCATGCGCCGTGGCCGAGGGCACCGA
gp140.modSF162       (2320) GCCGTGAGCCTGTTCGACGCCATGCGCCGTGGCCGAGGGCACCGA
gp140.mut7.modSF162  (2212) GCCGTGAGCCTGTTCGACGCCATGCGCCGTGGCCGAGGGCACCGA
gp140.mut8.modSF162  (2026) ---------------------------------------------
gp160.modSF162.delV2 (2026) ---------------------------------------------
gp140.modSF162.delV1V2 (2026) ------------------------------------------
gp120.modSF162       (1513) ---------------------------------------------
           Consensus (2401)
```

FIG. 66A-17

```
                              2500
gp160.modSF162        (2451) CCGCATCATCGAGGTGGGCCCAGCGCATCGGCCGCCTTCCTGCACATCC
gp160.modSF162.delV2  (2370) CCGCATCATCGAGGTGGGCCCAGCGCATCGGCCGCCTTCCTGCACATCC
gp160.modSF162.delV1V2 (2262) CCGCATCATCGAGGTGGGCCCAGCGCATCGGCCGCCTTCCTGCACATCC
gp140.modSF162        (2026) -------------------------------------------------
gp140.mut.modSF162    (2026) -------------------------------------------------
gp140.mut7.modSF162   (2026) -------------------------------------------------
gp140.mut8.modSF162   (2026) -------------------------------------------------
gp120.modSF162        (1513) -------------------------------------------------
Consensus             (2451)

2547
gp160.modSF162        (2501) CCGCCCGCATCCGCCAGGGCTTCGAGCGCCCTGCTGTAACTCGAG
gp160.modSF162.delV2  (2420) CCCGCCCGCATCCGCCAGGGCTTCGAGCGCCCTGCTGTAACTCGAG
gp160.modSF162.delV1V2 (2312) CCGCCCGCATCCGCCAGGGCTTCGAGCGCCCTGCTGTAACTCGAG
gp140.modSF162        (2026) ---------------------------------------------
gp140.mut.modSF162    (2026) ---------------------------------------------
gp140.mut7.modSF162   (2026) ---------------------------------------------
gp140.mut8.modSF162   (2026) ---------------------------------------------
gp120.modSF162        (1513) ---------------------------------------------
Consensus             (2501)
```

FIG. 66A-18

```
                                               Start of tPA
                              1         ↓                   40
         gp160          (1)  GAATTCGCCACCATGGATGCAATGAAGAGAGGGCTCTGCT
      gp160 del V1     (1)  GAATTCGCCACCATGGATGCAATGAAGAGAGGGCTCTGCT
      gp160 del V2     (1)  GAATTCGCCACCATGGATGCAATGAAGAGAGGGCTCTGCT
     gp160 del V1-2    (1)  GAATTCGCCACCATGGATGCAATGAAGAGAGGGCTCTGCT
    gp 160 del 128-194 (1)  GAATTCGCCACCATGGATGCAATGAAGAGAGGGCTCTGCT
           gp140TM     (1)  GAATTCGCCACCATGGATGCAATGAAGAGAGGGCTCTGCT
            gp140      (1)  GAATTCGCCACCATGGATGCAATGAAGAGAGGGCTCTGCT
          gp140mut     (1)  GAATTCGCCACCATGGATGCAATGAAGAGAGGGCTCTGCT
            gp120      (1)  GAATTCGCCACCATGGATGCAATGAAGAGAGGGCTCTGCT
         Consensus     (1)  GAATTCGCCACCATGGATGCAATGAAGAGAGGGCTCTGCT
                              41                            80
         gp160         (41) GTGTGCTGCTGCTGTGTGGAGCAGTCTTCGTTTCGCCCAG
      gp160 del V1    (41) GTGTGCTGCTGCTGTGTGGAGCAGTCTTCGTTTCGCCCAG
      gp160 del V2    (41) GTGTGCTGCTGCTGTGTGGAGCAGTCTTCGTTTCGCCCAG
     gp160 del V1-2   (41) GTGTGCTGCTGCTGTGTGGAGCAGTCTTCGTTTCGCCCAG
   gp 160 del 128-194 (41) GTGTGCTGCTGCTGTGTGGAGCAGTCTTCGTTTCGCCCAG
           gp140TM    (41) GTGTGCTGCTGCTGTGTGGAGCAGTCTTCGTTTCGCCCAG
            gp140     (41) GTGTGCTGCTGCTGTGTGGAGCAGTCTTCGTTTCGCCCAG
          gp140mut    (41) GTGTGCTGCTGCTGTGTGGAGCAGTCTTCGTTTCGCCCAG
            gp120     (41) GTGTGCTGCTGCTGTGTGGAGCAGTCTTCGTTTCGCCCAG
         Consensus    (41) GTGTGCTGCTGCTGTGTGGAGCAGTCTTCGTTTCGCCCAG end  of tPA ↓
                              81                           120
         gp160         (81) CGCCACCACCGTGCTGTGGGTGACCGTGTACTACGGCGTG
      gp160 del V1    (81) CGCCACCACCGTGCTGTGGGTGACCGTGTACTACGGCGTG
      gp160 del V2    (81) CGCCACCACCGTGCTGTGGGTGACCGTGTACTACGGCGTG
     gp160 del V1-2   (81) CGCCACCACCGTGCTGTGGGTGACCGTGTACTACGGCGTG
   gp 160 del 128-194 (81) CGCCACCACCGTGCTGTGGGTGACCGTGTACTACGGCGTG
           gp140TM    (81) CGCCACCACCGTGCTGTGGGTGACCGTGTACTACGGCGTG
            gp140     (81) CGCCACCACCGTGCTGTGGGTGACCGTGTACTACGGCGTG
          gp140mut    (81) CGCCACCACCGTGCTGTGGGTGACCGTGTACTACGGCGTG
            gp120     (81) CGCCACCACCGTGCTGTGGGTGACCGTGTACTACGGCGTG
         Consensus    (81) CGCCACCACCGTGCTGTGGGTGACCGTGTACTACGGCGTG
                             121                           160
          gp 160     (121) CCCGTGTGGAAGGAGGCCACCACCACCCTGTTCTGCGCCA
      gp160 del V1   (121) CCCGTGTGGAAGGAGGCCACCACCACCCTGTTCTGCGCCA
      gp160 del V2   (121) CCCGTGTGGAAGGAGGCCACCACCACCCTGTTCTGCGCCA
     gp160 del V1-2  (121) CCCGTGTGGAAGGAGGCCACCACCACCCTGTTCTGCGCCA
   gp 160 del 128-194(121) CCCGTGTGGAAGGAGGCCACCACCACCCTGTTCTGCGCCA
           gp140TM   (121) CCCGTGTGGAAGGAGGCCACCACCACCCTGTTCTGCGCCA
            gp140    (121) CCCGTGTGGAAGGAGGCCACCACCACCCTGTTCTGCGCCA
          gp140mut   (121) CCCGTGTGGAAGGAGGCCACCACCACCCTGTTCTGCGCCA
            gp120    (121) CCCGTGTGGAAGGAGGCCACCACCACCCTGTTCTGCGCCA
         Consensus   (121) CCCGTGTGGAAGGAGGCCACCACCACCCTGTTCTGCGCCA
```

FIG. 66B-1

```
                         161                                        200
        gp160     (161)  GCGACGCCAAGGCTTACAAGGCCGAGGCCCACAACGTGTG
   gp160 del V1   (161)  GCGACGCCAAGGCTTACAAGGCCGAGGCCCACAACGTGTG
   gp160 del V2   (161)  GCGACGCCAAGGCTTACAAGGCCGAGGCCCACAACGTGTG
  gp160 del V1-2  (161)  GCGACGCCAAGGCTTACAAGGCCGAGGCCCACAACGTGTG
gp 160 del 128-194 (161) GCGACGCCAAGGCTTACAAGGCCGAGGCCCACAACGTGTG
       gp140TM    (161)  GCGACGCCAAGGCTTACAAGGCCGAGGCCCACAACGTGTG
        gp140     (161)  GCGACGCCAAGGCTTACAAGGCCGAGGCCCACAACGTGTG
       gp140mut   (161)  GCGACGCCAAGGCTTACAAGGCCGAGGCCCACAACGTGTG
        gp120     (161)  GCGACGCCAAGGCTTACAAGGCCGAGGCCCACAACGTGTG
      Consensus   (161)  GCGACGCCAAGGCTTACAAGGCCGAGGCCCACAACGTGTG
                         201                                        240
        gp160     (201)  GGCCACCCACGCCTGCGTGCCCACCGACCCCAACCCCCAG
   gp160 del V1   (201)  GGCCACCCACGCCTGCGTGCCCACCGACCCCAACCCCCAG
   gp160 del V2   (201)  GGCCACCCACGCCTGCGTGCCCACCGACCCCAACCCCCAG
  gp160 del V1-2  (201)  GGCCACCCACGCCTGCGTGCCCACCGACCCCAACCCCCAG
gp 160 del 128-194 (201) GGCCACCCACGCCTGCGTGCCCACCGACCCCAACCCCCAG
       gp140TM    (201)  GGCCACCCACGCCTGCGTGCCCACCGACCCCAACCCCCAG
        gp140     (201)  GGCCACCCACGCCTGCGTGCCCACCGACCCCAACCCCCAG
       gp140mut   (201)  GGCCACCCACGCCTGCGTGCCCACCGACCCCAACCCCCAG
        gp120     (201)  GGCCACCCACGCCTGCGTGCCCACCGACCCCAACCCCCAG
      Consensus   (201)  GGCCACCCACGCCTGCGTGCCCACCGACCCCAACCCCCAG
                         241                                        280
        gp160     (241)  GAGGTGAACCTGACCAACGTGACCGAGAACTTCAACATGT
   gp160 del V1   (241)  GAGGTGAACCTGACCAACGTGACCGAGAACTTCAACATGT
   gp160 del V2   (241)  GAGGTGAACCTGACCAACGTGACCGAGAACTTCAACATGT
  gp160 del V1-2  (241)  GAGGTGAACCTGACCAACGTGACCGAGAACTTCAACATGT
gp 160 del 128-194 (241) GAGGTGAACCTGACCAACGTGACCGAGAACTTCAACATGT
       gp140TM    (241)  GAGGTGAACCTGACCAACGTGACCGAGAACTTCAACATGT
        gp140     (241)  GAGGTGAACCTGACCAACGTGACCGAGAACTTCAACATGT
       gp140mut   (241)  GAGGTGAACCTGACCAACGTGACCGAGAACTTCAACATGT
        gp120     (241)  GAGGTGAACCTGACCAACGTGACCGAGAACTTCAACATGT
      Consensus   (241)  GAGGTGAACCTGACCAACGTGACCGAGAACTTCAACATGT
                         281                                        320
        gp160     (281)  GGAAGAACAACATGGTGGAGCAGATGCATGAGGACATCAT
   gp160 del V1   (281)  GGAAGAACAACATGGTGGAGCAGATGCATGAGGACATCAT
   gp160 del V2   (281)  GGAAGAACAACATGGTGGAGCAGATGCATGAGGACATCAT
  gp160 del V1-2  (281)  GGAAGAACAACATGGTGGAGCAGATGCATGAGGACATCAT
gp 160 del 128-194 (281) GGAAGAACAACATGGTGGAGCAGATGCATGAGGACATCAT
       gp140TM    (281)  GGAAGAACAACATGGTGGAGCAGATGCATGAGGACATCAT
        gp140     (281)  GGAAGAACAACATGGTGGAGCAGATGCATGAGGACATCAT
       gp140mut   (281)  GGAAGAACAACATGGTGGAGCAGATGCATGAGGACATCAT
        gp120     (281)  GGAAGAACAACATGGTGGAGCAGATGCATGAGGACATCAT
      Consensus   (281)  GGAAGAACAACATGGTGGAGCAGATGCATGAGGACATCAT
                         321                                        360
        gp160     (321)  CAGCCTGTGGGACCAGAGCCTGAAGCCCTGCGTGAAGCTG
   gp160 del V1   (321)  CAGCCTGTGGGACCAGAGCCTGAAGCCCTGCGTGAAGCTG
   gp160 del V2   (321)  CAGCCTGTGGGACCAGAGCCTGAAGCCCTGCGTGAAGCTG
  gp160 del V1-2  (321)  CAGCCTGTGGGACCAGAGCCTGAAGCCCTGCGTGGGCGCC
gp 160 del 128-194 (321) CAGCCTGTGGGACCAGAGCCTGAAGCCCTGCGTGAAGCTG
       gp140TM    (321)  CAGCCTGTGGGACCAGAGCCTGAAGCCCTGCGTGAAGCTG
        gp140     (321)  CAGCCTGTGGGACCAGAGCCTGAAGCCCTGCGTGAAGCTG
       gp140mut   (321)  CAGCCTGTGGGACCAGAGCCTGAAGCCCTGCGTGAAGCTG
        gp120     (321)  CAGCCTGTGGGACCAGAGCCTGAAGCCCTGCGTGAAGCTG
      Consensus   (321)  CAGCCTGTGGGACCAGAGCCTGAAGCCCTGCGTGAAGCTG
```

FIG. 66B-2

```
                        361                                        400
      gp160      (361) ACCCCCTGTGCGTGACCCTGAACTGCACCGACAAGCTGA
   gp160 del V1  (361) ACCCCCTGTGCGTGACCCTGAACTGCACCGACAAGCTGG
   gp160 del V2  (361) ACCCCCTGTGCGTGACCCTGAACTGCACCGACAAGCTGA
  gp160 del V1-2 (361) GGC-------------------------------------
gp 160 del 128-194 (361) ACCCCCTGTGCGTGGGGGCAGGG-----------------
     gp140TM     (361) ACCCCCTGTGCGTGACCCTGAACTGCACCGACAAGCTGA
      gp140      (361) ACCCCCTGTGCGTGACCCTGAACTGCACCGACAAGCTGA
     gp140mut    (361) ACCCCCTGTGCGTGACCCTGAACTGCACCGACAAGCTGA
      gp120      (361) ACCCCCTGTGCGTGACCCTGAACTGCACCGACAAGCTGA
    Consensus    (361) ACCCCCTGTGCGTGACCCTGAACTGCACCGACAAGCTGA
                        401                                        440
      gp160      (401) CCGGCAGCACCAACGGCACCAACAGCACCAGCGGCACCAA
   gp160 del V1  (401) GCGCCGGC--------------------------------
   gp160 del V2  (401) CCGGCAGCACCAACGGCACCAACAGCACCAGCGGCACCAA
  gp160 del V1-2 (364) ----------------------------------------
gp 160 del 128-194 (385) ----------------------------------------
     gp140TM     (401) CCGGCAGCACCAACGGCACCAACAGCACCAGCGGCACCAA
      gp140      (401) CCGGCAGCACCAACGGCACCAACAGCACCAGCGGCACCAA
     gp140mut    (401) CCGGCAGCACCAACGGCACCAACAGCACCAGCGGCACCAA
      gp120      (401) CCGGCAGCACCAACGGCACCAACAGCACCAGCGGCACCAA
    Consensus    (401) CCGGCAGCACCAACGGCACCAACAGCACCAGCGGCACCAA
                        441                                        480
      gp160      (441) CAGCACCAGCGGCACCAACAGCACCAGCACCAACAGCACC
   gp160 del V1  (409) ----------------------------------------
   gp160 del V2  (441) CAGCACCAGCGGCACCAACAGCACCAGCACCAACAGCACC
  gp160 del V1-2 (364) ----------------------------------------
gp 160 del 128-194 (385) ----------------------------------------
     gp140TM     (441) CAGCACCAGCGGCACCAACAGCACCAGCACCAACAGCACC
      gp140      (441) CAGCACCAGCGGCACCAACAGCACCAGCACCAACAGCACC
     gp140mut    (441) CAGCACCAGCGGCACCAACAGCACCAGCACCAACAGCACC
      gp120      (441) CAGCACCAGCGGCACCAACAGCACCAGCACCAACAGCACC
    Consensus    (441) CAGCACCAGCGGCACCAACAGCACCAGCACCAACAGCACC
                        481                                        520
      gp160      (481) GACAGCTGGGAGAAGATGCCCGAGGGCGAGATCAAGAACT
   gp160 del V1  (409) -----------------------GGCGAGATCAAGAACT
   gp160 del V2  (481) GACAGCTGGGAGAAGATGCCCGAGGGCGAGATCAAGAACT
  gp160 del V1-2 (364) ----------------------------------------
gp 160 del 128-194 (385) ----------------------------------------
     gp140TM     (481) GACAGCTGGGAGAAGATGCCCGAGGGCGAGATCAAGAACT
      gp140      (481) GACAGCTGGGAGAAGATGCCCGAGGGCGAGATCAAGAACT
     gp140mut    (481) GACAGCTGGGAGAAGATGCCCGAGGGCGAGATCAAGAACT
      gp120      (481) GACAGCTGGGAGAAGATGCCCGAGGGCGAGATCAAGAACT
    Consensus    (481) GACAGCTGGGAGAAGATGCCCGAGGGCGAGATCAAGAACT
                        521                                        560
      gp160      (521) GCAGCTTCAACATCACCACCAGCGTGCGCGACAAGGTGCA
   gp160 del V1  (521) GCAGCTTCAACATCACCACCAGCGTGCGCGACAAGGTGCA
   gp160 del V2  (521) GCAGCTTCAACATCGGCGCCGGC-----------------
  gp160 del V1-2 (521) ----------------------------------------
gp 160 del 128-194 (521) ----------------------------------------
     gp140TM     (521) GCAGCTTCAACATCACCACCAGCGTGCGCGACAAGGTGCA
      gp140      (521) GCAGCTTCAACATCACCACCAGCGTGCGCGACAAGGTGCA
     gp140mut    (521) GCAGCTTCAACATCACCACCAGCGTGCGCGACAAGGTGCA
      gp120      (521) GCAGCTTCAACATCACCACCAGCGTGCGCGACAAGGTGCA
    Consensus    (521) GCAGCTTCAACATCACCACCAGCGTGCGCGACAAGGTGCA
```

FIG. 66B-3

```
                          561                                        600
         gp160      (561) GAAGGAGTACAGCCTGTTCTACAAGCTGGACGTGGTGCCC
   gp160 del V1    (465) GAAGGAGTACAGCCTGTTCTACAAGCTGGACGTGGTGCCC
   gp160 del V2    (544) ----------------------------------------
   gp160 del V1-2  (364) ----------------------------------------
 gp 160 del 128-194 (385) ----------------------------------------
         gp140TM   (561) GAAGGAGTACAGCCTGTTCTACAAGCTGGACGTGGTGCCC
         gp140     (561) GAAGGAGTACAGCCTGTTCTACAAGCTGGACGTGGTGCCC
         gp140mut  (561) GAAGGAGTACAGCCTGTTCTACAAGCTGGACGTGGTGCCC
         gp120     (561) GAAGGAGTACAGCCTGTTCTACAAGCTGGACGTGGTGCCC
      Consensus    (561) GAAGGAGTACAGCCTGTTCTACAAGCTGGACGTGGTGCCC
                          601                                        640
         gp160      (601) ATCGACAACGACAACGCCAGCTACCGCCTGATCAACTGCA
   gp160 del V1    (505) ATCGACAACGACAACGCCAGCTACCGCCTGATCAACTGCA
   gp160 del V2    (544) ------------------CGCCTGATCAACTGCA
   gp160 del V1-2  (364) ----------------------------------------
 gp 160 del 128-194 (385) ---------------------------------AACTGCG
         gp140TM   (601) ATCGACAACGACAACGCCAGCTACCGCCTGATCAACTGCA
         gp140     (601) ATCGACAACGACAACGCCAGCTACCGCCTGATCAACTGCA
         gp140mut  (601) ATCGACAACGACAACGCCAGCTACCGCCTGATCAACTGCA
         gp120     (601) ATCGACAACGACAACGCCAGCTACCGCCTGATCAACTGCA
      Consensus    (601) ATCGACAACGACAACGCCAGCTACCGCCTGATCAACTGCA
                          641                                        680
         gp160      (641) ACACCAGCGTGATCACCCAGGCCTGCCCCAAGGTGAGCTT
   gp160 del V1    (545) ACACCAGCGTGATCACCCAGGCCTGCCCCAAGGTGAGCTT
   gp160 del V2    (560) ACACCAGCGTGATCACCCAGGCCTGCCCCAAGGTGAGCTT
   gp160 del V1-2  (364) ------------------CAGGCCTGCCCCAAGGTGAGCTT
 gp 160 del 128-194 (392) AGACCAGCGTGATCACCCAGGCCTGCCCCAAGGTGAGCTT
         gp140TM   (641) ACACCAGCGTGATCACCCAGGCCTGCCCCAAGGTGAGCTT
         gp140     (641) ACACCAGCGTGATCACCCAGGCCTGCCCCAAGGTGAGCTT
         gp140mut  (641) ACACCAGCGTGATCACCCAGGCCTGCCCCAAGGTGAGCTT
         gp120     (641) ACACCAGCGTGATCACCCAGGCCTGCCCCAAGGTGAGCTT
      Consensus    (641) ACACCAGCGTGATCACCCAGGCCTGCCCCAAGGTGAGCTT
                          681                                        720
         gp160      (681) CGAGCCCATCCCCATCCACTACTGCGCCCCCGCCGGCTTC
   gp160 del V1    (585) CGAGCCCATCCCCATCCACTACTGCGCCCCCGCCGGCTTC
   gp160 del V2    (600) CGAGCCCATCCCCATCCACTACTGCGCCCCCGCCGGCTTC
   gp160 del V1-2  (387) CGAGCCCATCCCCATCCACTACTGCGCCCCCGCCGGCTTC
 gp 160 del 128-194 (432) CGAGCCCATCCCCATCCACTACTGCGCCCCCGCCGGCTTC
         gp140TM   (681) CGAGCCCATCCCCATCCACTACTGCGCCCCCGCCGGCTTC
         gp140     (681) CGAGCCCATCCCCATCCACTACTGCGCCCCCGCCGGCTTC
         gp140mut  (681) CGAGCCCATCCCCATCCACTACTGCGCCCCCGCCGGCTTC
         gp120     (681) CGAGCCCATCCCCATCCACTACTGCGCCCCCGCCGGCTTC
      Consensus    (681) CGAGCCCATCCCCATCCACTACTGCGCCCCCGCCGGCTTC
                          721                                        760
         gp160      (721) GCCATCCTGAAGTGCAAGGACAAGAAGTTCAACGGCACCG
   gp160 del V1    (625) GCCATCCTGAAGTGCAAGGACAAGAAGTTCAACGGCACCG
   gp160 del V2    (640) GCCATCCTGAAGTGCAAGGACAAGAAGTTCAACGGCACCG
   gp160 del V1-2  (427) GCCATCCTGAAGTGCAAGGACAAGAAGTTCAACGGCACCG
 gp 160 del 128-194 (472) GCCATCCTGAAGTGCAAGGACAAGAAGTTCAACGGCACCG
         gp140TM   (721) GCCATCCTGAAGTGCAAGGACAAGAAGTTCAACGGCACCG
         gp140     (721) GCCATCCTGAAGTGCAAGGACAAGAAGTTCAACGGCACCG
         gp140mut  (721) GCCATCCTGAAGTGCAAGGACAAGAAGTTCAACGGCACCG
         gp120     (721) GCCATCCTGAAGTGCAAGGACAAGAAGTTCAACGGCACCG
      Consensus    (721) GCCATCCTGAAGTGCAAGGACAAGAAGTTCAACGGCACCG
```

FIG. 66B-4

|  |  | 761 | 800 |
|---|---|---|---|
| gp160 | (761) | GCCCCTGCAAGAACGTGAGCACCGTGCAGTGCACCCACGG | |
| gp160 del V1 | (665) | GCCCCTGCAAGAACGTGAGCACCGTGCAGTGCACCCACGG | |
| gp160 del V2 | (680) | GCCCCTGCAAGAACGTGAGCACCGTGCAGTGCACCCACGG | |
| gp160 del V1-2 | (467) | GCCCCTGCAAGAACGTGAGCACCGTGCAGTGCACCCACGG | |
| gp 160 del 128-194 | (512) | GCCCCTGCAAGAACGTGAGCACCGTGCAGTGCACCCACGG | |
| gp140TM | (761) | GCCCCTGCAAGAACGTGAGCACCGTGCAGTGCACCCACGG | |
| gp140 | (761) | GCCCCTGCAAGAACGTGAGCACCGTGCAGTGCACCCACGG | |
| gp140mut | (761) | GCCCCTGCAAGAACGTGAGCACCGTGCAGTGCACCCACGG | |
| gp120 | (761) | GCCCCTGCAAGAACGTGAGCACCGTGCAGTGCACCCACGG | |
| Consensus | (761) | GCCCCTGCAAGAACGTGAGCACCGTGCAGTGCACCCACGG | |
|  |  | 801 | 840 |
| gp160 | (801) | CATCCGCCCCGTGGTGAGCACCCAGCTGCTGCTGAACGGC | |
| gp160 del V1 | (705) | CATCCGCCCCGTGGTGAGCACCCAGCTGCTGCTGAACGGC | |
| gp160 del V2 | (720) | CATCCGCCCCGTGGTGAGCACCCAGCTGCTGCTGAACGGC | |
| gp160 del V1-2 | (507) | CATCCGCCCCGTGGTGAGCACCCAGCTGCTGCTGAACGGC | |
| gp 160 del 128-194 | (552) | CATCCGCCCCGTGGTGAGCACCCAGCTGCTGCTGAACGGC | |
| gp140TM | (801) | CATCCGCCCCGTGGTGAGCACCCAGCTGCTGCTGAACGGC | |
| gp140 | (801) | CATCCGCCCCGTGGTGAGCACCCAGCTGCTGCTGAACGGC | |
| gp140mut | (801) | CATCCGCCCCGTGGTGAGCACCCAGCTGCTGCTGAACGGC | |
| gp120 | (801) | CATCCGCCCCGTGGTGAGCACCCAGCTGCTGCTGAACGGC | |
| Consensus | (801) | CATCCGCCCCGTGGTGAGCACCCAGCTGCTGCTGAACGGC | |
|  |  | 841 | 880 |
| gp160 | (841) | AGCCTGGCCGAGGAGGAGATCGTGCTGCGCTCCGAGAACT | |
| gp160 del V1 | (745) | AGCCTGGCCGAGGAGGAGATCGTGCTGCGCTCCGAGAACT | |
| gp160 del V2 | (760) | AGCCTGGCCGAGGAGGAGATCGTGCTGCGCTCCGAGAACT | |
| gp160 del V1-2 | (547) | AGCCTGGCCGAGGAGGAGATCGTGCTGCGCTCCGAGAACT | |
| gp 160 del 128-194 | (592) | AGCCTGGCCGAGGAGGAGATCGTGCTGCGCTCCGAGAACT | |
| gp140TM | (841) | AGCCTGGCCGAGGAGGAGATCGTGCTGCGCTCCGAGAACT | |
| gp140 | (841) | AGCCTGGCCGAGGAGGAGATCGTGCTGCGCTCCGAGAACT | |
| gp140mut | (841) | AGCCTGGCCGAGGAGGAGATCGTGCTGCGCTCCGAGAACT | |
| gp120 | (841) | AGCCTGGCCGAGGAGGAGATCGTGCTGCGCTCCGAGAACT | |
| Consensus | (841) | AGCCTGGCCGAGGAGGAGATCGTGCTGCGCTCCGAGAACT | |
|  |  | 881 | 920 |
| gp160 | (881) | TCACCGACAACGCCAAGACCATCATCGTGCAGCTGAACGA | |
| gp160 del V1 | (785) | TCACCGACAACGCCAAGACCATCATCGTGCAGCTGAACGA | |
| gp160 del V2 | (800) | TCACCGACAACGCCAAGACCATCATCGTGCAGCTGAACGA | |
| gp160 del V1-2 | (587) | TCACCGACAACGCCAAGACCATCATCGTGCAGCTGAACGA | |
| gp 160 del 128-194 | (632) | TCACCGACAACGCCAAGACCATCATCGTGCAGCTGAACGA | |
| gp140TM | (881) | TCACCGACAACGCCAAGACCATCATCGTGCAGCTGAACGA | |
| gp140 | (881) | TCACCGACAACGCCAAGACCATCATCGTGCAGCTGAACGA | |
| gp140mut | (881) | TCACCGACAACGCCAAGACCATCATCGTGCAGCTGAACGA | |
| gp120 | (881) | TCACCGACAACGCCAAGACCATCATCGTGCAGCTGAACGA | |
| Consensus | (881) | TCACCGACAACGCCAAGACCATCATCGTGCAGCTGAACGA | |
|  |  | 921 | 960 |
| gp160 | (921) | GTCCGTGGAGATCAACTGCATCCGCCCCAACAACAACACG | |
| gp160 del V1 | (825) | GTCCGTGGAGATCAACTGCATCCGCCCCAACAACAACACG | |
| gp160 del V2 | (840) | GTCCGTGGAGATCAACTGCATCCGCCCCAACAACAACACG | |
| gp160 del V1-2 | (627) | GTCCGTGGAGATCAACTGCATCCGCCCCAACAACAACACG | |
| gp 160 del 128-194 | (672) | GTCCGTGGAGATCAACTGCATCCGCCCCAACAACAACACG | |
| gp140TM | (921) | GTCCGTGGAGATCAACTGCATCCGCCCCAACAACAACACG | |
| gp140 | (921) | GTCCGTGGAGATCAACTGCATCCGCCCCAACAACAACACG | |
| gp140mut | (921) | GTCCGTGGAGATCAACTGCATCCGCCCCAACAACAACACG | |
| gp120 | (921) | GTCCGTGGAGATCAACTGCATCCGCCCCAACAACAACACG | |
| Consensus | (921) | GTCCGTGGAGATCAACTGCATCCGCCCCAACAACAACACG | |

FIG. 66B-5

```
                           961                                    1000
         gp160      (961)  CGTAAGAGCATCCACATCGGCCCCGGCCGCGCCTTCTACG
     gp160 del V1   (865)  CGTAAGAGCATCCACATCGGCCCCGGCCGCGCCTTCTACG
     gp160 del V2   (880)  CGTAAGAGCATCCACATCGGCCCCGGCCGCGCCTTCTACG
    gp160 del V1-2  (667)  CGTAAGAGCATCCACATCGGCCCCGGCCGCGCCTTCTACG
 gp 160 del 128-194 (712)  CGTAAGAGCATCCACATCGGCCCCGGCCGCGCCTTCTACG
         gp140TM    (961)  CGTAAGAGCATCCACATCGGCCCCGGCCGCGCCTTCTACG
         gp140      (961)  CGTAAGAGCATCCACATCGGCCCCGGCCGCGCCTTCTACG
         gp140mut   (961)  CGTAAGAGCATCCACATCGGCCCCGGCCGCGCCTTCTACG
         gp120      (961)  CGTAAGAGCATCCACATCGGCCCCGGCCGCGCCTTCTACG
       Consensus    (961)  CGTAAGAGCATCCACATCGGCCCCGGCCGCGCCTTCTACG
                           1001                                   1040
         gp160     (1001)  CCACCGGCGACATCATCGGCGACATCCGCCAGGCCCACTG
     gp160 del V1   (905)  CCACCGGCGACATCATCGGCGACATCCGCCAGGCCCACTG
     gp160 del V2   (920)  CCACCGGCGACATCATCGGCGACATCCGCCAGGCCCACTG
    gp160 del V1-2  (707)  CCACCGGCGACATCATCGGCGACATCCGCCAGGCCCACTG
 gp 160 del 128-194 (752)  CCACCGGCGACATCATCGGCGACATCCGCCAGGCCCACTG
         gp140TM   (1001)  CCACCGGCGACATCATCGGCGACATCCGCCAGGCCCACTG
         gp140     (1001)  CCACCGGCGACATCATCGGCGACATCCGCCAGGCCCACTG
         gp140mut  (1001)  CCACCGGCGACATCATCGGCGACATCCGCCAGGCCCACTG
         gp120     (1001)  CCACCGGCGACATCATCGGCGACATCCGCCAGGCCCACTG
       Consensus   (1001)  CCACCGGCGACATCATCGGCGACATCCGCCAGGCCCACTG
                           1041                                   1080
         gp160     (1041)  CAACATCAGCAAGGCCAACTGGACCAACACCCTCGAGCAG
     gp160 del V1   (945)  CAACATCAGCAAGGCCAACTGGACCAACACCCTCGAGCAG
     gp160 del V2   (960)  CAACATCAGCAAGGCCAACTGGACCAACACCCTCGAGCAG
    gp160 del V1-2  (747)  CAACATCAGCAAGGCCAACTGGACCAACACCCTCGAGCAG
 gp 160 del 128-194 (792)  CAACATCAGCAAGGCCAACTGGACCAACACCCTCGAGCAG
         gp140TM   (1041)  CAACATCAGCAAGGCCAACTGGACCAACACCCTCGAGCAG
         gp140     (1041)  CAACATCAGCAAGGCCAACTGGACCAACACCCTCGAGCAG
         gp140mut  (1041)  CAACATCAGCAAGGCCAACTGGACCAACACCCTCGAGCAG
         gp120     (1041)  CAACATCAGCAAGGCCAACTGGACCAACACCCTCGAGCAG
       Consensus   (1041)  CAACATCAGCAAGGCCAACTGGACCAACACCCTCGAGCAG
                           1081                                   1120
         gp160     (1081)  ATCGTGGAGAAGCTGCGCGAGCAGTTCGGCAACAACAAGA
     gp160 del V1   (985)  ATCGTGGAGAAGCTGCGCGAGCAGTTCGGCAACAACAAGA
     gp160 del V2  (1000)  ATCGTGGAGAAGCTGCGCGAGCAGTTCGGCAACAACAAGA
    gp160 del V1-2  (787)  ATCGTGGAGAAGCTGCGCGAGCAGTTCGGCAACAACAAGA
 gp 160 del 128-194 (832)  ATCGTGGAGAAGCTGCGCGAGCAGTTCGGCAACAACAAGA
         gp140TM   (1081)  ATCGTGGAGAAGCTGCGCGAGCAGTTCGGCAACAACAAGA
         gp140     (1081)  ATCGTGGAGAAGCTGCGCGAGCAGTTCGGCAACAACAAGA
         gp140mut  (1081)  ATCGTGGAGAAGCTGCGCGAGCAGTTCGGCAACAACAAGA
         gp120     (1081)  ATCGTGGAGAAGCTGCGCGAGCAGTTCGGCAACAACAAGA
       Consensus   (1081)  ATCGTGGAGAAGCTGCGCGAGCAGTTCGGCAACAACAAGA
                           1121                                   1160
         gp160     (1121)  CCATCATCTTCAACAGCAGCAGCGGCGGCGACCCCGAGAT
     gp160 del V1  (1025)  CCATCATCTTCAACAGCAGCAGCGGCGGCGACCCCGAGAT
     gp160 del V2  (1040)  CCATCATCTTCAACAGCAGCAGCGGCGGCGACCCCGAGAT
    gp160 del V1-2  (827)  CCATCATCTTCAACAGCAGCAGCGGCGGCGACCCCGAGAT
 gp 160 del 128-194 (872)  CCATCATCTTCAACAGCAGCAGCGGCGGCGACCCCGAGAT
         gp140TM   (1121)  CCATCATCTTCAACAGCAGCAGCGGCGGCGACCCCGAGAT
         gp140     (1121)  CCATCATCTTCAACAGCAGCAGCGGCGGCGACCCCGAGAT
         gp140mut  (1121)  CCATCATCTTCAACAGCAGCAGCGGCGGCGACCCCGAGAT
         gp120     (1121)  CCATCATCTTCAACAGCAGCAGCGGCGGCGACCCCGAGAT
       Consensus   (1121)  CCATCATCTTCAACAGCAGCAGCGGCGGCGACCCCGAGAT
```

FIG. 66B-6

```
                           1161                                  1200
         gp160      (1161) CGTGTTCCACAGCTTCAACTGCGGCGGCGAGTTCTTCTAC
  gp160 del V1      (1065) CGTGTTCCACAGCTTCAACTGCGGCGGCGAGTTCTTCTAC
  gp160 del V2      (1080) CGTGTTCCACAGCTTCAACTGCGGCGGCGAGTTCTTCTAC
gp160 del V1-2       (867) CGTGTTCCACAGCTTCAACTGCGGCGGCGAGTTCTTCTAC
gp 160 del 128-194   (912) CGTGTTCCACAGCTTCAACTGCGGCGGCGAGTTCTTCTAC
        gp140TM     (1161) CGTGTTCCACAGCTTCAACTGCGGCGGCGAGTTCTTCTAC
          gp140     (1161) CGTGTTCCACAGCTTCAACTGCGGCGGCGAGTTCTTCTAC
       gp140mut     (1161) CGTGTTCCACAGCTTCAACTGCGGCGGCGAGTTCTTCTAC
          gp120     (1161) CGTGTTCCACAGCTTCAACTGCGGCGGCGAGTTCTTCTAC
      Consensus     (1161) CGTGTTCCACAGCTTCAACTGCGGCGGCGAGTTCTTCTAC
                           1201                                  1240
         gp160      (1201) TGCAACACCAGCCAGCTGTTCAACAGCACCTGGAACATCA
  gp160 del V1      (1105) TGCAACACCAGCCAGCTGTTCAACAGCACCTGGAACATCA
  gp160 del V2      (1120) TGCAACACCAGCCAGCTGTTCAACAGCACCTGGAACATCA
gp160 del V1-2       (907) TGCAACACCAGCCAGCTGTTCAACAGCACCTGGAACATCA
gp 160 del 128-194   (952) TGCAACACCAGCCAGCTGTTCAACAGCACCTGGAACATCA
        gp140TM     (1201) TGCAACACCAGCCAGCTGTTCAACAGCACCTGGAACATCA
          gp140     (1201) TGCAACACCAGCCAGCTGTTCAACAGCACCTGGAACATCA
       gp140mut     (1201) TGCAACACCAGCCAGCTGTTCAACAGCACCTGGAACATCA
          gp120     (1201) TGCAACACCAGCCAGCTGTTCAACAGCACCTGGAACATCA
      Consensus     (1201) TGCAACACCAGCCAGCTGTTCAACAGCACCTGGAACATCA
                           1241                                  1280
         gp160      (1241) CCGAGGAGGTGAACAAGACCAAGGAGAACGACACCATCAT
  gp160 del V1      (1145) CCGAGGAGGTGAACAAGACCAAGGAGAACGACACCATCAT
  gp160 del V2      (1160) CCGAGGAGGTGAACAAGACCAAGGAGAACGACACCATCAT
gp160 del V1-2       (947) CCGAGGAGGTGAACAAGACCAAGGAGAACGACACCATCAT
gp 160 del 128-194   (992) CCGAGGAGGTGAACAAGACCAAGGAGAACGACACCATCAT
        gp140TM     (1241) CCGAGGAGGTGAACAAGACCAAGGAGAACGACACCATCAT
          gp140     (1241) CCGAGGAGGTGAACAAGACCAAGGAGAACGACACCATCAT
       gp140mut     (1241) CCGAGGAGGTGAACAAGACCAAGGAGAACGACACCATCAT
          gp120     (1241) CCGAGGAGGTGAACAAGACCAAGGAGAACGACACCATCAT
      Consensus     (1241) CCGAGGAGGTGAACAAGACCAAGGAGAACGACACCATCAT
                           1281                                  1320
         gp160      (1281) CCTGCCCTGCCGCATCCGCCAGATCATCAACATGTGGCAG
  gp160 del V1      (1185) CCTGCCCTGCCGCATCCGCCAGATCATCAACATGTGGCAG
  gp160 del V2      (1200) CCTGCCCTGCCGCATCCGCCAGATCATCAACATGTGGCAG
gp160 del V1-2       (987) CCTGCCCTGCCGCATCCGCCAGATCATCAACATGTGGCAG
gp 160 del 128-194  (1032) CCTGCCCTGCCGCATCCGCCAGATCATCAACATGTGGCAG
        gp140TM     (1281) CCTGCCCTGCCGCATCCGCCAGATCATCAACATGTGGCAG
          gp140     (1281) CCTGCCCTGCCGCATCCGCCAGATCATCAACATGTGGCAG
       gp140mut     (1281) CCTGCCCTGCCGCATCCGCCAGATCATCAACATGTGGCAG
          gp120     (1281) CCTGCCCTGCCGCATCCGCCAGATCATCAACATGTGGCAG
      Consensus     (1281) CCTGCCCTGCCGCATCCGCCAGATCATCAACATGTGGCAG
                           1321                                  1360
         gp160      (1321) GAGGTGGGCAAGGCCATGTACGCCCCCCCCATCCGCGGCC
  gp160 del V1      (1225) GAGGTGGGCAAGGCCATGTACGCCCCCCCCATCCGCGGCC
  gp160 del V2      (1240) GAGGTGGGCAAGGCCATGTACGCCCCCCCCATCCGCGGCC
gp160 del V1-2      (1027) GAGGTGGGCAAGGCCATGTACGCCCCCCCCATCCGCGGCC
gp 160 del 128-194  (1072) GAGGTGGGCAAGGCCATGTACGCCCCCCCCATCCGCGGCC
        gp140TM     (1321) GAGGTGGGCAAGGCCATGTACGCCCCCCCCATCCGCGGCC
          gp140     (1321) GAGGTGGGCAAGGCCATGTACGCCCCCCCCATCCGCGGCC
       gp140mut     (1321) GAGGTGGGCAAGGCCATGTACGCCCCCCCCATCCGCGGCC
          gp120     (1321) GAGGTGGGCAAGGCCATGTACGCCCCCCCCATCCGCGGCC
      Consensus     (1321) GAGGTGGGCAAGGCCATGTACGCCCCCCCCATCCGCGGCC
```

FIG. 66B-7

```
                                1361                                    1400
          gp160        (1361)   AGATCAAGTGCAGCAGCAATATTACCGGCCTGCTGCTGAC
      gp160 del V1     (1265)   AGATCAAGTGCAGCAGCAATATTACCGGCCTGCTGCTGAC
      gp160 del V2     (1280)   AGATCAAGTGCAGCAGCAATATTACCGGCCTGCTGCTGAC
     gp160 del V1-2    (1067)   AGATCAAGTGCAGCAGCAATATTACCGGCCTGCTGCTGAC
    gp 160 del 128-194 (1112)   AGATCAAGTGCAGCAGCAATATTACCGGCCTGCTGCTGAC
         gp140TM       (1361)   AGATCAAGTGCAGCAGCAATATTACCGGCCTGCTGCTGAC
          gp140        (1361)   AGATCAAGTGCAGCAGCAATATTACCGGCCTGCTGCTGAC
         gp140mut      (1361)   AGATCAAGTGCAGCAGCAATATTACCGGCCTGCTGCTGAC
          gp120        (1361)   AGATCAAGTGCAGCAGCAATATTACCGGCCTGCTGCTGAC
        Consensus      (1361)   AGATCAAGTGCAGCAGCAATATTACCGGCCTGCTGCTGAC
                                1401                                    1440
          gp160        (1401)   CCGCGACGGCGGCACCAACAACAACCGCACCAACGACACC
      gp160 del V1     (1305)   CCGCGACGGCGGCACCAACAACAACCGCACCAACGACACC
      gp160 del V2     (1320)   CCGCGACGGCGGCACCAACAACAACCGCACCAACGACACC
     gp160 del V1-2    (1107)   CCGCGACGGCGGCACCAACAACAACCGCACCAACGACACC
    gp 160 del 128-194 (1152)   CCGCGACGGCGGCACCAACAACAACCGCACCAACGACACC
         gp140TM       (1401)   CCGCGACGGCGGCACCAACAACAACCGCACCAACGACACC
          gp140        (1401)   CCGCGACGGCGGCACCAACAACAACCGCACCAACGACACC
         gp140mut      (1401)   CCGCGACGGCGGCACCAACAACAACCGCACCAACGACACC
          gp120        (1401)   CCGCGACGGCGGCACCAACAACAACCGCACCAACGACACC
        Consensus      (1401)   CCGCGACGGCGGCACCAACAACAACCGCACCAACGACACC
                                1441                                    1480
          gp160        (1441)   GAGACCTTCCGCCCCGGCGGCGGCAACATGAAGGACAACT
      gp160 del V1     (1345)   GAGACCTTCCGCCCCGGCGGCGGCAACATGAAGGACAACT
      gp160 del V2     (1360)   GAGACCTTCCGCCCCGGCGGCGGCAACATGAAGGACAACT
     gp160 del V1-2    (1147)   GAGACCTTCCGCCCCGGCGGCGGCAACATGAAGGACAACT
    gp 160 del 128-194 (1192)   GAGACCTTCCGCCCCGGCGGCGGCAACATGAAGGACAACT
         gp140TM       (1441)   GAGACCTTCCGCCCCGGCGGCGGCAACATGAAGGACAACT
          gp140        (1441)   GAGACCTTCCGCCCCGGCGGCGGCAACATGAAGGACAACT
         gp140mut      (1441)   GAGACCTTCCGCCCCGGCGGCGGCAACATGAAGGACAACT
          gp120        (1441)   GAGACCTTCCGCCCCGGCGGCGGCAACATGAAGGACAACT
        Consensus      (1441)   GAGACCTTCCGCCCCGGCGGCGGCAACATGAAGGACAACT
                                1481                                    1520
          gp160        (1481)   GGCGCAGCGAGCTGTACAAGTACAAGGTGGTGCGCATCGA
      gp160 del V1     (1385)   GGCGCAGCGAGCTGTACAAGTACAAGGTGGTGCGCATCGA
      gp160 del V2     (1400)   GGCGCAGCGAGCTGTACAAGTACAAGGTGGTGCGCATCGA
     gp160 del V1-2    (1187)   GGCGCAGCGAGCTGTACAAGTACAAGGTGGTGCGCATCGA
    gp 160 del 128-194 (1232)   GGCGCAGCGAGCTGTACAAGTACAAGGTGGTGCGCATCGA
         gp140TM       (1481)   GGCGCAGCGAGCTGTACAAGTACAAGGTGGTGCGCATCGA
          gp140        (1481)   GGCGCAGCGAGCTGTACAAGTACAAGGTGGTGCGCATCGA
         gp140mut      (1481)   GGCGCAGCGAGCTGTACAAGTACAAGGTGGTGCGCATCGA
          gp120        (1481)   GGCGCAGCGAGCTGTACAAGTACAAGGTGGTGCGCATCGA
        Consensus      (1481)   GGCGCAGCGAGCTGTACAAGTACAAGGTGGTGCGCATCGA
                                1521                                    1560
          gp160        (1521)   GCCCTGGGCGTGGCCCCCACCCAGGCCAAGCGCCGCGTG
      gp160 del V1     (1425)   GCCCTGGGCGTGGCCCCCACCCAGGCCAAGCGCCGCGTG
      gp160 del V2     (1440)   GCCCTGGGCGTGGCCCCCACCCAGGCCAAGCGCCGCGTG
     gp160 del V1-2    (1227)   GCCCTGGGCGTGGCCCCCACCCAGGCCAAGCGCCGCGTG
    gp 160 del 128-194 (1272)   GCCCTGGGCGTGGCCCCCACCCAGGCCAAGCGCCGCGTG
         gp140TM       (1521)   GCCCTGGGCGTGGCCCCCACCCAGGCCAAGCGCCGCGTG
          gp140        (1521)   GCCCTGGGCGTGGCCCCCACCCAGGCCAAGCGCCGCGTG
         gp140mut      (1521)   GCCCTGGGCGTGGCCCCCACCCAGGCCAAGCGCCGCGTG
          gp120        (1521)   GCCCTGGGCGTGGCCCCCACCCAGGCCAAGCGCCGCGTG
        Consensus      (1521)   GCCCTGGGCGTGGCCCCCACCCAGGCCAAGCGCCGCGTG
```

FIG. 66B-8

```
                              1561                                    1600
          gp160      (1561)   GTGCAGCGCGAGAAGCGCGCCGTGGGCCTGGGCGCCCTGT
     gp160 del V1    (1465)   GTGCAGCGCGAGAAGCGCGCCGTGGGCCTGGGCGCCCTGT
     gp160 del V2    (1480)   GTGCAGCGCGAGAAGCGCGCCGTGGGCCTGGGCGCCCTGT
    gp160 del V1-2   (1267)   GTGCAGCGCGAGAAGCGCGCCGTGGGCCTGGGCGCCCTGT
   gp 160 del 128-194 (1312)  GTGCAGCGCGAGAAGCGCGCCGTGGGCCTGGGCGCCCTGT
         gp140TM     (1561)   GTGCAGCGCGAGAAGCGCGCCGTGGGCCTGGGCGCCCTGT
           gp140     (1561)   GTGCAGCGCGAGAAGCGCGCCGTGGGCCTGGGCGCCCTGT
         gp140mut    (1561)   GTGCAGCGCGAGAAGAGCGCCGTGGGCCTGGGCGCCCTGT
           gp120     (1561)   GTGCAGCGCGAGAAGCGCTAAG------------------
       Consensus     (1561)   GTGCAGCGCGAGAAGCGCGCCGTGGGCCTGGGCGCCCTGT
                              1601                                    1640
          gp160      (1601)   TCATCGGCTTC-CTGGGCGCCGCCGGGAGCACCATGGGCG
     gp160 del V1    (1505)   TCATCGGCTTC-CTGGGCGCCGCCGGGAGCACCATGGGCG
     gp160 del V2    (1520)   TCATCGGCTTC-CTGGGCGCCGCCGGGAGCACCATGGGCG
    gp160 del V1-2   (1307)   TCATCGGCTTC-CTGGGCGCCGCCGGGAGCACCATGGGCG
   gp 160 del 128-194 (1352)  TCATCGGCTTC-CTGGGCGCCGCCGGGAGCACCATGGGCG
         gp140TM     (1601)   TCATCGGCTTC-CTGGGCGCCGCCGGGAGCACCATGGGCG
           gp140     (1601)   TCATCGGCTTC-CTGGGCGCCGCCGGGAGCACCATGGGCG
         gp140mut    (1601)   TCATCGGCTTC-CTGGGCGCCGCCGGGAGCACCATGGGCG
           gp120     (1583)   ATATCGGATCCTCTAGA-----------------------
       Consensus     (1601)   TCATCGGCTTCNCTGGGCGCCGCCGGGAGCACCATGGGCG
                              1641                                    1680
          gp160      (1640)   CCGCCTCCGTGACCCTGACCGTGCAGGCCCGCCAGCTGCT
     gp160 del V1    (1544)   CCGCCTCCGTGACCCTGACCGTGCAGGCCCGCCAGCTGCT
     gp160 del V2    (1559)   CCGCCTCCGTGACCCTGACCGTGCAGGCCCGCCAGCTGCT
    gp160 del V1-2   (1346)   CCGCCTCCGTGACCCTGACCGTGCAGGCCCGCCAGCTGCT
   gp 160 del 128-194 (1391)  CCGCCTCCGTGACCCTGACCGTGCAGGCCCGCCAGCTGCT
         gp140TM     (1640)   CCGCCTCCGTGACCCTGACCGTGCAGGCCCGCCAGCTGCT
           gp140     (1640)   CCGCCTCCGTGACCCTGACCGTGCAGGCCCGCCAGCTGCT
         gp140mut    (1640)   CCGCCTCCGTGACCCTGACCGTGCAGGCCCGCCAGCTGCT
           gp120     (1600)   ----------------------------------------
       Consensus     (1641)   CCGCCTCCGTGACCCTGACCGTGCAGGCCCGCCAGCTGCT
                              1681                                    1720
          gp160      (1680)   GAGCGGCATCGTGCAGCAGCAGAACAACCTGCTGCGCGCC
     gp160 del V1    (1584)   GAGCGGCATCGTGCAGCAGCAGAACAACCTGCTGCGCGCC
     gp160 del V2    (1599)   GAGCGGCATCGTGCAGCAGCAGAACAACCTGCTGCGCGCC
    gp160 del V1-2   (1386)   GAGCGGCATCGTGCAGCAGCAGAACAACCTGCTGCGCGCC
   gp 160 del 128-194 (1431)  GAGCGGCATCGTGCAGCAGCAGAACAACCTGCTGCGCGCC
         gp140TM     (1680)   GAGCGGCATCGTGCAGCAGCAGAACAACCTGCTGCGCGCC
           gp140     (1680)   GAGCGGCATCGTGCAGCAGCAGAACAACCTGCTGCGCGCC
         gp140mut    (1680)   GAGCGGCATCGTGCAGCAGCAGAACAACCTGCTGCGCGCC
           gp120     (1600)   ----------------------------------------
       Consensus     (1681)   GAGCGGCATCGTGCAGCAGCAGAACAACCTGCTGCGCGCC
                              1721                                    1760
          gp160      (1720)   ATCGAGGCCCAGCAGCACCTGCTGCAGCTGACCGTGTGGG
     gp160 del V1    (1624)   ATCGAGGCCCAGCAGCACCTGCTGCAGCTGACCGTGTGGG
     gp160 del V2    (1639)   ATCGAGGCCCAGCAGCACCTGCTGCAGCTGACCGTGTGGG
    gp160 del V1-2   (1426)   ATCGAGGCCCAGCAGCACCTGCTGCAGCTGACCGTGTGGG
   gp 160 del 128-194 (1471)  ATCGAGGCCCAGCAGCACCTGCTGCAGCTGACCGTGTGGG
         gp140TM     (1720)   ATCGAGGCCCAGCAGCACCTGCTGCAGCTGACCGTGTGGG
           gp140     (1720)   ATCGAGGCCCAGCAGCACCTGCTGCAGCTGACCGTGTGGG
         gp140mut    (1720)   ATCGAGGCCCAGCAGCACCTGCTGCAGCTGACCGTGTGGG
           gp120     (1600)   ----------------------------------------
       Consensus     (1721)   ATCGAGGCCCAGCAGCACCTGCTGCAGCTGACCGTGTGGG
```

FIG. 66B-9

|  |  | 1761 | 1800 |
|---|---|---|---|
| gp160 | (1760) | GCATCAAGCAGCTGCAGGCCCGCATCCTGGCCGTGGAGCG | |
| gp160 del V1 | (1664) | GCATCAAGCAGCTGCAGGCCCGCATCCTGGCCGTGGAGCG | |
| gp160 del V2 | (1679) | GCATCAAGCAGCTGCAGGCCCGCATCCTGGCCGTGGAGCG | |
| gp160 del V1-2 | (1466) | GCATCAAGCAGCTGCAGGCCCGCATCCTGGCCGTGGAGCG | |
| gp 160 del 128-194 | (1511) | GCATCAAGCAGCTGCAGGCCCGCATCCTGGCCGTGGAGCG | |
| gp140TM | (1760) | GCATCAAGCAGCTGCAGGCCCGCATCCTGGCCGTGGAGCG | |
| gp140 | (1760) | GCATCAAGCAGCTGCAGGCCCGCATCCTGGCCGTGGAGCG | |
| gp140mut | (1760) | GCATCAAGCAGCTGCAGGCCCGCATCCTGGCCGTGGAGCG | |
| gp120 | (1600) | ---------------------------------------- | |
| Consensus | (1761) | GCATCAAGCAGCTGCAGGCCCGCATCCTGGCCGTGGAGCG | |
|  |  | 1801 | 1840 |
| gp160 | (1800) | CTACCTGAAGGACCAGCAGCTGCTGGGCATCTGGGGCTGC | |
| gp160 del V1 | (1704) | CTACCTGAAGGACCAGCAGCTGCTGGGCATCTGGGGCTGC | |
| gp160 del V2 | (1719) | CTACCTGAAGGACCAGCAGCTGCTGGGCATCTGGGGCTGC | |
| gp160 del V1-2 | (1506) | CTACCTGAAGGACCAGCAGCTGCTGGGCATCTGGGGCTGC | |
| gp 160 del 128-194 | (1551) | CTACCTGAAGGACCAGCAGCTGCTGGGCATCTGGGGCTGC | |
| gp140TM | (1800) | CTACCTGAAGGACCAGCAGCTGCTGGGCATCTGGGGCTGC | |
| gp140 | (1800) | CTACCTGAAGGACCAGCAGCTGCTGGGCATCTGGGGCTGC | |
| gp140mut | (1800) | CTACCTGAAGGACCAGCAGCTGCTGGGCATCTGGGGCTGC | |
| gp120 | (1600) | ---------------------------------------- | |
| Consensus | (1801) | CTACCTGAAGGACCAGCAGCTGCTGGGCATCTGGGGCTGC | |
|  |  | 1841 | 1880 |
| gp160 | (1840) | AGCGGCAAGCTGATCTGCACCACCACCGTGCCCTGGAACA | |
| gp160 del V1 | (1744) | AGCGGCAAGCTGATCTGCACCACCACCGTGCCCTGGAACA | |
| gp160 del V2 | (1759) | AGCGGCAAGCTGATCTGCACCACCACCGTGCCCTGGAACA | |
| gp160 del V1-2 | (1546) | AGCGGCAAGCTGATCTGCACCACCACCGTGCCCTGGAACA | |
| gp 160 del 128-194 | (1591) | AGCGGCAAGCTGATCTGCACCACCACCGTGCCCTGGAACA | |
| gp140TM | (1840) | AGCGGCAAGCTGATCTGCACCACCACCGTGCCCTGGAACA | |
| gp140 | (1840) | AGCGGCAAGCTGATCTGCACCACCACCGTGCCCTGGAACA | |
| gp140mut | (1840) | AGCGGCAAGCTGATCTGCACCACCACCGTGCCCTGGAACA | |
| gp120 | (1600) | ---------------------------------------- | |
| Consensus | (1841) | AGCGGCAAGCTGATCTGCACCACCACCGTGCCCTGGAACA | |
|  |  | 1881 | 1920 |
| gp160 | (1880) | GCAGCTGGAGCAACAAGAGCCTGACCGAGATCTGGGACAA | |
| gp160 del V1 | (1784) | GCAGCTGGAGCAACAAGAGCCTGACCGAGATCTGGGACAA | |
| gp160 del V2 | (1799) | GCAGCTGGAGCAACAAGAGCCTGACCGAGATCTGGGACAA | |
| gp160 del V1-2 | (1586) | GCAGCTGGAGCAACAAGAGCCTGACCGAGATCTGGGACAA | |
| gp 160 del 128-194 | (1631) | GCAGCTGGAGCAACAAGAGCCTGACCGAGATCTGGGACAA | |
| gp140TM | (1880) | GCAGCTGGAGCAACAAGAGCCTGACCGAGATCTGGGACAA | |
| gp140 | (1880) | GCAGCTGGAGCAACAAGAGCCTGACCGAGATCTGGGACAA | |
| gp140mut | (1880) | GCAGCTGGAGCAACAAGAGCCTGACCGAGATCTGGGACAA | |
| gp120 | (1600) | ---------------------------------------- | |
| Consensus | (1881) | GCAGCTGGAGCAACAAGAGCCTGACCGAGATCTGGGACAA | |
|  |  | 1921 | 1960 |
| gp160 | (1920) | CATGACCTGGATGGAGTGGGAGCGCGAGATCGGCAACTAC | |
| gp160 del V1 | (1824) | CATGACCTGGATGGAGTGGGAGCGCGAGATCGGCAACTAC | |
| gp160 del V2 | (1839) | CATGACCTGGATGGAGTGGGAGCGCGAGATCGGCAACTAC | |
| gp160 del V1-2 | (1626) | CATGACCTGGATGGAGTGGGAGCGCGAGATCGGCAACTAC | |
| gp 160 del 128-194 | (1671) | CATGACCTGGATGGAGTGGGAGCGCGAGATCGGCAACTAC | |
| gp140TM | (1920) | CATGACCTGGATGGAGTGGGAGCGCGAGATCGGCAACTAC | |
| gp140 | (1920) | CATGACCTGGATGGAGTGGGAGCGCGAGATCGGCAACTAC | |
| gp140mut | (1920) | CATGACCTGGATGGAGTGGGAGCGCGAGATCGGCAACTAC | |
| gp120 | (1600) | ---------------------------------------- | |
| Consensus | (1921) | CATGACCTGGATGGAGTGGGAGCGCGAGATCGGCAACTAC | |

FIG. 66B-10

|  |  | 1961 2000 |
|---|---|---|
| gp160 | (1960) | ACCGGCCTGATCTACAACCTGATCGAGATCGCCCAGAACC |
| gp160 del V1 | (1864) | ACCGGCCTGATCTACAACCTGATCGAGATCGCCCAGAACC |
| gp160 del V2 | (1879) | ACCGGCCTGATCTACAACCTGATCGAGATCGCCCAGAACC |
| gp160 del V1-2 | (1666) | ACCGGCCTGATCTACAACCTGATCGAGATCGCCCAGAACC |
| gp 160 del 128-194 | (1711) | ACCGGCCTGATCTACAACCTGATCGAGATCGCCCAGAACC |
| gp140TM | (1960) | ACCGGCCTGATCTACAACCTGATCGAGATCGCCCAGAACC |
| gp140 | (1960) | ACCGGCCTGATCTACAACCTGATCGAGATCGCCCAGAACC |
| gp140mut | (1960) | ACCGGCCTGATCTACAACCTGATCGAGATCGCCCAGAACC |
| gp120 | (1600) | ---------------------------------------- |
| Consensus | (1961) | ACCGGCCTGATCTACAACCTGATCGAGATCGCCCAGAACC |
|  |  | 2001 2040 |
| gp160 | (2000) | AGCAGGAGAAGAACGAGCAGGAGCTGCTGGAGCTGGACAA |
| gp160 del V1 | (1904) | AGCAGGAGAAGAACGAGCAGGAGCTGCTGGAGCTGGACAA |
| gp160 del V2 | (1919) | AGCAGGAGAAGAACGAGCAGGAGCTGCTGGAGCTGGACAA |
| gp160 del V1-2 | (1706) | AGCAGGAGAAGAACGAGCAGGAGCTGCTGGAGCTGGACAA |
| gp 160 del 128-194 | (1751) | AGCAGGAGAAGAACGAGCAGGAGCTGCTGGAGCTGGACAA |
| gp140TM | (2000) | AGCAGGAGAAGAACGAGCAGGAGCTGCTGGAGCTGGACAA |
| gp140 | (2000) | AGCAGGAGAAGAACGAGCAGGAGCTGCTGGAGCTGGACAA |
| gp140mut | (2000) | AGCAGGAGAAGAACGAGCAGGAGCTGCTGGAGCTGGACAA |
| gp120 | (1600) | ---------------------------------------- |
| Consensus | (2001) | AGCAGGAGAAGAACGAGCAGGAGCTGCTGGAGCTGGACAA |
|  |  | 2041 2080 |
| gp160 | (2040) | GTGGGCCAGCCTGTGGAACTGGTTCGACATCACCAACTGG |
| gp160 del V1 | (1944) | GTGGGCCAGCCTGTGGAACTGGTTCGACATCACCAACTGG |
| gp160 del V2 | (1959) | GTGGGCCAGCCTGTGGAACTGGTTCGACATCACCAACTGG |
| gp160 del V1-2 | (1746) | GTGGGCCAGCCTGTGGAACTGGTTCGACATCACCAACTGG |
| gp 160 del 128-194 | (1791) | GTGGGCCAGCCTGTGGAACTGGTTCGACATCACCAACTGG |
| gp140TM | (2040) | GTGGGCCAGCCTGTGGAACTGGTTCGACATCACCAACTGG |
| gp140 | (2040) | GTGGGCCAGCCTGTGGAACTGGTTCGACATCACCAACTGG |
| gp140mut | (2040) | GTGGGCCAGCCTGTGGAACTGGTTCGACATCACCAACTGG |
| gp120 | (1600) | ---------------------------------------- |
| Consensus | (2041) | GTGGGCCAGCCTGTGGAACTGGTTCGACATCACCAACTGG |
|  |  | 2081 2120 |
| gp160 | (2080) | CTGTGGTACATCCGCATCTTCATCATGATCGTGGGCGGCC |
| gp160 del V1 | (1984) | CTGTGGTACATCCGCATCTTCATCATGATCGTGGGCGGCC |
| gp160 del V2 | (1999) | CTGTGGTACATCCGCATCTTCATCATGATCGTGGGCGGCC |
| gp160 del V1-2 | (1786) | CTGTGGTACATCCGCATCTTCATCATGATCGTGGGCGGCC |
| gp 160 del 128-194 | (1831) | CTGTGGTACATCCGCATCTTCATCATGATCGTGGGCGGCC |
| gp140TM | (2080) | CTGTGGTACATCCGCATCTTCATCATGATCGTGGGCGGCC |
| gp140 | (2080) | CTGTGGTACATC---------------------------- |
| gp140mut | (2080) | CTGTGGTACATC---------------------------- |
| gp120 | (1600) | ---------------------------------------- |
| Consensus | (2081) | CTGTGGTACATCCGCATCTTCATCATGATCGTGGGCGGCC |
|  |  | 2121 2160 |
| gp160 | (2120) | TGATCGGCCTGCGCATCGTGTTCGCCGTGCTGAGCA---- |
| gp160 del V1 | (2024) | TGATCGGCCTGCGCATCGTGTTCGCCGTGCTGAGCA---- |
| gp160 del V2 | (2039) | TGATCGGCCTGCGCATCGTGTTCGCCGTGCTGAGCA---- |
| gp160 del V1-2 | (1826) | TGATCGGCCTGCGCATCGTGTTCGCCGTGCTGAGCA---- |
| gp 160 del 128-194 | (1871) | TGATCGGCCTGCGCATCGTGTTCGCCGTGCTGAGCA---- |
| gp140TM | (2120) | TGATCGGCCTGCGCATCGTGTTCGCCGTGCTGAGCATCGT |
| gp140 | (2092) | ---------------------------------------- |
| gp140mut | (2092) | ---------------------------------------- |
| gp120 | (1600) | ---------------------------------------- |
| Consensus | (2121) | TGATCGGCCTGCGCATCGTGTTCGCCGTGCTGAGCANNNN |

FIG. 66B-11

```
                              2161                                    2200
         gp160   (2156)  -TCGTGAACCGCGTGCGCCAGGGCTACAGCCCCATCAGCC
    gp160 del V1 (2060)  -TCGTGAACCGCGTGCGCCAGGGCTACAGCCCCATCAGCC
    gp160 del V2 (2075)  -TCGTGAACCGCGTGCGCCAGGGCTACAGCCCCATCAGCC
  gp160 del V1-2 (1862)  -TCGTGAACCGCGTGCGCCAGGGCTACAGCCCCATCAGCC
gp 160 del 128-194 (1907) -TCGTGAACCGCGTGCGCCAGGGCTACAGCCCCATCAGCC
         gp140TM (2160)  GTAAGATATCGGATCCTCTAGA------------------
           gp140 (2092)  -TAAGATATCGGATCCTCTAGA------------------
        gp140mut (2092)  -TAAGATATCGGATCCTCTAGA------------------
           gp120 (1600)  ----------------------------------------
       Consensus (2161)  NTCGTGAACCGCGTGCGCCAGGGCTACAGCCCCATCAGCC
                              2201                                    2240
         gp160   (2195)  TGCAGACCCGCCTGCCCGCCCAGCGCGGCCCCGACCGCCC
    gp160 del V1 (2099)  TGCAGACCCGCCTGCCCGCCCAGCGCGGCCCCGACCGCCC
    gp160 del V2 (2114)  TGCAGACCCGCCTGCCCGCCCAGCGCGGCCCCGACCGCCC
  gp160 del V1-2 (1901)  TGCAGACCCGCCTGCCCGCCCAGCGCGGCCCCGACCGCCC
gp 160 del 128-194 (1946) TGCAGACCCGCCTGCCCGCCCAGCGCGGCCCCGACCGCCC
         gp140TM (2182)  ----------------------------------------
           gp140 (2113)  ----------------------------------------
        gp140mut (2113)  ----------------------------------------
           gp120 (1600)  ----------------------------------------
       Consensus (2201)  TGCAGACCCGCCTGCCCGCCCAGCGCGGCCCCGACCGCCC
                              2241                                    2280
         gp160   (2235)  CGAGGGCATCGAGGAGGAGGGCGGCGAGCGCGACCGCGAC
    gp160 del V1 (2139)  CGAGGGCATCGAGGAGGAGGGCGGCGAGCGCGACCGCGAC
    gp160 del V2 (2154)  CGAGGGCATCGAGGAGGAGGGCGGCGAGCGCGACCGCGAC
  gp160 del V1-2 (1941)  CGAGGGCATCGAGGAGGAGGGCGGCGAGCGCGACCGCGAC
gp 160 del 128-194 (1986) CGAGGGCATCGAGGAGGAGGGCGGCGAGCGCGACCGCGAC
         gp140TM (2182)  ----------------------------------------
           gp140 (2113)  ----------------------------------------
        gp140mut (2113)  ----------------------------------------
           gp120 (1600)  ----------------------------------------
       Consensus (2241)  CGAGGGCATCGAGGAGGAGGGCGGCGAGCGCGACCGCGAC
                              2281                                    2320
         gp160   (2275)  CGCAGCAACCGCCTGGTGCACGGCCTGCTGGCCCTGATCT
    gp160 del V1 (2179)  CGCAGCAACCGCCTGGTGCACGGCCTGCTGGCCCTGATCT
    gp160 del V2 (2194)  CGCAGCAACCGCCTGGTGCACGGCCTGCTGGCCCTGATCT
  gp160 del V1-2 (1981)  CGCAGCAACCGCCTGGTGCACGGCCTGCTGGCCCTGATCT
gp 160 del 128-194 (2026) CGCAGCAACCGCCTGGTGCACGGCCTGCTGGCCCTGATCT
         gp140TM (2182)  ----------------------------------------
           gp140 (2113)  ----------------------------------------
        gp140mut (2113)  ----------------------------------------
           gp120 (1600)  ----------------------------------------
       Consensus (2281)  CGCAGCAACCGCCTGGTGCACGGCCTGCTGGCCCTGATCT
                              2321                                    2360
         gp160   (2315)  GGGACGACCTGCGCAGCCTGTGCCTGTTCAGCTACCACCG
    gp160 del V1 (2219)  GGGACGACCTGCGCAGCCTGTGCCTGTTCAGCTACCACCG
    gp160 del V2 (2234)  GGGACGACCTGCGCAGCCTGTGCCTGTTCAGCTACCACCG
  gp160 del V1-2 (2021)  GGGACGACCTGCGCAGCCTGTGCCTGTTCAGCTACCACCG
gp 160 del 128-194 (2066) GGGACGACCTGCGCAGCCTGTGCCTGTTCAGCTACCACCG
         gp140TM (2182)  ----------------------------------------
           gp140 (2113)  ----------------------------------------
        gp140mut (2113)  ----------------------------------------
           gp120 (1600)  ----------------------------------------
       Consensus (2321)  GGGACGACCTGCGCAGCCTGTGCCTGTTCAGCTACCACCG
```

FIG. 66B-12

|                    |        | 2361                                     2400 |
|---|---|---|
| gp160              | (2355) | CCTGCGCGACCTGCTGCTGATCGTGGCCCGCATCGTGGAG |
| gp160 del V1       | (2259) | CCTGCGCGACCTGCTGCTGATCGTGGCCCGCATCGTGGAG |
| gp160 del V2       | (2274) | CCTGCGCGACCTGCTGCTGATCGTGGCCCGCATCGTGGAG |
| gp160 del V1-2     | (2061) | CCTGCGCGACCTGCTGCTGATCGTGGCCCGCATCGTGGAG |
| gp 160 del 128-194 | (2106) | CCTGCGCGACCTGCTGCTGATCGTGGCCCGCATCGTGGAG |
| gp140TM            | (2182) | ---------------------------------------- |
| gp140              | (2113) | ---------------------------------------- |
| gp140mut           | (2113) | ---------------------------------------- |
| gp120              | (1600) | ---------------------------------------- |
| Consensus          | (2361) | CCTGCGCGACCTGCTGCTGATCGTGGCCCGCATCGTGGAG |

|                    |        | 2401                                     2440 |
|---|---|---|
| gp160              | (2395) | CTGCTGGGCCGCCGCGGCTGGGAGGCCCTGAAGTACTGGT |
| gp160 del V1       | (2299) | CTGCTGGGCCGCCGCGGCTGGGAGGCCCTGAAGTACTGGT |
| gp160 del V2       | (2314) | CTGCTGGGCCGCCGCGGCTGGGAGGCCCTGAAGTACTGGT |
| gp160 del V1-2     | (2101) | CTGCTGGGCCGCCGCGGCTGGGAGGCCCTGAAGTACTGGT |
| gp 160 del 128-194 | (2146) | CTGCTGGGCCGCCGCGGCTGGGAGGCCCTGAAGTACTGGT |
| gp140TM            | (2182) | ---------------------------------------- |
| gp140              | (2113) | ---------------------------------------- |
| gp140mut           | (2113) | ---------------------------------------- |
| gp120              | (1600) | ---------------------------------------- |
| Consensus          | (2401) | CTGCTGGGCCGCCGCGGCTGGGAGGCCCTGAAGTACTGGT |

|                    |        | 2441                                     2480 |
|---|---|---|
| gp160              | (2435) | GGAACCTGCTGCAGTACTGGAGCCAGGAGCTGAAGAGCAG |
| gp160 del V1       | (2339) | GGAACCTGCTGCAGTACTGGAGCCAGGAGCTGAAGAGCAG |
| gp160 del V2       | (2354) | GGAACCTGCTGCAGTACTGGAGCCAGGAGCTGAAGAGCAG |
| gp160 del V1-2     | (2141) | GGAACCTGCTGCAGTACTGGAGCCAGGAGCTGAAGAGCAG |
| gp 160 del 128-194 | (2186) | GGAACCTGCTGCAGTACTGGAGCCAGGAGCTGAAGAGCAG |
| gp140TM            | (2182) | ---------------------------------------- |
| gp140              | (2113) | ---------------------------------------- |
| gp140mut           | (2113) | ---------------------------------------- |
| gp120              | (1600) | ---------------------------------------- |
| Consensus          | (2441) | GGAACCTGCTGCAGTACTGGAGCCAGGAGCTGAAGAGCAG |

|                    |        | 2481                                     2520 |
|---|---|---|
| gp160              | (2475) | CGCCGTGAGCCTGTTCAACGCCACCGCCATCGCCGTGGCC |
| gp160 del V1       | (2379) | CGCCGTGAGCCTGTTCAACGCCACCGCCATCGCCGTGGCC |
| gp160 del V2       | (2394) | CGCCGTGAGCCTGTTCAACGCCACCGCCATCGCCGTGGCC |
| gp160 del V1-2     | (2181) | CGCCGTGAGCCTGTTCAACGCCACCGCCATCGCCGTGGCC |
| gp 160 del 128-194 | (2226) | CGCCGTGAGCCTGTTCAACGCCACCGCCATCGCCGTGGCC |
| gp140TM            | (2182) | ---------------------------------------- |
| gp140              | (2113) | ---------------------------------------- |
| gp140mut           | (2113) | ---------------------------------------- |
| gp120              | (1600) | ---------------------------------------- |
| Consensus          | (2481) | CGCCGTGAGCCTGTTCAACGCCACCGCCATCGCCGTGGCC |

|                    |        | 2521                                     2560 |
|---|---|---|
| gp160              | (2515) | GAGGGCACCGACCGCATCATCGAGATCGTGCAGCGCATCT |
| gp160 del V1       | (2419) | GAGGGCACCGACCGCATCATCGAGATCGTGCAGCGCATCT |
| gp160 del V2       | (2434) | GAGGGCACCGACCGCATCATCGAGATCGTGCAGCGCATCT |
| gp160 del V1-2     | (2221) | GAGGGCACCGACCGCATCATCGAGATCGTGCAGCGCATCT |
| gp 160 del 128-194 | (2266) | GAGGGCACCGACCGCATCATCGAGATCGTGCAGCGCATCT |
| gp140TM            | (2182) | ---------------------------------------- |
| gp140              | (2113) | ---------------------------------------- |
| gp140mut           | (2113) | ---------------------------------------- |
| gp120              | (1600) | ---------------------------------------- |
| Consensus          | (2521) | GAGGGCACCGACCGCATCATCGAGATCGTGCAGCGCATCT |

FIG. 66B-13

```
                               2561                              2600
          gp160       (2555)   TCCGCGCCGTGATCCACATCCCCCGCCGCATCCGCCAGGG
     gp160 del V1     (2459)   TCCGCGCCGTGATCCACATCCCCCGCCGCATCCGCCAGGG
     gp160 del V2     (2474)   TCCGCGCCGTGATCCACATCCCCCGCCGCATCCGCCAGGG
     gp160 del V1-2   (2261)   TCCGCGCCGTGATCCACATCCCCCGCCGCATCCGCCAGGG
    gp 160 del 128-194 (2306)  TCCGCGCCGTGATCCACATCCCCCGCCGCATCCGCCAGGG
          gp140TM     (2182)   ----------------------------------------
            gp140     (2113)   ----------------------------------------
         gp140mut     (2113)   ----------------------------------------
            gp120     (1600)   ----------------------------------------
        Consensus     (2561)   TCCGCGCCGTGATCCACATCCCCCGCCGCATCCGCCAGGG
                               2601                              2640
          gp160       (2595)   CCTGGAGCGCGCCCTGCTGTAAGATATCGGATCCTCTAGA
     gp160 del V1     (2499)   CCTGGAGCGCGCCCTGCTGTAAGATATCGGATCCTCTAGA
     gp160 del V2     (2514)   CCTGGAGCGCGCCCTGCTGTAAGATATCGGATCCTCTAGA
     gp160 del V1-2   (2301)   CCTGGAGCGCGCCCTGCTGTAAGATATCGGATCCTCTAGA
    gp 160 del 128-194 (2346)  CCTGGAGCGCGCCCTGCTGTAAGATATCGGATCCTCTAGA
          gp140TM     (2182)   ----------------------------------------
            gp140     (2113)   ----------------------------------------
         gp140mut     (2113)   ----------------------------------------
            gp120     (1600)   ----------------------------------------
        Consensus     (2601)   CCTGGAGCGCGCCCTGCTGTAAGATATCGGATCCTCTAGA
                               2641                              2680
          gp160       (2635)   AAGCCATGGATATCGGATCCACTACGCGTTAGAGCTCGCT
     gp160 del V1     (2539)   ----------------------------------------
     gp160 del V2     (2554)   ----------------------------------------
     gp160 del V1-2   (2341)   ----------------------------------------
    gp 160 del 128-194 (2386)  ----------------------------------------
          gp140TM     (2182)   ----------------------------------------
            gp140     (2113)   ----------------------------------------
         gp140mut     (2113)   ----------------------------------------
            gp120     (1600)   ----------------------------------------
        Consensus     (2641)   NNNNNNNNNNNNNNNNNNNNNNNNNNNNNNNNNNNNNNNN
                               2681
          gp160       (2675)   GATCAGCT
     gp160 del V1     (2539)   --------
     gp160 del V2     (2554)   --------
     gp160 del V1-2   (2341)   --------
    gp 160 del 128-194 (2386)  --------
          gp140TM     (2182)   --------
            gp140     (2113)   --------
         gp140mut     (2113)   --------
            gp120     (1600)   --------
        Consensus     (2681)   NNNNNNNN
```

FIG. 66B-14

HIV-1SF2 wt RT (PISPIET-->GIRKVL)
```
CCCATTAGTCCTATTGAAACTGTACCAGTAAAATTAAAGCCAGGAATGGATGGCCCAAAA
GTTAAGCAATGGCCATTGACAGAAGAAAAAATAAAAGCATTAGTAGAGATATGTACAGAA
ATGGAAAAGGAAGGGAAAATTTCAAAAATTGGGCCTGAAAATCCATACAATACTCCAGTA
TTTGCTATAAAGAAAAAGACAGTACTAAATGGAGAAAACTAGTAGATTTCAGAGAACTT
AATAAAAGAACTCAAGACTTCTGGGAAGTTCAGTTAGGAATACCACACCCCGCAGGGTTA
AAAAAGAAAAAATCAGTAACAGTATTGGATGTGGGTGATGCATACTTTTCAGTTCCCTTA
GATAAAGACTTTAGAAAGTATACTGCATTTACCATACCTAGTATAAACAATGAGACACCA
GGGATTAGATATCAGTACAATGTGCTGCCACAGGGATGGAAAGGATCACCAGCAATATTC
CAAAGTAGCATGACAAAAATCTTAGAGCCTTTTAGAAAACAGAATCCAGACATAGTTATC
TATCAAtacatggatgatTTGTATGTAGGATCTGACTTAGAAATAGGGCAGCATAGAACA
AAAATAGAGGAACTGAGACAGCATCTGTTGAGGTGGGGATTTACCACACCAGACAAAAAA
CATCAGAAAGAACCTCCATTCCTTtggatgggttatGAACTCCATCCTGATAAATGGACA
GTACAGCCTATAATGCTGCCAGAAAAAGACAGCTGGACTGTCAATGACATACAGAAGTTA
GTGGGAAAATTGAATTGGGCAAGTCAGATTTATGCAGGGATTAAAGTAAAGCAGTTATGT
AAACTCCTTAGAGGAACCAAAGCACTAACAGAAGTAATACCACTAACAGAAGAAGCAGAG
CTAGAACTGGCAGAAAACAGGGAGATTCTAAAAGAACCAGTACATGAAGTATATTATGAC
CCATCAAAAGACTTAGTAGCAGAAATACAGAAGCAGGGGCAAGGCCAATGGACATATCAA
ATTTATCAAGAGCCATTTAAAAATCTGAAAACAGGAAAGTATGCAAGGATGAGGGGTGCC
CACACTAATGATGTAAAACAGTTAACAGAGGCAGTGCAAAAAGTATCCACAGAAAGCATA
GTAATATGGGGAAAGATTCCTAAATTTAAACTACCCATACAAAAGGAAACATGGGAAGCA
TGGTGGATGGAGTATTGGCAAGCTACCTGGATTCCTGAGTGGGAGTTTGTCAATACCCCT
CCCTTAGTGAAATTATGGTACCAGTTAGAGAAAGAACCCATAGTAGGAGCAGAAACTTTC
TATGTAGATGGGGCAGCTAATAGGGAGACTAAATTAGGAAAAGCAGGATATGTTACTGAC
AGAGGAAGACAAAAAGTTGTCTCCATAGCTGACACAACAAATCAGAAGACTGAATTACAA
GCAATTCATCTAGCTTTGCAGGATTCGGGATTAGAAGTAAACATAGTAACAGACTCACAA
TATGCATTAGGAATCATTCAAGCACAACCAGATAAGAGTGAATCAGAGTTAGTCAGTCAA
ATAATAGAGCAGTTAATAAAAAAGGAAAAGGTCTACCTGGCATGGGTACCAGCACACAAA
GGAATTGGAGGAAATGAACAAGTAGATAAATTAGTCAGTGCTGGAATCAGGAAAGTACTA
```

FIG. 68
(SEQ ID NO:77)

GagProtMod.SF2(GP1)
GTCGACGCCACCATGGGCGCCCGCGCCAGCGTGCTGAGCGGCGGCGAGCTGGACAAGTGG
GAGAAGATCCGCCTGCGCCCCGGCGGCAAGAAGAAGTACAAGCTGAAGCACATCGTGTGG
GCCAGCCGCGAGCTGGAGCGCTTCGCCGTGAACCCCGGCCTGCTGGAGACCAGCGAGGGC
TGCCGCCAGATCCTGGGCCAGCTGCAGCCCAGCCTGCAGACCGGCAGCGAGGAGCTGCGC
AGCCTGTACAACACCGTGGCCACCCTGTACTGCGTGCACCAGCGCATCGACGTCAAGGAC
ACCAAGGAGGCCCTGGAGAAGATCGAGGAGGAGCAGAACAAGTCCAAGAAGAAGGCCCAG
CAGGCCGCCGCCGCCGGCACCGGCAACAGCAGCCAGGTGAGCCAGAACTACCCCATC
GTGCAGAACCTGCAGGGCCAGATGGTGCACCAGGCCATCAGCCCCGCACCCTGAACGCC
TGGGTGAAGGTGGTGGAGGAGAAGGCCTTCAGCCCCGAGGTGATCCCCATGTTCAGCGCC
CTGAGCGAGGGCGCCACCCCCAGGACCTGAACACGATGTTGAACACCGTGGGCGGCCAC
CAGGCCGCCATGCAGATGCTGAAGGAGACCATCAACGAGGAGGCCGCCGAGTGGGACCGC
GTGCACCCCGTGCACGCCGGCCCCATCGCCCCGGCCAGATGCGCGAGCCCCGCGGCAGC
GACATCGCCGGCACCACCAGCACCCTGCAGGAGCAGATCGGCTGGATGACCAACAACCCC
CCCATCCCCGTGGGCGAGATCTACAAGCGGTGGATCATCCTGGGCCTGAACAAGATCGTG
CGGATGTACAGCCCCACCAGCATCCTGGACATCGCCAGGGCCCCAAGGAGCCCTTCCGC
GACTACGTGGACCGCTTCTACAAGACCCTGCGCGCTGAGCAGGCCAGCCAGGACGTGAAG
AACTGGATGACCGAGACCCTGCTGGTGCAGAACGCCAACCCCGACTGCAAGACCATCCTG
AAGGCTCTCGGCCCCGCGGCCACCCTGGAGGAGATGATGACCGCCTGCCAGGGCGTGGGC
GGCCCCGGCCACAAGGCCCGCGTGCTGGCCGAGGCGATGAGCCAGGTGACGAACCCGGCG
ACCATCATGATGCAGCGCGGCAACTTCCGCAACCAGCGGAAGACCGTCAAGTGCTTCAAC
TGCGGCAAGGAGGGCCACACCGCCAGGAACTGCCGCGCCCCCGCAAGAAGGGCTGCTGG
CGCTGCGGCCGCGAAGGACACCAAATGAAAGATTGCACTGAGAGACAGGCTAATTTTTTA
GGGAAGATCTGGCCTTCCTACAAGGGAAGGCCAGGGAATTTTCTTCAGAGCAGACCAGAG
CCAACAGCCCCACCAGAAGAGAGCTTCAGGTTTGGGGAGGAGAAAACAACTCCCTCTCAG
AAGCAGGAGCCGATAGACAAGGAACTGTATCCTTTAACTTCCCTCAGATCACTCTTTGGC
AACGACCCCTCGTCACAGTAAGGATCGGCGGCCAGCTCAAGGAGGCGCTGCTCGACACCG
GCGCCGACGACACCGTGCTGGAGGAGATGAACCTGCCCGGCAAGTGGAAGCCCAAGATGA
TCGGCGGGATCGGGGGCTTCATCAAGGTGCGGCAGTACGACCAGATCCCCGTGGAGATCT
GCGGCCACAAGGCCATCGGCACCGTGCTGGTGGGCCCCACCCCCGTGAACATCATCGGCC
GCAACCTGCTGACCCAGATCGGCTGCACCCTGAACTTCCCCATCAGCCCCATCGAGACGG
TGCCCGTGAAGCTGAAGCCGGGGATGGACGGCCCCAAGGTCAAGCAGTGGCCCCTGTAAG
AATTC

FIG. 69
(SEQ ID NO:78)

GagProtMod.SF2(GP2)
GTCGACGCCACCATGGGCGCCCGCGCCAGCGTGCTGAGCGGCGGCGAGCTGGACAAGTGG
GAGAAGATCCGCCTGCGCCCCGGCGGCAAGAAGAAGTACAAGCTGAAGCACATCGTGTGG
GCCAGCCGCGAGCTGGAGCGCTTCGCCGTGAACCCCGGCCTGCTGGAGACCAGCGAGGGC
TGCCGCCAGATCCTGGGCCAGCTGCAGCCCAGCCTGCAGACCGGCAGCGAGGAGCTGCGC
AGCCTGTACAACACCGTGGCCACCCTGTACTGCGTGCACCAGCGCATCGACGTCAAGGAC
ACCAAGGAGGCCCTGGAGAAGATCGAGGAGGAGCAGAACAAGTCCAAGAAGAAGGCCCAG
CAGGCCGCCGCCGCCGCCGGCACCGGCAACAGCAGCCAGGTGAGCCAGAACTACCCCATC
GTGCAGAACCTGCAGGGCCAGATGGTGCACCAGGCCATCAGCCCCGCACCCTGAACGCC
TGGGTGAAGGTGGTGGAGGAGAAGGCCTTCAGCCCCGAGGTGATCCCCATGTTCAGCGCC
CTGAGCGAGGGCGCCACCCCCCAGGACCTGAACACGATGTTGAACACCGTGGGCGGCCAC
CAGGCCGCCATGCAGATGCTGAAGGAGACCATCAACGAGGAGGCCGCCGAGTGGGACCGC
GTGCACCCCGTGCACGCCGGCCCCATCGCCCCCGGCCAGATGCGCGAGCCCCGCGGCAGC
GACATCGCCGGCACCACCAGCACCCTGCAGGAGCAGATCGGCTGGATGACCAACAACCCC
CCCATCCCCGTGGGCGAGATCTACAAGCGGTGGATCATCCTGGGCCTGAACAAGATCGTG
CGGATGTACAGCCCCACCAGCATCCTGGACATCCGCCAGGGCCCCAAGGAGCCCTTCCGC
GACTACGTGGACCGCTTCTACAAGACCCTGCGCGCTGAGCAGGCCAGCCAGGACGTGAAG
AACTGGATGACCGAGACCCTGCTGGTGCAGAACGCCAACCCCGACTGCAAGACCATCCTG
AAGGCTCTCGGCCCCGCGGCCACCCTGGAGGAGATGATGACCGCCTGCCAGGGCGTGGGC
GGCCCCGGCCACAAGGCCCGCGTGCTGGCCGAGGCGATGAGCCAGGTGACGAACCCGGCG
ACCATCATGATGCAGCGCGGCAACTTCCGCAACCAGCGGAAGACCGTCAAGTGCTTCAAC
TGCGGCAAGGAGGGCCACACCGCCAGGAACTGCCGCGCCCCCGCAAGAAGGGCTGCTGG
CGCTGCGGCCGCGAAGGACACCAAATGAAAGATTGCACTGAGAGACAGGCTAATTTTTTA
GGGAAGATCTGGCCTTCCTACAAGGGAAGGCCAGGGAATTTTCTTCAGAGCAGACCAGAG
CCAACAGCCCCACCAGAAGAGAGCTTCAGGTTTGGGGAGGAGAAAACAACTCCCTCTCAG
AAGCAGGAGCCGATAGACAAGGAACTGTATCCTTTAACTTCCCTCAGATCACTCTTTGGC
AACGACCCCTCGTCACAGTAAGGATCGGGGGCAACTCAAGGAAGCGCTGCTCGATACAG
GAGCAGATGATACAGTATTAGAAGAAATGAATTTGCCAGGAAAATGGAAACCAAAAATGA
TAGGGGGGATCGGGGGCTTCATCAAGGTGAGGCAGTACGACCAGATACCTGTAGAAATCT
GTGGACATAAAGCTATAGGTACAGTATTAGTAGGACCTACACCTGTCAACATAATTGGAA
GAAATCTGTTGACCCAGATCGGCTGCACCTTGAACTTCCCCATCAGCCCTATTGAGACGG
TGCCCGTGAAGTTGAAGCCGGGGATGGACGGCCCCAAGGTCAAGCAATGGCCATTGTAAG
AATTC

FIG. 70
(SEQ ID NO:79)

FS(+)_ProtInact_RTopt_YM

GCGGCCGCGAAGGACACCAAATGAAAGATTGCACTGAGAGACAGGCTAATTTTTTAGGGA
AGATCTGGCCTTCCTACAAGGGAAGGCCAGGGAATTTTCTTCAGAGCAGACCAGAGCCAA
CAGCCCCACCAGAAGAGAGCTTCAGGTTTGGGGAGGAGAAAACAACTCCCTCTCAGAAGC
AGGAGCCGATAGACAAGGAACTGTATCCTTTAACTTCCCTCAGATCACTCTTTGGCAACG
ACCCCTCGTCACAATAAGGATCGGGGGCAACTCAAGGAAGCGCTGCTCGATACAGGAGC
AGATGATACAGTATTAGAAGAAATGAATTTGCCAGGAAAATGGAAACCAAAAATGATAGG
GGGGATCGGGGGCTTCATCAAGGTGAGGCAGTACGACCAGATACCTGTAGAAATCTGTGG
ACATAAAGCTATAGGTACAGTATTAGTAGGACCTACACCTGTCAACATAATTGGAAGAAA
TCTGTTGACCCAGATCGGCTGCACCTTGAACTTCCCCATCAGCCCTATTGAGACGGTGCC
CGTGAAGTTGAAGCCGGGGATGGACGGCCCCAAGGTCAAGCAATGGCCATTGACCGAGGA
GAAGATCAAGGCCCTGGTGGAGATCTGCACCGAGATGGAGAAGGAGGGCAAGATCAGCAA
GATCGGCCCCGAGAACCCCTACAACACCCCGTGTTCGCCATCAAGAAGAAGGACAGCAC
CAAGTGGCGCAAGCTGGTGGACTTCCGCGAGCTGAACAAGCGCACCCAGGACTTCTGGGA
GGTGCAGCTGGGCATCCCCCACCCCGCCGGCCTGAAGAAGAAGAAGAGCGTGACCGTGCT
GGACGTGGGCGACGCCTACTTCAGCGTGCCCCTGGACAAGGACTTCCGCAAGTACACCGC
CTTCACCATCCCCAGCATCAACAACGAGACCCCCGGCATCCGCTACCAGTACAACGTGCT
GCCCCAGGGCTGGAAGGGCAGCCCCGCCATCTTCCAGAGCAGCATGACCAAGATCCTGGA
GCCCTTCCGCAAGCAGAACCCCGACATCGTGATCTACCAGGCCCCCCTGTACGTGGGCAG
CGACCTGGAGATCGGCCAGCACCGCACCAAGATCGAGGAGCTGCGCCAGCACCTGCTGCG
CTGGGGCTTCACCACCCCCGACAAGAAGCACCAGAAGGAGCCCCCCTTCCTGTGGATGGG
CTACGAGCTGCACCCCGACAAGTGGACCGTGCAGCCCATCATGCTGCCCGAGAAGGACAG
CTGGACCGTGAACGACATCCAGAAGCTGGTGGGCAAGCTGAACTGGGCCAGCCAGATCTA
CGCCGGCATCAAGGTGAAGCAGCTGTGCAAGCTGCTGCGCGGCACCAAGGCCCTGACCGA
GGTGATCCCCCTGACCGAGGAGGCCGAGCTGGAGCTGGCCGAGAACCGCGAGATCCTGAA
GGAGCCCGTGCACGAGGTGTACTACGACCCCAGCAAGGACCTGGTGGCCGAGATCCAGAA
GCAGGGCCAGGGCCAGTGGACCTACCAGATCTACCAGGAGCCCTTCAAGAACCTGAAGAC
CGGCAAGTACGCCCGCATGCGCGGCGCCCACACCAACGACGTGAAGCAGCTGACCGAGGC
CGTGCAGAAGGTGAGCACCGAGAGCATCGTGATCTGGGGCAAGATCCCCAAGTTCAAGCT

FIG. 71A
(SEQ ID NO:80)

GCCCATCCAGAAGGAGACCTGGGAGGCCTGGTGGATGGAGTACTGGCAGGCCACCTGGAT
CCCCGAGTGGGAGTTCGTGAACACCCCCCCCTGGTGAAGCTGTGGTACCAGCTGGAGAA
GGAGCCCATCGTGGGCGCCGAGACCTTCTACGTGGACGGCGCCGCCAACCGCGAGACCAA
GCTGGGCAAGGCCGGCTACGTGACCGACCGGGGCCGGCAGAAGGTGGTGAGCATCGCCGA
CACCACCAACCAGAAGACCGAGCTGCAGGCCATCCACCTGGCCCTGCAGGACAGCGGCCT
GGAGGTGAACATCGTGACCGACAGCCAGTACGCCCTGGGCATCATCCAGGCCCAGCCCGA
CAAGAGCGAGAGCGAGCTGGTGAGCCAGATCATCGAGCAGCTGATCAAGAAGGAGAAGGT
GTACCTGGCCTGGGTGCCCGCCCACAAGGGCATCGGCGGCAACGAGCAGGTGGACAAGCT
GGTGAGCGCCGGCATCCGCAAGGTGCTGTTCCTGAACGGCATCGATGGCGGCATCGTGAT
CTACCAGTACATGGACGACCTGTACGTGGGCAGCGGCGGCCCTAGGATCGATTAAAAGCT
TCCCGGGGCTAGCACCGGTGAATTC

FIG. 71B
(SEQ ID NO:80)

FS(+)_ProtInact_RTopt_YMWM

GCGGCCGCGAAGGACACCAAATGAAAGATTGCACTGAGAGACAGGCTAATTTTTTAGGGA
AGATCTGGCCTTCCTACAAGGGAAGGCCAGGGAATTTTCTTCAGAGCAGACCAGAGCCAA
CAGCCCCACCAGAAGAGAGCTTCAGGTTTGGGGAGGAGAAAACAACTCCCTCTCAGAAGC
AGGAGCCGATAGACAAGGAACTGTATCCTTTAACTTCCCTCAGATCACTCTTTGGCAACG
ACCCCTCGTCACAATAAGGATCGGGGGCAACTCAAGGAAGCGCTGCTCGATACAGGAGC
AGATGATACAGTATTAGAAGAAATGAATTTGCCAGGAAAATGGAAACCAAAAATGATAGG
GGGGATCGGGGGCTTCATCAAGGTGAGGCAGTACGACCAGATACCTGTAGAAATCTGTGG
ACATAAAGCTATAGGTACAGTATTAGTAGGACCTACACCTGTCAACATAATTGGAAGAAA
TCTGTTGACCCAGATCGGCTGCACCTTGAACTTCCCCATCAGCCCTATTGAGACGGTGCC
CGTGAAGTTGAAGCCGGGGATGGACGGCCCCAAGGTCAAGCAATGGCCATTGACCGAGGA
GAAGATCAAGGCCCTGGTGGAGATCTGCACCGAGATGGAGAAGGAGGGCAAGATCAGCAA
GATCGGCCCCGAGAACCCCTACAACACCCCGTGTTCGCCATCAAGAAGAAGGACAGCAC
CAAGTGGCGCAAGCTGGTGGACTTCCGCGAGCTGAACAAGCGCACCCAGGACTTCTGGGA
GGTGCAGCTGGGCATCCCCCACCCCGCCGGCCTGAAGAAGAAGAAGAGCGTGACCGTGCT
GGACGTGGGCGACGCCTACTTCAGCGTGCCCCTGGACAAGGACTTCCGCAAGTACACCGC
CTTCACCATCCCCAGCATCAACAACGAGACCCCCGGCATCCGCTACCAGTACAACGTGCT
GCCCCAGGGCTGGAAGGGCAGCCCCGCCATCTTCCAGAGCAGCATGACCAAGATCCTGGA
GCCCTTCCGCAAGCAGAACCCCGACATCGTGATCTACCAGGCCCCCCTGTACGTGGGCAG
CGACCTGGAGATCGGCCAGCACCGCACCAAGATCGAGGAGCTGCGCCAGCACCTGCTGCG
CTGGGGCTTCACCACCCCCGACAAGAAGCACCAGAAGGAGCCCCCCTTCCTGCCCATCGA
GCTGCACCCCGACAAGTGGACCGTGCAGCCCATCATGCTGCCCGAGAAGGACAGCTGGAC
CGTGAACGACATCCAGAAGCTGGTGGGCAAGCTGAACTGGGCCAGCCAGATCTACGCCGG
CATCAAGGTGAAGCAGCTGTGCAAGCTGCTGCGCGGCACCAAGGCCCTGACCGAGGTGAT
CCCCCTGACCGAGGAGGCCGAGCTGGAGCTGGCCGAGAACCGCGAGATCCTGAAGGAGCC
CGTGCACGAGGTGTACTACGACCCCAGCAAGGACCTGGTGGCCGAGATCCAGAAGCAGGG
CCAGGGCCAGTGGACCTACCAGATCTACCAGGAGCCCTTCAAGAACCTGAAGACCGGCAA
GTACGCCCGCATGCGCGGCGCCCACACCAACGACGTGAAGCAGCTGACCGAGGCCGTGCA
GAAGGTGAGCACCGAGAGCATCGTGATCTGGGGCAAGATCCCCAAGTTCAAGCTGCCCAT

FIG. 72A
(SEQ ID NO:81)

CCAGAAGGAGACCTGGGAGGCCTGGTGGATGGAGTACTGGCAGGCCACCTGGATCCCCGA
GTGGGAGTTCGTGAACACCCCCCCCTGGTGAAGCTGTGGTACCAGCTGGAGAAGGAGCC
CATCGTGGGCGCCGAGACCTTCTACGTGGACGGCGCCGCCAACCGCGAGACCAAGCTGGG
CAAGGCCGGCTACGTGACCGACCGGGGCCGGCAGAAGGTGGTGAGCATCGCCGACACCAC
CAACCAGAAGACCGAGCTGCAGGCCATCCACCTGGCCCTGCAGGACAGCGGCCTGGAGGT
GAACATCGTGACCGACAGCCAGTACGCCCTGGGCATCATCCAGGCCCAGCCCGACAAGAG
CGAGAGCGAGCTGGTGAGCCAGATCATCGAGCAGCTGATCAAGAAGGAGAAGGTGTACCT
GGCCTGGGTGCCCGCCCACAAGGGCATCGGCGGCAACGAGCAGGTGGACAAGCTGGTGAG
CGCCGGCATCCGCAAGGTGCTGTTCCTGAACGGCATCGATGGCGGCATCGTGATCTACCA
GTACATGGACGACCTGTACGTGGGCAGCGGCGGCCCTAGGATCGATTAAAAGCTTCCCGG
GGCTAGCACCGGTGAATTC

FIG. 72B
(SEQ ID NO:81)

FS(-)_ProtMod_RTopt_YM

GCGGCCGCGAAGGACACCAAATGAAAGATTGCACTGAGAGACAGGCTAATTTCTTCCGCG
AGGACCTGGCCTTCCTGCAGGGCAAGGCCCGCGAGTTCAGCAGCGAGCAGACCCGCGCCA
ACAGCCCCACCCGCCGCGAGCTGCAGGTGTGGGGCGGCGAGAACAACAGCCTGAGCGAGG
CCGGCGCCGACCGCCAGGGCACCGTGAGCTTCAACTTCCCCCAGATCACCCTGTGGCAGC
GCCCCCTGGTGACCATCAGGATCGGCGGCCAGCTCAAGGAGGCGCTGCTCGACACCGGCG
CCGACGACACCGTGCTGGAGGAGATGAACCTGCCCGGCAAGTGGAAGCCCAAGATGATCG
GCGGGATCGGGGGCTTCATCAAGGTGCGGCAGTACGACCAGATCCCCGTGGAGATCTGCG
GCCACAAGGCCATCGGCACCGTGCTGGTGGGCCCCACCCCCGTGAACATCATCGGCCGCA
ACCTGCTGACCCAGATCGGCTGCACCCTGAACTTCCCCATCAGCCCCATCGAGACGGTGC
CCGTGAAGCTGAAGCCGGGGATGGACGGCCCCAAGGTCAAGCAGTGGCCCCTGACCGAGG
AGAAGATCAAGGCCCTGGTGGAGATCTGCACCGAGATGGAGAAGGAGGGCAAGATCAGCA
AGATCGGCCCCGAGAACCCCTACAACACCCCCGTGTTCGCCATCAAGAAGAAGGACAGCA
CCAAGTGGCGCAAGCTGGTGGACTTCGCGAGCTGAACAAGCGCACCCAGGACTTCTGGG
AGGTGCAGCTGGGCATCCCCCACCCCGCCGGCCTGAAGAAGAAGAAGAGCGTGACCGTGC
TGGACGTGGGCGACGCCTACTTCAGCGTGCCCCTGGACAAGGACTTCCGCAAGTACACCG
CCTTCACCATCCCCAGCATCAACAACGAGACCCCCGGCATCCGCTACCAGTACAACGTGC
TGCCCCAGGGCTGGAAGGGCAGCCCCGCCATCTTCCAGAGCAGCATGACCAAGATCCTGG
AGCCCTTCCGCAAGCAGAACCCCGACATCGTGATCTACCAGGCCCCCTGTACGTGGGCA
GCGACCTGGAGATCGGCCAGCACCGCACCAAGATCGAGGAGCTGCGCCAGCACCTGCTGC
GCTGGGGCTTCACCACCCCCGACAAGAAGCACCAGAAGGAGCCCCCCTTCCTGTGGATGG
GCTACGAGCTGCACCCCGACAAGTGGACCGTGCAGCCCATCATGCTGCCCGAGAAGGACA
GCTGGACCGTGAACGACATCCAGAAGCTGGTGGGCAAGCTGAACTGGGCCAGCCAGATCT
ACGCCGGCATCAAGGTGAAGCAGCTGTGCAAGCTGCTGCGCGGCACCAAGGCCCTGACCG
AGGTGATCCCCCTGACCGAGGAGGCCGAGCTGGAGCTGGCCGAGAACCGCGAGATCCTGA
AGGAGCCCGTGCACGAGGTGTACTACGACCCCAGCAAGGACCTGGTGGCCGAGATCCAGA
AGCAGGGCCAGGGCCAGTGGACCTACCAGATCTACCAGGAGCCCTTCAAGAACCTGAAGA
CCGGCAAGTACGCCCGCATGCGCGGCGCCCACACCAACGACGTGAAGCAGCTGACCGAGG
CCGTGCAGAAGGTGAGCACCGAGAGCATCGTGATCTGGGGCAAGATCCCCAAGTTCAAGC

FIG. 73A
(SEQ ID NO:82)

TGCCCATCCAGAAGGAGACCTGGGAGGCCTGGTGGATGGAGTACTGGCAGGCCACCTGGA
TCCCCGAGTGGGAGTTCGTGAACACCCCCCCCTGGTGAAGCTGTGGTACCAGCTGGAGA
AGGAGCCCATCGTGGGCGCCGAGACCTTCTACGTGGACGGCGCCGCCAACCGCGAGACCA
AGCTGGGCAAGGCCGGCTACGTGACCGACCGGGGCCGGCAGAAGGTGGTGAGCATCGCCG
ACACCACCAACCAGAAGACCGAGCTGCAGGCCATCCACCTGGCCCTGCAGGACAGCGGCC
TGGAGGTGAACATCGTGACCGACAGCCAGTACGCCCTGGGCATCATCCAGGCCCAGCCCG
ACAAGAGCGAGAGCGAGCTGGTGAGCCAGATCATCGAGCAGCTGATCAAGAAGGAGAAGG
TGTACCTGGCCTGGGTGCCCGCCCACAAGGGCATCGGCGGCAACGAGCAGGTGGACAAGC
TGGTGAGCGCCGGCATCCGCAAGGTGCTGTTCCTGAACGGCATCGATGGCGGCATCGTGA
TCTACCAGTACATGGACGACCTGTACGTGGGCAGCGGCGGCCCTAGGATCGATTAAAAGC
TTCCCGGGGCTAGCACCGGTGAATTC

FIG. 73B
(SEQ ID NO:82)

FS(-)_ProtMod_RTopt_YMWM

GCGGCCGCGAAGGACACCAAATGAAAGATTGCACTGAGAGACAGGCTAATTTCTTCCGCG
AGGACCTGGCCTTCCTGCAGGGCAAGGCCCGCGAGTTCAGCAGCGAGCAGACCCGCGCCA
ACAGCCCCACCCGCCGCGAGCTGCAGGTGTGGGCGGCGAGAACAACAGCCTGAGCGAGG
CCGGCGCCGACCGCCAGGGCACCGTGAGCTTCAACTTCCCCCAGATCACCCTGTGGCAGC
GCCCCCTGGTGACCATCAGGATCGGCGGCCAGCTCAAGGAGGCGCTGCTCGACACCGGCG
CCGACGACACCGTGCTGGAGGAGATGAACCTGCCCGGCAAGTGGAAGCCCAAGATGATCG
GCGGGATCGGGGGCTTCATCAAGGTGCGGCAGTACGACCAGATCCCCGTGGAGATCTGCG
GCCACAAGGCCATCGGCACCGTGCTGGTGGGCCCCACCCCGTGAACATCATCGGCCGCA
ACCTGCTGACCCAGATCGGCTGCACCCTGAACTTCCCCATCAGCCCCATCGAGACGGTGC
CCGTGAAGCTGAAGCCGGGGATGGACGGCCCCAAGGTCAAGCAGTGGCCCCTGACCGAGG
AGAAGATCAAGGCCCTGGTGGAGATCTGCACCGAGATGGAGAAGGAGGGCAAGATCAGCA
AGATCGGCCCCGAGAACCCCTACAACACCCCGTGTTCGCCATCAAGAAGAAGGACAGCA
CCAAGTGGCGCAAGCTGGTGGACTTCCGCGAGCTGAACAAGCGCACCCAGGACTTCTGGG
AGGTGCAGCTGGGCATCCCCCACCCCGCCGGCCTGAAGAAGAAGAAGAGCGTGACCGTGC
TGGACGTGGGCGACGCCTACTTCAGCGTGCCCCTGGACAAGGACTTCCGCAAGTACACCG
CCTTCACCATCCCCAGCATCAACAACGAGACCCCCGGCATCCGCTACCAGTACAACGTGC
TGCCCCAGGGCTGGAAGGGCAGCCCCGCCATCTTCCAGAGCAGCATGACCAAGATCCTGG
AGCCCTTCCGCAAGCAGAACCCCGACATCGTGATCTACCAGGCCCCCCTGTACGTGGGCA
GCGACCTGGAGATCGGCCAGCACCGCACCAAGATCGAGGAGCTGCGCCAGCACCTGCTGC
GCTGGGGCTTCACCACCCCCGACAAGAAGCACCAGAAGGAGCCCCCCTTCCTGCCCATCG
AGCTGCACCCCGACAAGTGGACCGTGCAGCCCATCATGCTGCCCGAGAAGGACAGCTGGA
CCGTGAACGACATCCAGAAGCTGGTGGGCAAGCTGAACTGGGCCAGCCAGATCTACGCCG
GCATCAAGGTGAAGCAGCTGTGCAAGCTGCTGCGCGGCACCAAGGCCCTGACCGAGGTGA
TCCCCCTGACCGAGGAGGCCGAGCTGGAGCTGGCCGAGAACCGCGAGATCCTGAAGGAGC
CCGTGCACGAGGTGTACTACGACCCCAGCAAGGACCTGGTGGCCGAGATCCAGAAGCAGG
GCCAGGGCCAGTGGACCTACCAGATCTACCAGGAGCCCTTCAAGAACCTGAAGACCGGCA
AGTACGCCCGCATGCGCGGCGCCCACACCAACGACGTGAAGCAGCTGACCGAGGCCGTGC
AGAAGGTGAGCACCGAGAGCATCGTGATCTGGGGCAAGATCCCCAAGTTCAAGCTGCCCA

FIG. 74A
(SEQ ID NO:83)

```
TCCAGAAGGAGACCTGGGAGGCCTGGTGGATGGAGTACTGGCAGGCCACCTGGATCCCCG
AGTGGGAGTTCGTGAACACCCCCCCCTGGTGAAGCTGTGGTACCAGCTGGAGAAGGAGC
CCATCGTGGGCGCCGAGACCTTCTACGTGGACGGCGCCGCCAACCGCGAGACCAAGCTGG
GCAAGGCCGGCTACGTGACCGACCGGGGCCGGCAGAAGGTGGTGAGCATCGCCGACACCA
CCAACCAGAAGACCGAGCTGCAGGCCATCCACCTGGCCCTGCAGGACAGCGGCCTGGAGG
TGAACATCGTGACCGACAGCCAGTACGCCCTGGGCATCATCCAGGCCCAGCCCGACAAGA
GCGAGAGCGAGCTGGTGAGCCAGATCATCGAGCAGCTGATCAAGAAGGAGAAGGTGTACC
TGGCCTGGGTGCCCGCCCACAAGGGCATCGGCGGCAACGAGCAGGTGGACAAGCTGGTGA
GCGCCGGCATCCGCAAGGTGCTGTTCCTGAACGGCATCGATGGCGGCATCGTGATCTACC
AGTACATGGACGACCTGTACGTGGGCAGCGGCGGCCCTAGGATCGATTAAAAGCTTCCCG
GGGCTAGCACCGGTGAATTC
```

FIG. 74B

(SEQ ID NO:83)

FS(-)_ProtMod_RTopt(+)

GCGGCCGCGAAGGACACCAAATGAAAGATTGCACTGAGAGACAGGCTAATTTCTTCCGCG
AGGACCTGGCCTTCCTGCAGGGCAAGGCCCGCGAGTTCAGCAGCGAGCAGACCCGCGCCA
ACAGCCCCACCCGCCGCGAGCTGCAGGTGTGGGGCGGCGAGAACAACAGCCTGAGCGAGG
CCGGCGCCGACCGCCAGGGCACCGTGAGCTTCAACTTCCCCCAGATCACCCTGTGGCAGC
GCCCCCTGGTGACCATCAGGATCGGCGGCCAGCTCAAGGAGGCGCTGCTCGACACCGGCG
CCGACGACACCGTGCTGGAGGAGATGAACCTGCCCGGCAAGTGGAAGCCCAAGATGATCG
GCGGGATCGGGGGCTTCATCAAGGTGCGGCAGTACGACCAGATCCCCGTGGAGATCTGCG
GCCACAAGGCCATCGGCACCGTGCTGGTGGGCCCCACCCCCGTGAACATCATCGGCCGCA
ACCTGCTGACCCAGATCGGCTGCACCCTGAACTTCCCCATCAGCCCCATCGAGACGGTGC
CCGTGAAGCTGAAGCCGGGGATGGACGGCCCCAAGGTCAAGCAGTGGCCCCTGACCGAGG
AGAAGATCAAGGCCCTGGTGGAGATCTGCACCGAGATGGAGAAGGAGGGCAAGATCAGCA
AGATCGGCCCCGAGAACCCCTACAACACCCCCGTGTTCGCCATCAAGAAGAAGGACAGCA
CCAAGTGGCGCAAGCTGGTGGACTTCCGCGAGCTGAACAAGCGCACCCAGGACTTCTGGG
AGGTGCAGCTGGGCATCCCCCACCCCGCCGGCCTGAAGAAGAAGAAGAGCGTGACCGTGC
TGGACGTGGGCGACGCCTACTTCAGCGTGCCCCTGGACAAGGACTTCCGCAAGTACACCG
CCTTCACCATCCCCAGCATCAACAACGAGACCCCCGGCATCCGCTACCAGTACAACGTGC
TGCCCCAGGGCTGGAAGGGCAGCCCCGCCATCTTCCAGAGCAGCATGACCAAGATCCTGG
AGCCCTTCCGCAAGCAGAACCCCGACATCGTGATCTACCAGTACATGGACGACCTGTACG
TGGGCAGCGACCTGGAGATCGGCCAGCACCGCACCAAGATCGAGGAGCTGCGCCAGCACC
TGCTGCGCTGGGGCTTCACCACCCCCGACAAGAAGCACCAGAAGGAGCCCCCCTTCCTGT
GGATGGGCTACGAGCTGCACCCCGACAAGTGGACCGTGCAGCCCATCATGCTGCCCGAGA
AGGACAGCTGGACCGTGAACGACATCCAGAAGCTGGTGGGCAAGCTGAACTGGGCCAGCC
AGATCTACGCCGGCATCAAGGTGAAGCAGCTGTGCAAGCTGCTGCGCGGCACCAAGGCCC
TGACCGAGGTGATCCCCCTGACCGAGGAGGCCGAGCTGGAGCTGGCCGAGAACCGCGAGA
TCCTGAAGGAGCCCGTGCACGAGGTGTACTACGACCCCAGCAAGGACCTGGTGGCCGAGA
TCCAGAAGCAGGGCCAGGGCCAGTGGACCTACCAGATCTACCAGGAGCCCTTCAAGAACC
TGAAGACCGGCAAGTACGCCCGCATGCGCGGCGCCCACACCAACGACGTGAAGCAGCTGA
CCGAGGCCGTGCAGAAGGTGAGCACCGAGAGCATCGTGATCTGGGGCAAGATCCCCAAGT
TCAAGCTGCCCATCCAGAAGGAGACCTGGGAGGCCTGGTGGATGGAGTACTGGCAGGCCA
CCTGGATCCCCGAGTGGGAGTTCGTGAACACCCCCCCCCTGGTGAAGCTGTGGTACCAGC
TGGAGAAGGAGCCCATCGTGGGCGCCGAGACCTTCTACGTGGACGGCGCCGCCAACCGCG

FIG. 75A
(SEQ ID NO:84)

AGACCAAGCTGGGCAAGGCCGGCTACGTGACCGACCGGGGCCGGCAGAAGGTGGTGAGCA
TCGCCGACACCACCAACCAGAAGACCGAGCTGCAGGCCATCCACCTGGCCCTGCAGGACA
GCGGCCTGGAGGTGAACATCGTGACCGACAGCCAGTACGCCCTGGGCATCATCCAGGCCC
AGCCCGACAAGAGCGAGAGCGAGCTGGTGAGCCAGATCATCGAGCAGCTGATCAAGAAGG
AGAAGGTGTACCTGGCCTGGGTGCCCGCCCACAAGGGCATCGGCGGCAACGAGCAGGTGG
ACAAGCTGGTGAGCGCCGGCATCCGCAAGGTGCTGTTCCTGAACGGCATCGATGGCGGCA
TCGTGATCTACCAGTACATGGACGACCTGTACGTGGGCAGCGGCGGCCCTAGGATCGATT
AAAAGCTTCCCGGGGCTAGCACCGGTGAATTC

FIG. 75B
(SEQ ID NO:84)

Tat_wt_SF162 (wildtype)

ATGGAGCCAGTAGATCCTAGATTAGAGCCCTGGAAGCATCCAGGAAGTCAGCCTAAGA
CTGCTTGTACAAATTGCTATTGTAAAAAGTGTTGCTTTCATTGCCAAGTTTGTTTCATAAC
AAAAGGCTTAGGCATCTCCTATGGCAGGAAGAAGCGGAGACAGCGACGAAGAGCTCCT
CCAGACAGTGAGGTTCATCAAGTTTCTCTACCAAAGCAACCCGCTTCCCAGCCCCAAGG
GGACCCGACAGGCCCGAAGGAATCGAAGAAGAAGGTGGAGAGAGAGACAGAGACAGA
TCCAGTCCATTAG

FIG. 76
(SEQ ID NO:85)

Tat_SF162

MEPVDPRLEPWKHPGSQPKTACTNCYCKKCCFHCQVCFITKGLGISYGRKKRRQRRRAPPDSE
VHQVSLPKQPASQPQGDPTGPKESKKKVERETETDPVH

FIG. 77
(SEQ ID NO:86)

Tat_SF162_opt

ATGGAGCCCGTGGACCCCGCCTGGAGCCCTGGAAGCACCCCGGCAGCCAGCCCAAGAC
CGCCTGCACCAACTGCTACTGCAAGAAGTGCTGCTTCCACTGCCAGGTGTGCTTCATCACC
AAGGGCCTGGGCATCAGCTACGGCCGCAAGAAGCGCCGCCAGCGCCGCCGCGCCCCCC
CGACAGCGAGGTGCACCAGGTGAGCCTGCCCAAGCAGCCCGCCAGCCAGCCCCAGGGCG
ACCCCACCGGCCCCAAGGAGAGCAAGAAGAAGGTGGAGCGCGAGACCGAGACCGACCCC
GTGCACTAG

FIG. 78
(SEQ ID NO:87)

Tat_Cys22_SF162_opt

ATGGAGCCCGTGGACCCCGCCTGGAGCCCTGGAAGCACCCCGGCAGCCAGCCCAAGAC
CGCCgGCACCAACTGCTACTGCAAGAAGTGCTGCTTCCACTGCCAGGTGTGCTTCATCACCA
AGGGCCTGGGCATCAGCTACGGCCGCAAGAAGCGCCGCCAGCGCCGCCGCGCCCCCCC
GACAGCGAGGTGCACCAGGTGAGCCTGCCCAAGCAGCCCGCCAGCCAGCCCCAGGGCGA
CCCCACCGGCCCCAAGGAGAGCAAGAAGAAGGTGGAGCGCGAGACCGAGACCGACCCCG
TGCACTAG

FIG. 79
(SEQ ID NO:88)

Alignment GagMod vs GP1_GP2

```
                                                                                   Section 1
                         (1) 1      10        20        30        40        50        60          76
          GagMod.SF2     (1) ATGGGCGCCCGCGCCAGCGTGCTGAGCGGCGGCGAGCTGGACAAGTGGGAGAAGATCCGCCTGCGCCCCGGCGGCA
GagProtMod.SF2(GP1)      (1) ATGGGCGCCCGCGCCAGCGTGCTGAGCGGCGGCGAGCTGGACAAGTGGGAGAAGATCCGCCTGCGCCCCGGCGGCA
GagProtMod.SF2(GP2)      (1) ATGGGCGCCCGCGCCAGCGTGCTGAGCGGCGGCGAGCTGGACAAGTGGGAGAAGATCCGCCTGCGCCCCGGCGGCA
           Consensus     (1) ATGGGCGCCCGCGCCAGCGTGCTGAGCGGCGGCGAGCTGGACAAGTGGGAGAAGATCCGCCTGCGCCCCGGCGGCA
                                                                                   Section 2
                        (77) 77           90        100       110       120       130       140     152
          GagMod.SF2    (77) AGAAGAAGTACAAGCTGAAGCACATCGTGTGGGCCAGCCGCGAGCTGGAGCGCTTCGCCGTGAACCCCGGCCTGCT
GagProtMod.SF2(GP1)     (77) AGAAGAAGTACAAGCTGAAGCACATCGTGTGGGCCAGCCGCGAGCTGGAGCGCTTCGCCGTGAACCCCGGCCTGCT
GagProtMod.SF2(GP2)     (77) AGAAGAAGTACAAGCTGAAGCACATCGTGTGGGCCAGCCGCGAGCTGGAGCGCTTCGCCGTGAACCCCGGCCTGCT
           Consensus    (77) AGAAGAAGTACAAGCTGAAGCACATCGTGTGGGCCAGCCGCGAGCTGGAGCGCTTCGCCGTGAACCCCGGCCTGCT
                                                                                   Section 3
                       (153) 153   160       170       180       190       200       210            228
          GagMod.SF2   (153) GGAGACCAGCGAGGGCTGCCGCCAGATCCTGGGCCAGCTGCAGCCCAGCCTGCAGACCGGCAGCGAGGAGCTGCGC
GagProtMod.SF2(GP1)    (153) GGAGACCAGCGAGGGCTGCCGCCAGATCCTGGGCCAGCTGCAGCCCAGCCTGCAGACCGGCAGCGAGGAGCTGCGC
GagProtMod.SF2(GP2)    (153) GGAGACCAGCGAGGGCTGCCGCCAGATCCTGGGCCAGCTGCAGCCCAGCCTGCAGACCGGCAGCGAGGAGCTGCGC
           Consensus   (153) GGAGACCAGCGAGGGCTGCCGCCAGATCCTGGGCCAGCTGCAGCCCAGCCTGCAGACCGGCAGCGAGGAGCTGCGC
                                                                                   Section 4
                       (229) 229         240       250       260       270       280       290      304
          GagMod.SF2   (229) AGCCTGTACAACACCGTGGCCACCCTGTACTGCGTGCACCAGCGCATCGACGTCAAGGACACCAAGGAGGCCCTGG
GagProtMod.SF2(GP1)    (229) AGCCTGTACAACACCGTGGCCACCCTGTACTGCGTGCACCAGCGCATCGACGTCAAGGACACCAAGGAGGCCCTGG
GagProtMod.SF2(GP2)    (229) AGCCTGTACAACACCGTGGCCACCCTGTACTGCGTGCACCAGCGCATCGACGTCAAGGACACCAAGGAGGCCCTGG
           Consensus   (229) AGCCTGTACAACACCGTGGCCACCCTGTACTGCGTGCACCAGCGCATCGACGTCAAGGACACCAAGGAGGCCCTGG
                                                                                   Section 5
                       (305) 305  310       320       330       340       350       360       370  380
          GagMod.SF2   (305) AGAAGATCGAGGAGGAGCAGAACAAGTCCAAGAAGAAGGCCCAGCAGGCCGCCGCCGCCGCCGGCACCGGCAACAG
GagProtMod.SF2(GP1)    (305) AGAAGATCGAGGAGGAGCAGAACAAGTCCAAGAAGAAGGCCCAGCAGGCCGCCGCCGCCGCCGGCACCGGCAACAG
GagProtMod.SF2(GP2)    (305) AGAAGATCGAGGAGGAGCAGAACAAGTCCAAGAAGAAGGCCCAGCAGGCCGCCGCCGCCGCCGGCACCGGCAACAG
           Consensus   (305) AGAAGATCGAGGAGGAGCAGAACAAGTCCAAGAAGAAGGCCCAGCAGGCCGCCGCCGCCGCCGGCACCGGCAACAG
```

FIG. 80A

Alignment GagMod vs GP1_GP2

```
                        381         390       400       410       420       430       440                Section 6
                                                                                                                456
       GagMod.SF2  (381) CAGCCAGGTGAGCCAGGTGAGCCAGAACTACCCCATCGTGCAGAACCTGCAGGGCCAGATGGTGCACCAGGCCATCAGCCCCGC
GagProtMod.SF2(GP1)(381) CAGCCAGGTGAGCCAGGTGAGCCAGAACTACCCCATCGTGCAGAACCTGCAGGGCCAGATGGTGCACCAGGCCATCAGCCCCGC
GagProtMod.SF2(GP2)(381) CAGCCAGGTGAGCCAGGTGAGCCAGAACTACCCCATCGTGCAGAACCTGCAGGGCCAGATGGTGCACCAGGCCATCAGCCCCGC
          Consensus(381) CAGCCAGGTGAGCCAGGTGAGCCAGAACTACCCCATCGTGCAGAACCTGCAGGGCCAGATGGTGCACCAGGCCATCAGCCCCGC 457         470       480       490       500       510       520               Section 7
                                                                                                                532
       GagMod.SF2  (457) ACCCTGAACGCCTGGGTGAAGGTGGTGGAGGAGAAGGCCTTCAGCCCCGAGGTGATCCCCATGTTCAGCGCCCTGA
GagProtMod.SF2(GP1)(457) ACCCTGAACGCCTGGGTGAAGGTGGTGGAGGAGAAGGCCTTCAGCCCCGAGGTGATCCCCATGTTCAGCGCCCTGA
GagProtMod.SF2(GP2)(457) ACCCTGAACGCCTGGGTGAAGGTGGTGGAGGAGAAGGCCTTCAGCCCCGAGGTGATCCCCATGTTCAGCGCCCTGA
          Consensus(457) ACCCTGAACGCCTGGGTGAAGGTGGTGGAGGAGAAGGCCTTCAGCCCCGAGGTGATCCCCATGTTCAGCGCCCTGA 533         540       550       560       570       580       590               Section 8
                                                                                                                608
       GagMod.SF2  (533) GCGAGGGGGCCACCCCCCAGGACCTGAACACCATGCTGAACACCGTGGGCGGCCACCAGGCCGCCATGCAGATGCT
GagProtMod.SF2(GP1)(533) GCGAGGGGGCCACCCCCCAGGACCTGAACACCATGCTGAACACCGTGGGCGGCCACCAGGCCGCCATGCAGATGCT
GagProtMod.SF2(GP2)(533) GCGAGGGGGCCACCCCCCAGGACCTGAACACCATGCTGAACACCGTGGGCGGCCACCAGGCCGCCATGCAGATGCT
          Consensus(533) GCGAGGGGGCCACCCCCCAGGACCTGAACACCATGCTGAACACCGTGGGCGGCCACCAGGCCGCCATGCAGATGCT 609         620       630       640       650       660       670               Section 9
                                                                                                                684
       GagMod.SF2  (609) GAAGGAGACCATCAACGAGGAGGCCGCCGAGTGGGACCGCCTGCACCCCGTGCACGCCGGCCCCATCGCCCCCGGC
GagProtMod.SF2(GP1)(609) GAAGGAGACCATCAACGAGGAGGCCGCCGAGTGGGACCGCCTGCACCCCGTGCACGCCGGCCCCATCGCCCCCGGC
GagProtMod.SF2(GP2)(609) GAAGGAGACCATCAACGAGGAGGCCGCCGAGTGGGACCGCCTGCACCCCGTGCACGCCGGCCCCATCGCCCCCGGC
          Consensus(609) GAAGGAGACCATCAACGAGGAGGCCGCCGAGTGGGACCGCCTGCACCCCGTGCACGCCGGCCCCATCGCCCCCGGC 685         700       710       720       730       740       750              Section 10
                                                                                                                760
       GagMod.SF2  (685) CAGATGCGCGAGCCCCGCGGCAGCGACATCGCCGGCACCACCAGCACCCTGCAGGAGCAGATCGGCTGGATGACCA
GagProtMod.SF2(GP1)(685) CAGATGCGCGAGCCCCGCGGCAGCGACATCGCCGGCACCACCAGCACCCTGCAGGAGCAGATCGGCTGGATGACCA
GagProtMod.SF2(GP2)(685) CAGATGCGCGAGCCCCGCGGCAGCGACATCGCCGGCACCACCAGCACCCTGCAGGAGCAGATCGGCTGGATGACCA
          Consensus(685) CAGATGCGCGAGCCCCGCGGCAGCGACATCGCCGGCACCACCAGCACCCTGCAGGAGCAGATCGGCTGGATGACCA
```

FIG. 80B

Alignment GagMod vs GP1_GP2

```
                                                                                                         Section 11
                     (761)    761         770        780        790        800        810        820        836
       GagMod.SF2    (761)   ACAACCCCCCCATCCCGTGGGCGAGATCATCCTGGGCCTGAACAAGATCGTGCGGATGTA
 GagProtMod.SF2(GP1) (761)   ACAACCCCCCCATCCCGTGGGCGAGATCATCCTGGGCCTGAACAAGATCGTGCGGATGTA
 GagProtMod.SF2(GP2) (761)   ACAACCCCCCCATCCCGTGGGCGAGATCATCCTGGGCCTGAACAAGATCGTGCGGATGTA
           Consensus (761)   ACAACCCCCCCATCCCGTGGGCGAGATCATCCTGGGCCTGAACAAGATCGTGCGGATGTA
                                                                                                         Section 12
                     (837)    837        850        860        870        880        890        900        912
       GagMod.SF2    (837)   CAGCCCCACCAGCAGCATCCTGGACATCCGCCAGGGCCCCAAGGAGCCCTTCCGCGACTACTGGACCGTTCTACAAG
 GagProtMod.SF2(GP1) (837)   CAGCCCCACCAGCAGCATCCTGGACATCCGCCAGGGCCCCAAGGAGCCCTTCCGCGACTACTGGACCGTTCTACAAG
 GagProtMod.SF2(GP2) (837)   CAGCCCCACCAGCAGCATCCTGGACATCCGCCAGGGCCCCAAGGAGCCCTTCCGCGACTACTGGACCGTTCTACAAG
           Consensus (837)   CAGCCCCACCAGCAGCATCCTGGACATCCGCCAGGGCCCCAAGGAGCCCTTCCGCGACTACTGGACCGTTCTACAAG
                                                                                                         Section 13
                     (913)    913        930        940        950        960        970        988
       GagMod.SF2    (913)   ACCCTGCGCGCTGAGCAGGCCAGCCAGGACGTGAAGAACTGGATGACCGAGACCCTGCTGGTGCAGAACGCCAACC
 GagProtMod.SF2(GP1) (913)   ACCCTGCGCGCTGAGCAGGCCAGCCAGGACGTGAAGAACTGGATGACCGAGACCCTGCTGGTGCAGAACGCCAACC
 GagProtMod.SF2(GP2) (913)   ACCCTGCGCGCTGAGCAGGCCAGCCAGGACGTGAAGAACTGGATGACCGAGACCCTGCTGGTGCAGAACGCCAACC
           Consensus (913)   ACCCTGCGCGCTGAGCAGGCCAGCCAGGACGTGAAGAACTGGATGACCGAGACCCTGCTGGTGCAGAACGCCAACC
                                                                                                         Section 14
                     (989)    989       1000       1010       1020       1030       1040       1050       1064
       GagMod.SF2    (989)   CCGACTGCAAGACCATCCTGAAGGCTCTCGGCCCGGCCACCCTGGAGGAGATGATGACCGCCTGCCAGGGCGT
 GagProtMod.SF2(GP1) (989)   CCGACTGCAAGACCATCCTGAAGGCTCTCGGCCCGGCCACCCTGGAGGAGATGATGACCGCCTGCCAGGGCGT
 GagProtMod.SF2(GP2) (989)   CCGACTGCAAGACCATCCTGAAGGCTCTCGGCCCGGCCACCCTGGAGGAGATGATGACCGCCTGCCAGGGCGT
           Consensus (989)   CCGACTGCAAGACCATCCTGAAGGCTCTCGGCCCGGCCACCCTGGAGGAGATGATGACCGCCTGCCAGGGCGT
                                                                                                         Section 15
                    (1065)   1065 1070   1080       1090       1100       1110       1120       1130      1140
       GagMod.SF2   (1065)   GGGCGGCCCCGGCCACAAGGCCCGCGTGCTGGCCGAGGCCATGAGCCAGGTGACGAACCCGGCGACCATCATGATG
 GagProtMod.SF2(GP1)(1065)   GGGCGGCCCCGGCCACAAGGCCCGCGTGCTGGCCGAGGCCATGAGCCAGGTGACGAACCCGGCGACCATCATGATG
 GagProtMod.SF2(GP2)(1065)   GGGCGGCCCCGGCCACAAGGCCCGCGTGCTGGCCGAGGCCATGAGCCAGGTGACGAACCCGGCGACCATCATGATG
          Consensus (1065)   GGGCGGCCCCGGCCACAAGGCCCGCGTGCTGGCCGAGGCCATGAGCCAGGTGACGAACCCGGCGACCATCATGATG
```

FIG. 80C

Alignment GagMod vs GP1_GP2

```
                              Section 16
                        1200           1216
GagMod.SF2         (1141) 1141      1150      1160      1170      1180      1190      1200
GagProtMod.SF2(GP1)(1141) CAGCGCGGGCAACTTCCGCAACCAGCGGAAGACCGTCAACTGCTTCAACTGGGCAAGGAGGGCCACACCGCCAGGA
GagProtMod.SF2(GP2)(1141) CAGCGCGGGCAACTTCCGCAACCAGCGGAAGACCGTCAACTGCTTCAACTGGGCAAGGAGGGCCACACCGCCAGGA
Consensus          (1141) CAGCGCGGGCAACTTCCGCAACCAGCGGAAGACCGTCAAGTGCTTCAAGTGGGCAAGGAGGGCCACACCGCCAGGA
                          CAGCGCGGGCAACTTCCGCAACCAGCGGAAGACCGTCAAGTGCTTCAAGTGGGCAAGGAGGGCCACACCGCCAGGA Section 17
                        1217                                                    1292
GagMod.SF2         (1217) ACTGCCGCGCGCCCCGCGCAAGAAGGGCTGCTGGCGCTGCGCCGAGGGCCACCAGATGAAGGACTGCACCGAGCG
GagProtMod.SF2(GP1)(1217) ACTGCCGCGCGCCCCGCGCAAGAAGGGCTGCTGGCGCTGCGCCGAGGGCCACCAGACCAAATGAAGATTGCACTGAGAG
GagProtMod Alignment GagMod vs GP1_GP2

```
                                                                                    Section 21
                   (1521) 1521      1530      1540      1550      1560      1570      1580      1596
           GagMod.SF2(1510) ----------------------------------------------------------------------------
GagProtMod.SF2(GP1)(1521) CAGCTCAAGGAGGCGCTGCTCGACACCGGCGCCGACGACACCGTGCTGGAGGAGATGAACCTGCCCGGCAAGTGGA
GagProtMod.SF2(GP2)(1521) CAACTCAAGGAAGCGCTGCTCGATACAGGAGCAGATGATACAGTATTAGAAGAAATCAATTTGCCAGGAAAATGGA
          Consensus(1521) CA CTCAAGGA GCGCTGCTCGA AC GG GC GA GA AC GT  T GA GA ATGAA  TGCC GG AA TGGA
                                                                                    Section 22
                   (1597) 1597        1610      1620      1630      1640      1650      1660    1672
           GagMod.SF2(1510) ----------------------------------------------------------------------------
GagProtMod.SF2(GP1)(1597) AGCCCAAGATGATCGGCGGGATCGGGGGCTTCATCAAGGTGCGGCAGTACGACCAGATCCCCGTGGAGATCTGCGG
GagProtMod.SF2(GP2)(1597) AACCAAAAATGATAGGGGGGATCGGGGGCTTCATCAAGGTGAGGCAGTACGACCAGATACCTGTAGAAATCTGTGG
          Consensus(1597) A CC AA ATGAT GG GGGATCGGGGGCTTCATCAAGGTG GGCAGTACGACCAGAT CC GT GA ATCTG GG
                                                                                    Section 23
                   (1673) 1673  1680      1690      1700      1710      1720      1730         1748
           GagMod.SF2(1510) ----------------------------------------------------------------------------
GagProtMod.SF2(GP1)(1673) CCACAAGGCCATCGGCACCGTGCTGGTGGGCCCCACCCCCGTGAACATCATCGGCCGCAACCTGCTGACCCAGATC
GagProtMod.SF2(GP2)(1673) ACATAAAGCTATAGGTACAGTATTAGTAGGACCTACACCTGTCAACATAATTGGAAGAAATCTGTTGACCCAGATC
          Consensus(1673)  CA AA GC AT GG AC GT  T GT GG CC AC CC GT AACAT AT GG  G AA CTG TGACCCAGATC
                                                                                    Section 24
                   (1749) 1749      1760      1770      1780      1790      1800      1810      1824
           GagMod.SF2(1510) ----------------------------------------------------------------------------
GagProtMod.SF2(GP1)(1749) GGCTGCACCCTGAACTTCCCCATCAGCCCCATCGAGACGGTGCCCGTGAAGCTGAAGCCGGGGATGGACGGCCCCA
GagProtMod.SF2(GP2)(1749) GGCTGCACCTTGAACTTCCCCATCAGCCCTATTGAGACGGTGCCCGTGAAGTTGAAGCCGGGGATGGACGGCCCCA
          Consensus(1749) GGCTGCACC TGAACTTCCCCATCAGCCC AT GAGACGGTGCCCGTGAAG TGAAGCCGGGGATGGACGGCCCCA
                                                                                    Section 25
                   (1825) 1825 1830          1847
           GagMod.SF2(1510) ----------------------
GagProtMod.SF2(GP1)(1825) AGGTCAAGCAGTGGCCCCTGTAA
GagProtMod.SF2(GP2)(1825) AGGTCAAGCAATGGCCATTGTAA
          Consensus(1825) AGGTCAAGCA TGGCC  TGTAA
```

FIG. 80E

TataminoSF162.opt

ATGGAGCCCGTGGACCCCCGGCCTGGAGCCCTGGAAGCACCCCGGCAGCCAGCCCAA
GACCGCCTGCACCAACTGCTACTGCAAGAAGTGCTGCTTCCACTGCCAGGTGTGCTT
CATCACCAAGGGCCTGGGCATCAGCTACGGCCGCAAGAAGCGCCGCCAGCGCCGC

FIG. 81
(SEQ ID NO:89)

Tat_Cys22_SF162

MEPVD

EXPRESSION OF HIV POLYPEPTIDES AND PRODUCTION OF VIRUS-LIKE PARTICLES

CROSS-REFERENCE TO RELATED APPLICATIONS

This application is a division of Ser. No. 12/026,619, filed Feb. 6, 2008, now U.S. Pat. No. 7,718,401, issued May 18, 2010, which is a division of Ser. No. 10/387,336 filed Mar. 11, 2003, now issued as U.S. Pat. No. 7,348,177, which is a continuation of Ser. No. 09/475,515, filed Dec. 30, 1999, now U.S. Pat. No. 6,602,705, and which claims the benefit of Ser. No. 60/114,495 filed Dec. 31, 1998 and Ser. No. 60/168,471 filed Dec. 1, 1999. Each of these applications is incorporated herein by reference in its entirety.

INCORPORATION OF SEQUENCE LISTING BY REFERENCE

This application incorporates by reference the contents of a 190 kb text file created on Nov. 24, 2010 and named "51381.txt," which is the sequence listing for this application.

TECHNICAL FIELD

Synthetic expression cassettes encoding the HIV polypeptides (e.g., Gag-, pol-, prot-, reverse transcriptase, Env- or tat-containing polypeptides) are described, as are uses of the expression cassettes. The present invention relates to the efficient expression of HIV polypeptides in a variety of cell types. Further, the invention provides methods of producing Virus-Like Particles (VLPs), as well as, uses of the VLPs and high level expression of oligomeric envelope proteins.

BACKGROUND OF THE INVENTION

Acquired immune deficiency syndrome (AIDS) is recognized as one of the greatest health threats facing modern medicine. There is, as yet, no cure for this disease.

In 1983-1984, three groups independently identified the suspected etiological agent of AIDS. See, e.g., Barre-Sinoussi et al. (1983) Science 220:868-871; Montagnier et al., in Human T-Cell Leukemia Viruses (Gallo, Essex & Gross, eds., 1984); Vilmer et al. (1984) The Lancet 1:753; Popovic et al. (1984) Science 224:497-500; Levy et al. (1984) Science 225: 840-842. These isolates were variously called lymphadenopathy-associated virus (LAV), human T-cell lymphotropic virus type III (HTLV-III), or AIDS-associated retrovirus (ARV). All of these isolates are strains of the same virus, and were later collectively named Human Immunodeficiency Virus (HIV). With the isolation of a related AIDS-causing virus, the strains originally called HIV are now termed HIV-1 and the related virus is called HIV-2 See, e.g., Guyader et al. (1987) Nature 326:662-669; Brun-Vezinet et al. (1986) 233: 343-346; Clavel et al. (1986) Nature 324:691-695.

A great deal of information has been gathered about the HIV virus, however, to date an effective vaccine has not been identified. Several targets for vaccine development have been examined including the env, Gag, poi and tat gene products encoded by HIV.

Haas, et al., (*Current Biology* 6(3):315-324, 1996) suggested that selective codon usage by HIV-1 appeared to account for a substantial fraction of the inefficiency of viral protein synthesis. Andre, et al., (*J. Virol.* 72(2):1497-1503, 1998) described an increased immune response elicited by DNA vaccination employing a synthetic gp120 sequence with optimized codon usage. Schneider, et al., (*J. Virol.* 71(7): 4892-4903, 1997) discuss inactivation of inhibitory (or instability) elements (INS) located within the coding sequences of the Gag and Gag-protease coding sequences.

The Gag proteins of HIV-1 are necessary for the assembly of virus-like particles. HIV-1 Gag proteins are involved in many stages of the life cycle of the virus including, assembly, virion maturation after particle release, and early post-entry steps in virus replication. The roles of HIV-1 Gag proteins are numerous and complex (Freed, E. O., *Virology* 251:1-15, 1998).

Wolf, et al., (PCT International Application, WO 96/30523, published 3 Oct. 1996; European Patent Application, Publication No. 0 449 116 A1, published 2 Oct. 1991) have described the use of altered pr55 Gag of HIV-1 to act as a non-infectious retroviral-like particulate carrier, in particular, for the presentation of immunologically important epitopes. Wang, et al., (*Virology* 200:524-534, 1994) describe a system to study assembly of HIV Gag-β-galactosidase fusion proteins into virions. They describe the construction of sequences encoding HIV Gag-β-galactosidase fusion proteins, the expression of such sequences in the presence of HIV Gag proteins, and assembly of these proteins into virus particles.

Recently, Shiver, et al., (PCT International Application, WO 98/34640, published 13 Aug. 1998) described altering HIV-1 (CAM1) Gag coding sequences to produce synthetic DNA molecules encoding HIV Gag and modifications of HIV Gag. The codons of the synthetic molecules were codons preferred by a projected host cell.

The envelope protein of HIV-1 is a glycoprotein of about 160 kD (gp160). During virus infection of the host cell, gp160 is cleaved by host cell proteases to form gp120 and the integral membrane protein, gp41. The gp41 portion is anchored in (and spans) the membrane bilayer of virion, while the gp120 segment protrudes into the surrounding environment. As there is no covalent attachment between gp120 and gp41, free gp120 is released from the surface of virions and infected cells.

Haas, et al., (*Current Biology* 6(3):315-324, 1996) suggested that selective codon usage by HIV-1 appeared to account for a substantial fraction of the inefficiency of viral protein synthesis. Andre, et al., (*J. Virol.* 72(2):1497-1503, 1998) described an increased immune response elicited by DNA vaccination employing a synthetic gp120 sequence with optimized codon usage.

SUMMARY OF THE INVENTION

The present invention relates to improved expression of HIV Env-, tat-, pol-, prot-, reverse transcriptase, or Gag-containing polypeptides and production of virus-like particles.

In one embodiment the present invention includes an expression cassette, comprising a polynucleotide encoding an HIV Gag polypeptide comprising a sequence having at least 90% sequence identity to the sequence presented as SEQ ID NO:20. In certain embodiments, the polynucleotide sequence encoding said Gag polypeptide comprises a sequence having at least 90% sequence identity to the sequence presented as SEQ ID NO:9 or SEQ ID NO:4. The expression cassettes may further include a polynucleotide sequence encoding an HIV protease polypeptide, for example a nucleotide sequence having at least 90% sequence identity to a sequence selected from the group consisting of: SEQ ID NO:5, SEQ ID NO:78, and SEQ ID NO:79. The expression cassettes may further include a polynucleotide sequence encoding an HIV reverse transcriptase polypeptide, for example a sequence having at least 90% sequence identity to a sequence selected from the group consisting of: SEQ ID NO:80, SEQ ID NO:81, SEQ ID NO:82, SEQ ID NO:83, and SEQ ID NO:84. The expression cassettes may further include a polynucleotide sequence encoding an HIV tat polypeptide, for example a sequence selected from the group consisting of: SEQ ID NO:87, SEQ ID NO:88, and SEQ ID NO:89. The expression cassettes may further include a polynucleotide sequence encoding an HIV polymerase polypeptide, for example a sequence having at least 90% sequence identity to the sequence presented as SEQ ID NO:6. The expression cassettes may include a polynucleotide sequence encoding an HIV polymerase polypeptide, wherein (i) the nucleotide sequence encoding said polypeptide comprises a sequence having at least 90% sequence identity to the sequence presented as SEQ ID NO:4, and (ii) wherein the sequence is modified by deletions of coding regions corresponding to reverse transcriptase and integrase. The expression cassettes described above may preserves T-helper cell and CTL epitopes. The expression cassettes may further include a polynucleotide sequence encoding an HCV core polypeptide, for example a sequence having at least 90% sequence identity to the sequence presented as SEQ ID NO:7.

In another aspect, the invention includes an expression cassette, comprising a polynucleotide sequence encoding a polypeptide including an HIV Env polypeptide, wherein the polynucleotide sequence encoding said Env polypeptide comprises a sequence having at least 90% sequence identity to SEQ ID NO:71 (FIG. 58) or SEQ ID NO:72 (FIG. 59). In certain embodiments, the Env expression cassettes includes sequences flanking a V1 region but have a deletion in the V1 region itself, for example the sequence presented as SEQ ID NO:65 (FIG. 52, gp160.modUS4.delV1). In certain embodiments, the Env expression cassettes, include sequences flanking a V2 region but have a deletion in the V2 region itself, for example the sequences shown in SEQ ID NO:60 (FIG. 47); SEQ ID NO:66 (FIG. 53); SEQ ID NO:34 (FIG. 20); SEQ ID NO:37 (FIG. 24); SEQ ID NO:40 (FIG. 27); SEQ ID NO:43 (FIG. 30); SEQ ID NO:46 (FIG. 33); SEQ ID NO:76 (FIG. 64) and SEQ ID NO:49 (FIG. 36). In certain embodiments, the Env expression cassettes include sequences flanking a V1/V2 region but have a deletion in the V1/V2 region itself, for example, SEQ ID NO:59 (FIG. 46); SEQ ID NO:61 (FIG. 48); SEQ ID NO:67 (FIG. 54); SEQ ID NO:75 (FIG. 63); SEQ ID NO:35 (FIG. 21); SEQ ID NO:38 (FIG. 25); SEQ ID NO:41 (FIG. 28); SEQ ID NO:44 (FIG. 31); SEQ ID NO:47 (FIG. 34) and SEQ ID NO:50 (FIG. 37). The Env-encoding expression cassettes may also include a mutated cleavage site that prevents the cleavage of a gp140 polypeptide into a gp120 polypeptide and a gp41 polypeptide, for example, SEQ ID NO:57 (FIG. 44); SEQ ID NO:61 (FIG. 48); SEQ ID NO:63 (FIG. 50); SEQ ID NO:39 (FIG. 26); SEQ ID NO:40 (FIG. 27); SEQ ID NO:41 (FIG. 28); SEQ ID NO:42 (FIG. 29); SEQ ID NO:43 (FIG. 30); SEQ ID NO:44 (FIG. 31); SEQ ID NO:45 (FIG. 32); SEQ ID NO:46 (FIG. 33); and SEQ ID NO:47 (FIG. 34). The Env expression cassettes may include a gp160 Env polypeptide or a polypeptide derived from a gp160 Env polypeptide, for example SEQ ID NO:64 (FIG. 51); SEQ ID NO:65 (FIG. 52); SEQ ID NO:66 (FIG. 53); SEQ ID NO:67 (FIG. 54); SEQ ID NO:68 (FIG. 55); SEQ ID NO:75 (FIG. 63); SEQ ID NO:73 (FIG. 61); SEQ ID NO:48 (FIG. 35); SEQ ID NO:49 (FIG. 36); SEQ ID NO:50 (FIG. 37); SEQ ID NO:76 (FIG. 64); and SEQ ID NO:74 (FIG. 62). The Env expression cassettes may include a gp140 Env polypeptide or a polypeptide derived from a gp140 Env polypeptide, for example SEQ ID NO:56 (FIG. 43); SEQ ID NO:57 (FIG. 44); SEQ ID NO:58 (FIG. 45); SEQ ID NO:59 (FIG. 46); SEQ ID NO:60 (FIG. 47); SEQ ID NO:61 (FIG. 48); SEQ ID NO:62 (FIG. 49); SEQ ID NO:63 (FIG. 50); SEQ ID NO:36 (FIG. 23); SEQ ID NO:37 (FIG. 24); SEQ ID NO:38 (FIG. 25); SEQ ID NO:39 (FIG. 26); SEQ ID NO:40 (FIG. 27); SEQ ID NO:41 (FIG. 28); SEQ ID NO:42 (FIG. 29); SEQ ID NO:43 (FIG. 30); SEQ ID NO:44 (FIG. 31); SEQ ID NO:45 (FIG. 32); SEQ ID NO:46 (FIG. 33); and SEQ ID NO:47 (FIG. 34). The Env expression cassettes may also include a gp120 Env polypeptide or a polypeptide derived from a gp120 Env polypeptide, for example SEQ ID NO:54 (FIG. 41); and SEQ ID NO:55 (FIG. 42); SEQ ID NO:33 (FIG. 19); SEQ ID NO:34 (FIG. 20); and SEQ ID NO:35 (FIG. 21). The Env expression cassettes may include an Env polypeptide lacking the amino acids corresponding to residues 128 to about 194, relative to strains SF162 or US4, for example, SEQ ID NO:55 (FIG. 42); SEQ ID NO:62 (FIG. 49); SEQ ID NO:63 (FIG. 50); and SEQ ID NO:68 (FIG. 55).

In another aspect, the invention includes a recombinant expression system for use in a selected host cell, comprising, one or more of the expression cassettes described herein operably linked to control elements compatible with expression in the selected host cell. The expression cassettes may be included on one or on multiple vectors and may use the same or different promoters. Exemplary control elements include a transcription promoter (e.g., CMV, CMV+intron A, SV40, RSV, HIV-Ltr, MMLV-ltr, and metallothionein), a transcription enhancer element, a transcription termination signal, polyadenylation sequences, sequences for optimization of initiation of translation, and translation termination sequences.

In another aspect, the invention includes a recombinant expression system for use in a selected host cell, comprising, any one of the expression cassettes described herein operably linked to control elements compatible with expression in the selected host cell. Exemplary control elements include, but are not limited to, a transcription promoter (e.g., CMV, CMV+intron A, SV40, RSV, HIV-LTR, MMLV-LTR, and metallothionein), a transcription enhancer element, a transcription termination signal, polyadenylation sequences, sequences for optimization of initiation of translation, and translation termination sequences.

In yet another aspect, the invention includes a cell comprising one or more of the expression cassettes described herein operably linked to control elements compatible with expression in the cell. The cell can be, for example, a mammalian cell (e.g., BHK, VERO, HT1080, 293, RD, COS-7, or CHO cells), an insect cell (e.g., *Trichoplusia ni* (Tn5) or Sf9), a bacterial cell, a plant cell, a yeast cell, an antigen presenting cell (e.g., primary, immortalized or tumor-derived lymphoid cells such as macrophages, monocytes, dendritic cells, B-cells, T-cells, stem cells, and progenitor cells thereof).

In another aspect, the invention includes methods for producing a polypeptide including HIV Gag-, prot-, pol-, reverse transcriptase, Env- or Tat-containing polypeptide sequences, said method comprising, incubating the cells comprising one or more the expression cassettes describe herein, under conditions for producing said polypeptide.

In yet another aspect, the invention includes compositions for generating an immunological response, comprising one or more of the expression cassettes described herein. In certain embodiments, the compositions also include an adjuvant.

In a still further aspect, the invention includes methods of generating an immune response in a subject, comprising introducing a composition comprising one or more of the expression cassettes described herein into the subject under conditions that are compatible with expression of said expression cassette in the subject. In certain embodiments, the expression cassette is introduced using a gene delivery vector. More than one expression cassette may be introduced using one or more gene delivery vectors.

In yet another aspect, the invention includes a purified polynucleotide comprising a polynucleotide sequence encoding a polypeptide including an HIV Env polypeptide, wherein the polynucleotide sequence encoding said Env polypeptide comprises a sequence having at least 90% sequence identity to SEQ ID NO:71 (FIG. 58) or SEQ ID NO:72 (FIG. 59). Further exemplary purified polynucleotide sequences were presented above.

The polynucleotides of the present invention can be produced by recombinant techniques, synthetic techniques, or combinations thereof.

In another embodiment, the invention includes a method for producing a polypeptide including HIV Gag polypeptide sequences, where the method comprises incubating any of the above cells containing an expression cassette of interest under conditions for producing the polypeptide.

The invention further includes, a method for producing virus-like particles (VLPs) where the method comprises incubating any of the above-described cells containing an expression cassette of interest under conditions for producing VLPs.

In another aspect the invention includes a method for producing a composition of virus-like particles (VLPs) where, any of the above-described cells containing an expression cassette of interest are incubated under conditions for producing VLPs, and the VLPs are substantially purified to produce a composition of VLPs.

In a further embodiment of the present invention, packaging cell lines are produced using the expression cassettes of the present invention. For example, a cell line useful for packaging lentivirus vectors comprises suitable host cells that have an expression vector containing an expression cassette of the present invention wherein said polynucleotide sequence is operably linked to control elements compatible with expression in the host cell. In a preferred embodiment, such host cells may be transfected with one or more expression cassettes having a polynucleotide sequence that encodes an HIV polymerase polypeptide or polypeptides derived therefrom, for example, where the nucleotide sequence encoding said polypeptide comprises a sequence having at least 90% sequence identity to the sequence presented as SEQ ID NO:6. Further, the HIV polymerase polypeptide may be modified by deletions of coding regions corresponding to reverse transcriptase and integrase. Such a polynucleotide sequence may preserve T-helper cell and CTL epitopes, for example when used in a vaccine application. In addition, the polynucleotide sequence may also include other polypeptides. Further, polynucleotide sequences encoding additional polypeptides whose expression are useful for packaging cell line function may also be utilized.

In another aspect, the present invention includes a gene delivery or vaccine vector for use in a subject, where the vector is a suitable gene delivery vector for use in the subject, and the vector comprises one or more of any of the expression cassettes of the present invention where the polynucleotide sequences of interest are operably linked to control elements compatible with expression in the subject. Such gene delivery vectors can be used in a method of DNA immunization of a subject, for example, by introducing a gene delivery vector into the subject under conditions that are compatible with expression of the expression cassette in the subject. Gene delivery vectors useful in the practice of the present invention include, but are not limited to, nonviral vectors, bacterial plasmid vectors, viral vectors, particulate carriers (where the vector is coated on a polylactide co-glycolide particles, gold or tungsten particle, for example, the coated particle can be delivered to a subject cell using a gene gun), liposome preparations, and viral vectors (e.g., vectors derived from alphaviruses, pox viruses, and vaccinia viruses, as well as, retroviral vectors, including, but not limited to, lentiviral vectors). Alphavirus-derived vectors include, for example, an alphavirus cDNA construct, a recombinant alphavirus particle preparation and a eukaryotic layered vector initiation system. In one embodiment, the subject is a vertebrate, preferably a mammal, and in a further embodiment the subject is a human.

The invention further includes a method of generating an immune response in a subject, where cells of a subject are transfected with any of the above-described gene delivery vectors (e.g., alphavirus constructs; alphavirus cDNA constructs; eukaryotic layered vector initiation systems (see, e.g., U.S. Pat. No. 5,814,482 for description of suitable eukaryotic layered vector initiation systems); alphavirus particle preparations; etc.) under conditions that permit the expression of a selected polynucleotide and production of a polypeptide of interest (i.e., encoded by any expression cassette of the present invention), thereby eliciting an immunological response to the polypeptide. Transfection of the cells may be performed ex vivo and the transfected cells are reintroduced into the subject. Alternately, or in addition, the cells may be transfected in vivo in the subject. The immune response may be humoral and/or cell-mediated (cellular).

Further embodiments of the present invention include purified polynucleotides. In one embodiment, the purified polynucleotide comprises a polynucleotide sequence having at least 90% sequence identity to the sequence presented as SEQ ID NO:20, and complements thereof. In another embodiment, the purified polynucleotide comprises a polynucleotide sequence encoding an HIV Gag polypeptide, wherein the polynucleotide sequence comprises a sequence having at least 90% sequence identity to the sequence presented as SEQ ID NO:20, and complements thereof. In still another embodiment, the purified polynucleotide comprises a polynucleotide sequence encoding an HIV Gag polypeptide, wherein the polynucleotide sequence comprises a sequence having at least 90% sequence identity to the sequence presented as SEQ ID NO:9, and complements thereof. In further embodiments the polynucleotide sequence comprises a sequence having at least 90% sequence identity to one of the following sequences: SEQ ID NO:4, SEQ ID NO:5, SEQ ID NO:6, SEQ ID NO:7, and complements thereof.

The polynucleotides of the present invention can be produced by recombinant techniques, synthetic techniques, or combinations thereof.

These and other embodiments of the present invention will readily occur to those of ordinary skill in the art in view of the disclosure herein.

BRIEF DESCRIPTION OF THE FIGURES

FIG. 1 shows the locations of the inactivation sites for the native HIV-1SF2 Gag protein coding sequence SEQ ID NO:1.

FIG. 2 shows the locations of the inactivation sites for the native HIV-1SF2 Gag-protease protein coding sequence SEQ ID NO:2.

FIG. 3A shows immature p55Gag virus-like particles in COS-7 cells transfected with a synthetic HIV-1$_{SF2}$ gag construct while FIG. 3B shows mature (arrows) and immature VLP in cells transfected with a modified HIV-1$_{SF2}$ gagprotease construct (GP2, SEQ ID NO:70). Transfected cells were fixed at 24 h (gag) or 48 h (gagprotease) post-transfection and subsequently analyzed by electron microscopy (magnification at 100,000×). Cells transfected with vector alone (pCMVKm2) served as negative control (data not shown).

FIG. 7 presents an alignment of modified coding sequences of the present invention including a synthetic Gag expression cassette (SEQ ID NO:4), a synthetic Gag-protease expression cassette (SEQ ID NO:5), and a synthetic Gag-polymerase expression cassette (SEQ ID NO:6). A common region (Gag-common; SEQ ID NO:9) extends from position 1 to position 1262.

FIG. 12 shows the location of the inactivation sites for the native HIV-1SF2 Gag-polymerase sequence SEQ ID NO:3.

FIG. 16 depicts the nucleotide sequence of wild-type gp120 from SF162 (SEQ ID NO:30).

FIG. 17 depicts the nucleotide sequence of the wild-type gp140 from SF162 (SEQ ID NO:31).

FIG. 18 depicts the nucleotide sequence of the wild-type gp160 from SF162 (SEQ ID NO:32).

FIG. 19 depicts the nucleotide sequence of the construct designated gp120.modSF162 (SEQ ID NO:33).

FIG. 20 depicts the nucleotide sequence of the construct designated gp120.modSF162.delV2 (SEQ ID NO:34).

FIG. 21 depicts the nucleotide sequence of the construct designated gp120.modSF162.delV1/V2 (SEQ ID NO:35).

FIG. 23 depicts the nucleotide sequence of the construct designated gp140.modSF162 (SEQ ID NO:36).

FIG. 24 depicts the nucleotide sequence of the construct designated gp140.modSF162.delV2 (SEQ ID NO:37).

FIG. 25 depicts the nucleotide sequence of the construct designated gp140.modSF162.delV1/V2 (SEQ ID NO:38).

FIG. 26 depicts the nucleotide sequence of the construct designated gp140.mut.modSF162 (SEQ ID NO:39).

FIG. 27 depicts the nucleotide sequence of the construct designated gp140.mut.modSF162.delV2 (SEQ ID NO:40).

FIG. 28 depicts the nucleotide sequence of the construct designated gp140.mut.modSF162.delV1/V2 (SEQ ID NO:41).

FIG. 29 depicts the nucleotide sequence of the construct designated gp140.mut7.modSF162 (SEQ ID NO:42).

FIG. 30 depicts the nucleotide sequence of the construct designated gp140.mut7.modSF162.delV2 (SEQ ID NO:43).

FIG. 31 depicts the nucleotide sequence of the construct designated gp140.mut7.modSF162.delV1/V2 (SEQ ID NO:44).

FIG. 32 depicts the nucleotide sequence of the construct designated gp140.mut8.modSF162 (SEQ ID NO:45).

FIG. 33 depicts the nucleotide sequence of the construct designated gp140.mut8.modSF162.delV2 (SEQ ID NO:46).

FIG. 34 depicts the nucleotide sequence of the construct designated gp140.mut8.modSF162.delV1/V2 (SEQ ID NO:47).

FIG. 35 depicts the nucleotide sequence of the construct designated gp160.modSF162 (SEQ ID NO:48).

FIG. 36 depicts the nucleotide sequence of the construct designated gp160.modSF162.delV2 (SEQ ID NO:49).

FIG. 37 depicts the nucleotide sequence of the construct designated gp160.modSF162.delV1/V2 (SEQ ID NO:50).

FIG. 38 depicts the nucleotide sequence of the wild-type gp120 from US4 (SEQ ID NO:51).

FIG. 39 depicts the nucleotide sequence of the wild-type gp140 from US4 (SEQ ID NO:52).

FIG. 40 depicts the nucleotide sequence of the wild-type gp160 from US4 (SEQ ID NO:53).

FIG. 41 depicts the nucleotide sequence of the construct designated gp120.modUS4 (SEQ ID NO:54).

FIG. 42 depicts the nucleotide sequence of the construct designated gp120.modUS4.del 128-194 (SEQ ID NO:55).

FIG. 43 depicts the nucleotide sequence of the construct designated gp140.modUS4 (SEQ ID NO:56).

FIG. 44 depicts the nucleotide sequence of the construct designated gp140.mut.modUS4 (SEQ ID NO:57).

FIG. 45 depicts the nucleotide sequence of the construct designated gp140.TM.modUS4 (SEQ ID NO:58).

FIG. 46 depicts the nucleotide sequence of the construct designated gp140.modUS4.delV1/V2 (SEQ ID NO:59).

FIG. 47 depicts the nucleotide sequence of the construct designated gp140.modUS4.delV2 (SEQ ID NO:60).

FIG. 48 depicts the nucleotide sequence of the construct designated gp140.mut.modUS4.delV1/V2 (SEQ ID NO:61).

FIG. 49 depicts the nucleotide sequence of the construct designated gp140.modUS4.del 128-194 (SEQ ID NO:62).

FIG. 50 depicts the nucleotide sequence of the construct designated gp140.mut.modUS4.del 128-194 (SEQ ID NO:63).

FIG. 51 depicts the nucleotide sequence of the construct designated gp160.modUS4 (SEQ ID NO:64).

FIG. 52 depicts the nucleotide sequence of the construct designated gp160.modUS4.delV1 (SEQ ID NO:65).

FIG. 53 depicts the nucleotide sequence of the construct designated gp160.modUS4.delV2 (SEQ ID NO:66).

FIG. 54 depicts the nucleotide sequence of the construct designated gp160.modUS4.delV1/V2 (SEQ ID NO:67).

FIG. 55 depicts the nucleotide sequence of the construct designated gp160.modUS4.del 128-194 (SEQ ID NO:68).

FIG. 56 depicts the nucleotide sequence of the common region of Env from wild-type US4 (SEQ ID NO:69).

FIG. 57 depicts the nucleotide sequence of the common region of Env from wild-type SF162 (SEQ ID NO:70).

FIG. 58 depicts the nucleotide sequence of synthetic sequences corresponding to the common region of Env from US4 (SEQ ID NO:71).

FIG. 59 depicts the nucleotide sequence of synthetic sequences corresponding to the common region of Env from SF162 (SEQ ID NO:72).

FIG. 61 depicts the nucleotide sequence of the bicistronic construct designated gp160.modUS4.Gag.modSF2 (SEQ ID NO:73).

FIG. 62 depicts the nucleotide sequence of the bicistronic construct designated gp160.modSF162.Gag.modSF2 (SEQ ID NO:74).

FIG. 63 depicts the nucleotide sequence of the bicistronic construct designated gp160.modUS4.-delV1/V2.Gag.modSF2 (SEQ ID NO:75).

FIG. 64 depicts the nucleotide sequence of the bicistronic construct designated gp160.modSF162.delV2.Gag.modSF2 (SEQ ID NO:76).

FIGS. 65A-65F show micrographs of 293T cells transfected with the following polypeptide encoding sequences: FIG. 65A, gag.modSF2; FIG. 65B, gp160.modUS4; FIG. 65C, gp160.modUS4.delV1/V2.gag.modSF2 (bicistronic Env and Gag); FIGS. 65D and 65E, gp160.modUS4.delV1/V2 and gag.modSF2; and FIG. 65F, gp120.modSF162.delV2 and gag.modSF2.

FIGS. 66A and 66B present alignments of selected modified coding sequences of the present invention including a common region defined for each group of synthetic Env expression cassettes. FIG. 66A presents alignments of modified SF162 sequences. gp160.modSF162, SEQ ID NO:48; gp160.modSF162.delV2, SEQ ID NO:49; gp160.modSF162.delV1V2, SEQ ID NO:50; gp140.mut.modSF162, SEQ ID NO:39; gp140.mut7.modSF162, SEQ ID NO:42; gp140.mut8.modSF162, SEQ ID NO:45; gp120.modSF162, SEQ ID NO:33. FIG. 66B presents alignments of modified US4 sequences. gp160, SEQ ID NO:53; gp160 del V1, SEQ ID NO:65; gp160 del V2, SEQ ID NO:66; gp160 del 128-194, SEQ ID NO:63; gp140™, SEQ ID NO:58; gp140, SEQ ID NO:52; gp140mut, SEQ ID NO:57; gp120, SEQ ID NO:51. The SEQ ID NOs for these sequences are presented in Tables 1A and 1B.

FIG. 68 (SEQ ID NO:77) depicts the wild-type nucleotide sequence of Gag reverse transcriptase from SF2.

FIG. 69 (SEQ ID NO:78) depicts the nucleotide sequence of the construct designated GP1.

FIG. 70 (SEQ ID NO:79) depicts the nucleotide sequence of the construct designated GP2.

FIG. 71 (SEQ ID NO:80) depicts the nucleotide sequence of the construct designated FS(+).protinact_RTopt.YM. FS(+) indicates that there is a frameshift in the GagPol coding sequence.

FIG. 72 (SEQ ID NO:81) depicts the nucleotide sequence of the construct designated FS(+).protinact.RTopt.YMWM.

FIG. 73 (SEQ ID NO:82) depicts the nucleotide sequence of the construct designated FS(−).protmod.RTopt.YM. FS(−) indicates that there is no frameshift in the GagPol coding sequence.

FIG. 74 (SEQ ID NO:83) depicts the nucleotide sequence of the construct designated FS(−).protmod.RTopt.YMWM.

FIG. 75 (SEQ ID NO:84) depicts the nucleotide sequence of the construct designated FS(−).protmod.RTopt(+).

FIG. 76 (SEQ ID NO:85) depicts the nucleotide sequence of wild type Tat from isolate SF162.

FIG. 77 (SEQ ID NO:86) depicts the amino acid sequence of the tat polypeptide.

FIG. 78 (SEQ ID NO:87) depicts the nucleotide sequence of a synthetic Tat construct designated Tat.SF162.opt.

FIG. 79 (SEQ ID NO:88) depicts the nucleotide sequence of a synthetic Tat construct designated tat.cys22.sf162.opt. The construct encodes a tat polypeptide in which the cystein residue at position 22 of the wild type Tat polypeptide is replaced by a glycine residue.

FIGS. 80A to 80E are an alignment of the nucleotide sequences of the constructs designated Gag.mod.SF2, GP1 (SEQ ID NO:78), and GP2 (SEQ ID NO:79).

FIG. 81 (SEQ ID NO:89) depicts the nucleotide sequence of the construct designated tataminoSF162.opt, which encodes the amino terminus of that tat protein. The codon encoding the cystein-22 residue is underlined.

FIG. 82 (SEQ ID NO:90) depicts the amino acid sequence of the polypeptide encoded by the construct designated tat.cys22.5F162.opt (SEQ ID NO:88).

DETAILED DESCRIPTION OF THE INVENTION

Figure 3A:
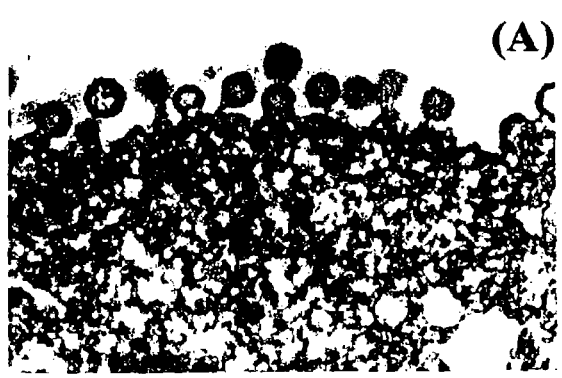
FIGS. 3A and 3B show electron micrographs of virus-like particles.

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences,* 18th Edition (Easton, Pa.: Mack Publishing Company, 1990); Methods In Enzymology (S. Colowick and N. Kaplan, eds., Academic Press, Inc.); and *Handbook of Experimental Immunology*, Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Short Protocols in Molecular Biology,* 4th ed. (Ausubel et al. eds., 1999, John Wiley & Sons); *Molecular Biology Techniques: An Intensive Laboratory Course*, (Ream et al., eds., 1998, Academic Press); PCR (*Introduction to Biotechniques Series*), 2nd ed. (Newton & Graham eds., 1997, Springer Verlag).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, reference to "an antigen" includes a mixture of two or more such agents.

1. Definitions

In describing the present invention, the following terms will be employed, and are intended to be defined as indicated below.

"Synthetic" sequences, as used herein, refers to Env-, tat- or Gag-encoding polynucleotides whose expression has been optimized as described herein, for example, by codon substitution, deletions, replacements and/or inactivation of inhibitory sequences. "Wild-type" or "native" sequences, as used herein, refers to polypeptide encoding sequences that are essentially as they are found in nature, e.g., Gag encoding sequences as found in the isolate HIV-1SF2 or Env encoding sequences as found in the isolates HIV-1SF162 or HIV1US4.

As used herein, the term "virus-like particle" or "VLP" refers to a nonreplicating, viral shell, derived from any of several viruses discussed further below. VLPs are generally composed of one or more viral proteins, such as, but not limited to those proteins referred to as capsid, coat, shell, surface and/or envelope proteins, or particle-forming polypeptides derived from these proteins. VLPs can forth spontaneously upon recombinant expression of the protein in an appropriate expression system. Methods for producing particular VLPs are known in the art and discussed more fully below. The presence of VLPs following recombinant expression of viral proteins can be detected using conventional techniques known in the art, such as by electron microscopy, biophysical characterization, and the like. See, e.g., Baker et al., *Biophys. J.* (1991) 60:1445-1456; Hagensee et al., *J. Virol.* (1994) 68:4503-4505. For example, VLPs can be isolated by density gradient centrifugation and/or identified by characteristic density banding (e.g., Example 7). Alternatively, cryoelectron microscopy can be performed on vitrified aqueous samples of the VLP preparation in question, and images recorded under appropriate exposure conditions.

By "particle-forming polypeptide" derived from a particular viral protein is meant a full-length or near full-length viral protein, as well as a fragment thereof, or a viral protein with internal deletions, which has the ability to form VLPs under conditions that favor VLP formation. Accordingly, the polypeptide may comprise the full-length sequence, fragments, truncated and partial sequences, as well as analogs and precursor forms of the reference molecule. The term therefore intends deletions, additions and substitutions to the sequence, so long as the polypeptide retains the ability to form a VLP. Thus, the term includes natural variations of the specified polypeptide since variations in coat proteins often occur between viral isolates. The term also includes deletions, additions and substitutions that do not naturally occur in the reference protein, so long as the protein retains the ability to form a VLP. Preferred substitutions are those which are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids.

An "antigen" refers to a molecule containing one or more epitopes (either linear, conformational or both) that will stimulate a host's immune system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature), as well as, killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

For purposes of the present invention, antigens can be derived from any of several known viruses, bacteria, parasites and fungi, as described more fully below. The term also intends any of the various tumor antigens. Furthermore, for purposes of the present invention, an "antigen" refers to a protein which includes modifications, such as deletions, additions and substitutions (generally conservative in nature), to the native sequence, so long as the protein maintains the ability to elicit an immunological response, as defined herein. These modifications may be deliberate, as through site-directed mutagenesis, or may be accidental, such as through mutations of hosts which produce the antigens.

An "immunological response" to an antigen or composition is the development in a subject of a humoral and/or a cellular immune response to an antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376. Recent methods of measuring cell-mediated immune response include measurement of intracellular cytokines or cytokine secretion by T-cell populations, or by measurement of epitope specific T-cells (e.g., by the tetramer technique)(reviewed by McMichael, A. J., and O'Callaghan, C. A., *J. Exp. Med.* 187(9)1367-1371, 1998; Mcheyzer-Williams, M. G., et al, *Immunol. Rev.* 150: 5-21, 1996; Lalvani, A., et al, *J. Exp. Med.* 186:859-865, 1997).

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic composition" is a composition that comprises an antigenic molecule where administration of the composition to a subject results in the development in the subject of a humoral and/or a cellular immune response to the antigenic molecule of interest.

By "subunit vaccine" is meant a vaccine composition which includes one or more selected antigens but not all antigens, derived from or homologous to, an antigen from a pathogen of interest such as from a virus, bacterium, parasite or fungus. Such a composition is substantially free of intact pathogen cells or pathogenic particles, or the lysate of such cells or particles. Thus, a "subunit vaccine" can be prepared from at least partially purified (preferably substantially purified) immunogenic polypeptides from the pathogen, or analogs thereof. The method of obtaining an antigen included in the subunit vaccine can thus include standard purification techniques, recombinant production, or synthetic production.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences, see e.g., McCaughan et al. (1995) *PNAS USA* 92:5431-5435; Kochetov et al (1998) *FEBS Letts.* 440:351-355.

A "nucleic acid" molecule can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "re-combinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

One of skill in the art can readily determine the proper search parameters to use for a given sequence in the above programs. For example, the search parameters may vary based on the size of the sequence in question. Thus, for example, a representative embodiment of the present invention would include an isolated polynucleotide having X contiguous nucleotides, wherein (i) the X contiguous nucleotides have at least about 50% identity to Y contiguous nucleotides derived from any of the sequences described herein, (ii) X equals Y, and (iii) X is greater than or equal to 6 nucleotides and up to 5000 nucleotides, preferably greater than or equal to 8 nucleotides and up to 5000 nucleotides, more preferably 10-12 nucleotides and up to 5000 nucleotides, and even more preferably 15-20 nucleotides, up to the number of nucleotides present in the full-length sequences described herein (e.g., see the Sequence Listing and claims), including all integer values falling within the above-described ranges.

The synthetic expression cassettes (and purified polynucleotides) of the present invention include related polynucleotide sequences having about 80% to 100%, greater than 80-85%, preferably greater than 90-92%, more preferably greater than 95%, and most preferably greater than 98% sequence (including all integer values falling within these described ranges) identity to the synthetic expression cassette sequences disclosed herein (for example, to the sequences presented in Tables 1A and 1B) when the sequences of the present invention are used as the query sequence.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N. Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N. Y.).

A first polynucleotide is "derived from" second polynucleotide if it has the same or substantially the same basepair sequence as a region of the second polynucleotide, its cDNA, complements thereof, or if it displays sequence identity as described above.

A first polypeptide is "derived from" a second polypeptide if it is (i) encoded by a first polynucleotide derived from a second polynucleotide, or (ii) displays sequence identity to the second polypeptides as described above.

Generally, a viral polypeptide is "derived from" a particular polypeptide of a virus (viral polypeptide) if it is (i) encoded by an open reading frame of a polynucleotide of that virus (viral polynucleotide), or (ii) displays sequence identity to polypeptides of that virus as described above.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

By "nucleic acid immunization" is meant the introduction of a nucleic acid molecule encoding one or more selected antigens into a host cell, for the in vivo expression of an antigen, antigens, an epitope, or epitopes. The nucleic acid molecule can be introduced directly into a recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses. When used for immunization, such gene delivery expression vectors may be referred to as vaccines or vaccine vectors.

"T lymphocytes" or "T cells" are non-antibody producing lymphocytes that constitute a part of the cell-mediated arm of the immune system. T cells arise from immature lymphocytes that migrate from the bone marrow to the thymus, where they undergo a maturation process under the direction of thymic hormones. Here, the mature lymphocytes rapidly divide increasing to very large numbers. The maturing T cells become immunocompetent based on their ability to recognize and bind a specific antigen. Activation of immunocompetent T cells is triggered when an antigen binds to the lymphocyte's surface receptors.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology,* 52:456, Sambrook et al. (1989) Molecular Cloning, a laboratory manual, Cold Spring Harbor Laboratories, New York, Davis et al. (1986) *Basic Methods in Molecular Biology,* Elsevier, and Chu et al. (1981) *Gene* 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring gene sequences to target cells (e.g., bacterial plasmid vectors, viral vectors, non-viral vectors, particulate carriers, and liposomes). Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as viral vectors.

Transfer of a "suicide gene" (e.g., a drug-susceptibility gene) to a target cell renders the cell sensitive to compounds or compositions that are relatively nontoxic to normal cells. Moolten, F. L. (1994) *Cancer Gene Ther.* 1:279-287. Examples of suicide genes are thymidine kinase of herpes simplex virus (HSV-tk), cytochrome P450 (Manome et al. (1996) *Gene Therapy* 3:513-520), human deoxycytidine kinase (Manome et al. (1996) *Nature Medicine* 2(5):567-573) and the bacterial enzyme cytosine deaminase (Dong et al. (1996) *Human Gene Therapy* 7:713-720). Cells which express these genes are rendered sensitive to the effects of the relatively nontoxic prodrugs ganciclovir (HSV-tk), cyclophosphamide (cytochrome P450 2B1), cytosine arabinoside (human deoxycytidine kinase) or 5-fluorocytosine (bacterial cytosine deaminase). Culver et al. (1992) *Science* 256:1550-1552, Huber et al. (1994) *Proc. Natl. Acad. Sci. USA* 91:8302-8306.

A "selectable marker" or "reporter marker" refers to a nucleotide sequence included in a gene transfer vector that has no therapeutic activity, but rather is included to allow for simpler preparation, manufacturing, characterization or testing of the gene transfer vector.

A "specific binding agent" refers to a member of a specific binding pair of molecules wherein one of the molecules specifically binds to the second molecule through chemical and/or physical means. One example of a specific binding agent is an antibody directed against a selected antigen.

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

As used herein, "treatment" refers to any of (I) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

"Lentiviral vector", and "recombinant lentiviral vector" are derived from the subset of retroviral vectors known as lentiviruses. Lentiviral vectors refer to a nucleic acid construct which carries, and within certain embodiments, is capable of directing the expression of a nucleic acid molecule of interest. The lentiviral vector includes at least one transcriptional promoter/enhancer or locus defining element(s), or other elements which control gene expression by other means such as alternate splicing, nuclear RNA export, post-translational modification of messenger, or post-transcriptional modification of protein. Such vector constructs must also include a packaging signal, long terminal repeats (LTRS) or portion thereof, and positive and negative strand primer binding sites appropriate to the lentiviral vector used (if these are not already present in the retroviral vector). Optionally, the recombinant lentiviral vector may also include a signal which directs polyadenylation, selectable markers such as Neo, TK, hygromycin, phleomycin, histidinol, or DHFR, as well as one or more restriction sites and a translation termination sequence. By way of example, such vectors typically include a 5' LTR, a tRNA binding site, a packaging signal, an origin of second strand DNA synthesis, and a 3'LTR or a portion thereof.

"Lentiviral vector particle" as utilized within the present invention refers to a lentivirus which carries at least one gene of interest. The retrovirus may also contain a selectable marker. The recombinant lentivirus is capable of reverse transcribing its genetic material (RNA) into DNA and incorporating this genetic material into a host cell's DNA upon infection. Lentiviral vector particles may have a lentiviral envelope, a non-lentiviral envelope (e.g., an ampho or VSV-G envelope), or a chimeric envelope.

"Nucleic acid expression vector" or "Expression cassette" refers to an assembly which is capable of directing the expression of a sequence or gene of interest. The nucleic acid expression vector includes a promoter which is operably linked to the sequences or gene(s) of interest. Other control elements may be present as well. Expression cassettes described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

"Packaging cell" refers to a cell which contains those elements necessary for production of infectious recombinant retrovirus (e.g., lentivirus) which are lacking in a recombinant retroviral vector. Typically, such packaging cells contain one or more expression cassettes which are capable of expressing proteins which encode Gag, pol and env proteins.

"Producer cell" or "vector producing cell" refers to a cell which contains all elements necessary for production of recombinant retroviral vector particles.

2. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

2.1 Synthetic Expression Cassettes 2.1.1 Modification of HIV-1 Gag Nucleic Acid Coding Sequences One aspect of the present invention is the generation of HIV-1 Gag protein coding sequences, and related sequences, having improved expression relative to the corresponding wild-type sequence. An exemplary embodiment of the present invention is illustrated herein modifying the Gag protein wild-type sequences obtained from the HIV-1SF2 strain (SEQ ID NO:1; Sanchez-Pescador, R., et al., Science 227 (4686): 484-492, 1985; Luciw, P. A., et al. U.S. Pat. No. 5,156,949, issued Oct. 20, 1992, herein incorporated by reference; Luciw, P. A., et al., U.S. Pat. No. 5,688,688, Nov. 18, 1997, herein incorporated by reference). Gag sequence obtained from other HIV variants may be manipulated in similar fashion following the teachings of the present specification. Such other variants include, but are not limited to, Gag protein encoding sequences obtained from the isolates. $HIV_{IIIb}$, $HIV_{SF2}$, $HIV-1_{SF162}$, $HIV-1_{SF170}$, $HIV_{LAV}$, $HIV_{LAI}$, $HIV_{MN}$, $HIV-1_{CM235}$, $HIV-1_{US4}$, other HIV-1 strains from diverse subtypes (e.g., subtypes, A through G, and O), HIV-2 strains and diverse subtypes (e.g., $HIV-2_{UC1}$ and $HIV-2_{UC2}$), and simian immunodeficiency virus (Sly). (See, e.g., Virology, 3rd Edition (W. K. Joklik ed. 1988); Fundamental Virology, 2nd Edition (B. N. Fields and D. M. Knipe, eds. 1991); Virology, 3rd Edition (Fields, B N, D M Knipe, P M Howley, Editors, 1996, Lippincott-Raven, Philadelphia, Pa.; for a description of these and other related viruses).

First, the HIV-1 codon usage pattern was modified so that the resulting nucleic acid coding sequence was comparable to codon usage found in highly expressed human genes (Example 1). The HIV codon usage reflects a high content of the nucleotides A or T of the codon-triplet. The effect of the HIV-1 codon usage is a high AT content in the DNA sequence that results in a decreased translation ability and instability of the mRNA. In comparison, highly expressed human codons prefer the nucleotides G or C. The Gag coding sequences were modified to be comparable to codon usage found in highly expressed human genes. In FIG. 11 (Example 1), the percent A-T content of cDNA sequences corresponding to the mRNA for a known unstable mRNA and a known stable mRNA are compared to the percent A-T content of native HIV-1SF2 Gag cDNA and to the synthetic Gag cDNA sequence of the present invention. Experiments performed in support of the present invention showed that the synthetic Gag sequences were capable of higher level of protein production (see the Examples) relative to the native Gag sequences. The data in FIG. 11 suggest that one reason for this increased production is increased stability of the mRNA corresponding to the synthetic Gag coding sequences versus the mRNA corresponding to the native Gag coding sequences.

Second, there are inhibitory (or instability) elements (INS) located within the coding sequences of the Gag coding sequences (Example 1). The RRE is a secondary RNA structure that interacts with the HIV encoded Rev-protein to overcome the expression down-regulating effects of the INS. To overcome the post-transcriptional activating mechanisms of RRE and Rev, the instability elements were inactivated by introducing multiple point mutations that did not alter the reading frame of the encoded proteins. FIG. 1 shows the original SF2 Gag sequence, the location of the INS sequences, and the modifications made to the INS sequences to reduce their effects. The resulting modified coding sequences are presented as a synthetic Gag expression cassette (SEQ ID NO:4).

Modification of the Gag polypeptide coding sequences resulted in improved expression relative to the wild-type coding sequences in a number of mammalian cell lines (as well as other types of cell lines, including, but not limited to, insect cells). Further, expression of the sequences resulted in production of virus-like particles (VLPs) by these cell lines (see below). Similar Gag polypeptide coding sequences can be obtained from a variety of isolates (families, sub-types, strains, etc.) including, but not limited to such other variants include, but are not limited to, Gag polypeptide encoding sequences obtained from the isolates $HIV_{IIIb}$, $HIV_{SF2}$, $HIV-1_{SF162}$, $HIV-1_{SF170}$, $HIV_{LAV}$, $HIV_{LAI}$, $HIV_{MN}$, $HIV-1_{CM235}$, $HIV-1_{US4}$, other HIV-1 strains from diverse subtypes(e.g., subtypes, A through G, and O), HIV-2 strains and diverse subtypes (e.g., $HIV-2_{UC1}$ and $HIV-2_{UC2}$), and simian immunodeficiency virus (SIV). (See, e.g., Virology, 3rd Edition (W. K. Joklik ed. 1988); *Fundamental Virology*, 2nd Edition (B. N. Fields and D. M. Knipe, eds. 1991; *Virology*, 3rd Edition (Fields, B N, D M Knipe, P M Howley, Editors, 1996, Lippincott-Raven, Philadelphia, Pa.). Gag polypeptide encoding sequences derived from these variants can be optimized and tested for improved expression in mammals by following the teachings of the present specification (see the Examples, in particular Example 1).

2.1.2 Further Modification of Sequences Including HIV-1 Gag Nucleic Acid Coding Sequences Experiments performed in support of the present invention have shown that similar modifications of HIV-1 Gag-protease, Gag-reverse transcriptase and Gag-polymerase sequences also result in improved expression of the polyproteins, as well as, the production of VLPs formed by polypeptides produced from such modified coding sequences.

For the Gag-protease sequence (wild type, SEQ ID NO:2; modified, SEQ ID NOs:5, 78, 79), the changes in codon usage were restricted to the regions upstream of the −1 frameshift (FIG. 2). Further, inhibitory (or instability) elements (INS) located within the coding sequences of the Gag-protease polypeptide coding sequence were altered as well (indicated in FIG. 2). Exemplary constructs (which include the −1 frameshift) encoding modified Gag-protease sequences include those shown in SEQ ID NOs:78 and 79 (FIGS. 69 and 70). These are: GP1 (SEQ ID NO:78) in which the protease region was also codon optimized and INS inactivated and GP2 (SEQ ID NO:79), in which the protease region was only subjected to INS inactivation.

For other Gag-containing sequences, for example the Gag-polymerase sequence (wild type, SEQ ID NO:3; modified, SEQ ID NO:6) or Gag-reverse transcriptase (wild type, SEQ ID NO:77; modified SEQ ID NOs:80-84), the changes in codon usage are similar to those for the Gag-protease sequence. Those expression cassettes which contain a frameshift in the GagPol coding sequence are designated "FS(+)" (SEQ ID NOs:80 and 81, FIGS. 71 and 72) while the designation "FS(−)" (SEQ ID Nos: 82, 83 and 84, FIGS. 73, 74 and 75) indicates that there is no frameshift utilized in this coding sequence.

In addition to polyproteins containing HIV-related sequences, the various Gag-, Gag-prot, Gag-pol, Gag-reverse transcriptase encoding sequences of the present invention can be fused to other polypeptides (creating chimeric polypeptides) for which an immunogenic response is desired. An example of such a chimeric protein is the joining of the improved expression Gag encoding sequences to the Hepatitis C Virus (HCV) core protein. In this case, the HCV-core encoding sequences were placed in-frame with the HIV-Gag encoding sequences, resulting in the Gag/HCV-core encoding sequence presented as SEQ ID NO:7 (wild type sequence presented as SEQ ID NO:8).

Further sequences useful in the practice of the present invention include, but are not limited to, sequences encoding viral epitopes/antigens {including but not limited to, HCV antigens (e.g., E1, E2; Houghton, M., et al., U.S. Pat. No. 5,714,596, issued Feb. 3, 1998; Houghton, M., et al., U.S. Pat. No. 5,712,088, issued Jan. 27, 1998; Houghton, M., et al., U.S. Pat. No. 5,683,864, issued Nov. 4, 1997; Weiner, A. J., et al., U.S. Pat. No. 5,728,520, issued Mar. 17, 1998; Weiner, A. J., et al., U.S. Pat. No. 5,766,845, issued Jun. 16, 1998; Weiner, A. J., et al., U.S. Pat. No. 5,670,152, issued Sep. 23, 1997; all herein incorporated by reference), HIV antigens (e.g., derived from nef, tat, rev, vpu, vif, vpr and/or env); and sequences encoding tumor antigens/epitopes. Additional sequences are described below. Also, variations on the orientation of the Gag and other coding sequences, relative to each other, are also described below.

Gag, Gag-protease, Gag-reverse transcriptase and/or Gag-polymerase polypeptide coding sequences can be obtained from any HIV isolates (different families, subtypes, and strains) including but not limited to the isolates $HIV_{IIIb}$, $HIV_{SF2}$, $HIV_{SF162}$, HIVus4, $HIV_{cm235}$, $HIV_{LAV}$, $HIV_{MN}$) (see, e.g., Myers et al. Los Alamos Database, Los Alamos National Laboratory, Los Alamos, N. Mex. (1992); Myers et al., *Human Retroviruses and Aids*, 1997, Los Alamos, N. Mex.: Los Alamos National Laboratory). Synthetic expression cassettes can be generated using such coding sequences as starting material by following the teachings of the present specification (e.g., see Example 1). Further, the synthetic expression cassettes of the present invention include related Gag polypeptide coding sequences having greater than 75%, preferably greater than 80-85%, more preferably greater than 90-95%, and most preferably greater than 98% sequence identity (or any integer value within these ranges) to the synthetic expression cassette sequences disclosed herein (for example, SEQ ID NO:4; SEQ ID NO:5; SEQ ID NO:6; and SEQ ID NO:20, the Gag Major Homology Region).

2.1.3 Expression of Synthetic Sequences Encoding HIV-1 Gag and Related Polypeptides Several synthetic Gag-encoding sequences (expression cassettes) of the present invention were cloned into a number of different expression vectors (Example 1) to evaluate levels of expression and production of VLPs. Two modified synthetic coding sequences are presented as a synthetic Gag expression cassette (SEQ ID NO:4) and a synthetic Gag-protease expression cassette (SEQ ID NOs:78 and 79). Other synthetic Gag-encoding proteins are presented, for example, as SEQ ID NOs:80 through 84. The synthetic DNA fragments for Gag-encoding polypeptides (e.g., Gag, Gag-protease, Gag-polymerase, Gag-reverse transcriptase) were cloned into expression vectors described in Example 1, including, a transient expression vector, CMV-promoter-based mammalian vectors, and a shuttle vector for use in baculovirus expression systems. Corresponding wild-type sequences were cloned into the same vectors.

These vectors were then transfected into a several different cell types, including a variety of mammalian cell lines, (293, RD, COS-7, and CHO, cell lines available, for example, from the A.T.C.C.). The cell lines were cultured under appropriate conditions and the levels of p24 (Gag) expression in supernatants were evaluated (Example 2). The results of these assays demonstrated that expression of synthetic Gag-encoding sequences were significantly higher than corresponding wild-type sequences (Example 2; Table 2).

Further, Western Blot analysis showed that cells containing the synthetic Gag expression cassette produced the expected 55 kD (p55) protein at higher per-cell concentrations than cells containing the native expression cassette. The Gag p55 protein was seen in both cell lysates and supernatants. The levels of production were significantly higher in cell supernatants for cells transfected with the synthetic Gag expression cassette of the present invention. Experiments performed in support of the present invention suggest that cells containing the synthetic Gag-prot expression cassettes produced the expected Gag-prot protein at comparably higher per-cell concentrations than cells containing the wild-type expression cassette.

Fractionation of the supernatants from mammalian cells transfected with the synthetic Gag expression cassette showed that it provides superior production of both p55 protein and VLPs, relative to the wild-type Gag sequences (Examples 6 and 7).

Efficient expression of these Gag-containing polypeptides in mammalian cell lines provides the following benefits: the Gag polypeptides are free of baculovirus contaminants; production by established methods approved by the FDA; increased purity; greater yields (relative to native coding sequences); and a novel method of producing the Gag-containing polypeptides in CHO or other mammalian cells which is not feasible in the absence of the increased expression obtained using the constructs of the present invention. Exemplary Mammalian cell lines include, but are not limited to, BHK, VERO, HT1080, 293, 293T, RD, COS-7, CHO, Jurkat, HUT, SUPT, C8166, MOLT4/clone8, MT-2, MT-4, H9, PM1, CEM, myeloma cells (e.g., SB20 cells) and CEMX174, such cell lines are available, for example, from the A.T.C.C.).

A synthetic Gag expression cassette of the present invention also demonstrated high levels of expression and VLP production when transfected into insect cells (Example 7). Further, in addition to a higher total protein yield, the final product from the synthetic p55-expressed Gag consistently contained lower amounts of contaminating baculovirus proteins than the final purified product from the native p55-expressed Gag.

Further, synthetic Gag expression cassettes of the present invention have also been introduced into yeast vectors which were transformed into and efficiently expressed by yeast cells (*Saccharomyces cerevisea*; using vectors as described in Rosenberg, S. and Tekamp-Olson, P., U.S. Pat. No. RE35, 749, issued, Mar. 17, 1998, herein incorporated by reference).

In addition to the mammalian and insect vectors described in the Examples, the synthetic expression cassettes of the present invention can be incorporated into a variety of expression vectors using selected expression control elements. Appropriate vectors and control elements for any given cell type can be selected by one having ordinary skill in the art in view of the teachings of the present specification and information known in the art about expression vectors.

For example, a synthetic Gag expression cassette can be inserted into a vector which includes control elements operably linked to the desired coding sequence, which allow for the expression of the gene in a selected cell-type. For example, typical promoters for mammalian cell expression include the SV40 early promoter, a CMV promoter such as the CMV immediate early promoter (a CMV promoter can include intron A), RSV, HIV-LTR, the mouse mammary tumor virus LTR promoter (MMLV-LTR), FIV-LTR, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook, et al., supra, as well as a bovine growth hormone terminator sequence. Introns, containing splice donor and acceptor sites, may also be designed into the constructs for use with the present invention (Chapman et al., *Nuc. Acids Res.* (1991) 19:3979-3986).

Enhancer elements may also be used herein to increase expression levels of the mammalian constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence (Chapman at al., *Nuc. Acids Res.* (1991) 19:3979-3986).

The desired synthetic Gag polypeptide encoding sequences can be cloned into any number of commercially available vectors to generate expression of the polypeptide in an appropriate host system. These systems include, but are not limited to, the following: baculovirus expression {Reilly, P. R., et al., *BACULOVIRUS EXPRESSION VECTORS: A LABORATORY MANUAL* (1992); Beames, et al., *Biotechniques* 11:378 (1991); Pharmingen; Clontech, Palo Alto, Calif.)}, vaccinia expression {Earl, P. L., et al., "Expression of proteins in mammalian cells using vaccinia" In *Current Protocols in Molecular Biology* (F. M. Ausubel, et al. Eds.), Greene Publishing Associates & Wiley Interscience, New York (1991); Moss, B., et al., U.S. Pat. No. 5,135,855, issued 4 Aug. 1992}, expression in bacteria {Ausubel, F. M., et al., *CURRENT PROTOCOLS IN MOLECULAR BIOLOGY*, John Wiley and Sons, Inc., Media PA; Clontech}, expression in yeast {Rosenberg, S. and Tekamp-Olson, P., U.S. Pat. No. RE35,749, issued, Mar. 17, 1998, herein incorporated by reference; Shuster, J. R., U.S. Pat. No. 5,629,203, issued May 13, 1997, herein incorporated by reference; Gellissen, G., et al., *Antonie Van Leeuwenhoek,* 62(1-2):79-93 (1992); Romanos, M. A., at al., *Yeast* 8(6):423-488 (1992); Goeddel, D. V., *Methods in Enzymology* 185 (1990); Guthrie, C., and G. R. Fink, *Methods in Enzymology* 194 (1991)}, expression in mammalian cells {Clontech; Gibco-BRL, Ground Island, N.Y.; e.g., Chinese hamster ovary (CHO) cell lines (Haynes, J., et al., *Nuc. Acid. Res.* 11:687-706 (1983); 1983, Lau, Y. F., et al., *Mol. Cell. Biol.* 4:1469-1475 (1984); Kaufman, R. J., "Selection and coamplification of heterologous genes in mammalian cells," in *Methods in Enzymology*, vol. 185, pp 537-566. Academic Press, Inc., San Diego Calif. (1991)}, and expression in plant cells {plant cloning vectors, Clontech Laboratories, Inc., Palo Alto, Calif., and Pharmacia LKB Biotechnology, Inc., Pistcataway, N.J.; Hood, E., et al., *J. Bacteriol.* 168:1291-1301 (1986); Nagel, R., et al., *FEMS Microbiol. Lett.* 67:325 (1990); An, et al., "Binary Vectors", and others in *Plant Molecular Biology Manual* A3:1-19 (1988); Miki, B. L. A., et al., pp. 249-265, and others in Plant DNA Infectious Agents (Hohn, T., et al., eds.) Springer-Verlag, Wien, Austria, (1987); *Plant Molecular Biology: Essential Techniques*, P. G. Jones and J. M. Sutton, New York, J. Wiley, 1997; Miglani, Gurbachan *Dictionary of Plant Genetics and Molecular Biology*, New York, Food Products Press, 1998; Henry, R. J., *Practical Applications of Plant Molecular Biology*, New York, Chapman & Hall, 1997}.

Also included in the invention is an expression vector, such as the CMV promoter-containing vectors described in Example 1, containing coding sequences and expression control elements which allow expression of the coding regions in a suitable host. The control elements generally include a promoter, translation initiation codon, and translation and transcription termination sequences, and an insertion site for introducing the insert into the vector. Translational control elements have been reviewed by M. Kozak (e.g., Kozak, M., *Mamm. Genome* 7(8):563-574, 1996; Kozak, M., *Biochimie* 76(9):815-821, 1994; Kozak, M., J *Cell Biol* 108(2):229-241, 1989; Kozak, M., and Shatkin, A. J., *Methods Enzymol* 60:360-375, 1979).

Expression in yeast systems has the advantage of commercial production. Recombinant protein production by vaccinia and CHO cell line have the advantage of being mammalian expression systems. Further, vaccinia virus expression has several advantages including the following: (i) its wide host range; (ii) faithful post-transcriptional modification, processing, folding, transport, secretion, and assembly of recombinant proteins; (iii) high level expression of relatively soluble recombinant proteins; and (iv) a large capacity to accommodate foreign DNA.

The recombinantly expressed polypeptides from synthetic Gag-encoding expression cassettes are typically isolated from lysed cells or culture media. Purification can be carried out by methods known in the art including salt fractionation, ion exchange chromatography, gel filtration, size-exclusion chromatography, size-fractionation, and affinity chromatography. Immunoaffinity chromatography can be employed using antibodies generated based on, for example, Gag antigens.

Advantages of expressing the Gag-containing proteins of the present invention using mammalian cells include, but are not limited to, the following: well-established protocols for scale-up production; the ability to produce VLPs; cell lines are suitable to meet good manufacturing process (GMP) standards; culture conditions for mammalian cells are known in the art.

2.1.4 Modification of HIV-1 Env Nucleic Acid Coding Sequences

One aspect of the present invention is the generation of HIV-1 Env protein coding sequences, and related sequences, having improved expression relative to the corresponding wild-type sequence. Exemplary embodiments of the present invention are illustrated herein modifying the Env protein wild-type sequences obtained from the HIV-1 subtype B strains HIV-1US4 and HIV-1SF162 (Myers et al., Los Alamos Database, Los Alamos National Laboratory, Los Alamos, N. Mex. (1992); Myers et al., *Human Retroviruses and Aids*, 1997, Los Alamos, N. Mex.: Los Alamos National Laboratory). Env sequence obtained from other HIV variants may be manipulated in similar fashion following the teachings of the present specification. Such other variants include those described above in Section 2.1.1 and on the World Wide Web (Internet), for example at http://hiv-web.lan1.gov/cgi-bin/hivDB3/public/wdb/ssampublic and http://hiv-web.lan1.gov.

First, the HIV-1 codon usage pattern was modified so that the resulting nucleic acid coding sequence was comparable to codon usage found in highly expressed human genes (Example 1). The HIV codon usage reflects a high content of the nucleotides A or T of the codon-triplet. The effect of the HIV-1 codon usage is a high AT content in the DNA sequence that results in a decreased translation ability and instability of the mRNA. In comparison, highly expressed human codons prefer the nucleotides G or C. The Env coding sequences were modified to be comparable to codon usage found in highly expressed human genes. Experiments performed in support of the present invention showed that the synthetic Env sequences were capable of higher level of protein production (see the Examples) relative to the native Env sequences. One reason for this increased production may be increased stability of the mRNA corresponding to the synthetic Env coding sequences versus the mRNA corresponding to the native Env coding sequences.

Modification of the Env polypeptide coding sequences resulted in improved expression relative to the wild-type coding sequences in a number of mammalian cell lines. Similar Env polypeptide coding sequences can be obtained from a variety of isolates (families, sub-types, etc.). Env polypeptide encoding sequences derived from these variants can be optimized and tested for improved expression in mammals by following the teachings of the present specification (see the Examples, in particular Example 2).

2.1.5 Further Modification of HIV-1 Env Nucleic Acid Coding Sequences

In addition to proteins containing HIV-related sequences, the Env encoding sequences of the present invention can be fused to other polypeptides (creating chimeric polypeptides). Also, variations on the orientation of the Env and other coding sequences, relative to each other, are contemplated. Further, the HIV protein encoding cassettes of the present invention can be co-expressed using one vector or multiple vectors. In addition, the polyproteins can be operably linked to the same or different promoters.

Env polypeptide coding sequences can be obtained from any HIV isolates (different families, subtypes, and strains) including but not limited to the isolates $HIV_{IIIb}$, $HIV_{SF2}$, $HIV_{us4}$, $HIV_{CM235}$, $HIV_{SF162}$, $HIV_{LAV}$, $HIV_{LAI}$, $HIV_{MN}$) (see, e.g., Myers et al., Los Alamos Database, Los Alamos National Laboratory, Los Alamos, N. Mex. (1992); Myers et al., *Human Retroviruses and Aids,* 1997, Los Alamos, N. Mex.: Los Alamos National Laboratory). Synthetic expression cassettes can be generated using such coding sequences as starting material by following the teachings of the present specification (e.g., see Example 1). Further, the synthetic expression cassettes (and purified polynucleotides) of the present invention include related Env polypeptide coding sequences having greater than 90%, preferably greater than 92%, more preferably greater than 95%, and most preferably greater than 98% sequence identity to the synthetic expression cassette sequences disclosed herein (for example, SEQ ID NOs:71-72; and/or the sequences presented in Tables 1A and 1B) when the sequences of the present invention are used as the query sequence.

2.1.6 Expression of Synthetic Sequences Encoding HIV-1 Env and Related Polypeptides Several synthetic Env-encoding sequences (expression cassettes) of the present invention were cloned into a number of different expression vectors (Example 1) to evaluate levels of expression and production of Env polypeptide. A modified synthetic coding sequence is presented as synthetic Env expression cassettes (Example 1, e.g., Tables 1A and 1B). The synthetic DNA fragments for Env were cloned into eucaryotic expression vectors described in Example 1 and in Section 2.1.3 above, including, a transient expression vector and CMV-promoter-based mammalian vectors. Corresponding wild-type sequences were cloned into the same vectors.

These vectors were then transfected into a several different cell types, including a variety of mammalian cell lines, (293, RD, COS-7, and CHO, cell lines available, for example, from the A.T.C.C.). The cell lines were cultured under appropriate conditions and the levels of gp120, gp140 and gp160 Env expression in supernatants were evaluated (Example 2). Env polypeptides include, but are not limited to, for example, native gp160, oligomeric gp140, monomeric gp120 as well as modified sequences of these polypeptides. The results of these assays demonstrated that expression of synthetic Env encoding sequences were significantly higher than corresponding wild-type sequences (Example 2; Tables 3 and 4).

Further, Western Blot analysis showed that cells containing the synthetic Env expression cassette produced the expected protein (gp120, gp140 or gp160) at higher per-cell concentrations than cells containing the native expression cassette. The Env proteins were seen in both cell lysates and supernatants. The levels of production were significantly higher in cell supernatants for cells transfected with the synthetic Env expression cassettes of the present invention as compared to wild type.

Fractionation of the supernatants from mammalian cells transfected with the synthetic Env expression cassettes showed that it provides superior production of Env proteins, relative to the wild-type Env sequences (Examples 2 and 3).

Efficient expression of these Env-containing polypeptides in mammalian cell lines provides the following benefits: the Env polypeptides are free of baculovirus or other viral contaminants; production by established methods approved by the FDA; increased purity; greater yields (relative to native coding sequences); and a novel method of producing the Env-containing polypeptides in CHO cells which is less feasible in the absence of the increased expression obtained using the constructs of the present invention.

Exemplary cell lines (e.g., mammalian, yeast, insect, etc.) include those described above in Section 2.1.3 for Gag-containing constructs. Further, appropriate vectors and control elements (e.g., promoters, enhancers, polyadenylation sequences, etc.) for any given cell type can be selected, as described above in Section 2.1.3, by one having ordinary skill in the art in view of the teachings of the present specification and information known in the art about expression vectors. In addition, the recombinantly expressed polypeptides from synthetic Env-encoding expression cassettes are typically isolated and purified from lysed cells or culture media, as described above for Gag-encoding expression cassettes. An exemplary purification is described in Example 4 and shown in FIG. 60.

2.1.7 Modification of HIV-1 Tat Nucleic Acid Coding Sequences

Another aspect of the present invention is the generation of HIV-1 tat protein coding sequences, and related sequences, having improved expression relative to the corresponding wild-type sequence. Exemplary embodiments of the present invention are illustrated herein modifying the tat wild-type nucleotide sequence (SEQ ID NO:85, FIG. 76) obtained from SF162 as described above. Exemplary synthetic tat constructs are shown in SEQ ID NO:87, which depicts a tat construct encoding a full-length tat polypeptide from strain SF162; SEQ ID NO:88, which depicts a tat construct encoding a tat polypeptide having the cystein residue at position 22 changed; and SEQ ID NO:89, which depicts a tat construct encoding the amino terminal portion of a tat polypeptide from strain SF162. The amino portion of the tat protein appears to contain many of the epitopes that induce an immune response. In addition, further modifications include replacement or deletion of the cystein residue at position 22, for example with a valine residue, an alanine residue or a glycine residue (SEQ ID Nos: 88 and 89, FIGS. 79 and 81), see, e.g., Caputo et al. (1996) *Gene Ther.* 3:235. In FIG. 81, which depicts a tat construct encoding the amino terminal portion of a tat polypeptide, the nucleotides (nucleotides 64-66) encoding the cystein residues are underlined. The design and construction of suitable construct can be readily done using the teachings of the present specification. As with Gag, pol, prot and Env, tat polypeptide coding sequences can be obtained from a variety of isolates (families, sub-types, etc.).

Modification of the tat polypeptide coding sequences result in improved expression relative to the wild-type coding sequences in a number of cell lines (e.g., mammalian, yeast, bacterial and insect cells). Tat polypeptide encoding sequences derived from these variants can be optimized and tested for improved expression in mammals by following the teachings of the present specification (see the Examples, in particular Example 2).

Various forms of the different embodiments of the invention, described herein, may be combined. For example, polynucleotides may be derived from the polynucleotide sequences of the present invention, including, but not limited to, coding sequences for Gag polypeptides, Env polypeptides, polymerase polypeptides, protease polypeptides, tat polypeptides, and reverse transcriptase polypeptides. Further, the polynucleotide coding sequences of the present invention may be combined into multi-cistronic expression cassettes where typically each coding sequence for each polypeptide is preceded by IRES sequences.

2.2 Production of Virus-Like Particles and Use of the Constructs of the Present Invention to Create Packaging Cell Lines The group-specific antigens (Gag) of human immunodeficiency virus type-1 (HIV-1) self-assemble into noninfectious virus-like particles (VLP) that are released from various eucaryotic cells by budding (reviewed by Freed, E. O., *Virology* 251:1-15, 1998). The synthetic expression cassettes of the present invention provide efficient means for the production of HIV-Gag virus-like particles (VLPs) using a variety of different cell types, including, but not limited to, mammalian cells.

Viral particles can be used as a matrix for the proper presentation of an antigen entrapped or associated therewith to the immune system of the host. For example, U.S. Pat. No. 4,722,840 describes hybrid particles comprised of a particle-forming fragment of a structural protein from a virus, such as a particle-forming fragment of hepatitis B virus (HBV) surface antigen (HBsAg), fused to a heterologous polypeptide. Tindle et al., *Virology* (1994) 200:547-557, describes the production and use of chimeric HBV core antigen particles containing epitopes of human papillomavirus (HPV) type 16 E7 transforming protein.

Adams et al., *Nature* (1987) 329:68-70, describes the recombinant production of hybrid HIVgp120:Ty VLPs in yeast and Brown et al., *Virology* (1994) 198:477-488, the production of chimeric proteins consisting of the VP2 protein of human parvovirus B19 and epitopes from human herpes simplex virus type 1, as well as mouse hepatitis virus A59. Wagner et al., (*Virology* (1994) 200:162-175, Brand et al., *J. Virol. Meth.* (1995) 51:153-168; Virology (1996) 220:128-140) and Wolf, et al., (EP 0 449 116 A1, published 2 Oct. 1991; WO 96/30523, published 3 Oct. 1996) describe the assembly of chimeric HIV-1 p55Gag particles. U.S. Pat. No.

5,503,833 describes the use of rotavirus VP6 spheres for encapsulating and delivering therapeutic agents.

2.2.1 VLP Production Using the Synthetic Expression Cassettes of the Present Invention Experiments performed in support of the present invention have demonstrated that the synthetic expression cassettes of the present invention provide superior production of both protein and VLPs, relative to native coding sequences (Examples 7 and 15). Further, electron microscopic evaluation of VLP production (Examples 6 and 15, FIGS. 3A-B and 65A-F) showed that free and budding immature virus particles of the expected size were produced by cells containing the synthetic expression cassettes.

Using the synthetic expression cassettes of the present invention, rather than native coding sequences, for the production of virus-like particles provide several advantages. First, VLPs can be produced in enhanced quantity making isolation and purification of the VLPs easier. Second, VLPs can be produced in a variety of cell types using the synthetic expression cassettes, in particular, mammalian cell lines can be used for VLP production, for example, CHO cells. Production using CHO cells provides (i) VLP formation; (ii) correct myristylation and budding; (iii) absence of non-mammalian cell contaminants (e.g., insect viruses and/or cells); and (iv) ease of purification. The synthetic expression cassettes of the present invention are also useful for enhanced expression in cell-types other than mammalian cell lines. For example, infection of insect cells with baculovirus vectors encoding the synthetic expression cassettes resulted in higher levels of total protein yield and higher levels of VLP production (relative to wild-type coding sequences). Further, the final product from insect cells infected with the baculovirus-Gag synthetic expression cassettes consistently contained lower amounts of contaminating insect proteins than the final product when wild-type coding sequences were used (Examples).

VLPs can spontaneously form when the particle-forming polypeptide of interest is recombinantly expressed in an appropriate host cell. Thus, the VLPs produced using the synthetic expression cassettes of the present invention are conveniently prepared using recombinant techniques. As discussed below, the Gag polypeptide encoding synthetic expression cassettes of the present invention can include other polypeptide coding sequences of interest (for example, Env, tat, rev, HIV protease, HIV polymerase, HCV core; see, Example 1). Expression of such synthetic expression cassettes yields VLPs comprising the product of the synthetic expression cassette, as well as, the polypeptide of interest.

Once coding sequences for the desired particle-forming polypeptides have been isolated or synthesized, they can be cloned into any suitable vector or replicon for expression. Numerous cloning vectors are known to those of skill in the art, and the selection of an appropriate cloning vector is a matter of choice. See, generally, Ausubel et al, supra or Sambrook et al, supra. The vector is then used to transform an appropriate host cell. Suitable recombinant expression systems include, but are not limited to, bacterial, mammalian, baculovirus/insect, vaccinia, Semliki Forest virus (SFV), Alphaviruses (such as, Sindbis, Venezuelan Equine Encephalitis (VEE)), mammalian, yeast and *Xenopus* expression systems, well known in the art. Particularly preferred expression systems are mammalian cell lines, vaccinia, Sindbis, insect and yeast systems.

For example, a number of mammalian cell lines are known in the art and include immortalized cell lines available from the American Type Culture Collection (A.T.C.C.), such as, but not limited to, Chinese hamster ovary (CHO) cells, 293 cells, HeLa cells, baby hamster kidney (BHK) cells, mouse myeloma (SB20), monkey kidney cells (COS), as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltose, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*. See, e.g., Summers and Smith, Texas Agricultural Experiment Station Bulletin No. 1555 (1987). Fungal hosts include, for example, *Aspergillus*.

Viral vectors can be used for the production of particles in eucaryotic cells, such as those derived from the pox family of viruses, including vaccinia virus and avian poxvirus. Additionally, a vaccinia based infection/transfection system, as described in Tomei et al., *J. Virol.* (1993) 67:4017-4026 and Selby et al., *J. Gen. Virol.* (1993) 74:1103-1113, will also find use with the present invention. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. Alternately, T7 can be added as a purified protein or enzyme as in the "Progenitor" system (Studier and Moffatt, *J. Mol. Biol.* (1986) 189:113-130). The method provides for high level, transient, cytoplasmic production of large quantities of RNA and its translation product(s).

Depending on the expression system and host selected, the VLPS are produced by growing host cells transformed by an expression vector under conditions whereby the particle-forming polypeptide is expressed and VLPs can be formed. The selection of the appropriate growth conditions is within the skill of the art. If the VLPs are formed intracellularly, the cells are then disrupted, using chemical, physical or mechanical means, which lyse the cells yet keep the VLPs substantially intact. Such methods are known to those of skill in the art and are described in, e.g., *Protein Purification Applications: A Practical Approach*, (E. L. V. Harris and S. Angal, Eds., 1990).

The particles are then isolated (or substantially purified) using methods that preserve the integrity thereof, such as, by density gradient centrifugation, e.g., sucrose gradients, PEG-precipitation, pelleting, and the like (see, e.g., Kirnbauer et al. *J. Virol.* (1993) 67:6929-6936), as well as standard purification techniques including, e.g., ion exchange and gel filtration chromatography.

VLPs produced by cells containing the synthetic expression cassettes of the present invention can be used to elicit an immune response when administered to a subject. One advantage of the present invention is that VLPs can be produced by mammalian cells carrying the synthetic expression cassettes at levels previously not possible. As discussed above, the VLPs can comprise a variety of antigens in addition to the Gag polypeptides (e.g., Env, tat, Gag-protease, Gag-polymerase, Gag-HCV-core). Purified VLPs, produced using the synthetic expression cassettes of the present invention, can be administered to a vertebrate subject, usually in the form of vaccine compositions. Combination vaccines may also be used, where such vaccines contain, for example, other subunit proteins derived from HIV or other organisms (e.g., env) or gene delivery vaccines encoding such antigens. Administration can take place using the VLPs formulated alone or formulated with other antigens. Further, the VLPs can be administered prior to, concurrent with, or subsequent to, delivery of the synthetic expression cassettes for DNA immunization (see below) and/or delivery of other vaccines. Also, the site of VLP administration may be the same or different as other vaccine compositions that are being administered. Gene delivery can be accomplished by a number of methods including, but are not limited to, immunization with DNA, alphavirus vectors, pox virus vectors, and vaccinia virus vectors.

VLP immune-stimulating (or vaccine) compositions can include various excipients, adjuvants, carriers, auxiliary substances, modulating agents, and the like. The immune stimulating compositions will include an amount of the VLP/antigen sufficient to mount an immunological response. An appropriate effective amount can be determined by one of skill in the art. Such an amount will fall in a relatively broad range that can be determined through routine trials and will generally be an amount on the order of about 0.1 µg to about 1000 µg, more preferably about 1 µg to about 300 µg, of VLP/antigen.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; McGee J P, et al., *J. Microencapsul.* 14(2):197-210, 1997; O'Hagan D T, et al., *Vaccine* 11(2):149-54, 1993. Such carriers are well known to those of ordinary skill in the art. Additionally, these carriers may function as immunostimulating agents ("adjuvants"). Furthermore, the antigen may be conjugated to a bacterial toxoid, such as toxoid from diphtheria, tetanus, cholera, etc., as well as toxins derived from *E. coli*.

Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), beta chemokines (MIP, 1-alpha, 1-beta Rantes, etc.); (6) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetyl-muramyl-L-alanyl-D-isogluatminyl-L-alanine-2-(1'-2'-dipalmitoyl-sn-glycero-3-huydroxyphosphoryloxy)-ethylamine (MTP-PE), etc.

Dosage treatment with the VLP composition may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1-4 months for a second dose, and if needed, a subsequent dose(s) after several months. The dosage regimen will also, at least in part, be determined by the potency of the modality, the vaccine delivery employed, the need of the subject and be dependent on the judgment of the practitioner.

If prevention of disease is desired (e.g., reduction of symptoms, recurrences or of disease progression), the antigen carrying VLPs are generally administered prior to primary infection with the pathogen of interest. If treatment is desired, e.g., the reduction of symptoms or recurrences, the VLP compositions are generally administered subsequent to primary infection.

2.2.2 Using the Synthetic Expression Cassettes of the Present Invention to Create Packaging Cell Lines A number of viral based systems have been developed for use as gene transfer vectors for mammalian host cells. For example, retroviruses (in particular, lentiviral vectors) provide a convenient platform for gene delivery systems. A coding sequence of interest (for example, a sequence useful for gene therapy applications) can be inserted into a gene delivery vector and packaged in retroviral particles using techniques known in the art. Recombinant virus can then be isolated and delivered to cells of the subject either in vivo or ex vivo. A number of retroviral systems have been described, including, for example, the following: (U.S. Pat. No. 5,219,740; Miller et al. (1989) *Biotechniques* 7:980; Miller, A. D. (1990) *Human Gene Therapy* 1:5; Scarpa et al. (1991) *Virology* 180:849; Burns et al. (1993) *Proc. Natl. Acad. Sci. USA* 90:8033; Boris-Lawrie et al. (1993) *Cur. Opin. Genet. Develop.* 3:102; GB 2200651; EP 0415731; EP 0345242; WO 89/02468; WO 89/05349; WO 89/09271; WO 90/02806; WO 90/07936; WO 90/07936; WO 94/03622; WO 93/25698; WO 93/25234; WO 93/11230; WO 93/10218; WO 91/02805; in U.S. Pat. No. 5,219,740; U.S. Pat. No. 4,405,712; U.S. Pat. No. 4,861,719; U.S. Pat. No. 4,980,289 and U.S. Pat. No. 4,777,127; in U.S. Ser. No. 07/800,921; and in Vile (1993) *Cancer Res* 53:3860-3864; Vile (1993) *Cancer Res* 53:962-

967; Ram (1993) *Cancer Res* 53:83-88; Takamiya (1992) *Neurosci Res* 33:493-503; Baba (1993) *J Neurosurg* 79:729-735; Mann (1983) *Cell* 33:153; Cane (1984) *Proc Natl Acad Sci USA* 81; 6349; and Miller (1990) *Human Gene Therapy* 1.

Sequences useful for gene therapy applications include, but are not limited to, the following. Factor VIII cDNA, including derivatives and deletions thereof (International Publication Nos. WO 96/21035, WO 97/03193, WO 97/03194, WO 97/03195, and WO 97/03191, all of which are hereby incorporated by reference). Factor IX cDNA (Kurachi et al. (1982) *Proc. Natl. Acad. Sci. USA* 79:6461-6464). Factor V cDNA can be obtained from pMT2-V (Jenny (1987) *Proc. Natl. Acad. Sci. USA* 84:4846, A.T.C.C. Deposit No. 40515). A full-length factor V cDNA, or a B domain deletion or B domain substitution thereof, can be used. B domain deletions of factor V, include those reported by Marquette (1995) *Blood* 86:3026 and Kane (1990) *Biochemistry* 29:6762. Antithrombin III cDNA (Prochownik (1983) *J. Biol. Chem.* 258:8389, A.T.C.C. Deposit No. 57224/57225). Protein C encoding cDNA (Foster (1984) *Proc. Natl. Acad. Sci. USA* 81:4766; Beckmann (1985) *Nucleic Acids Res.* 13:5233). Prothrombin cDNA can be obtained by restriction enzyme digestion of a published vector (Degen (1983) *Biochemistry* 22:2087). The endothelial cell surface protein, thrombomodulin, is a necessary cofactor for the normal activation of protein C by thrombin. A soluble recombinant form has been described (Parkinson (1990) *J. Biol. Chem.* 265:12602; Jackman (1987) *Proc. Natl. Acad. Sci. USA* 84:6425; Shirai (1988) *J. Biochem.* 103:281; Wen (1987) *Biochemistry* 26:4350; Suzuki (1987) *EMBO J.* 6:1891, A.T.C.C. Deposit No. 61348, 61349).

Many genetic diseases caused by inheritance of defective genes result in the failure to produce normal gene products, for example, thalassemia, phenylketonuria, Lesch-Nyhan syndrome, severe combined immunodeficiency (SCID), hemophilia A and B, cystic fibrosis, Duchenne's Muscular Dystrophy, inherited emphysema and familial hypercholesterolemia (Mulligan et al. (1993) *Science* 260:926; Anderson et al. (1992) *Science* 256:808; Friedman et al. (1989) *Science* 244:1275). Although genetic diseases may result in the absence of a gene product, endocrine disorders, such as diabetes and hypopituitarism, are caused by the inability of the gene to produce adequate levels of the appropriate hormone insulin and human growth hormone respectively.

In one aspect, gene therapy employing the constructs and methods of the present invention involves the introduction of normal recombinant genes into T cells so that new or missing proteins are produced by the T cells after introduction or reintroduction thereof into a patient. A number of genetic diseases have been selected for treatment with gene therapy, including adenine deaminase deficiency, cystic fibrosis, $\alpha_1$-antitrypsin deficiency, Gaucher's syndrome, as well as non-genetic diseases.

In particular, Gaucher's syndrome is a genetic disorder characterized by a deficiency of the enzyme glucocerebrosidase. This enzyme deficiency leads to the accumulation of glucocerebroside in the lysosomes of all cells in the body. For a review see *Science* 256:794 (1992) and Scriver et al., *The Metabolic Basis of Inherited Disease,* 6th ed., vol. 2, page 1677). Thus, gene transfer vectors that express glucocerebrosidase can be constructed for use in the treatment of this disorder. Likewise, gene transfer vectors encoding lactase can be used in the treatment of hereditary lactose intolerance, those expressing AD can be used for treatment of ADA deficiency, and gene transfer vectors encoding $\alpha_1$-antitrypsin can be used to treat $\alpha_1$-antitrypsin deficiency. See Ledley, F. D. (1987) *J. Pediatrics* 110:157-174, Verma, I. (November 1987) *Scientific American* pp. 68-84, and International Publication No. WO 95/27512 entitled "Gene Therapy Treatment for a Variety of Diseases and Disorders," for a description of gene therapy treatment of genetic diseases.

In still further embodiments of the invention, nucleotide sequences which can be incorporated into a gene transfer vector include, but are not limited to, proteins associated with enzyme-deficiency disorders, such as the cystic fibrosis transmembrane regulator (see, for example, U.S. Pat. No. 5,240,846 and Larrick et al. (1991) *Gene Therapy Applications of Molecular Biology,* Elsevier, New York and adenosine deaminase (ADA) (see U.S. Pat. No. 5,399,346); growth factors, or an agonist or antagonist of a growth factor (Bandara et al. (1992) *DNA and Cell Biology,* 11:227); one or more tumor suppressor genes such as p53, Rb, or C-CAMI (Kleinerman et al. (1995) *Cancer Research* 55:2831); a molecule that modulates the immune system of an organism, such as a HLA molecule (Nabel et al. (1993) *Proc. Natl. Acad. Sci. USA* 90:11307); a ribozyme (Larsson et al. (1996) *Virology* 219: 161); a peptide nucleic acid (Hirshman et al. (1996) *J. Invest. Med.* 44:347); an antisense molecule (Bordier et al. (1995) *Proc. Natl. Acad. Sci. USA* 92:9383) which can be used to down-regulate the expression or synthesis of aberrant or foreign proteins, such as HIV proteins or a wide variety of oncogenes such as p53 (Hesketh, *The Oncogene Facts Book,* Academic Press, New York, (1995); a biopharmaceutical agent or antisense molecule used to treat HIV-infection, such as an inhibitor of p24 (Nakashima et al. (1994) *Nucleic Acids Res.* 22:5004); or reverse-transcriptase (see, Bordier, supra).

Other proteins of therapeutic interest can be expressed in vivo by gene transfer vectors using the methods of the invention. For instance sustained in vivo expression of tissue factor inhibitory protein (TFPI) is useful for treatment of conditions including sepsis and DIC and in preventing reperfusion injury. (See International Publications Nos. WO 93/24143, WO 93/25230 and WO 96/06637). Nucleic acid sequences encoding various forms of TFPI can be obtained, for example, as described in U.S. Pat. Nos. 4,966,852; 5,106,833; and 5,466,783, and incorporated into the gene transfer vectors described herein.

Erythropoietin (EPO) and leptin can also be expressed in vivo from genetically modified T cells according to the methods of the invention. For instance EPO is useful in gene therapy treatment of a variety of disorders including anemia (see International Publication No. WO 95/13376 entitled "Gene Therapy for Treatment of Anemia"). Sustained delivery of leptin by the methods of the invention is useful in treatment of obesity. See International Publication No. WO 96/05309 for a description of the leptin gene and the use thereof in the treatment of obesity.

A variety of other disorders can also be treated by the methods of the invention. For example, sustained in vivo systemic production of apolipoprotein E or apolipoprotein A from genetically modified T cells can be used for treatment of hyperlipidemia (see Breslow et al. (1994) *Biotechnology* 12:365). Sustained production of angiotensin receptor inhibitor (Goodfriend et al. (1996) *N. Engl. J. Med.* 334:1469) can be provided by the methods described herein. As yet an additional example, the long term in vivo systemic production of angiostatin is useful in the treatment of a variety of tumors. (See O'Reilly et al. (1996) *Nature Med.* 2:689).

In other embodiments, gene transfer vectors can be constructed to encode a cytokine or other immunomodulatory molecule. For example, nucleic acid sequences encoding native IL-2 and gamma-interferon can be obtained as described in U.S. Pat. Nos. 4,738,927 and 5,326,859, respectively, while useful muteins of these proteins can be obtained as described in U.S. Pat. No. 4,853,332. Nucleic acid sequences encoding the short and long forms of mCSF can be obtained as described in U.S. Pat. Nos. 4,847,201 and 4,879,227, respectively. In particular aspects of the invention, retroviral vectors expressing cytokine or immunomodulatory genes can be produced as described herein (for example, employing the packaging cell lines of the present invention) and in International Application No. PCT US 94/02951, entitled "Compositions and Methods for Cancer Immunotherapy."

Examples of suitable immunomodulatory molecules for use herein include the following: IL-1 and IL-2 (Karupiah et al. (1990) *J. Immunology* 144:290-298, Weber et al. (1987). *J. Exp. Med.* 166:1716-1733, Gansbacher et al. (1990) *J. Exp. Med.* 172:1217-1224, and U.S. Pat. No. 4,738,927); IL-3 and IL-4 (Tepper et al. (1989) *Cell* 57:503-512, Golumbek et al. (1991) *Science* 254:713-716, and U.S. Pat. No. 5,017,691); IL-5 and IL-6 (Brakenhof et al. (1987) *J. Immunol.* 139:4116-4121, and International Publication No. WO 90/06370); IL-7 (U.S. Pat. No. 4,965,195); IL-8, IL-9, IL-10, IL-11, IL-12, and IL-13 (*Cytokine Bulletin*, Summer 1994); IL-14 and IL-15; alpha interferon (Finter et al. (1991) *Drugs* 42:749-765, U.S. Pat. Nos. 4,892,743 and 4,966,843, International Publication No. WO 85/02862, Nagata et al. (1980) *Nature* 284:316-320, Familletti et al. (1981) *Methods in Enz.* 78:387-394, Twu et al. (1989) *Proc. Natl. Acad. Sci. USA* 86:2046-2050, and Faktor et al. (1990) *Oncogene* 5:867-872); beta-interferon (Seif et al. (1991) *J. Virol.* 65:664-671); gamma-interferons (Radford et al. (1991) *The American Society of Hepatology* 20082015, Watanabe et al. (1989) *Proc. Natl. Acad. Sci. USA* 86:9456-9460, Gansbacher et al. (1990) *Cancer Research* 50:7820-7825, Maio et al. (1989) *Can. Immunol. Immunother.* 30:34-42, and U.S. Pat. Nos. 4,762,791 and 4,727,138); G-CSF (U.S. Pat. Nos. 4,999,291 and 4,810,643); GM-CSF (International Publication No. WO 85/04188); tumor necrosis factors (TNFs) (Jayaraman et al. (1990) *J. Immunology* 144:942-951); CD3 (Krissanen et al. (1987) *Immunogenetics* 26:258-266); ICAM-1 (Altman et al. (1989) *Nature* 338:512-514, Simmons et al. (1988) *Nature* 331:624-627); ICAM-2, LFA-1, LFA-3 (Wallner et al. (1987) *J. Exp. Med.* 166:923-932); MHC class I molecules, MHC class II molecules, B7.1-.3, $\beta_2$-microglobulin (Parnes et al. (1981) *Proc. Natl. Acad. Sci. USA* 78:2253-2257); chaperones such as calnexin; and MHC-linked transporter proteins or analogs thereof (Powis et al. (1991) *Nature* 354:528-531). Immunomodulatory factors may also be agonists, antagonists, or ligands for these molecules. For example, soluble forms of receptors can often behave as antagonists for these types of factors, as can mutated forms of the factors themselves.

Nucleic acid molecules that encode the above-described substances, as well as other nucleic acid molecules that are advantageous for use within the present invention, may be readily obtained from a variety of sources, including, for example, depositories such as the American Type Culture Collection, or from commercial sources such as British Bio-Technology Limited (Cowley, Oxford England). Representative examples include BBG 12 (containing the GM-CSF gene coding for the mature protein of 127 amino acids), BBG 6 (which contains sequences encoding gamma interferon), A.T.C.C. Deposit No. 39656 (which contains sequences encoding TNF), A.T.C.C. Deposit No. 20663 (which contains sequences encoding alpha-interferon), A.T.C.C. Deposit Nos. 31902, 31902 and 39517 (which contain sequences encoding beta-interferon), A.T.C.C. Deposit No. 67024 (which contains a sequence which encodes Interleukin-1b), A.T.C.C. Deposit Nos. 39405, 39452, 39516, 39626 and 39673 (which contain sequences encoding Interleukin-2), A.T.C.C. Deposit Nos. 59399, 59398, and 67326 (which contain sequences encoding Interleukin-3), A.T.C.C. Deposit No. 57592 (which contains sequences encoding Interleukin-4), A.T.C.C. Deposit Nos. 59394 and 59395 (which contain sequences encoding Interleukin-5), and A.T.C.C. Deposit No. 67153 (which contains sequences encoding Interleukin-6).

Plasmids containing cytokine genes or immunomodulatory genes (International Publication Nos. WO 94/02951 and WO 96/21015, both of which are incorporated by reference in their entirety) can be digested with appropriate restriction enzymes, and DNA fragments containing the particular gene of interest can be inserted into a gene transfer vector using standard molecular biology techniques. (See, e.g., Sambrook et al., supra., or Ausubel et al. (eds) *Current Protocols in Molecular Biology*, Greene Publishing and Wiley-Interscience).

Exemplary hormones, growth factors and other proteins which are useful for long term expression are described, for example, in European Publication No. 0437478B1, entitled "Cyclodextrin-Peptide Complexes." Nucleic acid sequences encoding a variety of hormones can be used, including those encoding human growth hormone, insulin, calcitonin, prolactin, follicle stimulating hormone (FSH), luteinizing hormone (LH), human chorionic gonadotropin (HCG), and thyroid stimulating hormone (TSH). A variety of different forms of IGF-1 and IGF-2 growth factor polypeptides are also well known the art and can be incorporated into gene transfer vectors for long term expression in vivo. See, e.g., European Patent No. 0123228B1, published for grant Sep. 19, 1993, entitled "Hybrid DNA Synthesis of Mature Insulin-like Growth Factors." As an additional example, the long term in vivo expression of different forms of fibroblast growth factor can also be effected employing the compositions and methods of invention. See, e.g., U.S. Pat. Nos. 5,464,774, 5,155,214, and 4,994,559 for a description of different fibroblast growth factors.

Polynucleotide sequences coding for the above-described molecules can be obtained using recombinant methods, such as by screening cDNA and genomic libraries from cells expressing the gene, or by deriving the gene from a vector known to include the same. For example, plasmids which contain sequences that encode altered cellular products may be obtained from a depository such as the A.T.C.C., or from commercial sources. Plasmids containing the nucleotide sequences of interest can be digested with appropriate restriction enzymes, and DNA fragments containing the nucleotide sequences can be inserted into a gene transfer vector using standard molecular biology techniques.

Alternatively, cDNA sequences for use with the present invention may be obtained from cells which express or contain the sequences, using standard techniques, such as phenol extraction and PCR of cDNA or genomic DNA. See, e.g., Sambrook et al., supra, for a description of techniques used to obtain and isolate DNA. Briefly, mRNA from a cell which expresses the gene of interest can be reverse transcribed with reverse transcriptase using oligo-dT or random primers. The single stranded cDNA may then be amplified by PCR (see U.S. Pat. Nos. 4,683,202, 4,683,195 and 4,800,159, see also *PCR Technology: Principles and Applications for DNA Amplification*, Erlich (ed.), Stockton Press, 1989)) using oligonucleotide primers complementary to sequences on either side of desired sequences.

The nucleotide sequence of interest can also be produced synthetically, rather than cloned, using a DNA synthesizer (e.g., an Applied Biosystems Model 392 DNA Synthesizer, available from ABI, Foster City, Calif.). The nucleotide sequence can be designed with the appropriate codons for the expression product desired. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

The synthetic expression cassettes of the present invention can be employed in the construction of packaging cell lines for use with retroviral vectors.

One type of retrovirus, the murine leukemia virus, or "MLV", has been widely utilized for gene therapy applications (see generally Mann et al. (*Cell* 33:153, 1993), Cane and Mulligan (Proc, Nat'l. Acad. Sci. USA 81:6349, 1984), and Miller et al., *Human Gene 2lerapy* 1:5-14, 1990.

Lentiviral vectors typically, comprise a 5' lentiviral LTR, a tRNA binding site, a packaging signal, a promoter operably linked to one or more genes of interest, an origin of second strand DNA synthesis and a 3' lentiviral LTR, wherein the lentiviral vector contains a nuclear transport element. The nuclear transport element may be located either upstream (5') or downstream (3') of a coding sequence of interest. Within certain embodiments, the nuclear transport element is not RRE. Within one embodiment the packaging signal is an extended packaging signal. Within other embodiments the promoter is a tissue specific promoter, or, alternatively, a promoter such as CMV. Within other embodiments, the lentiviral vector further comprises an internal ribosome entry site.

A wide variety of lentiviruses may be utilized within the context of the present invention, including for example, lentiviruses selected from the group consisting of HIV, HIV-1, HIV-2, FIV and SIV.

In one embodiment of the present invention synthetic Env and/or Gag-polymerase expression cassettes are provided comprising a promoter and a sequence encoding synthetic Gag-polymerase (SEQ ID NO:6) and at least one of vpr, vpu, nef or vif, wherein the promoter is operably linked to Gag-polymerase and vpr, vpu, nef or vif.

Within yet another aspect of the invention, host cells (e.g., packaging cell lines) are provided which contain any of the expression cassettes described herein. For example, within one aspect packaging cell line are provided comprising an expression cassette that comprises a sequence encoding synthetic Env and/or Gag-polymerase, and a nuclear transport element, wherein the promoter is operably linked to the sequence encoding Env and/or Gag-polymerase. Packaging cell lines may further comprise a promoter and a sequence encoding tat, rev, or an envelope, wherein the promoter is operably linked to the sequence encoding tat, rev, or, the envelope. The packaging cell line may further comprise a sequence encoding any one or more of nef, vif, vpu or vpr.

In one embodiment, the expression cassette (carrying, for example, the synthetic Env, synthetic tat and/or synthetic Gag-polymerase) is stably integrated. The packaging cell line, upon introduction of a lentiviral vector, typically produces viral particles. The promoter regulating expression of the synthetic expression cassette may be inducible. Typically, the packaging cell line, upon introduction of a lentiviral vector, produces viral particles that are essentially free of replication competent virus.

Packaging cell lines are provided comprising an expression cassette which directs the expression of a synthetic Env (or Gag-polymerase) gene, an expression cassette which directs the expression of a Gag (or Env) gene optimized for expression (e.g., Andre, S., et al., *Journal of Virology* 72(2):1497-1503, 1998; Haas, J., et al., *Current Biology* 6(3):315-324, 1996). A lentiviral vector is introduced into the packaging cell line to produce a vector particle producing cell line.

As noted above, lentiviral vectors can be designed to carry or express a selected gene(s) or sequences of interest. Lentiviral vectors may be readily constructed from a wide variety of lentiviruses (see RNA Tumor Viruses, Second Edition, Cold Spring Harbor Laboratory, 1985). Representative examples of lentiviruses included HIV, HIV-1, HIV-2, FIV and SIV. Such lentiviruses may either be obtained from patient isolates, or, more preferably, from depositories or collections such as the American Type Culture Collection, or isolated from known sources using available techniques.

Portions of the lentiviral gene delivery vectors (or vehicles) may be derived from different viruses. For example, in a given recombinant lentiviral vector, LTRs may be derived from an HIV, a packaging signal from SIV, and an origin of second strand synthesis from HrV-2. Lentiviral vector constructs may comprise a 5' lentiviral LTR, a tRNA binding site, a packaging signal, one or more heterologous sequences, an origin of second strand DNA synthesis and a 3' LTR, wherein said lentiviral vector contains a nuclear transport element that is not RRE.

Briefly, Long Terminal Repeats ("LTRs") are subdivided into three elements, designated U5, R and U3. These elements contain a variety of signals which are responsible for the biological activity of a retrovirus, including for example, promoter and enhancer elements which are located within U3. LTRs may be readily identified in the provirus (integrated DNA form) due to their precise duplication at either end of the genome. As utilized herein, a 5' LTR should be understood to include a 5' promoter element and sufficient LTR sequence to allow reverse transcription and integration of the DNA form of the vector. The 3' LTR should be understood to include a polyadenylation signal, and sufficient LTR sequence to allow reverse transcription and integration of the DNA form of the vector.

The tRNA binding site and origin of second strand DNA synthesis are also important for a retrovirus to be biologically active, and may be readily identified by one of skill in the art. For example, retroviral tRNA binds to a tRNA binding site by Watson-Crick base pairing, and is carried with the retrovirus genome into a viral particle. The tRNA is then utilized as a primer for DNA synthesis by reverse transcriptase. The tRNA binding site may be readily identified based upon its location just downstream from the 5'LTR. Similarly, the origin of second strand DNA synthesis is, as its name implies, important for the second strand DNA synthesis of a retrovirus. This region, which is also referred to as the poly-purine tract, is located just upstream of the 3'LTR.

In addition to a 5' and 3' LTR, tRNA binding site, and origin of second strand DNA synthesis, recombinant retroviral vector constructs may also comprise a packaging signal, as well as one or more genes or coding sequences of interest. In addition, the lentiviral vectors have a nuclear transport element which, in preferred embodiments is not RRE. Representative examples of suitable nuclear transport elements include the element in Rous sarcoma virus (Ogert, et al., *J. Virol.* 70, 3834-3843, 1996), the element in Rous sarcoma virus (Liu & Mertz, *Genes & Dev.,* 9, 1766-1789, 1995) and the element in the genome of simian retrovirus type I (Zolotukhin, et al., *J. Virol.* 68, 7944-7952, 1994). Other potential elements include the elements in the histone gene (Kedes, *Annu. Rev. Biochem.* 48, 837-870, 1970), the α-interferon gene (Nagata et al., *Nature* 287, 401-408, 1980), the β-adrenergic receptor gene (Koilka, et al., *Nature* 329, 75-79, 1987), and the c-Jun gene (Hattorie, et al., *Proc. Natl. Acad. Sci. USA* 85, 9148-9152, 1988).

Recombinant lentiviral vector constructs typically lack both Gag-polymerase and env coding sequences. Recombinant lentiviral vector typically contain less than 20, preferably 15, more preferably 10, and most preferably 8 consecutive nucleotides found in Gag-polymerase or env genes. One advantage of the present invention is that the synthetic Gag-polymerase expression cassettes, which can be used to construct packaging cell lines for the recombinant retroviral vector constructs, have little homology to wild-type Gag-polymerase sequences and thus considerably reduce or eliminate the possibility of homologous recombination between the synthetic and wild-type sequences.

Lentiviral vectors may also include tissue-specific promoters to drive expression of one or more genes or sequences of interest. For example, lentiviral vector particles of the invention can contain a liver specific promoter to maximize the potential for liver specific expression of the exogenous DNA sequence contained in the vectors. Preferred liver specific promoters include the hepatitis B X-gene promoter and the hepatitis B core protein promoter. These liver specific promoters are preferably employed with their respective enhancers. The enhancer element can be linked at either the 5' or the 3' end of the nucleic acid encoding the sequences of interest. The hepatitis B X gene promoter and its enhancer can be obtained from the viral genome as a 332 base pair EcoRV-NcoI DNA fragment employing the methods described in Twu, et al., *J. Virol.* 61:3448-3453, 1987. The hepatitis B core protein promoter can be obtained from the viral genome as a 584 base pair BamHI-BglII DNA fragment employing the methods described in Gerlach, et al., *Virol* 189:59-66, 1992. It may be necessary to remove the negative regulatory sequence in the BamHI-BglII fragment prior to inserting it. Other liver specific promoters include the AFP (alpha fetal protein) gene promoter and the albumin gene promoter, as disclosed in EP Patent Publication 0 415 731, the −1 antitrypsin gene promoter, as disclosed in Rettenger, et al., *Proc. Natl. Acad. Sci.* 91:1460-1464, 1994, the fibrinogen gene promoter, the APO-A1 (Apolipoprotein A1) gene promoter, and the promoter genes for liver transference enzymes such as, for example, SGOT, SGPT and glutamyle transferase. See also PCT Patent Publications WO 90/07936 and WO 91/02805 for a description of the use of liver specific promoters in lentiviral vector particles.

Lentiviral vector constructs may be generated such that more than one gene of interest is expressed. This may be accomplished through the use of di- or oligo-cistronic cassettes (e.g., where the coding regions are separated by 80 nucleotides or less, see generally Levin et al., *Gene* 108:167-174, 1991), or through the use of Internal Ribosome Entry Sites ("IRES").

Packaging cell lines suitable for use with the above described recombinant retroviral vector constructs may be readily prepared given the disclosure provided herein. Briefly, the parent cell line from which the packaging cell line is derived can be selected from a variety of mammalian cell lines, including for example, 293, RD, COS-7, CHO, BHK, VERO, HT1080, and myeloma cells.

After selection of a suitable host cell for the generation of a packaging cell line, one or more expression cassettes are introduced into the cell line in order to complement or supply in trans components of the vector which have been deleted.

Representative examples of suitable expression cassettes have been described herein and include synthetic Env, tat, Gag, synthetic Gag-protease, synthetic Gag-reverse transcriptase and synthetic Gag-polymerase expression cassettes, which comprise a promoter and a sequence encoding, e.g., Env, tat, or Gag-polymerase and at least one of vpr, vpu, nef or vif, wherein the promoter is operably linked to Env, tat or Gag-polymerase and vpr, vpu, nef or vif. As described above, optimized Env, Gag and/or tat coding sequences may also be utilized in various combinations in the generation of packaging cell lines.

Utilizing the above-described expression cassettes, a wide variety of packaging cell lines can be generated. For example, within one aspect packaging cell line are provided comprising an expression cassette that comprises a sequence encoding synthetic HIV (e.g., Gag, Env, tat, Gag-polymerase, Gag-reverse transcriptase or Gag-protease) polypeptide, and a nuclear transport element, wherein the promoter is operably linked to the sequence encoding the HIV polypeptide. Within other aspects, packaging cell lines are provided comprising a promoter and a sequence encoding Gag, tat, rev, or an envelope (e.g., HIV env), wherein the promoter is operably linked to the sequence encoding Gag, tat, rev, or, the envelope. Within further embodiments, the packaging cell line may comprise a sequence encoding any one or more of nef, vif, vpu or vpr. For example, the packaging cell line may contain only nef, vif, vpu, or vpr alone, nef and vif, nef and vpu, nef and vpr, vif and vpu, vif and vpr, vpu and vpr, nef vif and vpu, nef vif and vpr, nef vpu and vpr, vvir vpu and vpr, or, all four of nef vif vpu and vpr.

In one embodiment, the expression cassette is stably integrated. Within another embodiment, the packaging cell line, upon introduction of a lentiviral vector, produces particles. Within further embodiments the promoter is inducible. Within certain preferred embodiments of the invention, the packaging cell line, upon introduction of a lentiviral vector, produces particles that are free of replication competent virus.

The synthetic cassettes containing optimized coding sequences are transfected into a selected cell line. Transfected cells are selected that (i) carry, typically, integrated, stable copies of the Gag, Pol, and Env coding sequences, and (ii) are expressing acceptable levels of these polypeptides (expression can be evaluated by methods known in the prior art, e.g., see Examples 1-4). The ability of the cell line to produce VLPs may also be verified (Examples 6, 7 and 15).

A sequence of interest is constructed into a suitable viral vector as discussed above. This defective virus is then transfected into the packaging cell line. The packaging cell line provides the viral functions necessary for producing virus-like particles into which the defective viral genome, containing the sequence of interest, are packaged. These VLPs are then isolated and can be used, for example, in gene delivery or gene therapy.

Further, such packaging cell lines can also be used to produce VLPs alone, which can, for example, be used as adjuvants for administration with other antigens or in vaccine compositions. Also, co-expression of a selected sequence of interest encoding a polypeptide (for example, an antigen) in the packaging cell line can also result in the entrapment and/or association of the selected polypeptide in/with the VLPs.

2.3 DNA Immunization and Gene Delivery

A variety of polypeptide antigens can be used in the practice of the present invention. Polypeptide antigens can be included in DNA immunization constructs containing, for example, any of the synthetic expression cassettes described herein fused in-frame to a coding sequence for the polypeptide antigen, where expression of the construct results in VLPs presenting the antigen of interest. Antigens can be derived from a wide variety of viruses, bacteria, fungi, plants, protozoans and other parasites. For example, the present invention will find use for stimulating an immune response against a wide variety of proteins from the herpesvirus family, including proteins derived from herpes simplex virus (HSV) types 1 and 2, such as HSV-1 and HSV-2 gB, gD, gH, VP16 and VP22; antigens derived from varicella zoster virus (VZV), Epstein-Barr virus (EBV) and cytomegalovirus (CMV) including CMV gB and gH; and antigens derived from other human herpesviruses such as HHV6 and HHV7. (See, e.g. Chee et al., *Cytomegaloviruses* (J. K. McDougall, ed., Springer-Verlag 1990) pp. 125-169, for a review of the protein coding content of cytomegalovirus; McGeoch et al., *J. Gen. Virol.* (1988) 69:1531-1574, for a discussion of the various HSV-1 encoded proteins; U.S. Pat. No. 5,171,568 for a discussion of HSV-1 and HSV-2 gB and gD proteins and the genes encoding therefore; Baer et al., *Nature* (1984) 310:207-211, for the identification of protein coding sequences in an EBV genome; and Davison and Scott, *J. Gen. Virol.* (1986) 67:1759-1816, for a review of VZV.)

Additionally, immune responses to antigens from the hepatitis family of viruses, including hepatitis A virus (HAV), hepatitis B virus (HBV), hepatitis C virus (HCV), the delta hepatitis virus (HDV), hepatitis E virus (HEV), and hepatitis G virus, can also be stimulated using the constructs of the present invention. By way of example, the HCV genome encodes several viral proteins, including E1 (also known as E) and E2 (also known as E2/NSI), which will find use with the present invention (see, Houghton et al. *Hepatology* (1991) 14:381-388, for a discussion of HCV proteins, including E1 and E2). The δ-antigen from HDV can also be used (see, e.g., U.S. Pat. No. 5,389,528, for a description of the δ-antigen).

Similarly, influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al., *Virology* (1990) 179:759-767; Webster et al. "Antigenic variation among type A influenza viruses," p. 127-168. In: P. Palese and D. W. Kingsbury (ed.), *Genetics of influenza viruses.* Springer-Verlag, New York).

Other antigens of particular interest to be used in the practice of the present invention include antigens and polypeptides derived therefrom from human papillomavirus (HPV), such as one or more of the various early proteins including E6 and E7; tick-borne encephalitis viruses; and HIV-1 (also known as HTLV-III, LAV, ARV, etc.), including, but not limited to, antigens such as gp120, gp41, gp160, Gag and pol from a variety of isolates including, but not limited to, $HIV_{IIIb}$, $HIV_{SF2}$, $HIV-1_{SF162}$, $HIV-1_{SF170}$, $HIV_{LAV}$, $HIV_{LAI}$, $HIV_{MN}$, $HIV-1_{CM235}$, $HIV-1_{US4}$, other HIV-1 strains from diverse subtypes (e.g., subtypes, A through G, and O), HIV-2 strains and diverse subtypes (e.g., $HIV-2_{UC1}$ and $HIV-2_{UC2}$). See, e.g., Myers, et al., Los Alamos Database, Los Alamos National Laboratory, Los Alamos, N. Mex.; Myers, et al., *Human Retroviruses and Aids,* 1990, Los Alamos, N. Mex.: Los Alamos National Laboratory.

Proteins derived from other viruses will also find use in the claimed methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae, e.g., HTLV-I; HTLV-II; HIV-1; HIV-2; simian immunodeficiency virus (SIV) among others. See, e.g. Virology, 3rd Edition (W. K. Joklik ed. 1988); *Fundamental Virology,* 2nd Edition (B. N. Fields and D. M. Knipe, eds. 1991; *Virology,* 3rd Edition (Fields, B N, D M Knipe, P M Howley, Editors, 1996, Lippincott-Raven, Philadelphia, Pa.) for a description of these and other viruses.

Particularly preferred bacterial antigens are derived from organisms that cause diphtheria, tetanus, pertussis, meningitis, and other pathogenic states, including, without limitation, antigens derived from *Corynebacterium diphtheriae, Clostridium tetani, Bordetella pertusis, Neisseria meningitidis,* including serotypes *Meningococcus* A, B, C, Y and WI35 (MenA, B, C, Y and WI35), *Haemophilus influenza* type B (Hib), and *Helicobacter pylori.* Examples of parasitic antigens include those derived from organisms causing malaria, tuberculosis, and Lyme disease.

Furthermore, the methods described herein provide means for treating a variety of malignant cancers. For example, the system of the present invention can be used to enhance both humoral and cell-mediated immune responses to particular proteins specific to a cancer in question, such as an activated oncogene, a fetal antigen, or an activation marker. Such tumor antigens include any of the various MAGEs (melanoma associated antigen E), including MAGE 1, 2, 3, 4, etc. (Boon, T. *Scientific American* (March 1993):82-89); any of the various tyrosinases; MART 1 (melanoma antigen recognized by T cells), mutant ras; mutant p53; p97 melanoma antigen; CEA (carcinoembryonic antigen), among others.

DNA immunization using synthetic expression cassettes of the present invention has been demonstrated to be efficacious (Examples 8 and 10-12). Animals were immunized with both the synthetic expression cassette and the wild type expression cassette. The results of the immunizations with plasmid-DNAs showed that the synthetic expression cassettes provide a clear improvement of immunogenicity relative to the native expression cassettes. Also, the second boost immunization induced a secondary immune response, for example after two to eight weeks. Further, the results of CTL assays showed increased potency of synthetic expression cassettes for induction of cytotoxic T-lymphocyte (CTL) responses by DNA immunization.

It is readily apparent that the subject invention can be used to mount an immune response to a wide variety of antigens and hence to treat or prevent a large number of diseases.

2.3.1 Delivery of the Synthetic Expression Cassettes of the Present Invention

Polynucleotide sequences coding for the above-described molecules can be obtained using recombinant methods, such as by screening cDNA and genomic libraries from cells expressing the gene, or by deriving the gene from a vector known to include the same. The sequences can be analyzed by conventional sequencing techniques. Furthermore, the desired gene can be isolated directly from cells and tissues containing the same, using standard techniques, such as phenol extraction and PCR of cDNA or genomic DNA. See, e.g., Sambrook et al., supra, for a description of techniques used to obtain, isolate and sequence DNA. Once the sequence is known, the gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence is assembled from overlapping oligonucleotides prepared by standard methods and assembled into a complete coding sequence. See, e.g., Edge, *Nature* (1981) 292:756; Nambair et al., *Science* (1984) 223: 1299; Jay et al., *J. Biol. Chem.* (1984) 259:6311; Stemmer, W. P.C., (1995) *Gene* 164:49-53.

Next, the gene sequence encoding the desired antigen can be inserted into a vector containing a synthetic expression cassette of the present invention (e.g., see Example 1 for construction of various exemplary synthetic expression cassette). The antigen is inserted into the synthetic coding sequence such that when the combined sequence is expressed it results in the production of VLPs comprising the polypeptide and/or the antigen of interest. Insertions can be made within the Gag coding sequence or at either end of the coding sequence (5', amino terminus of the expressed polypeptide; or 3', carboxy terminus of the expressed polypeptide—e.g., see Example 1)(Wagner, R., et al., *Arch Virol.* 127:117-137, 1992; Wagner, R., et al., *Virology* 200:162-175, 1994; Wu, X., et al., *J. Virol.* 69(6):3389-3398, 1995; Wang, C-T., et al., *Virology* 200:524-534, 1994; Chazal, N., et al., *Virology* 68(1):111-122, 1994; Griffiths, J. C., et al., *J. Virol.* 67(6): 3191-3198, 1993; Reicin, A. S., et al., *J. Virol.* 69(2):642-650, 1995).

Up to 50% of the coding sequences of p55Gag can be deleted without affecting the assembly to virus-like particles and expression efficiency (Borsetti, A., et al, *J. Virol.* 72(11): 9313-9317, 1998; Garnier, L., et al., *J Virol* 72(6):4667-4677, 1998; Zhang, Y., et al., *J Virol* 72(3):1782-1789, 1998; Wang, C., et al., *J Virol* 72(10): 7950-7959, 1998). In one embodiment of the present invention, immunogenicity of the high level expressing synthetic p55GagMod and p55GagProtMod expression cassettes can be increased by the insertion of different structural or non-structural HIV antigens, multi-epitope cassettes, or cytokine sequences into deleted, mutated or truncated regions of p55GagMod sequence. In another embodiment of the present invention, immunogenicity of the high level expressing synthetic Env expression cassettes can be increased by the insertion of different structural or non-structural HIV antigens, multiepitope cassettes, or cytokine sequences into deleted regions of gp120Mod, gp140Mod or gp160Mod sequences. Such deletions may be generated following the teachings of the present invention and information available to one of ordinary skill in the art. One possible advantage of this approach, relative to using full-length modified Env sequences fused to heterologous polypeptides, can be higher expression/secretion efficiency and/or higher immunogenicity of the expression product. Such deletions may be generated following the teachings of the present invention and information available to one of ordinary skill in the art. One possible advantage of this approach, relative to using full-length Env, Gag or Tat sequences fused to heterologous polypeptides, can be higher expression/secretion efficiency and/or immunogenicity of the expression product.

When sequences are added to the amino terminal end of Gag (for example, when using the synthetic p55GagMod expression cassette of the present invention), the polynucleotide can contain coding sequences at the 5' end that encode a signal for addition of a myristic moiety to the Gag-containing polypeptide (e.g., sequences that encode Met-Gly).

The ability of Gag-containing polypeptide constructs to form VLPs can be empirically determined following the teachings of the present specification.

HIV polypeptide/antigen synthetic expression cassettes include control elements operably linked to the coding sequence, which allow for the expression of the gene in vivo in the subject species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence.

Enhancer elements may also be used herein to increase expression levels of the mammalian constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence.

Furthermore, plasmids can be constructed which include a chimeric antigen-coding gene sequences, encoding, e.g., multiple antigens/epitopes of interest, for example derived from a single or from more than one viral isolate.

Typically the antigen coding sequences precede or follow the synthetic coding sequences and the chimeric transcription unit will have a single open reading frame encoding both the antigen of interest and the synthetic Gag coding sequences. Alternatively, multi-cistronic cassettes (e.g., bi-cistronic cassettes) can be constructed allowing expression of multiple antigens from a single mRNA using the EMCV IRES, or the like. Lastly, antigens can be encoded on separate transcripts from independent promoters on a single plasmid or other vector.

Once complete, the constructs are used for nucleic acid immunization or the like using standard gene delivery protocols. Methods for gene delivery are known in the art. See, e.g., U.S. Pat. Nos. 5,399,346, 5,580,859, 5,589,466. Genes can be delivered either directly to the vertebrate subject or, alternatively, delivered ex vivo, to cells derived from the subject and the cells reimplanted in the subject.

A number of viral based systems have been developed for gene transfer into mammalian cells. For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, *BioTechniques* (1989) 7:980-990; Miller, A. D., *Human Gene Therapy* (1990) 1:5-14; Scarpa et al., *Virology* (1991) 180:849-852; Burns et al., *Proc. Natl. Acad. Sci. USA* (1993) 90:8033-8037; and Boris-Lawrie and Temin, *Cur. Opin. Genet. Develop.* (1993) 3:102-109.

A number of adenovirus vectors have also been described. Unlike retroviruses which integrate into the host genome, adenoviruses persist extrachromosomally thus minimizing the risks associated with insertional mutagenesis (Haj-Ahmad and Graham, *J. Virol.* (1986) 57:267-274; Bett et al., *J. Virol.* (1993) 67:5911-5921; Mittereder et al., *Human Gene Therapy* (1994) 5:717-729; Seth et al., *J. Virol.* (1994) 68:933-940; Barr et al., *Gene Therapy* (1994) 1:51-58; Berkner, K. L. *BioTechniques* (1988) 6:616-629; and Rich et al., *Human Gene Therapy* (1993) 4:461-476).

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., *Molec. Cell. Biol.* (1988) 8:3988-3996; Vincent et al.,

*Vaccines* 90 (1990) (Cold Spring Harbor Laboratory Press); Carter, B. J. *Current Opinion in Biotechnology* (1992) 3:533-539; Muzyczka, N. *Current Topics in Microbiol. and Immunol.* (1992) 158:97-129; Kotin, R. M. *Human Gene Therapy* (1994) 5:793-801; Shelling and Smith, *Gene Therapy* (1994) 1:165-169; and Zhou et al., *J. Exp. Med.* (1994) 179:1867-1875.

Another vector system useful for delivering the polynucleotides of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors which will find use for delivering the nucleic acid molecules encoding the antigens of interest include those derived from the pox family of viruses, including vaccinia virus and avian poxvirus. By way of example, vaccinia virus recombinants expressing the genes can be constructed as follows. The DNA encoding the particular synthetic Gag/antigen coding sequence is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the coding sequences of interest into the viral genome. The resulting TK$^-$ recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., *J. Biol. Chem.* (1993) 268:6866-6869 and Wagner et al., *Proc. Natl. Acad. Sci. USA* (1992) 89:6099-6103, can also be used for gene delivery.

Members of the Alphavirus genus, such as, but not limited to, vectors derived from the Sindbis, Semliki Forest, and Venezuelan Equine Encephalitis viruses, will also find use as viral vectors for delivering the polynucleotides of the present invention (for example, a synthetic Gag- or Env-polypeptide encoding expression cassette as described in Example 14 below). For a description of Sindbis-virus derived vectors useful for the practice of the instant methods, see, Dubensky et al., *J. Virol.* (1996) 70:508-519; and International Publication Nos. WO 95/07995 and WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference.

A vaccinia based infection/transfection system can be conveniently used to provide for inducible, transient, expression of the coding sequences of interest (for example, a synthetic Gag/HCV-core expression cassette) in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, *Proc. Natl. Acad. Sci. USA* (1990) 87:6743-6747; Fuerst et al., *Proc. Natl. Acad. Sci. USA* (1986) 83:8122-8126.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, *J. Mol. Biol.* (1986) 189:113-130; Deng and Wolff, Gene (1994) 143:245-249; Gao et al., *Biochem. Biophys. Res. Commun.* (1994) 200:1201-1206; Gao and Huang, *Nuc. Acids Res.* (1993) 21:2867-2872; Chen et al., *Nuc. Acids Res.* (1994) 22:2114-2120; and U.S. Pat. No. 5,135,855.

The synthetic expression cassette of interest can also be delivered without a viral vector. For example, the synthetic expression cassette can be packaged as DNA or RNA in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097:1-17; Straubinger et al., in *Methods of Enzymology* (1983), Vol. 101, pp. 512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Felgner et al., *Proc. Natl. Acad. Sci. USA* (1987) 84:7413-7416); mRNA (Malone et al., *Proc. Natl. Acad. Sci. USA* (1989) 86:6077-6081); and purified transcription factors (Debs et al., *J. Biol. Chem.* (1990) 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N. Y. (See, also, Feigner et al., *Proc. Natl. Acad. Sci. USA* (1987) 84:7413-7416). Other commercially available lipids include (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194-4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512-527; Szoka et al., *Proc. Natl. Acad. Sci. USA* (1978) 75:4194-4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem.* (1980) 255:10431; Szoka and Papahadjopoulos, *Proc. Natl. Acad. Sci. USA* (1978) 75:145; and Schaefer-Ridder et al., *Science* (1982) 215:166.

The DNA and/or protein antigen(s) can also be delivered in cochleate lipid compositions similar to those described by Papahadjopoulos et al., *Biochem. Biophys. Acta.* (1975) 394: 483-491. See, also, U.S. Pat. Nos. 4,663,161 and 4,871,488.

The synthetic expression cassette of interest (e.g., any of the synthetic expression cassettes described in Example 1) may also be encapsulated, adsorbed to, or associated with, particulate carriers. Such carriers present multiple copies of a selected antigen to the immune system and promote migration, trapping and retention of antigens in local lymph nodes. The particles can be taken up by profession antigen presenting cells such as macrophages and dendritic cells, and/or can enhance antigen presentation through other mechanisms such as stimulation of cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; McGee J P, et al., *J. Microencapsul.* 14(2):197-210, 1997; O'Hagan D T, et al., *Vaccine* 11(2):149-54, 1993.

Furthermore, other particulate systems and polymers can be used for the in vivo or ex vivo delivery of the gene of interest. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Feigner, P. L., *Advanced Drug Delivery Reviews* (1990) 5:163-187, for a review of delivery systems useful for gene transfer. Peptoids (Zuckerman, R. N., et al., U.S. Pat. No. 5,831,005, issued Nov. 3, 1998, herein incorporated by reference) may also be used for delivery of a construct of the present invention.

Additionally, biolistic delivery systems employing particulate carriers such as gold and tungsten, are especially useful for delivering synthetic expression cassettes of the present invention. The particles are coated with the synthetic expression cassette(s) to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371, 015; and 5,478,744. Also, needle-less injection systems can be used (Davis, H. L., et al, *Vaccine* 12:1503-1509, 1994; Bioject, Inc., Portland, Oreg.).

Recombinant vectors carrying a synthetic expression cassette of the present invention are formulated into compositions for delivery to the vertebrate subject. These compositions may either be prophylactic (to prevent infection) or therapeutic (to treat disease after infection). The compositions will comprise a "therapeutically effective amount" of the gene of interest such that an amount of the antigen can be produced in vivo so that an immune response is generated in the individual to which it is administered. The exact amount necessary will vary depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials.

The compositions will generally include one or more "pharmaceutically acceptable excipients or vehicles" such as water, saline, glycerol, polyethyleneglycol, hyaluronic acid, ethanol, etc. Additionally, auxiliary substances, such as wetting or emulsifying agents, pH buffering substances, surfactants and the like, may be present in such vehicles. Certain facilitators of immunogenicity or of nucleic acid uptake and/or expression can also be included in the compositions or coadministered, such as, but not limited to, bupivacaine, cardiotoxin and sucrose.

Once formulated, the compositions of the invention can be administered directly to the subject (e.g., as described above) or, alternatively, delivered ex vivo, to cells derived from the subject, using methods such as those described above. For example, methods for the ex vivo delivery and reimplantation of transformed cells into a subject are known in the art and can include, e.g., dextran-mediated transfection, calcium phosphate precipitation, polybrene mediated transfection, lipofectamine and LT-1 mediated transfection, protoplast fusion, electroporation, encapsulation of the polynucleotide(s) (with or without the corresponding antigen) in liposomes, and direct microinjection of the DNA into nuclei.

Direct delivery of synthetic expression cassette compositions in vivo will generally be accomplished with or without viral vectors, as described above, by injection using either a conventional syringe, needless devices such as Bioject® or a gene gun, such as the Accell® gene delivery system (PowderJect Technologies, Inc., Oxford, England). The constructs can be delivered (e.g., injected) either subcutaneously, epidermally, intradermally, intramuscularly, intravenous, intramucosally (such as nasally, rectally and vaginally), intraperitoneally or orally. Delivery of DNA into cells of the epidermis is particularly preferred as this mode of administration provides access to skin-associated lymphoid cells and provides for a transient presence of DNA in the recipient. Other modes of administration include oral ingestion and pulmonary administration, suppositories, needle-less injection, transcutaneous and transdermal applications. Dosage treatment may be a single dose schedule or a multiple dose schedule.

2.3.2 Ex Vivo Delivery of the Synthetic Expression Cassettes of the Present Invention In one embodiment, T cells, and related cell types (including but not limited to antigen presenting cells, such as, macrophage, monocytes, lymphoid cells, dendritic cells, B-cells, T-cells, stem cells, and progenitor cells thereof), can be used for ex vivo delivery of the synthetic expression cassettes of the present invention. T cells can be isolated from peripheral blood lymphocytes (PBLs) by a variety of procedures known to those skilled in the art. For example, T cell populations can be "enriched" from a population of PBLs through the removal of accessory and B cells. In particular, T cell enrichment can be accomplished by the elimination of non-T cells using anti-MHC class II monoclonal antibodies. Similarly, other antibodies can be used to deplete specific populations of non-T cells. For example, anti-Ig antibody molecules can be used to deplete B cells and anti-MacI antibody molecules can be used to deplete macrophages.

T cells can be further fractionated into a number of different subpopulations by techniques known to those skilled in the art. Two major subpopulations can be isolated based on their differential expression of the cell surface markers CD4 and CD8. For example, following the enrichment of T cells as described above, CD4+ cells can be enriched using antibodies specific for CD4 (see Coligan et al., supra). The antibodies may be coupled to a solid support such as magnetic beads. Conversely, CD8+ cells can be enriched through the use of antibodies specific for CD4 (to remove CD4+ cells), or can be isolated by the use of CD8 antibodies coupled to a solid support. CD4 lymphocytes from HIV-1 infected patients can be expanded ex vivo, before or after transduction as described by Wilson et. al. (1995) *J. Infect. Dis.* 172:88.

Following purification of T cells, a variety of methods of genetic modification known to those skilled in the art can be performed using non-viral or viral-based gene transfer vectors constructed as described herein. For example, one such approach involves transduction of the purified T cell population with vector-containing supernatant of cultures derived from vector producing cells. A second approach involves co-cultivation of an irradiated monolayer of vector-producing cells with the purified T cells. A third approach involves a similar co-cultivation approach; however, the purified T cells are pre-stimulated with various cytokines and cultured 48 hours prior to the co-cultivation with the irradiated vector producing cells. Pre-stimulation prior to such transduction increases effective gene transfer (Nolta et al. (1992) *Exp. Hematol.* 20:1065). Stimulation of these cultures to proliferate also provides increased cell populations for re-infusion into the patient. Subsequent to co-cultivation, T cells are collected from the vector producing cell monolayer, expanded, and frozen in liquid nitrogen.

Gene transfer vectors, containing one or more synthetic expression cassette of the present invention (associated with appropriate control elements for delivery to the isolated T cells) can be assembled using known methods.

Selectable markers can also be used in the construction of gene transfer vectors. For example, a marker can be used which imparts to a mammalian cell transduced with the gene transfer vector resistance to a cytotoxic agent. The cytotoxic agent can be, but is not limited to, neomycin, aminoglycoside, tetracycline, chloramphenicol, sulfonamide, actinomycin, netropsin, distamycin A, anthracycline, or pyrazinamide. For example, neomycin phosphotransferase II imparts resistance to the neomycin analogue geneticin (G418).

The T cells can also be maintained in a medium containing at least one type of growth factor prior to being selected. A variety of growth factors are known in the art which sustain the growth of a particular cell type. Examples of such growth factors are cytokine mitogens such as rIL-2, IL-10, IL-12, and IL-15, which promote growth and activation of lymphocytes. Certain types of cells are stimulated by other growth factors such as hormones, including human chorionic gonadotropin (hCG) and human growth hormone. The selection of an appropriate growth factor for a particular cell population is readily accomplished by one of skill in the art.

For example, white blood cells such as differentiated progenitor and stem cells are stimulated by a variety of growth factors. More particularly, IL-3, IL-4, IL-5, IL-6, IL-9, GM-CSF, M-CSF, and G-CSF, produced by activated $T_H$ and activated macrophages, stimulate myeloid stem cells, which then differentiate into pluripotent stem cells, granulocyte-monocyte progenitors, eosinophil progenitors, basophil progenitors, megakaryocytes, and erythroid progenitors. Differentiation is modulated by growth factors such as GM-CSF, IL-3, IL-6, IL-11, and EPO.

Pluripotent stem cells then differentiate into lymphoid stem cells, bone marrow stromal cells, T cell progenitors, B cell progenitors, thymocytes, $T_H$ Cells, $T_C$ cells, and B cells. This differentiation is modulated by growth factors such as IL-3, IL-4, IL-6, IL-7, GM-CSF, M-CSF, G-CSF, IL-2, and IL-5.

Granulocyte-monocyte progenitors differentiate to monocytes, macrophages, and neutrophils. Such differentiation is modulated by the growth factors GM-CSF, M-CSF, and IL-8. Eosinophil progenitors differentiate into eosinophils. This process is modulated by GM-CSF and IL-5.

The differentiation of basophil progenitors into mast cells and basophils is modulated by GM-CSF, IL-4, and IL-9. Megakaryocytes produce platelets in response to GM-CSF, EPO, and IL-6. Erythroid progenitor cells differentiate into red blood cells in response to EPO.

Thus, during activation by the CD3-binding agent, T cells can also be contacted with a mitogen, for example a cytokine such as IL-2. In particularly preferred embodiments, the IL-2 is added to the population of T cells at a concentration of about 50 to 100 µg/ml. Activation with the CD3-binding agent can be carried out for 2 to 4 days.

Once suitably activated, the T cells are genetically modified by contacting the same with a suitable gene transfer vector under conditions that allow for transfection of the vectors into the T cells. Genetic modification is carried out when the cell density of the T cell population is between about $0.1 \times 10^6$ and $5 \times 10^6$, preferably between about $0.5 \times 10^6$ and $2 \times 10^6$. A number of suitable viral and nonviral-based gene transfer vectors have been described for use herein.

After transduction, transduced cells are selected away from non-transduced cells using known techniques. For example, if the gene transfer vector used in the transduction includes a selectable marker which confers resistance to a cytotoxic agent, the cells can be contacted with the appropriate cytotoxic agent, whereby non-transduced cells can be negatively selected away from the transduced cells. If the selectable marker is a cell surface marker, the cells can be contacted with a binding agent specific for the particular cell surface marker, whereby the transduced cells can be positively selected away from the population. The selection step can also entail fluorescence-activated cell sorting (FACS) techniques, such as where FACS is used to select cells from the population containing a particular surface marker, or the selection step can entail the use of magnetically responsive particles as retrievable supports for target cell capture and/or background removal.

More particularly, positive selection of the transduced cells can be performed using a FACS cell sorter (e.g. a FACSVantage™ Cell Sorter, Becton Dickinson Immunocytometry Systems, San Jose, Calif.) to sort and collect transduced cells expressing a selectable cell surface marker. Following transduction, the cells are stained with fluorescent-labeled antibody molecules directed against the particular cell surface marker. The amount of bound antibody on each cell can be measured by passing droplets containing the cells through the cell sorter. By imparting an electromagnetic charge to droplets containing the stained cells, the transduced cells can be separated from other cells. The positively selected cells are then harvested in sterile collection vessels. These cell sorting procedures are described in detail, for example, in the FACSVantage™ Training Manual, with particular reference to sections 3-11 to 3-28 and 10-1 to 10-17.

Positive selection of the transduced cells can also be performed using magnetic separation of cells based on expression or a particular cell surface marker. In such separation techniques, cells to be positively selected are first contacted with specific binding agent (e.g., an antibody or reagent the interacts specifically with the cell surface marker). The cells are then contacted with retrievable particles (e.g., magnetically responsive particles) which are coupled with a reagent that binds the specific binding agent (that has bound to the positive cells). The cell-binding agent-particle complex can then be physically separated from non-labeled cells, for example using a magnetic field. When using magnetically responsive particles, the labeled cells can be retained in a container using a magnetic filed while the negative cells are removed. These and similar separation procedures are known to those of ordinary skill in the art.

Expression of the vector in the selected transduced cells can be assessed by a number of assays known to those skilled in the art. For example, Western blot or Northern analysis can be employed depending on the nature of the inserted nucleotide sequence of interest. Once expression has been established and the transformed T cells have been tested for the presence of the selected synthetic expression cassette, they are ready for infusion into a patient via the peripheral blood stream.

The invention includes a kit for genetic modification of an ex vivo population of primary mammalian cells. The kit typically contains a gene transfer vector coding for at least one selectable marker and at least one synthetic expression cassette contained in one or more containers, ancillary reagents or hardware, and instructions for use of the kit.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Generation of Synthetic Gag and Env Expression Cassettes

A. Modification of HIV-1 Gag, Gag-Protease, Gag-Reverse Transcriptase and Gag-Polymerase Nucleic Acid Coding Sequences The Gag (SEQ ID NO:1), Gag-protease (SEQ ID NO:2), Gag-polymerase (SEQ ID NO:3), and Gag-reverse transcriptase (SEQ ID NO:77) coding sequences were selected from the HIV-1SF2 strain (Sanchez-Pescador, R., et al., *Science* 227(4686): 484-492, 1985; Luciw, P. A., et al. U.S. Pat. No. 5,156,949, issued Oct. 20, 1992, herein incorporated by reference; Luciw, P. A., et al., U.S. Pat. No. 5,688,688, Nov. 18, 1997). These sequences were manipulated to maximize expression of their gene products.

First, the HIV-1 codon usage pattern was modified so that the resulting nucleic acid coding sequence was comparable to codon usage found in highly expressed human genes. The HIV codon usage reflects a high content of the nucleotides A or T of the codon-triplet. The effect of the HIV-1 codon usage is a high AT content in the DNA sequence that results in a high AU content in the RNA and in a decreased translation ability and instability of the mRNA. In comparison, highly expressed human codons prefer the nucleotides G or C. The Gag-encoding sequences were modified to be comparable to codon usage found in highly expressed human genes.

FIG. 11 presents a comparison of the percent A-T content for the cDNAs of stable versus unstable RNAs (comparison window size=50). Human IFNγ mRNA is known to (i) be unstable, (ii) have a short half-life, and (iii) have a high A-U content. Human GAPDH (glyceraldehyde-3-phosphate dehydrogenase) mRNA is known to (i) be a stable RNA, and (i) have a low A-U content. In FIG. 11, the percent A-T content of these two sequences are compared to the percent A-T content of native HIV-1SF2 Gag cDNA and to the synthetic Gag cDNA sequence of the present invention. The top two panels of the figure show the percent A-T content over the length of the sequences for IFNγ and native Gag. The bottom two panels of the figure show the percent A-T content over the length of the sequences for GAPDH and the synthetic Gag. Experiments performed in support of the present invention showed that the synthetic Gag sequences were capable of higher level of protein production (see the Examples) than the native Gag sequences. The data in FIG. 11 suggest that one reason for this increased production may be increased stability of the mRNA corresponding to the synthetic Gag coding sequences versus the mRNA corresponding to the native Gag coding sequences.

Second, there are inhibitory (or instability) elements (INS) located within the coding sequences of the Gag and Gag-protease coding sequences (Schneider R, et al., *J. Virol.* 71(7): 4892-4903, 1997). RRE is a secondary RNA structure that interacts with the HIV encoded Rev-protein to overcome the expression down-regulating effects of the INS. To overcome the requirement for post-transcriptional activating mechanisms of RRE and Rev, and to enhance independent expression of the Gag polypeptide, the INS were inactivated by introducing multiple point mutations that did not alter the reading frame of the encoded proteins. FIG. 1 shows the original SF2 Gag sequence, the location of the INS sequences, and the modifications made to the INS sequences to reduce their effects.

For the Gag-protease sequence (wild type, SEQ ID NO:2; synthetic, SEQ ID NOs:5, 78 and 79), the changes in codon usage were restricted to the regions up to the −1 frameshift and starting again at the end of the Gag reading frame (FIG. 2; the region indicated in lower case letters in FIG. 2 is the unmodified region). Further, inhibitory (or instability) elements (INS) located within the coding sequences of the Gag-protease polypeptide coding sequence were altered as well (indicated in FIG. 2). The synthetic coding sequences were assembled by the Midland Certified Reagent Company (Midland, Tex.).

Figure 12B:
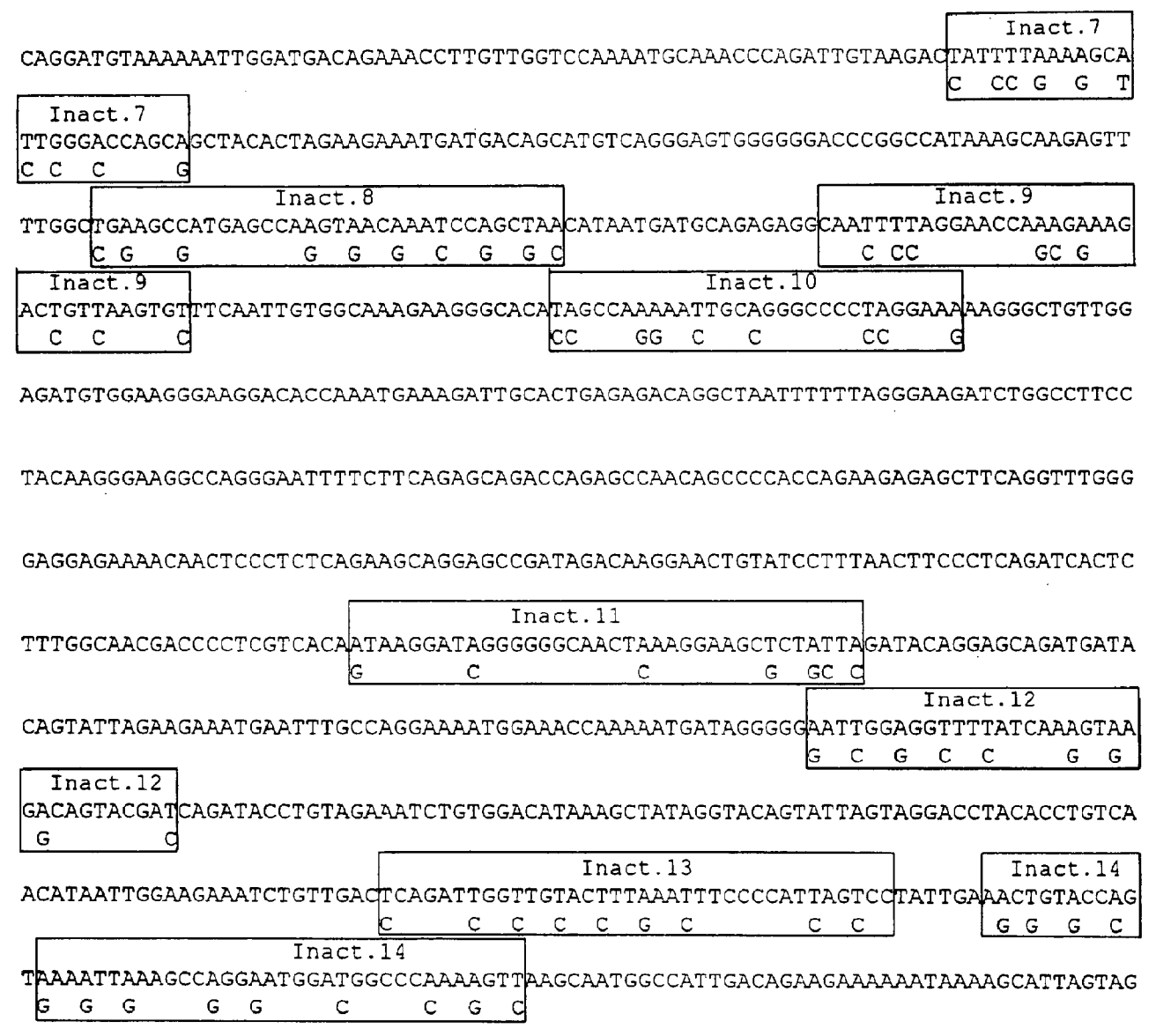

Modification of the Gag-polymerase sequences (wild type, SEQ ID NO:3; synthetic, SEQ ID NO:6) and Gag-reverse transcriptase sequences (SEQ ID NOs:80 through 84) include similar modifications as described for Gag-protease in order to preserve the frameshift region. Locations of the inactivation sites and changes to the sequence to alter the inactivation sites are presented in FIG. 12 for the native HIV-1$_{SF2}$ Gag-polymerase sequence.

In one embodiment of the invention, the full length polymerase coding region of the Gag-polymerase sequence is included with the synthetic Gag sequences in order to increase the number of epitopes for virus-like particles expressed by the synthetic, optimized Gag expression cassette. Because synthetic HIV-1 Gag-polymerase expresses the potentially deleterious functional enzymes reverse transcriptase (RT) and integrase (INT) (in addition to the structural proteins and protease), it is important to inactivate RT and INT functions. Several in-frame deletions in the RT and INT reading frame can be made to achieve catalytic nonfunctional enzymes with respect to their RT and INT activity. {Jay. A. Levy (Editor) (1995) *The Retroviridae*, Plenum Press, New York. ISBN 0-306-45033X. Pages 215-20; Grimison, B. and Laurence, J. (1995), *Journal Of Acquired Immune Deficiency Syndromes and Human Retrovirology* 9(1):58-68; Wakefield, J. K., et al., (1992) *Journal Of Virology* 66(11): 6806-6812; Esnouf, R., et al., (1995) *Nature Structural Biology* 2(4):303-308; Maignan, S., et al., (1998) *Journal Of Molecular Biology* 282(2):359-368; Katz, R. A. and Skalka, A. M. (1994) *Annual Review Of Biochemistry* 73 (1994); Jacobo-Molina, A., et al., (1993) *Proceedings Of the National Academy Of Sciences Of the United States Of America* 90(13):6320-6324; Hickman, A. B., et al., (1994) *Journal Of Biological Chemistry* 269(46):29279-29287; Goldgur, Y., et al., (1998) *Proceedings Of the National Academy Of Sciences Of the United States Of America* 95(16):9150-9154; Goette, M., et al., (1998) *Journal Of Biological Chemistry* 273(17): 10139-10146; Gorton, J. L., et al., (1998) *Journal of Virology* 72(6):5046-5055; Engelman, A., et al., (1997) *Journal Of Virology* 71(5):3507-3514; Dyda, F., et al., *Science* 266 (5193):1981-1986; Davies, J. F., et al., (1991) *Science* 252 (5002):88-95; Bujacz, G., et al., (1996) *Febs Letters* 398(2-3):175-178; Beard, W. A., et al., (1996) *Journal Of Biological Chemistry* 271(21):12213-12220; Kohlstaedt, L. A., et al., (1992) *Science* 256(5065):1783-1790; Krug, M. S, and Berger, S. L. (1991) *Biochemistry* 30(44):10614-10623; Mazumder, A., et al., (1996) *Molecular Pharmacology* 49(4): 621-628; Palaniappan, C., et al., (1997) *Journal Of Biological Chemistry* 272(17):11157-11164; Rodgers, D. W., et al., (1995) *Proceedings Of the National Academy Of Sciences Of the United States Of America* 92(4):1222-1226; Sheng, N. and Dennis, D. (1993) *Biochemistry* 32(18):4938-4942; Spence, R. A., et al., (1995) *Science* 267(5200):988-993.}

Furthermore selected B- and/or T-cell epitopes can be added to the Gag-polymerase constructs within the deletions of the RT- and INT-coding sequence to replace and augment any epitopes deleted by the functional modifications of RT and INT. Alternately, selected B- and T-cell epitopes (including CTL epitopes) from RT and INT can be included in a minimal VLP formed by expression of the synthetic Gag or synthetic GagProt cassette, described above. (For descriptions of known HIV B- and T-cell epitopes see, HIV Molecular Immunology Database CTL Search Interface; Los Alamos Sequence Compendia, 1987-1997;Internet address: http://hiv-web.lan1.gov/immunology/index.html.)

The resulting modified coding sequences are presented as a synthetic Gag expression cassette (SEQ ID NO:4), a synthetic Gag-protease expression cassette (SEQ ID NOs:5, 78 and 79), and a synthetic Gag-polymerase expression cassette (SEQ ID NO:6). Synthetic expression cassettes containing codon modifications in the reverse transcriptase region are shown in SEQ ID NOs:80 through 84. An alignment of selected sequences is presented in FIG. 7. A common region (Gag-common; SEQ ID NO:9) extends from position 1 to position 1262.

The synthetic DNA fragments for Gag and Gag-protease were cloned into the following expression vectors: pCMVKm2, for transient expression assays and DNA immunization studies, the pCMVKm2 vector was derived from pCMV6a (Chapman et al., *Nuc. Acids Res*. (1991) 19:3979-3986) and comprises a kanamycin selectable marker, a ColE1 origin of replication, a CMV promoter enhancer and Intron A, followed by an insertion site for the synthetic sequences described below followed by a polyadenylation signal derived from bovine growth hormone—the pCMVKm2 vector differs from the pCMV-link vector only in that a polylinker site was inserted into pCMVKm2 to generate pCMV-link (FIG. 14, polylinker at positions 1646 to 1697); pESN2dhfr (FIG. 13A) and pCMVPLEdhfr (also known as pCMVIII as shown in FIG. 13B), for expression in Chinese Hamster Ovary (CHO) cells; and, pAcC13, a shuttle vector for use in the Baculovirus expression system (pAcC13, was derived from pAcC12 which was described by Munemitsu S., et al., *Mol Cell Biol.* 10(11):5977-5982, 1990).

A restriction map for vector pCMV-link is presented in FIG. 14. In the figure, the CMV promoter (CMV IE ENH/PRO), bovine growth hormone terminator (BGH pA), kanamycin selectable marker (kan), and a ColE1 origin of replication (ColE1 ori) are indicated. A polycloning site is also indicated in the figure following the CMV promoter sequences.

A restriction map for vector pESN2dhfr is presented in FIG. 13A. In the figure, the CMV promoter (pCMV, hCMVIE), bovine growth hormone terminator (BGHpA), SV40 origin of replication (SV40ori), neomycin selectable marker (Neo), SV40 polyA (SV40pA), Adenovirus 2 late promoter (Ad2VLP), and the murine dhfr gene (mu dhfr) are indicated. A polycloning site is also indicated in the figure following the CMV promoter sequences.

Briefly, construction of pCMVPLEdhfr (pCMVIII) was as follows. To construct a DHFR cassette, the EMCV IRES (internal ribosome entry site) leader was PCR-amplified from pCite-4-a+ (Novagen, Inc., Milwaukee, Wis.) and inserted into pET-23d (Novagen, Inc., Milwaukee, Wis.) as an Xba-Nco fragment to give pET-EMCV. The dhfr gene was PCR-amplified from pESN2dhfr to give a product with a Gly-Gly-Gly-Ser spacer in place of the translation stop codon and inserted as an Nco-BamH1 fragment to give pET-E-DHFR. Next, the attenuated neo gene was PCR amplified from a pSV2Neo (Clontech, Palo Alto, Calif.) derivative and inserted into the unique BamH1 site of pET-E-DHFR to give pET-E-DHFR/$Neo_{(m2)}$. Then, the bovine growth hormone terminator from pcDNA3 (Invitrogen, Inc., Carlsbad, Calif.) was inserted downstream of the neo gene to give pET-E-DHFR/$Neo_{(m2)}$BGHt. The EMCV-dhfr/neo selectable marker cassette fragment was prepared by cleavage of pET-E-DHFR/$Neo_{(m2)}$BGHt. The CMV enhancer/promoter plus Intron A was transferred from pCMV6a (Chapman et al., *Nuc. Acids Res*. (1991) 19:3979-3986) as a HindIII-SalI fragment into pUC19 (New England Biolabs, Inc., Beverly, Mass.). The vector backbone of pUC19 was deleted from the Nde1 to the Sap1 sites. The above described DHFR cassette was added to the construct such that the EMCV IRES followed the CMV promoter to produce the final construct. The vector also contained an $amp^r$ gene and an SV40 origin of replication.

Selected pCMVKm2 vectors containing the synthetic expression cassettes have been designated as follows: pCMVKm2.GagMod.SF2, pCMVKm2.GagprotMod.SF2, and pCMVKm2.GagpolMod.SF2, pCMVKm2.GagprotMod.SF2.GP1 (SEQ ID NO:78) and pCMVKm2.GagprotMod.SF2.GP2 (SEQ ID NO:79). Other exemplary Gag-encoding expressing cassettes are shown in the Figures and as Sequence Listings.

B. Modification of HIV-1 Gag/Hepatitis C Core Chimeric Protein Nucleic Acid Coding Sequences Generation of Synthetic Expression Cassettes To facilitate the ligation of the Gag and HCV core coding sequences, PCR amplification was employed. The synthetic p55Gag expression cassette was used as a PCR template with the following primers: GAG5(SEQ ID NO:11) and P55-SAL3 (SEQ ID NO:12). The PCR amplification was conducted at 55° C. for 25 cycles using Stratagene's Pfu polymerase. The resulting PCR product was rendered free of nucleotides and primers using the Promega PCR clean-up kit and then subjected to EcoRI and SalI digestions. For HCV core coding sequences, the following primers were used with an HCV template (Houghton, M., et al., U.S. Pat. No. 5,714,596, issued Feb. 3, 1998; Houghton, M., et al., U.S. Pat. No. 5,712,088, issued Jan. 27, 1998; Houghton, M., et al., U.S. Pat. No. 5,683,864, issued Nov. 4, 1997; Weiner, A. J., et al., U.S. Pat. No. 5,728,520, issued Mar. 17, 1998; Weiner, A. J., et al., U.S. Pat. No. 5,766,845, issued Jun. 16, 1998; Weiner, A. J., et al., U.S. Pat. No. 5,670,152, issued Sep. 23, 1997; all herein incorporated by reference): CORESAL 5 (SEQ ID NO:13) and 173CORE(SEQ ID NO:14) using the conditions outlined above. The purified product was digested with SalI and BamHI restriction enzymes. The digested Gag and HCV core PCR products were ligated into the pCMVKm2 vector digested with EcoRI and BamHI. Ligation of the PCR products at the SalI site resulted in a direct fusion of the final amino acid of p55Gag to the second amino acid of HCV core, serine. Amino acid 173 of core is a serine and is followed immediately by a TAG termination codon. The sequence of the fusion clone was confirmed. The pCMVKm2 vector containing the synthetic expression cassette was designated as pCMVKm2.GagModHCVcore.

The EcoRI-BamHI fragment of p55Gag-core 173 was also cloned into EcoRI-BamHI-digested pAcC13 for baculovirus expression. Western blots confirmed expression and sucrose gradient sedimentation along with electron microscopy confirmed particle formation. To generate the above clone but containing the synthetic Gag sequences (instead of wild-type), the following steps were performed: pCMVKm2-modified p55Gag was used as template for PCR amplification with MS65 (SEQ ID NO:15) and MS66(SEQ ID NO:16) primers. The region amplified corresponds to the BspHI and SalI sites at the C-terminus of synthetic Gag sequence. The amplification product was digested with BspHI and SalI and ligated to SalI/BamHI digested pCMV-link along with the Sal/BspHI fragment from pCMV-Km-p55modGag, representing the amino terminal end of modified Gag, and the SalI/BamHI fragment from pCMV-p55Gag-core173. Thereafter, a T4-blunted-SalI partial/BamHI fragment was ligated into pAcC4-SmaI/BamHI to generate pAcC4-p55GagMod-core173 (containing the synthetic sequence presented as SEQ ID NO:7).

C. Defining of the Major Homology Region (MHR) of HIV-1 p55Gag

The Major Homology Region (MHR) of HIV-1 p55 (Gag) is located in the p24-CA sequence of Gag. It is a conserved stretch of 20 amino acids (SEQ ID NO:19). The position in the wild type HIV-1$_{SF2}$ Gag protein is from aa 286-305 and spans a region from nucleotides 856-915 in the native HIV-1$_{SF2}$ Gag DNA-sequence. The position in the synthetic Gag protein is from aa 288-307 and spans a region from nucleotides 862-921 for the synthetic Gag DNA-sequence. The nucleotide sequence for the MHR in the synthetic Gag-Mod.SF2 is presented as SEQ ID NO:20. Mutations or deletions in the amino acid sequence of the MHR can severely impair particle production (Borsetti, A., et al., J. Virol. 72(11): 9313-9317, 1998; Mammano, F., et al., J Virol 68(8):4927-4936, 1994).

Percent identity to the MHR nucleotide sequence can be determined, for example, using the MacDNAsis program (Hitachi Software Engineering America Limited, South San Francisco, Calif.), Higgins algorithm, with the following exemplary parameters: gap penalty=5, no. of top diagonals=5, fixed gap penalty=5, K-tuple=2, window size=5, and floating gap penalty=10.

D. Generation of Synthetic Env Expression Cassettes

Figure 15:
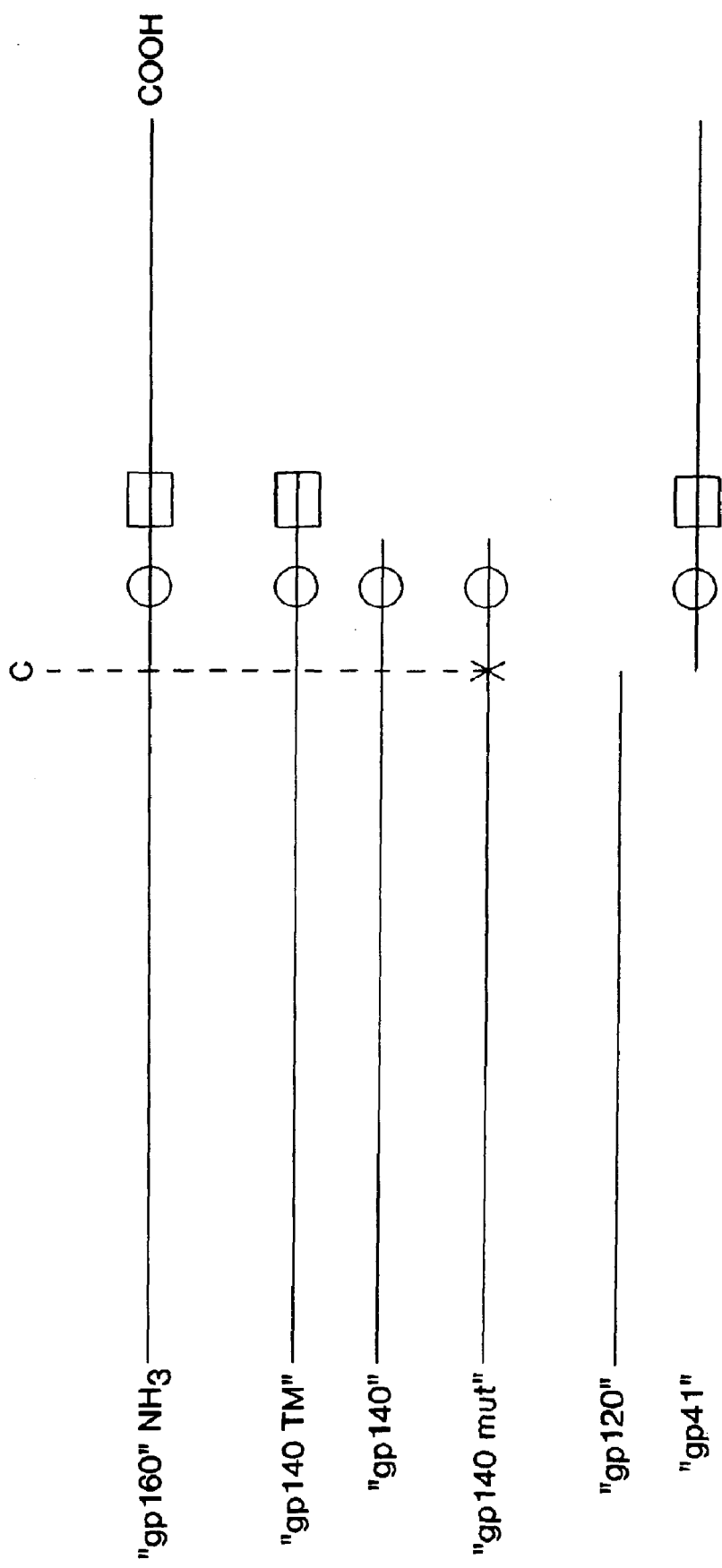
FIG. 15 presents a schematic diagram showing the relationships between the following forms of the HIV Env polypeptide: gp160, gp140, gp120, and gp41.

Env coding sequences of the present invention include, but are not limited to, polynucleotide sequences encoding the following HIV-encoded polypeptides: gp160, gp140, and gp120 (see, e.g., U.S. Pat. No. 5,792,459 for a description of the HIV-1$_{SF2}$ ("SF2") Env polypeptide). The relationships between these polypeptides is shown schematically in FIG. 15 (in the figure: the polypeptides are indicated as lines, the amino and carboxy termini are indicated on the gp160 line; the open circle represents the oligomerization domain; the open square represents a transmembrane spanning domain (TM); and "c" represents the location of a cleavage site, in gp140.mut the "X" indicates that the cleavage site has been mutated such that it no longer functions as a cleavage site). The polypeptide gp160 includes the coding sequences for gp120 and gp41. The polypeptide gp41 is comprised of several domains including an oligomerization domain (OD) and a transmembrane spanning domain (TM). In the native envelope, the oligomerization domain is required for the non-covalent association of three gp41 polypeptides to form a trimeric structure: through non-covalent interactions with the gp41 trimer (and itself), the gp120 polypeptides are also organized in a trimeric structure. A cleavage site (or cleavage sites) exists approximately between the polypeptide sequences for gp120 and the polypeptide sequences corresponding to gp41. This cleavage site(s) can be mutated to prevent cleavage at the site. The resulting gp140 polypeptide corresponds to a truncated form of gp160 where the transmembrane spanning domain of gp41 has been deleted. This gp140 polypeptide can exist in both monomeric and oligomeric (i.e. trimeric) forms by virtue of the presence of the oligomerization domain in the gp41 moiety. In the situation where the cleavage site has been mutated to prevent cleavage and the transmembrane portion of gp41 has been deleted the resulting polypeptide product is designated "mutated" gp140 (e.g., gp140.mut). As will be apparent to those in the field, the cleavage site can be mutated in a variety of ways. The native amino acid sequence in the SF162 cleavage sites is: APTKAKRRVVQREKR (SEQ ID NO:21), where KAKRR (SEQ ID NO:22) is termed the "second" site and REKR (SEQ ID NO:23) is the "first site". Exemplary mutations include the following constructs: gp140.mut7.modSF162 which encodes the amino acid sequence APTKAISSVVQSEKS (SEQ ID NO:24) in the cleavage site region; gp140.mut8.modSF162 which encodes the amino acid sequence APTIAISSVVQSEKS (SEQ ID NO:25) in the cleavage site region and gp140mut.modSF162 which encodes the amino acid sequence APTKAKRRVVQREKS (SEQ ID NO:26). Mutations are denoted in bold. The native amino acid sequence in the US4 cleavage sites is: APTQAKRRVVQREKR (SEQ ID NO:27), where QAKRR (SEQ ID NO:28) is termed the "second" site and REKR (SEQ ID NO:23) is the "first site". Exemplary mutations include the following construct: gp140.mut.modUS4 which encodes the amino acid sequence APTQAKRRVVQREKS (SEQ ID NO:29) in the cleavage site region. Mutations are denoted in bold.

E. Modification of HIV-1 Env (Envelope) Nucleic Acid Coding Sequences

In one embodiment of the present invention, wild-type Env coding sequences were selected from the HIV-1$_{SF162}$ ("SF162") strain (Cheng-Mayer (1989) *PNAS USA* 86:8575-8579). These SF162 sequences were as follows: gp120, SEQ ID NO:30 (FIG. 16); gp140, SEQ ID NO:31 (FIG. 17); and gp160, SEQ ID NO:32 (FIG. 18).

In another embodiment of the present invention, wild-type Env coding sequences were selected from the HIV-US4 strain (Mascola, et al. (1994) *J. Infect. Dis.* 169:48-54). These US4 sequences were as follows: gp120, SEQ ID NO:51 (FIG. 38); gp140, SEQ ID NO:52 (FIG. 39); and gp160, SEQ ID NO:53 (FIG. 40).

These Env coding sequences were manipulated to maximize expression of their gene products.

First, the wild-type coding region was modified in one or more of the following ways. In one embodiment, sequences encoding hypervariable regions of Env, particularly V1 and/or V2 were deleted. In other embodiments, mutations were introduced into sequences encoding the cleavage site in Env to abrogate the enzymatic cleavage of oligomeric gp140 into gp120 monomers. (See, e.g., Earl et al. (1990) *PNAS USA* 87:648-652; Earl et al. (1991) *J. Virol.* 65:31-41). In yet other embodiments, hypervariable region(s) were deleted, N-glycosylation sites were removed and/or cleavage sites mutated.

Second, the HIV-1 codon usage pattern was modified so that the resulting nucleic acid coding sequence was comparable to codon usage found in highly expressed human genes. The HIV codon usage reflects a high content of the nucleotides A or T in the codon-triplet. The effect of the HIV-1 codon usage is a high AT content in the DNA sequence that results in a decreased translation ability and instability of the mRNA. In comparison, highly expressed human codons prefer the nucleotides G or C. The Env coding sequences were modified to be comparable to codon usage found in highly expressed human genes.

Figure 22A:
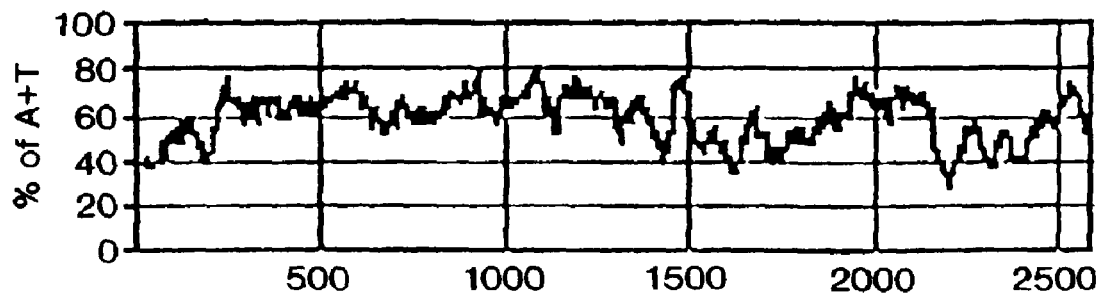
FIGS. 22A-H show the percent A-T content over the length of the sequences for IFNγ (FIGS. 2C and 2G); native gp160 Env US4 and SF162 (FIGS. 2A and 2E, respectively); GAPDH (FIGS. 2D and 2H); and the synthetic gp160 Env for US4 and SF162 (FIGS. 2B and 2F, respectively).
Figure 22B:
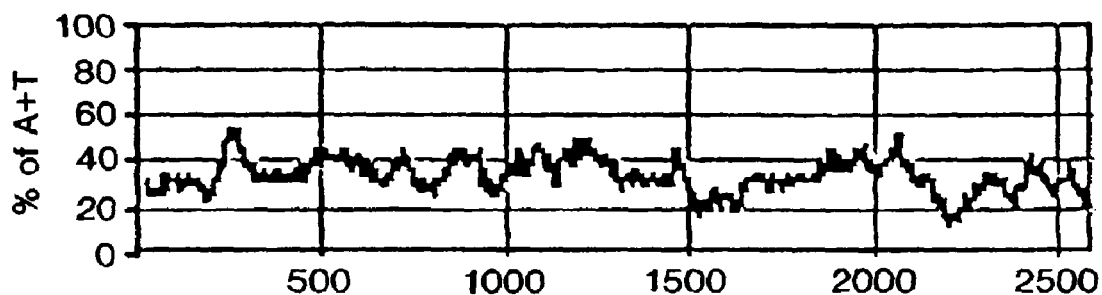
Figure 22C:
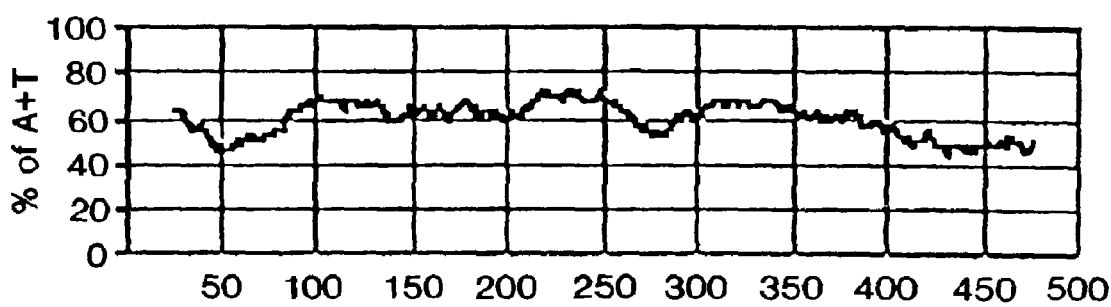
Figure 22D:
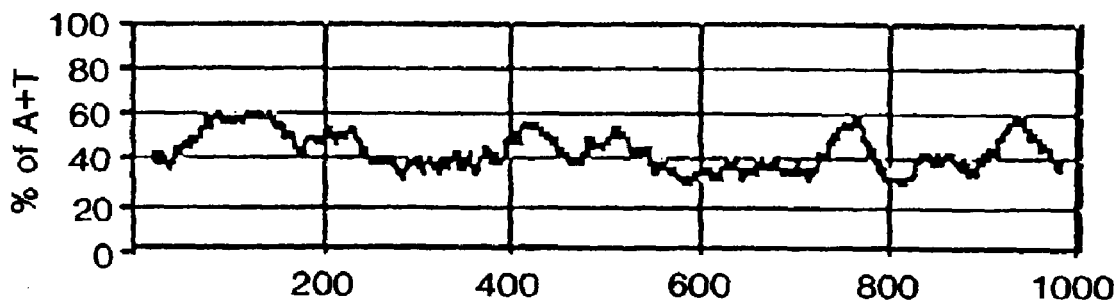
Figure 22E:
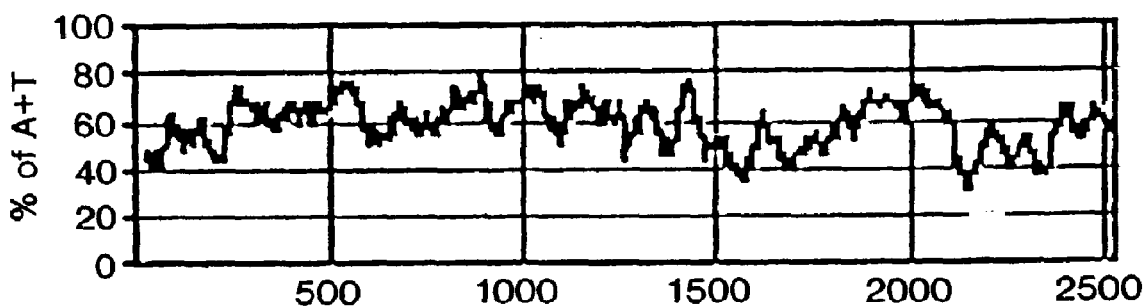
Figure 22F:
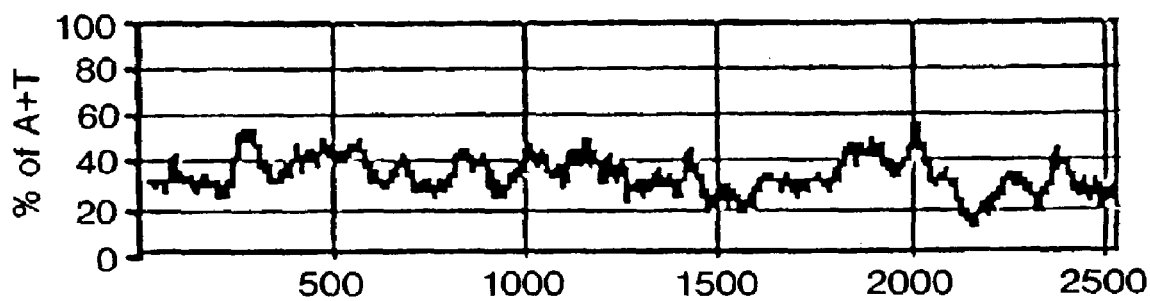
Figure 22G:
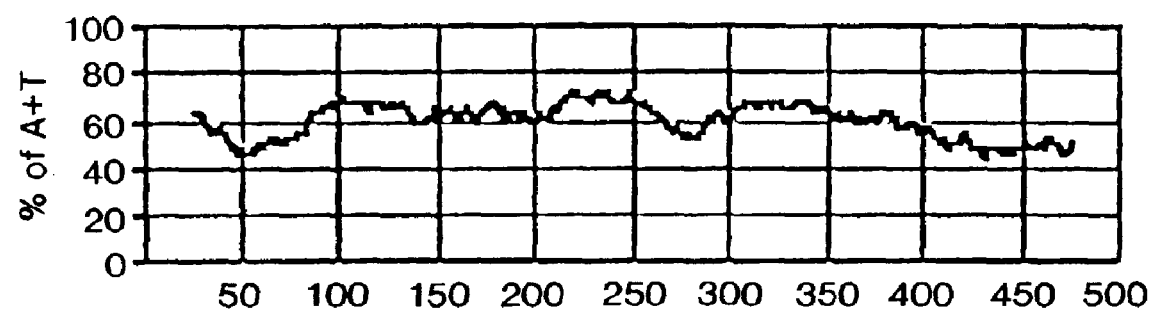
Figure 22H:
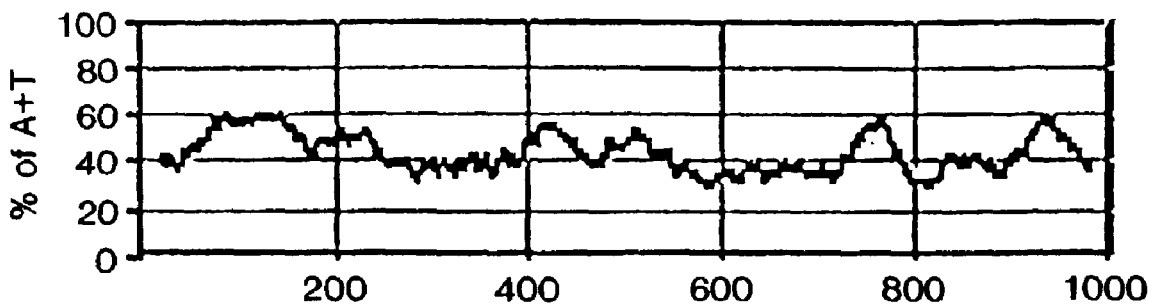

FIGS. 22A-22H present comparisons of the percent A-T content for the cDNAs of stable versus unstable RNAs (comparison window size=50). Human IFNγ mRNA is known to (i) be unstable, (ii) have a short half-life, and (iii) have a high A-U content. Human GAPDH (glyceraldehyde-3-phosphate dehydrogenase) mRNA is known to (i) be a stable RNA, and (i) have a low A-U content. In FIGS. 22A-H, the percent A-T content of these two sequences are compared to the percent A-T content of (1) native HIV-1 US4 Env gp160 cDNA, a synthetic US4 Env gp160 cDNA sequence (i.e., having modified codons) of the present invention; and (2) native HIV-1 SF162 Env gp160 cDNA, a synthetic SF162 Env gp160 cDNA sequence (i.e., having modified codons) of the present invention. FIGS. 22A-H show the percent A-T content over the length of the sequences for IFNγ (FIGS. 22C and 22G); native gp160 Env US4 and SF162 (FIGS. 22A and 22E, respectively); GAPDH (FIGS. 22D and 22H); and the synthetic gp160 Env for US4 and SF162 (FIGS. 22B and 22F). Experiments performed in support of the present invention showed that the synthetic Env sequences were capable of higher level of protein production (see the Examples) than the native Env sequences. The data in FIGS. 22A-H suggest that one reason for this increased production is increased stability of the mRNA corresponding to the synthetic Env coding sequences versus the mRNA corresponding to the native Env coding sequences.

To create the synthetic coding sequences of the present invention the gene cassettes were designed to comprise the entire coding sequence of interest. Synthetic gene cassettes were constructed by oligonucleotide synthesis and PCR amplification to generate gene fragments. Primers were chosen to provide convenient restriction sites for subcloning. The resulting fragments were then ligated to create the entire desired sequence which was then cloned into an appropriate vector. The final synthetic sequences were (i) screened by restriction endonuclease digestion and analysis, (ii) subjected to DNA sequencing in order to confirm that the desired sequence had been obtained and (iii) the identity and integrity of the expressed protein confirmed by SDS-PAGE and Western blotting (See, Examples. The synthetic coding sequences were assembled at Chiron Corp. or by the Midland Certified Reagent Company (Midland, Tex.).

Exemplary modified coding sequences are presented as synthetic Env expression cassettes in Table 1A and 1B. The following expression cassettes (i) have unique, terminal EcoRI and XbaI cloning sites; (ii) include Kozak sequences to promote optimal translation; (iii) tPA signal sequences (to direct the ENV polypeptide to the cell membrane, see, e.g., Chapman et al., infra); (iv) open reading frames optimized for expression in mammalian cells; and (v) a translational stop signal codon.

TABLE 1A

Exemplary Synthetic Env Expression Cassettes(SF162)

| Expression Cassette | Seq Id | Further Information |
|---|---|---|
| gp120 SF162 | 30 | wild-type; FIG. 16 |
| gp140 SF162 | 31 | wild-type; FIG. 17 |
| gp160 SF162 | 32 | wild-type; FIG. 18 |
| gp120.modSF162 | 33 | none; FIG. 19 |
| gp120.modSF162.delV2 | 34 | deleted V2 loop; FIG. 20 |
| gp120.modSF162.delV1/V2 | 35 | deleted V1 and V2; FIG. 21 |
| gp140.modSF162 | 36 | none; FIG. 23 |
| gp140.modSF162.delV2 | 37 | deleted V2 loop; FIG. 24 |
| gp140.modSF162.delV1/V2 | 38 | deleted V1 and V2; FIG. 25 |
| gp140.mut.modSF162 | 39 | mutated cleavage site; FIG. 26 |
| gp140.mut.modSF162.delV2 | 40 | deleted V2; mutated cleavage site; FIG. 27 |
| gp140.mut.modSF162.delV1/V2 | 41 | deleted V1 & V2; mutated cleavage site; FIG. 28 |
| gp140.mut7.modSF162 | 42 | mutated cleavage site; FIG. 29 |
| gp140.mut7.modSF162.delV2 | 43 | mutated cleavage site; deleted V2; FIG. 30 |
| gp140.mut7.modSF162.delV1/V2 | 44 | mutated cleavage site; deleted V1 and V2; FIG. 31 |
| gp140.mut8.modSF162 | 45 | mutated cleavage site; FIG. 32 |
| gp140.mut8.modSF162.delV2 | 46 | mutated cleavage site; deleted V2; FIG. 33 |
| gp140.mut8.modSF162.delV1/V2 | 47 | mutated cleavage site; deleted V1 and V2; FIG. 34 |
| gp160.modSF162 | 48 | none; FIG. 35 |
| gp160.modSF162.delV2 | 49 | deleted V2 loop; FIG. 36 |
| gp160.modSF162.delV1/V2 | 50 | deleted V1 & V2; FIG. 37 |

TABLE 1B

Exemplary Synthetic Env Expression Cassettes(US4)

| Expression Cassette | Seq Id | Further Information |
|---|---|---|
| gp120 US4 | 51 | wild-type; FIG. 38 |
| gp140 US4 | 52 | wild-type; FIG. 39 |
| gp160 US4 | 53 | wild-type; FIG. 40 |
| gp120.modUS4 | 54 | none; FIG. 41 |
| gp120.modUS4.del 128-194 | 55 | deletion in V1 and V2 regions; FIG. 42 |
| gp140.modUS4 | 56 | none; FIG. 43 |
| gp140.mut.modUS4 | 57 | mutated cleavage site; FIG. 44 |
| gp140TM.modUS4 | 58 | native transmembrane region; FIG. 45 |
| gp140.modUS4.delV1/V2 | 59 | deleted V1 and V2; FIG. 46 |
| gp140.modUS4.delV2 | 60 | deleted V1; FIG. 47 |
| gp140.mut.modUS4.delV1/V2 | 61 | mutated cleavage site; deleted V1 and V2; FIG. 48 |
| gp140.modUS4.del 128-194 | 62 | deletion in V1 and V2 regions; FIG. 49 |
| gp140.mut.modUS4.del 128-194 | 63 | mutated cleavage site; deletion in V1 and V2 regions; FIG. 50 |
| gp160.modUS4 | 64 | none; FIG. 51 |
| gp160.modUS4.delV1 | 65 | deleted V1; FIG. 52 |
| gp160.modUS4.delV2 | 66 | deleted V2; FIG. 53 |
| gp160.modUS4.delV1/V2 | 67 | deleted V1 and V2; FIG. 54 |
| gp160.modUS4del 128-194 | 68 | deletion in V1 and V2 regions; FIG. 55 |

Figure 66A-2:
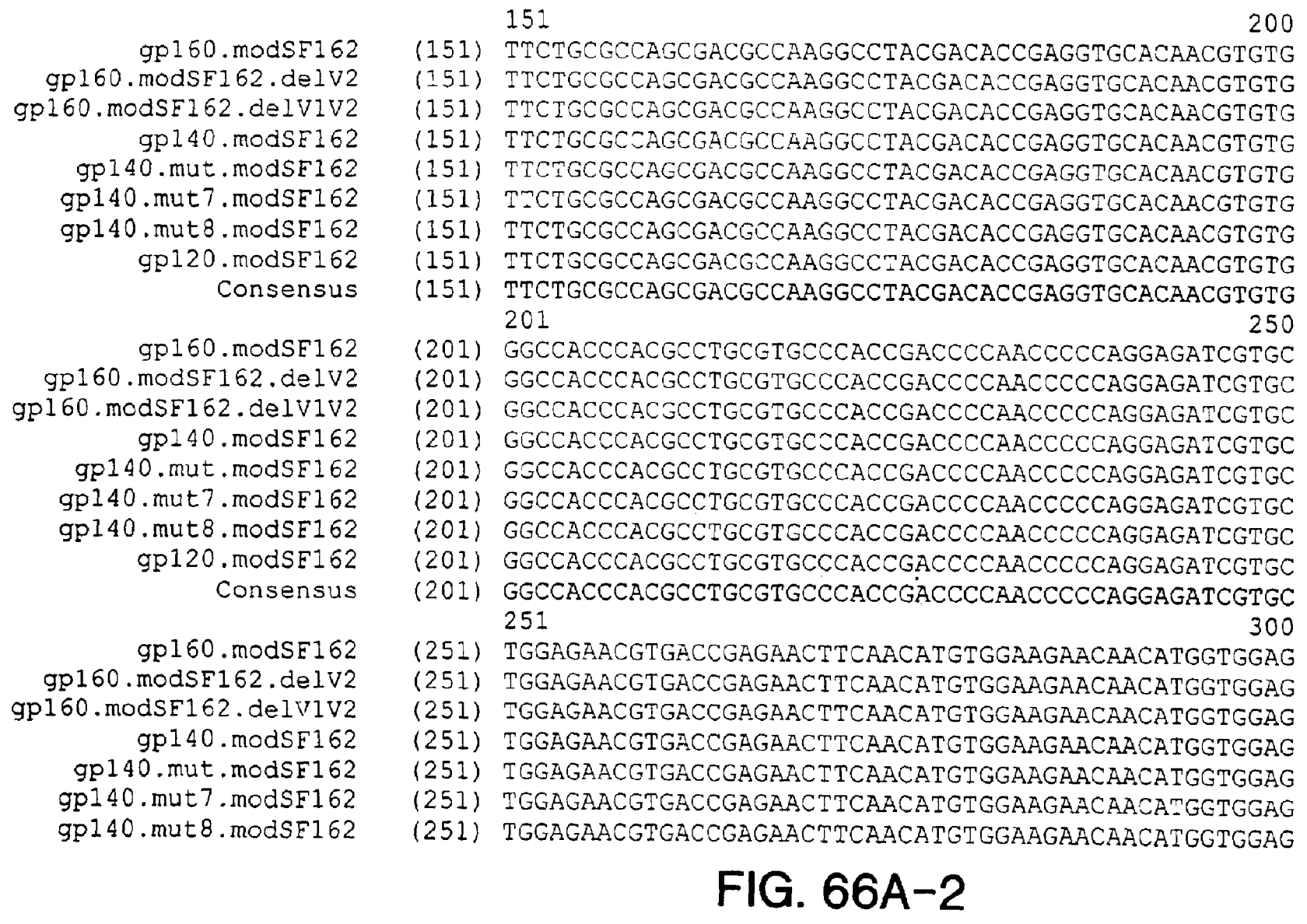
Figure 66A-5:
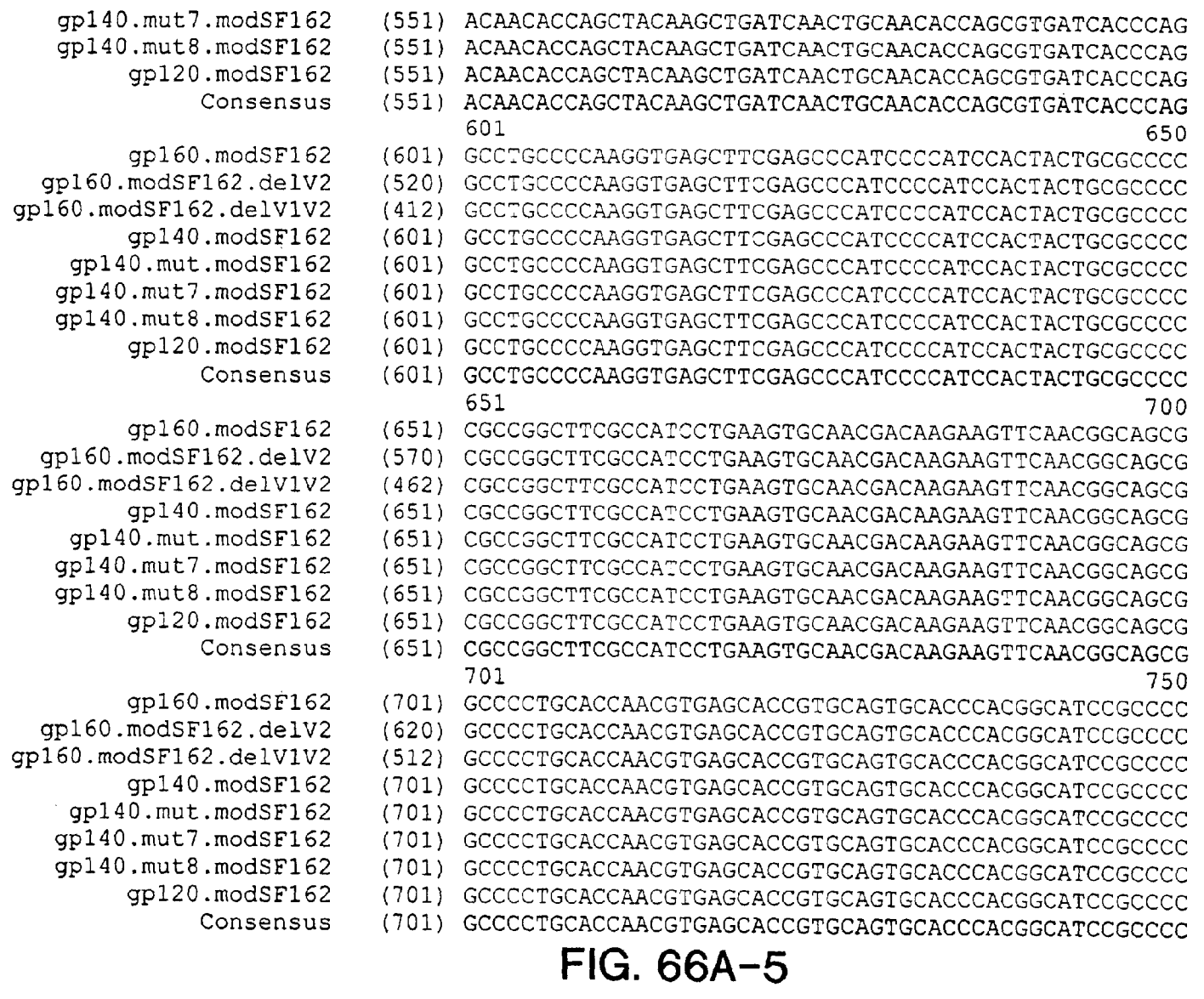

Alignments of the sequences presented in the above tables are presented in FIGS. 66A and 66B.

A common region (Env-common) extends from nucleotide position 1186 to nucleotide position 1329 (SEQ ID NO:69, FIG. 56) relative to the wild-type US4 sequence and from nucleotide position 1117 to position 1260 (SEQ ID NO:79, FIG. 57) relative to the wild-type SF162 sequence. The synthetic sequences of the present invention corresponding to these regions are presented, as SEQ ID NO:71 (FIG. 58) for the synthetic Env US4 common region and as SEQ ID NO:72 (FIG. 59) for the synthetic Env SF162 common region.

Percent identity to this sequence can be determined, for example, using the Smith-Waterman search algorithm (Time Logic, Incline Village, Nev.), with the following exemplary parameters: weight matrix=nuc4×4hb; gap opening penalty=20, gap extension penalty=5, reporting threshold=1; alignment threshold=20.

Various forms of the different embodiments of the present invention (e.g., constructs) may be combined.

F. Cloning Synthetic Env Expression Cassettes of the Present Invention.

Figure 13A:
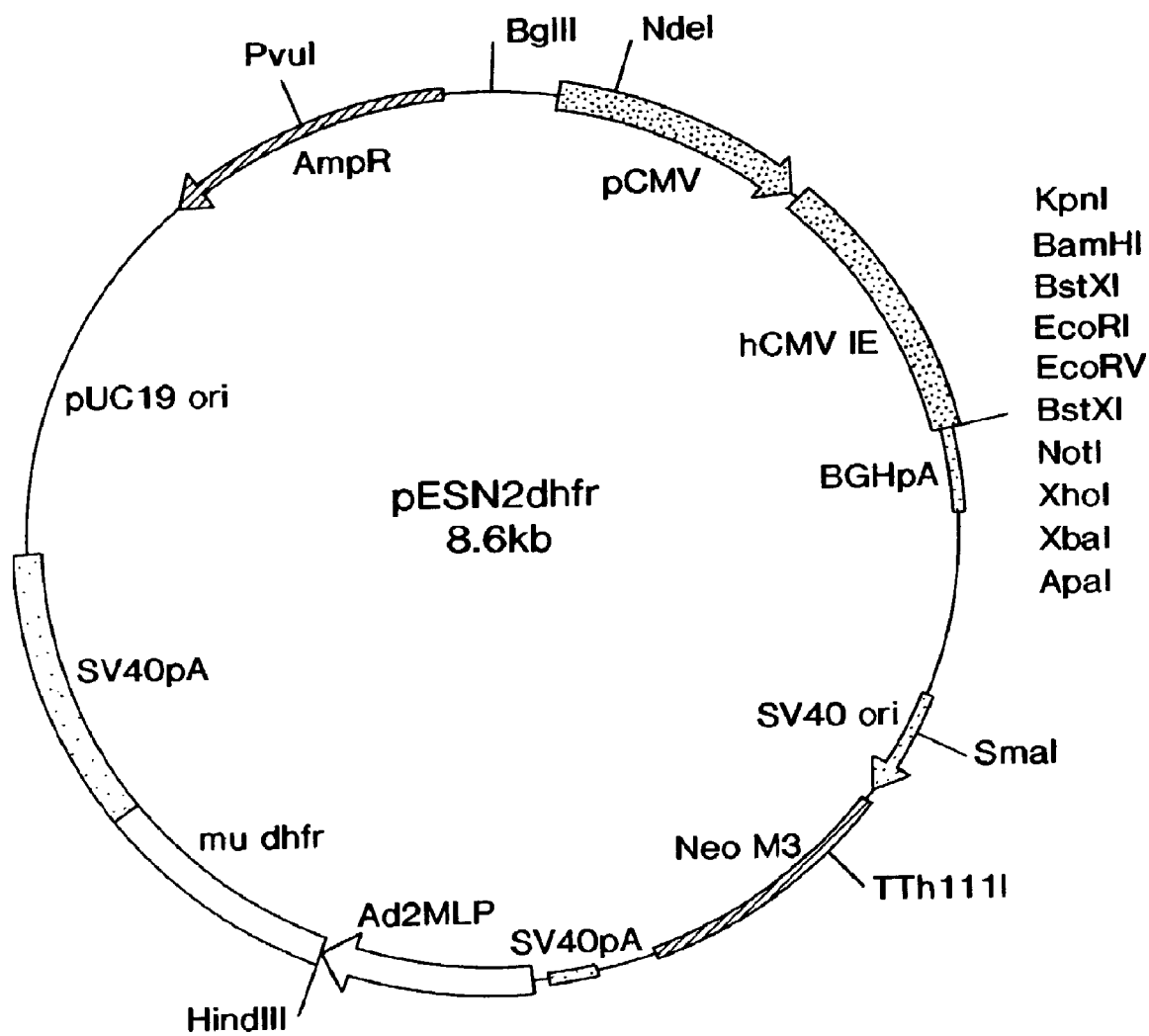
FIG. 13A presents a vector map of pESN2dhfr.
Figure 13B:
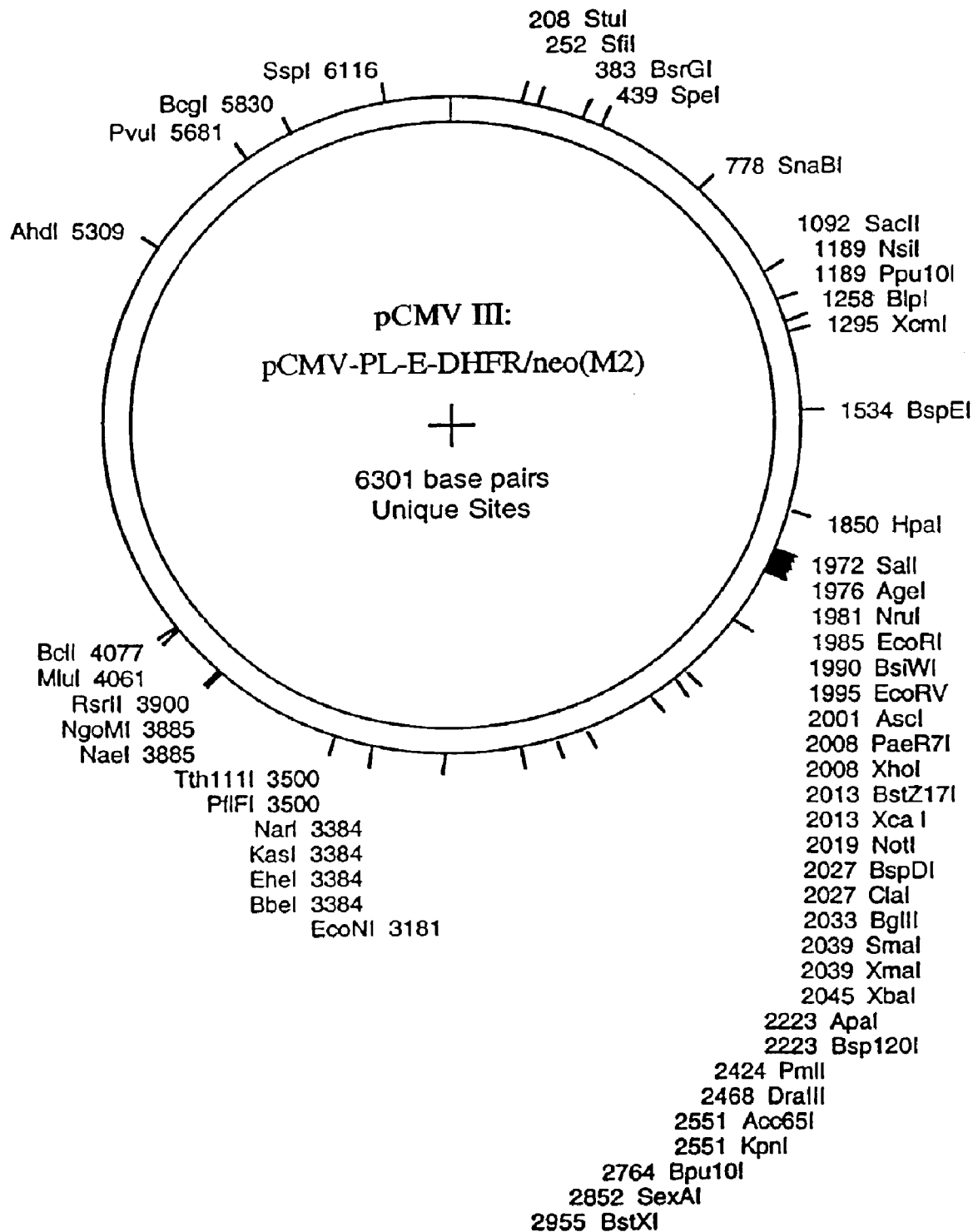
FIG. 13B presents a map of the pCMVIII vector.
Figure 14:
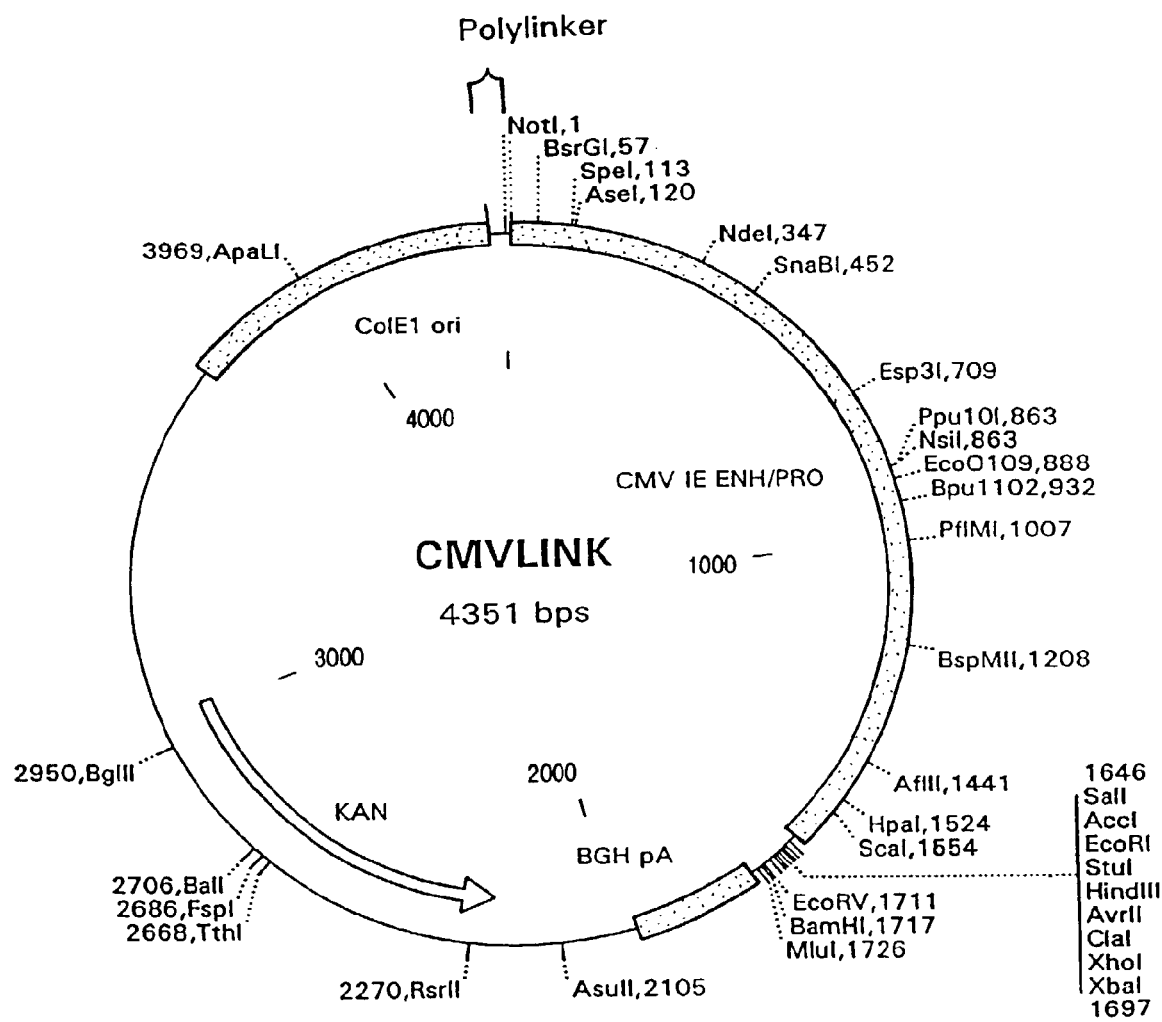
FIG. 14 presents a vector map of pCMV-LINK.

The synthetic DNA fragments encoding the Env polypeptides were typically cloned into the eucaryotic expression vectors described above for Gag, for example, pCMVKm2/pCMVlink (FIG. 4), pCMV6a, pESN2dhfr (FIG. 13A), pCMVIII (FIG. 13B; alternately designated as the pCMV-PL-E-dhfr/neo vector).

Exemplary designations for pCMVlink vectors containing synthetic expression cassettes of the present invention are as follows: pCMVlink.gp140.modSF162; pCMVlink.gp140.-modSF162.delV2; pCMVlink.gp140.mut.modSF162; pCMVlink.gp140.mut.modSF162.delV2; pCMVKm2.gp140modUS4; pCMVKm2.9p140.modUS4.delV2; pCMVKm2.gp140.mut.modUS4; and, pCMVKm2.gp140.mut.modUS4.delV1/V2.

G. Generation of Synthetic Tat Expression Cassettes

Tat coding sequences have also been modified according to the teachings of the present specification. The wild type nucleotide sequence encoding tat from variant SF162 is presented in FIG. 76 (SEQ ID NO:85). The corresponding wild-type amino acid sequence is presented in FIG. 77 (SEQ ID NO:86). FIG. 81 (SEQ ID NO:89) shows the nucleotide sequence encoding the amino terminal of the tat protein and the codon encoding cystein-22 is underlined. Other exemplary constructs encoding synthetic tat polypeptides are shown in FIGS. 78 and 79 (SEQ ID NOs:87 and 88). In one embodiment (SEQ ID NO:88), the cystein residue at position 22 is replaced by a glycine. Caputo et al. (1996) Gene Therapy 3:235 have shown that this mutation affects the trans activation domain of Tat.

Various forms of the different embodiments of the invention, described herein, may be combined.

H. Deposit of Vectors

Selected exemplary constructs shown below and described herein are deposited at Chiron Corporation, Emeryville, Calif., 94662-8097, and were sent to the American Type Culture Collection, 10801 University Boulevard, Manassas, Va. 20110-2209 on Dec. 27, 1999.

| Plasmid Name | Chiron Deposit # | Date Sent to ATCC |
|---|---|---|
| pCMVgp160.modUS4 | 5094 | 27 Dec 99 |
| pCMVgp160delI.modUS4 | 5095 | 27 Dec 99 |
| pCMVgp160del2.modUS4 | 5096 | 27 Dec 99 |
| pCMVgp160del-2.modUS4 | 5097 | 27 Dec 99 |
| pCMVgp160del128-194.mod.US4 | 5098 | 27 Dec 99 |
| pCMVgp140mut.modUS4del128-194 | 5100 | 27 Dec 99 |
| pCMVgp140.mut.mod.US | 5101 | 27 Dec 99 |
| pCMVgp160.modSF162 | 5125 | 27 Dec 99 |
| pCMVgp160.modSF162.delV2 | 5126 | 27 Dec 99 |
| pCMVgp160.modSF162.delV1V2 | 5127 | 27 Dec 99 |
| pCMVgp140.mut.modSF162delV2 | 5128 | 27 Dec 99 |
| pCMVgp140.mut7.modSF162 | 5129 | 27 Dec 99 |
| pCMVgp140.mut7.modSF162delV2 | 5130 | 27 Dec 99 |
| pCMVgp140.mut8.modSF162 | 5131 | 27 Dec 99 |
| pCMVgp140.mut8.modSF162delV2 | 5132 | 27 Dec 99 |
| pCMVgp140.mut8.modSF162delV1V2 | 5133 | 27 Dec 99 |
| pCMVKm2.Gagprot.Mod.SF2.GP1 | 5150 | 27 Dec 99 |
| pCMVKm2.Gagprot.Mod.SF2.GP2 | 5151 | 27 Dec 99 |

Example 2

Expression Assays for the Synthetic Gag, Env and Tat Coding Sequences

A. Gag and Gag-Protease Coding Sequences

The HIV-1SF2 wild-type Gag (SEQ ID NO:1) and Gag-protease (SEQ ID NO:2) sequences were cloned into expression vectors having the same features as the vectors into which the synthetic Gag (SEQ ID NO:4) and Gag-protease (SEQ ID NOs:5, 78 or 79)) sequences were cloned.

Expression efficiencies for various vectors carrying the HIV-15F2 wild-type and synthetic Gag sequences were evaluated as follows. Cells from several mammalian cell lines (293, RD, COS-7, and CHO; all obtained from the American Type Culture Collection, 10801 University Boulevard, Manassas, Va. 20110-2209) were transfected with 2 μg of DNA in transfection reagent LT1 (PanVera Corporation, 545 Science Dr., Madison, Wis.). The cells were incubated for 5 hours in reduced serum medium (Opti-MEM, Gibco-BRL, Gaithersburg, Md.). The medium was then replaced with normal medium as follows: 293 cells, IMDM, 10% fetal calf serum, 2% glutamine (BioWhittaker, Walkersville, Md.); RD and COS-7 cells, D-MEM, 10% fetal calf serum, 2% glutamine (Opti-MEM, Gibco-BRL, Gaithersburg, Md.); and CHO cells, Ham's F-12, 10% fetal calf serum, 2% glutamine (Opti-MEM, Gibco-BRL, Gaithersburg, Md.). The cells were incubated for either 48 or 60 hours. Supernatants were harvested and filtered through 0.45 μm syringe filters and, optionally, stored at −20° C.

Supernatants were evaluated using the Coulter p24-assay (Coulter Corporation, Hialeah, Fla., US), using 96-well plates coated with a murine monoclonal antibody directed against HIV core antigen. The HIV-1 p24 antigen binds to the coated wells. Biotinylated antibodies against HIV recognize the bound p24 antigen. Conjugated strepavidin-horseradish peroxidase reacts with the biotin. Color develops from the reaction of peroxidase with TMB substrate. The reaction is terminated by addition of $4NH_2SO_4$. The intensity of the color is directly proportional to the amount of HIV p24 antigen in a sample.

The results of these expression assays are presented in Tables 2A and 2B. Tables 2A and 2B shows data obtained using the synthetic Gag-protease expression cassette of SEQ ID NO:5. Similar results were obtained using the Gag-protease expression cassettes of SEQ ID NOs:78 and 79.

Table 2: In Vitro Gag and Gagprot p24 Expression

TABLE 2a

Increased in vitro expression from modified vs. native gag plasmids in supernatants and lysates from transiently transfected cells

| experiment | native (nat) [a] modified (mod) [b] | supernatant (sup) lysate (lys) | cell line | hours post transfection | total ng p24 (fold increase) |
|---|---|---|---|---|---|
| 1 | nat | sup | 293 | 48 | 3.4 |
|   | mod | sup | 293 | 48 | 1260 (371) |
|   | nat | sup | 293 | 60 | 3.2 |
|   | mod | sup | 293 | 60 | 2222 (694) |
| 2 | nat | sup | 293 | 60 | 1.8 |
|   | mod | sup | 293 | 60 | 1740 (966) |
| 3 | nat | sup | 293 | 60 | 1.8 |
|   | mod | sup | 293 | 60 | 580 (322) |
| 4 | nat | lys | 293 | 60 | 1.5 |
|   | mod | lys | 293 | 60 | 85 (57) |
| 1 | nat | sup | RD | 48 | 5.6 |
|   | mod | sup | RD | 48 | 66 (12) |
|   | nat | sup | RD | 60 | 7.8 |
|   | mod | sup | RD | 60 | 70.2 (9) |
| 2 | nat | lys | RD | 60 | 1.9 |
|   | mod | lys | RD | 60 | 7.8 (4) |
| 1 | nat | sup | COS-7 | 48 | 0.4 |
|   | mod | sup | COS-7 | 48 | 33.4 (84) |
| 2 | nat | sup | COS-7 | 48 | 0.4 |
|   | mod | sup | COS-7 | 48 | 10 (25) |
|   | nat | lys | COS-7 | 48 | 3 |
|   | mod | lys | COS-7 | 48 | 14 (5) |

[a] pCMVLink.Gag.SF2.PRE
[b] pCMVKm2.GagMod.SF2

TABLE 2B

In vitro expression from modified gag and gagprotease plasmids in supernatants and lysates from transiently transfected cells

| plasmid | supernatant (sup) lysate (lys) | cell line | hours post transfection | total ng p24[d] |
|---|---|---|---|---|
| Gag[a] | sup | 293 | 60 | 760 |
| GagProt(GP1)[b] | sup | 293 | 60 | 380 |
| GagProt(GP2)[c] | sup | 293 | 60 | 320 |
| Gag | lys | 293 | 60 | 78 |
| GagProt(GP1) | lys | 293 | 60 | 1250 |
| GagProt(GP2) | lys | 293 | 60 | 400 |
| Gag | sup | COS-7 | 72 | 40 |
| GagProt(GP1) | sup | COS-7 | 72 | 150 |
| GagProt(GP2) | sup | COS-7 | 72 | 290 |
| Gag | lys | COS-7 | 72 | 60 |
| GagProt(GP1) | lys | COS-7 | 72 | 63 |
| GagProt(GP2) | lys | COS-7 | 72 | 58 |

[a] pCMVKM2.GagMod.SF2
[b] pCMVKM2.GagProtMod.SF2(GP1) gagprotease with codon optimization and inactivation of INS in protease
[c] pCMVKm2.GagProtMod.SF2(GP2) gagprotease with only inactivation of INS in protease
[d] Shown are representative results from 3 independent experiments for each cell line tested.

The data showed that the synthetic Gag and Gag-protease expression cassettes provided dramatic increases in production of their protein products, relative to the native (HIV-1SF2 wild-type) sequences, when expressed in a variety of cell lines.

B. Env Coding Sequences

The HIV-SF162 ("SF162") wild-type Env (SEQ ID NO:1-3) and HIV-US4 ("US4") wild-type Env (SEQ ID NO:22-24) sequences were cloned into expression vectors having the same features as the vectors into which the synthetic Env sequences were cloned.

Expression efficiencies for various vectors carrying the SF162 and US4 wild-type and synthetic Env sequences were evaluated essentially as described above for Gag except that cell lysates were prepared in 40 μl lysis buffer (1.0% NP40, 0.1 M Tris pH 7.5) and frozen at −20° C. and capture ELISAs were performed as follows.

For Capture ELISAs, 250 ng of an ammonium sulfate IgG cut of goat polyclonal antibody to gp120SF2/env2-3 was used to coat each well of a 96-well plate (Corning, Corning, N.Y.). Serial dilutions of gp120/SF2 protein (MID 167) were used to set the quantitation curve from which expression of US4 or SF162 gp120 proteins from transfection supernatant and lysates were calculated. Samples were screened undiluted and, optionally, by serial 2-fold dilutions. A human polyclonal antibody to HIV-1 gp120/SF2 was used to detect bound gp120 envelope protein, followed by horse-radish peroxidase (HRP)-labeled goat anti-human IgG conjugates. TME (Pierce, Rockford, Ill.) was used as the substrate and the reaction is terminated by addition of $4N\ H_2SO_4$. The reaction was quantified by measuring the optical density (OD) at 450 nm. The intensity of the color is directly proportional to the amount of HIV gp120 antigen in a sample. Purified SF2 gp120 protein was diluted and used as a standard.

The results of the transient expression assays are presented in Tables 3 and 4. Table 3 depicts transient expression in 293 cells transfected with a pCMVKm2 vector carrying the Env cassette of interest. Table 4 depicts transient expression in RD cells transfected with a pCMVKm2 vector carrying the Env cassette of interest.

TABLE 3

| Native (N) Synthetic (S) | Cell Line | Total sup (ng) | Sup fold increase (S v. N) | Total cell lysate (ng) | Cell lysate fold increase (S v. N) | Total (ng) | Total fold increase (S v. N) |
|---|---|---|---|---|---|---|---|
| N-gp120.US4 | RD | 87 | | <1 | | 88 | |
| S-gp120.modUS4 | RD | 690 | 8 | 2 | 5 | 693 | 8 |
| N-gp140.US4 | RD | 526 | | 0 | | 526 | |
| S-gp140.modUS4 | RD | 1305 | 2 | 1 | 2 | 1306 | 2 |
| S-gp140mut.modUS4 | RD | 35 | N/A | 25 | N/A | 60 | N/A |
| S-gp140TM.modUS4 | RD | 0 | N/A | 5 | N/A | 5 | N/A |
| N-gp160.US4 | RD | 0 | | 8 | | 8 | |
| S-gp160.modUS4 | RD | 0 | 0 | 30 | 4 | 30 | 4 |

TABLE 4

CHO Cell Lines Expression Level of US4 Envelope Constructs

| Constructs | CHO Clone # | MTX Level | Expression Level* (ng/ml) |
|---|---|---|---|
| gp120.modUS4 | 1 | 3.2 µM | 250-450 |
| | 2 | 1.6 µM | 350-450 |
| | 3 | 200 nM | 230-580 |
| | 4 | 200 nM | 300-500 |
| gp140.modUS4 | 1 | 1 µM | 155-300 |
| | 2 | 1 µM | 100-260 |
| | 3 | 1 µM | 200-430 |
| gp140.mut.modUS4 | 1 | 1 µM | 110-270 |
| | 2 | 1 µM | 100-235 |
| | 3 | 1 µM | 100-220 |
| gp140.modUS4.delV1/V2 | 1 | 50 nM | 313-587** |
| | 2 | 50 nM | 237-667** |
| | 3 | 50 nM | 492-527** |
| gp140.mut.modUS4.delV1/V2 | 1 | 50 nM | 46-328** |
| | 2 | 50 nM | 82-318** |
| | 3 | 50 nM | 204-385** |

*All samples measured at T-75 flask stage unless otherwise indicated
**at 24 well and 6 well plate stages
***in a three liter bioreactor perfusion culture this clone yielded approximately 2-5 µg/ml.

The data showed that the synthetic Env and expression cassettes provided a significant increase in production of their protein products, relative to the native (HIV-1SF162 or US4 wild-type) sequences, when expressed in a variety of cell lines.

C. CHO Cell Line Env Expression Data

Chinese hamster ovary (CHO) cells were transfected with plasmid DNA encoding the synthetic HIV-1 gp120 or gp140 proteins (e.g., pESN2dhfr or pCMVIII vector backbone) using Mirus TransIT-LT1 polyamine transfection reagent (Pan Vera) according to the manufacturers instructions and incubated for 96 hours. After 96 hours, media was changed to selective media (F12 special with 250 µg/ml G418) and cells were split 1:5 and incubated for an additional 48 hours. Media was changed every 5-7 days until colonies started forming at which time the colonies were picked, plated into 96 well plates and screened by gp120 Capture ELISA. Positive clones were expanded in 24 well plates and screened several times for Env protein production by Capture ELISA, as described above. After reaching confluency in 24 well plates, positive clones were expanded to T25 flasks (Corning, Corning, N.Y.). These were screened several times after confluency and positive clones were expanded to T75 flasks.

Positive T75 clones were frozen in LN2 and the highest expressing clones amplified with 0-5 µM methotrexate (MTX) at several concentrations and plated in 100 mm culture dishes. Plates were screened for colony formation and all positive closed were again expanded as described above. Clones were expanded an amplified and screened at each step by gp120 capture ELISA. Positive clones were frozen at each methotrexate level. Highest producing clones were grown in perfusion bioreactors (3L, 100L) for expansion and adaptation to low serum suspension culture conditions for scale-up to larger bioreactors.

Tables 5 and 6 show Capture ELISA data from CHO cells transfected with pCMVIII vector carrying a cassette encoding synthetic HIV-US4 and SF162 Env polypeptides (e.g., mutated cleavage sites, modified codon usage and/or deleted hypervariable regions). Thus, stably transfected CHO cell lines which express Env polypeptides (e.g., gp120, gp140-monomeric, and gp140-oligomeric) have been produced.

TABLE 5

CHO Cell Lines Expression Level of US4 Envelope Constructs

| Constructs | CHO Clone # | MTX Level | Expression Level* (ng/ml) |
|---|---|---|---|
| gp120.modUS4 | 1 | 3.2 µM | 250-450 |
| | 2 | 1.6 µM | 350-450 |
| | 3 | 200 nM | 230-580*** |
| | 4 | 200 nM | 300-500 |
| gp140.modUS4 | 1 | 1 µM | 155-300 |
| | 2 | 1 µM | 100-260 |
| | 3 | 1 µM | 200-430 |
| gp140.mut.modUS4 | 1 | 1 µM | 110-270 |
| | 2 | 1 µM | 100-235 |
| | 3 | 1 µM | 100-220 |
| gp140.modUS4.delV1/V2 | 1 | 50 nM | 313-587** |
| | 2 | 50 nM | 237-667** |
| | 3 | 50 nM | 492-527** |
| gp140.mut.modUS4.delV1/V2 | 1 | 50 nM | 46-328** |
| | 2 | 50 nM | 82-318** |
| | 3 | 50 nM | 204-385** |

*All samples measured at T-75 flask stage unless otherwise indicated
**at 24 well and 6 well plate stages
***in a three liter bioreactor perfusion culture this clone yielded approximately 2-5 µg/ml.

TABLE 6

CHO Cell Lines Expression Level of SF162 Envelope Constructs

| Constructs | CHO Clone # | MTX Level | Expression Level* (ng/ml) |
|---|---|---|---|
| gp120.modSF162 | 1 | 0 | 755-2705 |
| | 2 | 0 | 928-1538 |
| | 3 | 0 | 538-1609 |
| gp140.modSF162 | 1 | 20 nM | 180-350 |
| gp140.mut.modSF162 | 1 | 20 nM | 164-451 |
| | 2 | 20 nM | 188-487 |
| | 3 | 20 nM | 233-804 |

TABLE 6-continued

CHO Cell Lines Expression Level of SF162 Envelope Constructs

| Constructs | CHO Clone # | MTX Level | Expression Level* (ng/ml) |
|---|---|---|---|
| gp120.modSF162.delV2 | 1 | 800 nM | 528-1560 |
| | 2 | 800 nM | 487-1878 |
| | 3 | 800 nM | 589-1212 |
| gp140.modSF162.delV2 | 1 | 800 nM | 300-600 |
| | 2 | 800 nM | 200-400 |
| | 3 | 800 nM | 200-500 |
| gp140.mut.modSF162.delV2 | 1 | 800 nM | 300-700 |
| | 2 | 400 nM | 1161 |
| | 3 | 800 nM | 400-600 |
| | 4 | 400 nM | 1600-2176 |

*All samples measured at T-75 flask stage unless otherwise indicated

The results presented above demonstrate the ability of the constructs of the present invention to provide expression of Env polypeptides in CHO cells. Production of polypeptides using CHO cells provides (i) correct glycosylation patterns and protein conformation (as determined by binding to panel of MAbs); (ii) correct binding to CD4 receptor molecules; (iii) absence of non-mammalian cell contaminants (e.g., insect viruses and/or cells); and (iv) ease of purification.

D. Tat Coding Sequences

The HIV-SF162 ("SF162") wild-type Tat (SEQ ID NO:85) sequences were cloned into expression vectors having the same features as the vectors into which the synthetic Tat sequences were cloned (SEQ ID NOs:87, 88 and 89).

Expression efficiencies for various vectors carrying the SF162 wild-type and synthetic Tat sequences are evaluated essentially as described above for Gag and Env using capture ELISAs with the appropriate anti-tat antibodies and/or CHO cell assays. Expression of the polypeptides encoded by the synthetic cassettes is improved relative to wild type.

Example 3

Western Blot Analysis of Expression

A. Gag and Gag-Protease Coding Sequences

Human 293 cells were transfected as described in Example 2 with pCMV6a-based vectors containing native or synthetic Gag expression cassettes. Cells were cultivated for 60 hours post-transfection. Supernatants were prepared as described. Cell lysates were prepared as follows. The cells were washed once with phosphate-buffered saline, lysed with detergent [1% NP40 (Sigma Chemical Co., St. Louis, Mo.) in 0.1 M Tris-HCl, pH 7.5], and the lysate transferred into fresh tubes. SDS-polyacrylamide gels (pre-cast 8-16%; Novex, San Diego, Calif.) were loaded with 20 µl of supernatant or 12.5 µl of cell lysate. A protein standard was also loaded (5 µl, broad size range standard; BioRad Laboratories, Hercules, Calif.). Electrophoresis was carried out and the proteins were transferred using a BioRad Transfer Chamber (BioRad Laboratories, Hercules, Calif.) to Immobilon P membranes (Millipore Corp., Bedford, Mass.) using the transfer buffer recommended by the manufacturer (Millipore), where the transfer was performed at 100 volts for 90 minutes. The membranes were exposed to HIV-1-positive human patient serum and immunostained using o-phenylenediamine dihydrochloride (OPD; Sigma).

The results of the immunoblotting analysis showed that cells containing the synthetic Gag expression cassette produced the expected p55 protein at higher per-cell concentrations than cells containing the native expression cassette. The Gag p55 protein was seen in both cell lysates and supernatants. The levels of production were significantly higher in cell supernatants for cells transfected with the synthetic Gag expression cassette of the present invention. Experiments performed in support of the present invention suggest that cells containing the synthetic Gag-prot expression cassette produced the expected Gag-prot protein at comparably higher per-cell concentrations than cells containing the native expression cassette.

In addition, supernatants from the transfected 293 cells were fractionated on sucrose gradients. Aliquots of the supernatant were transferred to Polyclear™ ultra-centrifuge tubes (Beckman Instruments, Columbia, Md.), under-laid with a solution of 20% (wt/wt) sucrose, and subjected to 2 hours centrifugation at 28,000 rpm in a Beckman SW28 rotor. The resulting pellet was suspended in PBS and layered onto a 20-60% (wt/wt) sucrose gradient and subjected to 2 hours centrifugation at 40,000 rpm in a Beckman SW41ti rotor.

The gradient was then fractionated into approximately 10×1 ml aliquots (starting at the top, 20%-end, of the gradient). Samples were taken from fractions 1-9 and were electrophoresed on 8-16% SDS polyacrylamide gels. Fraction number 4 (the peak fraction) corresponds to the expected density of Gag protein VLPs. The supernatants from 293/synthetic Gag cells gave much stronger p55 bands than supernatants from 293/native Gag cells, and, as expected, the highest concentration of p55 in either supernatant was found in fraction 4.

These results demonstrate that the synthetic Gag expression cassette provides superior production of both p55 protein and VLPs, relative to the native Gag coding sequences.

B. Env Coding Sequences

Human 293 cells were transfected as described in Example 2 with pCMVKm2-based; pCMVlink-based; p-CMVII-based or pESN2-based vectors containing native or synthetic Env expression cassettes. Cells were cultivated for 48 or 60 hours post-transfection. Cell lysates and supernatants were prepared as described (Example 2). Briefly, the cells were washed once with phosphate-buffered saline, lysed with detergent [1% NP40 (Sigma Chemical Co., St. Louis, Mo.)] in 0.1 M Tris-HCl, pH 7.5], and the lysate transferred into fresh tubes. SDS-polyacrylamide gels (pre-cast 8-16%; Novex, San Diego, Calif.) were loaded with 20 µl of supernatant or 12.5 µl of cell lysate. A protein molecular weight standard and an HIV SF2 gp120 positive control protein (5 µl, broad size range standard; BioRad Laboratories, Hercules, Calif.) were also loaded. Electrophoresis was carried out and the proteins were transferred using a BioRad Transfer Chamber (BioRad Laboratories, Hercules, Calif.) to Immobilon P membranes (Millipore Corp., Bedford, Mass.) using the transfer buffer recommended by the manufacturer (Millipore), where the transfer was performed at 100 volts for 90 minutes. The membranes were then reacted against polyclonal goat anti-gp120SF2/env2-3 anti-sera, followed by incubation with swine anti-goat IgG-peroxidase (POD) (Sigma, St. Louis, Mo.). Bands indicative of binding were visualized by adding DAB with hydrogen peroxide which deposits a brown precipitate on the membranes.

The results of the immunoblotting analysis showed that cells containing the synthetic Env expression cassette produced the expected Env gp proteins of the predicted molecular weights as determined by mobilities in SDS-polyacrylamide gels at higher per-cell concentrations than cells containing the native expression cassette. The Env proteins were seen in both cell lysates and supernatants. The levels of production were significantly higher in cell supernatants for cells transfected with the synthetic Env expression cassette of the present invention.

C. Tat Coding Sequences

Human 293 cells are transfected as described in Example 2 with various vectors containing native or synthetic Tat expression cassettes. Cells are cultivated and isolated proteins analyzed as described above. Immunoblotting analysis shows that cells containing the synthetic Tat expression cassette produced the expected Tat proteins of the predicted molecular weights as determined by mobilities in SDS-polyacrylamide gels at higher per-cell concentrations than cells containing the native expression cassette.

Example 4

Purification of Env Polypeptides

A. Purification of Oligomeric gp140

Figure 60:
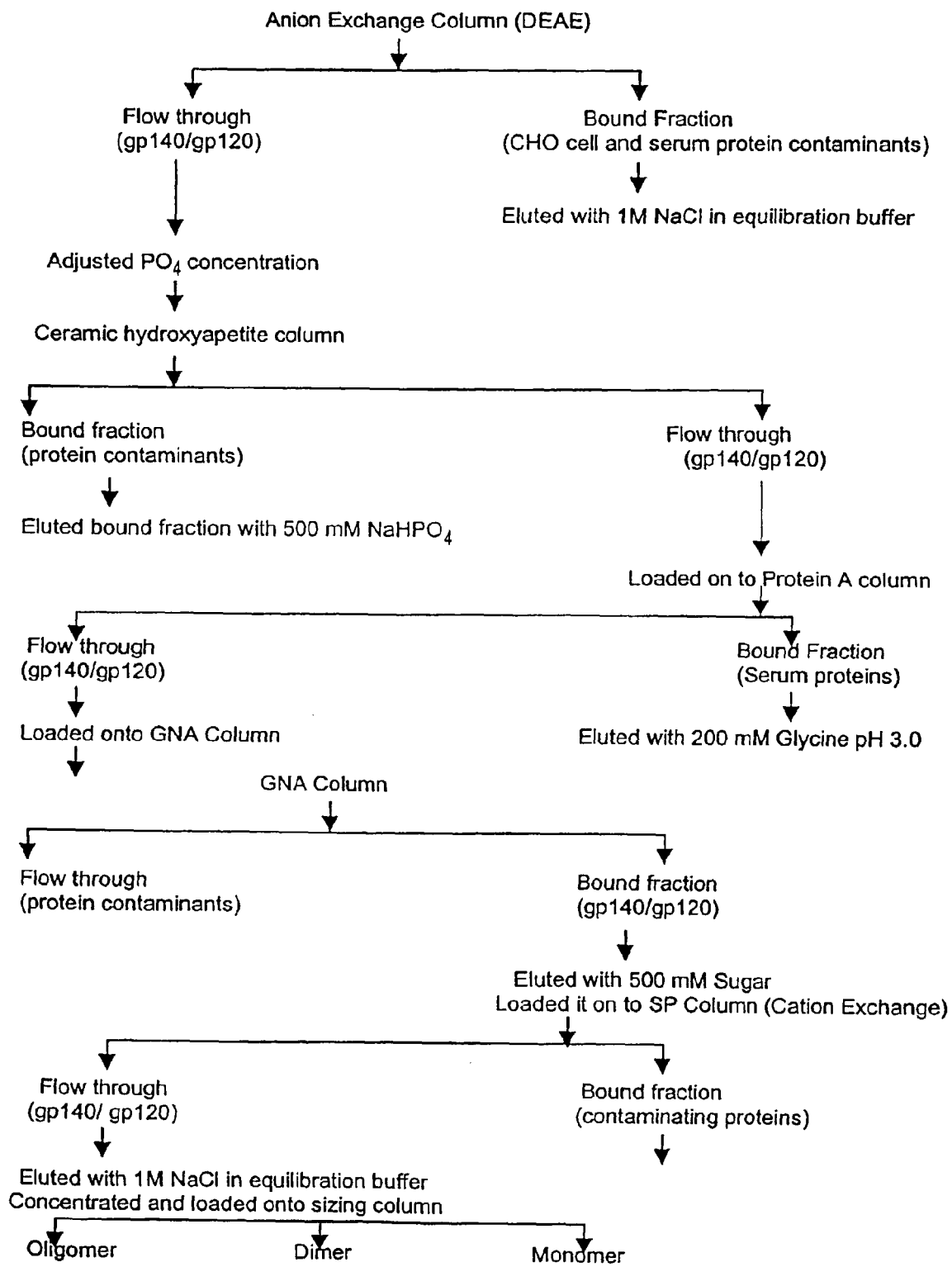
FIG. 60 presents a schematic representation of an Env polypeptide purification strategy.
Figure 67:
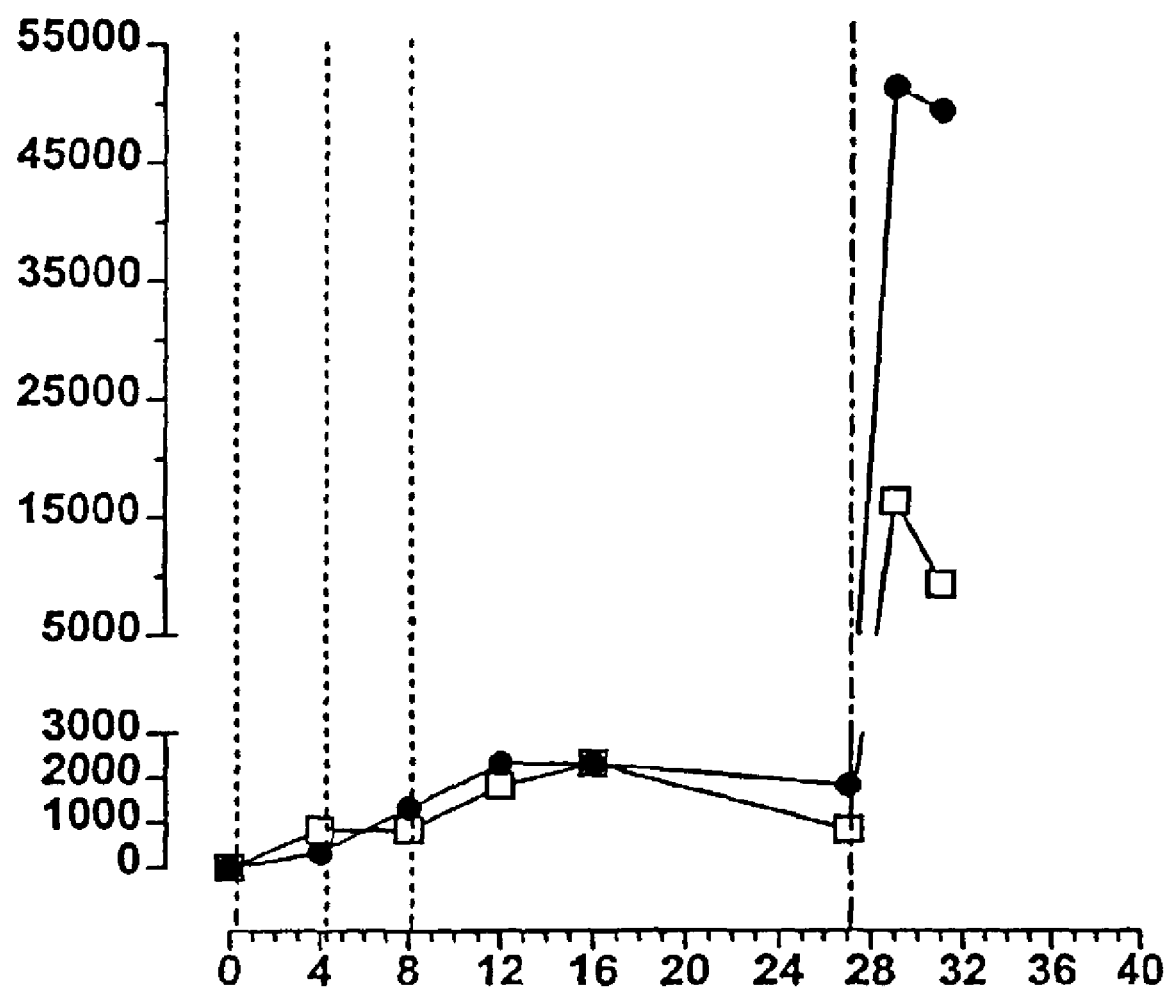
FIG. 67 shows the ELISA titers (binding antibodies) obtained in two rhesus macaques (H445, lines with solid black dots; and J408, lines with open squares). The y-axis is the end-point gp140 ELISA titers and the x-axis shows weeks post-immunization. The dashed lines at 0, 4, and 8 weeks represent DNA immunizations. The alternating dash/dotted line at 27 weeks indicates a DNA plus protein boost immunization.

Purification of oligomeric gp140 (o-gp140 US4) was conducted essentially as shown in FIG. 60. For the experiments described herein, o-gp140 refers to oligomeric gp140 in either native or modified (e.g., optimized expression sequences, deleted, mutated, truncated, etc.) form. Briefly, concentrated (30-50×) supernatants obtained from CHO cell cultures were loaded onto an anion exchange (DEAE) column which removed DNA and other serum proteins. The eluted material was loaded onto a ceramic hydroxyapatite column (CHAP) which bound serum proteins but not HIV Env proteins. The flow-through from the DEAE and CHAP columns was loaded onto a Protein A column as a precautionary step to remove any remaining serum immunoglobulins. The Env proteins in the flow-through were then captured using the lectin gluvanthus navalis (GNA, Vector Labs, Burlingame, Calif.). GNA has high affinity for mannose rich carbohydrates such as Env. The Env proteins were then eluted with GNA substrate. To remove other highly glycosylated proteins, a cation exchange column (SP) was used to purify gp140/gp120. In a final step, which separates gp120 from o-gp140, a gel filtration column was used to separate oligomers from monomers. Sizing and chromatography analysis of the final product revealed that this strategy lead to the successful isolation of oligomeric gp140.

B. Purification of gp120

Purification of gp120 was conducted essentially as previously described for other Env proteins. Briefly, concentrated supernatants obtained from CHO cell cultures were loaded onto an anion exchange (DEAF) column which removed DNA and other serum proteins. The eluted material was loaded onto a ceramic hydroxyapatite column (CHAP) which bound serum proteins but not HIV Env proteins. The flow-through from the CHAP column was loaded a cation exchange column (SP) where the flow-through was discarded and the bound fraction eluted with salt. The eluted fraction(s) were loaded onto a Suprose 12/Superdex 200 Tandem column (Pharmacia-Upjohn, Uppsala, Sweden) from which purified gp120 was obtained. Sizing and chromatography analysis of the final product revealed that this strategy successfully purified gp120 proteins.

Example 5

Analysis of Purified Env Polypeptides

A. Analysis of o-gp140

It is well documented that HIV Env protein binds to CD4 only in its correct conformation. Accordingly, the ability of o-gp140 US4 polypeptides, produced and purified as described above, to bind CD4 cells was tested. O-gp140 US4 was incubated for 15 minutes with FITC-labeled CD4 at room temperature and loaded onto a Biosil 250 (BioRad) size exclusion column using Waters HPLC. CD4-FITC has the longest retention time (2.67 minutes), followed by CD4-FITC-gp120 (2.167 min). The shortest retention time (1.9 min) was observed for CD4-FITC-o-gp140 US4 indicating that, as expected, o-gp140 US4 binds to CD4 forming a large complex which reduces retention time on the column. Thus, the o-gp140 US4 produced and purified as described above is of the correct size and conformation.

In addition, the US4 o-gp140, purified as described above, was also tested for its ability to bind to a variety of monoclonal antibodies with known epitope specificities for the CD4 binding site, the CD4 inducible site, the V3 loop and oligomer-specific gp41 epitope. O-gp140 bound strongly to these antibodies, indicating that the purified protein retains its structural integrity.

B. Analysis of gp120

As described above, CD4-FITC binds gp120, as demonstrated by the decreased retention time on the HPLC column. Thus, US4 gp120 purified by the above method retains its conformational integrity. In addition, the properties of purified gp120 can be tested by examining its integrity and identity on western blots, as well as, by examining protein concentration, pH, conductivity, endotoxin levels, bioburden and the like. US4 gp120, purified as described above, was also tested for its ability to bind to a variety of monoclonal antibodies with known epitope specificities for the CD4 binding site, the CD4 inducible site, the V3 loop and oligomer-specific gp41 epitope. The pattern of mAb binding to gp120 indicated that the purified protein retained its structural integrity, for example, the purified gp120 did not bind the mAb having the oligomer-specific gp41 epitope (as expected).

Example 6

Electron Microscopic Evaluation of VLP Production

The cells for electron microscopy were plated at a density of 50-70% confluence, one day before transfection. The cells were transfected with 10 μg of DNA using transfection reagent LT1 (Panvera) and incubated for 5 hours in serum-reduced medium (see Example 2). The medium was then replaced with normal medium (see Example 2) and the cells were incubated for 14 hours (COS-7) or 40 hours (CHO). After incubation the cells were washed twice with PBS and fixed with 2% glutaraldehyde. Electron microscopy was performed by Prof. T. S. Benedict Yen, Veterans Affairs, Medical Center, San Francisco, Calif.).

Electron microscopy was carried out using a transmission electron microscope (Zeiss 10c). The cells were pre-stained with osmium and stained with uranium acetate and lead citrate. The magnification was 100,000×.

Figure 3B:

FIGS. 3A and 3B show micrographs of CHO cells transfected with pCMVKM2 carrying the synthetic Gag expression cassette (SEQ ID NO:5) or carrying the Gag-prot expression cassette (SEQ ID NO:79). In the figure, free and budding immature virus-like-particles (VLP) of the expected size (100 nm) are seen for the Gag expression cassette (FIG. 3A) and both immature and mature VLPs are seen for the Gag-prot expression cassette (FIG. 38). COS-7 cells transfected with the same vector have the same expression pattern. VLP can also be found intracellularly in CHO and COS-7 cells.

Native and synthetic Gag expression cassettes were compared for their associated levels of VLP production when used to transfect human 293 cells. The comparison was performed by density gradient ultracentrifugation of cell supernatants and Western-blot analysis of the gradient fractions. There was a clear improvement in production of VLPs when using the synthetic Gag construct.

Example 7

Expression of Virus-Like Particles in the Baculovirus System

A. Expression of Native HIV p55 Gag

To construct the native HIV p55 Gag baculovirus shuttle vector, the prototype SF2 HIV p55 plasmid, pTM1-Gag (Selby M. J., et al., *J. Virol.* 71(10):7827-7831, 1997), was digested with restriction endonucleases NcoI and BamHI to extract a 1.5 Kb fragment that was subsequently subcloned into pAcC4 (*Bio/Technology* 6:47-55, 1988), a derivative of pAc436. Generation of the recombinant baculovirus was achieved by co-transfecting 2 µg of the HIV p55 Gag pAcC4 shuttle vector with 0.5 µg of linearized, *Autographa californica* baculovirus (AcNPV) wild-type viral DNA into *Spodoptera frugiperda* (Sf9) cells (Kitts, P. A., Ayres M. D., and Possee R. D., Nucleic Acids Res. 18:5667-5672, 1990). The isolation of recombinant virus expressing HIV p55 Gag was performed according to standard techniques (O'Reilly, D. R., L. K. Miller, and V. A. Luckow, *Baculovirus Expression Vector: A Laboratory Manual*, W.H. Freeman and Company, New York, 1992).

Expression of the HIV p55 Gag was achieved using a 500 ml suspension culture of, Sf9 cells grown in serum-free medium (Miaorella, B., D. Inlow, A. Shauger, and D. Harano, *Bio/Technology* 6:1506-1510, 1988) that had been infected with the HIV p55 Gag recombinant baculovirus at a multiplicity of infection (MOI) of 10. Forty-eight hours post-infection, the supernatant was separated by centrifugation and filtered through a 0.2 µm filter. Aliquots of the supernatant were then transferred to Polyclear™ (Beckman Instruments, Palo Alto, Calif.) ultracentrifuge tubes, underlaid with 20% (wt/wt) sucrose, and subjected to 2 hours centrifugation at 24,00 rpm using a Beckman SW28 rotor.

Figure 4:
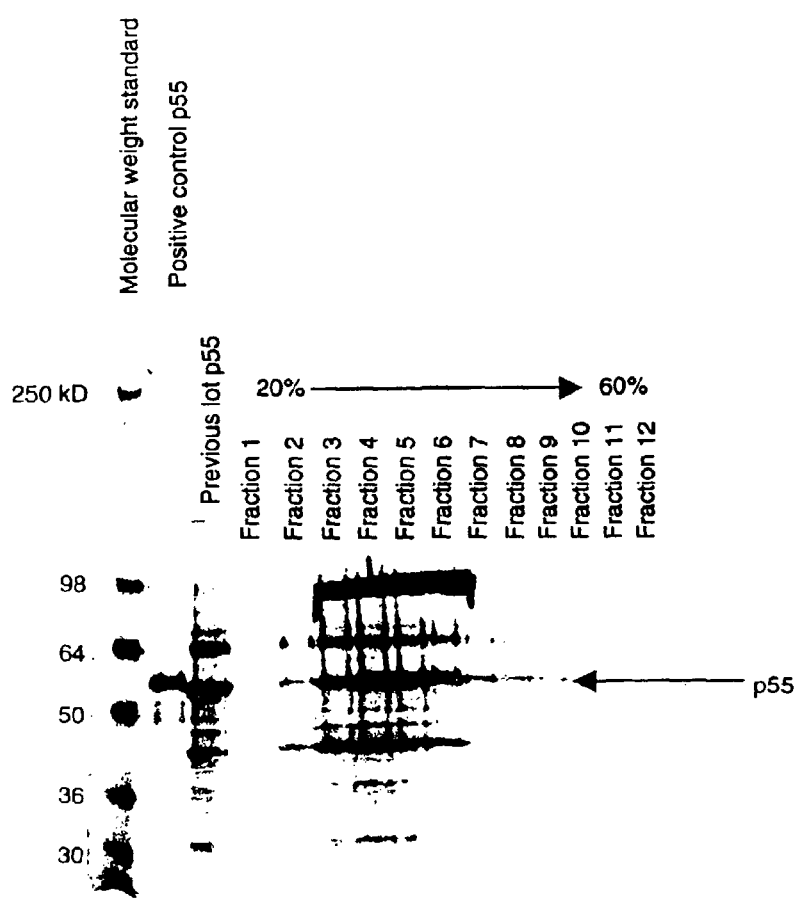
FIG. 4 presents an image of samples from a series of fractions which were electrophoresed on an 8-16% SDS polyacrylamide gel and the resulting bands visualized by commassie blue staining. The results show that the native p55 Gag virus-like particles (VLPs) banded at a sucrose density of range of 1.15-1.19 g/ml with the peak at approximately 1.17 g/ml.

The resulting pellet was suspended in Tris buffer (20 mM Tris HCl, pH 7.5, 250 mM NaCl, and 2.5 mM ethylenediaminetetraacetic acid [EDTA]), layered onto a 20-60% (wt/wt) sucrose gradient, and subjected to 2 hours centrifugation at 40,000 rpm using a Beckman SW41ti rotor. The gradient was then fractionated starting at the top (20% sucrose) of the gradient into approximately twelve 0.75 ml aliquots. A sample of each fraction was electrophoresed on 8-16% SDS polyacrylamide gels and the resulting bands were visualized after commassie staining (FIG. 4). Additional aliquots were subjected to refractive index analysis.

The results shown in FIG. 4 indicated that the p55 Gag virus-like particles banded at a sucrose density of range of 1.15-1.19 g/ml with the peak at approximately 1.17 g/ml. The peak fractions were pooled and concentrated by a second 20% sucrose pelleting. The resulting pellet was suspended in 1 ml of Tris buffer (described above). The total protein yield as estimated by Bicimchrominic Acid (BCA) (Pierce Chemical, Rockford, Ill.) was 1.6 mg.

B. Expression of Synthetic HIV p55 Gag

A baculovirus shuttle vector containing the synthetic p55 Gag sequence was constructed as follows. The synthetic HIV p55 expression cassette (Example 1) was digested with restriction enzyme SaiI followed by incubation with T4-DNA polymerase. The resulting fragment was isolated (PCR Clean-Up™, Promega, Madison, Wis.) and then digested with BamHI endonuclease. The shuttle vector pAcC13 (Munemitsu S., et al., *Mol Cell Biol.* 10(11):5977-5982, 1990) was linearized by digestion with EcoI, followed by incubation with T4-DNA polymerase, and then isolated (PCR Clean-Up™). The linearized vector was digested with BamHI, treated with alkaline phosphatase, and isolated by size fragmentation in an agarose gel. The isolated 1.5 kb fragment was ligated with the prepared pAcC13 vector. The resulting clone was designated pAcC13-Modif.p55Gag.

The expression conditions for the synthetic HIV p55 VLPs differed from those of the native p55 Gag as follows: a culture volume of 1 liter used instead of 500 ml; *Trichoplusia ni* (Tn5) (Wickham, T. J., and Nermerow, G. R., *BioTechnology Progress,* 9:25-30, 1993) insect cells were used instead of Sf9 insect cells; and, an MOI of 3 was instead of an MOI of 10. Experiments performed in support of the present invention showed that there was no appreciable difference in expression level between the Sf9 and Tn5 insect cells with the native p55 clone. In terms of MOI, experience with the native p55 clone suggested that an MOI of 10 resulted in higher expression (approximately 2-fold) of VLPs than a lower MOI.

Figure 5:
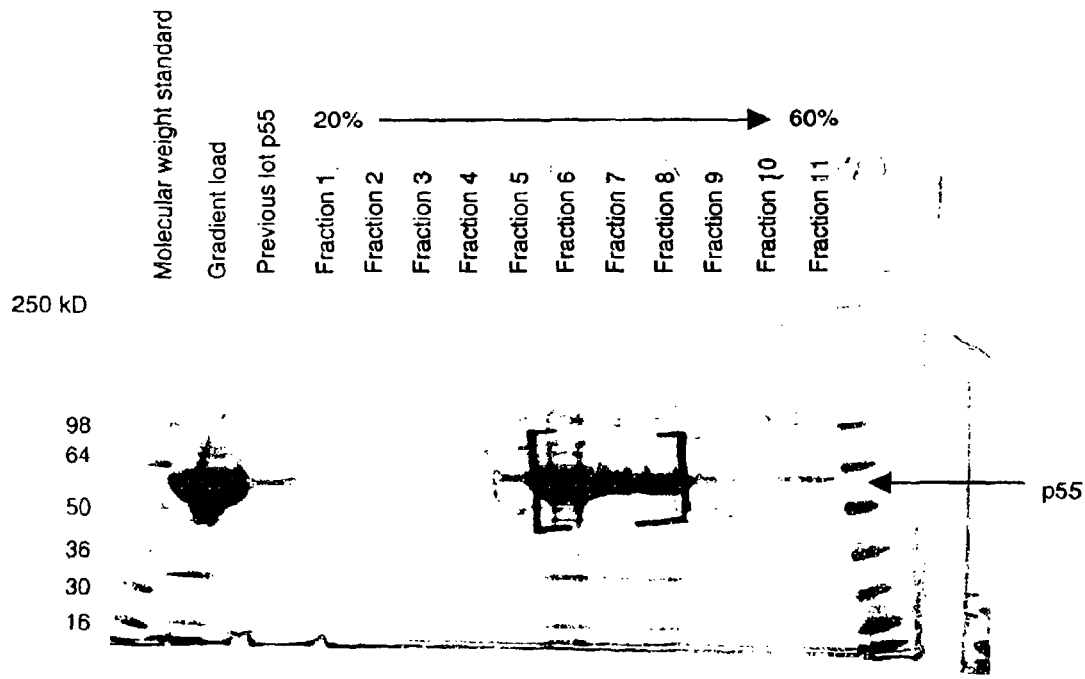
FIG. 5 presents an image similar to FIG. 4 where the analysis was performed using Gag VLPs produced by a synthetic Gag expression cassette.

The sucrose pelleting and banding methods used for the synthetic p55 VLPs were similar to those employed for the native p55 VLPs (described above), with the following exceptions: pelleted VLPs were suspended in 4 ml of phosphate buffered saline (PBS) instead of 1.0 ml of the Tris buffer; and four, 20-60% sucrose gradients were used instead of a single gradient. Also, due to the high concentration of banded VLPs, further concentration by pelleting was not required. The peak fractions from all 4 gradients were simply dialyzed against PBS. The approximate density of the banded VLPs ranged from 1.23-1.28 g/ml. A total protein yield as estimated by BCA was 46 mg. Results from the sucrose gradient banding of the synthetic p55 are shown in FIG. 5.

Figure 6:
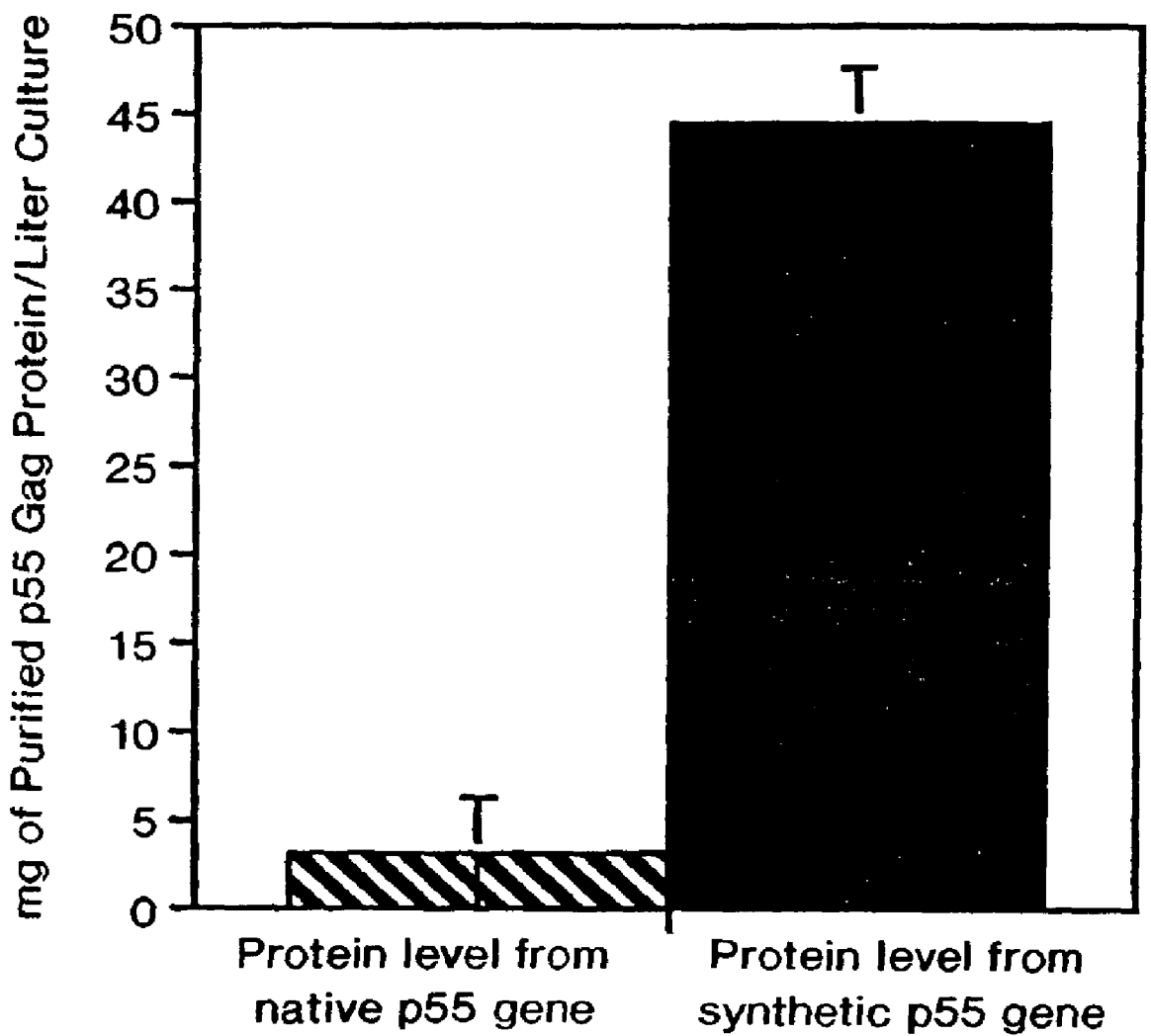
FIG. 6 presents a comparison of the total amount of purified HIV p55 Gag from several preparations obtained from two baculovirus expression cassettes encoding native and modified Gag.

A comparison of the total amount of purified HIV p55 Gag from several preparations obtained from the two baculovirus expression cassettes has been summarized in FIG. 6. The average yield from the native p55 was 3.16 mg/liter of culture (n=5, standard deviation (sd) ±1.07, range=1.8-4.8 mg/L) whereas the average yield from the synthetic p55 was more than ten-fold higher at 44.5 mg/liter of culture (n=2, sd=±6.4).

In addition to a higher total protein yield, the final product from the synthetic p55-expressed Gag consistently contained lower amounts of contaminating baculovirus proteins than the final product from the native p55-expressed Gag. This difference can be seen in the two commassie-stained gels FIGS. 4 and 5.

C. Expression of Native and Synthetic Gag-Core

Expression of the HIV p55 Gag/HCV Core 173 (SEQ ID NO:8) was achieved using a 2.5 liter suspension culture of Sf9 cells grown in serum-free medium (Miaorella, B., D. Inlow, A. Shauger, and D. Harano. 1988 Bio/Technology 6:1506-1510). The cells were infected with an HIV p55 Gag/HCV Core 173 recombinant baculovirus. Forty-eight hours post-infection, the supernatant was separated from the cells by centrifugation and filtered through a 0.2 µm filter. Aliquots of the supernatant were then transferred to a Polyclear™ (Beckman Instruments, Palo Alto, Calif.) ultracentrifuge tubes containing 30% (wt/wt) sucrose, and subjected to 2 hours of centrifugation at 24,000 rpm in a Beckman SW28 rotor and ultracentrifuge.

The resulting pellet was suspended in Tris buffer (50 mM Tris-HCl, pH 7.5, 500 mM NaCl) and layered onto a 30-60% (wt/wt) sucrose gradient and subjected to 2 hours centrifugation at 40,000 rpm in a Beckman SW41ti rotor and ultracentrifuge. The gradient was then fractionated starting at the top (30%) of the gradient into approximately 11×1.0 ml aliquots. A sample of each fraction was electrophoresed on 8-16% SDS polyacrylamide gels and the resulting bands were visualized after commassie staining.

A subset of aliquots were also subjected to Western blot analysis using monoclonal antibody 76C.5EG (Steimer, K. S., et al., *Virology* 150:283-290, 1986) which is specific for HIV p24 (a subunit of HIV p55). The peak fractions from the sucrose gradient were pooled and concentrated by a second 20% sucrose pelleting. The resulting pellet was suspended in 1 ml of buffer Tris buffer and the total protein yield as estimated by BCA (Pierce Chemical, Rockford, Ill.) was ~1.0 mg.

Figure 8:
FIG. 8 presents an image of wild-type Gag-HCV core expression samples from a series of fractions which were electrophoresed on an 8-16% SDS polyacrylamide gel and the resulting bands visualized by commassie staining.
Figure 9:
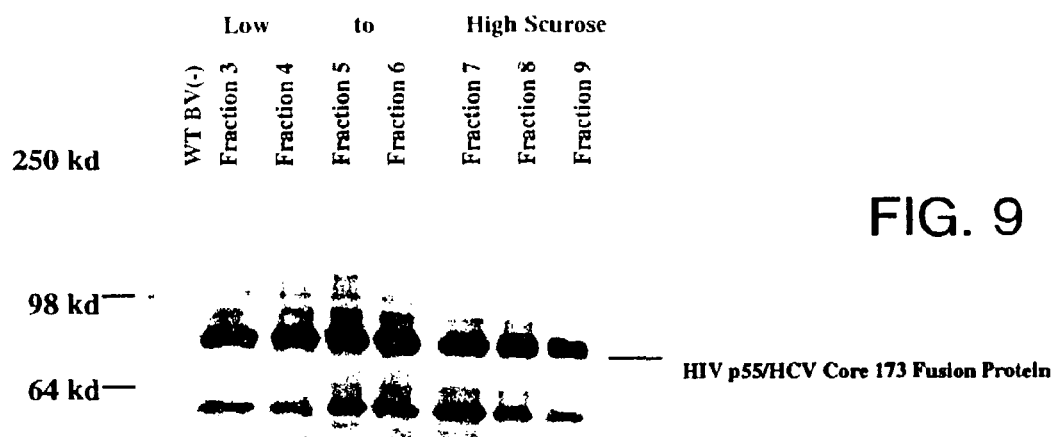
FIG. 9 shows the results of Western blot analysis of the gel shown presented in FIG. 8.

The results from the SDS PAGE are shown in FIG. 8 and the anti-p24 Western blot results are shown in FIG. 9. Taken together, these results indicate that the HIV p55 Gag/HCV Core 173 chimeric VLPs banded at a sucrose density similar to that of the HIV p55 Gag VLPs and the visible protein band that migrated at a molecular weight of ~72,000 kd was reactive with the HIV p24-specific monoclonal antibody. An additional immunoreactive band at approximately 55,000 kd also appeared to be reactive with the anti-p24 antibody and may be a degradation product.

Figure 10:
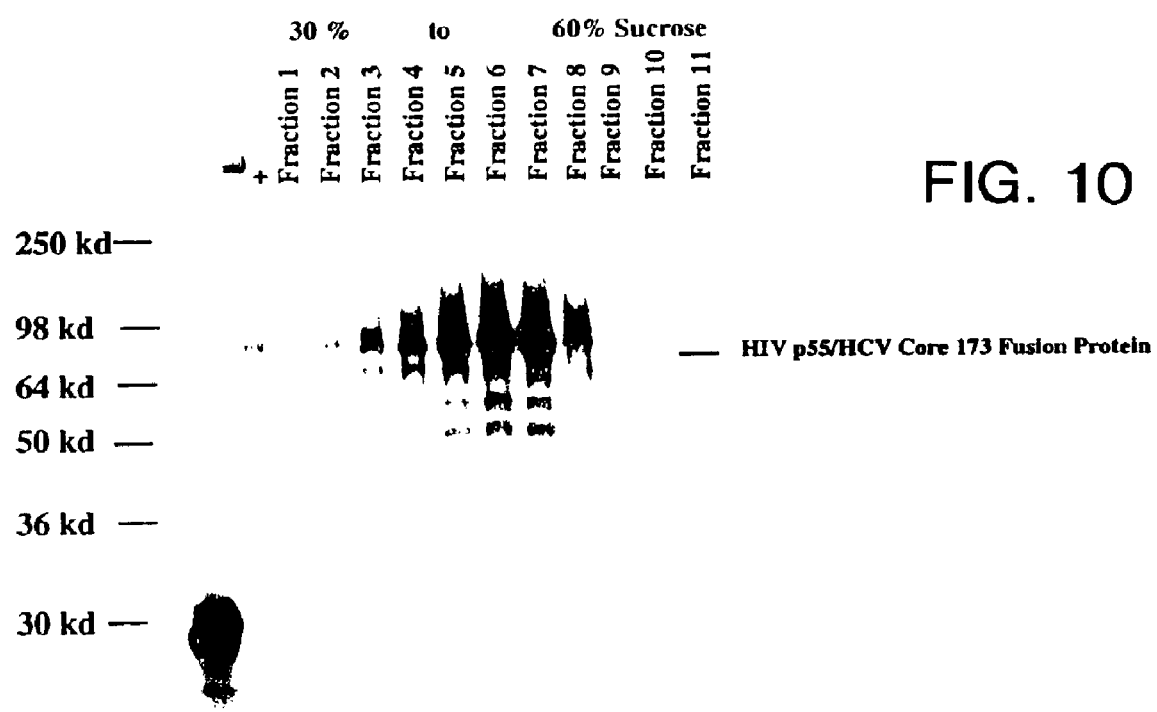
FIG. 10 presents results similar to those shown in FIG. 9. The results in FIG. 10 indicate that the main HCV Core-specific reactivity migrates at an approximate molecular weight of 72,000 kD, which is in accordance with the predicted molecular weight of the Gag-HCV core chimeric protein.
Figure 11A:
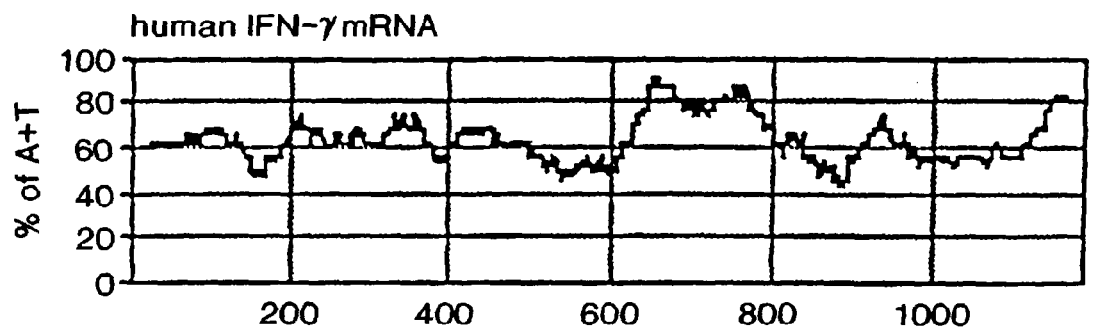
FIGS. 11A to 11D present a comparison of AT content, in percent, of cDNAs corresponding to an unstable human mRNA (human IFNγ mRNA; 11A), wild-type HIV Gag native RNA (11B), a stable human mRNA (human GAPDH mRNA; 11C), and synthetic HIV Gag RNA (11D).
Figure 11B:
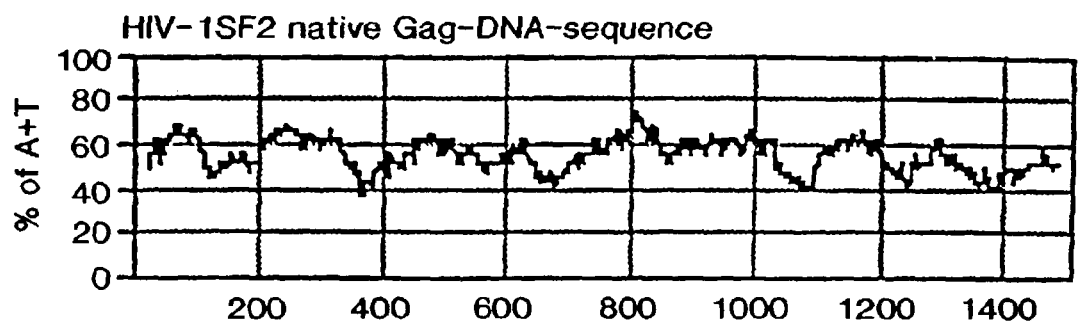
Figure 11C:
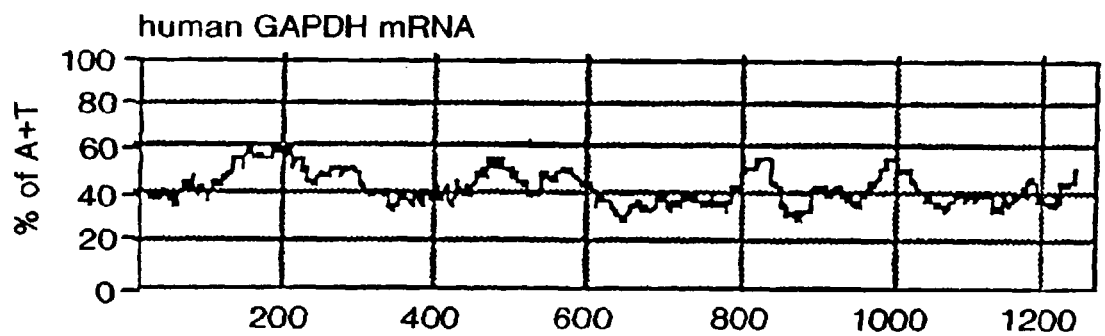
Figure 11D:
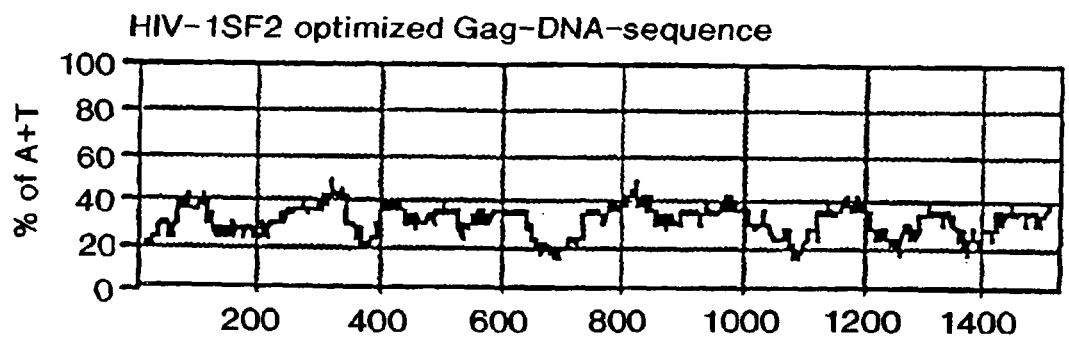

Although aliquots from the above preparation were not tested for reactivity with an HCV Core-specific antibody (an anti-CD22 rabbit serum), results from a similar preparation are shown in FIG. 10 and indicate that the main HCV Core-specific reactivity migrates at an approximate molecular weight of 72,000 kd which is in accordance with the predicted molecular weight of the chimeric protein.

The expression conditions for the synthetic HIV p55 Gag/HCV Core 173 (SEQ ID NO:8) VLPs differed from those of the native p55 Gag and are as follows: a culture volume of 1 liter used instead of 2.5 liters, *Trichoplusia ni* (Tn5) (Wickham, T. J., and Nemerow, G. R. 1993 BioTechnology Progress, 9:25-30) insect cells were used instead of Sf9 insect cells and an MOI of 3 was instead of an MOI of 10. The sucrose pelleting and banding methods used for the synthetic HIV p55 Gag/HCV Core 173 VLPs were similar to those employed for the native HIV p55 Gag/HCV Core 173 VLPs. However, differences included: pelleted VLPs were suspended in 1 ml of phosphate buffered saline (PBS) instead of 1.0 ml of the Tris buffer, and a single 20-60% sucrose gradients was used. A comparison of the total amount of purified HIV p55 Gag/HCV Core 173 from multiple preparations obtained from the two baculovirus expression cassettes showed that there was an increase in expression using the synthetic HIV p55 Gag/HCV Core 173 cassette.

D. Alternative Method for the Enrichment of HIV p55 Gag VLPs

In addition to purification from the media, p55 (Gag protein) expressed in baculovirus (e.g., using a synthetic expression cassette of the present invention) can also be purified as virus-like particles from the infected insect cells. For example, forty-eight hours post infection, the media and cell pellet are separated by centrifugation and the cell pellet is stored at −70° C. until future use. At the time of processing, the cell pellet is suspended in 5 volumes of hypotonic lysis buffer (20 mM Tris-HCl, pH 8.2, 1 mM EGTA; 1 mM MgCl, and Complete Protease Inhibitor® (Boehringer Mannheim Corp., Indianapolis, Ind.]). If needed, the cells are then dounced 8-10 times to complete cell lysis.

The lysate is then centrifuged at approximately 1000-1500×g for 20 minutes. The supernatant is decanted into UltraClear™ tubes, underlayed with 20% sucrose (w/w) and centrifuged at 24,000 rpm in SW28 buckets for 2 hours. The resulting pellet is suspended in Tris buffer (20 mM Tris HCl, pH 7.5, 250 mM NaCl, and 2.5 mM ethylene-diamine-tetraacetic acid (EDTA) with 0.1% IGEPAL detergent (Sigma Chemical, St. Louis, Mo.) and 250 units/ml of benzonase (American International Chemical, Inc., Natick, Mass.) and incubated at 4° C. for at least 30 minutes. The suspension is subsequently layered onto a 20-60% sucrose gradient and spun at 40,000 rpm using an SW41ti rotor for 20-24 hours.

After ultracentrifugation, the sucrose gradient is fractionated and aliquots run on SDS PAGE to identify peak fractions. The peak fractions are dialyzed against PBS and measured for protein content. Negatively stained electron mircographs typically show non-enveloped VLPs somewhat smaller in diameter (80-120 nm) than the budded VLPs. HIV Gag VLPs prepared in this manner are also capable of generating Gag-specific CTL responses in mice.

Example 8

In Vivo Immunogenicity of Synthetic Gag Expression Cassettes

A. Immunization

To evaluate the possibly improved immunogenicity of the synthetic Gag expression cassettes, a mouse study was performed. The plasmid DNA, pCMVKM2 carrying the synthetic Gag expression cassette, was diluted to the following final concentrations in a total injection volume of 100 μl: 20 μg, 2 μg, 0.2 μg, and 0.02 μg. To overcome possible negative dilution effects of the diluted DNA, the total DNA concentration in each sample was brought up to 20 μg using the vector (pCMVKM2) alone. As a control, plasmid DNA of the native Gag expression cassette was handled in the same manner. Twelve groups of four Balb/c mice (Charles River, Boston, Mass.) were intramuscularly immunized (50 μl per leg, intramuscular injection into the tibialis anterior) according to the schedule in Table 7.

TABLE 7

| Group | Gag Expression Cassette | Concentration of Gag plasmid DNA (μg) | Immunized at time (weeks): |
|---|---|---|---|
| 1 | Synthetic | 20 | 0[1], 4 |
| 2 | Synthetic | 2 | 0, 4 |
| 3 | Synthetic | 0.2 | 0, 4 |
| 4 | Synthetic | 0.02 | 0, 4 |
| 5 | Synthetic | 20 | 0 |
| 6 | Synthetic | 2 | 0 |
| 7 | Synthetic | 0.2 | 0 |
| 8 | Synthetic | 0.02 | 0 |
| 9 | Native | 20 | 0 |
| 10 | Native | 2 | 0 |
| 11 | Native | 0.2 | 0 |
| 12 | Native | 0.02 | 0 |

[1] = initial immunization at "week 0"
Groups 1-4 were bled at week 0 (before immunization), week 4, week 6, week 8, and week 12.
Groups 5-12 were bled at week 0 (before immunization) and at week 4.

B. Humoral Immune Response

The humoral immune response was checked with an anti-HIV Gag antibody ELISAs (enzyme-linked immunosorbent assays) of the mice sera 0 and 4 weeks post immunization (groups 5-12) and, in addition, 6 and 8 weeks post immunization, respectively, 2 and 4 weeks post second immunization (groups 1-4).

The antibody titers of the sera were determined by anti-Gag antibody ELISA. Briefly, sera from immunized mice were screened for antibodies directed against the HIV p55 Gag protein. ELISA microtiter plates were coated with 0.2 μg of HIV-1$_{SF2}$ p24-Gag protein per well overnight and washed four times; subsequently, blocking was done with PBS-0.2% Tween (Sigma) for 2 hours. After removal of the blocking solution, 100 μl of diluted mouse serum was added. Sera were tested at ⅕₂₅ dilutions and by serial 3-fold dilutions, thereafter. Microtiter plates were washed four times and incubated with a secondary, peroxidase-coupled anti-mouse IgG antibody (Pierce, Rockford, Ill.). ELISA plates were washed and 100 μl of 3,3',5,5'-tetramethyl benzidine (TMB; Pierce) was added per well. The optical density of each well was measured after 15 minutes. The titers reported are the reciprocal of the dilution of serum that gave a half-maximum optical density (O.D.). The ELISA results are presented in Table 8.

TABLE 8

| Group | Inoculum (μg) | Expression cassette | Sera - Week 4[3] | Sera - Week 6 | Sera - Week 8 |
|---|---|---|---|---|---|
| 1 | 20 | S[1] - gag | 98 | 455 | 551 |
| 2 | 2 | S - gag | 59 | 1408 | 227 |
| 3 | 0. | S - gag | 29 | 186 | 61 |
| 4 | 0.02 | S - gag | <20 | <20 | <20 |
| 5 | 20 | S - gag | 67 | n.a.[4] | n.a. |
| 6 | 2 | S - gag | 63 | n.a. | n.a. |
| 7 | 0. | S - gag | 57 | n.a. | n.a. |
| 8 | 0.02 | S - gag | <20 | n.a. | n.a. |
| 9 | 20 | N[2] - gag | 43 | n.a. | n.a. |
| 10 | 2 | N - gag | <20 | n.a. | n.a. |
| 11 | 0. | N - gag | <20 | n.a. | n.a. |
| 12 | 0.02 | N - gag | <20 | n.a. | n.a. |

[1] = synthetic gag expression cassette (SEQ ID NO: 4)
[2] = native gag expression cassette (SEQ ID NO: 1)
[3] = geometric mean antibody titer
[4] = not applicable The results of the mouse immunizations with plasmid-DNAs show that the synthetic expression cassettes provide a clear improvement of immunogenicity relative to the native expression cassettes. Also, the second boost immunization induced a secondary immune response after two weeks (groups 1-3).

C. Cellular Immune Response

The frequency of specific cytotoxic T-lymphocytes (CTL) was evaluated by a standard chromium release assay of peptide pulsed Balb/c mouse CD4 cells. Gag expressing vaccinia virus infected CD-8 cells were used as a positive control (vvGag). Briefly, spleen cells (Effector cells, E) were obtained from the BALB/c mice immunized, as described above (Table 8) were cultured, restimulated, and assayed for CTL activity against Gag peptide-pulsed target cells as described (Doe, B., and Walker, C. M., *AIDS* 10(7):793-794, 1996). The HIV-1$_{SF2}$ Gag peptide used was p7g SEQ ID NO:10. Cytotoxic activity was measured in a standard $^{51}$Cr release assay. Target (T) cells were cultured with effector (E) cells at various E:T ratios for 4 hours and the average cpm from duplicate wells was used to calculate percent specific $^{51}$Cr release. The results are presented in Table 9.

Cytotoxic T-cell (CTL) activity was measured in splenocytes recovered from the mice immunized with HIV Gag DNA (compare Effector column, Table 9, to immunization schedule, Table 8). Effector cells from the Gag DNA-immunized animals exhibited specific lysis of Gag p7g peptide-pulsed SV-BALB (MHC matched) targets cells indicative of a CTL response. Target cells that were peptide-pulsed and derived from an MHC-unmatched mouse strain (MC57) were not lysed (Table 9; MC/p7g).

TABLE 9

Cytotoxic T-lymphocyte (CTL) responses in mice immunized with HIV-1 gag DNA

| | | Percent specific lysis of target cells* | | |
|---|---|---|---|---|
| Immunization | E:T | SVBALB none | SVBALB p7g | RMA p7g |
| 20 μg DNA gagmod | 100:1 | 2 | 49 | <1 |
| | 30:1 | 3 | 30 | <1 |
| | 10:1 | <1 | 14 | <1 |
| 2 μg DNA gagmod | 100:1 | 2 | 37 | <1 |
| | 30:1 | 2 | 21 | <1 |
| | 10:1 | <1 | 13 | <1 |
| 0.2 μg DNA gagmod | 100:1 | 2 | 32 | <1 |
| | 30:1 | 3 | 25 | <1 |
| | 10:1 | 1 | 14 | <1 |
| 0.02 μg DNA gagmod | 100:1 | 1 | 17 | <1 |
| | 30:1 | 1 | 16 | <1 |
| | 10:1 | 1 | 8 | <1 |
| 20 μg DNA gag native | 100:1 | 2 | 49 | <1 |
| | 30:1 | 2 | 24 | <1 |
| | 10:1 | 1 | 12 | <1 |
| 2 μg DNA gag native | 100:1 | <1 | 18 | <1 |
| | 30:1 | 1 | 14 | <1 |
| | 10:1 | 1 | 7 | <1 |
| 0.2 μg DNA gag native | 100:1 | 3 | 30 | <1 |
| | 30:1 | 3 | 17 | <1 |
| | 10:1 | 2 | 7 | <1 |
| 0.02 μg DNA gag native | 100:1 | 4 | 2 | <1 |
| | 30:1 | 1 | 2 | <1 |
| | 10:1 | 1 | 2 | <1 |

*representative results of two animals per DNA-dose; positive CTL responses are indicated by boxed data The results of the CTL assays show increased potency of synthetic Gag expression cassettes for induction of cytotoxic T-lymphocyte (CTL) responses by DNA immunization.

Example 9

In Vivo Immunization with Env Polypeptides

A. Immunogenicity Study of US4 o-gp140 in Ras-3c Adjuvant System

Studies have been conducted using rabbits immunized with US4 o-gp140 purified as described above. Studies are also underway in animals to determine immunogenicity of US4 gp120, SF162 o-gp140 and SF162 gp120.

Two rabbits (#1 and #2) were immunized intramuscularly at 0, 4, 12 and 24 weeks with 50 μg of US4 o-gp140 in the Ribi™ adjuvant system (RAS-3c), (Ribi Immunochem, Hamilton, Mont.) containing 2% Squalene, 0.2% Tween 80, and one or more bacterial cell wall components from the group consisting of monophosphorylipid A (MPL, Ribi Immunochem, Hamilton, Mont.). In each experiment described herein, o-gp140 can be native, mutated and/or modified. Antibody responses directed against the US4 o-gp140 protein were measured by ELISA. Results are shown in Table 10.

TABLE 10

| Rabbit/sample | Approximate o-gp140 ELISA titer |
|---|---|
| pre-immunization | 0 |
| #1: post1 (0 week immuniz) | 400 |
| #1: post2 (4 week immuniz) | 15,000 |
| #1: post3 (12 week immuniz) | 50,000 |
| #1: post4 (24 week immuniz) | 100,000 |
| #2: post1 (0 week immuniz) | 600 |
| #2: post2 (4 week immuniz) | 12,000 |
| #2: post3 (12 week immuniz) | 25,000 |
| #2: post4 (24 week immuiz) | 55,000 |

The avidities of antibodies directed against the US4 o-gp140 protein were measured in a similar ELISA format employing successive washes with increasing concentrations of ammonium isothiocynate. Results are shown in Table 11.

TABLE 11

| Time of sample | Approx. Antibody avidity (NH$_4$HCN Conc. in M) |
|---|---|
| pre-immunization | 0.02 |
| post1 (0 week immuniz) | 1.8 |
| post2 (4 week immuniz) | 3.5 |
| post3 (12 week immuniz) | 5.5 |
| post4 (24 week immuniz) | 5.1 |

These results show that US4 o-gp140 is highly immunogenic and able to induce substantial antibody responses after only one or two immunizations.

B. Immunogenicity of US4 o-gp140 in MF59-Based Adjuvants

Groups of 4 rabbits were immunized intramuscularly at 0, 4, 12 and 24 weeks with various doses of US4 o-gp140 protein in three different MF59-based adjuvants (MF59 is described in International Publication No. WO 90/14837 and typically contains 5% Squalene, 0.5% Tween 80, and 0.5% Span 85). Antibody titers were measured post-third by ELISA using SF2 gp120 to coat the plates. QHC is a quill-based adjuvant (Iscotek, Uppsala, Sweden). Results are shown in Table 12.

TABLE 12

| Antigen dose (μg) | Adjuvant | Anti-gp120$_{SF2}$ Ab GMT* |
|---|---|---|
| 12.5 | MF59 | 7231 |
| 25 | MF59 | 8896 |
| 50 | MF59 | 12822 |
| 12.5 | MF59/MPL | 24146 |
| 25 | MF59/MPL | 27199 |
| 50 | MF59/MPL | 23059 |
| 50 | MF59/MPL/QHC | 31759 |

*GMT = geometric mean titer

Thus, adjuvanted o-gp140 generated antigen-specific antibodies. Further, the antibodies were shown to increased in avidity over time.

C. Neutralizing Antibodies

Neutralizing antibodies post-third immunization were measured against HIV-1 SF2 in a T-cell line adapted virus (TCLA) assay and against PBMC-grown HIV-1 variants SF2, SF162 and 119 using the CCR5+ CEMx174 LTR-GFP reporter cell line, 5.25 (provided by N. Landau, Salk Institute, San Diego, Calif.) as target cells. Results are shown in Table 13.

TABLE 13

Neutralizing antibody responses in rabbits immunized with o-gp140.modUS4 protein

| Group | Animal | SF2 TCLA* | SF2 PBMC[#] | SF162 PBMC[#] | 119 PBMC[#] |
|---|---|---|---|---|---|
| Experiment 1 | | | | | |
| o-gp140/ | 217 | >640 | 100% | 49 | 17 |
| Ras-3c | 218 | >640 | 96 | 37 | 29 |
| 50 mg | | | | | |
| Experiment 2 | | | | | |
| o-gp140/ | 792 | 45 | 71 | 39 | 26 |
| MF59 | 793 | 50 | 87 | 26 | 4 |
| 50 mg | 794 | 59 | 87 | 13 | 0 |
| | 795 | 128 | 92 | 15 | 0 |
| o-gp140/ | 804 | 173 | 91 | 47 | 18 |
| MF59 + MPL | 805 | 134 | 93 | 28 | 4 |
| 50 mg | 806 | N.D.** | 95 | 49 | 13 |
| | 807 | 441 | 100 | 31 | 15 |
| o-gp140/MF59 + | 808 | 465 | 98 | 46 | 40 |
| MPL + QHC | 809 | 496 | 100 | 44 | 39 |
| 50 mg | 810 | >640 | 101 | 27 | 4 |
| | 811 | 92 | 92 | 24 | 37 |

*TCLA neutralizing antibody titers (50% inhibition).
**Not Determined
[#]% Inhibition at 1:10 dilution of sera with any detectable non-specific inhibition in pre-bleeds subtracted.

The above studies in rabbits indicate that the US4 o-gp140 protein is highly immunogenic. When administered with adjuvant, this protein was able to induce substantial antibody responses after only one or two immunizations. Moreover, the adjuvanted o-gp140 protein was able to generate antigen-specific antibodies which increased in avidity after successive immunizations, and substantial neutralizing activity against T-cell line adapted HIV-1. Neutralizing activity was also observed against PBMC-grown primary HIV strains, including the difficult to neutralize CCR5 co-receptor (R5)-utilizing isolates, SF162 and 119.

Example 10

In Vivo Immunogenicity of Synthetic Env Expression Cassettes

A. General Immunization Methods

To evaluate the immunogenicity of the synthetic Env expression cassettes, studies using guinea pigs, rabbits, mice, rhesus macaques and baboons were performed. The studies were structured as follows: DNA immunization alone (single or multiple); DNA immunization followed by protein immunization (boost); DNA immunization followed by Sindbis particle immunization; immunization by Sindbis particles alone.

B. Humoral Immune Response

The humoral immune response was checked in serum specimens from immunized animals with an anti-HIV Env antibody ELISAs (enzyme-linked immunosorbent assays) at various times post-immunization. The antibody titers of the sera were determined by anti-Env antibody ELISA as described above. Briefly, sera from immunized animals were screened for antibodies directed against the HIV gp120 or gp140 Env protein. Wells of ELISA microtiter plates were coated overnight with the selected Env protein and washed four times; subsequently, blocking was done with PBS-0.2% Tween (Sigma) for 2 hours. After removal of the blocking solution, 100 μl of diluted mouse serum was added. Sera were tested at 1/25 dilutions and by serial 3-fold dilutions, thereafter. Microtiter plates were washed four times and incubated with a secondary, peroxidase-coupled anti-mouse IgG antibody (Pierce, Rockford, Ill.). ELISA plates were washed and 100 μl of 3,3', 5,5'-tetramethyl benzidine (TMB; Pierce) was added per well. The optical density of each well was measured after 15 minutes. Titers are typically reported as the reciprocal of the dilution of serum that gave a half-maximum optical density (O.D.).

Example 11

DNA-immunization of Baboons Using Synthetic Gag Expression Cassettes

A. Baboons

Four baboons were immunized 3 times (weeks 0, 4 and 8) bilaterally, intramuscular into the quadriceps using 1 mg pCMVKM2.GagMod.SF2 plasmid-DNA (Example 1). The animals were bled two weeks after each immunization and a p24 antibody ELISA was performed with isolated plasma. The ELISA was performed essentially as described in Example 5 except the second antibody-conjugate was an anti-human IgG, g-chain specific, peroxidase conjugate (Sigma Chemical Co., St. Louis, Md. 63178) used at a dilution of 1:500. Fifty μg/ml yeast extract was added to the dilutions of plasma samples and antibody conjugate to reduce non-specific background due to preexisting yeast antibodies in the baboons. The antibody titer results are presented in Table 14.

TABLE 14

| Immunization no. | Weeks | Antigen | wpi[a]/Baboon No. | Ab-titer[b] |
|---|---|---|---|---|
| 1 | 0 | gagmod DNA | 0 w/219 | <10 |
| | | | 0 w/220 | <10 |
| | | | 0 w/221 | <10 |
| | | | 0 w/222 | <10 |
| | 6 | | 2 wp 1st/219 | <10 |
| | | | 2 wp 1st/220 | <10 |
| | | | 2 wp 1st/221 | <10 |
| | | | 2 wp 1st/222 | 15 |
| 4 | 14 | gagmod DNA | 2 wp 4th/219 | <10 |
| | | | 2 wp 4th/220 | 88 |
| | | | 2 wp 4th/221 | <10 |
| | | | 2 wp 4th/222 | 56 |
| 5 | 30 | gagmod DNA | 2 wp 5th/219 | <10 |
| | | | 2 wp 5th/220 | 391 |
| | | | 2 wp 5th/221 | 237 |
| | | | 2 wp 5th/222 | 222 |
| 6 | 46 | gag VLP protein | 2 wp 6th/219 | 753 |
| | | | 2 wp 6th/219 | 4330 |
| | | | 2 wp 6th/219 | 5000 |
| | | | 2 wp 6th/219 | 2881 |

[a]wpi = weeks post immunization
[b]geometric mean antibody titer

In Table 14, pre-bleed data are given as Immunization No. 0; data for bleeds taken 2 weeks post-first immunization are given as Immunization No. 1; data for bleeds taken 2 weeks post-second immunization are given as Immunization No. 2; and, data for bleeds taken 2 weeks post-third immunization are given as Immunization No. 3.

Further, lymphoproliferative responses to p24 antigen were also observed in baboons 221 and 222 two weeks post-fourth immunization (at week 14), and enhanced substantially post-boosting with VLP (at week 44 and 76). Such proliferation results are indicative of induction of T-helper cell functions.

B. Rhesus Macaques

The improved potency of the codon-modified gag expression plasmid observed in mouse and baboon studies was confirmed in rhesus macaques. Four of four macaques had detectable Gag-specific CTL after two or three 1 mg doses of modified gag plasmid. In contrast, in a previous study, only one of four macaques given 1 mg doses of plasmid-DNA encoding the wild-type HIV-1$_{SF2}$ Gag showed strong CTL activity that was not apparent until after the seventh immunization. Further evidence of the potency of the modified gag plasmid was the observation that CTL from two of the four rhesus macaques reacted with three nonoverlapping Gag peptide pools, suggesting that as many as three different Gag peptides are recognized and indicating that the CTL response is polyclonal. Additional quantification and specificity studies are in progress to further characterize the T cell responses to Gag in the plasmid-immunized rhesus macaques. DNA immunization of macaques with the modified gag plasmid did not result in significant antibody responses, with only two of four animals seroconverting at low titers. In contrast, in the same study the majority of macaques in groups immunized with p55Gag protein seroconverted and had strong Gag-specific antibody titers. These data suggest that a prime-boost strategy (DNA-prime and protein-boost) could be very promising for the induction of a strong CTL and antibody response.

In sum, these results demonstrate that the synthetic Gag plasmid DNA is immunogenic in non-human primates. When similar experiments were carried out using wild-type Gag plasmid DNA no such induction of anti-p24 antibodies was observed after four immunizations.

Example 12

DNA- and Protein Immunizations of Animals Using Env Expression Cassettes and Polypeptides A. Guinea Pigs Groups comprising six guinea pigs each were immunized intramuscularly at 0, 4, and 12 weeks with plasmid DNAs encoding the gp120.modUS4, gp140.modUS4, gp140.modUS4.delV1, gp140.modUS4.delV2, gp140.modUS4.delV1/V2, or gp160.modUS4 coding sequences of the US4-derived Env. The animals were subsequently boosted at 18 weeks with a single intramuscular dose of US4 o-gp140.mut.modUS4 protein in MF59 adjuvant. Anti-gp120 SF2 antibody titers (geometric mean titers) were measured at two weeks following the third DNA immunization and at two weeks after the protein boost. Results are shown in Table 15.

TABLE 15

| Group | GMT post-DNA immuniz. | GMT post-protein boost |
|---|---|---|
| gp120.modUS4 | 2098 | 9489 |
| gp140.modUS4 | 190 | 5340 |
| gp140.modUS4.delV1 | 341 | 7808 |
| gp140.modUS4.delV2 | 386 | 8165 |
| gp140.modUS4.delV1/V2 | 664 | 8270 |
| gp160.modUS4 | 235 | 9928 |

These results demonstrate the usefulness of the synthetic constructs to generate immune responses, as well as, the advantage of providing a protein boost to enhance the immune response following DNA immunization.

B. Rabbits

Rabbits were immunized intramuscularly and intradermally using a Bioject needless syringe with plasmid DNAs encoding the following synthetic SF162 Env polypeptides: gp120.modSF162, gp120.modSF162.delV2, gp140.modSF162, gp140.modSF162.delV2, gp140.mut.modSF162, gp140.mut.modSF162.delV2, gp160.modSF162, and gp160.modSF162.delV2. Approximately 1 mg of plasmid DNA (pCMVlink) carrying the synthetic Env expression cassette was used to immunize the rabbits. Rabbits were immunized with plasmid DNA at 0, 4, and 12 weeks. At two weeks after the third immunization all of the constructs were shown to have generated significant antibody titers in the test animals. Further, rabbits immunized with constructs containing deletions of the V2 region generally generated similar antibody titers relative to rabbits immunized with the companion construct still containing the V2 region.

The nucleic acid immunizations are followed by protein boosting with o-gp140.modSF162.delV2 (0.1 mg of purified protein) at 24 weeks after the initial immunization. Results are shown in Table 16.

TABLE 16

| Group | GMT 2 wks post-2nd DNA immunization | GMT 2 wks post-3rd DNA immunization | GMT 2 wks post-protein boost |
|---|---|---|---|
| gp120.modSF162 | 4573 | 5899 | 26033 |
| gp120.modSF162.delV2 | 3811 | 3122 | 29606 |
| gp140.modSF162 | 1478 | 710 | 12882 |
| gp140.modSF162.delV2 | 1572 | 819 | 11067 |
| gp140.mut.modSF162 | 1417 | 788 | 8827 |
| gp140.mut.modSF162.delV2 | 1378 | 1207 | 13301 |
| gp160.modSF162 | 23 | 81 | 7050 |
| gp160.modSF162.delV2 | 85 | 459 | 11568 |

All constructs are highly immunogenic and generate substantial antigen binding antibody responses after only 2 immunizations in rabbits.

C. Baboons

Groups of four baboons were immunized intramuscularly with 1 mg doses of DNA encoding different forms of synthetic US4 gp140 (see the following table) at 0, 4, 8, 12, 28, and 44 weeks. The animals were also boosted twice with US4 o-gp140 protein (gp140.mut.modUS4) at 44 and 76 weeks using MF59 as adjuvant. Results are shown in Table 17.

TABLE 17

| Animal | Treatment | 2 Wks Post 5th DNA immunization | 2 Wks post 6th DNA (plus o-gp140 prot.immuniz.) | 2 Wks post 7th DNA (o-gp140 protein only) |
|---|---|---|---|---|
| CY 215 | gp140.modUS4 | 8.3 | 446 | 1813 |
| CY 216 | | 8.3 | 433 | 1236 |
| CY 217 | | 68 | 1660 | 2989 |
| CY 218 | | 101 | 2556 | 1610 |
| Geomean: | | 26.2 | 951.4 | 1812.1 |
| CY 219 | gp140.modUS4 + | 8.3 | 8.3 | 421 |
| CY 220 | p55gag.SF2 | 8.3 | 8.3 | 3117 |
| CY 221 | | 8.3 | 954 | 871 |
| CY 222 | | 8.3 | 71 | 916 |
| Geomean: | | 8.3 | 46.5 | 1011.5 |
| CY 223 | gp140.mut.modUS4 | 41.4 | 10497 | 46432 |
| CY 224 | | 8.3 | 979 | 470 |
| CY 225 | | 135 | 2935 | 3870 |
| CY 226 | | 47 | 1209 | 4009 |
| Geomean: | | 68.3 | 2457.4 | 4289.6 |
| CY 227 | gp140TM.modUS4 | 8.3 | 56 | 5001 |
| CY 228 | | 8.3 | 806 | 1170 |
| CY 229 | | 8.3 | 48 | 3402 |
| CY 230 | | 8.3 | 38 | 6520 |
| GMT*: | | 8.3 | 95.3 | 3375.3 |

*GMT = geometric mean titer

The results in Table 17 demonstrate the usefulness of the synthetic constructs to generate immune responses in primates such as baboons. In addition, all animals showed evidence of antigen-specific (Env antigen) lymphopro-liferative responses.

D. Rhesus Macaques

Two rhesus macaques (designated H445 and J408) were immunized with 1 mg of DNA encoding SF162 gp140 with a deleted V2 region (SF162.9p140.delV2) by intramuscular (IM) and intradermal (ID) routes at 0, 4, 8, and 28 weeks. Approximately 100 µg of the protein encoded by the SF162.gp140mut.delV2 construct was also administered in MF59 by IM delivery at 28 weeks.

ELISA titers are shown in FIG. 61. Neutralizing antibody activity is shown Tables 18 and 19. Neutralizing antibody activity was determined against a variety of primary HIV-1 isolates in a primary lymphocyte or "PBMC-based" assay (see the following tables). Further, the phenotypic co-receptor usage for each of the primary isolates is indicated. As can be seen in the tables neutralizing antibodies were detected against every isolate tested, including the HIV-1 primary isolates (i.e., SF128A, 92US660, 92HT593, 92US657, 92US714, 91US056, and 91US054).

TABLE 18

| | Treatment | | Bleed 0 | Bleed 1 | Bleed 2 |
|---|---|---|---|---|---|
| Animal | 1st Immunization | 2nd Immunization | 1st Imm'n | 2nd Imm'n | 2 Wks post 2nd |
| EO 456 | 25 µg 120mod | (None) | 8.3 | 45 | 309 |
| EO 457 | DNA | | 8.3 | 254 | 460 |
| EO 458 | | | 8.3 | 8.3 | 93 |
| EO 459 | | | 8.3 | 43 | 45 |
| EO 460 | | | 8.3 | 8.3 | 274 |
| EO 461 | 25 µg 120mod | 25 µg 120mod | 8.3 | 47 | 1502 |
| EO 462 | DNA | DNA | 8.3 | 80 | 5776 |
| EO 463 | | | 8.3 | 89 | 3440 |
| EO 464 | | | 8.3 | 8.3 | 3347 |
| EO 465 | | | 8.3 | 69 | 1127 |

TABLE 18-continued

| Animal | Treatment | | Bleed 0 1st Imm'n | Bleed 1 2nd Imm'n | Bleed 2 2 Wks post 2nd |
| --- | --- | --- | --- | --- | --- |
| | 1st Immunization | 2nd Immunization | | | |
| EO 466 | 50 µg 120mod | (None) | 8.3 | 63 | 102 |
| EO 467 | DNA | | 8.3 | 112 | 662 |
| EO 468 | | | 8.3 | 94 | 459 |
| EO 469 | | | 8.3 | 58 | 48 |
| EO 470 | | | 8.3 | 95 | 355 |
| EO 471 | 50 µg 120mod | 50 µg 120mod | 8.3 | 110 | 9074 |
| EO 472 | DNA | DNA | 8.3 | 8.3 | 4897 |
| EO 473 | | | 8.3 | 49 | 4089 |
| EO 474 | | | 8.3 | 59 | 5280 |
| EO 475 | | | 8.3 | 8.3 | 929 |
| EO 476 | 25 µg 120mod | Sindbis/Env | 8.3 | | 653 |
| EO 477 | DNA | | 8.3 | 87 | 22675 |
| EO 478 | | | 8.3 | 76 | 3869 |
| EO 479 | | | 8.3 | | 1004 |
| EO 480 | | | 8.3 | 71 | 7080 |

TABLE 19

| Animal | Treatment | | Bleed 0 1st Imm'n | Bleed 1 2nd Imm'n | Bleed 2 2 Wks post 2nd |
| --- | --- | --- | --- | --- | --- |
| | 1st Immunization | 2nd Immunization | | | |
| EO 481 | Sindbis/Env | (None) | 8.3 | 8.3 | 8.3 |
| EO 482 | | | 8.3 | 8.3 | 8.3 |
| EO 483 | | | 8.3 | 78 | 103 |
| EO 484 | | | 8.3 | 8.3 | 32 |
| EO 485 | | | 8.3 | 76 | 207 |
| EO 486 | Sindbis/Env | Sindbis/Env | 8.3 | 8.3 | 458 |
| EO 487 | | | 8.3 | 8.3 | 345 |
| EO 488 | | | 8.3 | 8.3 | 331 |
| EO 489 | | | 8.3 | 103 | 111 |
| EO 490 | | | 8.3 | 8.3 | 5636 |

Lymphoproliferative activity (LPA) was also determined by antigenic stimulation followed by uptake of $^3$H-thymidine in these animals and is shown in Table 20. Experiment 1 was performed at 14 weeks post third DNA immunization and Experiment 2 was performed at 2 weeks post fourth DNA immunization using DNA and protein. For gp120ThaiE, gp120SF2 and US4 o-gp140, appropriate background values were used to calculate Stimulation Indices (S. I.; Antigenic stimulation CPM/Background CPM).

TABLE 20

S.I.: Calculated as Ag CPM/Background CPM

| Animal/exp# | gp120ThaiE | gp120 SF2 | env2-3SF2 | o-gp140US4 |
| --- | --- | --- | --- | --- |
| J408/#1 | 2 | 1 | 1 | 5 |
| H445/#1 | 1 | 1 | 1 | 6 |
| J408/#2 | 1 | 1 | 2 | 3 |
| H445/#2 | 0 | 0 | 3 | 2 |

As can be seen by the results presented in Table 20 lymphoproliferative responses to o-gp140.US4 antigen were also in all four animals at both experimental time points. Such proliferation results are indicative of induction of T-helper cell functions.

The results presented above demonstrate that the synthetic gp140.modSF162.delV2 DNA and protein are immunogenic in non-human primates.

Example 13

In Vitro Expression of Recombinant Sindbis RNA and DNA Containing the Synthetic Gag or Env Expression Cassettes A. Synthetic Gag Expression Cassettes To evaluate the expression efficiency of the synthetic Gag expression cassette in Alphavirus vectors, the synthetic Gag expression cassette was subcloned into both plasmid DNA-based and recombinant vector particle-based Sindbis virus vectors. Specifically, a cDNA vector construct for in vitro transcription of Sindbis virus RNA vector replicons (pRSIN-luc; Dubensky, et al., *J Virol.* 70:508-519, 1996) was modified to contain a PmeI site for plasmid linearization and a polylinker for insertion of heterologous genes. A polylinker was generated using two oligonucleotides that contain the sites XhoI, PmlI, ApaI, NarI, XbaI, and NotI (XPANXNF, SEQ ID NO:17, and XPANXNR, SEQ ID NO:18).

The plasmid pRSIN-luc (Dubensky et al., supra) was digested with XhoI and NotI to remove the luciferase gene insert, blunt-ended using Klenow and dNTPs, and purified from an agarose get using GeneCleanII (Biol0l, Vista, Calif.). The oligonucleotides were annealed to each other and ligated into the plasmid. The resulting construct was digested with NotI and SacI to remove the minimal Sindbis 3'-end sequence and $A_{40}$ tract, and ligated with an approximately 0.4 kbp fragment from PKSSIN-BV (WO 97/38087). This 0.4 kbp fragment was obtained by digestion of pKSSIN-BV with NotI and SacI, and purification after size fractionation from an agarose gel. The fragment contained the complete Sindbis virus 3'-end, an $A_{40}$ tract and a PmeI site for linearization. This new vector construct was designated SINBVE.

The synthetic HIV Gag coding sequence was obtained from the parental plasmid by digestion with EcoRI, blunt-ending with Klenow and dNTPs, purification with GeneCleanII, digestion with Sail, size fractionation on an agarose gel, and purification from the agarose gel using GeneCleanII. The synthetic Gag coding fragment was ligated into the SINBVE vector that had been digested with XhoI and PmlI. The resulting vector was purified using GeneCleanII and designated SINBVGag. Vector RNA replicons may be transcribed in vitro (Dubensky et al., supra) from SINBVGag and used directly for transfection of cells. Alternatively, the replicons may be packaged into recombinant vector particles by co-transfection with defective helper RNAs or using an alphavirus packaging cell line as described, for example, in U.S. Pat. Nos. 5,843,723 and 5,789,245, and then administered in vivo as described.

The DNA-based Sindbis virus vector pDCMVSIN-beta-gal (Dubensky, et al., *J. Virol.* 70:508-519, 1996) was digested with Sail and XbaI, to remove the beta-galactosidase gene insert, and purified using GeneCleanII after agarose gel size fractionation. The HIV Gag gene was inserted into the pDCMVSIN-beta-gal by digestion of SINBVGag with SalI and XhoI, purification using GeneCleanII of the Gag-containing fragment after agarose gel size fractionation, and ligation. The resulting construct was designated pDSIN-Gag, and may be used directly for in vivo administration or formulated using any of the methods described herein.

BHK and 293 cells were transfected with recombinant Sindbis vector RNA and DNA, respectively. The supernatants and cell lysates were tested with the Coulter p24 capture ELISA (Example 2).

BHK cells were transfected by electroporation with recombinant Sindbis RNA. The expression of p24 (in ng/ml) is presented in Table 21. In the table, SINGag#1 and 2 represent duplicate measurements, and SINβgal represents a negative control. Supernatants and lysates were collected 24 h post transfection.

TABLE 21

| Construct | Supernatant | Lysate |
|---|---|---|
| SINβgal RNA | 0 | 0 |
| SINGag#1 RNA | 7 ng | Max (approx. 1 μg) |
| SINGag#2 RNA | 1 ng | 700 ng |

293 cells were transfected using LT-1 (Example 2) with recombinant Sindbis DNA. Synthetic pCMVKM2GagMod.SF2 was used as a positive control. Supernatants and lysates were collected 48 h post transfection. The expression of p24 (in ng/ml) is presented in Table 22.

TABLE 22

| Construct | Supernatant | Lysate |
|---|---|---|
| SINGag DNA | 3 | 30 |
| pCMVKM2.GagMod.SF2 DNA | 32 | 42 |

The results presented in Tables 21 and 22 demonstrate that Gag proteins can be efficiently expressed from both DNA and RNA-based Sindbis vector systems using the synthetic Gag expression cassette (p55Gag.mod).

B. Synthetic Env Expression Cassettes

To evaluate the expression efficiency of the synthetic Env expression cassette in Alphavirus vectors, synthetic Env expression cassettes were subcloned into both plasmid DNA-based and recombinant vector particle-based Sindbis virus vectors as described above for Gag.

The synthetic HIV Env coding sequence was obtained from the parental plasmid by digestion with SalI and XbaI, size fractionation on an agarose gel, and purification from the agarose gel using GeneCleanII. The synthetic Env coding fragment was ligated into the SINBVE vector that had been digested with XhoI and XbaI. The resulting vector was purified using GeneCleanII and designated SINBVEnv. Vector RNA replicons may be transcribed in vitro (Dubensky et al., supra) from SINBVEnv and used directly for transfection of cells. Alternatively, the replicons may be packaged into recombinant vector particles by co-transfection with defective helper RNAs or using an alphavirus packaging cell line and administered as described above for Gag.

The DNA-based Sindbis virus vector pDCMVSIN-beta-gal (Dubensky, et al., *J. Virol.* 70:508-519, 1996) was digested with SalI and XbaI, to remove the beta-galactosidase gene insert, and purified using GeneCleanII after agarose gel size fractionation. The HIV Env gene was inserted into the pDCMVSIN-beta-gal by digestion of SINBVEnv with XbaI and XhoI, purification using GeneCleanII of the Env-containing fragment after agarose gel size fractionation, and ligation. The resulting construct was designated pDSIN-Env, and may be used directly for in vivo administration or formulated using any of the methods described herein.

BHK and 293 cells were transfected with recombinant Sindbis vector RNA and DNA, respectively. The supernatants and cell lysates were tested by capture ELISA.

BHK cells were transfected by electroporation with recombinant Sindbis RNA. The expression of Env (in ng/ml) is presented in Table 23. In the table, the Sindbis RNA containing synthetic Env expression cassettes are indicated and βgal represents a negative control. Supernatants and lysates were collected 24 h post transfection.

TABLE 23

| Construct | Supernatant (Neat) ng/ml | Lysate (1:10 dilution) ng/ml |
|---|---|---|
| βgal RNA | 0 | 0 |
| gp140.modUS4 | 726 | 7147 |
| gp140.modSF162 | 3529 | 7772 |
| gp140.modUS4.delV1/V2 | 1738 | 6526 |
| gp140.modUS4.delV2 | 960 | 3023 |
| gp140.modSF162.delV2 | 2772 | 3359 |

293 cells were transfected using LT-1 mediated transfection (PanVera) with recombinant Sindbis DNA containing synthetic expression cassettes of the present invention and βgal sequences as a negative control. Supernatants and lysates were collected 48 h post transfection. The expression of Env (in ng/ml) is presented in Table 24.

TABLE 24

| Construct | Supernatant (Neat) ng/ml | Lysate (1:10 dilution) ng/ml |
|---|---|---|
| βgal | 0 | 0 |
| gp140.modSF162.delV2 | 1977 | 801 |
| gp140.modSF162 | 949 | 746 |

The results presented in Tables 23 and 24 demonstrated that Env proteins can be efficiently expressed from both DNA and RNA-based Sindbis vector systems using the synthetic Env expression cassettes of the present invention.

Example 14

A. In vivo Immunization with Gag-containing DNA and/or Sindbis Particles

CB6F1 mice were immunized intramuscularly at 0 and 4 weeks with plasmid DNA and/or Sindbis vector RNA-containing particles each containing GagMod.SF2 sequences as indicated in Table 25. Animals were challenged with recombinant vaccinia expressing SF2 Gag at 3 weeks post second immunization (at week 7). Spleens were removed from the immunized and challenged animals 5 days later for a standard $^{51}C$ release assay for CTL activity. Values shown in Table 25 indicate the results from the spleens of three mice from each group. The boxed values in Table 25 indicate that all groups of mice receiving immunizations with pCMVKm2.GagMod.SF2 DNA and/or SindbisGagMod.SF2 virus particles either alone or in combinations showed antigen-specific CTL activity.

TABLE 25

Cytotoxic T-lymphocyte (CTL) responses in mice immunized with HIV-1 gagmod DNA and Sindbis gagmod virus particles

| Immunization | E:T | Percent specific lysis of target cells* | | |
|---|---|---|---|---|
| | | SVBALB none | SVBALB p7g | RMA p7g |
| pCMVKm2.GagMod.SF2 | 100:1 | 5 | 20 | 1 |
| DNA[a] at 0, 4 wks | 25:1 | 5 | 20 | <1 |
| | 6:1 | 4 | 8 | <1 |
| SindbisGagMod.SF2 | 100:1 | 10 | 49 | <1 |
| virus particles[b] | 25:1 | 7 | 20 | <1 |
| at 0, 4 wks | 6:1 | 5 | 12 | <1 |
| pCMVKm2.GagMod.SF2 DNA at 0 | 100:1 | 9 | 58 | <1 |
| wks SindbisGagMod.SF2 virus | 25:1 | 7 | 42 | 2 |
| particles at 4 wks | 6:1 | 4 | 13 | <1 |
| SindbisGagMod.SF2 | 100:1 | 5 | 38 | <1 |
| virus particles at 4 wks | 25:1 | 4 | 18 | <1 |
| pCMVKm2.GagMod.SF2 DNA at 0 wks | 6:1 | 3 | 13 | 1 |

[a] 20 μg
[b] $10^7$ particles release assay.
* Challenge with recombinant vaccinia virus expressing HIV-1 SF2 Gag at 3 weeks post second immunization (week 7). Spleens taken 5 days later. Ex vivo CTL assay performed by standard $^{51}$Cr release assay. Values seen represent results from 3 pooled mouse spleens per group

B. In Vivo Immunization with Env-Containing DNA and/or Sindbis Particles

Balb/C mice were immunized intramuscularly at 0 and 4 weeks(as shown in the following table) with plasmid DNA and/or Sindbis-virus RNA-containing particles each containing gp120.modUS4 sequences. Treatment regimes and antibody titers are shown in Table 26. Antibody titers were determined by ELISA using gp120 SF2 protein to coat the plates.

TABLE 26

| Animal | Treatment | | Bleed 0 | Bleed 1 (8 wks) | Bleed 2 (10 wks) |
|---|---|---|---|---|---|
| | 1st Immunization | 2nd Immunization | 1st Imm'n | 2nd Imm'n | 2 Wks post 2nd |
| EO 456 | 25 μg 120mod | (None) | 8.3 | 45 | 309 |
| EO 457 | DNA | | 8.3 | 254 | 460 |
| EO 458 | | | 8.3 | 8.3 | 93 |
| EO 459 | | | 8.3 | 43 | 45 |
| EO 460 | | | 8.3 | 8.3 | 274 |
| EO 461 | 25 μg 120mod | 25 μg 120mod | 8.3 | 47 | 1502 |
| EO 462 | DNA | DNA | 8.3 | 80 | 5776 |
| EO 463 | | | 8.3 | 89 | 3440 |
| EO 464 | | | 8.3 | 8.3 | 3347 |
| EO 465 | | | 8.3 | 69 | 1127 |
| EO 466 | 50 μg 120mod | (None) | 8.3 | 63 | 102 |
| EO 467 | DNA | | 8.3 | 112 | 662 |
| EO 468 | | | 8.3 | 94 | 459 |
| EO 469 | | | 8.3 | 58 | 48 |
| EO 470 | | | 8.3 | 95 | 355 |
| EO 471 | 50 μg 120mod | 50 μg 120mod | 8.3 | 110 | 9074 |
| EO 472 | DNA | DNA | 8.3 | 8.3 | 4897 |
| EO 473 | | | 8.3 | 49 | 4089 |
| EO 474 | | | 8.3 | 59 | 5280 |
| EO 475 | | | 8.3 | 8.3 | 929 |
| EO 476 | 25 μg 120mod | Sindbis/Env | 8.3 | | 653 |
| EO 477 | DNA | | 8.3 | 87 | 22675 |
| EO 478 | | | 8.3 | 76 | 3869 |
| EO 479 | | | 8.3 | | 1004 |
| EO 480 | | | 8.3 | 71 | 7080 |
| EO 481 | Sindbis/Env | (None) | 8.3 | 8.3 | 8.3 |
| EO 482 | | | 8.3 | 8.3 | 8.3 |
| EO 483 | | | 8.3 | 78 | 103 |
| EO 484 | | | 8.3 | 8.3 | 32 |
| EO 485 | | | 8.3 | 76 | 207 |

TABLE 26-continued

| Animal | Treatment | | Bleed 0 | Bleed 1 (8 wks) | Bleed 2 (10 wks) |
|---|---|---|---|---|---|
| | 1st Immunization | 2nd Immunization | 1st Imm'n | 2nd Imm'n | 2 Wks post 2nd |
| EO 486 | Sindbis/Env | Sindbis/Env | 8.3 | 8.3 | 458 |
| EO 487 | | | 8.3 | 8.3 | 345 |
| EO 488 | | | 8.3 | 8.3 | 331 |
| EO 489 | | | 8.3 | 103 | 111 |
| EO 490 | | | 8.3 | 8.3 | 5636 |

As can be seen from the data presented above, all of the mice generally demonstrated substantial immunological responses by bleed number 2. For Env, the best results were obtained using either (i) 50 μg of gp120.modUS4 DNA for the first immunization followed by a second immunization using 50 μg of gp120.modUS4 DNA, or (ii) 25 μg of gp120.modUS4 DNA for the first immunization followed by a second immunization using $10^7$ pfus of Sindbis.

The results presented above demonstrate that the Env and Gag proteins of the present invention are effective to induce an immune response using Sindbis vector systems which include the synthetic Env (e.g., gp120.modUS4) or Gag expression cassettes.

Example 15

Co-Transfection of Env and Gag as Monocistronic and Bicistronic Constructs

DNA constructs encoding (i) wild-type US4 and SF162 Env polypeptides, (ii) synthetic US4 and SF162 Env polypeptides (gp160.modUS4, gp160.modUS4.delV1/V2, gp160.modSF162, and gp120.modSF162.delV2), and (iii) SF2-gag polypeptide (i.e., the Gag coding sequences obtained from the SF2 variant or optimized sequences corresponding to gagSF2-gag.modSF2) were prepared. These monocistronic constructs were co-transfected into 293T cells in a transient transfection protocol using the following combinations: gp160.modUS4; gp160.modUS4 and gag.modSF2; gp160.modUS4.delV1/V2; gp160.modUS4.delV1/V2 and gag.modSF2; gp160.modSF162 and gag.modSF2; gp120.modSF162.delV2 and gag.modSF2; and gag.modSF2 alone.

Further several bicistronic constructs were made where the coding sequences for Env and Gag were under the control of a single CMV promoter and, between the two coding sequences, an IRES (internal ribosome entry site (EMCV IRES); Kozak, M., Critical Reviews dn Biochemistry and Molecular Biology 27(45):385-402, 1992; Witherell, G. W., et al., Virology 214:660-663, 1995) sequence was introduced after the Env coding sequence and before the Gag coding sequence. Those constructs were as follows: gp160.modUS4.gag.modSF2, SEQ ID NO:73 (FIG. 61); gp160.modUSF162.gag.modSF2, SEQ ID NO:74 (FIG. 62); gp160.modUS4.delV1/V2.gag.modSF2, SEQ ID NO:75 (FIG. 63); and gp160.modSF162.delV2.gag.modSF2, SEQ ID NO:76 (FIG. 64).

Supernatants from cell culture were filtered through 0.45 μm filters then ultracentrifuged for 2 hours at 24,000 rpm (140,000×g) in an SW28 rotor through a 20% sucrose cushion. The pelleted materials were suspended and layered on a 20-60% sucrose gradient and spun for 2 hours at 40,000 rpm (285,000×g) in an SW41Ti rotor. Gradients were fractionated into 1.0 ml samples. A total of 9-10 fractions were typically collected from each DNA transfection group.

The fractions were tested for the presence of the Env and Gag proteins (across all fractions). These results demonstrated that the appropriate proteins were expressed in the transfected cells (i.e., if an Env coding sequence was present the corresponding Env protein was detected; if a Gag coding sequence was present the corresponding Gag protein was detected).

Virus like particles (VLPs) were known to be present through a selected range of sucrose densities. Chimeric virus like particles (VLPs) were formed using all the tested combinations of constructs containing both Env and Gag. Significantly more protein was found in the supernatant collected from the cells transfected with "gp160.modUS4.delV1/V2 and gag.modSF2" than in all the other supernatants.

Western blot analysis was also performed on sucrose gradient fractions from each transfection. The results show that bicistronic plasmids gave lower amounts of VLPs than the amounts obtained using co-transfection with monocistronic plasmids.

In order to verify the production of chimeric VLPs by these cell lines the following electron microscopic analysis was carried out.

293T cells were plated at a density of 60-70% confluence in 100 mm dishes on the day before transfection. The cells were transfected with 10 μg of DNA in transfection reagent LT1 (Panvera Corporation, 545 Science Dr., Madison, Wis.). The cells were incubated overnight in reduced serum medium (opti-MEM, Gibco-BRL, Gaithersburg, Md.). The medium was replaced with 10% fetal calf serum, 2% glutamine in IMDM in the morning of the next day and the cells were incubated for 65 hours. Supernatants and lysates were collected for analysis as described above (see Example 2).

The fixed, transfected 293T cells and purified ENV-GAG VLPs were analyzed by electron microscopy. The cells were fixed as follows. Cell monolayers were washed twice with PBS and fixed with 2% glutaraldehyde. For purified VLPs, gradient peak fractions were collected and concentrated by ultracentrifugation (24,000 rpm) for 2 hours. Electron microscopic analysis was performed by Prof. T. S. Benedict Yen (Veterans Affairs, Medical Center, San Francisco, Calif.).

Electron microscopy was carried out using a transmission electron microscope (Zeiss 10c). The cells were pre-stained with osmium and stained with uranium acetate and lead citrate. Immunostaining was performed to visualize envelope on the VLP. The magnification was 100,000×.

FIGS. 65A-65F show micrographs of 293T cells transfected with the following constructs: FIG. 65A, gag.modSF2; FIG. 65B, gp160.modUS4; FIG. 65C, gp160.modUS4.delV1/V2.gag.modSF2 (bicistronic Env and Gag); FIGS. 65D and 65E, gp160.modUS4.delV1/V2 and gag.modSF2; and FIG. 65F, gp120.modSF162.delV2 and gag.modSF2. In the figures, free and budding immature virus-like-particles (VLPs) of the expected size (approximately 100 nm) decorated with the Env protein were seen. In sum, gp160 polypeptides incorporate into Gag VLPs when constructs were co-transfected into cells. The efficiency of incorporation is 2-3 fold higher when constructs encoding V-deleted Env polypeptides from high synthetic expression cassettes are used.

Although preferred embodiments of the subject invention have been described in some detail, it is understood that obvious variations can be made without departing from the spirit and the scope of the invention as defined by the appended claims.

The invention claimed is:

1. A method for producing virus-like particles (VLPs), comprising incubating a cell under conditions for producing the VLPs, wherein the cell comprises an expression cassette, wherein the expression cassette comprises a polynucleotide sequence encoding a polypeptide including an HIV Gag polypeptide, wherein the polynucleotide sequence encoding the Gag polypeptide comprises a sequence having at least 90% sequence identity to SEQ ID NO: 9, and wherein the polynucleotide sequence is operably linked to control elements compatible with expression in the cell.

2. The method of claim 1 wherein the polynucleotide sequence further encodes an HIV polypeptide selected from the group consisting of:
   a protease polypeptide;
   a reverse transcriptase polypeptide;
   a tat polypeptide; and
   a polymerase polypeptide.

3. The method of claim 2 wherein the polynucleotide sequence further encodes the protease polypeptide.

4. The method of claim 2 wherein the polynucleotide sequence further encodes the reverse transcriptase polypeptide.

5. The method of claim 2 wherein the polynucleotide sequence further encodes the tat polypeptide.

6. The method of claim 1 wherein the cell is selected from:
   the group consisting of BHK, VERO, HT1080, 293, RD, COS-7, CHO cells, and insect cells;
   the group consisting of a bacterial cell, a yeast cell, a plant cell, and an antigen presenting cell; and
   the group consisting of an immortalized cell and a tumor-derived cell.

7. The method of claim 1 further comprising substantially purifying the VLPs to produce a composition of VLPs.

8. The method of claim 2 wherein the polynucleotide further encodes the polymerase polypeptide.

9. The method of claim 8 wherein the polynucleotide comprises a sequence at least 90% identical to SEQ ID NO:6.

10. The method of claim 1 wherein the polynucleotide sequence further encodes a polynucleotide sequence encoding an HCV core polypeptide.

11. The method of claim 10 wherein the polynucleotide comprises a sequence at least 90% identical to the nucleotide sequence SEQ ID NO:7.

12. The method of claim 3 wherein the polynucleotide sequence comprises a nucleotide sequence having at least 90% identity to a nucleotide sequence selected from the group consisting of SEQ ID NO:5, SEQ ID NO:78, and SEQ ID NO:79.

13. The method of claim 4 wherein the polynucleotide sequence encoding the reverse transcriptase polypeptide comprises a nucleotide sequence having at least 90% identity to a nucleotide sequence selected from the group consisting of SEQ ID NO:80, SEQ ID NO:81, SEQ ID NO:82, SEQ ID NO:83, and SEQ ID NO:84.

14. The method of claim 5 wherein the polynucleotide sequence encoding the tat polypeptide comprises a nucleotide sequence having at least 90% identity to a nucleotide sequence selected from the group consisting of SEQ ID NO:88 and SEQ ID NO:89.

* * * * *

SEQUENCE LISTING

```
<160> NUMBER OF SEQ ID NOS: 90

<210> SEQ ID NO 1
<211> LENGTH: 1509
<212> TYPE: DNA
<213> ORGANISM: Human immunodeficiency virus

<400> SEQUENCE: 1
atgggtgcga gagcgtcggt attaagcggg ggagaattag ataaatggga aaaaattcgg     60
ttaaggccag ggggaaagaa aaaatataag ttaaaacata tagtatgggc aagcagggag    120
ctagaacgat tcgcagtcaa tcctggcctg ttagaaacat cagaaggctg cagacaaata    180
ttgggacagc tacagccatc ccttcagaca ggatcagaag aacttagatc attatataat    240
```

| | |
|---|---|
| acagtagcaa ccctctattg tgtacatcaa aggatagatg taaaagacac caaggaagct | 300 |
| ttagagaaga tagaggaaga gcaaaacaaa agtaagaaaa aggcacagca agcagcagct | 360 |
| gcagctggca caggaaacag cagccaggtc agccaaaatt accctatagt gcagaaccta | 420 |
| caggggcaaa tggtacatca ggccatatca cctagaactt taaatgcatg ggtaaaagta | 480 |
| gtagaagaaa aggctttcag cccagaagta atacccatgt tttcagcatt atcagaagga | 540 |
| gccacccccac aagatttaaa caccatgcta aacacagtgg ggggacatca agcagccatg | 600 |
| caaatgttaa aagagactat caatgaggaa gctgcagaat gggatagagt gcatccagtg | 660 |
| catgcagggc ctattgcacc aggccaaatg agagaaccaa ggggaagtga catagcagga | 720 |
| actactagta cccttcagga acaaatagga tggatgacaa ataatccacc tatcccagta | 780 |
| ggagaaatct ataaaagatg gataatcctg ggattaaata aaatagtaag aatgtatagc | 840 |
| cctaccagca ttctggacat aagacaagga ccaaaggaac cctttagaga ttatgtagac | 900 |
| cggttctata aaactctaag agccgaacaa gcttcacagg atgtaaaaaa ttggatgaca | 960 |
| gaaaccttgt tggtccaaaa tgcaaaccca gattgtaaga ctattttaaa agcattggga | 1020 |
| ccagcagcta cactagaaga aatgatgaca gcatgtcagg gagtgggggg acccggccat | 1080 |
| aaagcaagag ttttggctga agccatgagc caagtaacaa atccagctaa cataatgatg | 1140 |
| cagagaggca attttaggaa ccaaagaaag actgttaagt gtttcaattg tggcaaagaa | 1200 |
| gggcacatag ccaaaaattg cagggcccct aggaaaaagg gctgttggag atgtggaagg | 1260 |
| gaaggacacc aaatgaaaga ttgcactgag agacaggcta attttttagg gaagatctgg | 1320 |
| ccttcctaca agggaaggcc agggaatttt cttcagagca gaccagagcc aacagcccca | 1380 |
| ccagaagaga gcttcaggtt tggggaggag aaaacaactc cctctcagaa gcaggagccg | 1440 |
| atagacaagg aactgtatcc tttaacttcc ctcagatcac tctttggcaa cgacccctcg | 1500 |
| tcacaataa | 1509 |

<210> SEQ ID NO 2
<211> LENGTH: 1845
<212> TYPE: DNA
<213> ORGANISM: Human immunodeficiency virus

<400> SEQUENCE: 2

| | |
|---|---|
| atgggtgcga gagcgtcggt attaagcggg ggagaattag ataaatggga aaaaattcgg | 60 |
| ttaaggccag ggggaaagaa aaaatataag ttaaaacata tagtatgggc aagcagggag | 120 |
| ctagaacgat tcgcagtcaa tcctggcctg ttagaaacat cagaaggctg cagacaaata | 180 |
| ttgggacagc tacagccatc ccttcagaca ggatcagaag aacttagatc attatataat | 240 |
| acagtagcaa ccctctattg tgtacatcaa aggatagatg taaaagacac caaggaagct | 300 |
| ttagagaaga tagaggaaga gcaaaacaaa agtaagaaaa aggcacagca agcagcagct | 360 |
| gcagctggca caggaaacag cagccaggtc agccaaaatt accctatagt gcagaaccta | 420 |
| caggggcaaa tggtacatca ggccatatca cctagaactt taaatgcatg ggtaaaagta | 480 |
| gtagaagaaa aggctttcag cccagaagta atacccatgt tttcagcatt atcagaagga | 540 |
| gccacccccac aagatttaaa caccatgcta aacacagtgg ggggacatca agcagccatg | 600 |
| caaatgttaa aagagactat caatgaggaa gctgcagaat gggatagagt gcatccagtg | 660 |
| catgcagggc ctattgcacc aggccaaatg agagaaccaa ggggaagtga catagcagga | 720 |
| actactagta cccttcagga acaaatagga tggatgacaa ataatccacc tatcccagta | 780 |
| ggagaaatct ataaaagatg gataatcctg ggattaaata aaatagtaag aatgtatagc | 840 |

-continued

```
cctaccagca ttctggacat aagacaagga ccaaaggaac cctttagaga ttatgtagac    900
cggttctata aaactctaag agccgaacaa gcttcacagg atgtaaaaaa ttggatgaca    960
gaaaccttgt tggtccaaaa tgcaaaccca gattgtaaga ctattttaaa agcattggga   1020
ccagcagcta cactagaaga aatgatgaca gcatgtcagg gagtggggggg acccggccat  1080
aaagcaagag ttttggctga agccatgagc caagtaacaa atccagctaa cataatgatg   1140
cagagaggca attttaggaa ccaaagaaag actgttaagt gtttcaattg tggcaaagaa   1200
gggcacatag ccaaaaattg cagggcccct aggaaaaagg gctgttggag atgtggaagg   1260
gaaggacacc aaatgaaaga ttgcactgag agacaggcta attttttagg gaagatctgg   1320
ccttcctaca agggaaggcc agggaatttt cttcagagca gaccagagcc aacagcccca   1380
ccagaagaga gcttcaggtt tggggaggag aaaacaactc cctctcagaa gcaggagccg   1440
atagacaagg aactgtatcc tttaacttcc ctcagatcac tctttggcaa cgacccctcg   1500
tcacaataag gatagggggg caactaaagg aagctctatt agatacagga gcagatgata   1560
cagtattaga agaaatgaat ttgccaggaa aatggaaacc aaaaatgata ggggaattg   1620
gaggttttat caaagtaaga cagtacgatc agatacctgt agaaatctgt ggacataaag   1680
ctataggtac agtattagta ggacctacac ctgtcaacat aattggaaga atctgttga   1740
ctcagattgg ttgtacttta aatttcccca ttagtcctat tgaaactgta ccagtaaaat   1800
taaagccagg aatggatggc ccaaaagtta agcaatggcc attga                    1845
```

<210> SEQ ID NO 3
<211> LENGTH: 4313
<212> TYPE: DNA
<213> ORGANISM: Human immunodeficiency virus

<400> SEQUENCE: 3

```
atgggtgcga gagcgtcggt attaagcggg ggagaattag ataaatggga aaaaattcgg     60
ttaaggccag ggggaaagaa aaaatataag ttaaaacata tagtatgggc aagcagggag    120
ctagaacgat tcgcagtcaa tcctggcctg ttagaaacat cagaaggctg cagacaaata    180
ttgggacagc tacagccatc ccttcagaca ggatcagaag aacttagatc attatataat    240
acagtagcaa ccctctattg tgtacatcaa aggatagatg taaaagacac caaggaagct    300
ttagagaaga tagaggaaga gcaaaacaaa agtaagaaaa aggcacagca agcagcagct    360
gcagctggca caggaaacag cagccaggtc agccaaaatt accctatagt gcagaaccta    420
caggggcaaa tggtacatca ggccatatca cctagaactt taaatgcatg gtaaaagta    480
gtagaagaaa aggctttcag cccagaagta atacccatgt tttcagcatt atcagaagga    540
gccaccccac aagatttaaa caccatgcta aacacagtgg ggggacatca agcagccatg    600
caaatgttaa aagagactat caatgaggaa gctgcagaat gggatagagt gcatccagtg    660
catgcagggc ctattgcacc aggccaaatg agagaaccaa gggaagtga catagcagga    720
actactagta cccttcagga caaatagga tgatgacaa ataatccacc tatcccagta    780
ggagaaatct ataaaagatg gataatcctg ggattaaata aaatagtaag aatgtatagc    840
cctaccagca ttctggacat aagacaagga ccaaaggaac cctttagaga ttatgtagac    900
cggttctata aaactctaag agccgaacaa gcttcacagg atgtaaaaaa ttggatgaca    960
gaaaccttgt tggtccaaaa tgcaaaccca gattgtaaga ctattttaaa agcattggga   1020
ccagcagcta cactagaaga aatgatgaca gcatgtcagg gagtggggggg acccggccat  1080
aaagcaagag ttttggctga agccatgagc caagtaacaa atccagctaa cataatgatg   1140
```

```
cagagaggca attttaggaa ccaaagaaag actgttaagt gtttcaattg tggcaaagaa    1200
gggcacatag ccaaaaattg cagggcccct aggaaaaagg gctgttggag atgtggaagg    1260
gaaggacacc aaatgaaaga ttgcactgag agacaggcta attttttagg gaagatctgg    1320
ccttcctaca agggaaggcc agggaatttt cttcagagca gaccagagcc aacagcccca    1380
ccagaagaga gcttcaggtt tggggaggag aaaacaactc cctctcagaa gcaggagccg    1440
atagacaagg aactgtatcc tttaacttcc ctcagatcac tctttggcaa cgacccctcg    1500
tcacaataag gatagggggg caactaaagg aagctctatt agatacagga gcagatgata    1560
cagtattaga agaaatgaat ttgccaggaa aatggaaacc aaaaatgata gggggaattg    1620
gaggttttat caaagtaaga cagtacgatc agatacctgt agaaatctgt ggacataaag    1680
ctataggtac agtattagta ggacctacac ctgtcaacat aattggaaga aatctgttga    1740
ctcagattgg ttgtactttta aatttcccca ttagtcctat tgaaactgta ccagtaaaat    1800
taaagccagg aatggatggc ccaaaagtta agcaatggcc attgacagaa gaaaaaataa    1860
aagcattagt agagatatgt acagaaatgg aaaaggaagg gaaaatttca aaaattgggc    1920
ctgaaaatcc atacaatact ccagtatttg ctataaagaa aaaagacagt actaaatgga    1980
gaaaactagt agatttcaga gaacttaata aaagaactca agacttctgg gaagttcagt    2040
taggaatacc acaccccgca gggttaaaaa agaaaaaatc agtaacagta ttggatgtgg    2100
gtgatgcata cttttcagtt cccttagata aagactttag aaagtatact gcatttacca    2160
tacctagtat aaacaatgag acaccaggga ttagatatca gtacaatgtg ctgccacagg    2220
gatggaaagg atcaccagca atattccaaa gtagcatgac aaaaatctta gagccttttta    2280 gaaaacagaa tccagacata gttatctatc aatacatgga tgatttgtat gtaggatctg    2340
acttagaaat agggcagcat agaacaaaaa tagaggaact gagacagcat ctgttgaggt    2400
ggggatttac cacaccagac aaaaaacatc agaaagaacc tccattcctt tggatgggtt    2460
atgaactcca tcctgataaa tggacagtac agcctataat gctgccagaa aaagacagct    2520
ggactgtcaa tgacatacag aagttagtgg gaaaattgaa ttgggcaagt cagatttatg    2580
cagggattaa agtaaagcag ttatgtaaac tccttagagg aaccaaagca ctaacagaag    2640
taataccact aacagaagaa gcagagctag aactggcaga aaacagggag attctaaaag    2700
aaccagtaca tgaagtatat tatgacccat caaaagactt agtagcagaa atacagaagc    2760
aggggcaagg ccaatggaca tatcaaattt atcaagagcc atttaaaaat ctgaaaacag    2820
gaaagtatgc aaggatgagg ggtgcccaca ctaatgatgt aaaacagtta acagaggcag    2880
tgcaaaaagt atccacagaa agcatagtaa tatggggaaa gattcctaaa tttaaactac    2940
ccatacaaaa ggaaacatgg gaagcatggt ggatggagta ttggcaagct acctggattc    3000
ctgagtggga gtttgtcaat accccctcccct tagtgaaatt atggtaccag ttagagaaag    3060
aacccatagt aggagcagaa actttctatg tagatggggc agctaatagg gagactaaat    3120
taggaaaagc aggatatgtt actgacagag gaagacaaaa agttgtctcc atagctgaca    3180
caacaaatca gaagactgaa ttacaagcaa ttcatctagc tttgcaggat tcgggattag    3240
aagtaaacat agtaacagac tcacaatatg cattaggaat cattcaagca caaccagata    3300
agagtgaatc agagttagtc agtcaaataa tagagcagtt aataaaaaag gaaaaggtct    3360
acctggcatg ggtaccagca cacaaaggaa ttggaggaaa tgaacaagta gataaattag    3420
tcagtgctgg aatcaggaaa gtactatttt tgaatggaat agataaggcc caagaagaac    3480
atgagaaata tcacagtaat tggagagcaa tggctagtga ttttaacctg ccacctgtag    3540
```

| | |
|---|---|
| tagcaaaaga aatagtagcc agctgtgata aatgtcagct aaaaggagaa gccatgcatg | 3600 |
| gacaagtaga ctgtagtcca ggaatatggc aactagattg tacacatcta gaaggaaaaa | 3660 |
| ttatcctggt agcagttcat gtagccagtg gatatataga agcagaagtt attccagcag | 3720 |
| agacagggca ggaaacagca tattttctct taaaattagc aggaagatgg ccagtaaaaa | 3780 |
| caatacatac agacaatggc agcaatttca ccagtactac ggttaaggcc gcctgttggt | 3840 |
| gggcagggat caagcaggaa tttggcattc cctacaatcc ccaaagtcaa ggagtagtag | 3900 |
| aatctatgaa taatgaatta agaaaaatta taggacaggt aagagatcag gctgaacacc | 3960 |
| ttaagacagc agtacaaatg gcagtattca tccacaattt taaaagaaaa ggggggattg | 4020 |
| ggggatacag tgcaggggaa agaatagtag acataatagc aacagacata caaactaaag | 4080 |
| aactacaaaa gcaaattaca aaattcaaa attttcgggt ttattacagg gacaacaaag | 4140 |
| atccccttg gaaaggacca gcaaagcttc tctggaaagg tgaaggggca gtagtaatac | 4200 |
| aagataatag tgacataaaa gtagtgccaa gaagaaaagc aaaaatcatt agggattatg | 4260 |
| gaaaacagat ggcaggtgat gattgtgtgg caagtagaca ggatgaggat tag | 4313 |

<210> SEQ ID NO 4
<211> LENGTH: 1515
<212> TYPE: DNA
<213> ORGANISM: Artificial Sequence
<220> FEATURE:
<223> OTHER INFORMATION: Synthetic HIV Gag

<400> SEQUENCE: 4

| | |
|---|---|
| gccaccatgg gcgcccgcgc cagcgtgctg agcggcggcg agctggacaa gtgggagaag | 60 |
| atccgcctgc gccccggcgg caagaagaag tacaagctga gcacatcgt gtgggccagc | 120 |
| cgcgagctgg agcgcttcgc cgtgaacccc ggcctgctgg agaccagcga gggctgccgc | 180 |
| cagatcctgg gccagctgca gcccagcctg cagaccggca gcgaggagct cgcagcctg | 240 |
| tacaacaccg tggccaccct gtactgcgtg caccagcgca tcgacgtcaa ggacaccaag | 300 |
| gaggccctgg agaagatcga ggaggagcag aacaagtcca agaagaaggc ccagcaggcc | 360 |
| gccgccgccg ccggcaccgg caacagcagc caggtgagcc agaactaccc catcgtgcag | 420 |
| aacctgcagg gccagatggt gcaccaggcc atcagccccc gcaccctgaa cgcctgggtg | 480 |
| aaggtggtgg aggagaaggc cttcagcccc gaggtgatcc ccatgttcag cgccctgagc | 540 |
| gagggcgcca ccccccagga cctgaacacg atgttgaaca ccgtgggcgg ccaccaggcc | 600 |
| gccatgcaga tgctgaagga gaccatcaac gaggaggccg ccgagtggga ccgcgtgcac | 660 |
| cccgtgcacg ccggccccat cgcccccggc cagatgcgcg agcccgcgg cagcgacatc | 720 |
| gccggcacca ccagcaccct gcaggagcag atcggctgga tgaccaacaa ccccccccatc | 780 |
| cccgtgggcg agatctacaa gcggtggatc atcctgggcc tgaacaagat cgtgcggatg | 840 |
| tacagcccca ccagcatcct ggacatccgc cagggcccca aggagcccttt ccgcgactac | 900 |
| gtggaccgct tctacaagac cctgcgcgct gagcaggcca gccaggacgt gaagaactgg | 960 |
| atgaccgaga ccctgctggt gcagaacgcc aaccccgact gcaagaccat cctgaaggct | 1020 |
| ctcggccccg cggccaccct ggaggagatg atgaccgcct gcagggcgt gggcggcccc | 1080 |
| ggccacaagg cccgcgtgct ggccgaggcg atgagccagg tgacgaaccc ggcgaccatc | 1140 |
| atgatgcagc gcggcaactt ccgcaaccag cggaagaccg tcaagtgctt caactgcggc | 1200 |
| aaggagggcc acaccgccag gaactgccgc gcccccgca agaagggctg ctggcgctgc | 1260 |
| ggccgcgagg ccaccagat gaaggactgc accgagcgcc aggccaactt cctgggcaag | 1320 |

| | |
|---|---|
| atctggccca gctacaaggg ccgccccggc aacttcctgc agagccgccc cgagcccacc | 1380 |
| gccccccccg aggagagctt ccgcttcggc gaggagaaga ccaccccag ccagaagcag | 1440 |
| gagcccatcg acaaggagct gtaccccctg accagcctgc gcagcctgtt cggcaacgac | 1500 |
| cccagcagcc agtaa | 1515 |

<210> SEQ ID NO 5
<211> LENGTH: 1853
<212> TYPE: DNA
<213> ORGANISM: Artificial Sequence
<220> FEATURE:
<223> OTHER INFORMATION: Synthetic HIV-Gag-Protease

<400> SEQUENCE: 5

| | |
|---|---|
| gccaccatgg gcgcccgcgc cagcgtgctg agcggcggcg agctggacaa gtgggagaag | 60 |
| atccgcctgc gccccggcgg caagaagaag tacaagctga gcacatcgt gtgggccagc | 120 |
| cgcgagctgg agcgcttcgc cgtgaacccc ggcctgctgg agaccagcga gggctgccgc | 180 |
| cagatcctgg ccagctgca gcccagcctg cagaccggca gcgaggagct gcgcagcctg | 240 |
| tacaacaccg tggccaccct gtactgcgtg caccagcgca tcgacgtcaa ggacaccaag | 300 |
| gaggccctgg agaagatcga ggaggagcag aacaagtcca gaagaaggc ccagcaggcc | 360 |
| gccgccgccg ccggcaccgg caacagcagc caggtgagcc agaactaccc catcgtgcag | 420 |
| aacctgcagg gccagatggt gcaccaggcc atcagccccc gcaccctgaa cgcctgggtg | 480 |
| aaggtggtgg aggagaaggc cttcagcccc gaggtgatcc ccatgttcag cgccctgagc | 540 |
| gagggcgcca ccccccagga cctgaacacg atgttgaaca ccgtgggcgg ccaccaggcc | 600 |
| gccatgcaga tgctgaagga gaccatcaac gaggaggccg ccgagtggga ccgcgtgcac | 660 |
| cccgtgcacg ccggccccat cgccccggc cagatgcgcg agccccgcgg cagcgacatc | 720 |
| gccggcacca ccagcaccct gcaggagcag atcggctgga tgaccaacaa ccccccccatc | 780 |
| cccgtgggcg agatctacaa gcggtggatc atcctgggcc tgaacaagat cgtgcggatg | 840 |
| tacagcccca ccagcatcct ggacatccgc caggcccca aggagcccctt ccgcgactac | 900 |
| gtggaccgct tctacaagac cctgcgcgct gagcaggcca ccaggacgt gaagaactgg | 960 |
| atgaccgaga ccctgctggt gcagaacgcc aaccccgact gcaagaccat cctgaaggct | 1020 |
| ctcggccccg cggccaccct ggaggagatg atgaccgcct gccagggcgt gggcggcccc | 1080 |
| ggccacaagg cccgcgtgct ggccgaggcg atgagccagg tgacgaaccc ggcgaccatc | 1140 |
| atgatgcagc gcggcaactt ccgcaaccag cggaagaccg tcaagtgctt caactgcggc | 1200 |
| aaggagggcc acaccgccag gaactgccgc gccccccgca agaagggctg ctggcgctgc | 1260 |
| ggccgcgaag acaccaaaat gaagattgc actgagagac aggctaattt tttagggaag | 1320 |
| atctggcctt cctacaaggg aaggccaggg aatttctc agagcagacc agagccaaca | 1380 |
| gccccaccag aagagagctt caggtttggg gaggagaaaa caactccctc tcagaagcag | 1440 |
| gagccgatag acaaggaact gtatccttta acttccctca gatcactctt tggcaacgac | 1500 |
| ccctcgtcac agtaaggatc ggcggccagc tcaaggaggc gctgctcgac accgcgccg | 1560 |
| acgacaccgt gctggaggag atgaacctgc ccggcaagtg gaagcccaag atgatcggcg | 1620 |
| ggatcggggg cttcatcaag gtgcggcagt acgaccagat ccccgtggag atctgcggcc | 1680 |
| acaaggccat cggcaccgtg ctggtgggcc ccacccccgt gaacatcatc ggccgcaacc | 1740 |
| tgctgaccca gatcggctgc accctgaact tccccatcag ccccatcgag acggtgcccg | 1800 |
| tgaagctgaa gccggggatg gacggcccca aggtcaagca gtggcccctg taa | 1853 |

<210> SEQ ID NO 6
<211> LENGTH: 4319
<212> TYPE: DNA
<213> ORGANISM: Artificial Sequence
<220> FEATURE:
<223> OTHER INFORMATION: Synthetic HIV-Gag-Polymerase

<400> SEQUENCE: 6

```
gccaccatgg gcgcccgcgc cagcgtgctg agcggcggcg agctggacaa gtgggagaag      60
atccgcctgc gccccggcgg caagaagaag tacaagctga agcacatcgt gtgggccagc     120
cgcgagctgc agcgcttcgc cgtgaaccc ggcctgctgg agaccagcga gggctgccgc      180
cagatcctgg gccagctgca gcccagcctg cagaccggca gcgaggagct cgcagcctg      240
tacaacaccg tggccaccct gtactgcgtg caccagcgca tcgacgtcaa ggacaccaag     300
gaggccctgg agaagatcga ggaggagcag aacaagtcca agaagaaggc ccagcaggcc     360
gccgccgccg ccggcaccgg caacagcagc caggtgagcc agaactaccc catcgtgcag     420
aacctgcagg gccagatggt gcaccaggcc atcagccccc gcaccctgaa cgcctgggtg     480
aaggtggtgg aggagaaggc cttcagcccc gaggtgatcc ccatgttcag cgccctgagc     540
gagggcgcca ccccccagga cctgaacacg atgttgaaca ccgtgggcgg ccaccaggcc     600
gccatgcaga tgctgaagga gaccatcaac gaggaggccg ccgagtggga ccgcgtgcac     660
cccgtgcacg ccggccccat cgcccccggc cagatgcgcg agccccgcgg cagcgacatc     720
gccggcacca ccagcaccct gcaggagcag atcggctgga tgaccaacaa cccccccatc     780
cccgtgggcg agatctacaa gcggtggatc atcctgggcc tgaacaagat cgtgcggatg     840
tacagcccca ccagcatcct ggacatccgc cagggcccca aggagccctt ccgcgactac     900
gtggaccgct tctacaagac cctgcgcgct gagcaggcca ccaggacgt gaagaactgg     960
atgaccgaga ccctgctggt gcagaacgcc aaccccgact gcaagaccat cctgaaggct    1020
ctcggccccg cggccaccct ggaggagatg atgaccgcct gccagggcgt gggcggcccc    1080
ggccacaagg cccgcgtgct ggccgaggcg atgagccagg tgacgaaccc ggcgaccatc    1140
atgatgcagc gcggcaactt ccgcaaccag cggaagaccg tcaagtgctt caactgcggc    1200
aaggagggcc acaccgccag gaactgccgc gcccccgca agaagggctg ctggcgctgc    1260
ggccgcgaag gacaccaaat gaaagattgc actgagagac aggctaattt tttagggaag    1320
atctggcctt cctacaaggg aaggccaggg aattttcttc agagcagacc agagccaaca    1380
gccccaccag aagagagctt caggtttggg gaggagaaaa caactccctc tcagaagcag    1440
gagccgatag acaaggaact gtatccttta acttccctca gatcactctt tggcaacgac    1500
ccctcgtcac agtaaggatc ggcggccagc tcaaggaggc gctgctcgac accgcgccg    1560
acgacaccgt gctggaggag atgaacctgc ccggcaagtg gaagcccaag atgatcggcg    1620
ggatcggggg cttcatcaag gtgcggcagt acgaccagat ccccgtggag atctgcggcc    1680
acaaggccat cggcaccgtg ctggtgggcc cccccccgt gaacatcatc ggccgcaacc    1740
tgctgacccc gatcggctgc accctgaact tcccccatcag ccccatcgag acggtgcccg    1800
tgaagctgaa gccggggatg gacggccca aggtcaagca gtggcccctg accgaggaga    1860
agatcaaggc cctggtggag atctgcaccg agatggagaa ggaggcaag atcagcaaga    1920
tcggccccga gaaccccctac aacaccccg tgttcgccat caagaagaag gacagcacca    1980
agtggcgcaa gctggtggac ttccgcgagc tgaacaagcg cacccaggac ttctggggag    2040
tgcagctggg catcccccac cccgccggcc tgaagaagaa gaagagcgtg accgtgctgg    2100
```

-continued

| | |
|---|---|
| acgtgggcga cgcctacttc agcgtgcccc tggacaagga cttccgcaag tacaccgcct | 2160 |
| tcaccatccc cagcatcaac aacgagaccc ccggcatccg ctaccagtac aacgtgctgc | 2220 |
| cccagggctg aagggcagc cccgccatct tccagagcag catgaccaag atcctggagc | 2280 |
| ccttccgcaa gcagaacccc gacatcgtga tctaccagta catggacgac ctgtacgtgg | 2340 |
| gcagcgacct ggagatcggc cagcaccgca ccaagatcga ggagctgcgc cagcacctgc | 2400 |
| tgcgctgggg cttcaccacc cccgacaaga agcaccagaa ggagcccccc ttcctgtgga | 2460 |
| tgggctacga gctgcacccc gacaagtgga ccgtgcagcc catcatgctg cccgagaagg | 2520 |
| acagctggac cgtgaacgac atccagaagc tggtgggcaa gctgaactgg gccagccaga | 2580 |
| tctacgccgg catcaaggtg aagcagctgt gcaagctgct gcgcggcacc aaggccctga | 2640 |
| ccgaggtgat ccccctgacc gaggaggccg agctggagct ggccgagaac cgcgagatcc | 2700 |
| tgaaggagcc cgtgcacgag gtgtactacg accccagcaa ggacctggtg ccgagatcc | 2760 |
| agaagcaggg ccagggccag tggacctacc agatctacca ggagcccttc aagaacctga | 2820 |
| agaccggcaa gtacgcccgc atgcgcggcg cccacaccaa cgacgtgaag cagctgaccg | 2880 |
| aggccgtgca gaaggtgagc accgagagca tcgtgatctg gggcaagatc cccaagttca | 2940 |
| agctgcccat ccagaaggag acctgggagg cctggtggat ggagtactgg caggccacct | 3000 |
| ggatccccga gtgggagttc gtgaacaccc cccccctggt gaagctgtgg taccagctgg | 3060 |
| agaaggagcc catcgtgggc gccgagacct tctacgtgga cggcgccgcc aaccgcgaga | 3120 |
| ccaagctggg caaggccggc tacgtgaccg accgcggccg ccagaaggtg gtgagcatcg | 3180 |
| ccgacaccac caaccagaag accgagctgc aggccatcca cctggccctg caggacagcg | 3240 |
| gcctggaggt gaacatcgtg accgacagcc agtacgccct gggcatcatc caggcccagc | 3300 |
| ccgacaagag cgagagcgag ctggtgagcc agatcatcga gcagctgatc aagaaggaga | 3360 |
| aggtgtacct ggcctgggtg cccgcccaca gggcatcgg cggcaacgag caggtggaca | 3420 |
| agctggtgag cgccggcatc cgcaaggtgc tgttcctgaa cggcatcgac aaggcccagg | 3480 |
| aggagcacga gaagtaccac agcaactggc gcgccatggc cagcgacttc aacctgcccc | 3540 |
| ccgtggtggc caaggagatc gtggccagct gcgacaagtg ccagctgaag ggcgaggcca | 3600 |
| tgcacggcca ggtggactgc agccccggca tctggcagct ggactgcacc cacctggagg | 3660 |
| gcaagatcat cctggtggcc gtgcacgtgg ccagcggcta catcgaggcc gaggtgatcc | 3720 |
| ccgccgagac cggccaggag accgcctact tcctgctgaa gctggccggc cgctggcccg | 3780 |
| tgaagaccat ccacaccgac aacggcagca acttcaccag caccaccgtg aaggccgcct | 3840 |
| gctggtgggc cggcatcaag caggagttcg gcatccccta caacccccag agccagggcg | 3900 |
| tggtggagag catgaacaac gagctgaaga agatcatcgg ccaggtgcgc gaccaggccg | 3960 |
| agcacctgaa gaccgccgtg cagatggccg tgttcatcca caacttcaag cgcaagggcg | 4020 |
| gcatcggcgg ctacagcgcc ggcgagcgca tcgtggacat catcgccacc gacatccaga | 4080 |
| ccaaggagct gcagaagcag atcaccaaga tccagaactt ccgcgtgtac taccgcgaca | 4140 |
| acaaggaccc cctgtggaag ggccccgcca agctgctgtg gaagggcgag ggcgccgtgg | 4200 |
| tgatccagga caacagcgac atcaaggtgg tgccccgccg caaggccaag atcatccgcg | 4260 |
| actacggcaa gcagatggcc ggcgacgact gcgtggccag ccgccaggac gaggactag | 4319 |

<210> SEQ ID NO 7
<211> LENGTH: 2031
<212> TYPE: DNA
<213> ORGANISM: Artificial Sequence
<220> FEATURE:

<223> OTHER INFORMATION: synthetic HIV-Gag/HCV-core fusion polypeptide

<400> SEQUENCE: 7

```
gccaccatgg gcgcccgcgc cagcgtgctg agcggcggcg agctggacaa gtgggagaag      60
atccgcctgc gccccggcgg caagaagaag tacaagctga agcacatcgt gtgggccagc     120
cgcgagctgg agcgcttcgc cgtgaacccc ggcctgctgg agaccagcga gggctgccgc     180
cagatcctgg gccagctgca gcccagcctg cagaccggca gcgaggagct cgcgcagcctg    240
tacaacaccg tggccaccct gtactgcgtg caccagcgca tcgacgtcaa ggacaccaag     300
gaggccctgg agaagatcga ggaggagcag aacaagtcca agaagaaggc ccagcaggcc     360
gccgccgccg ccggcaccgg caacagcagc caggtgagcc agaactaccc catcgtgcag     420
aacctgcagg gccagatggt gcaccaggcc atcagccccc gcaccctgaa cgcctgggtg     480
aaggtggtgg aggagaaggc cttcagcccc gaggtgatcc ccatgttcag cgccctgagc     540
gagggcgcca ccccccagga cctgaacacg atgttgaaca ccgtgggcgg ccaccaggcc     600
gccatgcaga tgctgaagga gaccatcaac gaggaggccg ccgagtggga ccgcgtgcac     660
cccgtgcacg ccggccccat cgcccccggc cagatgcgcg agccccgcgg cagcgacatc     720
gccggcacca ccagcaccct gcaggagcag atcggctgga tgaccaacaa ccccccccatc     780
cccgtgggcg agatctacaa gcggtggatc atcctgggcc tgaacaagat cgtgcggatg     840
tacagcccca ccagcatcct ggacatccgc cagggcccca aggagccctt ccgcgactac     900
gtggaccgct tctacaagac cctgcgcgct gagcaggcca gccaggacgt gaagaactgg     960
atgaccgaga ccctgctggt gcagaacgcc aaccccgact gcaagaccat cctgaaggct    1020
ctcggccccg cggccaccct ggaggagatg atgaccgcct gccagggcgt gggcggcccc    1080
ggccacaagg cccgcgtgct ggccgaggcg atgagccagg tgacgaaccc ggccgaccatc    1140
atgatgcagc gcggcaactt ccgcaaccag cggaagaccg tcaagtgctt caactgcggc    1200
aaggagggcc acaccgccag gaactgccgc gcccccccgca agaagggctg ctggcgctgc    1260
ggccgcgagg gccaccagat gaaggactgc accgagcgcc aggccaactt cctgggcaag    1320
atctggccca gctacaaggg ccgccccggc aacttcctgc agagccgccc cgagcccacc    1380
gcccccccccg aggagagctt ccgcttcggc gaggagaaga ccaccccag ccagaagcag    1440
gagcccatcg acaaggagct gtaccccctg accagcctgc gcagcctgtt cggcaacgac    1500
cccagcagcc agtcgacgaa tcctaaacct caaagaaaaa acaaacgtaa caccaaccgt    1560
cgcccacagg acgtcaagtt cccgggtggc ggtcagatcg ttggtggagt ttacttgttg    1620
ccgcgcaggg gccctagatt gggtgtgcgc gcgacgagaa agacttccga gcggtcgcaa    1680
cctcgaggta gacgtcagcc tatccccaag gctcgtcggc ccgagggcag gacctgggct    1740
cagcccgggt acccttggcc cctctatggc aatgagggct gcggtgggc gggatggctc    1800
ctgtctcccc gtggctctcg gcctagctgg ggcccacag accccggcg taggtcgcgc     1860
aatttgggta aggtcatcga tacccttacg tgcggcttcg ccgacctcat ggggtacata    1920
ccgctcgtcg gcgccccctct tggaggcgct gccaggccc tggcgcatgg cgtccgggtt    1980
ctggaagacg gcgtgaacta tgcaacaggg aaccttcctg gttgctctta g             2031
```

<210> SEQ ID NO 8
<211> LENGTH: 2025
<212> TYPE: DNA
<213> ORGANISM: Artificial Sequence
<220> FEATURE:
<223> OTHER INFORMATION: synthetic HIV-Gag/HCV-Core fusion polypeptide

<400> SEQUENCE: 8

```
atgggtgcga gagcgtcggt attaagcggg ggagaattag ataaatggga aaaaattcgg     60
ttaaggccag ggggaaagaa aaatataag ttaaaacata tagtatgggc aagcagggag    120
ctagaacgat tcgcagtcaa tcctggcctg ttagaaacat cagaaggctg cagacaaata    180
ttgggacagc tacagccatc ccttcagaca ggatcagaag aacttagatc attatataat    240
acagtagcaa ccctctattg tgtacatcaa aggatagatg taaaagacac caaggaagct    300
ttagagaaga tagaggaaga gcaaaacaaa agtaagaaaa aggcacagca agcagcagct    360
gcagctggca caggaaacag cagccaggtc agccaaaatt accctatagt gcagaaccta    420
caggggcaaa tggtacatca ggccatatca cctagaactt taaatgcatg ggtaaaagta    480
gtagaagaaa aggctttcag cccagaagta atacccatgt tttcagcatt atcagaagga    540
gccaccccac aagatttaaa caccatgcta aacacagtgg ggggacatca agcagccatg    600
caaatgttaa aagagactat caatgaggaa gctgcagaat gggatagagt gcatccagtg    660
catgcagggc ctattgcacc aggccaaatg agagaaccaa ggggaagtga catagcagga    720
actactagta cccttcagga acaaatagga tggatgacaa ataatccacc tatcccagta    780
ggagaaatct ataaaagatg gataatcctg ggattaaata aaatagtaag aatgtatagc    840
cctaccagca ttctggacat aagacaagga ccaaaggaac cctttagaga ttatgtagac    900
cggttctata aaactctaag agccgaacaa gcttcacagg atgtaaaaaa ttggatgaca    960
gaaaccttgt tggtccaaaa tgcaaaccca gattgtaaga ctatttttaaa agcattggga   1020
ccagcagcta cactagaaga aatgatgaca gcatgtcagg gagtgggggg acccggccat   1080
aaagcaagag ttttggctga agccatgagc caagtaacaa atccagctaa cataatgatg   1140
cagagaggca attttaggaa ccaaagaaag actgttaagt gtttcaattg tggcaaagaa   1200
gggcacatag ccaaaaattg cagggcccct aggaaaaagg gctgttggag atgtggaagg   1260
gaaggacacc aaatgaaaga ttgcactgag agacaggcta attttttagg gaagatctgg   1320
ccttcctaca agggaaggcc agggaatttt cttcagagca gaccagagcc aacagcccca   1380
ccagaagaga gcttcaggtt tggggaggag aaaacaactc cctctcagaa gcaggagccg   1440
atagacaagg aactgtatcc tttaacttcc ctcagatcac tctttggcaa cgacccctcg   1500
tcacagtcga cgaatcctaa acctcaaaga aaaacaaac gtaacaccaa ccgtcgccca    1560
caggacgtca agttcccggg tggcggtcag atcgttggtg agtttacttt gttgccgcgc   1620
aggggcccta gattgggtgt gcgcgcgacg agaaagactt ccgagcggtc gcaacctcga   1680
ggtagacgtc agcctatccc caaggctcgt cggcccgagg gcaggacctg ggctcagccc   1740
gggtaccctt ggcccctcta tggcaatgag ggctgcgggt gggcgggatg gctcctgtct   1800
ccccgtggct ctcggcctag ctggggcccc acagaccccc ggcgtaggtc gcgcaatttg   1860
ggtaaggtca tcgatacccct tacgtgcggc ttcgccgacc tcatgggta cataccgctc    1920
gtcggcgccc ctcttggagg cgctgccagg gccctggcgc atggcgtccg ggttctggaa   1980
gacggcgtga actatgcaac agggaaccttt cctggttgct cttag                   2025
```

<210> SEQ ID NO 9
<211> LENGTH: 1268
<212> TYPE: DNA
<213> ORGANISM: Artificial Sequence
<220> FEATURE:
<223> OTHER INFORMATION: synthetic Gag common region

<400> SEQUENCE: 9

```
gccaccatgg gcgcccgcgc cagcgtgctg agcggcggcg agctggacaa gtgggagaag    60
atccgcctgc gccccggcgg caagaagaag tacaagctga agcacatcgt gtgggccagc   120
cgcgagctgg agcgcttcgc cgtgaacccc ggcctgctgg agaccagcga gggctgccgc   180
cagatcctgg gccagctgca gcccagcctg cagaccggca gcgaggagct cgcagcctg    240 tacaacaccg tggccaccct gtactgcgtg caccagcgca tcgacgtcaa ggacaccaag   300
gaggccctgg agaagatcga ggaggagcag aacaagtcca agaagaaggc ccagcaggcc   360
gccgccgccg ccggcaccgg caacagcagc caggtgagcc agaactaccc catcgtgcag   420
aacctgcagg gccagatggt gcaccaggcc atcagccccc gcaccctgaa cgcctgggtg   480
aaggtggtgg aggagaaggc cttcagcccc gaggtgatcc ccatgttcag cgccctgagc   540
gagggcgcca ccccccagga cctgaacacg atgttgaaca ccgtgggcgg ccaccaggcc   600
gccatgcaga tgctgaagga gaccatcaac gaggaggccg ccgagtggga ccgcgtgcac   660
cccgtgcacg ccggccccat cgccccggc cagatgcgcg agccccgcgg cagcgacatc   720
gccggcacca ccagcaccct gcaggagcag atcggctgga tgaccaacaa ccccccatc   780 cccgtgggcg agatctacaa gcggtggatc atcctgggcc tgaacaagat cgtgcggatg   840
tacagcccca ccagcatcct ggacatccgc cagggcccca aggagccctt ccgcgactac   900
gtggaccgct tctacaagac cctgcgcgct gagcaggcca gccaggacgt gaagaactgg   960
atgaccgaga ccctgctggt gcagaacgcc aaccccgact gcaagaccat cctgaaggct  1020
ctcggccccg cggccaccct ggaggagatg atgaccgcct gccagggcgt gggcggcccc  1080
ggccacaagg cccgcgtgct ggccgaggcg atgagccagg tgacgaaccc ggcgaccatc  1140
atgatgcagc gcggcaactt ccgcaaccag cggaagaccg tcaagtgctt caactgcggc  1200
aaggagggcc acaccgccag gaactgccgc gccccccgca gaaagggctg ctggcgctgc  1260
ggccgcga                                                           1268
```

```
<210> SEQ ID NO 10
<211> LENGTH: 20
<212> TYPE: PRT
<213> ORGANISM: Artificial Sequence
<220> FEATURE:
<223> OTHER INFORMATION: HIV-Gag peptide p7G

<400> SEQUENCE: 10

Gly Gly His Gln Ala Ala Met Gln Met Leu Lys Glu Thr Ile Asn Glu
1               5                   10                  15

Glu Ala Ala Glu
            20

<210> SEQ ID NO 11
<211> LENGTH: 30
<212> TYPE: DNA
<213> ORGANISM: Artificial Sequence
<220> FEATURE:
<223> OTHER INFORMATION: primer GAG5

<400> SEQUENCE: 11
aagaattcca tgggtgcgag agcgtcggta                                    30

<210> SEQ ID NO 12
<211> LENGTH: 30
<212> TYPE: DNA
<213> ORGANISM: Artificial Sequence
<220> FEATURE:
<223> OTHER INFORMATION: primer p55-SAL3
```

-continued

<400> SEQUENCE: 12
attcgtcgac tgtgacgagg ggtcgttgcc                                              30

<210> SEQ ID NO 13
<211> LENGTH: 34
<212> TYPE: DNA
<213> ORGANISM: Artificial Sequence
<220> FEATURE:
<223> OTHER INFORMATION: primer CORESAL5

<400> SEQUENCE: 13
atttgtcgac gaatcctaaa cctcaaagaa aaac                                         34

<210> SEQ ID NO 14
<211> LENGTH: 31
<212> TYPE: DNA
<213> ORGANISM: Artificial Sequence
<220> FEATURE:
<223> OTHER INFORMATION: primer 173CORE

<400> SEQUENCE: 14
tattggatcc taagagcaac caggaaggtt c                                            31

<210> SEQ ID NO 15
<211> LENGTH: 21
<212> TYPE: DNA
<213> ORGANISM: Artificial Sequence
<220> FEATURE:
<223> OTHER INFORMATION: primer MS65

<400> SEQUENCE: 15
cgaccatcat ggatgcagcg c                                                       21

<210> SEQ ID NO 16
<211> LENGTH: 30
<212> TYPE: DNA
<213> ORGANISM: Artificial Sequence
<220> FEATURE:
<223> OTHER INFORMATION: primer MS66

<400> SEQUENCE: 16
aggattcgtc gagtcgctgc tggggtcgtt                                              30

<210> SEQ ID NO 17
<211> LENGTH: 26
<212> TYPE: DNA
<213> ORGANISM: Artificial Sequence
<220> FEATURE:
<223> OTHER INFORMATION: primer XPANXNF

<400> SEQUENCE: 17
gcacgtgggc ccggcgcctc tagagc                                                  26

<210> SEQ ID NO 18
<211> LENGTH: 26
<212> TYPE: DNA
<213> ORGANISM: Artificial Sequence
<220> FEATURE:
<223> OTHER INFORMATION: primer XPANXNR

<400> SEQUENCE: 18
gctctagagg cgccgggccc acgtgc                                                  26

<210> SEQ ID NO 19
<211> LENGTH: 20
<212> TYPE: PRT

```
<213> ORGANISM: Artificial Sequence
<220> FEATURE:
<223> OTHER INFORMATION: HIV p55 Gag Major Homology Region

<400> SEQUENCE: 19

Asp Ile Arg Gln Gly Pro Lys Glu Pro Phe Arg Asp Tyr Val Asp Arg
1               5                   10                  15

Phe Tyr Lys Thr
            20

<210> SEQ ID NO 20
<211> LENGTH: 60
<212> TYPE: DNA
<213> ORGANISM: Artificial Sequence
<220> FEATURE:
<223> OTHER INFORMATION: synthetic p55 Gag Major Homology Region

<400> SEQUENCE: 20
gacatccgcc agggccccaa ggagcccttc cgcgactacg tggaccgctt ctacaagacc    60

<210> SEQ ID NO 21
<211> LENGTH: 15
<212> TYPE: PRT
<213> ORGANISM: Human immunodeficiency virus

<400> SEQUENCE: 21

Ala Pro Thr Lys Ala Lys Arg Arg Val Val Gln Arg Glu Lys Arg
1               5                   10                  15

<210> SEQ ID NO 22
<211> LENGTH: 5
<212> TYPE: PRT
<213> ORGANISM: Human immunodeficiency virus

<400> SEQUENCE: 22

Lys Ala Lys Arg Arg
1               5

<210> SEQ ID NO 23
<211> LENGTH: 4
<212> TYPE: PRT
<213> ORGANISM: Human immunodeficiency virus

<400> SEQUENCE: 23

Arg Glu Lys Arg
1

<210> SEQ ID NO 24
<211> LENGTH: 15
<212> TYPE: PRT
<213> ORGANISM: Artificial Sequence
<220> FEATURE:
<223> OTHER INFORMATION: aa of mut7.SF162 cleavage site

<400> SEQUENCE: 24

Ala Pro Thr Lys Ala Ile Ser Ser Val Val Gln Ser Glu Lys Ser
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: aa of mut8.SF162 cleavage site

<400> SEQUENCE: 25
```

-continued

```
Ala Pro Thr Ile Ala Ile Ser Ser Val Val Gln Ser Glu Lys Ser
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: aa of mut.SF162 cleavage site

<400> SEQUENCE: 26

Ala Pro Thr Lys Ala Lys Arg Arg Val Val Gln Arg Glu Lys Ser
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: aa of native cleavage site in US4

<400> SEQUENCE: 27

Ala Pro Thr Gln Ala Lys Arg Arg Val Val Gln Arg Glu Lys Arg
1               5                   10                  15

<210> SEQ ID NO 28
<211> LENGTH: 5
<212> TYPE: PRT
<213> ORGANISM: Artificial Sequence
<220> FEATURE:
<223> OTHER INFORMATION: aa of second cleavage site in US4

<400> SEQUENCE: 28

Gln Ala Lys Arg Arg
1               5

<210> SEQ ID NO 29
<211> LENGTH: 15
<212> TYPE: PRT
<213> ORGANISM: Artificial Sequence
<220> FEATURE:
<223> OTHER INFORMATION: aa of mut.US4 cleavage site

<400> SEQUENCE: 29

Ala Pro Thr Gln Ala Lys Arg Arg Val Val Gln Arg Glu Lys Ser
1               5                   10                  15

<210> SEQ ID NO 30
<211> LENGTH: 1419
<212> TYPE: DNA
<213> ORGANISM: Human immunodeficiency virus

<400> SEQUENCE: 30
gtagaaaaat tgtgggtcac agtctattat ggggtacctg tgtggaaaga agcaaccacc      60
actctatttt gtgcatcaga tgctaaagcc tatgacacag aggtacataa tgtctgggcc     120
acacatgcct gtgtacccac agaccctaac ccacaagaaa tagtattgga aaatgtgaca     180
gaaaatttta acatgtggaa aaataacatg gtagaacaga tgcatgagga tataatcagt     240
ttatgggatc aaagtctaaa gccatgtgta agttaaccc cactctgtgt tactctacat      300
tgcactaatt tgaagaatgc tactaatacc aagagtagta ttggaaaga gatggacaga     360 ggagaaataa aaaattgctc tttcaaggtc accacaagca taagaaataa gatgcagaaa     420
gaatatgcac ttttttataa acttgatgta gtaccaatag ataatgataa tacaagctat     480
aaattgataa attgtaacac ctcagtcatt acacaggcct gtccaaaggt atcctttgaa     540
```

```
ccaattccca tacattattg tgccccggct ggttttgcga ttctaaagtg taatgataag      600
aagttcaatg gatcaggacc atgtacaaat gtcagcacag tacaatgtac acatggaatt      660
aggccagtag tgtcaactca attgctgtta aatggcagtc tagcagaaga agggtagta       720 attagatctg aaaatttcac agacaatgct aaaactataa tagtacagct gaaggaatct      780
gtagaaatta attgtacaag acctaacaat aatacaagaa aaagtataac tataggaccg      840
gggagagcat tttatgcaac aggagacata ataggagata taagacaagc acattgtaac      900
attagtggag aaaaatggaa taacacttta aaacagatag ttacaaaatt acaagcacaa      960
tttgggaata aacaatagt ctttaagcaa tcctcaggag gggacccaga aattgtaatg      1020 cacagttta attgtggagg ggaattttc tactgtaatt caacacagct ttttaatagt      1080
acttggaata atactatagg gccaaataac actaatggaa ctatcacact cccatgcaga      1140
ataaaacaaa ttataaacag gtggcaggaa gtaggaaaag caatgtatgc ccctcccatc      1200
agaggacaaa ttagatgctc atcaaatatt acaggactgc tattaacaag atggtggt       1260 aaagagatca gtaacaccac cgagatcttc agacctggag gtggagatat gagggacaat      1320
tggagaagtg aattatataa atataaagta gtaaaaattg agccattagg agtagcaccc      1380
accaaggcaa agagaagagt ggtgcagaga gaaaaaaga                            1419
```

<210> SEQ ID NO 31
<211> LENGTH: 1932
<212> TYPE: DNA
<213> ORGANISM: Human immunodeficiency virus

<400> SEQUENCE: 31

```
gtagaaaaat tgtgggtcac agtctattat ggggtacctg tgtggaaaga agcaaccacc       60
actctatttt gtgcatcaga tgctaaagcc tatgacacag aggtacataa tgtctgggcc      120
acacatgcct gtgtacccac agaccctaac ccacaagaaa tagtattgga aaatgtgaca      180
gaaaatttta acatgtggaa aaataacatg gtagaacaga tgcatgagga tataatcagt      240
ttatgggatc aaagtctaaa gccatgtgta aagttaaccc cactctgtgt tactctacat      300
tgcactaatt tgaagaatgc tactaatacc aagagtagta attggaaaga gatggacaga      360
ggagaaataa aaaattgctc tttcaaggtc accacaagca taagaaataa gatgcagaaa      420
gaatatgcac ttttttataa acttgatgta gtaccaatag ataatgataa tacaagctat      480
aaattgataa attgtaacac ctcagtcatt acacaggcct gtccaaaggt atcctttgaa      540
ccaattccca tacattattg tgccccggct ggttttgcga ttctaaagtg taatgataag      600
aagttcaatg gatcaggacc atgtacaaat gtcagcacag tacaatgtac acatggaatt      660
aggccagtag tgtcaactca attgctgtta aatggcagtc tagcagaaga agggtagta       720 attagatctg aaaatttcac agacaatgct aaaactataa tagtacagct gaaggaatct      780
gtagaaatta attgtacaag acctaacaat aatacaagaa aaagtataac tataggaccg      840
gggagagcat tttatgcaac aggagacata ataggagata taagacaagc acattgtaac      900
attagtggag aaaaatggaa taacacttta aaacagatag ttacaaaatt acaagcacaa      960
tttgggaata aacaatagt ctttaagcaa tcctcaggag gggacccaga aattgtaatg      1020 cacagttta attgtggagg ggaattttc tactgtaatt caacacagct ttttaatagt      1080
acttggaata atactatagg gccaaataac actaatggaa ctatcacact cccatgcaga      1140
ataaaacaaa ttataaacag gtggcaggaa gtaggaaaag caatgtatgc ccctcccatc      1200
agaggacaaa ttagatgctc atcaaatatt acaggactgc tattaacaag atggtggt       1260
```

```
aaagagatca gtaacaccac cgagatcttc agacctggag gtggagatat gagggacaat    1320
tggagaagtg aattatataa atataaagta gtaaaaattg agccattagg agtagcaccc    1380
accaaggcaa agagaagagt ggtgcagaga gaaaaaagag cagtgacgct aggagctatg    1440
ttccttgggt tcttgggagc agcaggaagc actatgggcg cacggtcact gacgctgacg    1500
gtacaggcca gacaattatt gtctggtata gtgcaacagc agaacaattt gctgagagct    1560
attgaggcgc aacagcatct gttgcaactc acagtctggg gcatcaagca gctccaggca    1620
agagtcctgg ctgtggaaag atacctaaag gatcaacagc tcctagggat ttggggttgc    1680
tctgaaaaac tcatttgcac cactgctgtg ccttggaatg ctagttggag taataaatct    1740
ctggatcaga tttggaataa catgacctgg atggagtggg agagagaaat tgacaattac    1800
acaaacttaa tatacacctt aattgaagaa tcgcagaacc aacaagaaaa gaatgaacaa    1860
gaattattag aattggataa gtgggcaagt ttgtggaatt ggtttgacat atcaaaatgg    1920
ctgtggtata ta                                                       1932

<210> SEQ ID NO 32
<211> LENGTH: 2457
<212> TYPE: DNA
<213> ORGANISM: Human immunodeficiency virus

<400> SEQUENCE: 32
gtagaaaaat tgtgggtcac agtctattat ggggtacctg tgtggaaaga agcaaccacc      60
actctatttt gtgcatcaga tgctaaagcc tatgacacag aggtacataa tgtctgggcc     120
acacatgcct gtgtacccac agaccctaac ccacaagaaa tagtattgga aaatgtgaca     180
gaaaatttta acatgtggaa aaataacatg gtagaacaga tgcatgagga tataatcagt     240
ttatgggatc aaagtctaaa gccatgtgta agttaaccc cactctgtgt tactctacat     300
tgcactaatt tgaagaatgc tactaatacc aagagtagta attggaaaga gatggacaga     360
ggagaaataa aaaattgctc tttcaaggtc accacaagca taagaaataa gatgcagaaa     420
gaatatgcac ttttttataa acttgatgta gtaccaatag ataatgataa tacaagctat     480
aaattgataa attgtaacac ctcagtcatt acacaggcct gtccaaaggt atcctttgaa     540
ccaattccca tacattattg tgccccggct ggttttgcga ttctaaagtg taatgataag     600
aagttcaatg gatcaggacc atgtacaaat gtcagcacag tacaatgtac acatggaatt     660
aggccagtag tgtcaactca attgctgtta aatggcagtc tagcagaaga agggtagta     720 attagatctg aaaatttcac agacaatgct aaaactataa tagtacagct gaaggaatct     780
gtagaaatta ttgtacaag acctaacaat aatacaagaa aaagtataac tataggaccg     840
gggagagcat tttatgcaac aggagacata ataggagata agacaagc acattgtaac     900 attagtggag aaaatggaa taacacttta aaacagatag ttacaaaatt acaagcacaa     960
tttgggaata aaacaatagt ctttaagcaa tcctcaggag gggacccaga aattgtaatg    1020
cacagtttta attgtggagg ggaatttttc tactgtaatt caacacagct tttaatagt    1080 acttggaata atactatagg gccaaataac actaatggaa ctatcacact cccatgcaga    1140
ataaaacaaa ttataaacag gtggcaggaa gtaggaaaag caatgtatgc ccctcccatc    1200
agaggacaaa ttagatgctc atcaaatatt acaggactgc tattaacaag atggtggt     1260 aaagagatca gtaacaccac cgagatcttc agacctggag gtggagatat gagggacaat    1320
tggagaagtg aattatataa atataaagta gtaaaaattg agccattagg agtagcaccc    1380
accaaggcaa agagaagagt ggtgcagaga gaaaaaagag cagtgacgct aggagctatg    1440
```

```
ttccttgggt tcttgggagc agcaggaagc actatgggcg cacgtcact gacgctgacg    1500 gtacaggcca gacaattatt gtctggtata gtgcaacagc agaacaattt gctgagagct    1560
attgaggcgc aacagcatct gttgcaactc acagtctggg gcatcaagca gctccaggca    1620
agagtcctgg ctgtggaaag atacctaaag gatcaacagc tcctagggat ttggggttgc    1680
tctggaaaac tcatttgcac cactgctgtg ccttggaatg ctagttggag taataaatct    1740
ctggatcaga tttggaataa catgacctgg atggagtggg agagagaaat tgacaattac    1800
acaaacttaa tatacacctt aattgaagaa tcgcagaacc aacaagaaaa gaatgaacaa    1860
gaattattag aattggataa gtgggcaagt ttgtggaatt ggtttgacat atcaaaatgg    1920
ctgtggtata taaaaatatt cataatgata gtaggaggtt tagtaggttt aaggatagtt    1980
tttactgtgc tttctatagt gaatagagtt aggcaggat actcaccatt atcatttcag     2040
acccgcttcc cagccccaag ggacccgac aggcccgaag gaatcgaaga agaaggtgga     2100
gagagagaca gagacagatc cagtccatta gtgcatggat tattagcact catctgggac    2160
gatctacgga gcctgtgcct cttcagctac accgcttga gagacttaat cttgattgca     2220
gcgaggattg tggaacttct gggacgcagg ggtgggaag ccctcaagta ttggggggaat    2280 ctcctgcagt attggattca ggaactaaag aatagtgctg ttagtttgtt tgatgccata    2340
gctatagcag tagctgaggg gacagatagg attatagaag tagcacaaag aattggtaga    2400
gcttttctcc acatacctag aagaataaga cagggctttg aaagggcttt gctataa       2457

<210> SEQ ID NO 33
<211> LENGTH: 1453
<212> TYPE: DNA
<213> ORGANISM: Artificial Sequence
<220> FEATURE:
<223> OTHER INFORMATION: gp120.modSF162

<400> SEQUENCE: 33
gaattcgcca ccatggatgc aatgaagaga gggctctgct gtgtgctgct gctgtgtgga    60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg gaccaccac gcctgcgtgc ccaccgaccc caaccccag    240 gagatcgtgc tggagaacgt gaccgagaac ttcaacatgt ggaagaacaa catggtggag    300
cagatgcacg aggacatcat cagcctgtgg gaccagagcc tgaagccctg cgtgaagctg    360 accccccctgt gcgtgacccct gcactgcacc aacctgaaga cgccaccaa caccaagagc    420 agcaactgga aggagatgga ccgcggcgag atcaagaact gcagcttcaa ggtgaccacc    480
agcatccgca caagatgca aaggagtac gccctgttct acaagctgga cgtggtgccc    540
atcgacaacg acaaccacag ctacaagctg atcaactgca acaccagcgt gatcacccag    600
gcctgcccca aggtgagctt cgagcccatc cccatccact actgcgcccc cgccggcttc    660
gccatcctga gtgcaacga caagaagttc aacggcagcg gccctgcac caacgtgagc    720 accgtgcagt gcacccacgg catccgcccc gtggtgagca cccagctgct gctgaacggc    780
agcctggccg aggagggcgt ggtgatccgc agcgagaact tcaccgacaa cgccaagacc    840
atcatcgtgc agctgaagga gagcgtggag atcaactgca ccgcccccaa caacaacacc    900
cgcaagagca tcaccatcgg ccccggccgc gccttctacg ccaccggcga catcatcggc    960
gacatccgcc aggcccactg caacatcagc ggcgagaagt ggaacaacac cctgaagcag    1020
atcgtgacca gctgcaggc ccagttcggc aacaagacca tcgtgttcaa gcagagcagc    1080
```

```
ggcggcgacc ccgagatcgt gatgcacagc ttcaactgcg gcggcgagtt cttctactgc    1140
aacagcaccc agctgttcaa cagcacctgg aacaacacca tcggcccaa caacaccaac     1200 ggcaccatca ccctgccctg ccgcatcaag cagatcatca accgctggca ggaggtgggc    1260
aaggccatgt acgcccccc catccgcggc cagatccgct gcagcagcaa catcaccggc    1320
ctgctgctga cccgcgacgg cggcaaggag atcagcaaca ccaccgagat cttccgcccc    1380
ggcggcggcg acatgcgcga caactggcgc agcgagctgt acaagtacaa ggtggtgaag    1440
atcgagcccc tgg                                                       1453
```

<210> SEQ ID NO 34
<211> LENGTH: 1387
<212> TYPE: DNA
<213> ORGANISM: Artificial Sequence
<220> FEATURE:
<223> OTHER INFORMATION: gp120.modSF162.delV2

<400> SEQUENCE: 34

```
gaattcgcca ccatggatgc aatgaagaga gggctctgct gtgtgctgct gctgtgtgga    60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg gaccaccac gcctgcgtgc ccaccgaccc caaccccag    240 agatcgtgc tggagaacgt gaccgagaac ttcaacatgt ggaagaacaa catggtggag    300
cagatgcacg aggacatcat cagcctgtgg gaccagagcc tgaagccctg cgtgaagctg    360
acccccctgt gcgtgaccct gcactgcacc aacctgaaga cgccaccaa caccaagagc    420 agcaactgga aggagatgga ccgcggcgag atcaagaact gcagcttcaa ggtgggcgcc    480
ggcaagctga tcaactgcaa caccagcgtg atcacccagg cctgccccaa ggtgagcttc    540
gagcccatcc ccatccacta ctgcgcccc gccggcttcg ccatcctgaa gtgcaacgac    600
aagaagttca cggcagcgg ccctgcacc aacgtgagca ccgtgcagtg caccccacggc    660 atccgccccg tggtgagcac ccagctgctg ctgaacggca gcctggccga gagggcgtg    720 gtgatccgca gcgagaactt caccgacaac gccaagacca tcatcgtgca gctgaaggag    780
agcgtggaga tcaactgcac ccgccccaac aacaacaccc gcaagagcat caccatcggc    840
cccggccgcg ccttctacgc caccggcgac atcatcggcg acatccgcca ggcccactgc    900
aacatcagcg gcgagaagtg gaacaacacc ctgaagcaga tcgtgaccaa gctgcaggcc    960
cagttcggca acaagaccat cgtgttcaag cagagcagcg gcggcgaccc cgagatcgtg    1020
atgcacagct tcaactgcgg cggcgagttc ttctactgca acagcaccca gctgttcaac    1080
agcacctgga caacaccat cggccccaac aacaccaacg gcaccatcac cctgccctgc    1140
cgcatcaagc agatcatcaa ccgctggcag gaggtgggca aggccatgta cgcccccc    1200 atccgcggcc agatccgctg cagcagcaac atcaccggc tgctgctgac ccgcgacggc    1260
ggcaaggaga tcagcaacac caccgagatc ttccgccccg gcggcggcga catgcgcgac    1320
aactggcgca gcgagctgta caagtacaag gtggtgaaga tcgagcccct gggcgtggcc    1380
cccacca                                                              1387
```

<210> SEQ ID NO 35
<211> LENGTH: 1323
<212> TYPE: DNA
<213> ORGANISM: Artificial Sequence
<220> FEATURE:
<223> OTHER INFORMATION: gp120.modSF162.delV1V2

<400> SEQUENCE: 35

```
gaattcgcca ccatggatgc aatgaagaga gggctctgct gtgtgctgct gctgtgtgga      60
gcagtcttcg tttcgcccag cgccgtggag aagctgtggg tgaccgtgta ctacggcgtg     120
cccgtgtgga aggaggccac caccaccctg ttctgcgcca gcgacgccaa ggcctacgac     180
accgaggtgc acaacgtgtg gccaccac gcctgcgtgc ccaccgaccc caaccccag        240
gagatcgtgc tggagaacgt gaccgagaac ttcaacatgt ggaagaacaa catggtggag     300
cagatgcacg aggacatcat cagcctgtgg gaccagagcc tgaagccctg cgtgaagctg     360
accccctgt gcgtgggcgc cggcaactgc agaccagcg tgatcaccca ggcctgcccc       420
aaggtgagct tcgagcccat ccccatccac tactgcgccc ccgccggctt cgccatcctg     480
aagtgcaacg acaagaagtt caacggcagc ggcccctgca ccaacgtgag caccgtgcag     540
tgcacccacg gcatccgccc cgtggtgagc acccagctgc tgctgaacgg cagcctggcc     600
gaggagggcg tggtgatccg cagcgagaac ttcaccgaca cgccaagac catcatcgtg     660
cagctgaagg agagcgtgga gatcaactgc acccgcccca acaacaacac ccgcaagagc     720
atcaccatcg gccccggccg cgccttctac gccaccggcg acatcatcgg cgacatccgc     780
caggcccact gcaacatcag cggcgagaag tggaacaaca ccctgaagca gatcgtgacc     840
aagctgcagg cccagttcgg caacaagacc atcgtgttca gcagagcag cggcggcgac     900
cccgagatcg tgatgcacag cttcaactgc ggcggcgagt tcttctactg caacagcacc     960
cagctgttca acagcacctg gaacaacacc atcggcccca caacaccaa cggcaccatc    1020
accctgccct gccgcatcaa gcagatcatc aaccgctggc aggaggtggg caaggccatg    1080
tacgccccc ccatccgcgg ccagatccgc tgcagcagca catcaccgg cctgctgctg      1140
acccgcgacg cggcaagga gatcagcaac accaccgaga tcttccgccc cggcggcggc    1200
gacatgcgcg acaactggcg cagcgagctg tacaagtaca aggtggtgaa gatcgagccc    1260
ctgggcgtgg ccccaccaa ggccaagcgc cgcgtggtgc agcgcgagaa cgctaactc     1320
gag                                                                 1323
```

<210> SEQ ID NO 36
<211> LENGTH: 2025
<212> TYPE: DNA
<213> ORGANISM: Artificial Sequence
<220> FEATURE:
<223> OTHER INFORMATION: gp140.modSF162

<400> SEQUENCE: 36

```
gaattcgcca ccatggatgc aatgaagaga gggctctgct gtgtgctgct gctgtgtgga      60
gcagtcttcg tttcgcccag cgccgtggag aagctgtggg tgaccgtgta ctacggcgtg     120
cccgtgtgga aggaggccac caccaccctg ttctgcgcca gcgacgccaa ggcctacgac     180
accgaggtgc acaacgtgtg gccaccac gcctgcgtgc ccaccgaccc caaccccag        240
gagatcgtgc tggagaacgt gaccgagaac ttcaacatgt ggaagaacaa catggtggag     300
cagatgcacg aggacatcat cagcctgtgg gaccagagcc tgaagccctg cgtgaagctg     360
accccctgt gcgtgaccct gcactgcacc aacctgaaga cgccaccaa caccaagagc      420
agcaactgga aggagatgga ccgcggcgag atcaagaact gcagcttcaa ggtgaccacc    480
agcatccgca caagatgca gaaggagtac gccctgttct acaagctgga cgtggtgccc    540
atcgacaacg acaacaccag ctacaagctg atcaactgca caccagcgt gatcacccag    600
gcctgcccca aggtgagctt cgagcccatc cccatccact actgcgcccc cgccggcttc    660
```

```
gccatcctga agtgcaacga caagaagttc aacggcagcg cccctgcac caacgtgagc        720 accgtgcagt gcacccacgg catccgcccc gtggtgagca cccagctgct gctgaacggc        780
agcctggccg aggagggcgt ggtgatccgc agcgagaact tcaccgacaa cgccaagacc        840
atcatcgtgc agctgaagga gagcgtggag atcaactgca cccgccccaa caacaacacc        900
cgcaagagca tcaccatcgg ccccggccgc gccttctacg ccaccggcga catcatcggc        960
gacatccgcc aggcccactg caacatcagc ggcgagaagt ggaacaacac cctgaagcag       1020
atcgtgacca gctgcaggc ccagttcggc aacaagacca tcgtgttcaa gcagagcagc       1080
ggcggcgacc ccgagatcgt gatgcacagc ttcaactgcg gcggcgagtt cttctactgc       1140
aacagcaccc agctgttcaa cagcacctgg aacaacacca tcggcccca caacaccaac       1200 ggcaccatca ccctgccctg ccgcatcaag cagatcatca ccgctggca ggaggtgggc        1260 aaggccatgt acgcccccccc catccgcggc cagatccgct gcagcagcaa catcaccggc       1320
ctgctgctga cccgcgacgg cggcaaggag atcagcaaca ccaccgagat cttccgcccc       1380
ggcggcggcg acatgcgcga caactggcgc agcgagctgt acaagtacaa ggtggtgaag       1440
atcgagcccc tgggcgtggc ccccaccaag gccaagcgcc gcgtggtgca gcgcgagaag       1500
cgcgccgtga ccctgggcgc catgttcctg ggcttcctgg gcgccgccgg cagcaccatg       1560
ggcgcccgca gcctgaccct gaccgtgcag gcccgccagc tgctgagcgg catcgtgcag       1620
cagcagaaca acctgctgcg cgccatcgag gcccagcagc acctgctgca gctgaccgtg       1680
tggggcatca gcagctgca ggcccgcgtg ctggccgtgg agcgctacct gaaggaccag       1740
cagctgctgg gcatctgggg ctgcagcggc aagctgatct gcaccaccgc cgtgccctgg       1800
aacgccagct ggagcaacaa gagcctggac cagatctgga caacatgac ctggatggag        1860 tgggagcgcg agatcgacaa ctacaccaac ctgatctaca ccctgatcga ggagagccag       1920
aaccagcagg agaagaacga gcaggagctg ctggagctgg acaagtgggc cagcctgtgg       1980
aactggttcg acatcagcaa gtggctgtgg tacatctaac tcgag                       2025
```

<210> SEQ ID NO 37
<211> LENGTH: 1944
<212> TYPE: DNA
<213> ORGANISM: Artificial Sequence
<220> FEATURE:
<223> OTHER INFORMATION: gp140.modSF162.delV2

<400> SEQUENCE: 37

```
gaattcgcca ccatggatgc aatgaagaga gggctctgct gtgtgctgct gctgtgtgga         60
gcagtcttcg tttcgcccag cgccgtggag aagctgtggg tgaccgtgta ctacggcgtg        120
cccgtgtgga aggaggccac caccaccctg ttctgcgcca gcgacgccaa ggcctacgac        180
accgaggtgc acaacgtgtg gccaccac gcctgcgtgc ccaccgaccc caaccccag         240 gagatcgtgc tggagaacgt gaccgagaac ttcaacatgt ggaagaacaa catggtggag        300
cagatgcacg aggacatcat cagcctgtgg gaccagagcc tgaagccctg cgtgaagctg        360
acccccctgt gcgtgaccct gcactgcacc aacctgaaga acgccaccaa caccaagagc        420
agcaactgga aggagatgga ccgcggcgag atcaagaact gcagcttcaa ggtgggcgcc        480
ggcaagctga tcaactgcaa caccagcgtg atcacccagg cctgccccaa ggtgagcttc        540
gagcccatcc ccatccacta ctgcgcccccc gccggcttcg ccatcctgaa gtgcaacgac        600
aagaagttca cgcagcgg cccctgcacc aacgtgagca ccgtgcagtg cacccacggc        660
atccgccccg tggtgagcac ccagctgctg ctgaacggca gcctggccga ggagggcgtg        720
```

```
gtgatccgca gcgagaactt caccgacaac gccaagacca tcatcgtgca gctgaaggag      780
agcgtggaga tcaactgcac ccgccccaac aacaacaccc gcaagagcat caccatcggc      840
cccggccgcg ccttctacgc caccggcgac atcatcggcg acatccgcca ggcccactgc      900
aacatcagcg gcgagaagtg gaacaacacc ctgaagcaga tcgtgaccaa gctgcaggcc      960
cagttcggca caagaccat cgtgttcaag cagagcagcg gcggcgaccc cgagatcgtg      1020
atgcacagct tcaactgcgg cggcgagttc ttctactgca cagcaccca gctgttcaac      1080 agcacctgga caacaccat cggcccaac aacaccaacg gcaccatcac cctgcccctgc      1140 cgcatcaagc agatcatcaa ccgctggcag gaggtgggca aggccatgta cgcccccccc      1200
atccgcggcc agatccgctg cagcagcaac atcaccggcc tgctgctgac ccgcgacggc      1260
ggcaaggaga tcagcaacac caccgagatc ttccgccccg gcggcggcga catgcgcgac      1320
aactggcgca gcgagctgta caagtacaag gtggtgaaga tcgagcccct gggcgtggcc      1380
cccaccaagg ccagcgccg cgtggtgcag cgcgagaagc gcgccgtgac cctgggcgcc      1440
atgttcctgg gcttcctggg cgccgccggc agcaccatgg gcgcccgcag cctgaccctg      1500
accgtgcagg cccgccagct gctgagcggc atcgtgcagc agcagaacaa cctgctgcgc      1560
gccatcgagg cccagcagca cctgctgcag ctgaccgtgt ggggcatcaa gcagctgcag      1620
gcccgcgtgc tggccgtgga gcgctacctg aaggaccagc agctgctggg catctgggc      1680 tgcagcggca gctgatctg caccaccgcc gtgccctgga acgccagctg gagcaacaag      1740
agcctggacc agatctggaa caacatgacc tggatggagt gggagcgcga gatcgacaac      1800
tacaccaacc tgatctacac cctgatcgag gagagccaga accagcagga agaacgag       1860 caggagctgc tggagctgga caagtgggcc agcctgtgga ctggttcga catcagcaag      1920 tggctgtggt acatctaact cgag                                            1944
```

<210> SEQ ID NO 38
<211> LENGTH: 1944
<212> TYPE: DNA
<213> ORGANISM: Artificial Sequence
<220> FEATURE:
<223> OTHER INFORMATION: gp140.modSF162.delV1/V2

<400> SEQUENCE: 38

```
gaattcgcca ccatggatgc aatgaagaga gggctctgct gtgtgctgct gctgtgtgga      60
gcagtcttcg tttcgcccag cgccgtggag aagctgtggg tgaccgtgta ctacggcgtg      120
cccgtgtgga aggaggccac caccaccctg ttctgcgcca gcgacgccaa ggcctacgac      180
accgaggtgc acaacgtgtg gccaccac gcctgcgtgc ccaccgaccc caacccccag      240
gagatcgtgc tggagaacgt gaccgagaac ttcaacatgt ggaagaacaa catggtggag      300
cagatgcacg aggacatcat cagcctgtgg gaccagagcc tgaagccctg cgtgaagctg      360
acccccctgt gcgtgaccct gcactgcacc aacctgaaga cgccaccaa caccaagagc      420 agcaactgga aggagatgga ccgcggcgag atcaagaact gcagcttcaa ggtgggcgcc      480
ggcaagctga tcaactgcaa caccagcgtg atcacccagg cctgccccaa ggtgagcttc      540
gagcccatcc ccatccacta ctgcgcccc gccggcttcg ccatcctgaa gtgcaacgac      600
aagaagttca cggcagcgg cccctgcacc aacgtgagca ccgtgcagtg cacccacggc      660
atccgccccg tggtgagcac ccagctgctg ctgaacggca gcctggccga gggggcgtg      720 gtgatccgca gcgagaactt caccgacaac gccaagacca tcatcgtgca gctgaaggag      780
agcgtggaga tcaactgcac ccgccccaac aacaacaccc gcaagagcat caccatcggc      840
```

```
cccggccgcg ccttctacgc caccggcgac atcatcggcg acatccgcca ggcccactgc    900
aacatcagcg gcgagaagtg gaacaacacc ctgaagcaga tcgtgaccaa gctgcaggcc    960
cagttcggca acaagaccat cgtgttcaag cagagcagcg gcggcgaccc cgagatcgtg   1020
atgcacagct tcaactgcgg cggcgagttc ttctactgca acagcaccca gctgttcaac   1080
agcacctgga acaacaccat cggccccaac aacaccaacg gcaccatcac cctgccctgc   1140
cgcatcaagc agatcatcaa ccgctggcag gaggtgggca aggccatgta cgccccccc    1200 atccgcggcc agatccgctg cagcagcaac atcaccggcc tgctgctgac ccgcgacggc   1260
ggcaaggaga tcagcaacac caccgagatc ttccgccccg gcggcggcga catgcgcgac   1320
aactggcgca gcgagctgta caagtacaag gtggtgaaga tcgagcccct gggcgtggcc   1380
cccaccaagg ccaagcgccg cgtggtgcag cgcgagaagc gcgccgtgac cctgggcgcc   1440
atgttcctgg gcttcctggg cgccgccggc agcaccatgg gcgcccgcag cctgacccctg   1500 accgtgcagg cccgccagct gctgagcggc atcgtgcagc agcagaacaa cctgctgcgc   1560
gccatcgagg cccagcagca cctgctgcag ctgaccgtgt ggggcatcaa gcagctgcag   1620
gcccgcgtgc tggccgtgga gcgctacctg aaggaccagc agctgctggg catctggggc   1680
tgcagcggca agctgatctg caccaccgcc gtgccctgga cgccagctg gagcaacaag   1740 agcctggacc agatctggaa caacatgacc tggatggagt gggagcgcga gatcgacaac   1800
tacaccaacc tgatctacac cctgatcgag gagagccaga accagcagga agaacgag    1860 caggagctgc tggagctgga caagtgggcc agcctgtgga actggttcga catcagcaag   1920
tggctgtggt acatctaact cgag                                          1944

<210> SEQ ID NO 39
<211> LENGTH: 2025
<212> TYPE: DNA
<213> ORGANISM: Artificial Sequence
<220> FEATURE:
<223> OTHER INFORMATION: gp140.mut.modSF162

<400> SEQUENCE: 39
gaattcgcca ccatggatgc aatgaagaga gggctctgct gtgtgctgct gctgtgtgga     60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg gccaccac gcctgcgtgc ccaccgaccc caacccccag    240
gagatcgtgc tggagaacgt gaccgagaac ttcaacatgt ggaagaacaa catggtggag    300
cagatgcacg aggacatcat cagcctgtgg gaccagagcc tgaagccctg cgtgaagctg    360 accccccctgt gcgtgaccct gcactgcacc aacctgaaga cgccaccaa caccaagagc    420 agcaactgga aggagatgga ccgcggcgag atcaagaact gcagcttcaa ggtgaccacc    480
agcatccgca caagatgca aaggagtac gccctgttct acaagctgga cgtggtgccc    540
atcgacaacg acaacaccag ctacaagctg atcaactgca acaccagcgt gatcacccag    600
gcctgcccca aggtgagctt cgagcccatc cccatccact actgcgcccc cgccggcttc    660
gccatcctga gtgcaacga caagaagttc aacggcagcg gccctgcac caacgtgagc    720 accgtgcagt gcacccacgg catccgcccc gtggtgagca cccagctgct gctgaacggc    780
agcctggccg aggaggggcgt ggtgatccgc agcgagaact tcaccgacaa cgccaagacc    840
atcatcgtgc agctgaagga gagcgtggag atcaactgca cccgccccaa caacaacacc    900
cgcaagagca tcaccatcgg ccccggccgc gccttctacg ccaccggcga catcatcggc    960
```

```
gacatccgcc aggcccactg caacatcagc ggcgagaagt ggaacaacac cctgaagcag      1020
atcgtgacca agctgcaggc ccagttcggc aacaagacca tcgtgttcaa gcagagcagc      1080
ggcggcgacc ccgagatcgt gatgcacagc ttcaactgcg gcggcgagtt cttctactgc      1140
aacagcaccc agctgttcaa cagcacctgg aacaacacca tcggcccaa  caacaccaac      1200 ggcaccatca ccctgccctg ccgcatcaag cagatcatca accgctggca ggaggtgggc      1260
aaggccatgt acgccccccc catccgcggc cagatccgct gcagcagcaa catcaccggc      1320
ctgctgctga cccgcgacgg cggcaaggag atcagcaaca ccaccgagat cttccgcccc      1380
ggcggcggcg acatgcgcga caactggcgc agcgagctgt acaagtacaa ggtggtgaag      1440
atcgagcccc tgggcgtggc ccccaccaag gccaagcgcc gcgtggtgca gcgcgagaag      1500
agcgccgtga ccctgggcgc catgttcctg ggcttcctgg gcgccgccgg cagcaccatg      1560
ggcgcccgca gcctgacccct gaccgtgcag gcccgccagc tgctgagcgg catcgtgcag      1620
cagcagaaca acctgctgcg cgccatcgag gcccagcagc acctgctgca gctgaccgtg      1680
tggggcatca gcagctgca  ggcccgcgtg ctggccgtgg agcgctacct gaaggaccag      1740
cagctgctgg gcatctgggg ctgcagcggc aagctgatct gcaccaccgc cgtgccctgg      1800
aacgccagct ggagcaacaa gagcctggac cagatctgga caacatgac  ctggatggag      1860 tgggagcgcg agatcgacaa ctacaccaac ctgatctaca ccctgatcga ggagagccag      1920
aaccagcagg agaagaacga gcaggagctg ctggagctgg acaagtgggc cagcctgtgg      1980
aactggttcg acatcagcaa gtggctgtgg tacatctaac tcgag                     2025

<210> SEQ ID NO 40
<211> LENGTH: 1944
<212> TYPE: DNA
<213> ORGANISM: Artificial Sequence
<220> FEATURE:
<223> OTHER INFORMATION: gp140.mut.modSF162.delV2

<400> SEQUENCE: 40
gaattcgcca ccatggatgc aatgaagaga gggctctgct gtgtgctgct gctgtgtgga        60
gcagtcttcg tttcgcccag cgccgtggag aagctgtggg tgaccgtgta ctacggcgtg       120
cccgtgtgga aggaggccac caccaccctg ttctgcgcca cgacgccaa  ggcctacgac       180 accgaggtgc acaacgtgtg gccccaccac gcctgcgtgc caccgaccc  caaccccag       240 gagatcgtgc tggagaacgt gaccgagaac ttcaacatgt ggaagaacaa catggtggag       300
cagatgcacg aggacatcat cagcctgtgg gaccagagcc tgaagccctg cgtgaagctg       360 accccccctgt gcgtgaccct gcactgcacc aacctgaaga cgccaccaa  caccaagagc       420 agcaactgga aggagatgga ccgcggcgag atcaagaact gcagcttcaa ggtgggcgcc       480
ggcaagctga tcaactgcaa caccagcgtg atcacccagg cctgcccaa  ggtgagcttc       540 gagcccatcc ccatccacta ctgcgccccc gccggcttcg ccatcctgaa gtgcaacgac       600
aagaagttca cggcagcgg cccctgcacc aacgtgagca ccgtgcagtg cacccacggc       660
atccgccccg tggtgagcac ccagctgctg ctgaacggca gcctggccga ggagggcgtg       720
gtgatccgca gcgagaactt caccgacaac gccaagacca tcatcgtgca gctgaaggag       780
agcgtggaga tcaactgcac ccgccccaac aacaaccccc gcaagagcat caccatcggc       840
cccggccgcg ccttctacgc caccggcgac atcatcggcg acatccgcca ggcccactgc       900
aacatcagcg gcgagaagtg aacaacacc ctgaagcaga tcgtgaccaa gctgcaggcc       960
cagttcggca acaagaccat cgtgttcaag cagagcagcg gcggcgaccc cgagatcgtg      1020
```

```
atgcacagct tcaactgcgg cggcgagttc ttctactgca acagcaccca gctgttcaac    1080
agcacctgga acaacaccat cggccccaac aacaccaacg gcaccatcac cctgccctgc    1140
cgcatcaagc agatcatcaa ccgctggcag gaggtgggca aggccatgta cgccccccc    1200 atccgcggcc agatccgctg cagcagcaac atcaccggcc tgctgctgac ccgcgacggc    1260
ggcaaggaga tcagcaacac caccgagatc ttccgcccccg cggcggcga catgcgcgac    1320 aactggcgca gcgagctgta caagtacaag gtggtgaaga tcgagcccct gggcgtggcc    1380
cccaccaagg ccaagcgccg cgtggtgcag cgcgagaaga gcgccgtgac cctgggcgcc    1440
atgttcctgg gcttcctggg cgccgccggc agcaccatgg gcgcccgcag cctgaccctg    1500
accgtgcagg cccgccagct gctgagcggc atcgtgcagc agcagaacaa cctgctgcgc    1560
gccatcgagg cccagcagca cctgctgcag ctgaccgtgt ggggcatcaa gcagctgcag    1620
gcccgcgtgc tggccgtgga gcgctacctg aaggaccagc agctgctggg catctggggc    1680
tgcagcggca gctgatctg caccaccgcc gtgccctgga cgccagctg gagcaacaag    1740 agcctggacc agatctggaa caacatgacc tggatggagt gggagcgcga gatcgacaac    1800
tacaccaacc tgatctacac cctgatcgag gagagccaga accagcagga gaagaacgag    1860
caggagctgc tggagctgga caagtgggcc agcctgtgga actggttcga catcagcaag    1920
tggctgtggt acatctaact cgag                                            1944
```

<210> SEQ ID NO 41  
<211> LENGTH: 1836  
<212> TYPE: DNA  
<213> ORGANISM: Artificial Sequence  
<220> FEATURE:  
<223> OTHER INFORMATION: gp140.mut.modSF162.delV1/V2

<400> SEQUENCE: 41

```
gaattcgcca ccatggatgc aatgaagaga gggctctgct gtgtgctgct gctgtgtgga      60
gcagtcttcg tttcgcccag cgccgtggag aagctgtggg tgaccgtgta ctacggcgtg     120
cccgtgtgga aggaggccac caccaccctg ttctgcgcca cgacgccaa ggcctacgac     180 accgaggtgc acaacgtgtg gccacccac gcctgcgtgc ccaccgaccc caacccccag     240
gagatcgtgc tggagaacgt gaccgagaac ttcaacatgt ggaagaacaa catggtggag     300
cagatgcacg aggacatcat cagcctgtgg gaccagagcc tgaagccctg cgtgaagctg     360
acccccctgt gcgtgggcgc cggcaactgc cagaccagcg tgatcaccca ggcctgcccc     420
aaggtgagct tcgagcccat ccccatccac tactgcgccc ccgccggctt cgccatcctg     480
aagtgcaacg acaagaagtt caacggcagc ggccccctgca caacgtgag caccgtgcag     540 tgcacccacg gcatccgccc cgtggtgagc acccagctgc tgctgaacgg cagcctggcc     600
gaggagggcg tggtgatccg cagcgagaac ttcaccgaca cgccaagac catcatcgtg     660 cagctgaagg agagcgtgga gatcaactgc acccgcccca caacaacac ccgcaagagc     720 atcaccatcg cccccggccg cgccttctac gccaccggcg acatcatcgg cgacatccgc     780
caggcccact gcaacatcag cggcgagaag tggaacaaca ccctgaagca gatcgtgacc     840
aagctgcagg cccagttcgg caacaagacc atcgtgttca gcagagcag cggcggcgac     900 cccgagatcg tgatgcacag cttcaactgc ggcggcgagt tcttctactg caacagcacc     960
cagctgttca acagcacctg gaacaacacc atcggcccca acaacaccaa cggcaccatc    1020
accctgccct gccgcatcaa gcagatcatc aaccgctggc aggaggtggg caaggccatg    1080 tacgccccccc ccatccgcgg ccagatccgc tgcagcagca acatcaccgg cctgctgctg    1140
```

```
acccgcgacg gcggcaagga gatcagcaac accaccgaga tcttccgccc cggcggcggc   1200
gacatgcgcg acaactggcg cagcgagctg tacaagtaca aggtggtgaa gatcgagccc   1260
ctgggcgtgg cccccaccaa ggccaagcgc cgcgtggtgc agcgcgagaa gagcgccgtg   1320
accctgggcg ccatgttcct gggcttcctg ggcgccgccg gcagcaccat gggcgcccgc   1380
agcctgaccc tgaccgtgca ggcccgccag ctgctgagcg gcatcgtgca gcagcagaac   1440
aacctgctgc gcgccatcga ggcccagcag cacctgctgc agctgaccgt gtggggcatc   1500
aagcagctgc aggcccgcgt gctggccgtg gagcgctacc tgaaggacca gcagctgctg   1560
ggcatctggg gctgcagcgg caagctgatc tgcaccaccg ccgtgccctg gaacgccagc   1620
tggagcaaca gagcctgga ccagatctgg aacaacatga cctggatgga gtgggagcgc   1680
gagatcgaca actacaccaa cctgatctac accctgatcg aggagagcca gaaccagcag   1740
gagaagaacg agcaggagct gctggagctg gacaagtggg ccagcctgtg gaactggttc   1800
gacatcagca gtggctgtg gtacatctaa ctcgag                              1836

<210> SEQ ID NO 42
<211> LENGTH: 2025
<212> TYPE: DNA
<213> ORGANISM: Artificial Sequence
<220> FEATURE:
<223> OTHER INFORMATION: gp140.mut7.modSF162

<400> SEQUENCE: 42
gaattcgcca ccatggatgc aatgaagaga gggctctgct gtgtgctgct gctgtgtgga     60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg ggccacccac gcctgcgtgc ccaccgaccc caaccccag    240 gagatcgtgc tggagaacgt gaccgagaac ttcaacatgt ggaagaacaa catggtggag    300
cagatgcacg aggacatcat cagcctgtgg gaccagagcc tgaagccctg cgtgaagctg    360 accccctgt gcgtgaccct gcactgcacc aacctgaaga cgccaccaa caccaagagc    420 agcaactgga aggagatgga ccgcggcgag atcaagaact gcagcttcaa ggtgaccacc    480
agcatccgca caagatgca gaaggagtac gccctgttct acaagctgga cgtggtgccc    540
atcgacaacg acaacaccag ctacaagctg atcaactgca caccagcgt gatcacccag    600 gcctgcccca ggtgagcttc gagcccatcc ccatccact actgcgcccc cgccggcttc    660
gccatcctga gtgcaacga caagaagttc aacggcagcg gcccctgcac caacgtgagc    720
accgtgcagt gcacccacgg catccgcccc gtggtgagca cccagctgct gctgaacggc    780
agcctggccg aggagggcgt ggtgatccgc agcgagaact tcaccgacaa cgccaagacc    840
atcatcgtgc agctgaagga gagcgtggag atcaactgca cccgcccaa caacaacacc    900 cgcaagagca tcaccatcgg ccccggccgc gccttctacg ccaccggcga catcatcggc    960
gacatccgcc aggcccactg caacatcagc ggcgagaagt ggaacaacac cctgaagcag   1020
atcgtgacca agctgcaggc ccagttcggc aacaagacca tcgtgttcaa gcagagcagc   1080
ggcggcgacc ccgagatcgt gatgcacagc ttcaactgcg gcggcgagtt cttctactgc   1140
aacagccccc agctgttcaa cagcacctgg aacaacacca tcggcccaa caacaccaac   1200 ggcaccatca ccctgccctg ccgcatcaag cagatcatca accgctggca ggaggtgggc   1260
aaggccatgt acgcccccc catccgcggc cagatccgct gcagcagcaa catcaccggc   1320
ctgctgctga cccgcgacgg cggcaaggag atcagcaaca ccaccgagat cttccgcccc   1380
```

```
ggcggcggcg acatgcgcga caactggcgc agcgagctgt acaagtacaa ggtggtgaag    1440
atcgagcccc tgggcgtggc ccccaccaag gccatcagca gcgtggtgca gagcgagaag    1500
agcgccgtga ccctgggcgc catgttcctg ggcttcctgg gcgccgccgg cagcaccatg    1560
ggcgcccgca gcctgacccct gaccgtgcag gcccgccagc tgctgagcgg catcgtgcag    1620
cagcagaaca acctgctgcg cgccatcgag gcccagcagc acctgctgca gctgaccgtg    1680
tggggcatca agcagctgca ggcccgcgtg ctggccgtgg agcgctacct gaaggaccag    1740
cagctgctgg gcatctgggg ctgcagcggc aagctgatct gcaccaccgc cgtgccctgg    1800
aacgccagct ggagcaacaa gagcctggac cagatctgga caacatgac ctggatggag     1860 tgggagcgcg agatcgacaa ctacaccaac ctgatctaca ccctgatcga ggagagccag    1920
aaccagcagg agaagaacga gcaggagctg ctggagctgg acaagtgggc cagcctgtgg    1980
aactggttcg acatcagcaa gtggctgtgg tacatctaac tcgag                     2025
```

<210> SEQ ID NO 43
<211> LENGTH: 1944
<212> TYPE: DNA
<213> ORGANISM: Artificial Sequence
<220> FEATURE:
<223> OTHER INFORMATION: gp140.mut7.modSF162.delV2

<400> SEQUENCE: 43

```
gaattcgcca ccatggatgc aatgaagaga gggctctgct gtgtgctgct gctgtgtgga     60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg gccaccac gcctgcgtgc ccaccgaccc caaccccag      240 gagatcgtgc tggagaacgt gaccgagaac ttcaacatgt ggaagaacaa catggtggag    300
cagatgcacg aggacatcat cagcctgtgg gaccagagcc tgaagcccctg cgtgaagctg    360 accccccctgt gcgtgaccct gcactgcacc aacctgaaga cgccaccaa caccaagagc    420 agcaactgga aggagatgga ccgcggcgag atcaagaact gcagcttcaa ggtgggcgcc    480
ggcaagctga tcaactgcaa caccagcgtg atcacccagg cctgccccaa ggtgagcttc    540
gagcccatcc ccatccacta ctgcgccccc gccggcttcg ccatcctgaa gtgcaacgac    600
aagaagttca cggcagcggc ccctgcacc aacgtgagca ccgtgcagtg cacccacggc    660
atccgccccg tggtgagcac ccagctgctg ctgaacggca gcctggccga gggggcgtg    720 gtgatccgca gcgagaactt caccgacaac gccaagacca tcatcgtgca gctgaaggag    780
agcgtggaga tcaactgcac ccgccccaac aacaacaccc gcaagagcat caccatcggc    840
cccggccgcg ccttctacgc caccggcgac atcatcggcg acatccgcca ggcccactgc    900
aacatcagcg gcgagaagtg gaacaacacc ctgaagcaga tcgtgaccaa gctgcaggcc    960
cagttcggca caagaccat cgtgttcaag cagagcagcg gcggcgaccc cgagatcgtg    1020
atgcacagct tcaactgcgg cggcgagttc ttctactgca acagcaccca gctgttcaac    1080
agcacctgga acaacaccat cggccccaac aacaccaacg caccatcac cctgccctgc    1140 cgcatcaagc agatcatcaa ccgctggcag gaggtgggca aggccatgta cgcccccccc    1200
atccgcggcc agatccgctg cagcagcaac atcaccggcc tgctgctgac ccgcgacggc    1260
ggcaaggaga tcagcaacac caccgagatc ttccgccccg gcggcggcga catgcgcgac    1320
aactggcgca gcgagctgta caagtacaag gtggtgaaga tcgagcccct gggcgtggcc    1380
cccaccaagg ccatcagcag cgtggtgcag agcgagaaga gcgccgtgac cctgggcgcc    1440
```

| | |
|---|---|
| atgttcctgg gcttcctggg cgccgccggc agcaccatgg gcgcccgcag cctgaccctg | 1500 |
| accgtgcagg cccgccagct gctgagcggc atcgtgcagc agcagaacaa cctgctgcgc | 1560 |
| gccatcgagg cccagcagca cctgctgcag ctgaccgtgt ggggcatcaa gcagctgcag | 1620 |
| gcccgcgtgc tggccgtgga gcgctacctg aaggaccagc agctgctggg catctggggc | 1680 |
| tgcagcggca agctgatctg caccaccgcc gtgccctgga acgccagctg gagcaacaag | 1740 |
| agcctggacc agatctggaa caacatgacc tggatggagt gggagcgcga gatcgacaac | 1800 |
| tacaccaacc tgatctacac cctgatcgag gagagccaga accagcagga agaacgag | 1860 |
| caggagctgc tggagctgga caagtgggcc agcctgtgga actggttcga catcagcaag | 1920 |
| tggctgtggt acatctaact cgag | 1944 |

<210> SEQ ID NO 44
<211> LENGTH: 1836
<212> TYPE: DNA
<213> ORGANISM: Artificial Sequence
<220> FEATURE:
<223> OTHER INFORMATION: gp140.mut7.modSF162.delV1/V2

<400> SEQUENCE: 44

| | |
|---|---|
| gaattcgcca ccatggatgc aatgaagaga gggctctgct gtgtgctgct gctgtgtgga | 60 |
| gcagtcttcg tttcgcccag cgccgtggag aagctgtggg tgaccgtgta ctacggcgtg | 120 |
| cccgtgtgga aggaggccac caccaccctg ttctgcgcca gcgacgccaa ggcctacgac | 180 |
| accgaggtgc acaacgtgtg gccaccac gcctgcgtgc ccaccgaccc caaccccag | 240 |
| gagatcgtgc tggagaacgt gaccgagaac ttcaacatgt ggaagaacaa catggtggag | 300 |
| cagatgcacg aggacatcat cagcctgtgg gaccagagcc tgaagccctg cgtgaagctg | 360 |
| accccctgt gcgtgggcgc cggcaactgc agaccagcg tgatcaccca ggcctgcccc | 420 |
| aaggtgagct tcgagcccat ccccatccac tactgcgccc ccgccggctt cgccatcctg | 480 |
| aagtgcaacg acaagaagtt caacggcagc ggcccctgca ccaacgtgag caccgtgcag | 540 |
| tgcacccacg gcatccgccc cgtggtgagc acccagctgc tgctgaacgg cagcctggcc | 600 |
| gaggagggcg tggtgatccg cagcgagaac ttcaccgaca acgccaagac catcatcgtg | 660 |
| cagctgaagg agagcgtgga gatcaactgc acccgcccca caacaacac ccgcaagagc | 720 |
| atcaccatcg gccccggccg cgccttctac gccaccggcg acatcatcgg cgacatccgc | 780 |
| caggcccact gcaacatcag cggcgagaag tggaacaaca ccctgaagca gatcgtgacc | 840 |
| aagctgcagg cccagttcgg caacaagacc atcgtgttca gcagagcag cggcggcgac | 900 |
| cccgagatcg tgatgcacag cttcaactgc ggcggcgagt tcttctactg caacagcacc | 960 |
| cagctgttca acagcacctg gaacaacacc atcgccccca acaaccaa cggcaccatc | 1020 |
| accctgccct gccgcatcaa gcagatcatc aaccgctggc aggaggtggg caaggccatg | 1080 |
| tacgccccc ccatccgcgg ccagatccgc tgcagcagca acatcaccgg cctgctgctg | 1140 |
| acccgcgacg gcggcaagga gatcagcaac accaccgaga tcttccgccc cggcggcggc | 1200 |
| gacatgcgcg acaactggcg cagcgagctg tacaagtaca aggtggtgaa gatcgagccc | 1260 |
| ctgggcgtgg cccccaccaa ggccatcagc agcgtggtgc agagcgagaa gagcgccgtg | 1320 |
| accctggccg ccatgttcct gggcttcctg ggcgccgccg gcagcaccat gggcgcccgc | 1380 |
| agcctgaccc tgaccgtgca ggcccgccag ctgctgagcg gcatcgtgca gcagcagaac | 1440 |
| aacctgctgc gcgccatcga ggcccagcag cacctgctgc agctgaccgt gtggggcatc | 1500 |
| aagcagctgc aggcccgcgt gctggccgtg gagcgctacc tgaaggacca gcagctgctg | 1560 |

| | |
|---|---|
| ggcatctggg gctgcagcgg caagctgatc tgcaccaccg ccgtgccctg gaacgccagc | 1620 |
| tggagcaaca agagcctgga ccagatctgg aacaacatga cctggatgga gtgggagcgc | 1680 |
| gagatcgaca actacaccaa cctgatctac accctgatcg aggagagcca gaaccagcag | 1740 |
| gagaagaacg agcaggagct gctggagctg gacaagtggg ccagcctgtg gaactggttc | 1800 |
| gacatcagca gtggctgtg gtacatctaa ctcgag | 1836 |

<210> SEQ ID NO 45
<211> LENGTH: 2025
<212> TYPE: DNA
<213> ORGANISM: Artificial Sequence
<220> FEATURE:
<223> OTHER INFORMATION: gp140.mut8.modSF162

<400> SEQUENCE: 45

| | |
|---|---|
| gaattcgcca ccatggatgc aatgaagaga gggctctgct gtgtgctgct gctgtgtgga | 60 |
| gcagtcttcg tttcgcccag cgccgtggag aagctgtggg tgaccgtgta ctacggcgtg | 120 |
| cccgtgtgga aggaggccac caccaccctg ttctgcgcca gcgacgccaa ggcctacgac | 180 |
| accgaggtgc acaacgtgtg gccaccac gcctgcgtgc ccaccgaccc caaccccag | 240 |
| gagatcgtgc tggagaacgt gaccgagaac ttcaacatgt ggaagaacaa catggtggag | 300 |
| cagatgcacg aggacatcat cagcctgtgg gaccagagcc tgaagccctg cgtgaagctg | 360 |
| accccccctgt gcgtgaccct gcactgcacc aacctgaaga cgccaccaa caccaagagc | 420 |
| agcaactgga aggagatgga ccgcggcgag atcaagaact gcagcttcaa ggtgaccacc | 480 |
| agcatccgca caagatgca aaggagtac gccctgttct acaagctgga cgtggtgccc | 540 |
| atcgacaacg acaacaccag ctacaagctg atcaactgca acaccagcgt gatcacccag | 600 |
| gcctgcccca aggtgagctt cgagcccatc cccatccact actgcgcccc cgccggcttc | 660 |
| gccatcctga gtgcaacga caagaagttc aacggcagcg gccctgcac caacgtgagc | 720 |
| accgtgcagt gcacccacgg catccgcccc gtggtgagca cccagctgct gctgaacggc | 780 |
| agcctggccg aggagggcgt ggtgatccgc agcgagaact tcaccgacaa cgccaagacc | 840 |
| atcatcgtgc agctgaagga gagcgtggag atcaactgca cccgccccaa caacaacacc | 900 |
| cgcaagagca tcaccatcgg ccccggccgc gccttctacg ccaccggcga catcatcggc | 960 |
| gacatccgcc aggcccactg caacatcagc ggcgagaagt ggaacaacac cctgaagcag | 1020 |
| atcgtgacca gctgcaggc ccagttcggc aacaagacca tcgtgttcaa gcagagcagc | 1080 |
| ggcggcgacc ccgagatcgt gatgcacagc ttcaactgcg gcggcgagtt cttctactgc | 1140 |
| aacagcaccc agctgttcaa cagcacctgg aacaacacca tcggcccccaa caacaccaac | 1200 |
| ggcaccatca ccctgccctg ccgcatcaag cagatcatca ccgctggca ggaggtgggc | 1260 |
| aaggccatgt acgccccccc catccgcggc cagatccgct gcagcagcaa catcaccggc | 1320 |
| ctgctgctga cccgcgacgg cggcaaggag atcagcaaca ccaccgagat cttccgcccc | 1380 |
| ggcggcggcg acatgcgcga caactggcgc agcgagctgt acaagtacaa ggtggtgaag | 1440 |
| atcgagcccc tgggcgtggc ccccaccatc gccatcagca gcgtggtgca gagcgagaag | 1500 |
| agcgccgtga ccctgggcgc catgttcctg ggcttcctgg gcgccgccgg cagcaccatg | 1560 |
| ggcgcccgca gcctgaccct gaccgtgcag gcccgccagc tgctgagcgg catcgtgcag | 1620 |
| cagcagaaca acctgctgcg cgccatcgag gcccagcagc acctgctgca gctgaccgtg | 1680 |
| tggggcatca gcagctgca ggcccgcgtg ctggccgtgg agcgctacct gaaggaccag | 1740 |
| cagctgctgg gcatctgggg ctgcagcggc aagctgatct gcaccaccgc cgtgccctgg | 1800 |

| | |
|---|---|
| aacgccagct ggagcaacaa gagcctggac cagatctgga acaacatgac ctggatggag | 1860 |
| tgggagcgcg agatcgacaa ctacaccaac ctgatctaca ccctgatcga ggagagccag | 1920 |
| aaccagcagg agaagaacga gcaggagctg ctggagctgg acaagtgggc cagcctgtgg | 1980 |
| aactggttcg acatcagcaa gtggctgtgg tacatctaac tcgag | 2025 |

<210> SEQ ID NO 46
<211> LENGTH: 1944
<212> TYPE: DNA
<213> ORGANISM: Artificial Sequence
<220> FEATURE:
<223> OTHER INFORMATION: gp140.mut8.modSF162.delV2

<400> SEQUENCE: 46

| | |
|---|---|
| gaattcgcca ccatggatgc aatgaagaga gggctctgct gtgtgctgct gctgtgtgga | 60 |
| gcagtcttcg tttcgcccag cgccgtggag aagctgtggg tgaccgtgta ctacggcgtg | 120 |
| cccgtgtgga aggaggccac caccaccctg ttctgcgcca cgacgccaa ggcctacgac | 180 |
| accgaggtgc acaacgtgtg gccaccac gcctgcgtgc ccaccgaccc caaccccag | 240 |
| gagatcgtgc tggagaacgt gaccgagaac ttcaacatgt ggaagaacaa catggtggag | 300 |
| cagatgcacg aggacatcat cagcctgtgg gaccagagcc tgaagccctg cgtgaagctg | 360 |
| accccctgt gcgtgaccct gcactgcacc aacctgaaga cgccaccaa caccaagagc | 420 |
| agcaactgga aggagatgga ccgcggcgag atcaagaact gcagcttcaa ggtgggcgcc | 480 |
| ggcaagctga tcaactgcaa caccagcgtg atcacccagg cctgccccaa ggtgagcttc | 540 |
| gagcccatcc ccatccacta ctgcgccccc gccggcttcg ccatcctgaa gtgcaacgac | 600 |
| aagaagttca cggcagcgg cccctgcacc aacgtgagca ccgtgcagtg cacccacggc | 660 |
| atccgccccg tggtgagcac ccagctgctg ctgaacggca gcctggccga ggagggcgtg | 720 |
| gtgatccgca gcgagaactt caccgacaac gccaagacca tcgtgca gctgaaggag | 780 |
| agcgtggaga tcaactgcac ccgcccccaac aacaacaccc gcaagagcat caccatcggc | 840 |
| cccgccgcg ccttctacgc caccggcgac atcatcggcg acatccgcca ggcccactgc | 900 |
| aacatcagcg gcgagaagtg gaacaacacc ctgaagcaga tcgtgaccaa gctgcaggcc | 960 |
| cagttcggca caagaccat cgtgttcaag cagagcagcg gcggcgaccc cgagatcgtg | 1020 |
| atgcacagct tcaactgcgg cggcgagttc ttctactgca cagcacccca gctgttcaac | 1080 |
| agcacctgga caacaccat cggccccaac aacaccaacg gcaccatcac cctgccctgc | 1140 |
| cgcatcaagc agatcatcaa ccgctggcag gaggtgggca aggccatgta cgcccccccc | 1200 |
| atccgcggcc agatccgctg cagcagcaac atcaccggcc tgctgctgac ccgcgacggc | 1260 |
| ggcaaggaga tcagcaacac caccgagatc ttccgccccg gcggcggcga catgcgcgac | 1320 |
| aactggcgca gcgagctgta caagtacaag gtggtgaaga tcgagcccct gggcgtggcc | 1380 |
| cccaccatcg ccatcagcag cgtggtgcag agcgagaaga gcgccgtgac cctgggcgcc | 1440 |
| atgttcctgg gcttcctggg cgccgccggc agcaccatgg gcgcccgcag cctgaccctg | 1500 |
| accgtgcagg cccgccagct gctgagcggc atcgtgcagc agcagaacaa cctgctgcgc | 1560 |
| gccatcgagg cccagcagca cctgctgcag ctgaccgtgt ggggcatcaa gcagctgcag | 1620 |
| gcccgcgtgc tggccgtgga gcgctacctg aaggaccagc agctgctggg catctggggc | 1680 |
| tgcagcggca agctgatctg caccaccgcc gtgccctgga acgccagctg agcaacaag | 1740 |
| agcctggacc agatctggaa caacatgacc tggatggagt gggagcgcga gatcgacaac | 1800 |
| tacaccaacc tgatctacac cctgatcgag gagagccaga accagcagga gaagaacgag | 1860 |

```
caggagctgc tggagctgga caagtgggcc agcctgtgga actggttcga catcagcaag    1920
tggctgtggt acatctaact cgag                                            1944

<210> SEQ ID NO 47
<211> LENGTH: 1836
<212> TYPE: DNA
<213> ORGANISM: Artificial Sequence
<220> FEATURE:
<223> OTHER INFORMATION: gp140.mut8.modSF162.delV1/V2

<400> SEQUENCE: 47
gaattcgcca ccatggatgc aatgaagaga gggctctgct gtgtgctgct gctgtgtgga      60
gcagtcttcg tttcgcccag cgccgtggag aagctgtggg tgaccgtgta ctacggcgtg     120
cccgtgtgga aggaggccac caccaccctg ttctgcgcca cgacgccaa ggcctacgac      180 accgaggtgc acaacgtgtg gccaccac gcctgcgtgc ccaccgaccc caaccccag       240 gagatcgtgc tggagaacgt gaccgagaac ttcaacatgt ggaagaacaa catggtggag     300
cagatgcacg aggacatcat cagcctgtgg gaccagagcc tgaagccctg cgtgaagctg     360 accccctgt gcgtgggcgc cggcaactgc agaccagcg tgatcaccca ggcctgcccc      420
aaggtgagct tcgagcccat ccccatccac tactgcgccc ccgccggctt cgccatcctg     480
aagtgcaacg acaagaagtt caacggcagc ggccccctgca caacgtgag cccgtgcag     540 tgcacccacg gcatccgccc cgtggtgagc acccagctgc tgctgaacgg cagcctggcc     600
gaggagggcg tggtgatccg cagcgagaac ttcaccgaca cgccaagac catcatcgtg     660 cagctgaagg agagcgtgga gatcaactgc acccgcccca caacaacac ccgcaagagc     720 atcaccatcg gccccggccg cgccttctac gccaccggcg acatcatcgg cgacatccgc    780
caggcccact gcaacatcag cggcgagaag tggaacaaca ccctgaagca gatcgtgacc    840
aagctgcagg cccagttcgg caacaagacc atcgtgttca gcagagcag cggcggcgac     900 cccgagatcg tgatgcacag cttcaactgc ggcggcgagt tcttctactg caacagcacc    960
cagctgttca acagcacctg gaacaacacc atcggcccca caacaccaa cggcaccatc    1020 accctgccct gccgcatcaa gcagatcatc aaccgctggc aggaggtggg caaggccatg   1080 tacgccccc ccatccgcgg ccagatccgc tgcagcagca catcaccgg cctgctgctg    1140 acccgcgacg gcggcaagga gatcagcaac accaccgaga tcttccgccc cggcggcggc   1200
gacatgcgcg acaactggcg cagcgagctg tacaagtaca aggtggtgaa gatcgagccc   1260
ctgggcgtgg ccccaccat cgccatcagc agcgtggtgc agagcgagaa gagcgccgtg    1320
accctgggcg ccatgttcct gggcttcctg ggcgccgccg cagcaccat gggcgcccgc   1380 agcctgaccc tgaccgtgca ggcccgccag ctgctgagcg gcatcgtgca gcagcagaac   1440
aacctgctgc gcgccatcga ggcccagcag caccggctgc agctgaccgt gtggggcatc   1500
aagcagctgc aggcccgcgt gctggccgtg agcgcctacc tgaaggacca gcagctgctg   1560
ggcatctggg gctgcagcgg caagctgatc tgcaccaccg ccgtgccctg gaacgccagc   1620
tggagcaaca agagcctgga ccagatctgg aacaacatga cctggatgga gtgggagcgc   1680
gagatcgaca actacaccaa cctgatctac accctgatcg aggagagcca gaaccagcag   1740
gagaagaacg agcaggagct gctggagctg gacaagtggg ccagcctgtg gaactggttc   1800
gacatcagca gtggctgtg gtacatctaa ctcgag                                1836

<210> SEQ ID NO 48
<211> LENGTH: 2547
```

-continued

```
<212> TYPE: DNA
<213> ORGANISM: Artificial Sequence
<220> FEATURE:
<223> OTHER INFORMATION: gp160.modSF162

<400> SEQUENCE: 48
gaattcgcca ccatggatgc aatgaagaga gggctctgct gtgtgctgct gctgtgtgga    60
gcagtcttcg tttcgcccag cgccgtggag aagctgtggg tgaccgtgta ctacggcgtg   120
cccgtgtgga aggaggccac caccaccctg ttctgcgcca gcgacgccaa ggcctacgac   180
accgaggtgc acaacgtgtg gccaccacac gcctgcgtgc ccaccgaccc caaccccag   240 gagatcgtgc tggagaacgt gaccgagaac ttcaacatgt ggaagaacaa catggtggag   300
cagatgcacg aggacatcat cagcctgtgg gaccagagcc tgaagccctg cgtgaagctg   360
acccccctgt gcgtgaccct gcactgcacc aacctgaaga acgccaccaa caccaagagc   420
agcaactgga aggagatgga ccgcggcgag atcaagaact gcagcttcaa ggtgaccacc   480
agcatccgca caagatgca aggagtac gccctgttct acaagctgga cgtggtgccc   540
atcgacaacg acaacaccag ctacaagctg atcaactgca acaccagcgt gatcacccag   600
gcctgcccca aggtgagctt cgagcccatc cccatccact actgcgcccc cgccggcttc   660
gccatcctga gtgcaacga caagaagttc aacggcagcg cccctgcac caacgtgagc   720 accgtgcagt gcacccacgg catccgcccc gtggtgagca cccagctgct gctgaacggc   780
agcctggccg aggagggcgt ggtgatccgc agcgagaact tcaccgacaa cgccaagacc   840
atcatcgtgc agctgaagga gagcgtggag atcaactgca ccgcccaa caacaacacc   900 cgcaagagca tcaccatcgg ccccggccgc gccttctacg ccaccggcga catcatcggc   960
gacatccgcc aggcccactg caacatcagc ggcgagaagt ggaacaacac cctgaagcag  1020
atcgtgacca agctgcaggc ccagttcggc aacaagacca tcgtgttcaa gcagagcagc  1080
ggcggcgacc ccgagatcgt gatgcacagc ttcaactgcg gcggcgagtt cttctactgc  1140
aacagcaccc agctgttcaa cagcacctgg aacaacacca tcggccccaa caccaccaac  1200
ggcaccatca ccctgccctg ccgcatcaag cagatcatca accgctggca ggaggtgggc  1260
aaggccatgt acgccccccc catccgcggc cagatccgct gcagcagcaa catcaccggc  1320
ctgctgctga cccgcgacgg cggcaaggag atcagcaaca ccaccgagat cttccgcccc  1380
ggcggcggcg acatgcgcga caactggcgc agcgagctgt acaagtacaa ggtggtgaag  1440
atcgagcccc tgggcgtggc ccccaccaag gccaagcgcc gcgtggtgca gcgcgagaag  1500
cgcgccgtga cccctgggcgc catgttcctg ggcttcctgg gcgccgccgg cagcaccatg  1560
ggcgcccgca gcctgacccct gaccgtgcag gcccgccagc tgctgagcgg catcgtgcag  1620
cagcagaaca acctgctgcg cgccatcgag gcccagcagc acctgctgca gctgaccgtg  1680
tggggcatca gcagctgca ggcccgcgtg ctggccgtgg agcgctacct gaaggaccag  1740
cagctgctgg gcatctgggg ctgcagcggc aagctgatct gcaccaccgc cgtgccctgg  1800
aacgccagct ggagcaacaa gagcctggac cagatctgga caacatgac ctggatggag  1860 tgggagcgcg agatcgacaa ctacaccaac ctgatctaca ccctgatcga ggagagccag  1920
aaccagcagg agaagaacga gcaggagctg ctggagctgg acaagtgggc cagcctgtgg  1980
aactggttcg acatcagcaa gtggctgtgg tacatcaaga tcttcatcat gatcgtgggc  2040
ggcctggtgg gcctgcgcat cgtgttcacc gtgctgagca tcgtgaaccg cgtgcgccag  2100
ggctacagcc ccctgagctt ccagacccgc ttccccgccc ccgcggccc cgaccgcccc  2160 gagggcatcg aggaggaggg cggcgagcgc gaccgcgacc gcagcagccc cctggtgcac  2220
```

```
ggcctgctgg ccctgatctg gacgacctg cgcagcctgt gcctgttcag ctaccaccgc    2280
ctgcgcgacc tgatcctgat cgccgcccgc atcgtggagc tgctgggccg ccgcggctgg    2340
gaggccctga gtactggggg caacctgctg cagtactgga tccaggagct gaagaacagc    2400
gccgtgagcc tgttcgacgc catcgccatc gccgtggccg agggcaccga ccgcatcatc    2460
gaggtggccc agcgcatcgg ccgcgccttc ctgcacatcc ccgccgcat ccgccagggc     2520 ttcgagcgcg ccctgctgta actcgag                                       2547

<210> SEQ ID NO 49
<211> LENGTH: 2466
<212> TYPE: DNA
<213> ORGANISM: Artificial Sequence
<220> FEATURE:
<223> OTHER INFORMATION: gp160.modSF162.delV2

<400> SEQUENCE: 49
gaattcgcca ccatggatgc aatgaagaga gggctctgct gtgtgctgct gctgtgtgga      60
gcagtcttcg tttcgcccag cgccgtggag aagctgtggg tgaccgtgta ctacggcgtg     120
cccgtgtgga aggaggccac caccaccctg ttctgcgcca cgacgccaa ggcctacgac      180 accgaggtgc acaacgtgtg gccaccac gcctgcgtgc ccaccgaccc caaccccag       240 gagatcgtgt ggagaacgt gaccgagaac ttcaacatgt ggaagaacaa catggtggag      300
cagatgcacg aggacatcat cagcctgtgg gaccagagcc tgaagccctg cgtgaagctg     360 accccctgt gcgtgaccct gcactgcacc aacctgaaga cgccaccaa caccaagagc      420 agcaactgga aggagatgga ccgcggcgag atcaagaact gcagcttcaa ggtgggcgcc    480
ggcaagctga tcaactgcaa caccagcgtg atcacccagg cctgccccaa ggtgagcttc    540
gagcccatcc ccatccacta ctgcgccccc gccggcttcg ccatcctgaa gtgcaacgac    600
aagaagttca cggcagcgg ccctgcacc aacgtgagca ccgtgcagtg caccacggc       660 atccgccccg tggtgagcac ccagctgctg ctgaacggca gcctggccga ggagggcgtg    720
gtgatccgca gcgagaactt caccgacaac gccaagacca tcatcgtgca gctgaaggag    780
agcgtggaga tcaactgcac ccgccccaac aacaacaccc gcaagagcat caccatcggc    840
cccggccgcg ccttctacgc caccggcgac atcatcggcg acatccgcca ggcccactgc    900
aacatcagcg gcgagaagtg gaacaacacc ctgaagcaga tcgtgaccaa gctgcaggcc    960
cagttcggca acaagaccat cgtgttcaag cagagcagcg gcggcgaccc cgagatcgtg    1020
atgcacagct tcaactgcgg cggcgagttc ttctactgca acagcaccca gctgttcaac    1080
agcacctgga caacaccat cggccccaac aacaccaacg gcaccatcac cctgcccctg    1140
cgcatcaagc agatcatcaa ccgctggcag gaggtgggca aggccatgta cgccccccc     1200 atccgcggcc agatccgctg cagcagcaac atcaccggcc tgctgctgac ccgcgacggc    1260
ggcaaggaga tcagcaacac caccgagatc ttccgccccg cggcggcga catgcgcgac     1320 aactggcgca gcgagctgta caagtacaag gtggtgaaga tcgagcccct gggcgtggcc    1380
cccaccaagg ccaagcgccg cgtggtgcag cgcgagaagc gcgccgtgac cctgggcgcc    1440
atgttcctgg gcttcctggg cgccgccggc agcaccatgg gcgcccgcag cctgaccctg    1500
accgtgcagg cccgccagct gctgagcggc atcgtgcagc agcagaacaa cctgctgcgc    1560
gccatcgagg cccagcagca cctgctgcag ctgaccgtgt ggggcatcaa gcagctgcag    1620
gcccgcgtgc tggccgtgga gcgctacctg aaggaccagc agctgctggg catctgggc     1680 tgcagcggca agctgatctg caccaccgcc gtgcctgga acgccagctg gagcaacaag    1740
```

| | |
|---|---|
| agcctggacc agatctggaa caacatgacc tggatggagt gggagcgcga gatcgacaac | 1800 |
| tacaccaacc tgatctacac cctgatcgag gagagccaga accagcagga gaagaacgag | 1860 |
| caggagctgc tggagctgga caagtgggcc agcctgtgga actggttcga catcagcaag | 1920 |
| tggctgtggt acatcaagat cttcatcatg atcgtgggcg gcctggtggg cctgcgcatc | 1980 |
| gtgttcaccg tgctgagcat cgtgaaccgc gtgcgccagg gctacagccc cctgagcttc | 2040 |
| cagacccgct tccccgcccc ccgcggcccc gaccgccccg agggcatcga ggaggagggc | 2100 |
| ggcgagcgcg accgcgaccg cagcagcccc ctggtgcacg gcctgctggc cctgatctgg | 2160 |
| gacgacctgc gcagcctgtg cctgttcagc taccaccgcc tgcgcgacct gatcctgatc | 2220 |
| gccgcccgca tcgtggagct gctgggccgc gcggctggg aggccctgaa gtactggggc | 2280 |
| aacctgctgc agtactggat ccaggagctg aagaacagcg ccgtgagcct gttcgacgcc | 2340 |
| atcgccatcg ccgtggccga gggcaccgac cgcatcatcg aggtggccca gcgcatcggc | 2400 |
| cgcgccttcc tgcacatccc ccgccgcatc cgccagggct cgagcgcgc cctgctgtaa | 2460 |
| ctcgag | 2466 |

<210> SEQ ID NO 50
<211> LENGTH: 2358
<212> TYPE: DNA
<213> ORGANISM: Artificial Sequence
<220> FEATURE:
<223> OTHER INFORMATION: gp160.modSF162.delV1/V2

<400> SEQUENCE: 50

| | |
|---|---|
| gaattcgcca ccatggatgc aatgaagaga gggctctgct gtgtgctgct gctgtgtgga | 60 |
| gcagtcttcg tttcgcccag cgccgtggag aagctgtggg tgaccgtgta ctacggcgtg | 120 |
| cccgtgtgga aggaggccac caccaccctg ttctgcgcca gcgacgccaa ggcctacgac | 180 |
| accgaggtgc acaacgtgtg gccaccac gcctgcgtgc ccaccgaccc caaccccag | 240 |
| gagatcgtgc tggagaacgt gaccgagaac ttcaacatgt ggaagaacaa catggtggag | 300 |
| cagatgcacg aggacatcat cagcctgtgg gaccagagcc tgaagccctg cgtgaagctg | 360 |
| accccctgt gcgtgggcgc cggcaactgc cagaccagcg tgatcaccca ggcctgcccc | 420 |
| aaggtgagct tcgagcccat ccccatccac tactgcgccc ccgccggctt cgccatcctg | 480 |
| aagtgcaacg acaagaagtt caacggcagc ggcccctgca ccaacgtgag caccgtgcag | 540 |
| tgcacccacg gcatccgccc cgtggtgagc acccagctgc tgctgaacgg cagcctggcc | 600 |
| gaggagggcg tggtgatccg cagcgagaac ttcaccgaca acgccaagac catcatcgtg | 660 |
| cagctgaagg agagcgtgga gatcaactgc acccgcccca caacaacac cgcaagagc | 720 |
| atcaccatcg cccccggccg cgccttctac gccaccggcg acatcatcgg cgacatccgc | 780 |
| caggcccact gcaacatcag cggcgagaag tggaacaaca ccctgaagca gatcgtgacc | 840 |
| aagctgcagg cccagttcgg caacaagacc atcgtgttca gcagagcag cggcggcgac | 900 |
| cccgagatcg tgatgcacag cttcaactgc ggcggcgagt tcttctactg caacagcacc | 960 |
| cagctgttca acagcacctg gaacaacac atcgccccca caacaccaa cggcaccatc | 1020 |
| accctgccct gccgcatcaa gcagatcatc aaccgctggc aggaggtggg caaggccatg | 1080 |
| tacgcccccc ccatccgcgg ccagatccgc tgcagcagca catcaccgg cctgctgctg | 1140 |
| acccgcgacg gcggcaagga gatcagcaac accaccgaga tcttccgccc cggcggcggc | 1200 |
| gacatgcgcg acaactggcg cagcgagctg tacaagtaca aggtggtgaa gatcgagccc | 1260 |
| ctgggcgtgg cccccaccaa ggccaagcgc cgcgtggtgc agcgcgagaa gcgcgccgtg | 1320 |

| | |
|---|---|
| accctgggcg ccatgttcct gggcttcctg ggcgccgccg gcagcaccat gggcgcccgc | 1380 |
| agcctgaccc tgaccgtgca ggcccgccag ctgctgagcg gcatcgtgca gcagcagaac | 1440 |
| aacctgctgc gcgccatcga ggcccagcag cacctgctgc agctgaccgt gtggggcatc | 1500 |
| aagcagctgc aggcccgcgt gctggccgtg gagcgctacc tgaaggacca gcagctgctg | 1560 |
| ggcatctggg gctgcagcgg caagctgatc tgcaccaccg ccgtgccctg gaacgccagc | 1620 |
| tggagcaaca gagcctgga ccagatctgg aacaacatga cctggatgga gtgggagcgc | 1680 |
| gagatcgaca actacaccaa cctgatctac accctgatcg aggagagcca gaaccagcag | 1740 |
| gagaagaacg agcaggagct gctggagctg gacaagtggg ccagcctgtg gaactggttc | 1800 |
| gacatcagca gtggctgtg gtacatcaag atcttcatca tgatcgtggg cggcctggtg | 1860 |
| ggcctgcgca tcgtgttcac cgtgctgagc atcgtgaacc gcgtgcgcca gggctacagc | 1920 |
| cccctgagct tccagacccg cttccccgcc ccccgcggcc ccgaccgccc cgagggcatc | 1980 |
| gaggaggagg gcggcgagcg cgaccgcgac cgcagcagcc ccctggtgca cggcctgctg | 2040 |
| gccctgatct gggacgacct gcgcagcctg tgcctgttca gctaccaccg cctgcgcgac | 2100 |
| ctgatcctga tcgccgcccg catcgtggag ctgctgggcc gccgcggctg ggaggccctg | 2160 |
| aagtactggg gcaacctgct gcagtactgg atccaggagc tgaagaacag cgccgtgagc | 2220 |
| ctgttcgacg ccatcgccat cgccgtggcc gagggcaccg accgcatcat cgaggtggcc | 2280 |
| cagcgcatcg gccgcgcctt cctgcacatc ccccgccgca tccgccaggg cttcgagcgc | 2340 |
| gccctgctgt aactcgag | 2358 |

<210> SEQ ID NO 51
<211> LENGTH: 1494
<212> TYPE: DNA
<213> ORGANISM: Human immunodeficiency virus

<400> SEQUENCE: 51

| | |
|---|---|
| acaacagtct tgtgggtcac agtctattat ggggtacctg tgtggaaaga agcaaccacc | 60 |
| actctgtttt gtgcatcaga tgctaaagca tacaaagcag aggcacataa cgtctgggct | 120 |
| acacatgcct gtgtacccac agaccccaac ccacaggaag taaatttaac aaatgtgaca | 180 |
| gaaaatttta acatgtggaa aaataacatg gtggaacaga tgcatgagga tataatcagt | 240 |
| ttatgggatc aaagcctaaa gccatgtgta aaattaaccc cactctgtgt tactttaaat | 300 |
| tgtactgata gttgacagg tagtactaat ggcacaaata gtactagtgg cactaatagt | 360 |
| actagtggca ctaatagtac tagtactaat agtactgata gttgggaaaa gatgccagaa | 420 |
| ggagaaataa aaaactgctc tttcaatatc accacaagtg taagagataa agtgcagaaa | 480 |
| gaatattctc tcttctataa acttgatgta gtaccaatag ataatgataa tgctagctat | 540 |
| agattgataa attgtaatac ctcagtcatt acacaagcct gtccaaaggt atctttgaa | 600 |
| ccaattccca tacattattg tgccccggct ggttttgcga ttctaaagtg taaagataag | 660 |
| aagttcaatg gaacaggacc atgtaaaaat gtcagcacag tacaatgcac acatggaatt | 720 |
| agaccagtag tatcaactca actgctgtta aatggcagtc tagcagaaga agagatagta | 780 |
| cttagatctg aaaatttcac agacaatgct aaaaccataa tagtacagct gaatgaatct | 840 |
| gtagaaatta ttgtataag acccaacaat aatacaagaa aaagtataca tataggacca | 900 |
| gggagagcat tttatgcaac aggtgatata ataggagaca taagacaagc acattgtaac | 960 |
| attagtaaag caaactggac taacactta gaacagatag ttgaaaaatt aagagaacaa | 1020 |
| tttgggaata taaaacaat aatctttaat tcatcctcag gaggggaccc agaaattgta | 1080 |

```
tttcacagtt ttaattgtgg aggggaattt ttctattgta atacatcaca actatttaat    1140
agtacctgga atattactga agaggtaaat aagactaaag aaaatgacac tatcatactc    1200
ccatgcagaa taagacaaat tataaacatg tggcaagaag taggaaaagc aatgtatgcc    1260
cctcccatca gaggacaaat taaatgttca tcaaatatta cagggctgct attaactaga    1320
gatggtggta ctaacaataa taggacgaac gacaccgaga ccttcagacc tgggggagga    1380
aacatgaagg acaattggag aagtgaatta tataaatata agtagtaag aattgaacca     1440 ttaggagtag cacccaccca ggcaaagaga agagtggtgc aaagagagaa aaga          1494
```

<210> SEQ ID NO 52
<211> LENGTH: 2007
<212> TYPE: DNA
<213> ORGANISM: Human immunodeficiency virus

<400> SEQUENCE: 52

```
acaacagtct tgtgggtcac agtctattat ggggtacctg tgtggaaaga agcaaccacc     60
actctgtttt gtgcatcaga tgctaaagca tacaaagcag aggcacataa cgtctgggct    120
acacatgcct gtgtacccac agaccccaac ccacaggaag taaatttaac aaatgtgaca    180
gaaaatttta acatgtggaa aataacatg gtggaacaga tgcatgagga tataatcagt     240
ttatgggatc aaagcctaaa gccatgtgta aaattaaccc cactctgtgt tactttaaat    300
tgtactgata agttgacagg tagtactaat ggcacaaata gtactagtgg cactaatagt    360
actagtggca ctaatagtac tagtactaat agtactgata gttgggaaaa gatgccagaa    420
ggagaaataa aaaactgctc tttcaatatc accacaagtg taagagataa agtgcagaaa    480
gaatattctc tcttctataa acttgatgta gtaccaatag ataatgataa tgctagctat    540
agattgataa attgtaatac ctcagtcatt acacaagcct gtccaaaggt atcttttgaa    600
ccaattccca tacattattg tgccccggct ggttttgcga ttctaaagtg taaagataag    660
aagttcaatg gaacaggacc atgtaaaaat gtcagcacag tacaatgcac acatggaatt    720
agaccagtag tatcaactca actgctgtta aatggcagtc tagcagaaga agagatagta    780
cttagatctg aaaatttcac agacaatgct aaaaccataa tagtacagct gaatgaatct    840
gtagaaatta attgtataag acccaacaat aatacaagaa aaagtataca tataggacca    900
gggagagcat tttatgcaac aggtgatata ataggagaca taagacaagc acattgtaac    960
attagtaaag caaactggac taacacttta gaacagatag ttgaaaaatt aagagaacaa   1020
tttgggaata taaaacaat aatctttaat tcatcctcag gaggggaccc agaaattgta    1080
tttcacagtt ttaattgtgg aggggaattt ttctattgta atacatcaca actatttaat    1140
agtacctgga atattactga agaggtaaat aagactaaag aaaatgacac tatcatactc    1200
ccatgcagaa taagacaaat tataaacatg tggcaagaag taggaaaagc aatgtatgcc    1260
cctcccatca gaggacaaat taaatgttca tcaaatatta cagggctgct attaactaga    1320
gatggtggta ctaacaataa taggacgaac gacaccgaga ccttcagacc tgggggagga    1380
aacatgaagg acaattggag aagtgaatta tataaatata agtagtaag aattgaacca     1440 ttaggagtag cacccaccca ggcaaagaga agagtggtgc aaagagagaa aagagcagtg   1500
ggactaggag ctttgttcat tgggttcttg ggagcagcag gaagcactat gggcgcagcg    1560
tcagtgacgc tgacggtaca ggccagacaa ttattgtctg gtatagtgca acagcagaac    1620
aatttgctga gagctattga ggcgcaacag catctgttgc aactcacggt ctggggcatc    1680
aaacagctcc aggcaagaat cctggctgtg gaaagatacc taaaggatca acagctccta   1740
```

| gggatttggg gttgctctgg aaaactcatt tgcaccacta ctgtgccttg aactctagt | 1800 |
| tggagtaata aatctctgac tgagatttgg gataatatga cctggatgga gtgggaaaga | 1860 |
| gaaattggca attatacagg cttaatatac aatttaattg aaatagcaca aaaccagcaa | 1920 |
| gaaaagaatg aacaagaatt attggaatta gacaagtggg caagtttgtg gaattggttt | 1980 |
| gatataacaa actggctgtg gtatata | 2007 |

<210> SEQ ID NO 53
<211> LENGTH: 2532
<212> TYPE: DNA
<213> ORGANISM: Human immunodeficiency virus

<400> SEQUENCE: 53

| acaacagtct tgtgggtcac agtctattat ggggtacctg tgtggaaaga agcaaccacc | 60 |
| actctgtttt gtgcatcaga tgctaaagca tacaaagcag aggcacataa cgtctgggct | 120 |
| acacatgcct gtgtacccac agaccccaac ccacaggaag taaatttaac aaatgtgaca | 180 |
| gaaaatttta acatgtggaa aaataacatg gtggaacaga tgcatgagga tataatcagt | 240 |
| ttatgggatc aaagcctaaa gccatgtgta aaattaaccc cactctgtgt tactttaaat | 300 |
| tgtactgata agttgacagg tagtactaat ggcacaaata gtactagtgg cactaatagt | 360 |
| actagtggca ctaatagtac tagtactaat agtactgata gttgggaaaa gatgccagaa | 420 |
| ggagaaataa aaaactgctc tttcaatatc accacaagtg taagagataa agtgcagaaa | 480 |
| gaatattctc tcttctataa acttgatgta gtaccaatag ataatgataa tgctagctat | 540 |
| agattgataa attgtaatac ctcagtcatt acacaagcct gtccaaaggt atcttttgaa | 600 |
| ccaattccca tacattattg tgccccggct ggttttgcga ttctaaagtg taaagataag | 660 |
| aagttcaatg gaacaggacc atgtaaaaat gtcagcacag tacaatgcac acatggaatt | 720 |
| agaccagtag tatcaactca actgctgtta aatggcagtc tagcagaaga agagatagta | 780 |
| cttagatctg aaaatttcac agacaatgct aaaaccataa tagtacagct gaatgaatct | 840 |
| gtagaaatta ttgtataag acccaacaat aatacaagaa aaagtataca tataggacca | 900 |
| gggagagcat tttatgcaac aggtgatata ataggagaca taagacaagc acattgtaac | 960 |
| attagtaaag caaactggac taacacttta gaacagatag ttgaaaaatt aagagaacaa | 1020 |
| tttgggaata taaaacaat aatctttaat tcatcctcag gaggggaccc agaaattgta | 1080 |
| tttcacagtt ttaattgtgg aggggaattt ttctattgta atacatcaca actatttaat | 1140 |
| agtacctgga atattactga agaggtaaat aagactaaag aaaatgacac tatcatactc | 1200 |
| ccatgcagaa taagacaaat tataaacatg tggcaagaag taggaaaagc aatgtatgcc | 1260 |
| cctcccatca gaggacaaat taaatgttca tcaaatatta cagggctgct attaactaga | 1320 |
| gatggtggta ctaacaataa taggacgaac gacaccgaga ccttcagacc tgggggagga | 1380 |
| aacatgaagg acaattggag aagtgaatta tataaatata aagtagtaag aattgaacca | 1440 |
| ttaggagtag cacccacccc aggcaaagaga agagtggtgc aaagagagaa aagagcagtg | 1500 |
| ggactaggag ctttgttcat tgggttcttg ggagcagcag gaagcactat gggcgcagcg | 1560 |
| tcagtgacgc tgacggtaca ggccagacaa ttattgtctg gtatagtgca acagcagaac | 1620 |
| aatttgctga gagctattga ggcgcaacag catctgttgc aactcacggt ctggggcatc | 1680 |
| aaacagctcc aggcaagaat cctggctgtg gaaagatacc taaaggatca acagctccta | 1740 |
| gggatttggg gttgctctgg aaaactcatt tgcaccacta ctgtgccttg aactctagt | 1800 |
| tggagtaata aatctctgac tgagatttgg gataatatga cctggatgga gtgggaaaga | 1860 |

```
gaaattggca attatacagg cttaatatac aatttaattg aaatagcaca aaaccagcaa      1920
gaaaagaatg aacaagaatt attggaatta gacaagtggg caagtttgtg gaattggttt      1980
gatataacaa actggctgtg gtatataaga atattcataa tgatagtagg aggcttgata      2040
ggtttaagaa tagttttgc tgtactttct atagtgaata gagttaggca gggatactca       2100
ccaatatcat tgcagacccg cctcccagct cagaggggac cgacaggcc cgaaggaatc       2160 gaagaagaag gtggagagag agacagagac agatccaatc gattagtgca tggattattg      2220
gcactcatct gggacgatct gcggagcctg tgcctcttca gctaccaccg cttgagagac      2280
ttactcttga ttgtagcgag gattgtggaa cttctggac gcaggggtg ggaagccctc        2340 aagtattggt ggaatctcct gcagtattgg agtcaggagc taagagtag tgctgttagt      2400 ttgtttaatg ccacagcaat agcagtagct gaagggacag ataggattat agaaatagta      2460
caaagaattt ttagagctgt aattcacata cctagaagaa taagacaggg cttggagagg      2520
gctttactat aa                                                          2532

<210> SEQ ID NO 54
<211> LENGTH: 1599
<212> TYPE: DNA
<213> ORGANISM: Artificial Sequence
<220> FEATURE:
<223> OTHER INFORMATION: gp120.modUS4

<400> SEQUENCE: 54
gaattcgcca ccatggatgc aatgaagaga gggctctgct gtgtgctgct gctgtgtgga        60
gcagtcttcg tttcgcccag cgccaccacc gtgctgtggg tgaccgtgta ctacggcgtg       120
cccgtgtgga aggaggccac caccaccctg ttctgcgcca cgacgccaa ggcttacaag        180 gccgaggccc acaacgtgtg gccacccac gcctgcgtgc ccaccgaccc caacccccag        240
gaggtgaacc tgaccaacgt gaccgagaac ttcaacatgt ggaagaacaa catggtggag       300
cagatgcatg aggacatcat cagcctgtgg gaccagagcc tgaagccctg cgtgaagctg       360 accccctgt gcgtgaccct gaactgcacc gacaagctga ccggcagcac caacggcacc        420
aacagcacca gcggcaccaa cagcaccagc ggcaccaaca gcaccagcac caacagcacc       480
gacagctggg agaagatgcc cgagggcgag atcaagaact gcagcttcaa catcaccacc       540
agcgtgcgcg acaaggtgca gaaggagtac agcctgttct acaagctgga cgtggtgccc       600
atcgacaacg acaacgccag ctaccgcctg atcaactgca caccagcgt gatcacccag        660 gcctgcccca aggtgagctt cgagcccatc cccatccact actgcgcccc cgccggcttc       720
gccatcctga gtgcaagga caagaagttc aacggcaccg gccctgcaa gaacgtgagc         780 accgtgcagt gcacccacgg catccgcccc gtggtgagca cccagctgct gctgaacggc       840
agcctggccg aggaggagat cgtgctgcgc tccgagaact tcaccgacaa cgccaagacc       900
atcatcgtgc agctgaacga gtccgtggag atcaactgca tccgccccaa caacaacacg      960
cgtaagagca tccacatcgg ccccggccgc gccttctacg ccaccggcga catcatcggc      1020
gacatccgcc aggcccactg caacatcagc aaggccaact ggaccaacac cctcgagcag      1080
atcgtggaga gctgcgcga gcagttcggc aacaacaaga ccatcatctt caacagcagc      1140
agcggcggcg accccgagat cgtgttccac agcttcaact cggcggcga gttcttctac      1200 tgcaacacca gccagctgtt caacagcacc tggaacatca ccgaggaggt gaacaagacc      1260
aaggagaacg acaccatcat cctgccctgc cgcatccgcc agatcatcaa catgtggcag      1320
gaggtgggca aggccatgta cgccccccc atccgcggcc agatcaagtg cagcagcaat      1380
```

-continued

```
attaccggcc tgctgctgac ccgcgacggc ggcaccaaca caaccgcac caacgacacc      1440 gagaccttcc gccccggcgg cggcaacatg aaggacaact ggcgcagcga gctgtacaag      1500
tacaaggtgg tgcgcatcga gcccctgggc gtggccccca cccaggccaa gcgccgcgtg      1560
gtgcagcgcg agaagcgcta agatatcgga tcctctaga                            1599
```

<210> SEQ ID NO 55
<211> LENGTH: 1350
<212> TYPE: DNA
<213> ORGANISM: Artificial Sequence
<220> FEATURE:
<223> OTHER INFORMATION: gp120.modUS4.del 128-194

<400> SEQUENCE: 55

```
gaattcgcca ccatggatgc aatgaagaga gggctctgct gtgtgctgct gctgtgtgga      60
gcagtcttcg tttcgcccag cgccaccacc gtgctgtggg tgaccgtgta ctacggcgtg      120
cccgtgtgga aggaggccac caccaccctg ttctgcgcca gcgacgccaa ggcttacaag      180
gccgaggccc acaacgtgtg gccacccac gcctgcgtgc ccaccgaccc aaccccag       240 gaggtgaacc tgaccaacgt gaccgagaac ttcaacatgt ggaagaacaa catggtggag      300
cagatgcatg aggacatcat cagcctgtgg gaccagagcc tgaagccctg cgtgaagctg      360 accccctgt gcgtggggc agggaactgc gagaccagcg tgatcaccca ggcctgcccc      420
aaggtgagct tcgagcccat ccccatccac tactgcgccc cgccggctt cgccatcctg      480 aagtgcaagg acaagaagtt caacggcacc ggccctgca agaacgtgag caccgtgcag      540
tgcacccacg gcatccgccc cgtggtgagc acccagctgc tgctgaacgg cagcctggcc      600
gaggaggaga tcgtgctgcg ctccgagaac ttcaccgaca cgccaagac catcatcgtg      660 cagctgaacg agtccgtgga gatcaactgc atccgcccca caacaacac gcgtaagagc      720 atccacatcg gccccggccg cgccttctac gccaccggcg acatcatcgg cgacatccgc      780
caggcccact gcaacatcag caaggccaac tggaccaaca ccctcgagca gatcgtggag      840
aagctgcgcg agcagttcgg caacaacaag accatcatct tcaacagcag cagcggcggc      900
gaccccgaga tcgtgttcca gcttcaac tgcggcggcg agttcttcta ctgcaacacc      960
agccagctgt tcaacagcac ctggaacatc accgaggagg tgaacaagac caaggagaac      1020
gacaccatca tcctgcctg ccgcatccgc cagatcatca acatgtggca ggaggtgggc      1080
aaggccatgt acgccccccc catccgcggc cagatcaagt gcagcagcaa tattaccggc      1140
ctgctgctga cccgcgacgg cggcaccaac aacaaccgca ccaacgacac cgagaccttc      1200
cgccccggcg gcggcaacat gaaggacaac tggcgcagcg agctgtacaa gtacaaggtg      1260
gtgcgcatcg agcccctggg cgtggccccc acccaggcca gcgccgcgt ggtgcagcgc      1320 gagaagcgct aagatatcgg atcctctaga                                      1350
```

<210> SEQ ID NO 56
<211> LENGTH: 2112
<212> TYPE: DNA
<213> ORGANISM: Artificial Sequence
<220> FEATURE:
<223> OTHER INFORMATION: gp140.modUS4

<400> SEQUENCE: 56

```
gaattcgcca ccatggatgc aatgaagaga gggctctgct gtgtgctgct gctgtgtgga      60
gcagtcttcg tttcgcccag cgccaccacc gtgctgtggg tgaccgtgta ctacggcgtg      120
cccgtgtgga aggaggccac caccaccctg ttctgcgcca gcgacgccaa ggcttacaag      180
```

```
gccgaggccc acaacgtgtg ggccacccac gcctgcgtgc ccaccgaccc caacccccag      240
gaggtgaacc tgaccaacgt gaccgagaac ttcaacatgt ggaagaacaa catggtggag      300
cagatgcatg aggacatcat cagcctgtgg gaccagagcc tgaagccctg cgtgaagctg      360
acccccctgt gcgtgaccct gaactgcacc gacaagctga ccggcagcac caacggcacc      420
aacagcacca gcggcaccaa cagcaccagc ggcaccaaca gcaccagcac caacagcacc      480
gacagctggg agaagatgcc cgagggcgag atcaagaact gcagcttcaa catcaccacc      540
agcgtgcgcg acaaggtgca gaaggagtac agcctgttct acaagctgga cgtggtgccc      600
atcgacaacg acaacgccag ctaccgcctg atcaactgca acaccagcgt gatcacccag      660
gcctgcccca aggtgagctt cgagcccatc cccatccact actgcgcccc cgccggcttc      720
gccatcctga gtgcaagga caagaagttc aacggcaccg cccctgcaa gaacgtgagc      780 accgtgcagt gcacccacgg catccgcccc gtggtgagca cccagctgct gctgaacggc      840
agcctggccg aggaggagat cgtgctgcgc tccgagaact tcaccgacaa cgccaagacc      900
atcatcgtgc agctgaacga gtccgtggag atcaactgca tccgccccaa caacaacacg      960
cgtaagagca tccacatcgg ccccggccgc gccttctacg ccaccggcga catcatcggc     1020
gacatccgcc aggcccactg caacatcagc aaggccaact ggaccaacac cctcgagcag     1080
atcgtggaga gctgcgcga gcagttcggc aacaacaaga ccatcatctt caacagcagc     1140
agcggcggcg accccgagat cgtgttccac agcttcaact gcggcggcga gttcttctac     1200
tgcaacacca gccagctgtt caacagcacc tggaacatca ccgaggaggt gaacaagacc     1260
aaggagaacg acaccatcat cctgccctgc cgcatccgcc agatcatcaa catgtggcag     1320
gaggtgggca aggccatgta cgcccccccc atccgcggcc agatcaagtg cagcagcaat     1380
attaccggcc tgctgctgac ccgcgacggc ggcaccaaca caaccgcac caacgacacc     1440 gagaccttcc gccccggcgg cggcaacatg aaggacaact ggcgcagcga gctgtacaag     1500
tacaaggtgg tgcgcatcga gcccctgggc gtggcccca cccaggccaa gcgccgcgtg     1560
gtgcagcgcg agaagcgcgc cgtgggcctg ggcgccctgt tcatcggctt cctgggcgcc     1620
gccgggagca ccatgggcgc cgcctccgtg accctgaccg tgcaggcccg ccagctgctg     1680
agcggcatcg tgcagcagca gaacaacctg ctgcgcgcca tcgaggccca gcagcacctg     1740
ctgcagctga ccgtgtgggg catcaagcag ctgcaggccc gcatcctggc cgtggagcgc     1800
tacctgaagg accagcagct gctgggcatc tggggctgca gcggcaagct gatctgcacc     1860
accaccgtgc cctggaacag cagctggagc aacaagagcc tgaccgagat ctgggacaac     1920
atgacctgga tggagtggga gcgcgagatc ggcaactaca ccggcctgat ctacaacctg     1980
atcgagatcg cccagaacca gcaggagaag aacgagcagg agctgctgga gctggacaag     2040
tgggccagcc tgtggaactg gttcgacatc accaactggc tgtggtacat ctaagatatc     2100
ggatcctcta ga                                                         2112

<210> SEQ ID NO 57
<211> LENGTH: 2112
<212> TYPE: DNA
<213> ORGANISM: Artificial Sequence
<220> FEATURE:
<223> OTHER INFORMATION: gp140.mut.modUS4

<400> SEQUENCE: 57
gaattcgcca ccatggatgc aatgaagaga gggctctgct gtgtgctgct gctgtgtgga       60
gcagtcttcg tttcgcccag cgccaccacc gtgctgtggg tgaccgtgta ctacggcgtg      120
```

```
cccgtgtgga aggaggccac caccaccctg ttctgcgcca gcgacgccaa ggcttacaag      180
gccgaggccc acaacgtgtg gyccacccac gcctgcgtgc ccaccgaccc caaccccag       240 gaggtgaacc tgaccaacgt gaccgagaac ttcaacatgt ggaagaacaa catggtggag      300
cagatgcatg aggacatcat cagcctgtgg gaccagagcc tgaagccctg cgtgaagctg      360 accccctgt gcgtgaccct gaactgcacc gacaagctga ccggcagcac caacggcacc      420
aacagcacca gcggcaccaa cagcaccagc ggcaccaaca gcaccagcac caacagcacc      480
gacagctggg agaagatgcc cgagggcgag atcaagaact gcagcttcaa catcaccacc      540
agcgtgcgcg acaaggtgca aaggagtac agcctgttct acaagctgga cgtggtgccc      600
atcgacaacg acaacgccag ctaccgcctg atcaactgca caccagcgt gatcacccag      660 gcctgcccca aggtgagctt cgagcccatc cccatccact actgcgcccc cgccggcttc      720
gccatcctga gtgcaagga caagaagttc aacggcaccg cccctgcaa gaacgtgagc      780 accgtgcagt gcacccacgg catccgcccc gtggtgagca cccagctgct gctgaacggc      840
agcctggccg aggaggagat cgtgctgcgc tccgagaact tcaccgacaa cgccaagacc      900
atcatcgtgc agctgaacga gtccgtggag atcaactgca tccgcccaa caacaacacg      960 cgtaagagca tccacatcgg ccccggccgc gccttctacg ccaccggcga catcatcggc     1020
gacatccgcc aggcccactg caacatcagc aaggccaact ggaccaacac cctcgagcag     1080
atcgtggaga gctgcgcga gcagttcggc aacaacaaga ccatcatctt caacagcagc     1140
agcggcggcg accccgagat cgtgttccac agcttcaact gcggcggcga gttcttctac     1200
tgcaacacca gccagctgtt caacagcacc tggaacatca ccgaggaggt gaacaagacc     1260
aaggagaacg acaccatcat cctgccctgc cgcatccgcc agatcatcaa catgtggcag     1320
gaggtgggca aggccatgta cgcccccccc atccgcggcc agatcaagtg cagcagcaat     1380
attaccggcc tgctgctgac ccgcgacggc ggcaccaaca caaccgcac caacgacacc     1440 gagaccttcc gccccggcgg cggcaacatg aaggacaact ggcgcagcga gctgtacaag     1500
tacaaggtgg tgcgcatcga gccccgtgggc gtggcccca cccaggccaa cgccgcgtg     1560 gtgcagcgcg agaagagcgc cgtgggcctg ggcgccctgt tcatcggctt cctgggcgcc     1620
gccgggagca ccatgggcgc cgcctccgtg accctgaccg tgcaggcccg ccagctgctg     1680
agcggcatcg tgcagcagca gaacaacctg ctgcgcgcca tcgaggccca gcagcacctg     1740
ctgcagctga ccgtgtgggg catcaagcag ctgcaggccc gcatcctggc cgtggagcgc     1800
tacctgaagg accagcagct gctgggcatc tggggctgca gcggcaagct gatctgcacc     1860
accaccgtgc cctggaacag cagctggagc aacaagagcc tgaccgagat ctgggacaac     1920
atgacctgga tggagtggga gcgcgagatc ggcaactaca ccggcctgat ctacaacctg     1980
atcgagatcg cccagaacca gcaggagaag aacgagcagg agctgctgga gctggacaag     2040
tgggccagcc tgtggaactg gttcgacatc accaactggc tgtggtacat ctaagatatc     2100
ggatcctcta ga                                                         2112
```

<210> SEQ ID NO 58
<211> LENGTH: 2181
<212> TYPE: DNA
<213> ORGANISM: Artificial Sequence
<220> FEATURE:
<223> OTHER INFORMATION: gp140TM.modUS4

<400> SEQUENCE: 58

```
gaattcgcca ccatggatgc aatgaagaga gggctctgct gtgtgctgct gctgtgtgga      60
```

```
gcagtcttcg tttcgcccag cgccaccacc gtgctgtggg tgaccgtgta ctacggcgtg      120
cccgtgtgga aggaggccac caccaccctg ttctgcgcca gcgacgccaa ggcttacaag      180
gccgaggccc acaacgtgtg gccaccac gcctgcgtgc ccaccgaccc caaccccag       240 gaggtgaacc tgaccaacgt gaccgagaac ttcaacatgt ggaagaacaa catggtggag      300
cagatgcatg aggacatcat cagcctgtgg gaccagagcc tgaagccctg cgtgaagctg      360
acccccctgt gcgtgaccct gaactgcacc gacaagctga ccggcagcac caacggcacc      420
aacagcacca gcggcaccaa cagcaccagc ggcaccaaca gcaccagcac caacagcacc      480
gacagctggg agaagatgcc cgagggcgag atcaagaact gcagcttcaa catcaccacc      540
agcgtgcgcg acaaggtgca gaaggagtac agcctgttct acaagctgga cgtggtgccc      600
atcgacaacg acaacgccag ctaccgcctg atcaactgca caccagcgt gatcacccag       660 gcctgcccca aggtgagctt cgagcccatc cccatccact actgcgcccc cgccggcttc      720
gccatcctga gtgcaagga caagaagttc aacggcaccg cccctgcaa gaacgtgagc        780 accgtgcagt gcacccacgg catccgcccc gtggtgagca cccagctgct gctgaacggc      840
agcctggccg aggaggagat cgtgctgcgc tccgagaact tcaccgacaa cgccaagacc      900
atcatcgtgc agctgaacga gtccgtggag atcaactgca tccgccccaa caacaacacg      960
cgtaagagca tccacatcgg cccccggccgc gccttctacg ccaccggcga catcatcggc     1020
gacatccgcc aggcccactg caacatcagc aaggccaact ggaccaacac cctcgagcag     1080
atcgtggaga gctgcgcga gcagttcggc aacaacaaga ccatcatctt caacagcagc      1140
agcggcggcg accccgagat cgtgttccac agcttcaact gcggcggcga gttcttctac     1200
tgcaacacca gccagctgtt caacagcacc tggaacatca ccgaggaggt gaacaagacc     1260
aaggagaacg acaccatcat cctgccctgc cgcatccgcc agatcatcaa catgtggcag     1320
gaggtgggca aggccatgta cgcccccccc atccgcggcc agatcaagtg cagcagcaat     1380
attaccggcc tgctgctgac ccgcgacggc ggcaccaaca caaccgcac caacgacacc       1440 gagaccttcc gccccggcgg cggcaacatg aaggacaact ggcgcagcga gctgtacaag     1500
tacaaggtgg tgcgcatcga gcccctgggc gtggcccca cccaggccaa gcgccgcgtg       1560
gtgcagcgcg agaagcgcgc cgtgggcctg ggcgccctgt tcatcggctt cctgggcgcc     1620
gccgggagca ccatgggcgc cgcctccgtg accctgaccg tgcaggcccg ccagctgctg     1680
agcggcatcg tgcagcagca gaacaacctg ctgcgcgcca tcgaggccca gcagcacctg     1740
ctgcagctga ccgtgtgggg catcaagcag ctgcaggccc gcatcctggc cgtggagcgc     1800
tacctgaagg accagcagct gctgggcatc tgggctgca gcggcaagct gatctgcacc      1860
accaccgtgc cctggaacag cagctggagc aacaagagcc tgaccgagat ctgggacaac     1920
atgacctgga tggagtggga gcgcgagatc ggcaactaca ccggcctgat ctacaacctg     1980
atcgagatcg cccagaacca gcaggagaag aacgagcagg agctgctgga gctggacaag     2040
tgggccagcc tgtggaactg gttcgacatc accaactggc tgtggtacat ccgcatcttc      2100
atcatgatcg tgggcggcct gatcggcctg cgcatcgtgt tcgccgtgct gagcatcgtg      2160
taagatatcg gatcctctag a                                                2181

<210> SEQ ID NO 59
<211> LENGTH: 1818
<212> TYPE: DNA
<213> ORGANISM: Artificial Sequence
<220> FEATURE:
<223> OTHER INFORMATION: gp140.modUS4.delV1/V2
```

<400> SEQUENCE: 59

```
gaattcgcca ccatggatgc aatgaagaga gggctctgct gtgtgctgct gctgtgtgga      60
gcagtcttcg tttcgcccag cgccaccacc gtgctgtggg tgaccgtgta ctacggcgtg     120
cccgtgtgga aggaggccac caccaccctg ttctgcgcca gcgacgccaa ggcttacaag     180
gccgaggccc acaacgtgtg gccaccac gcctgcgtgc ccaccgaccc caaccccag      240
gaggtgaacc tgaccaacgt gaccgagaac ttcaacatgt ggaagaacaa catggtggag     300
cagatgcatg aggacatcat cagcctgtgg gaccagagcc tgaagccctg cgtgggcgcc     360
ggccaggcct gccccaaggt gagcttcgag cccatcccca tccactactg cgcccccgcc     420
ggcttcgcca tcctgaagtg caaggacaag aagttcaacg gcaccggccc ctgcaagaac     480
gtgagcaccg tgcagtgcac ccacggcatc cgccccgtgg tgagcaccca gctgctgctg     540
aacggcagcc tggccgagga ggagatcgtg ctgcgctccg agaacttcac cgacaacgcc     600
aagaccatca tcgtgcagct gaacgagtcc gtggagatca actgcatccg ccccaacaac     660
aacacgcgta agagcatcca catcggcccc ggccgcgcct tctacgccac cggcgacatc     720
atcggcgaca tccgccaggc ccactgcaac atcagcaagg ccaactggac caacaccctc     780
gagcagatcg tggagaagct gcgcgagcag ttcggcaaca acaagaccat catcttcaac     840
agcagcagcg gcggcgaccc cgagatcgtg ttccacagct tcaactgcgg cggcgagttc     900
ttctactgca caccagcca gctgttcaac agcacctgga acatcaccga ggaggtgaac     960
aagaccaagg agaacgacac catcatcctg ccctgccgca tccgccagat catcaacatg    1020
tggcaggagg tgggcaaggc catgtacgcc ccccccatcc gcggccagat caagtgcagc    1080
agcaatatta ccggcctgct gctgaccgc gacggcggca ccaacaacaa ccgcaccaac    1140
gacaccgaga ccttccgccc cggcggcggc aacatgaagg acaactggcg cagcgagctg    1200
tacaagtaca aggtggtgcg catcgagccc ctgggcgtgg cccccaccca ggccaagcgc    1260
cgcgtggtgc agcgcgagaa cgcgccgtg gcctgggcg ccctgttcat cggcttcctg    1320
ggcgccgccg ggagcaccat gggcgccgcc tccgtgaccc tgaccgtgca ggcccgccag    1380
ctgctgagcg gcatcgtgca gcagcagaac aacctgctgc gcgccatcga ggcccagcag    1440
cacctgctgc agctgaccgt gtggggcatc aagcagctgc aggcccgcat cctggccgtg    1500
gagcgctacc tgaaggacca gcagctgctg ggcatctggg gctgcagcgg caagctgatc    1560
tgcaccacca ccgtgccctg gaacagcagc tggagcaaca gagcctgac cgagatctgg    1620
gacaacatga cctggatgga gtgggagcgc gagatcggca actacaccgg cctgatctac    1680
aacctgatcg agatcgccca gaaccagcag gagaagaacg agcaggagct gctggagctg    1740
gacaagtggg ccagcctgtg gaactggttc gacatcacca ctggctgtg gtacatctaa    1800
gatatcggat cctctaga                                                 1818
```

<210> SEQ ID NO 60
<211> LENGTH: 2031
<212> TYPE: DNA
<213> ORGANISM: Artificial Sequence
<220> FEATURE:
<223> OTHER INFORMATION: gp140.modUS4.delV2

<400> SEQUENCE: 60

```
gaattcgcca ccatggatgc aatgaagaga gggctctgct gtgtgctgct gctgtgtgga      60
gcagtcttcg tttcgcccag cgccaccacc gtgctgtggg tgaccgtgta ctacggcgtg     120
cccgtgtgga aggaggccac caccaccctg ttctgcgcca gcgacgccaa ggcttacaag     180
```

```
gccgaggccc acaacgtgtg gccacccac gcctgcgtgc ccaccgaccc caacccccag      240
gaggtgaacc tgaccaacgt gaccgagaac ttcaacatgt ggaagaacaa catggtggag      300
cagatgcatg aggacatcat cagcctgtgg gaccagagcc tgaagccctg cgtgaagctg      360
acccccctgt gcgtgaccct gaactgcacc gacaagctga ccggcagcac caacggcacc      420
aacagcacca gcggcaccaa cagcaccagc ggcaccaaca gcaccagcac caacagcacc      480
gacagctggg agaagatgcc cgagggcgag atcaagaact gcagcttcaa catcggcgcc      540
ggccgcctga tcaactgcaa caccagcgtg atcacccagg cctgccccaa ggtgagcttc      600
gagcccatcc ccatccacta ctgcgcccc gccggcttcg ccatcctgaa gtgcaaggac      660
aagaagttca cggcaccgg ccctgcaag acgtgagca ccgtgcagtg cacccacggc      720
atccgccccg tggtgagcac ccagctgctg ctgaacggga gcctggccga ggaggagatc      780
gtgctgcgct ccgagaactt caccgacaac gccaagacca tcatcgtgca gctgaacgag      840
tccgtggaga tcaactgcat ccgccccaac aacaacacgc gtaagagcat ccacatcggc      900
cccggccgcg ccttctacgc caccggcgac atcatcggcg acatccgcca ggcccactgc      960
aacatcagca aggccaactg gaccaacacc ctcgagcaga tcgtggagaa gctgcgcgag     1020
cagttcggca caacaagac catcatcttc aacagcagca gcggcggcga ccccgagatc     1080
gtgttccaca gcttcaactg cggcggcgag ttcttctact gcaacaccag ccagctgttc     1140
aacagcacct ggaacatcac cgaggaggtg aacaagacca aggagaacga caccatcatc     1200
ctgccctgcc gcatccgcca gatcatcaac atgtggcagg aggtgggcaa ggccatgtac     1260 gccccccccca tccgcggcca gatcaagtgc agcagcaata ttaccggcct gctgctgacc     1320
cgcgacggcg gcaccaacaa caaccgcacc aacgacaccg agaccttccg ccccggcggc     1380
ggcaacatga aggacaactg gcgcagcgag ctgtacaagt acaaggtggt gcgcatcgag     1440
cccctgggcg tggcccccac ccaggccaag cgccgcgtgg tgcagcgcga aagcgcgcc     1500 gtgggcctgg cgccctgtt catcggcttc ctgggcgccg ccgggagcac catgggcgcc     1560
gcctccgtga ccctgaccgt gcaggcccgc cagctgctga gcggcatcgt gcagcagcag     1620
aacaacctgc tgcgcgccat cgaggcccag cagcacctgc tgcagctgac cgtgtggggc     1680
atcaagcagc tgcaggcccg catcctggcc gtggagcgct acctgaagga ccagcagctg     1740
ctgggcatct ggggctgcag cggcaagctg atctgcacca ccaccgtgcc ctggaacagc     1800
agctggagca acaagagcct gaccgagatc tgggacaaca tgacctggat ggagtgggag     1860
cgcgagatcg gcaactacac cggcctgatc tacaacctga tcgagatcgc ccagaaccag     1920
caggagaaga cgagcagga gctgctggag ctggacaagt gggccagcct gtggaactgg     1980
ttcgacatca ccaactggct gtggtacatc taagatatcg gatcctctag a              2031
```

<210> SEQ ID NO 61
<211> LENGTH: 1818
<212> TYPE: DNA
<213> ORGANISM: Artificial Sequence
<220> FEATURE:
<223> OTHER INFORMATION: gp140.mut.modUS4.delV1/V2

<400> SEQUENCE: 61

```
gaattcgcca ccatggatgc aatgaagaga gggctctgct gtgtgctgct gctgtgtgga       60
gcagtcttcg tttcgcccag cgccaccacc gtgctgtggg tgaccgtgta ctacggcgtg      120
cccgtgtgga aggaggccac caccaccctg ttctgcgcca gcgacgccaa ggcttacaag      180
gccgaggccc acaacgtgtg gccacccac gcctgcgtgc ccaccgaccc caacccccag      240
```

```
gaggtgaacc tgaccaacgt gaccgagaac ttcaacatgt ggaagaacaa catggtggag      300
cagatgcatg aggacatcat cagcctgtgg gaccagagcc tgaagccctg cgtgggcgcc      360
ggccaggcct gccccaaggt gagcttcgag cccatcccca tccactactg cgcccccgcc      420
ggcttcgcca tcctgaagtg caaggacaag aagttcaacg gcaccggccc ctgcaagaac      480
gtgagcaccg tgcagtgcac ccacggcatc cgcccgtgg tgagcaccca gctgctgctg      540
aacggcagcc tggccgagga ggagatcgtg ctgcgctccg agaacttcac cgacaacgcc      600
aagaccatca tcgtgcagct gaacgagtcc gtggagatca actgcatccg ccccaacaac      660
aacacgcgta agagcatcca catcggcccc ggccgcgcct ctacgccac cggcgacatc      720 atcggcgaca tccgccaggc ccactgcaac atcagcaagg ccaactggac caacaccctc      780
gagcagatcg tggagaagct gcgcgagcag ttcggcaaca caagaccat catcttcaac      840 agcagcagcg gcggcgaccc cgagatcgtg ttccacagct tcaactgcgg cggcgagttc      900
ttctactgca caccagcca gctgttcaac agcacctgga acatcaccga ggaggtgaac      960
aagaccaagg agaacgacac catcatcctg ccctgccgca tccgccagat catcaacatg     1020
tggcaggagg tgggcaaggc catgtacgcc ccccccatcc gcggccagat caagtgcagc     1080
agcaatatta ccggcctgct gctgacccgc gacggcggca ccaacaacaa ccgcaccaac     1140
gacaccgaga ccttccgccc cggcggcggc aacatgaagg acaactggcg cagcgagctg     1200
tacaagtaca aggtggtgcg catcgagccc ctgggcgtgg cccccaccca ggccaagcgc     1260
cgcgtggtgc agcgcgagaa gagcgccgtg ggcctgggcg ccctgttcat cggcttcctg     1320
ggcgccgccg ggagcaccat gggcgccgcc tccgtgaccc tgaccgtgca ggcccgccag     1380
ctgctgagcg gcatcgtgca gcagcagaac aacctgctgc gcgccatcga ggcccagcag     1440
cacctgctgc agctgaccgt gtggggcatc aagcagctgc aggcccgcat cctggccgtg     1500
gagcgctacc tgaaggacca gcagctgctg ggcatctggg gctgcagcgg caagctgatc     1560
tgcaccacca ccgtgccctg gaacagcagc tggagcaaca gagcctgac cgagatctgg     1620 gacaacatga cctggatgga gtgggagcgc gagatcggca actacaccgg cctgatctac     1680
aacctgatcg agatcgccca gaaccagcag gagaagaacg agcaggagct gctggagctg     1740
gacaagtggg ccagcctgtg gaactggttc gacatcacca ctggctgtg gtacatctaa     1800 gatatcggat cctctaga                                                   1818
```

<210> SEQ ID NO 62
<211> LENGTH: 1818
<212> TYPE: DNA
<213> ORGANISM: Artificial Sequence
<220> FEATURE:
<223> OTHER INFORMATION: gp140.modUS4.del 128-194

<400> SEQUENCE: 62

```
gaattcgcca ccatggatgc aatgaagaga gggctctgct gtgtgctgct gctgtgtgga       60
gcagtcttcg tttcgcccag cgccaccacc gtgctgtggg tgaccgtgta ctacggcgtg      120
cccgtgtgga aggaggccac caccaccctg ttctgcgcca cgacgccaa ggcttacaag      180 gccgaggccc acaacgtgtg gggccaccac gcctgcgtgc ccaccgaccc caacccccag      240
gaggtgaacc tgaccaacgt gaccgagaac ttcaacatgt ggaagaacaa catggtggag      300
cagatgcatg aggacatcat cagcctgtgg gaccagagcc tgaagccctg cgtgggcgcc      360
ggccaggcct gccccaaggt gagcttcgag cccatcccca tccactactg cgcccccgcc      420
ggcttcgcca tcctgaagtg caaggacaag aagttcaacg gcaccggccc ctgcaagaac      480
```

```
gtgagcaccg tgcagtgcac ccacggcatc cgccccgtgg tgagcaccca gctgctgctg      540
aacggcagcc tggccgagga ggagatcgtg ctgcgctccg agaacttcac cgacaacgcc      600
aagaccatca tcgtgcagct gaacgagtcc gtggagatca actgcatccg ccccaacaac      660
aacacgcgta agagcatcca catcggcccc ggccgcgcct tctacgccac cggcgacatc      720
atcggcgaca tccgccaggc ccactgcaac atcagcaagg ccaactggac caacaccctc      780
gagcagatcg tggagaagct gcgcgagcag ttcggcaaca acaagaccat catcttcaac      840
agcagcagcg gcggcgaccc cgagatcgtg ttccacagct caactgcgg cggcgagttc       900 ttctactgca acaccagcca gctgttcaac agcacctgga acatcaccga ggaggtgaac      960
aagaccaagg agaacgacac catcatcctg ccctgccgca tccgccagat catcaacatg     1020
tggcaggagg tgggcaaggc catgtacgcc ccccccatcc gcggcagat caagtgcagc      1080 agcaatatta ccggcctgct gctgaccccg gacggcggca ccaacaacaa ccgcaccaac     1140
gacaccgaga ccttccgccc cggcggcggc aacatgaagg acaactggcg cagcgagctg     1200
tacaagtaca aggtggtgcg catcgagccc ctgggcgtgg ccccaccca ggccaagcgc      1260 cgcgtggtgc agcgcgagaa gagcgccgtg ggcctgggcg ccctgttcat cggcttcctg     1320
ggcgccgccg ggagcaccat gggcgccgcc tccgtgaccc tgaccgtgca ggcccgccag     1380
ctgctgagcg gcatcgtgca gcagcagaac aacctgctgc gcgccatcga ggcccagcag     1440
cacctgctgc agctgaccgt gtggggcatc aagcagctgc aggcccgcat cctggccgtg     1500
gagcgctacc tgaaggacca gcagctgctg ggcatctggg gctgcagcgg caagctgatc     1560
tgcaccacca ccgtgccctg aacagcagc tggagcaaca agagcctgac cgagatctgg     1620
gacaacatga cctggatgga gtgggagcgc gagatcggca ctacaccgg cctgatctac      1680 aacctgatcg agatcgccca gaaccagcag gagaagaacg agcaggagct gctggagctg     1740
gacaagtggg ccagcctgtg gaactggttc gacatcacca ctggctgtg gtacatctaa      1800 gatatcggat cctctaga                                                  1818
```

<210> SEQ ID NO 63
<211> LENGTH: 1863
<212> TYPE: DNA
<213> ORGANISM: Artificial Sequence
<220> FEATURE:
<223> OTHER INFORMATION: gp140.mut.modUS4.del 128-194

<400> SEQUENCE: 63

```
gaattcgcca ccatggatgc aatgaagaga gggctctgct gtgtgctgct gctgtgtgga       60
gcagtcttcg tttcgcccag cgccaccacc gtgctgtggg tgaccgtgta ctacggcgtg      120
cccgtgtgga aggaggccac caccaccctg ttctgcgcca gcgacgccaa ggcttacaag      180
gccgaggccc acaacgtgtg gccaccac gcctgcgtgc ccaccgaccc caaccccag      240 gaggtgaacc tgaccaacgt gaccgagaac ttcaacatgt ggaagaacaa catggtggag      300
cagatgcatg aggacatcat cagcctgtgg gaccagagcc tgaagccctg cgtgaagctg      360 accccctgt gcgtggggc agggaactgc gagaccagc tgatcaccca ggcctgccc       420 aaggtgagct tcgagcccat ccccatccac tactgcgccc ccgccggctt cgccatcctg      480
aagtgcaagg acaagaagtt caacggcacc ggcccctgca gaacgtgag caccgtgcag      540 tgcacccacg gcatccgccc cgtggtgagc acccagctgc tgctgaacgg cagcctggcc      600
gaggaggaga tcgtgctgcg ctccgagaac ttcaccgaca cgccaagac catcatcgtg      660 cagctgaacg agtccgtgga gatcaactgc atccgcccca caacaacac gcgtaagagc      720
```

| | |
|---|---:|
| atccacatcg gccccggccg cgccttctac gccaccggcg acatcatcgg cgacatccgc | 780 |
| caggcccact gcaacatcag caaggccaac tggaccaaca ccctcgagca gatcgtggag | 840 |
| aagctgcgcg agcagttcgg caacaacaag accatcatct caacagcag cagcggcggc | 900 |
| gaccccgaga tcgtgttcca cagcttcaac tgcggcggcg agttcttcta ctgcaacacc | 960 |
| agccagctgt tcaacagcac ctggaacatc accgaggagg tgaacaagac caaggagaac | 1020 |
| gacaccatca tcctgccctg ccgcatccgc cagatcatca catgtggca ggaggtgggc | 1080 |
| aaggccatgt acgccccccc catccgcggc cagatcaagt gcagcagcaa tattaccggc | 1140 |
| ctgctgctga cccgcgacgg cggcaccaac aacaaccgca ccaacgacac cgagaccttc | 1200 |
| cgccccggcg gcggcaacat gaaggacaac tggcgcagcg agctgtacaa gtacaaggtg | 1260 |
| gtgcgcatcg agcccctggg cgtggccccc acccaggcca agccgcgt ggtgcagcgc | 1320 |
| gagaagagcg ccgtgggcct gggcgccctt ttcatcggct cctgggcgc cgccgggagc | 1380 |
| accatgggcg ccgcctccgt gaccctgacc gtgcaggccc ccagctgct gagcggcatc | 1440 |
| gtgcagcagc agaacaacct gctgcgcgcc atcgaggccc agcagcacct gctgcagctg | 1500 |
| accgtgtggg gcatcaagca gctgcaggcc cgcatcctgg ccgtggagcg ctacctgaag | 1560 |
| gaccagcagc tgctgggcat ctggggctgc agcggcaagc tgatctgcac caccaccgtg | 1620 |
| ccctggaaca gcagctggag caacaagagc ctgaccgaga tctgggacaa catgacctgg | 1680 |
| atggagtggg agcgcgagat cggcaactac accggcctga tctacaacct gatcgagatc | 1740 |
| gcccagaacc agcaggagaa gaacgagcag gagctgctgg agctggacaa gtgggccagc | 1800 |
| ctgtggaact ggttcgacat caccaactgg ctgtggtaca tctaagatat cggatcctct | 1860 |
| aga | 1863 |

<210> SEQ ID NO 64
<211> LENGTH: 2634
<212> TYPE: DNA
<213> ORGANISM: Artificial Sequence
<220> FEATURE:
<223> OTHER INFORMATION: gp160.modUS4

<400> SEQUENCE: 64

| | |
|---|---:|
| gaattcgcca ccatggatgc aatgaagaga gggctctgct gtgtgctgct gctgtgtgga | 60 |
| gcagtcttcg tttcgcccag cgccaccacc gtgctgtggg tgaccgtgta ctacggcgtg | 120 |
| cccgtgtgga aggaggccac caccaccctg ttctgcgcca gcgacgccaa ggcttacaag | 180 |
| gccgaggccc acaacgtgtg gaccacccac gcctgcgtgc ccaccgaccc caacccccag | 240 |
| gaggtgaacc tgaccaacgt gaccgagaac ttcaacatgt ggaagaacaa catggtggag | 300 |
| cagatgcatg aggacatcat cagcctgtgg gaccagagcc tgaagccctg cgtgaagctg | 360 |
| accccccctgt gcgtgaccct gaactgcacc gacaagctga ccggcagcac caacggcacc | 420 |
| aacagcacca gcggcaccaa cagcaccagc ggcaccaaca gcaccagcac caacagcacc | 480 |
| gacagctggg agaagatgcc cgagggcgag atcaagaact gcagcttcaa catcaccacc | 540 |
| agcgtgcgcg acaaggtgca gaaggagtac agcctgttct acaagctgga cgtggtgccc | 600 |
| atcgacaacg acaacgccag ctaccgcctg atcaactgca acaccagcgt gatcacccag | 660 |
| gcctgcccca aggtgagctt cgagcccatc cccatccact actgcgcccc gccggcttc | 720 |
| gccatcctga gtgcaagga caagaagttc aacggcaccg gccctgcaa gaacgtgagc | 780 |
| accgtgcagt gcacccacgg catccgcccc gtggtgagca cccagctgct gctgaacggc | 840 |
| agcctggccg aggaggagat cgtgctgcgc tccgagaact tcaccgacaa cgccaagacc | 900 |

| | |
|---|---:|
| atcatcgtgc agctgaacga gtccgtggag atcaactgca tccgcccaa caacaacacg | 960 |
| cgtaagagca tccacatcgg ccccggccgc gccttctacg ccaccggcga catcatcggc | 1020 |
| gacatccgcc aggcccactg caacatcagc aaggccaact ggaccaacac cctcgagcag | 1080 |
| atcgtggaga agctgcgcga gcagttcggc aacaacaaga ccatcatctt caacagcagc | 1140 |
| agcggcggcg accccgagat cgtgttccac agcttcaact gcggcggcga gttcttctac | 1200 |
| tgcaacacca gccagctgtt caacagcacc tggaacatca ccgaggaggt gaacaagacc | 1260 |
| aaggagaacg acaccatcat cctgccctgc cgcatccgcc agatcatcaa catgtggcag | 1320 |
| gaggtgggca aggccatgta cgccccccc atccgcggcc agatcaagtg cagcagcaat | 1380 |
| attaccggcc tgctgctgac ccgcgacggc ggcaccaaca caaccgcac caacgacacc | 1440 |
| gagaccttcc gccccggcgg cggcaacatg aaggacaact ggcgcagcga gctgtacaag | 1500 |
| tacaaggtgg tgcgcatcga gcccctgggc gtggccccca cccaggccaa cgccgcgtg | 1560 |
| gtgcagcgcg agaagcgcgc cgtgggcctg gcgccctgt tcatcggctt cctgggcgcc | 1620 |
| gccgggagca ccatgggcgc cgcctccgtg accctgaccg tgcaggcccg ccagctgctg | 1680 |
| agcggcatcg tgcagcagca gaacaacctg ctgcgcgcca tcgaggccca gcagcacctg | 1740 |
| ctgcagctga ccgtgtgggg catcaagcag ctgcaggccc gcatcctggc cgtggagcgc | 1800 |
| tacctgaagg accagcagct gctgggcatc tgggcctgca cggcaagct gatctgcacc | 1860 |
| accaccgtgc cctggaacag cagctggagc aacaagagcc tgaccgagat ctgggacaac | 1920 |
| atgacctgga tggagtggga gcgcgagatc ggcaactaca ccggcctgat ctacaacctg | 1980 |
| atcgagatcg cccagaacca gcaggagaag aacgagcagg agctgctgga gctggacaag | 2040 |
| tgggccagcc tgtggaactg gttcgacatc accaactggc tgtggtacat ccgcatcttc | 2100 |
| atcatgatcg tgggcggcct gatcggcctg cgcatcgtgt tcgccgtgct gagcatcgtg | 2160 |
| aaccgcgtgc gccagggcta cagccccatc agcctgcaga cccgcctgcc cgcccagcgc | 2220 |
| ggccccgacc gccccgaggg catcgaggag gagggcggcg agcgcgaccg cgaccgcagc | 2280 |
| aaccgcctgg tgcacggcct gctggccctg atctgggacg acctgcgcag cctgtgcctg | 2340 |
| ttcagctacc accgcctgcg cgacctgctg ctgatcgtgg cccgcatcgt ggagctgctg | 2400 |
| ggccgccgcg gctgggaggc cctgaagtac tggtggaacc tgctgcagta ctggagccag | 2460 |
| gagctgaaga gcagcgccgt gagcctgttc aacgccaccg ccatcgccgt ggccgagggc | 2520 |
| accgaccgca tcatcgagat cgtgcagcgc atcttccgcg ccgtgatcca catccccgc | 2580 |
| cgcatccgcc agggcctgga gcgcgccctg ctgtaagata tcggatcctc taga | 2634 |

<210> SEQ ID NO 65
<211> LENGTH: 2538
<212> TYPE: DNA
<213> ORGANISM: Artificial Sequence
<220> FEATURE:
<223> OTHER INFORMATION: gp160.modUS4.delV1

<400> SEQUENCE: 65

| | |
|---|---:|
| gaattcgcca ccatggatgc aatgaagaga gggctctgct gtgtgctgct gctgtgtgga | 60 |
| gcagtcttcg tttcgcccag cgccaccacc gtgctgtggg tgaccgtgta ctacggcgtg | 120 |
| cccgtgtgga aggaggccac caccaccctg ttctgcgcca cgacgccaa ggcttacaag | 180 |
| gccgaggccc acaacgtgtg ggccacccac gcctgcgtgc ccaccgaccc caacccccag | 240 |
| gaggtgaact gaccaacgt gaccgagaac ttcaacatgt ggaagaacaa catggtggag | 300 |
| cagatgcatg aggacatcat cagcctgtgg gaccagagcc tgaagccctg cgtgaagctg | 360 |

```
accccccctgt gcgtgaccct gaactgcacc gacaagctgg gcgccggcgg cgagatcaag    420
aactgcagct tcaacatcac caccagcgtg cgcgacaagg tgcagaagga gtacagcctg    480
ttctacaagc tggacgtggt gcccatcgac aacgacaacg ccagctaccg cctgatcaac    540
tgcaacacca gcgtgatcac ccaggcctgc cccaaggtga gcttcgagcc catccccatc    600
cactactgcg ccccgccgg cttcgccatc ctgaagtgca aggacaagaa gttcaacggc    660
accggcccct gcaagaacgt gagcaccgtg cagtgcaccc acggcatccg ccccgtggtg    720
agcacccagc tgctgctgaa cggcagcctg gccgaggagg agatcgtgct cgctccgag    780 aacttcaccg acaacgccaa gaccatcatc gtgcagctga cgagtccgt ggagatcaac    840 tgcatccgcc ccaacaacaa cacgcgtaag agcatccaca tcggcccggg ccgcgccttc    900
tacgccaccg cgacatcat cggcgacatc cgccaggccc actgcaacat cagcaaggcc    960
aactggacca cacccctcga gcagatcgtg gagaagctgc gcgagcagtt cggcaacaac    1020
aagaccatca tcttcaacag cagcagcggc ggcgaccccg agatcgtgtt ccacagcttc    1080
aactgcggcg gcgagttctt ctactgcaac accagccagc tgttcaacag cacctggaac    1140
atcaccgagg aggtgaacaa gaccaaggag aacgacacca tcatcctgcc ctgccgcatc    1200
cgccagatca tcaacatgtg gcaggaggtg ggcaaggcca tgtacgcccc ccccatccgc    1260
ggccagatca agtgcagcag caatattacc ggcctgctgc tgacccgcga cggcggcacc    1320
aacaacaacc gcaccaacga caccgagacc ttccgccccg gcggcggcaa catgaaggac    1380
aactggcgca gcgagctgta caagtacaag gtggtgcgca tcgagcccct gggcgtggcc    1440
cccacccagg ccaagcgccg cgtggtgcag cgcgagaagc gcgccgtggg cctgggcgcc    1500
ctgttcatcg gcttcctggg cgccgccggg agcaccatgg gcgccgcctc cgtgaccctg    1560
accgtgcagg cccgccagct gctgagcggc atcgtgcagc agcagaacaa cctgctgcgc    1620
gccatcgagg cccagcagca cctgctgcag ctgaccgtgt ggggcatcaa gcagctgcag    1680
gcccgcatcc tggccgtgga gcgctacctg aaggaccagc agctgctggg catctggggc    1740
tgcagcggca agctgatctg caccaccacc gtgccctgga acagcagctg gagcaacaag    1800
agcctgaccg agatctggga caacatgacc tggatggagt gggagcgcga gatcggcaac    1860
tacaccggcc tgatctacaa cctgatcgag atcgcccaga accagcagga gaagaacgag    1920
caggagctgc tggagctgga caagtgggcc agcctgtgga actggttcga catcaccaac    1980
tggctgtggt acatccgcat cttcatcatg atcgtgggcg gcctgatcgg cctgcgcatc    2040
gtgttcgccg tgctgagcat cgtgaaccgc gtgcgccagg gctacagccc catcagcctg    2100
cagacccgcc tgcccgccca gcgcggcccc gaccgcccg agggcatcga ggaggagggc    2160
ggcgagcgcg accgcgaccg cagcaaccgc ctggtgcacg gcctgctggc cctgatctgg    2220
gacgacctgc gcagcctgtg cctgttcagc taccaccgcc tgcgcgacct gctgctgatc    2280
gtggcccgca tcgtggagct gctgggccgc cgcggctggg aggccctgaa gtactggtgg    2340
aacctgctgc agtactggag ccaggagctg aagagcagcg ccgtgagcct gttcaacgcc    2400
accgccatcg ccgtggccga gggcaccgac cgcatcatcg agatcgtgca gcgcatcttc    2460
cgcgccgtga tccacatccc ccgccgcatc cgccagggcc tggagcgcgc cctgctgtaa    2520
gatatcggat cctctaga                                                  2538
```

```
<210> SEQ ID NO 66
<211> LENGTH: 2553
<212> TYPE: DNA
<213> ORGANISM: Artificial Sequence
```

<220> FEATURE:
<223> OTHER INFORMATION: gp160.modUS4.delV2

<400> SEQUENCE: 66

```
gaattcgcca ccatggatgc aatgaagaga gggctctgct gtgtgctgct gctgtgtgga      60
gcagtcttcg tttcgcccag cgccaccacc gtgctgtggg tgaccgtgta ctacggcgtg     120
cccgtgtgga aggaggccac caccaccctg ttctgcgcca cgacgccaa ggcttacaag      180
gccgaggccc acaacgtgtg gccaccac gcctgcgtgc caccgaccc caaccccag        240
gaggtgaacc tgaccaacgt gaccgagaac ttcaacatgt ggaagaacaa catggtggag    300
cagatgcatg aggacatcat cagcctgtgg gaccagagcc tgaagccctg cgtgaagctg    360
accccctgt gcgtgaccct gaactgcacc gacaagctga ccggcagcac caacggcacc     420
aacagcacca gcggcaccaa cagcaccagc ggcaccaaca gcaccagcac caacagcacc    480
gacagctggg agaagatgcc cgagggcgag atcaagaact gcagcttcaa catcggcgcc    540
ggccgcctga tcaactgcaa caccagcgtg atcacccagg cctgcccaa ggtgagcttc     600
gagcccatcc ccatccacta ctgcgccccc gccggcttcg ccatcctgaa gtgcaaggac    660
aagaagttca acggcaccgg ccctgcaag aacgtgagca ccgtgcagtg cacccacggc    720
atccgccccg tggtgagcac ccagctgctg ctgaacggca gcctggccga ggaggagatc    780
gtgctgcgct ccgagaactt caccgacaac gccaagacca tcatcgtgca gctgaacgag    840
tccgtggaga tcaactgcat ccgccccaac aacaacacgc gtaagagcat ccacatcggc    900
cccgccgcg ccttctacgc caccggcgac atcatcggcg acatccgcca ggcccactgc    960
aacatcagca aggccaactg gaccaacacc ctcgagcaga tcgtggagaa gctgcgcgag   1020
cagttcggca caacaagac catcatcttc aacagcagca cgcggcgga cccgagatc     1080
gtgttccaca gcttcaactg cggcggcgag ttcttctact gcaacaccag ccagctgttc   1140
aacagcacct ggaacatcac cgaggaggtg aacaagacca aggagaacga caccatcatc   1200
ctgccctgcc gcatccgcca gatcatcaac atgtggcagg aggtgggcaa ggccatgtac   1260
gccccccca tccgcggcca gatcaagtgc agcagcaata ttaccggcct gctgctgacc    1320
cgcgacggcg gcaccaacaa caaccgcacc aacgacaccg agaccttccg ccccggcggc   1380
ggcaacatga aggacaactg gcgcagcgag ctgtacaagt acaaggtggt gcgcatcgag   1440
cccctgggcg tggccccac ccaggccaag cgccgcgtgg tgcagcgcga aagcgcgcc    1500
gtgggcctgg cgccctgtt catcggcttc ctgggcgccg ccgggagcac catgggcgcc    1560
gcctccgtga ccctgaccgt gcaggcccgc cagctgctga cgggcatcgt gcagcagcag   1620
aacaacctgc tgcgcgccat cgaggcccag cagcacctgc tgcagctgac cgtgtgggc    1680
atcaagcagc tgcaggcccg catcctggcc gtggagcgct acctgaagga ccagcagctg   1740
ctgggcatct ggggctgcag cggcaagctg atctgcacca ccaccgtgcc ctggaacagc   1800
agctggagca acaagagcct gaccgagatc tgggacaaca tgacctggat ggagtgggag   1860
cgcgagatcg gcaactacac cggcctgatc tacaacctga tcgagatcgc ccagaaccag   1920
caggagaaga acgagcagga gctgctggag ctggacaagt gggccagcct gtggaactgg   1980
ttcgacatca ccaactggct gtggtacatc cgcatcttca tcatgatcgt gggcggcctg   2040
atcggcctgc gcatcgtgtt cgccgtgctg agcatcgtga accgcgtgcg ccagggctac   2100
agccccatca gcctgcagac ccgctgcccc gccagcgcg gcccgaccg cccgagggc     2160
atcgaggagg agggcggcga gcgcgaccgc gaccgcagca accgcctggt gcacggcctg   2220
ctggccctga tctgggacga cctgcgcagc ctgtgcctgt tcagctacca ccgcctgcgc   2280
```

```
gacctgctgc tgatcgtggc ccgcatcgtg gagctgctgg gccgccgcgg ctggaggcc    2340 ctgaagtact ggtggaacct gctgcagtac tggagccagg agctgaagag cagcgccgtg    2400
agcctgttca cgccaccgc catcgccgtg gccgagggca ccgaccgcat catcgagatc     2460
gtgcagcgca tcttccgcgc cgtgatccac atcccccgcc gcatccgcca gggcctggag    2520
cgcgccctgc tgtaagatat cggatcctct aga                                 2553

<210> SEQ ID NO 67
<211> LENGTH: 2340
<212> TYPE: DNA
<213> ORGANISM: Artificial Sequence
<220> FEATURE:
<223> OTHER INFORMATION: gp160.modUS4.delV1/V2

<400> SEQUENCE: 67
gaattcgcca ccatggatgc aatgaagaga gggctctgct gtgtgctgct gctgtgtgga      60
gcagtcttcg tttcgcccag cgccaccacc gtgtgtgggg tgaccgtgta ctacggcgtg     120
cccgtgtgga aggaggccac caccacccctg ttctgcgcca gcgacgccaa ggcttacaag    180
gccgaggccc acaacgtgtg gccaccac gcctgcgtgc ccaccgaccc caacccccag       240
gaggtgaacc tgaccaacgt gaccgagaac ttcaacatgt ggaagaacaa catggtggag    300
cagatgcatg aggacatcat cagcctgtgg gaccagagcc tgaagccctg cgtgggcgcc    360
ggccaggcct gccccaaggt gagcttcgag cccatcccca tccactactg cgcccccgcc    420
ggcttcgcca tcctgaagtg caaggacaag aagttcaacg gcaccggccc ctgcaagaac    480
gtgagcaccg tgcagtgcac ccacggcatc cgcccgtgg tgagcaccca gctgctgctg     540
aacggcagcc tggccgagga ggagatcgtg ctgcgctccg agaacttcac cgacaacgcc    600
aagaccatca tcgtgcagct gaacgagtcc gtggagatca actgcatccg ccccaacaac    660
aacacgcgta agagcatcca catcggcccc ggccgcgcct tctacgccac cggcgacatc    720
atcggcgaca tccgccaggc ccactgcaac atcagcaagg ccaactggac caacacccctc    780 gagcagatcg tggagaagct cgcgcagcag ttcggcaaca caagaccat catcttcaac    840 agcagcagcg gcggcgaccc cgagatcgtg ttccacagct tcaactgcgg cggcgagttc    900
ttctactgca caccagcca gctgttcaac agcacctgga acatcaccga ggaggtgaac    960
aagaccaagg agaacgacac catcatcctg ccctgccgca tccgccagat catcaacatg   1020
tggcaggagg tgggcaaggc catgtacgcc ccccccatcc gcggccagat caagtgcagc   1080
agcaatatta ccggcctgct gctgacccgc gacgcggca ccaacaacaa ccgcaccaac    1140
gacaccgaga ccttccgccc cggcggcggc aacatgaagg acaactggcg cagcgagctg   1200
tacaagtaca aggtggtgcg catcgagccc ctgggcgtgg cccccaccca ggccaagcgc   1260
cgcgtggtgc agcgcgagaa cgcgccgtg gccctgggcg ccctgttcat cggcttcctg   1320
ggcgccgccg ggagcaccat gggcgccgcc tccgtgaccc tgaccgtgca ggcccgccag   1380
ctgctgagcg gcatcgtgca gcagcagaac aacctgctgc gcgccatcga ggcccagcag   1440
cacctgctgc agctgaccgt gtggggcatc aagcagctgc aggcccgcat cctggccgtg   1500
gagcgctacc tgaaggacca gcagctgctg ggcatctggg gctgcagcgg caagctgatc   1560
tgcaccacca ccgtgccctg gaacagcagc tggagcaaca gagcctgac cgagatctgg   1620 gacaacatga cctggatgga gtgggagcgc gagatcggca actacaccgg cctgatctac   1680
aacctgatcg agatcgccca gaaccagcag gagaagaacg agcaggagct gctggagctg   1740
gacaagtggg ccagcctgtg gaactggttc gacatcacca ctggctgtg gtacatccgc    1800
```

| atcttcatca tgatcgtggg cggcctgatc ggcctgcgca tcgtgttcgc cgtgctgagc | 1860 |
| atcgtgaacc gcgtgcgcca gggctacagc cccatcagcc tgcagacccg cctgcccgcc | 1920 |
| cagcgcggcc ccgaccgccc cgagggcatc gaggaggagg cggcgagcg cgaccgcgac | 1980 |
| cgcagcaacc gcctggtgca cggcctgctg ccctgatct gggacgacct gcgcagcctg | 2040 |
| tgcctgttca gctaccaccg cctgcgcgac ctgctgctga tcgtggcccg catcgtggag | 2100 |
| ctgctgggcc gccgcggctg ggaggccctg aagtactggt ggaacctgct gcagtactgg | 2160 |
| agccaggagc tgaagagcag cgccgtgagc ctgttcaacg ccaccgccat cgccgtggcc | 2220 |
| gagggcaccg accgcatcat cgagatcgtg cagcgcatct ccgcgccgt gatccacatc | 2280 |
| ccccgccgca tccgccaggg cctggagcgc gccctgctgt aagatatcgg atcctctaga | 2340 |

<210> SEQ ID NO 68
<211> LENGTH: 2385
<212> TYPE: DNA
<213> ORGANISM: Artificial Sequence
<220> FEATURE:
<223> OTHER INFORMATION: gp160.modUS4del 128-194

<400> SEQUENCE: 68

| gaattcgcca ccatggatgc aatgaagaga gggctctgct gtgtgctgct gctgtgtgga | 60 |
| gcagtcttcg tttcgcccag cgccaccacc gtgctgtggg tgaccgtgta ctacggcgtg | 120 |
| cccgtgtgga aggaggccac caccaccctg ttctgcgcca gcgacgccaa ggcttacaag | 180 |
| gccgaggccc acaacgtgtg gccaccac gcctgcgtgc ccaccgaccc caaccccag | 240 |
| gaggtgaacc tgaccaacgt gaccgagaac ttcaacatgt ggaagaacaa catggtggag | 300 |
| cagatgcatg aggacatcat cagcctgtgg gaccagagcc tgaagccctg cgtgaagctg | 360 |
| acccccctgt gcgtggggc agggaactgc gagaccagcg tgatcaccca ggcctgcccc | 420 |
| aaggtgagct cgagcccat ccccatccac tactgcgccc ccgccggctt cgccatcctg | 480 |
| aagtgcaagg acaagaagtt caacggcacc ggcccctgca agaacgtgag caccgtgcag | 540 |
| tgcacccacg gcatccgccc cgtggtgagc acccagctgc tgctgaacgg cagcctggcc | 600 |
| gaggaggaga tcgtgctgcg ctccgagaac ttcaccgaca cgccaagac catcatcgtg | 660 |
| cagctgaaca gtccgtgga gatcaactgc atccgcccca caacaacac gcgtaagagc | 720 |
| atccacatcg gccccggccg cgccttctac gccaccggcg acatcatcgg cgacatccgc | 780 |
| caggcccact gcaacatcag caaggccaac tggaccaaca cctcgagca gatcgtggag | 840 |
| aagctgcgcg agcagttcgg caacaacaag accatcatct tcaacagcag cagcggcggc | 900 |
| gaccccgaga tcgtgttcca gcttcaac tgcggcggcg agttcttcta ctgcaacacc | 960 |
| agccagctgt tcaacagcac ctggaacatc accgaggagg tgaacaagac caaggagaac | 1020 |
| gacaccatca tcctgccctg ccgcatccgc cagatcatca acatgtggca ggaggtgggc | 1080 |
| aaggccatgt acgccccccc catccgcggc cagatcaagt gcagcagcaa tattaccggc | 1140 |
| ctgctgctga cccgcgacgg cggcaccaac aacaaccgca ccaacgacac cgagaccttc | 1200 |
| cgccccggcg gcggcaacat gaaggacaac tggcgcagcg agctgtacaa gtacaaggtg | 1260 |
| gtgcgcatcg agcccctggg cgtggccccc acccaggcca gcgccgcgt ggtgcagcgc | 1320 |
| gagaagcgcg ccgtgggcct gggcgccctg ttcatcggct tcctgggcgc cgccgggagc | 1380 |
| accatgggcg ccgcctccgt gaccctgacc gtgcaggccc gccagctgct gagcggcatc | 1440 |
| gtgcagcagc agaacaacct gctgcgcgcc atcgaggccc agcagcacct gctgcagctg | 1500 |
| accgtgtggg gcatcaagca gctgcaggcc cgcatcctgg ccgtggagcg ctacctgaag | 1560 |

```
gaccagcagc tgctgggcat ctggggctgc agcggcaagc tgatctgcac caccaccgtg    1620
ccctggaaca gcagctggag caacaagagc ctgaccgaga tctgggacaa catgacctgg    1680
atggagtggg agcgcgagat cggcaactac accggcctga tctacaacct gatcgagatc    1740
gcccagaacc agcaggagaa gaacgagcag gagctgctgg agctggacaa gtgggccagc    1800
ctgtggaact ggttcgacat caccaactgg ctgtggtaca tccgcatctt catcatgatc    1860
gtgggcggcc tgatcggcct gcgcatcgtg ttcgccgtgc tgagcatcgt gaaccgcgtg    1920
cgccagggct acagcccat cagcctgcag accgcctgc cgcccagcg cggccccgac      1980 cgccccgagg catcgagga ggaggcggc gagcgcgacc gcgaccgcag caaccgcctg      2040
gtgcacggcc tgctggccct gatctgggac gacctgcgca gcctgtgcct gttcagctac    2100
caccgcctgc gcgacctgct gctgatcgtg gcccgcatcg tggagctgct gggccgccgc    2160
ggctgggagg ccctgaagta ctggtggaac ctgctgcagt actggagcca ggagctgaag    2220
agcagcgccg tgagcctgtt caacgccacc gccatcgccg tggccgaggg caccgaccgc    2280
atcatcgaga tcgtgcagcg catcttccgc gccgtgatcc acatccccg ccgcatccgc    2340 cagggcctgg agcgcgccct gctgtaagat atcggatcct ctaga                   2385
```

<210> SEQ ID NO 69
<211> LENGTH: 144
<212> TYPE: DNA
<213> ORGANISM: Human immunodeficiency virus

<400> SEQUENCE: 69

```
gacaccatca tcctgccctg ccgcatccgc cagatcatca acatgtggca ggaggtgggc     60
aaggccatgt acgccccccc catccgcggc cagatcaagt gcagcagcaa catcaccggc    120
ctgctgctga cccgcgacgg cggc                                           144
```

<210> SEQ ID NO 70
<211> LENGTH: 144
<212> TYPE: DNA
<213> ORGANISM: Human immunodeficiency virus

<400> SEQUENCE: 70

```
ggaactatca cactcccatg cagaataaaa caaattataa acaggtggca ggaagtagga     60
aaagcaatgt atgcccctcc catcagagga caaattagat gctcatcaaa tattacagga    120
ctgctattaa caagagatgg tggt                                           144
```

<210> SEQ ID NO 71
<211> LENGTH: 144
<212> TYPE: DNA
<213> ORGANISM: Artificial Sequence
<220> FEATURE:
<223> OTHER INFORMATION: synthetic Env US4 common region

<400> SEQUENCE: 71

```
gacaccatca tcctgccctg ccgcatccgc cagatcatca acatgtggca ggaggtgggc     60
aaggccatgt acgccccccc catccgcggc cagatcaagt gcagcagcaa catcaccggc    120
ctgctgctga cccgcgacgg cggc                                           144
```

<210> SEQ ID NO 72
<211> LENGTH: 144
<212> TYPE: DNA
<213> ORGANISM: Artificial Sequence
<220> FEATURE:
<223> OTHER INFORMATION: synthetic Env SF162 common region -continued

<400> SEQUENCE: 72

```
ggcaccatca ccctgccctg ccgcatcaag cagatcatca accgctggca ggaggtgggc      60
aaggccatgt acgccccccc catccgcggc cagatccgct gcagcagcaa catcaccggc     120
ctgctgctga cccgcgacgg cggc                                            144
```

<210> SEQ ID NO 73
<211> LENGTH: 4766
<212> TYPE: DNA
<213> ORGANISM: Artificial Sequence
<220> FEATURE:
<223> OTHER INFORMATION: gp160.modUS4.gag.modSF2

<400> SEQUENCE: 73

```
gaattcgcca ccatggatgc aatgaagaga gggctctgct gtgtgctgct gctgtgtgga      60
gcagtcttcg tttcgcccag cgccaccacc gtgctgtggg tgaccgtgta ctacggcgtg     120
cccgtgtgga aggaggccac caccaccctg ttctgcgcca cgacgccaa ggcttacaag      180
gccgaggccc acaacgtgtg gccacccac gcctgcgtgc ccaccgaccc caaccccag      240
gaggtgaacc tgaccaacgt gaccgagaac ttcaacatgt ggaagaacaa catggtggag    300
cagatgcatg aggacatcat cagcctgtgg gaccagagcc tgaagccctg cgtgaagctg    360
accccctgt gcgtgacct gaactgcacc gacaagctga ccggcagcac caacggcacc      420
aacagcacca gcggcaccaa cagcaccagc ggcaccaaca gcaccagcac caacagcacc     480
gacagctggg agaagatgcc cgagggcgag atcaagaact gcagcttcaa catcaccacc    540
agcgtgcgcg acaaggtgca gaaggagtac agcctgttct acaagctgga cgtggtgccc    600
atcgacaacg acaacgccag ctaccgcctg atcaactgca caccagcgt gatcacccag      660
gcctgccca aggtgagctt cgagcccatc cccatccact actgcgcccc cgccggcttc      720
gccatcctga gtgcaagga caagaagttc aacggcaccg cccctgcaa gaacgtgagc      780
accgtgcagt gcacccacgg catccgcccc gtggtgagca cccagctgct gctgaacggc    840
agcctggccg aggaggagat cgtgctgcgc tccgagaact tcaccgacaa cgccaagacc     900
atcatcgtgc agctgaacga gtccgtggag atcaactgca tccgccccaa caacaacacg     960
cgtaagagca tccacatcgg ccccggccgc gccttctacg ccaccggcga catcatcggc    1020
gacatccgcc aggcccactg caacatcagc aaggccaact ggaccaacac cctcgagcag    1080
atcgtggaga gctgcgcga gcagttcggc aacaacaaga ccatcatctt caacagcagc    1140
agcggcggcg accccgagat cgtgttccac agcttcaact gcggcggcga gttcttctac    1200
tgcaacacca gccagctgtt caacagcacc tggaacatca ccgaggaggt gaacaagacc    1260
aaggagaacg acaccatcat cctgccctgc cgcatccgcc agatcatcaa catgtggcag    1320
gaggtgggca aggccatgta cgccccccc catccgcggc agatcaagtg cagcagcaat    1380
attaccggcc tgctgctgac ccgcgacggc ggcaccaaca caaccgcac caacgacacc     1440
gagaccttcc gccccggcgg cggcaacatg aaggacaact ggcgcagcga gctgtacaag    1500
tacaaggtgg tgcgcatcga gcccctgggc gtggcccca cccaggccaa cgccgcgtg    1560
gtgcagcgcg agaagcgcgc cgtgggcctg ggcgccctgt tcatcggctt cctgggcgcc    1620
gccgggagca ccatgggcgc cgcctccgtg accctgaccg tgcaggcccg ccagctgctg    1680
agcggcatcg tgcagcagca gaacaacctg ctgcgcgcca tcgaggccca gcagcacctg    1740
ctgcagctga ccgtgtgggg catcaagcag ctgcaggccc gcatcctggc cgtggagcgc    1800
tacctgaagg accagcagct gctgggcatc tggggctgca gcggcaagct gatctgcacc    1860
```

```
accaccgtgc cctggaacag cagctggagc aacaagagcc tgaccgagat ctgggacaac   1920
atgacctgga tggagtggga gcgcgagatc ggcaactaca ccggcctgat ctacaacctg   1980
atcgagatcg cccagaacca gcaggagaag aacgagcagg agctgctgga gctggacaag   2040
tgggccagcc tgtggaactg gttcgacatc accaactggc tgtggtacat ccgcatcttc   2100
atcatgatcg tgggcggcct gatcggcctg cgcatcgtgt tcgccgtgct gagcatcgtg   2160
aaccgcgtgc gccagggcta cagccccatc agcctgcaga cccgcctgcc cgcccagcgc   2220
ggccccgacc gccccgaggg catcgaggag gagggcggcg agcgcgaccg cgaccgcagc   2280
aaccgcctgg tgcacggcct gctggccctg atctgggacg acctgcgcag cctgtgcctg   2340
ttcagctacc accgcctgcg cgacctgctg ctgatcgtgg cccgcatcgt ggagctgctg   2400
ggccgccgcg gctgggaggc cctgaagtac tggtggaacc tgctgcagta ctggagccag   2460
gagctgaaga gcagcgccgt gagcctgttc aacgccaccg ccatcgccgt ggccgagggc   2520
accgaccgca tcatcgagat cgtgcagcgc atcttccgcg ccgtgatcca catccccgc   2580 cgcatccgcc agggcctgga gcgcgccctg ctgtaagata tcggatcctc tagagaattc   2640 cgccccccc cccccccccc ctctccctcc cccccccta acgttactgg ccgaagccgc   2700
ttggaataag gccggtgtgc gtttgtctat atgttatttt ccaccatatt gccgtctttt   2760
ggcaatgtga gggcccggaa acctggccct gtcttcttga cgagcattcc taggggtctt   2820
tcccctctcg ccaaaggaat gcaaggtctg ttgaatgtcg tgaaggaagc agttcctctg   2880
gaagcttctt gaagacaaac aacgtctgta gcgacccttt gcaggcagcg aaccccccca   2940
cctggcgaca ggtgcctctg cggccaaaag ccacgtgtat aagatacacc tgcaaaggcg   3000
gcacaacccc agtgccacgt tgtgagttgg atagttgtgg aaagagtcaa atggctctcc   3060
tcaagcgtat tcaacaaggg gctgaaggat gcccagaagg taccccattg tatgggatct   3120
gatctggggc ctcggtgcac atgctttaca tgtgtttagt cgaggttaaa aaaacgtcta   3180
ggccccccga accacgggga cgtggttttc ctttgaaaaa cacgataata ccatgggcgc   3240
ccgcgccagc gtgctgagcg gcggcgagct ggacaagtgg gagaagatcc gcctgcgccc   3300
cggcggcaag aagaagtaca agctgaagca catcgtgtgg gccagccgcg agctggagcg   3360
cttcgccgtg aaccccggcc tgctggagac cagcgagggc tgccgccaga tcctgggcca   3420
gctgcagccc agcctgcaga ccggcagcga ggagctgcgc agcctgtaca caccgtggc   3480 caccctgtac tgcgtgcacc agcgcatcga cgtcaaggac accaaggagg ccctggagaa   3540
gatcgaggag gagcagaaca gtccaagaa gaaggcccag caggccgccg ccgccgccgg   3600
caccggcaac agcagccagg tgagccgaa ctaccccatc gtgcagaacc tgcagggcca   3660
gatggtgcac caggccatca gcccccgcac cctgaacgcc tgggtgaagg tggtggagga   3720
gaaggccttc agccccgagg tgatccccat gttcagcgcc ctgagcgagg gcgccacccc   3780
ccaggacctg aacacgatgt tgaacaccgt gggcggccac caggccgcca tgcagatgct   3840
gaaggagacc atcaacgagg aggccgccga gtgggaccgc gtgcaccccg tgcacgccgg   3900
ccccatcgcc cccggccaga tgcgcgagcc ccgcggcagc gacatcgccg gcaccaccag   3960
caccctgcag gagcagatcg gctggatgac caacaacccc cccatccccg tgggcgagat   4020
ctacaagcgg tggatcatcc tgggcctgaa caagatcgtg cggatgtaca gccccaccag   4080
catcctggac atccgccagg gccccaagga gcccttccgc gactacgtgg accgcttcta   4140
caagaccctg cgcgctgagc aggccagcca ggacgtgaag aactggatga ccgagaccct   4200
gctggtgcag aacgccaacc ccgactgcaa gaccatcctg aaggctctcg ccccgcggc   4260
```

```
cacccctggag gagatgatga ccgcctgcca gggcgtgggc ggccccggcc acaaggcccg    4320
cgtgctggcc gaggcgatga gccaggtgac gaacccggcg accatcatga tgcagcgcgg    4380
caacttccgc aaccagcgga agaccgtcaa gtgcttcaac tgcggcaagg agggccacac    4440
cgccaggaac tgccgcgccc cccgcaagaa gggctgctgg cgctgcggcc gcgagggcca    4500
ccagatgaag gactgcaccg agcgccaggc caacttcctg ggcaagatct ggcccagcta    4560
caagggccgc cccggcaact tcctgcagag ccgccccgag cccaccgccc ccccgaggag    4620
gagcttccgc ttcggcgagg agaagaccac ccccagccag aagcaggagc ccatcgacaa    4680
ggagctgtac cccctgacca gcctgcgcag cctgttcggc aacgacccca gcagccagta    4740
agaattcaga ctcgagcaag tctaga                                         4766

<210> SEQ ID NO 74
<211> LENGTH: 4689
<212> TYPE: DNA
<213> ORGANISM: Artificial Sequence
<220> FEATURE:
<223> OTHER INFORMATION: gp160.modSF162.gag.modSF2

<400> SEQUENCE: 74
gaattcgcca ccatggatgc aatgaagaga gggctctgct gtgtgctgct gctgtgtgga      60
gcagtcttcg tttcgcccag cgccgtggag aagctgtggg tgaccgtgta ctacggcgtg     120
cccgtgtgga aggaggccac caccaccctg ttctgcgcca gcgacgccaa ggcctacgac     180
accgaggtgc acaacgtgtg gccaccccac gcctgcgtgc ccaccgaccc caaccccag      240 gagatcgtgc tggagaacgt gaccgagaac ttcaacatgt ggaagaacaa catggtggag     300
cagatgcacg aggacatcat cagcctgtgg gaccagagcc tgaagccctg cgtgaagctg     360
acccccctgt gcgtgaccct gcactgcacc aacctgaaga cgccaccaa caccaagagc      420 agcaactgga aggagatgga ccgcggcgag atcaagaact gcagcttcaa ggtgaccacc     480
agcatccgca caagatgca aaggagtac gccctgttct acaagctgga cgtggtgccc       540
atcgacaacg acaacaccag ctacaagctg atcaactgca caccagcgt gatcacccag      600 gcctgcccca aggtgagctt cgagcccatc cccatccact actgcgcccc cgccggcttc     660
gccatcctga gtgcaacga caagaagttc aacggcagcg gccctgcac caacgtgagc      720 accgtgcagt gcacccacgg catccgcccc gtggtgagca cccagctgct gctgaacggc    780
agcctggccg aggagggcgt ggtgatccgc agcgagaact tcaccgacaa cgccaagacc    840
atcatcgtgc agctgaagga gagcgtggag atcaactgca cccgccccaa caacaacacc    900
cgcaagagca tcaccatcgg ccccggccgc gccttctacg ccaccggcga catcatcggc    960
gacatccgcc aggcccactg caacatcagc ggcgagaagt ggaacaacac cctgaagcag   1020
atcgtgacca gctgcaggc ccagttcggc aacaagacca tcgtgttcaa gcagagcagc    1080
ggcggcgacc ccgagatcgt gatgcacagc ttcaactgcg gcggcgagtt cttctactgc   1140
aacagcaccc agctgttcaa cagcacctgg aacaacacca tcggccccaa caccaccaac   1200
ggcaccatca ccctgcccg ccgcatcaag cagatcatca accgctggca ggaggtgggc   1260
aaggccatgt acgccccccc catccgcggc cagatccgct gcagcagcaa catcaccggc   1320
ctgctgctga cccgcgacgg cggcaaggag atcagcaaca ccaccgagat cttccgcccc   1380
ggcggcggcg acatgcgcga caactggcgc agcgagctgt acaagtacaa ggtggtgaag   1440
atcgagcccc tgggcgtggc ccccaccaag gccaagcgcc gcgtggtgca gcgcgagaag   1500
cgcgccgtga cctgggcgc catgttcctg ggcttcctgg gcgccgccgg cagcaccatg   1560
```

```
ggcgcccgca gcctgaccct gaccgtgcag gcccgccagc tgctgagcgg catcgtgcag    1620
cagcagaaca acctgctgcg cgccatcgag gcccagcagc acctgctgca gctgaccgtg    1680
tggggcatca agcagctgca gcccgcgtg ctggccgtgg agcgctacct gaaggaccag     1740
cagctgctgg gcatctgggg ctgcagcggc aagctgatct gcaccaccgc cgtgccctgg    1800
aacgccagct ggagcaacaa gagcctggac cagatctgga caacatgac ctggatggag     1860 tgggagcgcg agatcgacaa ctacaccaac ctgatctaca ccctgatcga ggagagccag    1920
aaccagcagg agaagaacga gcaggagctg ctggagctgg acaagtgggc cagcctgtgg    1980
aactggttcg acatcagcaa gtggctgtgg tacatcaaga tcttcatcat gatcgtgggc    2040
ggcctggtgg gcctgcgcat cgtgttcacc gtgctgagca tcgtgaaccg cgtgcgccag    2100
ggctacagcc ccctgagctt ccagacccgc ttccccgccc ccgcggccc cgaccgcccc     2160 gagggcatcg aggaggaggg cggcgagcgc gaccgcgacc gcagcagccc cctggtgcac    2220
ggcctgctgg ccctgatctg gacgacctg cgcagcctgt gcctgttcag ctaccaccgc     2280
ctgcgcgacc tgatcctgat cgccgcccgc atcgtggagc tgctgggccg ccgcggctgg    2340
gaggccctga agtactgggg caacctgctg cagtactgga tccaggagct gaagaacagc    2400
gccgtgagcc tgttcgacgc catcgccatc gccgtggccg agggcaccga ccgcatcatc    2460
gaggtggccc agcgcatcgg ccgcgccttc ctgcacatcc ccgccgcat ccgccagggc     2520 ttcgagcgcg ccctgctgta actcgagcaa gtctagagaa ttccgccccc ccccccccc    2580 cccctctccc tcccccccc ctaacgttac tggccgaagc gcttggaat aaggccggtg     2640 tgcgtttgtc tatatgttat tttccaccat attgccgtct tttggcaatg tgagggcccg    2700
gaaacctggc cctgtcttct tgacgagcat tcctagggt ctttcccctc tcgccaaagg     2760
aatgcaaggt ctgttgaatg tcgtgaagga agcagttcct ctggaagctt cttgaagaca    2820
aacaacgtct gtagcgaccc tttgcaggca gcggaacccc ccacctggcg acaggtgcct    2880
ctgcggccaa aagccacgtg tataagatac acctgcaaag gcggcacaac cccagtgcca    2940
cgttgtgagt tggatagttg tggaaagagt caaatggctc tcctcaagcg tattcaacaa    3000
ggggctgaag gatgcccaga aggtacccca ttgtatggga tctgatctgg ggcctcggtg    3060
cacatgcttt acatgtgttt agtcgaggtt aaaaaaaacgt ctaggccccc cgaaccacgg    3120
ggacgtggtt ttcctttgaa aaacacgata ataccatggg cgcccgcgcc agcgtgctga    3180
gcggcggcga gctggacaag tgggagaaga tccgcctgcg ccccggcggc aagaagaagt    3240
acaagctgaa gcacatcgtg tgggccagcc gcgagctgga gcgcttcgcc gtgaaccccg    3300
gcctgctgga accagcgag ggctgccgcc agatcctggg ccagctgcag cccagcctgc     3360
agaccggcag cgaggagctg cgcagcctgt acaacaccgt ggccaccctg tactgcgtgc    3420
accagcgcat cgacgtcaag gacaccaagg aggccctgga aagatcgag gaggagcaga    3480 acaagtccaa gaagaaggcc cagcaggccg ccgccgccgc cggcaccggc aacagcagcc    3540
aggtgagcca gaactacccc atcgtgcaga acctgcaggg ccagatggtg caccaggcca    3600
tcagcccccg caccctgaac gcctgggtga aggtggtgga ggagaaggcc ttcagccccg    3660
aggtgatccc catgttcagc gccctgagcg agggcgccac ccccaggac ctgaacacga     3720 tgttgaacac cgtgggcggc caccaggccg ccatgcagat gctgaaggag accatcaacg    3780
aggaggccgc cgagtgggac cgagtgcacc ccgtgcacgc cggccccatc gccccggcc     3840 agatgcgcga gccccgcggc agcgacatcg ccggcaccac cagcacccatg caggagcaga    3900 tcggctggat gaccaacaac cccccatcc ccgtgggcga gatctacaag cggtggatca     3960
```

```
tcctgggcct gaacaagatc gtgcggatgt acagccccac cagcatcctg gacatccgcc    4020
agggccccaa ggagcccttc cgcgactacg tggaccgctt ctacaagacc ctgcgcgctg    4080
agcaggccag ccaggacgtg aagaactgga tgaccgagac cctgctggtg cagaacgcca    4140
accccgactg caagaccatc ctgaaggctc tcggccccgc ggccaccctg aggagatga     4200 tgaccgcctg ccaggcgtg gcggccccg gccacaaggc ccgcgtgctg ccgaggcga      4260 tgagccaggt gacgaacccg cgaccatca tgatgcagcg cggcaacttc cgcaaccagc    4320
ggaagaccgt caagtgcttc aactgcggca aggagggcca caccgccagg aactgccgcg    4380
ccccccgcaa gaagggctgc tggcgctgcg gccgcgaggg ccaccagatg aaggactgca    4440
ccgagcgcca ggccaacttc ctgggcaaga tctggcccag ctacaagggc cgccccggca    4500
acttcctgca gagccgcccc gagcccaccg ccccccccga ggagagcttc cgcttcggcg    4560
aggagaagac cacccccagc cagaagcagg agcccatcga caaggagctg taccccctga    4620
ccagcctgcg cagcctgttc ggcaacgacc ccagcagcca gtaagaattc agactcgagc    4680
aagtctaga                                                             4689
```

<210> SEQ ID NO 75
<211> LENGTH: 4472
<212> TYPE: DNA
<213> ORGANISM: Artificial Sequence
<220> FEATURE:
<223> OTHER INFORMATION: gp160.modUS4.delV1/V2.gag.modSF2

<400> SEQUENCE: 75

```
gaattcgcca ccatggatgc aatgaagaga gggctctgct gtgtgctgct gctgtgtgga     60
gcagtcttcg tttcgcccag cgccaccacc gtgctgtggg tgaccgtgta ctacggcgtg    120
cccgtgtgga aggaggccac caccaccctg ttctgcgcca gcgacgccaa ggcttacaag    180
gccgaggccc acaacgtgtg ggccacccac gcctgcgtgc ccaccgaccc caacccccag    240
gaggtgaacc tgaccaacgt gaccgagaac ttcaacatgt ggaagaacaa catggtggag    300
cagatgcatg aggacatcat cagcctgtgg gaccagagcc tgaagccctg cgtgggcgcc    360
ggccaggcct gccccaaggt gagcttcgag cccatcccca tccactactg cgcccccgcc    420
ggcttcgcca tcctgaagtg caaggacaag aagttcaacg gcaccggccc ctgcaagaac    480
gtgagcaccg tgcagtgcac ccacggcatc cgccccgtgg tgagcaccca gctgctgctg    540
aacggcagcc tggccgagga ggagatcgtg ctgcgctccg agaacttcac cgacaacgcc    600
aagaccatca tcgtgcagct gaacgagtcc gtggagatca actgcatccg ccccaacaac    660
aacacgcgta agagcatcca catcggcccc ggcgcgcct tctacgccac cggcgacatc    720
atcggcgaca tccgccaggc ccactgcaac atcagcaagg ccaactggac caacaccctc    780
gagcagatcg tggagaagct gcgcgagcag ttcggcaaca acaagaccat catcttcaac    840
agcagcagcg gcggcgaccc cgagatcgtg ttccacagct tcaactgcgg cggcgagttc    900
ttctactgca caccagcca gctgttcaac agcacctgga acatcaccga ggaggtgaac    960
aagaccaagg agaacgacac catcatcctg ccctgccgca tccgcagat catcaacatg   1020 tggcaggagg tgggcaaggc catgtacgcc ccccccatcc gcggccagat caagtgcagc    1080
agcaatatta ccggcctgct gctgacccgc gacggcggca acaacaa ccgcaccaac     1140 gacaccgaga ccttccgccc cggcggcggc aacatgaagg acaactggcg cagcgagctg    1200
tacaagtaca aggtggtgcg catcgagccc ctggcgtgg cccccaccca ggccaagcgc    1260
cgcgtggtgc agcgcgagaa gcgcgccgtg ggcctgggcg ccctgttcat cggcttcctg    1320
```

```
ggcgccgccg ggagcaccat gggcgccgcc tccgtgaccc tgaccgtgca ggcccgccag    1380
ctgctgagcg gcatcgtgca gcagcagaac aacctgctgc gcgccatcga ggcccagcag    1440
cacctgctgc agctgaccgt gtggggcatc aagcagctgc aggcccgcat cctggccgtg    1500
gagcgctacc tgaaggacca gcagctgctg ggcatctggg gctgcagcgg caagctgatc    1560
tgcaccacca ccgtgccctg gaacagcagc tggagcaaca gagcctgac cgagatctgg    1620
gacaacatga cctggatgga gtgggagcgc gagatcggca actacaccgg cctgatctac    1680
aacctgatcg agatcgccca gaaccagcag gagaagaacg agcaggagct gctggagctg    1740
gacaagtggg ccagcctgtg gaactggttc gacatcacca ctggctgtg gtacatccgc    1800
atcttcatca tgatcgtggg cggcctgatc ggcctgcgca tcgtgttcgc cgtgctgagc    1860
atcgtgaacc gcgtgcgcca gggctacagc cccatcagcc tgcagacccg cctgcccgcc    1920
cagcgcggcc ccgaccgccc cgagggcatc gaggaggagg cggcgagcg cgaccgcgac    1980
cgcagcaacc gcctggtgca cggcctgctg gccctgatct gggacgacct gcgcagcctg    2040
tgcctgttca gctaccaccg cctgcgcgac ctgctgctga tcgtggcccg catcgtggag    2100
ctgctgggcc gccgcggctg ggaggccctg aagtactggt ggaacctgct gcagtactgg    2160
agccaggagc tgaagagcag cgccgtgagc ctgttcaacg ccaccgccat cgccgtggcc    2220
gagggcaccg accgcatcat cgagatcgtg cagcgcatct ccgcgccgt gatccacatc    2280
ccccgccgca tccgccaggg cctggagcgc gccctgctgt aagatatcgg atcctctaga    2340
gaattccgcc cccccccccc ccccccctct ccctccccc cccctaacgt tactggccga    2400
agccgcttgg aataaggccg gtgtgcgttt gtctatatgt tattttccac catattgccg    2460
tcttttggca atgtgagggc ccggaaacct ggccctgtct tcttgacgag cattcctagg    2520
ggtctttccc ctctcgccaa aggaatgcaa ggtctgttga atgtcgtgaa ggaagcagtt    2580
cctctgaag cttcttgaag acaaacaacg tctgtagcga ccctttgcag gcagcggaac    2640
cccccacctg gcgacaggtg cctctgcggc caaaagccac gtgtataaga tacacctgca    2700
aaggcggcac aaccccagtg ccacgttgtg agttggatag ttgtggaaag agtcaaatgg    2760
ctctcctcaa gcgtattcaa caaggggctg aaggatgccc agaaggtacc ccattgtatg    2820
ggatctgatc tggggcctcg gtgcacatgc tttacatgtg tttagtcgag gttaaaaaaa    2880
cgtctaggcc ccccgaacca cggggacgtg gttttccttt gaaaaacacg ataataccat    2940
gggcgcccgc gccagcgtgc tgagcggcgg cgagctggac aagtgggaga gatccgcct    3000
gcgccccggc ggcaagaaga agtacaagct gaagcacatc gtgtgggcca ccgcgagct    3060
ggagcgcttc gccgtgaacc ccggcctgct ggagaccagc gagggctgcc gccagatcct    3120
gggccagctg cagcccagcc tgcagaccgg cagcgaggag ctgcgcagcc tgtacaacac    3180
cgtggccacc ctgtactgcg tgcaccagcc catcgacgtc aaggacacca aggaggccct    3240
ggagaagatc gaggaggagc agaacaagtc caagaagaag gcccagcagg ccgccgccgc    3300
cgccggcacc ggcaacagca gccaggtgag ccagaactac cccatcgtgc agaacctgca    3360
gggccagatg gtgcaccagg ccatcagccc ccgcaccctg aacgcctggg tgaaggtggt    3420
ggaggagaag gccttcagcc ccgaggtgat ccccatgttc agcgccctga gcgagggcgc    3480
cacccccag gacctgaaca cgatgttgaa caccgtgggc ggccaccagg ccgccatgca    3540
gatgctgaag gagaccatca acgaggaggc cgccgagtgg gaccgcgtgc accccgtgca    3600
cgccggcccc atcgccccca ccagatgcg cgagccccgc ggcagcgaca tcgccggcac    3660
caccagcacc ctgcaggagc agatcggctg gatgaccaac aaccccccca tccccgtggg    3720
```

| | |
|---|---|
| cgagatctac aagcggtgga tcatcctggg cctgaacaag atcgtgcgga tgtacagccc | 3780 |
| caccagcatc ctggacatcc gccagggccc caaggagccc ttccgcgact acgtggaccg | 3840 |
| cttctacaag accctgcgcg ctgagcaggc cagccaggac gtgaagaact ggatgaccga | 3900 |
| gaccctgctg gtgcagaacg ccaaccccga ctgcaagacc atcctgaagg ctctcggccc | 3960 |
| cgcggccacc ctggaggaga tgatgaccgc ctgccaggc gtgggcggcc ccggccacaa | 4020 |
| ggcccgcgtg ctggccgagg cgatgagcca ggtgacgaac ccggcgacca tcatgatgca | 4080 |
| gcgcggcaac ttccgcaacc agcggaagac cgtcaagtgc ttcaactgcg gcaaggaggg | 4140 |
| ccacaccgcc aggaactgcc gcgcccccg caagaagggc tgctggcgct gcggccgcga | 4200 |
| gggccaccag atgaaggact gcaccgagcg ccaggccaac ttcctgggca agatctggcc | 4260 |
| cagctacaag ggccgccccg gcaacttcct gcagagccgc cccgagccca ccgcccccc | 4320 |
| cgaggagagc ttccgcttcg gcgaggagaa gaccaccccc agccagaagc aggagcccat | 4380 |
| cgacaaggag ctgtaccccc tgaccagcct gcgcagcctg ttcggcaacg accccagcag | 4440 |
| ccagtaagaa ttcagactcg agcaagtcta ga | 4472 |

<210> SEQ ID NO 76
<211> LENGTH: 4608
<212> TYPE: DNA
<213> ORGANISM: Artificial Sequence
<220> FEATURE:
<223> OTHER INFORMATION: gp160.modSF162.delV2.gag.modSF2

<400> SEQUENCE: 76
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgaagctg 360 accccccctgt gcgtgaccct gcactgcacc aacctgaaga acgccaccaa caccaagagc 420
agcaactgga aggagatgga ccgcggcgag atcaagaact gcagcttcaa ggtgggcgcc 480
ggcaagctga tcaactgcaa caccagcgtg atcacccagg cctgccccaa ggtgagcttc 540
gagcccatcc ccatccacta ctgcgccccc gccggcttcg ccatcctgaa gtgcaacgac 600
aagaagttca acggcagcgg cccctgcacc aacgtgagca ccgtgcagtg cacccacggc 660
atccgccccg tggtgagcac ccagctgctg ctgaacggca gcctggccga ggagggcgtg 720
gtgatccgca gcgagaactt caccgacaac gccaagacca tcatcgtgca gctgaaggag 780
agcgtggaga tcaactgcac ccgccccaac aacaacaccc gcaagagcat caccatcggc 840
cccggccgcg ccttctacgc caccggcgac atcatcggcg acatccgcca ggcccactgc 900
aacatcagcg gcgagaagtg gaacaacacc ctgaagcaga tcgtgaccaa gctgcaggcc 960
cagttcggca acaagaccat cgtgttcaag cagagcagcg gcggcgaccc cgagatcgtg 1020
atgcacagct tcaactgcgg cggcgagttc ttctactgca acagcaccca gctgttcaac 1080
agcacctgga acaacaccat cggccccaac aacaccaacg gcaccatcac cctgccctgc 1140
cgcatcaagc agatcatcaa ccgctggcag gaggtgggca aggccatgta cgcccccccc 1200
atccgcggcc agatccgctg cagcagcaac atcaccggcc tgctgctgac ccgcgacggc 1260
ggcaaggaga tcagcaacac caccgagatc ttccgccccg gcggcggcga catgcgcgac 1320

```
aactggcgca gcgagctgta caagtacaag gtggtgaaga tcgagcccct gggcgtggcc    1380
cccaccaagg ccaagcgccg cgtggtgcag cgcgagaagc gcgccgtgac cctgggcgcc    1440
atgttcctgg gcttcctggg cgccgccggc agcaccatgg gcgcccgcag cctgaccctg    1500
accgtgcagg cccgccagct gctgagcggc atcgtgcagc agcagaacaa cctgctgcgc    1560
gccatcgagg cccagcagca cctgctgcag ctgaccgtgt ggggcatcaa gcagctgcag    1620
gcccgcgtgc tggccgtgga gcgctacctg aaggaccagc agctgctggg catctggggc    1680
tgcagcggca gctgatctg caccaccgcc gtgccctgga cgccagctg gagcaacaag    1740 agcctggacc agatctggaa caacatgacc tggatggagt gggagcgcga gatcgacaac    1800
tacaccaacc tgatctacac cctgatcgag gagagccaga accagcagga gaagaacgag    1860
caggagctgc tggagctgga caagtgggcc agcctgtgga actggttcga catcagcaag    1920
tggctgtggt acatcaagat cttcatcatg atcgtgggcg gcctggtggg cctgcgcatc    1980
gtgttcaccg tgctgagcat cgtgaaccgc gtgcgccagg gctacagccc cctgagcttc    2040
cagacccgct tccccgcccc cgcggcccc gaccgccccg agggcatcga ggaggagggc    2100
ggcgagcgca ccgcgaccg cagcagcccc ctggtgcacg gcctgctggc cctgatctgg    2160
gacgacctgc gcagcctgtg cctgttcagc taccaccgcc tgcgcgacct gatcctgatc    2220
gccgcccgca tcgtggagct gctgggccgc gcggctgggg aggccctgaa gtactggggc    2280
aacctgctgc agtactggat ccaggagctg aagaacagcg ccgtgagcct gttcgacgcc    2340
atcgccatcg ccgtggccga gggcaccgac cgcatcatcg aggtggccca gcgcatcggc    2400
cgcgccttcc tgcacatccc ccgccgcatc cgccagggct cgagcgcgc cctgctgtaa    2460 ctcgagcaag tctagagaat tccgccccc ccccccccc ccctctccct ccccccccc    2520 taacgttact ggccgaagcc gcttggaata aggccggtgt gcgtttgtct atatgttatt    2580
ttccaccata ttgccgtctt ttggcaatgt gagggcccgg aaacctggcc ctgtcttctt    2640
gacgagcatt cctaggggtc tttcccctct cgccaaagga atgcaaggtc tgttgaatgt    2700
cgtgaaggaa gcagttcctc tggaagcttc ttgaagacaa acaacgtctg tagcgaccct    2760
ttgcaggcag cggaaccccc cacctggcga caggtgcctc tgcggccaaa agccacgtgt    2820
ataagataca cctgcaaagg cggcacaacc ccagtgccac gttgtgagtt ggatagttgt    2880
ggaaagagtc aaatggctct cctcaagcgt attcaacaag gggctgaagg atgcccagaa    2940
ggtaccccat tgtatgggat ctgatctggg gcctcggtgc acatgcttta catgtgttta    3000
gtcgaggtta aaaaaacgtc taggccccccc gaaccacggg gacgtggttt tcctttgaaa    3060
aacacgataa taccatgggc gcccgcgcca gcgtgctgag cggcggcgag ctggacaagt    3120
gggagaagat ccgcctgcgc cccggcggca agaagaagta caagctgaag cacatcgtgt    3180
gggccagccg cgagctggag cgcttcgccg tgaaccccgg cctgctggag accagcgagg    3240
gctgccgcca gatcctgggc cagctgcagc ccagcctgca gaccggcagc gaggagctgc    3300
gcagcctgta caacaccgtg gccaccctgt actgcgtgca ccagcgcatc gacgtcaagg    3360
acaccaagga ggccctggag aagatcgagg aggagcagaa caagtccaag aagaaggccc    3420
agcaggccgc cgccgccgcc ggaccggca acagcagcca ggtgagccag aactacccca    3480
tcgtgcagaa cctgcagggc cagatggtgc accaggccat cagcccccgc accctgaacg    3540
cctgggtgaa ggtggtggag gagaaggcct tcagccccga ggtgatcccc atgttcagcg    3600
ccctgagcga gggcgccacc ccccaggacc tgaacacgat gttgaacacc gtgggcggcc    3660
accaggccgc catgcagatg ctgaaggaga ccatcaacga ggaggccgcc gagtgggacc    3720
```

```
gcgtgcaccc cgtgcacgcc ggccccatcg cccccggcca gatgcgcgag ccccgcggca    3780
gcgacatcgc cggcaccacc agcaccctgc aggagcagat cggctggatg accaacaacc    3840
cccccatccc cgtgggcgag atctacaagc ggtggatcat cctgggcctg aacaagatcg    3900
tgcggatgta cagccccacc agcatcctgg acatccgcca gggccccaag gagcccttcc    3960
gcgactacgt ggaccgcttc tacaagaccc tgcgcgctga gcaggccagc caggacgtga    4020
agaactggat gaccgagacc ctgctggtgc agaacgccaa ccccgactgc aagaccatcc    4080
tgaaggctct cggccccgcg ccacccctgg aggagatgat gaccgcctgc agggcgtgg     4140
gcggccccgg ccacaaggcc cgcgtgctgg ccgaggcgat gagccaggtg acgaacccgg    4200
cgaccatcat gatgcagcgc ggcaacttcc gcaaccagcg gaagaccgtc aagtgcttca    4260
actgcggcaa ggagggccac accgccagga actgccgcgc cccccgcaag aagggctgct    4320
ggcgctgcgg ccgcgagggc caccagatga aggactgcac cgagcgccag gccaacttcc    4380
tgggcaagat ctggcccagc tacaagggcc gccccggcaa cttcctgcag agccgccccg    4440
agcccaccgc cccccccgag gagagcttcc gcttcggcga ggagaagacc accccccagcc   4500
agaagcagga gcccatcgac aaggagctgt acccccctgac cagcctgcgc agcctgttcg   4560
gcaacgaccc cagcagccag taagaattca gactcgagca agtctaga                4608

<210> SEQ ID NO 77
<211> LENGTH: 1680
<212> TYPE: DNA
<213> ORGANISM: Human immunodeficiency virus

<400> SEQUENCE: 77
cccattagtc ctattgaaac tgtaccagta aaattaaagc caggaatgga tggcccaaaa      60
gttaagcaat ggccattgac agaagaaaaa ataaaagcat tagtagagat atgtacagaa     120
atggaaaagg aagggaaaat ttcaaaaatt gggcctgaaa atccatacaa tactccagta     180
tttgctataa agaaaaaaga cagtactaaa tggagaaaac tagtagattt cagagaactt     240
aataaaagaa ctcaagactt ctgggaagtt cagttaggaa taccacaccc cgcagggtta     300
aaaaagaaaa aatcagtaac agtattggat gtgggtgatg catactttc agttccctta      360
gataaagact ttagaaagta tactgcattt accataccta gtataaacaa tgagacacca     420
gggattagat atcagtacaa tgtgctgcca cagggatgga aaggatcacc agcaatattc     480
caaagtagca tgacaaaaat cttagagcct tttagaaaac agaatccaga catagttatc     540
tatcaataca tggatgattt gtatgtagga tctgacttag aaatagggca gcatagaaca     600
aaaatagagg aactgagaca gcatctgttg aggtggggat ttaccacacc agacaaaaaa     660
catcagaaag aacctccatt cctttggatg ggttatgaac tccatcctga taatggaca      720
gtacagccta ataatgctgcc agaaaaagac agctggactg tcaatgacat acagaagtta    780
gtgggaaaat tgaattgggc aagtcagatt tatgcaggga ttaaagtaaa gcagttatgt    840
aaactcctta gaggaaccaa agcactaaca gaagtaatac cactaacaga agaagcagag     900
ctagaactgg cagaaaacag ggagattcta aaagaaccag tacatgaagt atattatgac     960
ccatcaaaag acttagtagc agaaatacag aagcagggc aaggccaatg gacatatcaa    1020
atttatcaag agccatttaa aaatctgaaa acaggaaagt atgcaaggat gaggggtgcc    1080
cacactaatg atgtaaaaca gttaacagag gcagtgcaaa aagtatccac agaaagcata    1140
gtaatatggg gaaagattcc taaatttaaa ctacccatac aaaaggaaac atgggaagca    1200
tggtggatgg agtattggca agctacctgg attcctgagt gggagtttgt caatacccct    1260
```

```
ccccttagtga aattatggta ccagttagag aaagaaccca tagtaggagc agaaactttc    1320
tatgtagatg gggcagctaa tagggagact aaattaggaa aagcaggata tgttactgac    1380
agaggaagac aaaaagttgt ctccatagct gacacaacaa atcagaagac tgaattacaa    1440
gcaattcatc tagctttgca ggattcggga ttagaagtaa acatagtaac agactcacaa    1500
tatgcattag gaatcattca agcacaacca gataagagtg aatcagagtt agtcagtcaa    1560
ataatagagc agttaataaa aaaggaaaag gtctacctgg catgggtacc agcacacaaa    1620
ggaattggag gaaatgaaca agtagataaa ttagtcagtg ctggaatcag gaaagtacta    1680
```

<210> SEQ ID NO 78
<211> LENGTH: 1865
<212> TYPE: DNA
<213> ORGANISM: Artificial Sequence
<220> FEATURE:
<223> OTHER INFORMATION: GP1

<400> SEQUENCE: 78

```
gtcgacgcca ccatgggcgc ccgcgccagc gtgctgagcg gcggcgagct ggacaagtgg      60
gagaagatcc gcctgcgccc cggcggcaag aagaagtaca agctgaagca catcgtgtgg    120
gccagccgcg agctggagcg cttcgccgtg aaccccggcc tgctggagac cagcgagggc    180
tgccgccaga tcctgggcca gctgcagccc agcctgcaga ccggcagcga ggagctgcgc    240
agcctgtaca caccgtggc caccctgtac tgcgtgcacc agcgcatcga cgtcaaggac    300
accaaggagg ccctggagaa gatcgaggag gagcagaaca gtccaagaa gaaggcccag    360 caggccgccg ccgccgccgg caccggcaac agcagccagg tgagccagaa ctaccccatc    420
gtgcagaacc tgcagggcca gatggtgcac caggccatca gcccccgcac cctgaacgcc    480
tgggtgaagg tggtggagga aaggccttc agccccgagg tgatcccat gttcagcgcc    540 ctgagcgagg gcgccacccc ccaggacctg aacacgatgt tgaacaccgt gggcggccac    600
caggccgcca tgcagatgct gaaggagacc atcaacgagg aggccgccga gtgggaccgc    660
gtgcaccccg tgcacgccgg ccccatcgcc ccgggccaga tgcgcgagcc ccgcggcagc    720
gacatcgccg gcaccaccag caccctgcag gagcagatcg gctggatgac caacaacccc    780
cccatccccg tgggcgagat ctacaagcgg tggatcatcc tgggcctgaa caagatcgtg    840
cggatgtaca gccccaccag catcctggac atccgccagg gccccaagga gcccttccgc    900
gactacgtgg accgcttcta caagaccctg cgcgctgagc aggccagcca ggacgtgaag    960
aactggatga ccgagaccct gctggtgcag aacgccaacc ccgactgcaa gaccatcctg   1020
aaggctctcg gccccgcggc caccctggag gagatgatga ccgcctgcca gggcgtgggc   1080
ggccccggcc acaaggcccg cgtgctggcc gaggcgatga gccaggtgac gaacccggcg   1140
accatcatga tgcagcgcgg caacttccgc aaccagcgga agaccgtcaa gtgcttcaac   1200
tgcggcaagg agggccacac cgccaggaac tgccgcgccc ccgcaagaa gggctgctgg   1260 cgctgcggcc gcgaaggaca ccaaatgaaa gattgcactg agagacaggc taatttttta   1320
gggaagatct ggccttccta aagggaagg ccagggaatt tcttcagag cagaccagag   1380 ccaacagccc caccagaaga gagcttcagg tttggggagg agaaaacaac tccctctcag   1440
aagcaggagc cgatagacaa ggaactgtat cctttaactt ccctcagatc actctttggc   1500
aacgacccct cgtcacagta aggatcggcg gccagctcaa ggaggcgctg ctcgacaccg   1560
gcgccgacga caccgtgctg gaggagatga acctgcccgg caagtggaag cccaagatga   1620
tcggcgggat cggggcttc atcaaggtgc ggcagtacga ccagatcccc gtggagatct   1680
```

| | |
|---|---:|
| gcggccacaa ggccatcggc accgtgctgg tgggccccac cccgtgaac atcatcggcc | 1740 |
| gcaacctgct gacccagatc ggctgcaccc tgaacttccc catcagcccc atcgagacgg | 1800 |
| tgcccgtgaa gctgaagccg gggatggacg gccccaaggt caagcagtgg ccctgtaag | 1860 |
| aattc | 1865 |

<210> SEQ ID NO 79
<211> LENGTH: 1865
<212> TYPE: DNA
<213> ORGANISM: Artificial Sequence
<220> FEATURE:
<223> OTHER INFORMATION: GP2

<400> SEQUENCE: 79

| | |
|---|---:|
| gtcgacgcca ccatgggcgc ccgcgccagc gtgctgagcg gcggcgagct ggacaagtgg | 60 |
| gagaagatcc gcctgcgccc cggcggcaag aagaagtaca agctgaagca catcgtgtgg | 120 |
| gccagccgcg agctggagcg cttcgccgtg aaccccggcc tgctggagac cagcgagggc | 180 |
| tgccgccaga tcctgggcca gctgcagccc agcctgcaga ccggcagcga ggagctgcgc | 240 |
| agcctgtaca acaccgtggc caccctgtac tgcgtgcacc agcgcatcga cgtcaaggac | 300 |
| accaaggagg ccctggagaa gatcgaggag gagcagaaca agtccaagaa gaaggcccag | 360 |
| caggccgccg ccgccgccgg caccggcaac agcagccagg tgagccagaa ctaccccatc | 420 |
| gtgcagaacc tgcagggcca gatggtgcac caggccatca gcccccgcac cctgaacgcc | 480 |
| tgggtgaagg tggtggagga aaggccttc agccccgagg tgatccccat gttcagcgcc | 540 |
| ctgagcgagg gcgccacccc ccaggacctg aacacgatgt tgaacaccgt gggcggccac | 600 |
| caggccgcca tgcagatgct gaaggagacc atcaacgagg aggccgccga gtgggaccgc | 660 |
| gtgcaccccg tgcacgccgg ccccatcgcc cccggccaga tgcgcgagcc ccgcggcagc | 720 |
| gacatcgccg gcaccaccag caccctgcag gagcagatcg gctggatgac caacaacccc | 780 |
| cccatccccg tgggcgagat ctacaagcgg tggatcatcc tgggcctgaa caagatcgtg | 840 |
| cggatgtaca gccccaccag catcctggac atccgccagg gccccaagga gcccttccgc | 900 |
| gactacgtgg accgcttcta caagaccctg cgcgctgagc aggccagcca ggacgtgaag | 960 |
| aactggatga ccgagaccct gctggtgcag aacgccaacc ccgactgcaa gaccatcctg | 1020 |
| aaggctctcg gcccgcggc caccctggag gagatgatga ccgcctgcca gggcgtgggc | 1080 |
| ggccccggcc acaaggcccg cgtgctggcc gaggcgatga ccaggtgac gaacccggcg | 1140 |
| accatcatga tgcagcgcgg caacttccgc aaccagcgga gaccgtcaa gtgcttcaac | 1200 |
| tgcggcaagg agggccacac cgccaggaac tgccgcgccc ccgcaagaa gggctgctgg | 1260 |
| cgctgcggcc gcgaaggaca ccaaatgaaa gattgcactg agagacaggc taattttta | 1320 |
| gggaagatct ggccttccta aagggaagg ccagggaatt ttcttcagag cagaccagag | 1380 |
| ccaacagccc caccagaaga gagcttcagg tttgggagg agaaaacaac tccctctcag | 1440 |
| aagcaggagc cgatagacaa ggaactgtat cctttaactt ccctcagatc actctttggc | 1500 |
| aacgacccct cgtcacagta aggatcgggg ggcaactcaa ggaagcgctg ctcgatacag | 1560 |
| gagcagatga tacagtatta gaagaaatga atttgccagg aaaatggaaa ccaaaaatga | 1620 |
| tagggggat cggggcttc atcaaggtga ggcagtacga ccagatacct gtagaaatct | 1680 |
| gtggacataa agctataggt acagtattag taggacctac acctgtcaac ataattggaa | 1740 |
| gaaatctgtt gacccagatc ggctgcacct tgaacttccc catcagccct attgagacgg | 1800 |
| tgcccgtgaa gttgaagccg gggatggacg gccccaaggt caagcaatgg ccattgtaag | 1860 | aattc                                                                        1865

<210> SEQ ID NO 80
<211> LENGTH: 2305
<212> TYPE: DNA
<213> ORGANISM: Artificial Sequence
<220> FEATURE:
<223> OTHER INFORMATION: FS(+).proinact.RTopt.YM

<400> SEQUENCE: 80

```
gcggccgcga aggacaccaa atgaaagatt gcactgagag acaggctaat ttttaggga      60
agatctggcc ttcctacaag ggaaggccag ggaattttct tcagagcaga ccagagccaa    120
cagccccacc agaagagagc ttcaggtttg gggaggagaa acaactccc tctcagaagc     180
aggagccgat agacaaggaa ctgtatcctt taacttccct cagatcactc tttggcaacg    240
acccctcgtc acaataagga tcgggggca actcaaggaa gcgctgctcg atacaggagc     300
agatgataca gtattagaag aaatgaattt gccaggaaaa tggaaaccaa aaatgatagg    360
ggggatcggg ggcttcatca aggtgaggca gtacgaccag atacctgtag aaatctgtgg    420
acataaagct ataggtacag tattagtagg acctacacct gtcaacataa ttggaagaaa    480
tctgttgacc cagatcggct gcaccttgaa cttccccatc agccctattg agacggtgcc    540
cgtgaagttg aagccgggga tggacggccc caaggtcaag caatggccat tgaccgagga    600
gaagatcaag gccctggtgg agatctgcac cgagatggag aaggagggca agatcagcaa    660
gatcggcccc gagaaccccct acaacacccc cgtgttcgcc atcaagaaga aggacagcac    720
caagtggcgc aagctggtgg acttccgcga gctgaacaag cgcacccagg acttctggga    780
ggtgcagctg gcatccccc accccgccgg cctgaagaag aagaagagcg tgaccgtgct    840
ggacgtgggc gacgcctact tcagcgtgcc cctggacaag gacttccgca gtacaccgc     900
cttcaccatc cccagcatca acaacgagac ccccggcatc cgctaccagt acaacgtgct    960
gccccagggc tggaagggca gccccgccat cttccagagc agcatgacca agatcctgga   1020
gcccttccgc aagcagaaac ccgacatcgt gatctaccag gccccctgt acgtgggcag    1080
cgacctggag atcggccagc accgcaccaa gatcgaggag ctgcgccagc acctgctgcg   1140
ctggggcttc accacccccg acaagaagca ccagaaggag cccccttcc tgtggatggg   1200
ctacgagctg caccccgaca gtggaccgt gcagcccatc atgctgcccg agaaggacag   1260
ctggaccgtg aacgacatcc agaagctggt gggcaagctg aactgggcca gcagatcta   1320
cgccggcatc aaggtgaagc agctgtgcaa gctgctgcgc ggcaccaagg ccctgaccga   1380
ggtgatcccc ctgaccgagg aggccgagct ggagctggcc gagaaccgcg agatcctgaa   1440
ggagcccgtg cacgaggtgt actacgaccc cagcaaggac ctggtggccg agatccagaa   1500
gcagggccag ggccagtgga cctaccagat ctaccaggag cccttcaaga acctgaagac   1560
cggcaagtac gcccgcatgc gcggcgccca caacagcag gtgaagcagc tgaccgaggc   1620
cgtgcagaag gtgagcaccg agagcatcgt gatctgggc aagatcccca gttcaagct    1680
gcccatccag aaggagacct gggaggcctg gtggatggag tactggcagg ccacctggat   1740
ccccgagtgg gagttcgtga caccccccc cctggtgaag ctgtggtacc agctggagaa   1800
ggagcccatc gtgggcgccg agaccttcta cgtggacggc gccgcaacc gcgagaccaa   1860
gctgggcaag gccggctacg tgaccgaccg gggccggcag aaggtggtga gcatcgccga   1920
caccaccaac cagaagaccg agctgcaggc catccacctg gccctgcagg acagcggcct   1980
ggaggtgaac atcgtgaccg acagccagta cgccctgggc atcatccagg cccagcccga   2040
```

| | |
|---|---|
| caagagcgag agcgagctgg tgagccagat catcgagcag ctgatcaaga aggagaaggt | 2100 |
| gtacctggcc tgggtgcccg cccacaaggg catcggcggc aacgagcagg tggacaagct | 2160 |
| ggtgagcgcc ggcatccgca aggtgctgtt cctgaacggc atcgatggcg gcatcgtgat | 2220 |
| ctaccagtac atggacgacc tgtacgtggg cagcggcggc cctaggatcg attaaaagct | 2280 |
| tcccggggct agcaccggtg aattc | 2305 |

<210> SEQ ID NO 81
<211> LENGTH: 2299
<212> TYPE: DNA
<213> ORGANISM: Artificial Sequence
<220> FEATURE:
<223> OTHER INFORMATION: FS(+).proinact.RTopt.YMWM

<400> SEQUENCE: 81

| | |
|---|---|
| gcggccgcga aggacaccaa atgaaagatt gcactgagag acaggctaat ttttagggga | 60 |
| agatctggcc ttcctacaag ggaaggccag ggaattttct tcagagcaga ccagagccaa | 120 |
| cagccccacc agaagagagc ttcaggtttg ggaggagaa acaactccc tctcagaagc | 180 |
| aggagccgat agacaaggaa ctgtatcctt aacttccct cagatcactc tttggcaacg | 240 |
| accccctcgtc acaataagga tcgggggggca actcaaggaa gcgctgctcg atacaggagc | 300 |
| agatgataca gtattagaag aaatgaattt gccaggaaaa tggaaaccaa aaatgatagg | 360 |
| ggggatcggg ggcttcatca aggtgaggca gtacgaccag atacctgtag aaatctgtgg | 420 |
| acataaagct ataggtacag tattagtagg acctacacct gtcaacataa ttggaagaaa | 480 |
| tctgttgacc cagatcggct gcaccttgaa cttccccatc agccctattg agacggtgcc | 540 |
| cgtgaagttg aagccgggga tggacggccc caaggtcaag caatggccat tgaccgagga | 600 |
| gaagatcaag gccctggtgg agatctgcac cgagatggag aaggagggca agatcagcaa | 660 |
| gatcggcccc gagaacccct acaacacccc cgtgttcgcc atcaagaaga aggacagcac | 720 |
| caagtggcgc aagctggtgg acttccgcga gctgaacaag cgcacccagg acttctggga | 780 |
| ggtgcagctg ggcatccccc accccgccgg cctgaagaag aagaagagcg tgaccgtgct | 840 |
| ggacgtgggc gacgcctact tcagcgtgcc cctggacaag gacttccgca gtacaccgc | 900 |
| cttcaccatc cccagcatca acaacgagac ccccggcatc cgctaccagt acaacgtgct | 960 |
| gccccagggc tggaagggca gccccgccat cttccagagc agcatgacca agatcctgga | 1020 |
| gcccttccgc aagcagaacc ccgacatcgt gatctaccag gccccccgtgt acgtgggcag | 1080 |
| cgacctggag atcggccagc accgcaccaa gatcgaggag ctgcgccagc acctgctgcg | 1140 |
| ctggggcttc accaccccg acaagaagca ccagaaggag cccccttcc tgccatcga | 1200 |
| gctgcacccc gacaagtgga ccgtgcagcc catcatgctg cccgagaagg acagctggac | 1260 |
| cgtgaacgac atccagaagc tggtgggcaa gctgaactgg gccagccaga tctacgccgg | 1320 |
| catcaaggtg aagcagctgt gcaagctgct gcgcggcacc aaggccctga ccgaggtgat | 1380 |
| ccccctgacc gaggaggccg agctggagct ggccgagaac cgcgagatcc tgaaggagcc | 1440 |
| cgtgcacgag gtgtactacg accccagcaa ggacctggtg gccgagatcc agaagcaggg | 1500 |
| ccagggccag tggaccctac agatctacca ggagcccttc aagaacctga agaccggcaa | 1560 |
| gtacgcccgc atgcgcggcg cccacaccaa cgacgtgaaa cagctgaccg aggccgtgca | 1620 |
| gaaggtgagc accgagagca tcgtgatctg ggcaagatc cccaagttca agctgcccat | 1680 |
| ccagaaggag acctgggagg cctggtggat ggagtactgg caggccacct ggatcccga | 1740 |
| gtgggagttc gtgaacaccc cccccctggt gaagctgtgg taccagctgg agaaggagcc | 1800 |

```
catcgtgggc gccgagacct tctacgtgga cggcgccgcc aaccgcgaga ccaagctggg    1860
caaggccggc tacgtgaccg accggggccg gcagaaggtg gtgagcatcg ccgacaccac    1920
caaccagaag accgagctgc aggccatcca cctggccctg caggacagcg gcctggaggt    1980
gaacatcgtg accgacagcc agtacgccct gggcatcatc caggcccagc ccgacaagag    2040
cgagagcgag ctggtgagcc agatcatcga gcagctgatc aagaaggaga aggtgtacct    2100
ggcctgggtg cccgcccaca agggcatcgg cggcaacgag caggtggaca agctggtgag    2160
cgccggcatc cgcaaggtgc tgttcctgaa cggcatcgat gcggcatcg tgatctacca    2220 gtacatggac gacctgtacg tgggcagcgg cggccctagg atcgattaaa agcttcccgg    2280
ggctagcacc ggtgaattc                                                 2299

<210> SEQ ID NO 82
<211> LENGTH: 2306
<212> TYPE: DNA
<213> ORGANISM: Artificial Sequence
<220> FEATURE:
<223> OTHER INFORMATION: FS(-).protmod.RTopt.YM

<400> SEQUENCE: 82
gcggccgcga aggacaccaa atgaaagatt gcactgagag acaggctaat ttcttccgcg      60
aggacctggc cttcctgcag ggcaaggccc gcgagttcag cagcgagcag acccgcgcca    120
acagccccac ccgccgcgag ctgcaggtgt ggggcggcga gaacaacagc ctgagcgagg    180
ccggcgccga ccgccagggc accgtgagct tcaacttccc ccagatcacc ctgtggcagc    240
gccccctggt gaccatcagg atcggcggcc agctcaagga ggcgctgctc gacaccggcg    300
ccgacgacac cgtgctggag gagatgaacc tgcccggcaa gtggaagccc aagatgatcg    360
gcgggatcgg gggcttcatc aaggtgcggc agtacgacca gatccccgtg gagatctgcg    420
gccacaaggc catcggcacc gtgctggtgg cccccacccc cgtgaacatc atcggccgca    480
acctgctgac ccagatcggc tgcaccctga acttccccat cagccccatc gagacggtgc    540
ccgtgaagct gaagccgggg atggacggcc ccaaggtcaa gcagtggccc ctgaccgagg    600
agaagatcaa ggccctggtg gagatctgca ccgagatgga aaggagggc aagatcagca    660 agatcggccc cgagaacccc tacaacaccc ccgtgttcgc catcaagaag aaggacagca    720
ccaagtggcg caagctggtg gacttccgcg agctgaacaa gcgcacccag gacttctggg    780
aggtgcagct gggcatcccc caccccgccg gcctgaagaa gaagaagagc gtgaccgtgc    840
tggacgtggg cgacgcctac ttcagcgtgc ccctggacaa ggacttccgc aagtacaccg    900
ccttcaccat ccccagcatc aacaacgaga ccccggcat ccgctaccag tacaacgtgc    960
tgccccaggg ctggaagggc agccccgcca tcttccagag cagcatgacc aagatcctgg    1020
agcccttccg caagcagaac cccgacatcg tgatctacca ggccccctg tacgtgggca    1080 gcgacctgga gatcggccag caccgcacca agatcgagga gctgcgccag cacctgctgc    1140 gctgggctt caccaccccc gacaagaagc accagaagga gccccccttc ctgtggatgg    1200
gctacgagct gcacccgac aagtggaccg tgcagcccat catgctgccc gagaaggaca    1260
gctggaccgt gaacgacatc cagaagctgg tgggcaagct gaactgggcc agccagatct    1320 acgcggcat caaggtgaag cagctgtgca agctgctgcg cggcaccaag gccctgaccg    1380
aggtgatccc cctgaccgag gaggccgagc tggagctggc cgagaaccgc gagatcctga    1440
aggagcccgt gcacgaggtg tactacgacc ccagcaagga cctggtggcc gagatccaga    1500
agcagggcca gggccagtgg acctaccaga tctaccagga gcccttcaag aacctgaaga    1560
```

```
ccggcaagta cgcccgcatg cgcggcgccc acaccaacga cgtgaagcag ctgaccgagg    1620
ccgtgcagaa ggtgagcacc gagagcatcg tgatctgggg caagatcccc aagttcaagc    1680
tgcccatcca gaaggagacc tgggaggcct ggtggatgga gtactggcag gccacctgga    1740
tccccgagtg ggagttcgtg aacacccccc ccctggtgaa gctgtggtac cagctggaga    1800
aggagcccat cgtgggcgcc gagaccttct acgtggacgg cgccgccaac cgcgagacca    1860
agctgggcaa ggccggctac gtgaccgacc ggggccggca aaggtggtg agcatcgccg    1920 acaccaccaa ccagaagacc gagctgcagg ccatccacct ggccctgcag acagcggcc    1980 tggaggtgaa catcgtgacc gacagccagt acgccctggg catcatccag gcccagcccg    2040
acaagagcga gagcgagctg gtgagccaga tcatcgagca gctgatcaag aaggagaagg    2100
tgtacctggc ctgggtgccc gcccacaagg gcatcggcgg caacgagcag gtggacaagc    2160
tggtgagcgc cggcatccgc aaggtgctgt tcctgaacgg catcgatggc ggcatcgtga    2220
tctaccagta catggacgac ctgtacgtgg gcagcggcgg ccctaggatc gattaaaagc    2280
ttcccggggc tagcaccggt gaattc                                         2306

<210> SEQ ID NO 83
<211> LENGTH: 2300
<212> TYPE: DNA
<213> ORGANISM: Artificial Sequence
<220> FEATURE:
<223> OTHER INFORMATION: FS(-).protmod.RTopt.YMWM

<400> SEQUENCE: 83
gcggccgcga aggacaccaa atgaaagatt gcactgagag acaggctaat ttcttccgcg      60
aggacctggc cttcctgcag ggcaaggccc gcgagttcag cagcgagcag acccgcgcca     120
acagccccac ccgccgcgag ctgcaggtgt ggggcggcga gaacaacagc ctgagcgagg     180
ccggcgccga ccgccaggc accgtgagct tcaacttccc ccagatcacc ctgtggcagc      240
gccccctggt gaccatcagg atcggcggcc agctcaagga ggcgctgctc gacaccggcg     300
ccgacgacac cgtgctggag gagatgaacc tgccccggcaa gtggaagccc aagatgatcg     360
gcgggatcgg gggcttcatc aaggtgcggc agtacgacca gatccccgtg gagatctgcg     420
gccacaaggc catcggcacc gtgctggtgg ccccaccccc cgtgaacatc atcgccgcca     480
acctgctgac ccagatcggc tgcaccctga acttccccat cagccccatc gagacggtgc     540
ccgtgaagct gaagccgggg atggacggcc ccaaggtcaa gcagtggccc ctgaccgagg     600
agaagatcaa ggccctggtg gagatctgca ccgagatgga aaggagggc aagatcagca     660 agatcggccc cgagaacccc tacaacaccc ccgtgttcgc catcaagaag aaggacagca     720
ccaagtggcg caagctggtg gacttccgcg agctgaacaa gcgcacccag gacttctggg     780
aggtgcagct gggcatcccc cacccgccg gcctgaagaa gaagaagagc gtgaccgtgc     840
tggacgtggg cgacgcctac ttcagcgtgc cctggacaa ggacttccgc aagtacaccg     900
ccttcaccat ccccagcatc aacaacgaga cccccggcat ccgctaccag tacaacgtgc     960 tgcccccaggg ctggaagggc agcccccgcca tcttccagag cagcatgacc aagatcctgg    1020
agcccttccg caagcagaac cccgacatcg tgatctacca ggccccccctg tacgtgggca    1080 gcgacctgga gatcggccag caccgcacca agatcgagga gctgcgccag cacctgctgc    1140 gctgggggctt caccaccccc cgacaagaagc accagaagga gccccccttc ctgcccatcg    1200
agctgcaccc cgacaagtgg accgtgcagc ccatcatgct gccccgagaag acagctgga    1260 ccgtgaacga catccagaag ctggtgggca agctgaactg ggccagccag atctacgccg    1320
```

```
gcatcaaggt gaagcagctg tgcaagctgc tgcgcggcac caaggccctg accgaggtga   1380 tcccctgac cgaggaggcc gagctggagc tggccgagaa ccgcgagatc ctgaaggagc    1440
ccgtgcacga ggtgtactac gaccccagca aggacctggt ggccgagatc cagaagcagg   1500
gccagggcca gtggacctac cagatctacc aggagccctt caagaacctg aagaccggca   1560
agtacgcccg catgcgcggc gcccacacca cgacgtgaa gcagctgacc gaggccgtgc    1620
agaaggtgag caccgagagc atcgtgatct ggggcaagat ccccaagttc aagctgccca   1680
tccagaagga gacctgggag cctggtggga tggagtactg gcaggccacc tggatccccg   1740
agtgggagtt cgtgaacacc ccccccctgg tgaagctgtg gtaccagctg gagaaggagc   1800
ccatcgtggg cgccgagacc ttctacgtga cggcgccgc caaccgcgag accaagctgg    1860
gcaaggccgg ctacgtgacc gaccggggcc ggcagaaggt ggtgagcatc gccgacacca   1920
ccaaccagaa gaccgagctg caggccatcc acctggccct gcaggacagc ggcctggagg   1980
tgaacatcgt gaccgacagc cagtacgccc tgggcatcat ccaggcccag cccgacaaga   2040
gcgagagcga gctggtgagc cagatcatcg agcagctgat caagaaggag aaggtgtacc   2100
tggcctgggt gcccgcccac aagggcatcg gcggcaacga gcaggtggac aagctggtga   2160
gcgccggcat ccgcaaggtg ctgttcctga acggcatcga tggcggcatc gtgatctacc   2220
agtacatgga cgacctgtac gtgggcagcg cggccctag gatcgattaa aagcttcccg    2280
gggctagcac cggtgaattc                                               2300
```

<210> SEQ ID NO 84
<211> LENGTH: 2312
<212> TYPE: DNA
<213> ORGANISM: Artificial Sequence
<220> FEATURE:
<223> OTHER INFORMATION: FS(-).protmod.RTopt(+)

<400> SEQUENCE: 84

```
gcggccgcga aggacaccaa atgaaagatt gcactgagag acaggctaat ttcttccgcg   60
aggacctggc cttcctgcag ggcaaggccc gcgagttcag cagcgagcag acccgcgcca   120
acagccccac ccgccgcgag ctgcaggtgt ggggcggcga gaacaacagc ctgagcgagg   180
ccggcgccga ccgccagggc accgtgagct tcaacttccc ccagatcacc ctgtggcagc   240 gcccccctggt gaccatcagg atcggcggcc agctcaagga ggcgctgctc gacaccggcg   300
ccgacgacac cgtgctggag gagatgaacc tgcccggcaa gtggaagccc aagatgatcg   360
gcgggatcgg gggcttcatc aaggtgcggc agtacgacca gatccccgtg gagatctgcg   420
gccacaaggc catcggcacc gtgctggtgg gccccacccc cgtgaacatc atcggccgca   480
acctgctgac ccagatcggc tgcaccctga acttccccat cagccccatc gagacggtgc   540
ccgtgaagct gaagccgggg atggacggcc ccaaggtcaa gcagtggccc ctgaccgagg   600
agaagatcaa ggccctggtg gagatctgca ccgagatgga aggagggc aagatcagca   660 agatcggccc cgagaacccc tacaacaccc ccgtgttcgc catcaagaag aaggacagca   720
ccaagtggcg caagctggtg gacttccgcg agctgaacaa gcgcacccag gacttctggg   780
aggtgcagct gggcatcccc caccccgccg gcctgaagaa gaagaagagc gtgaccgtgc   840
tggacgtggg cgacgcctac ttcagcgtgc cctggacaa ggacttccgc aagtacaccg    900
ccttcaccat ccccagcatc aacaacgaga cccccggcat ccgctaccag tacaacgtgc   960
tgccccaggg ctggaagggc agcccgcca tcttccagag cagcatgacc aagatcctgg   1020
agcccttccg caagcagaac cccgacatcg tgatctacca gtacatggac gacctgtacg   1080
```

```
tgggcagcga cctggagatc ggccagcacc gcaccaagat cgaggagctg cgccagcacc   1140
tgctgcgctg gggcttcacc accccgaca agaagcacca aaggagccc ccttcctgt    1200 ggatgggcta cgagctgcac cccgacaagt ggaccgtgca gcccatcatg ctgcccgaga   1260
aggacagctg gaccgtgaac gacatccaga agctggtggg caagctgaac tgggccagcc   1320
agatctacgc cggcatcaag gtgaagcagc tgtgcaagct gctgcgcggc accaaggccc   1380
tgaccgaggt gatccccctg accgaggagg ccgagctgga gctggccgag aaccgcgaga   1440
tcctgaagga gcccgtgcac gaggtgtact acgaccccag caaggacctg gtggccgaga   1500
tccagaagca gggccagggc cagtggacct accagatcta ccaggagccc ttcaagaacc   1560
tgaagaccgg caagtacgcc cgcatgcgcg gcgcccacac caacgacgtg aagcagctga   1620
ccgaggccgt gcagaaggtg agcaccgaga gcatcgtgat ctggggcaag atccccaagt   1680
tcaagctgcc catccagaag gagacctggg aggcctggtg gatggagtac tggcaggcca   1740
cctggatccc cgagtgggag ttcgtgaaca ccccccccct ggtgaagctg tggtaccagc   1800
tggagaagga gcccatcgtg ggcgccgaga ccttctacgt ggacggcgcc gccaaccgcg   1860
agaccaagct gggcaaggcc ggctacgtga ccgaccgggg ccggcagaag gtggtgagca   1920
tcgccgacac caccaaccag aagaccgagc tgcaggccat ccacctggcc ctgcaggaca   1980
gcggcctgga ggtgaacatc gtgaccgaca gccagtacgc cctgggcatc atccaggccc   2040
agcccgacaa gagcgagagc gagctggtga gccagatcat cgagcagctg atcaagaagg   2100
agaaggtgta cctggcctgg gtgcccgccc acaagggcat cggcggcaac gagcaggtgg   2160
acaagctggt gagcgccggc atccgcaagg tgctgttcct gaacggcatc gatggcggca   2220
tcgtgatcta ccagtacatg gacgacctgt acgtgggcag cggcggccct aggatcgatt   2280
aaaagcttcc cggggctagc accggtgaat tc                                2312

<210> SEQ ID NO 85
<211> LENGTH: 306
<212> TYPE: DNA
<213> ORGANISM: Human immunodeficiency virus

<400> SEQUENCE: 85
atggagccag tagatcctag attagagccc tggaagcatc caggaagtca gcctaagact     60
gcttgtacaa attgctattg taaaaagtgt tgctttcatt gccaagtttg tttcataaca    120
aaaggcttag gcatctccta tggcaggaag aagcggagac agcgacgaag agctcctcca    180
gacagtgagg ttcatcaagt ttctctacca aagcaacccg cttcccagcc ccaaggggac    240
ccgacaggcc cgaaggaatc gaagaagaag gtggagagag agacagagac agatccagtc    300
cattag                                                               306

<210> SEQ ID NO 86
<211> LENGTH: 101
<212> TYPE: PRT
<213> ORGANISM: Human immunodeficiency virus

<400> SEQUENCE: 86

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
                20                  25                  30

His Cys Gln Val Cys Phe Ile Thr Lys Gly Leu Gly Ile Ser Tyr Gly
            35                  40                  45
```

```
                        Arg Lys Lys Arg Arg Gln Arg Arg Arg Ala Pro Pro Asp Ser Glu Val
                            50                  55                  60

His Gln Val Ser Leu Pro Lys Gln Pro Ala Ser Gln Pro Gln Gly Asp
                         65                  70                  75                  80

Pro Thr Gly Pro Lys Glu Ser Lys Lys Lys Val Glu Arg Glu Thr Glu
                                        85                  90                  95

Thr Asp Pro Val His
                                    100

<210> SEQ ID NO 87
<211> LENGTH: 306
<212> TYPE: DNA
<213> ORGANISM: Artificial Sequence
<220> FEATURE:
<223> OTHER INFORMATION: tat.SF162.opt

<400> SEQUENCE: 87
atggagcccg tggaccccg  cctggagccc tggaagcacc ccggcagcca gcccaagacc     60
gcctgcacca actgctactg caagaagtgc tgcttccact gccaggtgtg cttcatcacc    120
aagggcctgg gcatcagcta cggccgcaag aagcgccgcc agcgccgccg cgccccccc     180 gacagcgagg tgcaccaggt gagcctgccc aagcagcccg ccagccagcc caggggcgac    240
cccaccggcc caaggagag  caagaagaag gtggagcgcg agaccgagac cgaccccgtg    300
cactag                                                               306

<210> SEQ ID NO 88
<211> LENGTH: 306
<212> TYPE: DNA
<213> ORGANISM: Artificial Sequence
<220> FEATURE:
<223> OTHER INFORMATION: tat.cys22.SF162.opt

<400> SEQUENCE: 88
atggagcccg tggaccccg  cctggagccc tggaagcacc ccggcagcca gcccaagacc     60
gccggcacca actgctactg caagaagtgc tgcttccact gccaggtgtg cttcatcacc    120
aagggcctgg gcatcagcta cggccgcaag aagcgccgcc agcgccgccg cgccccccc     180 gacagcgagg tgcaccaggt gagcctgccc aagcagcccg ccagccagcc caggggcgac    240
cccaccggcc caaggagag  caagaagaag gtggagcgcg agaccgagac cgaccccgtg    300
cactag                                                               306

<210> SEQ ID NO 89
<211> LENGTH: 168
<212> TYPE: DNA
<213> ORGANISM: Artificial Sequence
<220> FEATURE:
<223> OTHER INFORMATION: tatamino.SF162.opt

<400> SEQUENCE: 89
atggagcccg tggaccccg  cctggagccc tggaagcacc ccggcagcca gcccaagacc     60
gcctgcacca actgctactg caagaagtgc tgcttccact gccaggtgtg cttcatcacc    120
aagggcctgg gcatcagcta cggccgcaag aagcgccgcc agcgccgc                 168

<210> SEQ ID NO 90
<211> LENGTH: 102
<212> TYPE: PRT
<213> ORGANISM: Artificial Sequence
<220> FEATURE:
<223> OTHER INFORMATION: tat cys22 SF162 protein
```

```
<400> SEQUENCE: 90

Met Glu Pro Val Asp Pro Arg Leu Glu Pro Trp Lys His Pro Gly Ser
1               5                   10                  15

Gln Pro Lys Thr Ala Gly Thr Asn Cys Tyr Cys Lys Lys Cys Cys Phe
                20                  25                  30

His Cys Gln Val Cys Phe Ile Thr Lys Gly Leu Gly Ile Ser Tyr Gly
            35                  40                  45

Arg Lys Lys Arg Arg Gln Arg Arg Ala Pro Pro Asp Ser Glu Val
        50                  55                  60

His Gln Val Ser Leu Pro Lys Gln Pro Ala Ser Gln Pro Gln Gly Asp
65                  70                  75                  80

Pro Thr Gly Pro Lys Glu Ser Lys Lys Lys Val Glu Arg Glu Thr Glu
                85                  90                  95

Thr Asp Pro Val His Glx
            100
```